(12) United States Patent
Shioda et al.

(10) Patent No.: US 9,521,848 B2
(45) Date of Patent: Dec. 20, 2016

(54) TETRAZOLINONE COMPOUND AND USE THEREFOR

(71) Applicant: Sumitomo Chemical Company, Limited, Tokyo (JP)

(72) Inventors: Takayuki Shioda, Takarazuka (JP); Sadayuki Arimori, Takarazuka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

(21) Appl. No.: 14/907,883

(22) PCT Filed: Jul. 29, 2014

(86) PCT No.: PCT/JP2014/070413
§ 371 (c)(1),
(2) Date: Jan. 27, 2016

(87) PCT Pub. No.: WO2015/016372
PCT Pub. Date: Feb. 5, 2015

(65) Prior Publication Data
US 2016/0157489 A1    Jun. 9, 2016

(30) Foreign Application Priority Data

Jul. 31, 2013 (JP) ................................ 2013-158729
Nov. 19, 2013 (JP) ................................ 2013-238579

(51) Int. Cl.
*A01N 43/713* (2006.01)
*C07D 401/14* (2006.01)
*C07D 401/12* (2006.01)

(52) U.S. Cl.
CPC ........... *A01N 43/713* (2013.01); *C07D 401/12* (2013.01); *C07D 401/14* (2013.01)

(58) Field of Classification Search
None
See application file for complete search history.

(56) References Cited

U.S. PATENT DOCUMENTS

| 6,583,090 B1 | 6/2003 | Gewehr et al. |
| 6,790,810 B2 | 9/2004 | Yanagi et al. |
| 2015/0051171 A1 | 2/2015 | Yoshimoto et al. |
| 2015/0203511 A1 | 7/2015 | Arimori et al. |
| 2015/0223460 A1 | 8/2015 | Arimori et al. |

FOREIGN PATENT DOCUMENTS

| JP | H09208565 A | 8/1997 |
| JP | 2001114769 A | 4/2001 |
| JP | 2002506060 A | 2/2002 |
| JP | 2003137876 A | 5/2003 |
| WO | 9636229 A1 | 11/1996 |
| WO | 2013092224 A1 | 6/2013 |
| WO | 2013162072 A1 | 10/2013 |
| WO | 2014051161 A1 | 4/2014 |
| WO | 2014051165 A1 | 4/2014 |

OTHER PUBLICATIONS

Int'l Preliminary Report on Patentability issued Oct. 21, 2014 in Int'l Application No. PCT/JP2014/070413.

*Primary Examiner* — Brian J Davis
(74) *Attorney, Agent, or Firm* — Panitch Schwarze Belisario & Nadel LLP

(57) ABSTRACT

A tetrazolinone compound represented by formula (1):

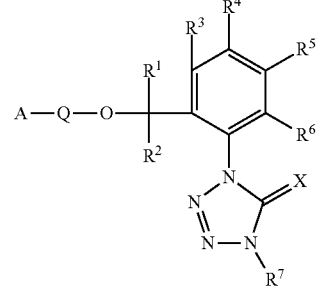

wherein $R^1$ and $R^2$ are the same or different and represent a hydrogen atom, etc.; $R^3$ represents a C1-C6 alkyl group, etc.; $R^4$, $R^5$, and $R^6$ are the same or different and represent a hydrogen atom, etc.; A represents a C6-C10 aryl group optionally having one or more atoms or groups selected from Group $P^1$, etc.; Q represents the following group Q1; and X represents an oxygen atom, has excellent control activity against pests.

10 Claims, No Drawings

TETRAZOLINONE COMPOUND AND USE THEREFOR

CROSS-REFERENCE TO RELATED APPLICATION

This application is a Section 371 of International Application No. PCT/JP2014/070413, filed Jul. 29, 2014, which was published in the Japanese language on Feb. 5, 2015, under International Publication No. WO 2015/016372 A1, and the disclosure of which is incorporated herein by reference.

TECHNICAL FIELD

The present invention relates to a tetrazolinone compound and use therefor.

BACKGROUND ART

Heretofore, various chemicals have been developed so as to control pests and provided in practice use, but in some cases, these chemicals may not exert enough activity.

Meanwhile, there have been known, as compounds having a tetrazolinone ring, compounds represented by formula (a):

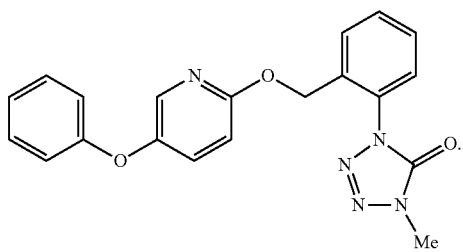

(see WO 96/036229 A)

The present invention provides compounds having excellent control activity against pests.

DISCLOSURE OF THE INVENTION

The present inventors have intensively studied so as to find compounds having excellent control activity against pests, and found that a tetrazolinone compound represented by the following formula (1) has excellent control activity against pests, thus completing the present invention.

The present invention includes the followings [1] to [11].

[1] A tetrazolinone compound represented by formula (1):

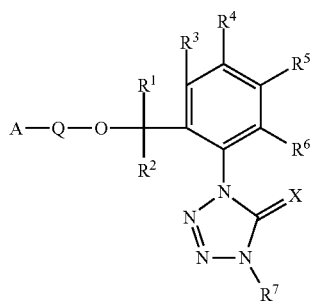

wherein
$R^1$ and $R^2$ each independently represents a hydrogen atom, a halogen atom, or a C1-C3 alkyl group;

$R^3$ represents a C1-C6 alkyl group, a C3-C6 cycloalkyl group, a halogen atom, a C1-C6 haloalkyl group, a C2-C6 alkenyl group, a C1-C6 alkoxy group, a C1-C6 alkylthio group, a C2-C6 alkynyl group, a nitro group, a cyano group, an aminocarbonyl group optionally having a C1-C6 alkyl group, a C2-C6 haloalkenyl group, a C2-C6 haloalkynyl group, a C3-C6 halocycloalkyl group, a C1-C6 haloalkoxy group, a C1-C6 haloalkylthio group, a C3-C6 cycloalkyloxy group, a C3-C6 halocycloalkyloxy group, a C3-C6 cycloalkylthio group, a C2-C6 alkenyloxy group, a C2-C6 alkynyloxy group, a C2-C6 haloalkenyloxy group, a C2-C6 haloalkynyloxy group, a C2-C6 alkenylthio group, a C2-C6 alkynylthio group, a C2-C6 haloalkenylthio group, a C2-C6 haloalkynylthio group, a C2-C6 alkylcarbonyl group, a C2-C6 haloalkylcarbonyl group, a C2-C6 alkylcarbonyloxy group, a C2-C6 alkylcarbonylthio group, a C2-C6 alkoxycarbonyl group, a hydroxy group, a sulfanyl group, an amino group optionally having a C1-C6 alkyl group, a pentafluorosulfanyl group, a C3-C9 trialkylsilyl group, a C5-C14 trialkylsilylethynyl group, a C1-C4 alkylsulfonyl group, a C1-C4 haloalkylsulfonyl group, a C1-C4 alkylsulfinyl group, a C1-C4 haloalkylsulfinyl group, a C2-C5 alkoxyalkyl group, or a C2-C5 alkylthioalkyl group;

$R^4$, $R^5$, and $R^6$ each independently represents a hydrogen atom, a halogen atom, a C1-C3 alkyl group, a C1-C3 haloalkyl group, or a C1-C3 alkoxy group;

$R^7$ represents a C1-C3 alkyl group optionally having one or more halogen atoms;

Q represents the following group:

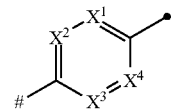

in which $X^1$, $X^2$, $X^3$, and X each independently represents a nitrogen atom or $CR^x$, $R^x$ represents a hydrogen atom, or one or more atoms or groups selected from Group $P^2$ (provided that one or more of $X^1$, $X^2$, $X^3$, and $X^4$ represent a nitrogen atom), the symbol # represents a binding site for A, and the symbol ● represents a binding site for an oxygen atom;

X represents an oxygen atom or a sulfur atom; and

A represents a C6-C10 aryl group optionally having one or more atoms or groups selected from Group $P^1$,
a C6-C10 aryloxy group optionally having one or more atoms or groups selected from Group $P^1$,
a C6-C10 arylthio group optionally having one or more atoms or groups selected from $P^1$,
a C6-C10 arylamino group optionally having one or more atoms or groups selected from Group $P^1$,
a 6-membered aromatic heterocyclic group having one, two, three, or four nitrogen atoms as a ring-constituent atom, provided that the heterocyclic group optionally has one or more groups or atoms selected from Group $P^1$,
a 5-membered heterocyclic group optionally having one or more atoms or groups selected from Group $P^1$, provided that the 5-membered heterocyclic group has, as a ring-constituent atom, one or more atoms selected from the group consisting of a nitrogen atom, an oxygen atom, and a sulfur atom and, when the 5-membered heterocyclic group has two or more atoms selected from the group consisting of a nitrogen atom, an oxygen atom, and a sulfur atom, the atoms may be the same or different to each other, an aliphatic C2-C9 heterocyclic group optionally having one or more atoms or groups selected from Group P¹, provided that the aliphatic C2-C9 heterocyclic group has, as a ring-constituent atom, one or more atoms selected from the group consisting of a nitrogen atom, an oxygen atom, and a sulfur atom and, when the aliphatic C2-C9 heterocyclic group has two or more atoms selected from the group consisting of a nitrogen atom, an oxygen atom, and a sulfur atom, the atoms may be the same or different to each other, and also a carbon or nitrogen atom constituting a ring of the aliphatic C2-C9 heterocyclic group is bound to Q,
a C3-C10 cycloalkyl group optionally having one or more atoms or groups selected from Group P¹,
a C7-C18 aralkyl group, a C7-C18 haloaralkyl group, a C7-C18 arylalkoxy group, a C7-C18 haloarylalkoxy group, or an oxime ether group optionally having one or more groups selected from Group P³:

Group P¹: Group consisting of a halogen atom, a C1-C6 alkyl group, a C1-C6 haloalkyl group, a C2-C6 alkenyl group, a C2-C6 haloalkenyl group, a C2-C6 alkynyl group, a C2-C6 haloalkynyl group, a C3-C6 cycloalkyl group, a C3-C6 halocycloalkyl group, a C1-C6 alkoxy group, a C1-C6 haloalkoxy group, a C1-C6 alkylthio group, a C1-C6 haloalkylthio group, a C3-C6 cycloalkyloxy group, a C3-C6 halocycloalkyloxy group, a C3-C6 cycloalkylthio group, a C3-C6 alkenyloxy group, a C3-C6 alkynyloxy group, a C3-C6 haloalkenyloxy group, a C3-C6 haloalkynyloxy group, a C3-C6 alkenylthio group, a C3-C6 alkynylthio group, a C3-C6 haloalkenylthio group, a C3-C6 haloalkynylthio group, a C2-C6 alkylcarbonyl group, a C2-C6 haloalkylcarbonyl group, a C2-C6 alkylcarbonyloxy group, a C2-C6 alkylcarbonylthio group, a hydroxycarbonyl group, a formyl group, a C2-C6 alkoxycarbonyl group, a nitro group, a cyano group, a hydroxy group, a C1-C6 alkylsulfonyl group, a C1-C6 haloalkylsulfonyl group, a C6-C10 arylsulfonyl group, a C6-C10 haloarylsulfonyl group, a C1-C6 alkylsulfinyl group, a C1-C6 haloalkylsulfinyl group, an amino group optionally having a C1-C6 alkyl group, an aminosulfonyl group optionally having a C1-C6 alkyl group, and an aminocarbonyl group optionally having a C1-C6 alkyl group;

Group P²: Group consisting of a C1-C4 alkyl group, a C1-C4 haloalkyl group, a halogen atom, a cyano group, a nitro group, a C3-C6 cycloalkyl group, a C3-C6 halocycloalkyl group, a C1-C4 alkoxy group, a C1-C4 haloalkoxy group, a C1-C4 alkylthio group, and a C1-C4 haloalkylthio group; and Group P³: Group consisting of a halogen atom, a C1-C6 alkyl group, a C1-C6 haloalkyl group, a C1-C6 cycloalkyl group, and a C1-C6 halocycloalkyl group.

[2] The tetrazolinone compound according to [1], wherein R¹, R², R⁴, R⁵, and R⁶ are hydrogen atoms, R³ is a C1-C6 alkyl group, a C3-C6 cycloalkyl group, a halogen atom, a C1-C6 haloalkyl group, or a C1-C6 alkoxy group, and Q is the following group Q11:

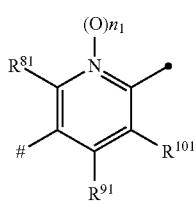

(Q11)

in which R⁸¹, R⁹¹, and R¹⁰¹ each independently represents a hydrogen atom, a halogen atom, a C1-C4 alkyl group, or a C1-C4 haloalkyl group, $n_1$ represents 0, X represents an oxygen atom, the symbol # represents a binding site for A, and the symbol ● represents a binding site for an oxygen atom.

[3] The tetrazolinone compound according to [1] or [2], wherein A is the following group A111:

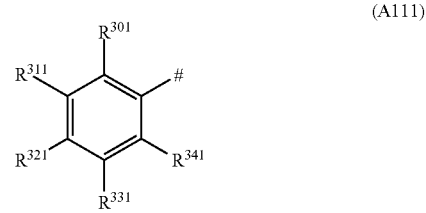

(A111)

in which R³⁰¹, R³¹¹, R³²¹, R³³¹, and R³⁴¹ each independently represents a hydrogen atom, a halogen atom, a C1-C6 alkyl group, a C1-C6 haloalkyl group, a C1-C6 alkoxy group, a C1-C6 haloalkoxy group, a C1-C6 alkylthio group, a C1-C6 haloalkylthio group, a C1-C6 alkylsulfinyl group, a C1-C6 haloalkylsulfinyl group, a C1-C6 alkylsulfonyl group, a C1-C6 haloalkylsulfonyl group, or a cyano group, and the symbol # represents a binding site for Q.

[4] The tetrazolinone compound according to [1] or [2], wherein A is the following group A131:

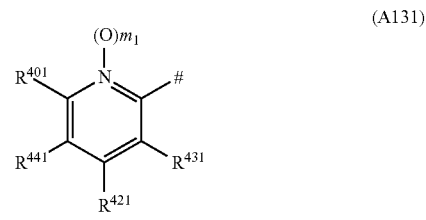

(A131)

in which $m_1$ represents 0, R⁴⁰¹, R⁴¹¹, R⁴²¹, and R⁴³¹ each independently represents a hydrogen atom, a halogen atom, a C1-C6 alkyl group, a C1-C6 haloalkyl group, a C1-C6 alkoxy group, a C1-C6 haloalkoxy group, a C1-C6 alkylthio group, a C1-C6 haloalkylthio group, a C1-C6 alkylsulfinyl group, a C1-C6 haloalkylsulfinyl group, a C1-C6 alkylsulfonyl group, a C1-C6 haloalkylsulfonyl group, or a cyano group, and the symbol # represents a binding site for Q.

[5] The tetrazolinone compound according to [1] or [2], wherein A is the following group A311:

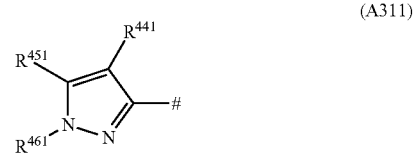

(A311)

in which R⁴⁴¹ represents a hydrogen atom, a C1-C3 alkyl group, or a halogen atom, R⁴⁵¹ represents a hydrogen atom, a halogen atom, a C1-C6 alkyl group, a C1-C3 alkoxy group, a C1-C3 alkylthio group, or a cyano group, R⁴⁶¹ represents a C1-C3 alkyl group, and the symbol # represents a binding site for Q.

[6] The tetrazolinone compound according to [1] or [2], wherein R¹, R², R⁴, R⁵, and R⁶ are hydrogen atoms, R³ is a C1-C6 alkyl group, a C3-C6 cycloalkyl group, a halogen atom, or a C1-C6 alkoxy group,
Q is Q11, R⁸¹, R⁹¹, and R¹⁰¹ each independently represents a hydrogen atom, a halogen atom, or a C1-C4 alkyl group,
A is a group A111, and R³⁰¹, R³¹¹, R³²¹, R³³¹, and R³⁴¹ each independently represents a hydrogen atom, a halogen atom, a C1-C6 alkyl group, a C1-C6 haloalkyl group, a C1-C6 alkoxy group, or a cyano group.

[7] The tetrazolinone compound according to [1] or [2], wherein $R^1$, $R^2$, $R^4$, $R^5$, and $R^6$ are hydrogen atoms, $R^3$ is a C1-C6 alkyl group, a C3-C6 cycloalkyl group, a halogen atom, or a C1-C6 alkoxy group,
Q is Q11, $R^{81}$, $R^{91}$, and $R^{101}$ each independently represents a hydrogen atom or a C1-C4 alkyl group, A is a group A131, and $R^{401}$, $R^{411}$, $R^{421}$, and $R^{431}$ each independently represents a hydrogen atom, a halogen atom, a C1-C6 alkyl group, a C1-C6 haloalkyl group, a C1-C6 alkoxy group, or a cyano group.

[8] The tetrazolinone compound according to [1], wherein $R^1$, $R^2$, $R^4$, $R^5$, and $R^6$ are hydrogen atoms, $R^3$ is a C1-C6 alkyl group,
Q is the following group Q21:

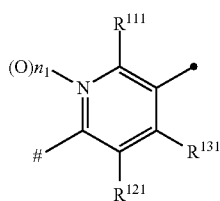

(Q21)

(in which $R^{121}$ and $R^{131}$ represent a hydrogen atom, $R^{111}$ represents a C1-C4 alkyl group, $n_1$ is 0, the symbol # represents a binding site for A, and the symbol ● represents a binding site for an oxygen atom), X is an oxygen atom, A is a group A111, and $R^{301}$, $R^{311}$, $R^{321}$, $R^{331}$, and $R^{341}$ each independently represents a hydrogen atom, a C1-C6 alkyl group, a C1-C6 alkoxy group, or a cyano group.

[9] A pest control agent comprising the tetrazolinone compound according to any one of [1] to [8].

[10] A method for controlling pests, which comprises treating plants or soil with an effective amount of the tetrazolinone compound according to any one of [1] to [8].

[11] Use of the tetrazolinone compound according to any one of [1] to [8] for controlling pests.

According to the present invention, pests can be controlled.

MODE FOR CARRYING OUT THE INVENTION

A compound of the present invention is a tetrazolinone compound represented by formula (1) (hereinafter sometimes referred to as the present compound (1)).
Formula (1)

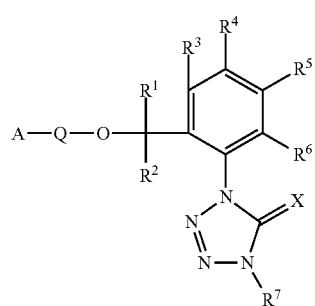

(1)

wherein symbols are the same as defined above.
Substituents as used herein will be mentioned below.
Examples of the halogen atom include a fluorine atom, a chlorine atom, a bromine atom, and an iodine atom.

The C1-C6 alkyl group represents a straight or branched alkyl group having 1-6 carbon atoms, and examples thereof include a methyl group, an ethyl group, a propyl group, an isopropyl group, a butyl group, a tert-butyl group, and a hexyl group.

The C1-C6 haloalkyl group represents a group in which at least one hydrogen atom of a straight or branched alkyl group having 1-6 carbon atoms is substituted with a halogen atom, and examples thereof include a fluoromethyl group, a chloromethyl group, a difluoromethyl group, a trifluoromethyl group, a 2,2,2-trifluoroethyl group, a pentafluoroethyl group, a 3-fluoropropyl group, a 2,2-difluoropropyl group, a 3,3,3-trifluoropropyl group, a 3-(fluoromethyl)-2-fluoroethyl group, a 4-fluorobutyl group, and a 2,2-difluorohexyl group.

The C2-C6 alkenyl group represents a straight or branched alkenyl group having 2-6 carbon atoms, and examples thereof include a vinyl group, a 1-propenyl group, an isopropenyl group, a 2-propenyl group, a 1-butenyl group, a 1-methyl-1-propenyl group, a 2-butenyl group, a 1,3-butadienyl group, a 1-pentenyl group, a 1-ethyl-2-propenyl group, a 2-pentenyl group, a 1-hexenyl group, and a 5-hexenyl group.

The C2-C6 haloalkenyl group represents a group in which at least one hydrogen atom of a straight or branched alkenyl group having 2-6 carbon atoms is substituted with a halogen atom, and examples thereof include a 2-chlorovinyl group, a 2-bromovinyl group, a 2-iodovinyl group, a 3-chloro-2-propenyl group, a 3-bromo-2-propenyl group, a 1-chloromethylvinyl group, a 2-bromo-1-methylvinyl group, a 1-trifluoromethylvinyl group, a 4,4,4-trifluoro-2-butenyl group, and a 5-bromo-4,5,5-trifluoro-4-trifluoromethyl-2-pentenyl group.

The C2-C6 alkynyl group represents a straight or branched alkynyl group having 2-6 carbon atoms, and examples thereof include an ethynyl group, a propargyl group, a 1-butyn-3-yl group, a 3-methyl-1-butyn-3-yl group, a 2-butynyl group, a 3-butynyl group, a 2-pentynyl group, a 3-pentynyl group, a 4-pentynyl group, a 1-hexynyl group, and a 5-hexynyl group.

The C2-C6 haloalkynyl group represents a group in which at least one hydrogen atom of a straight or branched alkynyl group having 2-6 carbon atoms is substituted with a halogen atom, and examples thereof include a fluoroethynyl group, a 3-chloro-2-propynyl group, a 3-bromo-2-propynyl group, a 3-iodo-2-propynyl group, a perfluoro-2-butynyl group, a perfluoro-2-pentynyl group, a perfluoro-3-pentynyl group, and a perfluoro-1-hexynyl group.

Examples of the C3-C6 cycloalkyl group include a cyclopropyl group, a cyclobutyl group, a cyclopentyl group, and a cyclohexyl group.

The C3-C6 halocycloalkyl group represents a group in which at least one hydrogen atom of a cycloalkyl group having 3-6 carbon atoms is substituted with a halogen atom, and examples thereof include a 2-fluorocyclopropyl group, a 2,2-difluorocyclopropyl group, a 2-chloro-2-fluorocyclopropyl group, a 2,2-dichlorocyclopropyl group, a 2-chlorocyclohexyl group, a 4,4-difluorocyclohexyl group, and a 4-chlorocyclohexyl group.

The C1-C6 alkoxy group represents a straight or branched alkoxy group having 1-6 carbon atoms, and examples thereof include a methoxy group, an ethoxy group, a propoxy group, an isopropoxy group, a butoxy group, an isobutoxy group, a sec-butoxy group, a tert-butoxy group, a pentyloxy group, and a hexyloxy group.

The C1-C6 haloalkoxy group represents a group in which at least one hydrogen atom of a straight or branched alkoxy group having 1-6 carbon atoms is substituted with a halogen atom, and examples thereof include a trifluoromethoxy group, a trichloromethoxy group, a chloromethoxy group, a dichloromethoxy group, a fluoromethoxy group, a difluoromethoxy group, a chlorofluoromethoxy group, a dichlorofluoromethoxy group, a pentafluoroethoxy group, a 2,2,2-trifluoroethoxy group, and a periodohexyloxy group.

The C1-C6 alkylthio group represents a straight or branched alkylthio group having 1-6 carbon atoms, and examples thereof include a methylthio group, an ethylthio group, a propylthio group, an isopropylthio group, a butylthio group, a sec-butylthio group, a tert-butylthio group, a hexylthio group, an isohexylthio group, and a sec-hexylthio group.

The C1-C6 haloalkylthio group represents a group in which at least one hydrogen atom of a straight or branched alkylthio group having 1-6 carbon atoms is substituted with a halogen atom, and examples thereof include a monofluoromethylthio group, a difluoromethylthio group, a trifluoromethylthio group, a trichloromethylthio group, a tribromomethylthio group, a triiodomethylthio group, a chlorofluoromethylthio group, a pentafluoroethylthio group, a 2,2,2-trifluoroethylthio group, and a periodohexylthio group.

Examples of the C3-C6 cycloalkyloxy group include a cyclopropyloxy group, a cyclobutyloxy group, a cyclopentyloxy group, and a cyclohexyloxy group.

The C3-C6 halocycloalkyloxy group represents a group in which at least one hydrogen atom of a cycloalkyloxy group having 3-6 carbon atoms is substituted with a halogen atom, and examples thereof include a 2-fluorocyclopropyloxy group, a 2,2-difluorocyclopropyloxy group, a 2-chloro-2-fluorocyclopropyloxy group, a 2,2-dichlorocyclopropyloxy group, a 2-chlorocyclohexyloxy group, a 4,4-difluorocyclohexyloxy group, and a 4-chlorocyclohexyloxy group.

Examples of the C3-C6 cycloalkylthio group include a cyclopropylthio group, a cyclobutylthio group, a cyclopentylthio group, and a cyclohexylthio group.

The C2-C6 alkenyloxy group represents a straight or branched alkenyloxy group having 2-6 carbon atoms, and examples thereof include a 2-propenyloxy group, a 2-butenyloxy group, a 1-methyl-2-propenyloxy group, a 3-butenyloxy group, a 2-methyl-2-propenyloxy group, a 2-pentenyloxy group, a 3-pentenyloxy group, a 4-pentenyloxy group, and a 5-hexenyloxy group.

The C2-C6 alkynyloxy group represents a straight or branched alkynyloxy group having 2-6 carbon atoms, and examples thereof include a propargyloxy group, a 1-butyn-3-yloxy group, a 3-methyl-1-butyn-3-yloxy group, a 2-butynyloxy group, a 3-butynyloxy group, a 2-pentynyloxy group, a 3-pentynyloxy group, a 4-pentynyloxy group, and a 5-hexynyloxy group.

The C2-C6 haloalkenyloxy group represents a group in which at least one hydrogen atom of a straight or branched alkenyloxy group having 2-6 carbon atoms is substituted with a halogen atom, and examples thereof include a 3-chloro-2-propenyloxy group, a 3-bromo-2-propenyloxy group, a 3-bromo-3,3-difluoro-1-propenyloxy group, a 2,3,3,3-tetrachloro-1-propenyloxy group, and a 5-bromo-4,5,5-trifluoro-4-trifluoromethyl-2-pentenyloxy group.

The C2-C6 haloalkynyloxy group represents a group in which at least one hydrogen atom of a straight or branched alkynyloxy group having 2-6 carbon atoms is substituted with a halogen atom, and examples thereof include a 3-chloro-2-propynyloxy group, a 3-bromo-2-propynyloxy group, a 3-iodo-2-propynyloxy group, a 5-chloro-4-pentynyloxy group, a 3-fluoro-2-propynyloxy group, and a perfluoro-5-hexynyloxy group.

The C2-C6 alkenylthio group represents a straight or branched alkenylthio group having 2-6 carbon atoms, and examples thereof include a 2-propenylthio group, a 2-butenylthio group, a 1-methyl-2-propenylthio group, a 3-butenylthio group, a 2-methyl-2-propenylthio group, a 2-pentenylthio group, a 3-pentenylthio group, a 4-pentenylthio group, and a 5-hexenylthio group.

The C2-C6 alkynylthio group represents a straight or branched alkynylthio group having 2-6 carbon atoms, and examples thereof include a propargylthio group, a 1-butyn-3-ylthio group, a 3-methyl-1-butyn-3-ylthio group, a 2-butynylthio group, a 3-butynylthio group, a 2-pentynylthio group, a 3-pentynylthio group, a 4-pentynylthio group, and a 5-hexynylthio group.

The C2-C6 haloalkenylthio group represents a group in which at least one hydrogen atom of a straight or branched alkenylthio group having 2-6 carbon atoms is substituted with a halogen atom, and examples thereof include a 3-chloro-2-propenylthio group, a 3-bromo-2-propenylthio group, a 3-bromo-3,3-difluoro-1-propenylthio group, a 2,3,3,3-tetrachloro-1-propenylthio group, a 2-chloro-2-propenylthio group, a 3,3-difluoro-2-propenylthio group, and a 5-bromo-4,5,5-trifluoro-4-trifluoromethyl-2-pentenylthio group.

The C2-C6 haloalkynylthio group represents a group in which at least one hydrogen atom of a straight or branched alkynylthio group having 2-6 carbon atoms is substituted with a halogen atom, and examples thereof include a 3-chloro-2-propynylthio group, a 3-bromo-2-propynylthio group, a 3-iodo-2-propynylthio group, a 5-chloro-4-pentynylthio group, a 3-fluoro-2-propynylthio group, and a perfluoro-5-hexynylthio group.

The C2-C6 alkylcarbonyl group represents an alkylcarbonyl group having 2-6 carbon atoms, which has a straight or branched alkyl group having 1-5 carbon atoms, and examples thereof include a methylcarbonyl group, an ethylcarbonyl group, a propylcarbonyl group, an isopropylcarbonyl group, a pivaloyl group, a butylcarbonyl group, and a pentylcarbonyl group.

The C2-C6 haloalkylcarbonyl group represents a group in which at least one hydrogen atom of a straight or branched alkylcarbonyl group having 2-6 carbon atoms is substituted with a halogen atom, and examples thereof include a trichloroacetyl group, a fluoroacetyl group, a difluoroacetyl group, a trifluoroacetyl group, a pentafluoropropionyl group, and a perfluorohexanoyl group.

The C2-C6 alkylcarbonyloxy group may be either straight or branched, and examples thereof include an acetoxy group, a propionyloxy group, a butanoyloxy group, a pentanoyloxy group, and a hexanoyloxy group.

The C2-C6 alkylcarbonylthio group may be either straight or branched, and examples thereof include an acetylthio group, a propionylthio group, a butanoylthio group, a pentanoylthio group, and a hexanoylthio group.

The C2-C6 alkoxycarbonyl group may be either straight or branched, and examples thereof include a methoxycarbonyl group, an ethoxycarbonyl group, a propyloxycarbonyl group, an isopropyloxycarbonyl group, a butyloxycarbonyl group, a tert-butyloxycarbonyl group, and a 2-methylbutyloxycarbonyl group.

The aminocarbonyl group optionally having a C1-C6 alkyl group represents an aminocarbonyl group in which one or two hydrogen atoms on nitrogen are optionally substituted with the same or different C1-C6 alkyl groups, and examples thereof include an aminocarbonyl group, a methylaminocarbonyl group, an ethylaminocarbonyl group, a propylaminocarbonyl group, an isopropylaminocarbonyl group, a butylaminocarbonyl group, a dimethylaminocarbonyl group, a diethylaminocarbonyl group, and a hexylaminocarbonyl group.

The aminosulfonyl group optionally having a C1-C6 alkyl group represents an aminosulfonyl group in which one or two hydrogen atoms on nitrogen are optionally substituted with the same or different C1-C6 alkyl groups, and examples thereof include an aminosulfonyl group, a methylaminosulfonyl group, an ethylaminosulfonyl group, a propylaminosulfonyl group, an isopropylaminosulfonyl group, a butylaminosulfonyl group, a dimethylaminosulfonyl group, a diethylaminosulfonyl group, and a hexylaminosulfonyl group.

The "6-membered aromatic heterocyclic group having one, two, three, or four nitrogen atoms as a ring-constituent atom" represents an aromatic 6-membered heterocyclic group in which one, two, three, or four atoms constituting the ring are nitrogen atoms, and examples thereof include a 2-pyridyl group, a 3-pyridyl group, a 4-pyridyl group, a 3-pyridazinyl group, a 2-pyrazinyl group, a 2-pyrimidinyl group, a 3-pyrimidinyl group, a 4-pyrimidinyl group, a 2,3,5-triazinyl group, a 2,3,6-triazinyl group, and a 2,3,5,6-tetrazinyl group.

The "6-membered aromatic heterocyclic group having one, two, three, or four nitrogen atoms as a ring-constituent atom (provided that the heterocyclic group optionally has one or more groups or atoms selected from Group $P^2$)" represents a group in which hydrogen atoms of the 6-membered aromatic heterocyclic group having one, two, three, or four nitrogen atoms as a ring-constituent atom are optionally substituted with one or more atoms or groups selected from Group $P^2$ and, when the number of atoms or groups selected from Group $P^2$ is 2 or more, those atoms or groups may be the same or different, and examples thereof include the following Q (Q1, Q2, Q3, Q4, Q5, Q6, Q7, Q8, and Q9):

Q:

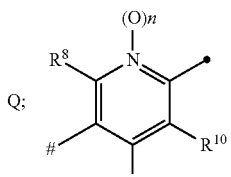 (Q1)

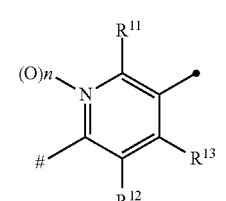 (Q2)

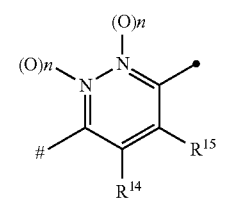 (Q3)

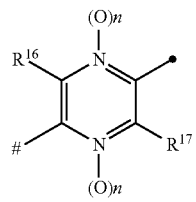 (Q4)

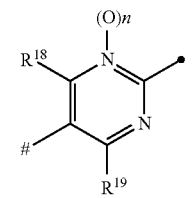 (Q5)

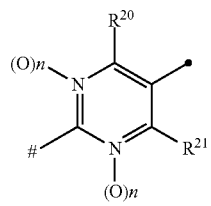 (Q6)

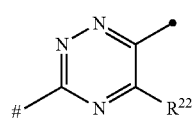 (Q7)

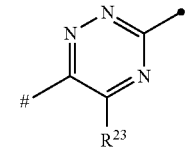 (Q8)

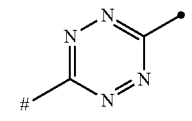 (Q9)

wherein n represents 0 or 1, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, and $R^{23}$ each independently represents a hydrogen atom, a C1-C4 alkyl group, a C1-C4 haloalkyl group, a halogen atom, a cyano group, a nitro group, a C3-C6 cycloalkyl group, a C3-C6 halocycloalkyl group, a C1-C4 alkoxy group, a C1-C4 haloalkoxy group, a C1-C4 alkylthio group, or a C1-C4 haloalkylthio group, the symbol # represents a binding site for A, the symbol ● represents a binding site for an oxygen atom, and n represents 0 or 1.

Examples of the C6-C10 aryl group include a phenyl group, a 1-naphthyl group, and a 2-naphthyl group.

The C6-C10 aryl group optionally having one or more atoms or groups selected from Group $P^1$ represents a C6-C10 aryl group in which hydrogen atoms of a C6-C10 aryl group are optionally substituted with one or more atoms or groups selected from Group $P^1$ and, when the number of atoms or groups selected from Group $P^1$ is 2 or more, those atoms or groups may be the same or different to each other.

Examples of the C6-C10 aryl group optionally having one or more atoms or groups selected from Group $P^1$ include the following A1, A2, and A3:

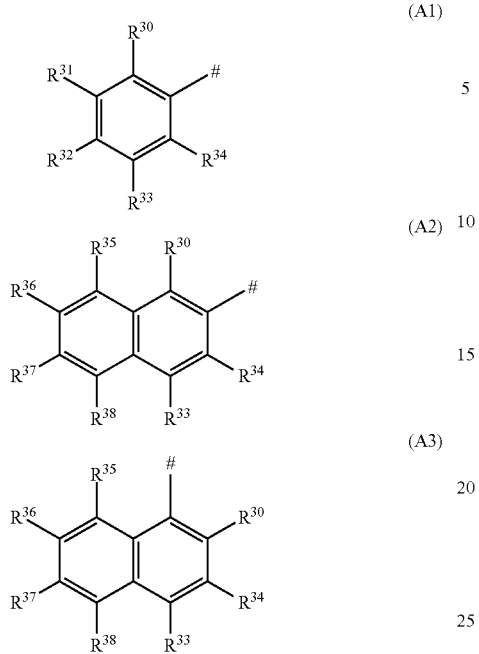

(A1)
(A2)
(A3)
(A4)
(A5)
(A6)

wherein $R^{30}$, $R^{31}$, $R^{32}$, $R^{33}$, $R^{34}$, $R^{35}$, $R^{36}$, $R^{37}$, and $R^{38}$ each independently represents a hydrogen atom, a halogen atom, a C1-C6 alkyl group, a C1-C6 haloalkyl group, a C2-C6 alkenyl group, a C2-C6 haloalkenyl group, a C2-C6 alkynyl group, a C2-C6 haloalkynyl group, a C3-C6 cycloalkyl group, a C3-C6 halocycloalkyl group, a C1-C6 alkoxy group, a C1-C6 haloalkoxy group, a C1-C6 alkylthio group, a C1-C6 haloalkylthio group, a C3-C6 cycloalkyloxy group, a C3-C6 halocycloalkyloxy group, a C3-C6 cycloalkylthio group, a C2-C6 alkenyloxy group, a C2-C6 alkynyloxy group, a C2-C6 haloalkenyloxy group, a C2-C6 haloalkynyloxy group, a C2-C6 alkenylthio group, a C2-C6 alkynylthio group, a C2-C6 haloalkenylthio group, a C2-C6 haloalkynylthio group, a C2-C6 alkylcarbonyl group, a C2-C6 haloalkylcarbonyl group, a C2-C6 alkylcarbonyloxy group, a C2-C6 alkylcarbonylthio group, a hydroxycarbonyl group, a formyl group, a C2-C6 alkoxycarbonyl group, a nitro group, a cyano group, a hydroxy group, a C1-C6 alkylsulfonyl group, a C1-C6 haloalkylsulfonyl group, a C6-C10 arylsulfonyl group, a C6-C10 haloarylsulfonyl group, a C1-C6 alkylsulfinyl group, a C1-C6 haloalkylsulfinyl group, an amino group optionally having a C1-C6 alkyl group, an aminosulfonyl group optionally having a C1-C6 alkyl group, or an aminocarbonyl group optionally having a C1-C6 alkyl group, and the symbol # represents a binding site for Q.

Examples of the C6-C10 aryloxy group include a phenyloxy group, a 1-naphthyloxy group, and a 2-naphthyloxy group.

The C6-C10 aryloxy group optionally having one or more atoms or groups selected from Group $P^1$ represents a C6-C10 aryloxy group in which hydrogen atoms of a C6-C10 aryl group are optionally substituted with one or more atoms or groups selected from Group $P^1$ and, when the number of atoms or groups selected from Group $P^1$ is 2 or more, those atoms or groups may be the same or different to each other. Examples of the C6-C10 aryloxy group optionally having one or more atoms or groups selected from Group $P^1$ include the following A4, A5, and A6:

wherein $R^{30}$, $R^{31}$, $R^3$, $R^{33}$, $R^{34}$, $R^{35}$, $R^{36}$, $R^{37}$, $R^{38}$, and the symbol # are the same as defined above.

Examples of the C6-C10 arylthio group include a phenylthio group, a 1-naphthylthio group, and a 2-naphthylthio group.

The C6-C10 arylthio group optionally having one or more atoms or groups selected from Group $P^1$ represents a C6-C10 arylthio group in which hydrogen atoms of a C6-C10 aryl group are optionally substituted with one or more atoms or groups selected from Group $P^1$ and, when the number of atoms or groups selected from Group $P^1$ is 2 or more, those atoms or groups may be the same or different to each other. Examples of the C6-C10 arylthio group optionally having one or more atoms or groups selected from Group $P^1$ include the following A7, A8, and A9 {the symbol # represents a binding site for Q}:

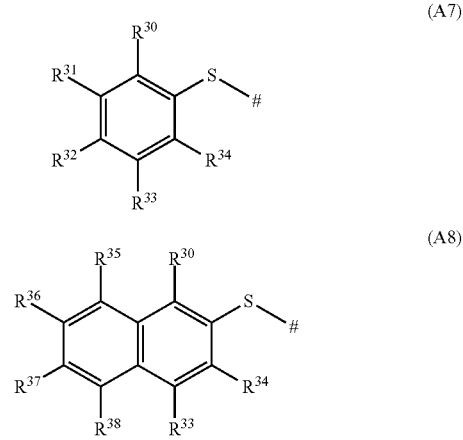

(A7)
(A8)

-continued

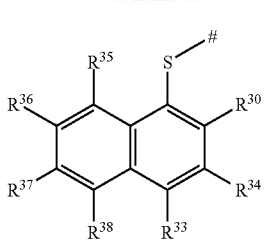
(A9)

wherein $R^{30}$, $R^{31}$, $R^{32}$, $R^{33}$, $R^{34}$, $R^{35}$, $R^{36}$, $R^{37}$, $R^{38}$, and the symbol # are the same as defined above.

Examples of the C6-C10 arylamino group include a phenylamino group, a 1-naphthylamino group, and a 2-naphthylamino group.

The C6-C10 arylamino group optionally having one or more atoms or groups selected from Group $P^1$ represents a C6-C10 arylamino group in which hydrogen atoms of a C6-C10 arylamino group are optionally substituted with one or more atoms or groups selected from Group $P^1$ and, when the number of atoms or groups selected from Group $P^1$ is 2 or more, those atoms or groups may be the same or different to each other. Examples of the C6-C10 arylamino group optionally having one or more atoms or groups selected from Group $P^1$ include the following A10, A11, and A12:

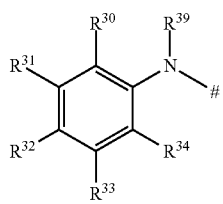
(A10)

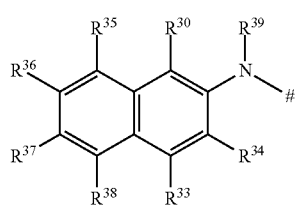
(A11)

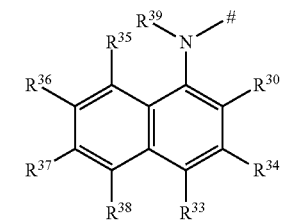
(A12)

wherein $R^{30}$, $R^{31}$, $R^{32}$, $R^{33}$, $R^{34}$, $R^{35}$, $R^{36}$, $R^{37}$, $R^{38}$, and $R^{39}$ each independently represents a hydrogen atom, a halogen atom, a C1-C6 alkyl group, a C1-C6 haloalkyl group, a C2-C6 alkenyl group, a C2-C6 haloalkenyl group, a C2-C6 alkynyl group, a C2-C6 haloalkynyl group, a C3-C6 cycloalkyl group, a C3-C6 halocycloalkyl group, a C1-C6 alkoxy group, a C1-C6 haloalkoxy group, a C1-C6 alkylthio group, a C1-C6 haloalkylthio group, a C3-C6 cycloalkyloxy group, a C3-C6 halocycloalkyloxy group, a C3-C6 cycloalkylthio group, a C2-C6 alkenyloxy group, a C2-C6 alkynyloxy group, a C2-C6 haloalkenyloxy group, a C2-C6 haloalkynyloxy group, a C2-C6 alkenylthio group, a C2-C6 alkynylthio group, a C2-C6 haloalkenylthio group, a C2-C6 haloalkynylthio group, a C2-C6 alkylcarbonyl group, a C2-C6 haloalkylcarbonyl group, a C2-C6 alkylcarbonyloxy group, a C2-C6 alkylcarbonylthio group, a hydroxycarbonyl group, a formyl group, a C2-C6 alkoxycarbonyl group, a nitro group, a cyano group, a hydroxy group, a C1-C6 alkylsulfonyl group, a C1-C6 haloalkylsulfonyl group, a C6-C10 arylsulfonyl group, a C6-C10 haloarylsulfonyl group, a C1-C6 alkylsulfinyl group, a C1-C6 haloalkylsulfinyl group, an amino group optionally having a C1-C6 alkyl group, an aminosulfonyl group optionally having a C1-C6 alkyl group, or an aminocarbonyl group optionally having a C1-C6 alkyl group, and the symbol # represents a binding site for Q.

The C7-C18 aralkyl group represents a group in which a C6-C10 aryl group and a C1-C6 alkyl group are bound to each other, and examples of the C7-C18 aralkyl group include a benzyl group, a phenethyl group, a 3-phenylpropyl group, a 12-phenyldodecyl group, a 1-naphthylmethyl group, a 2-(1-naphthyl)ethyl group, and a 4-(9-anthryl)butyl group.

The C7-C18 haloaralkyl group represents a group in which at least one hydrogen atom of the aryl moiety and/or the alkyl moiety of an aralkyl group having 7-18 carbon atoms is substituted with a halogen atom, and examples thereof include a 2-fluorobenzyl group, a 3-fluorobenzyl group, a 4-fluorobenzyl group, a 2-chlorobenzyl group, a 3-chlorobenzyl group, a 4-chlorobenzyl group, a 2,4-difluorobenzyl group, a 2,5-dichlorobenzyl group, a 2,4,6-trifluorobenzyl group, a 2-(4-bromophenyl)ethyl group, a 3-(4-iodophenyl)propyl group, a 12-(4-fluorophenyl)dodecyl group, a 6-fluoro-1-naphthylmethyl group, a 4-chloro-2-naphthylmethyl group, and a difluoro(phenyl)methyl group.

The C7-C18 arylalkoxy group represents a group in which a C6-C10 aryl group and a C1-C6 alkoxy group are bound to each other, and examples of the C7-C18 arylalkoxy group include a benzyloxy group, a phenethyloxy group, a 3-phenylpropyloxy group, a naphthylmethyloxy group, a naphthylethyloxy group, a naphthylpropyloxy group, and an anthrylbutyloxy group.

The C7-C18 haloarylalkoxy group represents a group in which at least one hydrogen atom of the aryl moiety and/or the alkoxy moiety of an aryl alkoxy group having 7-18 carbon atoms is substituted with a halogen atom, and examples thereof include a 4-fluorobenzyloxy group, a 2-chlorobenzyloxy group, a 3-bromobenzyloxy group, a 4-iodobenzyloxy group, a 2,4-difluorobenzyloxy group, a 2,5-dichlorobenzyloxy group, a 3,4,5-trifluorobenzyloxy group, a 2-(4-fluorophenyl)ethyloxy group, a 2-(3-chlorophenyl)ethyloxy group, and a 1,1-difluoro-1-phenylmethyloxy group.

The C3-C9 trialkylsilyl group represents an alkylsilyl group in which three hydrogen atoms on a silyl group are substituted with the same or different alkyl groups, and the total number of carbon atoms of alkyl groups on a silyl group is within a range of 3 to 9. Examples of the C3-C9 trialkylsilyl group include a trimethylsilyl group, a tert-butyldimethylsilyl group, a triethylsilyl group, an isopropyldimethylsilyl group, and a triisopropylsilyl group.

The C5-C14 trialkylsilylethynyl group represents an ethynyl group in which three hydrogen atoms on a silyl group are bound to an alkylsilyl group substituted with the same or different alkyl groups, and the alkyl group is either straight or branched and the total number of carbon atoms of an alkylsilyl group and an ethynyl group is within a range of 5 to 14. Examples of the C5-C14 trialkylsilylethynyl group include a trimethylsilylethynyl group, a tert-butyldimethylsilylethynyl group, a triethylsilylethynyl group, an isopropyldimethylsilylethynyl group, a triisopropylsilylethynyl group, a tri(tert-butyl)silylethynyl group, and a tributylsilylethynyl group.

The C1-C6 alkylsulfonyl group may be either straight or branched, and examples thereof include a methylsulfonyl group, an ethylsulfonyl group, a propylsulfonyl group, an isopropylsulfonyl group, a butylsulfonyl group, and a 4-methylpentylsulfonyl group.

The C1-C6 haloalkylsulfonyl group represents a group in which at least one hydrogen atom of a straight or branched alkylsulfonyl group having 1-6 carbon atoms is substituted with a halogen atom, and examples thereof include a trifluoromethylsulfonyl group, a trichloromethylsulfonyl group, a pentafluoroethylsulfonyl group, a 2,2,2-trifluoroethylsulfonyl group, and a periodohexylsulfonyl group.

Examples of the C6-C10 arylsulfonyl group include a phenylsulfonyl group, a 1-naphthylsulfonyl group, and a 2-naphthylsulfonyl group.

The C6-C10 haloarylsulfonyl group represents a group in which at least one hydrogen atom of an arylsulfonyl group having 6-10 carbon atoms is substituted with a halogen atom, and examples thereof include a 2-fluorophenylsulfonyl group, a 3-fluorophenylsulfonyl group, a 4-fluorophenylsulfonyl group, a 2-chlorophenylsulfonyl group, a 4-iodophenylsulfonyl group, a 2,4-difluorophenylsulfonyl group, a 2,4-dichlorophenylsulfonyl group, a 2,6-dichlorophenylsulfonyl group, a 2,4,6-trifluorophenylsulfonyl group, and a 3-bromo-2-naphthylsulfonyl group.

The C1-C6 alkylsulfinyl group may be either straight or branched, and examples thereof include a methylsulfinyl group, an ethylsulfinyl group, a propylsulfinyl group, an isopropylsulfinyl group, a butylsulfinyl group, and a 4-methylpentylsulfinyl group.

The C1-C6 haloalkylsulfinyl group represents a group in which at least one hydrogen atom of a straight or branched alkylsulfinyl group having 1-6 carbon atoms is substituted with a halogen atom, and examples thereof include a trifluoromethylsulfinyl group, a trichloromethylsulfinyl group, a tribromomethylsulfinyl group, a triiodomethylsulfinyl group, a pentafluoroethylsulfinyl group, a 2,2,2-trifluoroethylsulfinyl group, and a periodohexylsulfinyl group.

Examples of the C1-C3 alkyl group include a methyl group, an ethyl group, a propyl group, and an isopropyl group.

Examples of the C1-C3 haloalkyl group include a chloromethyl group, a dichloromethyl group, a fluoromethyl group, a difluoromethyl group, a trifluoromethyl group, a trichloromethyl group, a tribromomethyl group, a 2-fluoroethyl group, a 2,2-difluoroethyl group, a 2,2,2-trifluoroethyl group, a 2-chloroethyl group, and a 1-(fluoromethyl)-2-fluoroethyl group.

Examples of the C1-C3 alkyl group optionally having one or more halogen atoms include a methyl group, an ethyl group, a propyl group, an isopropyl group, a chloromethyl group, a dichloromethyl group, a fluoromethyl group, a difluoromethyl group, a trifluoromethyl group, a trichloromethyl group, a tribromomethyl group, a 2-fluoroethyl group, a 2,2-difluoroethyl group, a 2,2,2-trifluoroethyl group, a 2-chloroethyl group, and a 1-(fluoromethyl)-2-fluoroethyl group.

The C1-C4 alkyl group may be either straight or branched, and examples thereof include a methyl group, an ethyl group, a propyl group, an isopropyl group, a butyl group, an isobutyl group, a sec-butyl group, and a tert-butyl group.

The C1-C4 haloalkyl group represents a group in which at least one hydrogen atom of a straight or branched alkyl group having 1-4 carbon atoms is substituted with a halogen atom, and examples thereof include a monofluoromethyl group, a monochloromethyl group, a dichloromethyl group, a difluoromethyl group, a trifluoromethyl group, a trichloromethyl group, a tribromomethyl group, a 2,2,2-trifluoroethyl group, a 2,2,2-trichloroethyl group, a pentafluoroethyl group, and a 4-fluorobutyl group.

The C3-C5 cycloalkyl group also includes a cycloalkyl group having an alkyl group, and examples thereof include a cyclopropyl group, a cyclobutyl group, a cyclopentyl group, a 2-methylcyclopropyl group, a 2,2-dimethylcyclopropyl group, and a 2,3-dimethylcyclopropyl group.

The C1-C4 alkoxy group may be either straight or branched, and examples thereof include a methoxy group, an ethoxy group, a propyloxy group, an isopropyloxy group, a butyloxy group, an isobutyloxy group, a sec-butyloxy group, and a tert-butyloxy group.

The C1-C4 haloalkoxy group represents a group in which at least one hydrogen atom of a straight or branched alkoxy group having 1-4 carbon atoms is substituted with a halogen atom, and examples thereof include a trifluoromethoxy group, a trichloromethoxy group, a chloromethoxy group, a dichloromethoxy group, a fluoromethoxy group, a difluoromethoxy group, a chlorofluoromethoxy group, a dichlorofluoromethoxy group, a chlorodifluoromethoxy group, a pentafluoroethoxy group, a 2,2,2-trifluoroethoxy group, and a nonaiodobutoxy group.

The amino group optionally having a C1-C6 alkyl group represents an amino group in which one or two hydrogen atoms on nitrogen are substituted with the same or different alkyl groups, and represents a group in which the total number of carbon atoms of alkyl groups on nitrogen is within a range of 1 to 6. Examples of the amino group optionally having a C1-C6 alkyl group include an amino group, an N-methylamino group, an N-ethylamino group, an N-propylamino group, an N-isopropylamino group, an N-butylamino group, an N,N-dimethylamino group, an N,N-diethylamino group, an N,N-dipropylamino group, an N-ethyl-N-methylamino group, and an N-propyl-N-methylamino group.

Examples of the C3-C9 trialkylsilyl group include a trimethylsilyl group, a tert-butyldimethylsilyl group, a triethylsilyl group, an isopropyldimethylsilyl group, and a triisopropylsilyl group.

The C1-C4 alkylsulfonyl group may be either straight or branched, and examples thereof include a methylsulfonyl group, an ethylsulfonyl group, a propylsulfonyl group, an isopropylsulfonyl group, a butylsulfonyl group, an isobutylsulfonyl group, and a sec-butylsulfonyl group.

The C1-C4 haloalkylsulfonyl group represents a group in which at least one hydrogen atom of a straight or branched alkylsulfonyl group having 1-4 carbon atoms is substituted with a halogen atom, and examples thereof include a trifluoromethylsulfonyl group, a trichloromethylsulfonyl group, a tribromomethylsulfonyl group, a triiodomethylsulfonyl group, a pentafluoroethylsulfonyl group, a 2,2,2-trifluoroethylsulfonyl group, and a nonaiodobutylsulfonyl group.

The C1-C4 alkylsulfinyl group may be either straight or branched, and examples thereof include a methylsulfinyl group, an ethylsulfinyl group, a propylsulfinyl group, an isopropylsulfinyl group, a butylsulfinyl group, an isobutylsulfinyl group, and a sec-butylsulfinyl group.

The C1-C4 haloalkylsulfinyl group represents a group in which at least one hydrogen atom of a straight or branched alkylsulfinyl group having 1-4 carbon atoms is substituted with a halogen atom, and examples thereof include a trifluoromethylsulfinyl group, a trichloromethylsulfinyl group, a tribromomethylsulfinyl group, a triiodomethylsulfinyl group, a pentafluoroethylsulfinyl group, a 2,2,2-trifluoroethylsulfinyl group, and a nonaiodobutylsulfinyl group.

The C2-C5 alkoxyalkyl group represents a group in which the total number of carbon atoms of the alkoxy moiety and the alkyl moiety is within a range of 2 to 5, and may be either straight or branched, and examples thereof include a methoxymethyl group, an ethoxymethyl group, a propyloxymethyl group, an isopropyloxymethyl group, a butyloxymethyl group, an isobutyloxymethyl group, a sec-butyloxymethyl group, a 1-methoxyethyl group, a 2-methoxyethyl group, a 2-propyloxyethyl group, a 2-isopropyloxyethyl group, a 3-methoxypropyl group, a 3-ethoxypropyl group, a 3-methoxybutyl group, and a 4-methoxybutyl group.

The C2-C5 alkylthioalkyl group may be either straight or branched, and examples thereof include a methylthiomethyl group, an ethylthiomethyl group, a propylthiomethyl group, an isopropylthiomethyl group, a butylthiomethyl group, an isobutylthiomethyl group, a sec-butylthiomethyl group, a 1-methylthioethyl group, a 2-methylthioethyl group, a 2-propylthioethyl group, a 2-isopropylthioethyl group, a 3-methylthiopropyl group, a 3-ethylthiopropyl group, a 3-methylthiobutyl group, and a 4-methylthiobutyl group.

Examples of the C1-C3 alkoxy group include a methoxy group, an ethoxy group, a propyloxy group, and an isopropyloxy group.

The C1-C3 haloalkoxy group represents a group in which at least one hydrogen atom of a straight or branched alkyl group having 1-3 carbon atoms is substituted with a halogen atom, and examples thereof include a trifluoromethoxy group, a trichloromethoxy group, a chloromethoxy group, a dichloromethoxy group, a fluoromethoxy group, a difluoromethoxy group, a chlorofluoromethoxy group, a dichlorofluoromethoxy group, a chlorodifluoromethoxy group, a pentafluoroethoxy group, a 2,2,2-trifluoroethoxy group, and a 3,3,3-trifluoropropoxy group.

Examples of the C1-C3 alkylthio group include a methylthio group, an ethylthio group, a propylthio group, and an isopropylthio group.

Examples of the C1-C4 alkylthio group include a methylthio group, an ethylthio group, a propylthio group, an isopropylthio group, a butylthio group, an isobutylthio group, ad a tert-butylthio group.

The C1-C3 haloalkylthio group represents a group in which at least one hydrogen atom of a straight or branched alkylthio group having 1-3 carbon atoms is substituted with a halogen atom, and examples thereof include a monofluoromethylthio group, a difluoromethylthio group, a trifluoromethylthio group, a trichloromethylthio group, a tribromomethylthio group, a triiodomethylthio group, a chlorofluoromethylthio group, a 2,2,2-trifluoroethylthio group, and a 2,2-difluoroethylthio group.

The C1-C4 haloalkylthio group represents a group in which at least one hydrogen atom of a straight or branched alkylthio group having 1-4 carbon atoms is substituted with a halogen atom, and examples thereof include a monofluoromethylthio group, a difluoromethylthio group, a trifluoromethylthio group, a trichloromethylthio group, a tribromomethylthio group, a triiodomethylthio group, a chlorofluoromethylthio group, a pentafluoroethylthio group, and a 2,2-difluoroethylthio group.

Examples of the C3-C10 cycloalkyl group include a cyclopropyl group, a cyclobutyl group, a cyclopentyl group, a cyclohexyl group, a cycloheptyl group, and a cyclooctyl group.

The C3-C10 cycloalkyl group optionally having one or more atoms or groups selected from Group $P^1$ represents a C3-C10 cycloalkyl group in which one or more hydrogen atoms of a C3-C10 cycloalkyl group are optionally substituted with one or more atoms or groups selected from Group $P^1$, and examples thereof include a cyclopropyl group, a cyclobutyl group, a cyclopentyl group, a cyclohexyl group, a cycloheptyl group, a cyclooctyl group, a 2-fluorocyclopropyl group, a 2,2-difluorocyclopropyl group, a 2-chloro-2-fluorocyclopropyl group, a 2,2,3,3-tetrafluorocyclobutyl group, a 2-chlorocyclohexyl group, a 4,4-difluorocyclohexyl group, and a 4-trifluoromethylcyclohexyl group.

The "6-membered aromatic heterocyclic group having one, two, three, or four nitrogen atoms as a ring-constituent atom (provided that the heterocyclic group optionally has one or more groups or atoms selected from Group $P^1$)" represents a group in which hydrogen atoms of the 6-membered aromatic heterocyclic group having one, two, three, or four nitrogen atoms as a ring-constituent atom are optionally substituted with one or more atoms or groups selected from Group $P^1$ and, when the number of atoms or groups selected from Group $P^1$ is 2 or more, those atoms or groups may be the same or different to each other, and examples thereof include the following A13, A14, A15, A16, A17, A18, A19, A20, and A21:

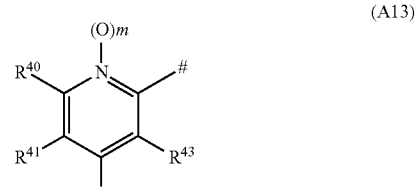

(A13)

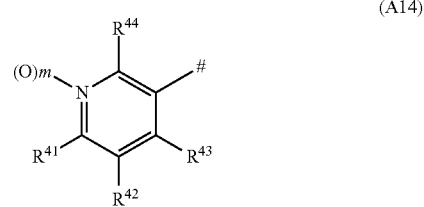

(A14)

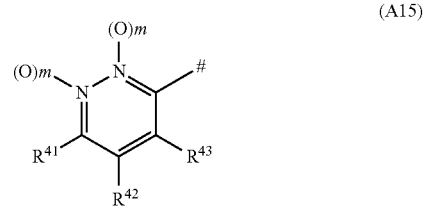

(A15)

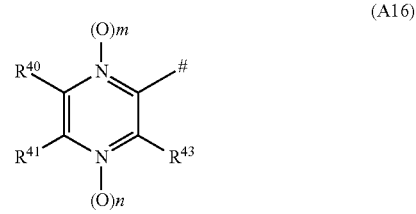

(A16)

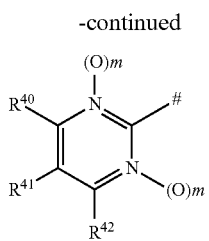

(A17)

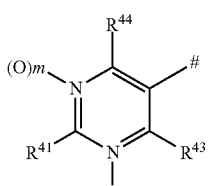

(A18)

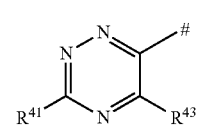

(A19)

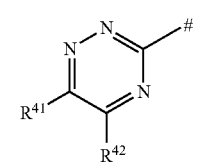

(A20)

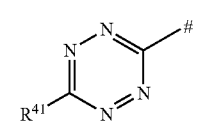

(A21)

wherein $R^{40}$, $R^{41}$, $R^{42}$, and $R^{43}$ each independently represents a hydrogen atom, a halogen atom, a C1-C6 alkyl group, a C1-C6 haloalkyl group, a C2-C6 alkenyl group, a C2-C6 haloalkenyl group, a C2-C6 alkynyl group, a C2-C6 haloalkynyl group, a C3-C6 cycloalkyl group, a C3-C6 halocycloalkyl group, a C1-C6 alkoxy group, a C1-C6 haloalkoxy group, a C1-C6 alkylthio group, a C1-C6 haloalkylthio group, a C3-C6 cycloalkyloxy group, a C3-C6 halocycloalkyloxy group, a C3-C6 cycloalkylthio group, a C2-C6 alkenyloxy group, a C2-C6 alkynyloxy group, a C2-C6 haloalkenyloxy group, a C2-C6 haloalkynyloxy group, a C2-C6 alkenylthio group, a C2-C6 alkynylthio group, a C2-C6 haloalkenylthio group, a C2-C6 haloalkynylthio group, a C2-C6 alkylcarbonyl group, a C2-C6 haloalkylcarbonyl group, a C2-C6 alkylcarbonyloxy group, a C2-C6 alkylcarbonylthio group, a hydroxycarbonyl group, a formyl group, a C2-C6 alkoxycarbonyl group, a nitro group, a cyano group, a hydroxy group, a C1-C6 alkylsulfonyl group, a C1-C6 haloalkylsulfonyl group, a C6-C10 arylsulfonyl group, a C6-C10 haloarylsulfonyl group, a C1-C6 alkylsulfinyl group, a C1-C6 haloalkylsulfinyl group, an amino group optionally having a C1-C6 alkyl group, a aminosulfonyl group optionally having a C1-C6 alkyl group, or an aminocarbonyl group optionally having a C1-C6 alkyl group, the symbol # represents a binding site for Q, and m represents 0 or 1.

The "5-membered heterocyclic group (provided that the 5-membered heterocyclic group has, as a ring-constituent atom, one or more atoms selected from the group consisting of a nitrogen atom, an oxygen atom, and a sulfur atom and, when the 5-membered heterocyclic group has two or more atoms selected from the group consisting of a nitrogen atom, an oxygen atom, and a sulfur atom, the atoms may be the same or different to each other)" represents a 5-membered ring aromatic heterocyclic group having one or more nitrogen atoms, oxygen atoms, and/or sulfur atoms as a ring-constituent atom, and examples thereof include a furan-2-yl group, a furan-3-yl group, a thiophen-2-yl group, a thiophen-3-yl group, a pyrazol-1-yl group, a pyrazol-3-yl group, a pyrazol-5-yl group, a thiazol-2-yl group, a thiazol-4-yl group, a thiazol-5-yl group, an oxazol-2-yl group, an oxazol-4-yl group, an oxazol-5-yl group, an imidazol-1-yl group, an imidazol-2-yl group, an imidazol-3-yl group, a 1,2,4-triazol-1-yl group, a 1,2,4-triazol-3-yl group, a 1,2,4-triazol-4-yl group, a 1,2,4-triazol-5-yl group, a 1,3,4-oxadiazole group, a 1,2,4-oxadiazole group, a 1,3,4-thiadiazole group, a 1,2,4-thiadiazole group, a 1,2,3-triazol-1-yl group, a 1,2,3-triazol-2-yl group, a 1,2,3,4-tetrazol-1-yl group, a 1,2,3,4-tetrazol-2-yl group, an isoxazol-3-yl group, an isoxazol-4-yl group, and an isoxazol-5-yl group.

The "5-membered heterocyclic group optionally having one or more atoms or groups selected from Group $P^1$ (provided that the 5-membered heterocyclic group has, as a ring-constituent atom, one or more atoms selected from the group consisting of a nitrogen atom, an oxygen atom, and a sulfur atom and, when the 5-membered heterocyclic group has two or more atoms selected from the group consisting of a nitrogen atom, an oxygen atom, and a sulfur atom, the atoms may be the same or different to each other)" represents a group in which hydrogen atoms of the 5-membered heterocyclic group are optionally substituted with one or more atoms or groups selected from Group $P^1$ and, when the number of atoms or groups selected from Group $P^1$ is 2 or more, those atoms or groups may be the same or different to each other, and examples thereof include the following A22, A23, A24, A25, A26, A27, A28, A29, A30, A31, A32, A33, A34, A35, A36, A37, A38, A39, A40, A41, A42, A43, A44, A45, A46, A47, A48, A49, A50, A51, A52, and A53:

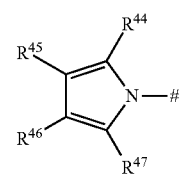

(A22)

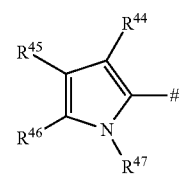

(A23)

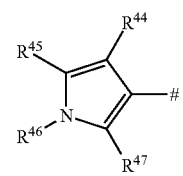

(A24)

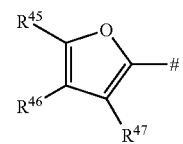

(A25)

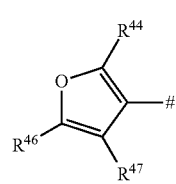 (A26)
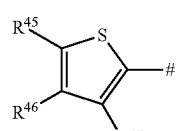 (A27)
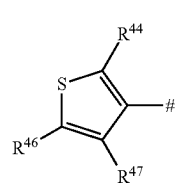 (A28)
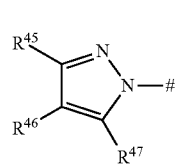 (A29)
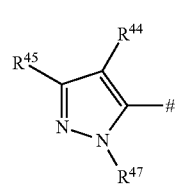 (A30)
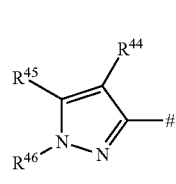 (A31)
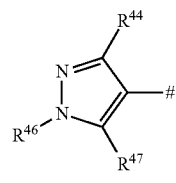 (A32)
 (A33)
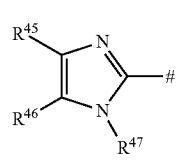 (A34)
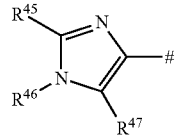 (A35)
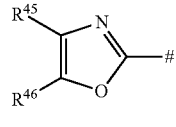 (A36)
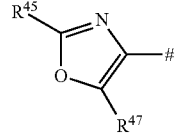 (A37)
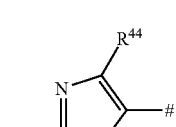 (A38)
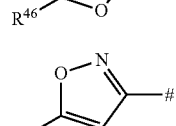 (A39)
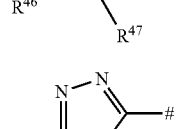 (A40)
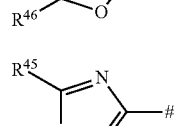 (A41)
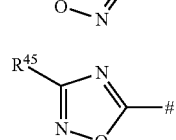 (A42)
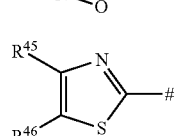 (A43)
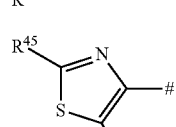 (A44)
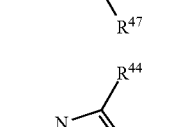 (A45)
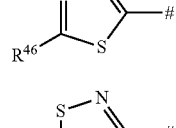 (A46)
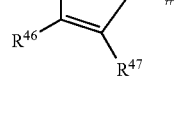

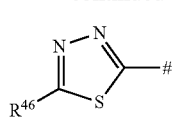 (A47)

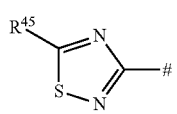 (A48)

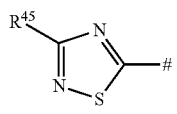 (A49)

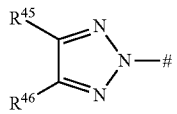 (A50)

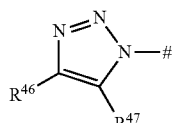 (A51)

 (A52)

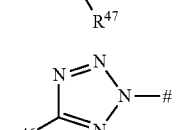 (A53)

wherein $R^{44}$, $R^{45}$, $R^{46}$, and $R^{47}$ each independently represents a hydrogen atom, a halogen atom, a C1-C6 alkyl group, a C1-C6 haloalkyl group, a C2-C6 alkenyl group, a C2-C6 haloalkenyl group, a C2-C6 alkynyl group, a C2-C6 haloalkynyl group, a C3-C6 cycloalkyl group, a C3-C6 halocycloalkyl group, a C1-C6 alkoxy group, a C1-C6 haloalkoxy group, a C1-C6 alkylthio group, a C1-C6 haloalkylthio group, a C3-C6 cycloalkyloxy group, a C3-C6 halocycloalkyloxy group, a C3-C6 cycloalkylthio group, a C2-C6 alkenyloxy group, a C2-C6 alkynyloxy group, a C2-C6 haloalkenyloxy group, a C2-C6 haloalkynyloxy group, a C2-C6 alkenylthio group, a C2-C6 alkynylthio group, a C2-C6 haloalkenylthio group, a C2-C6 haloalkynylthio group, a C2-C6 alkylcarbonyl group, a C2-C6 haloalkylcarbonyl group, a C2-C6 alkylcarbonyloxy group, a C2-C6 alkylcarbonylthio group, a hydroxycarbonyl group, a formyl group, a C2-C6 alkoxycarbonyl group, a nitro group, a cyano group, a hydroxy group, a C1-C6 alkylsulfonyl group, a C1-C6 haloalkylsulfonyl group, a C6-C10 arylsulfonyl group, a C6-C10 haloarylsulfonyl group, a C1-C6 alkylsulfinyl group, a C1-C6 haloalkylsulfinyl group, an amino group optionally having a C1-C6 alkyl group, a aminosulfonyl group optionally having a C1-C6 alkyl group, or an aminocarbonyl group optionally having a C1-C6 alkyl group, and the symbol # represents a binding site for Q.

The "aliphatic C2-C9 heterocyclic group (provided that the aliphatic C2-C9 heterocyclic group has, as a ring-constituent atom, one or more atoms selected from the group consisting of a nitrogen atom, an oxygen atom, and a sulfur atom and when the aliphatic C2-C9 heterocyclic group has two or more atoms selected from the group consisting of a nitrogen atom, an oxygen atom, and a sulfur atom, the atoms may be the same or different to each other, and also a carbon or nitrogen atom constituting a ring of the aliphatic C2-C9 heterocyclic group is bound to Q)" represents an aliphatic heterocyclic group having 2-9 carbon atoms, and examples thereof include an oxacyclopropyl group, an oxacyclobutyl group, an oxacyclopentyl group, an oxacyclohexyl group, an azacyclopropyl group, an azacyclobutyl group, a pyrrolidinyl group, a piperazinyl group, a morpholyl group, a thiocyclopropyl group, a thiocyclobutyl group, a thiocyclopentyl group, an oxazolyl group, an isoxazolyl group, a thiazolyl group, a thiazolyl group, and an oxazinyl group.

The "aliphatic C2-C9 heterocyclic group optionally having one or more atoms or groups selected from Group $P^1$ (provided that the aliphatic C2-C9 heterocyclic group has, as a ring-constituent atom, one or more atoms selected from the group consisting of a nitrogen atom, an oxygen atom, and a sulfur atom and, when the aliphatic C2-C9 heterocyclic group has two or more atoms selected from the group consisting of a nitrogen atom, an oxygen atom, and a sulfur atom, the atoms may be the same or different to each other, and also a carbon or nitrogen atom constituting a ring of the aliphatic C2-C9 heterocyclic group is bound to Q)" represents a group in which hydrogen atoms of the aliphatic C2-C9 heterocyclic groups are optionally substituted with one or more atoms or groups selected from Group $P^1$ and, when the number of atoms or groups selected from Group $P^1$ is 2 or more, those atoms or groups may be the same or different to each other, and examples thereof include the following A54, A55, A56, A57, A58, A59, A60, A61, A62, A63, A64, A65, A66, A67, A68, A69, A70, A71, A72, A73,

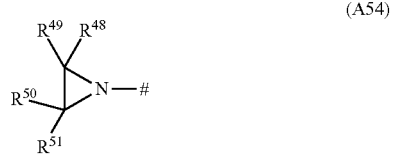 (A54)

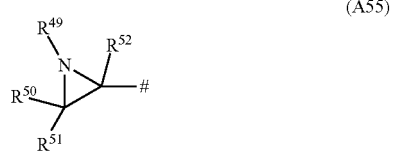 (A55)

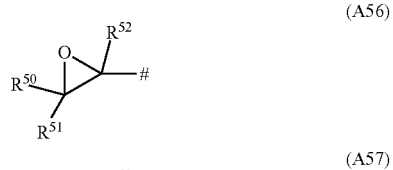 (A56)

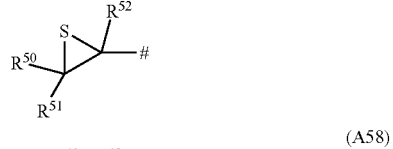 (A57)

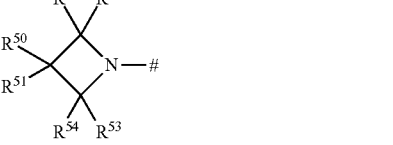 (A58)

-continued
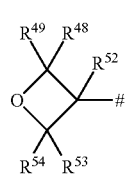 (A59)
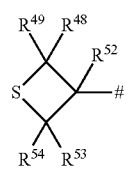 (A60)
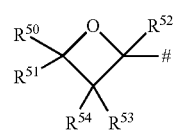 (A61)
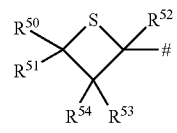 (A62)
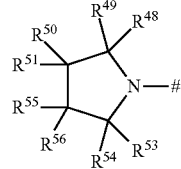 (A63)
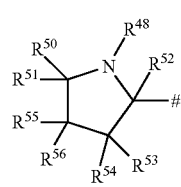 (A64)
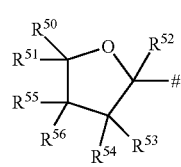 (A65)
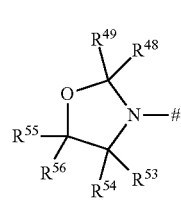 (A66)
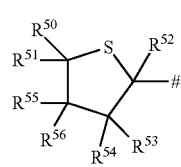 (A67)
-continued
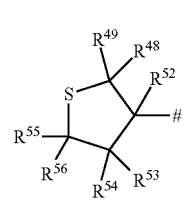 (A68)
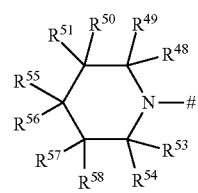 (A69)
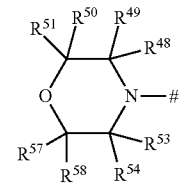 (A70)
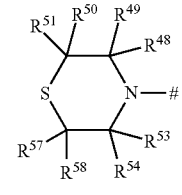 (A71)
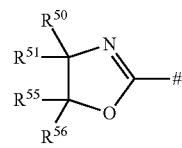 (A72)
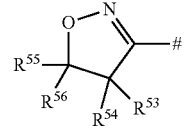 (A73)
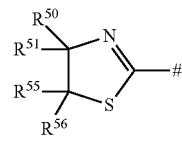 (A74)
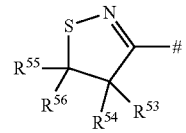 (A75)
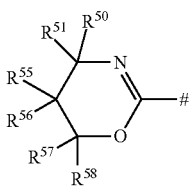 (A76)

(A77)

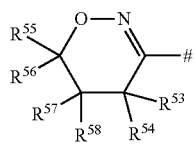

(A78)

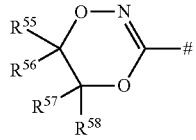

(A79)

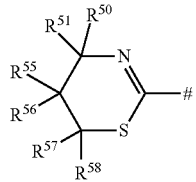

(A80)

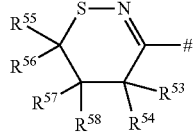

(A81)

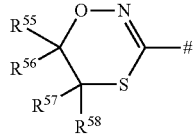

wherein $R^{48}$, $R^{49}$, $R^{50}$, $R^{51}$, $R^{52}$, $R^{53}$, $R^{54}$, $R^{55}$, $R^{56}$, $R^{57}$, and $R^{58}$ each independently represents a hydrogen atom, a halogen atom, a C1-C6 alkyl group, a C1-C6 haloalkyl group, a C2-C6 alkenyl group, a C2-C6 haloalkenyl group, a C2-C6 alkynyl group, a C2-C6 haloalkynyl group, a C3-C6 cycloalkyl group, a C3-C6 halocycloalkyl group, a C1-C6 alkoxy group, a C1-C6 haloalkoxy group, a C1-C6 alkylthio group, a C1-C6 haloalkylthio group, a C3-C6 cycloalkyloxy group, a C3-C6 halocycloalkyloxy group, a C3-C6 cycloalkylthio group, a C2-C6 alkenyloxy group, a C2-C6 alkynyloxy group, a C2-C6 haloalkenyloxy group, a C2-C6 haloalkynyloxy group, a C2-C6 alkenylthio group, a C2-C6 alkynylthio group, a C2-C6 haloalkenylthio group, a C2-C6 haloalkynylthio group, a C2-C6 alkylcarbonyl group, a C2-C6 haloalkylcarbonyl group, a C2-C6 alkylcarbonyloxy group, a C2-C6 alkylcarbonylthio group, a hydroxycarbonyl group, a formyl group, a C2-C6 alkoxycarbonyl group, a nitro group, a cyano group, a hydroxy group, a C1-C6 alkylsulfonyl group, a C1-C6 haloalkylsulfonyl group, a C6-C10 arylsulfonyl group, a C6-C10 haloarylsulfonyl group, a C1-C6 alkylsulfinyl group, a C1-C6 haloalkylsulfinyl group, an amino group optionally having a C1-C6 alkyl group, an aminosulfonyl group optionally having a C1-C6 alkyl group, or an aminocarbonyl group optionally having a C1-C6 alkyl group, and the symbol # represents a binding site for Q.

Examples of the oxime ether group optionally having one or more groups selected from Group $P^3$ include the following (A82):

(A82)

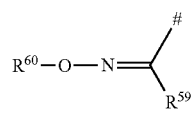

wherein $R^{59}$ and $R^{60}$ each independently represents a hydrogen atom, a C1-C6 alkyl group, a C1-C6 haloalkyl group, a C1-C6 cycloalkyl group, or a 1-C6 halocycloalkyl group, and the symbol # represents a binding site for Q.

Examples of the aspect of the present compound (1) are compounds in which the substituent is shown below.

A compound in which $R^1$ and $R^2$ are hydrogen atoms.

A compound in which $R^3$ is a C1-C6 alkyl group, a C3-C6 cycloalkyl group, a halogen atom, a C1-C6 haloalkyl group, a C2-C6 alkenyl group, a C1-C6 alkoxy group, a C1-C6 alkylthio group, a C1-C6 haloalkoxy group, a C1-C6 haloalkylthio group, a C2-C6 alkynyl group, a nitro group, or a cyano group.

A compound in which $R^3$ is a C1-C6 alkyl group, a C3-C6 cycloalkyl group, a halogen atom, a C1-C6 haloalkyl group, a C1-C6 alkoxy group, a C1-C6 alkylthio group, a C1-C6 haloalkoxy group, or a C1-C6 haloalkylthio group.

A compound in which $R^3$ is a C1-C3 alkyl group, a C3-C5 cycloalkyl group, a halogen atom, a C1-C3 haloalkyl group, a C1-C3 alkoxy group, a C1-C3 alkylthio group, a C1-C3 haloalkoxy group, or a C1-C3 haloalkylthio group.

A compound in which $R^4$, $R^5$, and $R^6$ are hydrogen atoms.

A compound in which $R^7$ is a C1-C3 alkyl group.

A compound in which Q is Q1, n is 0, and $R^8$, $R^9$, and $R^{10}$ are the same or different and represent a hydrogen atom, a halogen atom, a C1-C4 alkyl group, or a C1-C4 haloalkyl group.

A compound in which Q is Q2, n is 0, and $R^{11}$, $R^{12}$, and $R^{13}$ are the same or different and represent a hydrogen atom, a halogen atom, a C1-C4 alkyl group, or a C1-C4 haloalkyl group.

A compound in which Q is Q3, n is 0, and $R^{14}$ and $R^{15}$ are the same or different and represent a hydrogen atom, a halogen atom, a C1-C4 alkyl group, or a C1-C4 haloalkyl group.

A compound in which Q is Q4, n is 0, and $R^{16}$ and $R^{17}$ are the same or different and represent a hydrogen atom, a halogen atom, a C1-C4 alkyl group, or a C1-C4 haloalkyl group.

A compound in which Q is Q5, n is 0, and $R^{16}$ and $R^{17}$ are the same or different and represent a hydrogen atom, a halogen atom, a C1-C4 alkyl group, or a C1-C4 haloalkyl group.

A compound in which A is A1, and $R^{30}$, $R^{31}$, $R^{32}$, $R^{33}$, and $R^{34}$ are the same or different and represent a hydrogen atom, a halogen atom, a C1-C6 alkyl group, a C1-C6 haloalkyl group, a C1-C6 alkoxy group, a C1-C6 haloalkoxy group, a C1-C6 alkylthio group, a C1-C6 haloalkylthio group, or a cyano group.

A compound in which A is A4, and $R^{30}$, $R^{31}$, $R^{32}$, $R^{33}$, and $R^{34}$ are the same or different and represent a hydrogen atom, a halogen atom, a C1-C6 alkyl group, a C1-C6 haloalkyl group, a C1-C6 alkoxy group, a C1-C6 haloalkoxy group, a C1-C6 alkylthio group, a C1-C6 haloalkylthio group, or a cyano group.

A compound in which A is A13, m is 0, and $R^{40}$, $R^{41}$, $R^{42}$, and $R^{43}$ are the same or different and represent a hydrogen atom, a halogen atom, a C1-C6 alkyl group, a C1-C6 haloalkyl group, a C1-C6 alkoxy group, a C1-C6 haloalkoxy group, a C1-C6 alkylthio group, a C1-C6 haloalkylthio group, or a cyano group.

A compound in which A is A14, m is 0, and $R^{41}$, $R^{42}$, $R^{43}$, and $R^{44}$ are the same or different and represent a hydrogen atom, a halogen atom, a C1-C6 alkyl group, a C1-C6 haloalkyl group, a C1-C6 alkoxy group, a C1-C6 haloalkoxy group, a C1-C6 alkylthio group, a C1-C6 haloalkylthio group, or a cyano group.

A compound in which A is A15, m is 0, and $R^{41}$, $R^{42}$, and $R^{43}$ are the same or different and represent a hydrogen atom, a halogen atom, a C1-C6 alkyl group, a C1-C6 haloalkyl group, a C1-C6 alkoxy group, a C1-C6 haloalkoxy group, a C1-C6 alkylthio group, a C1-C6 haloalkylthio group, or a cyano group.

A compound in which A is A16, m is 0, and $R^{4'}$, $R^{41}$, and $R^{43}$ are the same or different and represent a hydrogen atom, a halogen atom, a C1-C6 alkyl group, a C1-C6 haloalkyl group, a C1-C6 alkoxy group, a C1-C6 haloalkoxy group, a C1-C6 alkylthio group, a C1-C6 haloalkylthio group, or a cyano group.

A compound in which A is A17, m is 0, and $R^{41}$, $R^{42}$, and $R^{43}$ are the same or different and represent a hydrogen atom, a halogen atom, a C1-C6 alkyl group, a C1-C6 haloalkyl group, a C1-C6 alkoxy group, a C1-C6 haloalkoxy group, a C1-C6 alkylthio group, a C1-C6 haloalkylthio group, or a cyano group.

A compound in which A is A29, $R^{45}$ is a hydrogen atom or a C1-C3 alkyl group, $R^{46}$ is a hydrogen atom, a halogen atom, a C1-C6 alkyl group, a C1-C3 alkoxy group, a C1-C3 alkylthio group, or a cyano group, and $R^{47}$ is a hydrogen atom or a C1-C3 alkyl group.

A compound in which A is A31, $R^{44}$ is a hydrogen atom, a C1-C3 alkyl group, or a halogen atom, $R^{45}$ is a hydrogen atom, a halogen atom, a C1-C6 alkyl group, a C1-C3 alkoxy group, a C1-C3 alkylthio group, or a cyano group, and $R^{46}$ is a hydrogen atom or a C1-C3 alkyl group.

A compound in which A is A36, $R^{45}$ is a hydrogen atom, a C1-C3 alkyl group, or a halogen atom, and $R^{46}$ is a hydrogen atom, a halogen atom, or a C1-C6 alkyl group.

A compound in which A is A37, $R^{45}$ is a hydrogen atom, a C1-C3 alkyl group, or a halogen atom, and $R^{46}$ is a hydrogen atom, a halogen atom, or a C1-C6 alkyl group.

A compound in which A is A43, $R^{45}$ is a hydrogen atom, a C1-C3 alkyl group, or a halogen atom, and $R^{46}$ is a hydrogen atom, a halogen atom, or a C1-C6 alkyl group.

A compound in which A is A44, $R^{45}$ is a hydrogen atom, a C1-C3 alkyl group, or a halogen atom, and $R^{47}$ is a hydrogen atom, a halogen atom, or a C1-C6 alkyl group.

A compound in which A is A72, and $R^{50}$, $R^{51}$, $R^{55}$, and $R^{56}$ are the same or different and represent a hydrogen atom or a C1-C3 alkyl group.

A compound in which A is A74, and $R^{50}$, $R^{51}$, $R^{55}$, and $R^{56}$ are the same or different and represent a hydrogen atom or a C1-C3 alkyl group.

A compound in which A is A82, $R^{49}$ is a hydrogen atom, a halogen atom, or a C1-C6 alkyl group, and $R^{60}$ is a hydrogen atom, a halogen atom, or a C1-C6 alkyl group.

A compound in which $R^1$, $R^2$, $R^4$, $R^5$, and $R^6$ are hydrogen atoms, $R^3$ is a C1-C3 alkyl group, a C3-C5 cycloalkyl group, a halogen atom, a C1-C3 haloalkyl group, a C1-C3 alkoxy group, a C1-C3 alkylthio group, a C1-C3 haloalkoxy group, or a C1-C3 haloalkylthio group, $R^7$ is a C1-C3 alkyl group, Q is Q1, n is 0, $R^8$, $R^9$, and $R^{10}$ are the same or different and represent a hydrogen atom, a halogen atom, a C1-C4 alkyl group, or a C1-C4 haloalkyl group, A is A1, $R^{30}$, $R^3$, $R^{32}$, $R^{33}$, and $R^{34}$ are the same or different and represent a hydrogen atom, a halogen atom, a C1-C6 alkyl group, a C1-C6 haloalkyl group, a C1-C6 alkoxy group, a C1-C6 haloalkoxy group, a C1-C6 alkylthio group, a C1-C6 haloalkylthio group, or a cyano group, and X is an oxygen atom.

A compound in which $R^1$, $R^2$, $R^4$, $R^5$, and $R^6$ are hydrogen atoms, $R^3$ is a C1-C3 alkyl group, a C3-C5 cycloalkyl group, a halogen atom, a C1-C3 haloalkyl group, a C1-C3 alkoxy group, a C1-C3 alkylthio group, a C1-C3 haloalkoxy group, or a C1-C3 haloalkylthio group, $R^7$ is a C1-C3 alkyl group, Q is Q1, n is 0, $R^8$, $R^9$, and $R^{10}$ are the same or different and represent a hydrogen atom, a halogen atom, a C1-C4 alkyl group, or a C1-C4 haloalkyl group, A is A13, m is 0, $R^{40}$, $R^{41}$, $R^{42}$, and $R^{43}$ are the same or different and represent a hydrogen atom, a halogen atom, a C1-C6 alkyl group, a C1-C6 haloalkyl group, a C1-C6 alkoxy group, a C1-C6 haloalkoxy group, a C1-C6 alkylthio group, a C1-C6 haloalkylthio group, or a cyano group, and X is an oxygen atom.

A compound in which $R^1$, $R^2$, $R^4$, $R^5$, and $R^6$ are hydrogen atoms, $R^3$ is a C1-C3 alkyl group, a C3-C5 cycloalkyl group, a halogen atom, a C1-C3 haloalkyl group, a C1-C3 alkoxy group, a C1-C3 alkylthio group, a C1-C3 haloalkoxy group, or a C1-C3 haloalkylthio group, $R^7$ is a C1-C3 alkyl group, Q is Q1, n is 0, $R^8$, $R^9$, and $R^{10}$ are the same or different and represent a hydrogen atom, a halogen atom, a C1-C4 alkyl group, or a C1-C4 haloalkyl group, A is A14, m is 0, $R^{41}$, $R^{42}$, $R^{43}$, and $R^{44}$ are the same or different and represent a hydrogen atom, a halogen atom, a C1-C6 alkyl group, a C1-C6 haloalkyl group, a C1-C6 alkoxy group, a C1-C6 haloalkoxy group, a C1-C6 alkylthio group, a C1-C6 haloalkylthio group, or a cyano group, and X is an oxygen atom.

A compound in which $R^1$, $R^2$, $R^4$, $R^5$, and $R^6$ are hydrogen atoms, $R^3$ is a C1-C3 alkyl group, a C3-C5 cycloalkyl group, a halogen atom, a C1-C3 haloalkyl group, a C1-C3 alkoxy group, a C1-C3 alkylthio group, a C1-C3 haloalkoxy group, or a C1-C3 haloalkylthio group, $R^7$ is a C1-C3 alkyl group, Q is Q1, n is 0, $R^8$, $R^9$, and $R^{10}$ are the same or different and represent a hydrogen atom, a halogen atom, a C1-C4 alkyl group, or a C1-C4 haloalkyl group, A is A17, m is 0, $R^{41}$, $R^{42}$, and $R^{43}$ are the same or different and represent a hydrogen atom, a halogen atom, a C1-C6 alkyl group, a C1-C6 haloalkyl group, a C1-C6 alkoxy group, a C1-C6 haloalkoxy group, a C1-C6 alkylthio group, a C1-C6 haloalkylthio group, or a cyano group, and X is an oxygen atom.

A compound in which $R^1$, $R^2$, $R^4$, $R^5$, and $R^6$ are hydrogen atoms, $R^3$ is a C1-C3 alkyl group, a C3-C5 cycloalkyl group, a halogen atom, a C1-C3 haloalkyl group, a C1-C3 alkoxy group, a C1-C3 alkylthio group, a C1-C3 haloalkoxy group, or a C1-C3 haloalkylthio group, $R^7$ is a C1-C3 alkyl group, Q is Q1, n is 0, $R^8$, $R^9$, and $R^{10}$ are the same or different and represent a hydrogen atom, a halogen atom, a C1-C4 alkyl group, or a C1-C4 haloalkyl group, A is A29, $R^{45}$ is a hydrogen atom or a C1-C3 alkyl group, $R^{46}$ is a hydrogen atom, a halogen atom, a C1-C6 alkyl group, a C1-C3 alkoxy group, a C1-C3 alkylthio group, or a cyano group, $R^{47}$ is a hydrogen atom or a C1-C3 alkyl group, and X is an oxygen atom.

A compound in which $R^1$, $R^2$, $R^4$, $R^5$, and $R^6$ are hydrogen atoms, $R^3$ is a C1-C3 alkyl group, a C3-C5 cycloalkyl group, a halogen atom, a C1-C3 haloalkyl group, a C1-C3 alkoxy group, a C1-C3 alkylthio group, a C1-C3 haloalkoxy group, or a C1-C3 haloalkylthio group, $R^7$ is a C1-C3 alkyl group, Q is Q1, n is 0, $R^8$, $R^9$, and $R^{10}$ are the same or different and represent a hydrogen atom, a halogen atom, a C1-C4 alkyl group, or a C1-C4 haloalkyl group, A is A31, $R^{44}$ is a hydrogen atom, a C1-C3 alkyl group, or a halogen atom, $R^{45}$ is a hydrogen atom, a halogen atom, a C1-C6 alkyl group, a C1-C3 alkoxy group, a C1-C3 alkylthio group, or a cyano group, $R^{46}$ is a hydrogen atom or a C1-C3 alkyl group, and X is an oxygen atom.

A compound in which $R^1$, $R^2$, $R^4$, $R^5$, and $R^6$ are hydrogen atoms, $R^3$ is a C1-C3 alkyl group, a C3-C5 cycloalkyl group, a halogen atom, a C1-C3 haloalkyl group, a C1-C3 alkoxy group, a C1-C3 alkylthio group, a C1-C3 haloalkoxy group, or a C1-C3 haloalkylthio group, $R^7$ is a C1-C3 alkyl group, Q is Q1, n is 0, $R^8$, $R^9$, and $R^{10}$ are the same or different and represent a hydrogen atom, a halogen atom, a C1-C4 alkyl group, or a C1-C4 haloalkyl group, A is A36, $R^{45}$ is a hydrogen atom, a C1-C3 alkyl group, or a halogen atom, $R^{46}$ is a hydrogen atom, a halogen atom, or a C1-C6 alkyl group, and X is an oxygen atom.

A compound in which $R^1$, $R^2$, $R^4$, $R^5$, and $R^6$ are hydrogen atoms, $R^3$ is a C1-C3 alkyl group, a C3-C5 cycloalkyl group, a halogen atom, a C1-C3 haloalkyl group, a C1-C3 alkoxy group, a C1-C3 alkylthio group, a C1-C3 haloalkoxy group, or a C1-C3 haloalkylthio group, $R^7$ is a C1-C3 alkyl group, Q is Q1, n is 0, $R^8$, $R^9$, and $R^{10}$ are the same or different and represent a hydrogen atom, a halogen atom, a C1-C4 alkyl group, or a C1-C4 haloalkyl group, A is A37, $R^{45}$ is a hydrogen atom, a C1-C3 alkyl group, or a halogen atom, $R^{47}$ is a hydrogen atom, a halogen atom, or a C1-C6 alkyl group, and X is an oxygen atom.

A compound in which $R^1$, $R^2$, $R^4$, $R^5$, and $R^6$ are hydrogen atoms, $R^3$ is a C1-C3 alkyl group, a C3-C5 cycloalkyl group, a halogen atom, a C1-C3 haloalkyl group, a C1-C3 alkoxy group, a C1-C3 alkylthio group, a C1-C3 haloalkoxy group, or a C1-C3 haloalkylthio group, $R^7$ is a C1-C3 alkyl group, Q is Q1, n is 0, $R^8$, $R^9$, and $R^{10}$ are the same or different and represent a hydrogen atom, a halogen atom, a C1-C4 alkyl group, or a C1-C4 haloalkyl group, A is A43, $R^{45}$ is a hydrogen atom, a C1-C3 alkyl group, or a halogen atom, $R^{46}$ is a hydrogen atom, a halogen atom, or a C1-C6 alkyl group, and X is an oxygen atom.

A compound in which $R^1$, $R^2$, $R^4$, $R^5$, and $R^6$ are hydrogen atoms, $R^3$ is a C1-C3 alkyl group, a C3-C5 cycloalkyl group, a halogen atom, a C1-C3 haloalkyl group, a C1-C3 alkoxy group, a C1-C3 alkylthio group, a C1-C3 haloalkoxy group, or a C1-C3 haloalkylthio group, $R^7$ is a C1-C3 alkyl group, Q is Q1, n is 0, $R^8$, $R^9$, and $R^{10}$ are the same or different and represent a hydrogen atom, a halogen atom, a C1-C4 alkyl group, or a C1-C4 haloalkyl group, A is A44, $R^{45}$ is a hydrogen atom, a C1-C3 alkyl group, or a halogen atom, $R^{47}$ is a hydrogen atom, a halogen atom, or a C1-C6 alkyl group, and X is an oxygen atom.

A compound in which $R^1$, $R^2$, $R^4$, $R^5$, and $R^6$ are hydrogen atoms, $R^3$ is a C1-C3 alkyl group, a C3-C5 cycloalkyl group, a halogen atom, a C1-C3 haloalkyl group, a C1-C3 alkoxy group, a C1-C3 alkylthio group, a C1-C3 haloalkoxy group, or a C1-C3 haloalkylthio group, $R^7$ is a C1-C3 alkyl group, Q is Q1, n is 0, $R^8$, $R^9$, and $R^{10}$ are the same or different and represent a hydrogen atom, a halogen atom, a C1-C4 alkyl group, or a C1-C4 haloalkyl group, A is A72, $R^{50}$, $R^{51}$, $R^{55}$, and $R^{56}$ are the same or different and represent a hydrogen atom or a C1-C3 alkyl group, and X is an oxygen atom.

A compound in which $R^1$, $R^2$, $R^4$, $R^5$, and $R^6$ are hydrogen atoms, $R^3$ is a C1-C3 alkyl group, a C3-C5 cycloalkyl group, a halogen atom, a C1-C3 haloalkyl group, a C1-C3 alkoxy group, a C1-C3 alkylthio group, a C1-C3 haloalkoxy group, or a C1-C3 haloalkylthio group, $R^7$ is a C1-C3 alkyl group, Q is Q1, n is 0, RU, $R^9$, and $R^{10}$ are the same or different and represent a hydrogen atom, a halogen atom, a C1-C4 alkyl group, or a C1-C4 haloalkyl group, A is A74, $R^5$, $R^{51}$, $R^{55}$, and $R^{56}$ are the same or different and represent a hydrogen atom or a C1-C3 alkyl group, and X is an oxygen atom.

A compound in which $R^1$, $R^2$, $R^4$, $R^5$, and $R^6$ are hydrogen atoms, $R^3$ is a C1-C3 alkyl group, a C3-C5 cycloalkyl group, a halogen atom, a C1-C3 haloalkyl group, a C1-C3 alkoxy group, a C1-C3 alkylthio group, a C1-C3 haloalkoxy group, or a C1-C3 haloalkylthio group, $R^7$ is a C1-C3 alkyl group, Q is Q1, n is 0, $R^8$, $R^9$, and $R^{10}$ are the same or different and represent a hydrogen atom, a halogen atom, a C1-C4 alkyl group, or a C1-C4 haloalkyl group, A is A82, $R^{49}$ is a hydrogen atom, a halogen atom, or a C1-C6 alkyl group, $R^{60}$ is a hydrogen atom, a halogen atom, or a C1-C6 alkyl group, and X is an oxygen atom.

A compound in which $R^1$, $R^2$, $R^4$, $R^5$, and $R^6$ are hydrogen atoms, $R^3$ is a C1-C3 alkyl group, a C3-C5 cycloalkyl group, a halogen atom, a C1-C3 haloalkyl group, a C1-C3 alkoxy group, a C1-C3 alkylthio group, a C1-C3 haloalkoxy group, or a C1-C3 haloalkylthio group, $R^7$ is a C1-C3 alkyl group, Q is Q2, n is 0, $R^{11}$, $R^{12}$, and $R^{13}$ are the same or different and represent a hydrogen atom, a halogen atom, a C1-C4 alkyl group, or a C1-C4 haloalkyl group, A is A1, $R^{30}$, $R^{31}$, $R^{32}$, $R^{33}$, and $R^{34}$ are the same or different and represent a hydrogen atom, a halogen atom, a C1-C6 alkyl group, a C1-C6 haloalkyl group, a C1-C6 alkoxy group, a C1-C6 haloalkoxy group, a C1-C6 alkylthio group, a C1-C6 haloalkylthio group, or a cyano group, and X is an oxygen atom.

A compound in which $R^1$, $R^2$, $R^4$, $R^5$, and $R^6$ are hydrogen atoms, $R^3$ is a C1-C3 alkyl group, a C3-C5 cycloalkyl group, a halogen atom, a C1-C3 haloalkyl group, a C1-C3 alkoxy group, a C1-C3 alkylthio group, a C1-C3 haloalkoxy group, or a C1-C3 haloalkylthio group, $R^7$ is a C1-C3 alkyl group, Q is Q2, n is 0, $R^{11}$, $R^{12}$, and $R^{13}$ are the same or different and represent a hydrogen atom, a halogen atom, a C1-C46 alkyl group, or a C1-C4 haloalkyl group, A is A13, m is 0, $R^{40}$, $R^{41}$, $R^{42}$, and $R^{43}$ are the same or different and represent a hydrogen atom, a halogen atom, a C1-C6 alkyl group, a C1-C6 haloalkyl group, a C1-C6 alkoxy group, a C1-C6 haloalkoxy group, a C1-C6 alkylthio group, a C1-C6 haloalkylthio group, or a cyano group, and X is an oxygen atom.

A compound in which $R^1$, $R^2$, $R^4$, $R^5$, and $R^6$ are hydrogen atoms, $R^3$ is a C1-C3 alkyl group, a C3-C5 cycloalkyl group, a halogen atom, a C1-C3 haloalkyl group, a C1-C3 alkoxy group, a C1-C3 alkylthio group, a C1-C3 haloalkoxy group, or a C1-C3 haloalkylthio group, $R^7$ is a C1-C3 alkyl group, Q is Q2, n is 0, $R^{11}$, $R^{12}$, and $R^{13}$ are the same or different and represent a hydrogen atom, a halogen atom, a C1-C4 alkyl group, or a C1-C4 haloalkyl group, A is A14, m is 0, $R^{41}$, $R^{42}$, $R^{43}$, and $R^{44}$ are the same or different and represent a hydrogen atom, a halogen atom, a C1-C6 alkyl group, a C1-C6 haloalkyl group, a C1-C6 alkoxy group, a C1-C6 haloalkoxy group, a C1-C6 alkylthio group, a C1-C6 haloalkylthio group, or a cyano group, and X is an oxygen atom.

A compound in which $R^1$, $R^2$, $R^4$, $R^5$, and $R^6$ are hydrogen atoms, $R^3$ is a C1-C3 alkyl group, a C3-C5 cycloalkyl group, a halogen atom, a C1-C3 haloalkyl group, a C1-C3 alkoxy group, a C1-C3 alkylthio group, a C1-C3 haloalkoxy group, or a C1-C3 haloalkylthio group, $R^7$ is a C1-C3 alkyl group, Q is Q2, n is 0, $R^{11}$, $R^{12}$, and $R^{13}$ are the same or different and represent a hydrogen atom, a halogen atom, a C1-C4 alkyl group, or a C1-C4 haloalkyl group, A is A17, m is 0, $R^{41}$, $R^{42}$, and $R^{43}$ are the same or different and represent a hydrogen atom, a halogen atom, a C1-C6 alkyl group, a C1-C6 haloalkyl group, a C1-C6 alkoxy group, a C1-C6 haloalkoxy group, a C1-C6 alkylthio group, a C1-C6 haloalkylthio group, or a cyano group, and X is an oxygen atom.

A compound in which $R^1$, $R^2$, $R^4$, $R^5$, and $R^6$ are hydrogen atoms, $R^3$ is a C1-C3 alkyl group, a C3-C5 cycloalkyl group, a halogen atom, a C1-C3 haloalkyl group, a C1-C3 alkoxy group, a C1-C3 alkylthio group, a C1-C3 haloalkoxy group, or a C1-C3 haloalkylthio group, $R^7$ is a C1-C3 alkyl group, Q is Q2, n is 0, $R^{11}$, $R^{12}$, and $R^{13}$ are the same or different and represent a hydrogen atom, a halogen atom, a C1-C4 alkyl group, or a C1-C4 haloalkyl group, A is A29, $R^{45}$ is a hydrogen atom or a C1-C3 alkyl group, $R^{46}$ is a hydrogen atom, a halogen atom, a C1-C6 alkyl group, a C1-C3 alkoxy group, a C1-C3 alkylthio group, or a cyano group, $R^{47}$ is a hydrogen atom or a C1-C3 alkyl group, and X is an oxygen atom.

A compound in which $R^1$, $R^2$, $R^4$, $R^5$, and $R^6$ are hydrogen atoms, $R^3$ is a C1-C3 alkyl group, a C3-C5 cycloalkyl group, a halogen atom, a C1-C3 haloalkyl group, a C1-C3 alkoxy group, a C1-C3 alkylthio group, a C1-C3 haloalkoxy group, or a C1-C3 haloalkylthio group, $R^7$ is a C1-C3 alkyl group, Q is Q2, n is 0, $R^{11}$, $R^{12}$, and $R^{13}$ are the same or different and represent a hydrogen atom, a halogen atom, a C1-C4 alkyl group, or a C1-C4 haloalkyl group, A is A31, $R^{44}$ is a hydrogen atom, a C1-C3 alkyl group, or a halogen atom, $R^{45}$ is a hydrogen atom, a halogen atom, a C1-C6 alkyl group, a C1-C3 alkoxy group, a C1-C3 alkylthio group, or a cyano group, $R^{46}$ is a hydrogen atom or a C1-C3 alkyl group, and X is an oxygen atom.

A compound in which $R^1$, $R^2$, $R^4$, $R^5$, and $R^6$ are hydrogen atoms, $R^3$ is a C1-C3 alkyl group, a C3-C5 cycloalkyl group, a halogen atom, a C1-C3 haloalkyl group, a C1-C3 alkoxy group, a C1-C3 alkylthio group, a C1-C3 haloalkoxy group, or a C1-C3 haloalkylthio group, $R^7$ is a C1-C3 alkyl group, Q is Q2, n is 0, $R^{11}$, $R^{12}$, and $R^{13}$ are the same or different and represent a hydrogen atom, a halogen atom, a C1-C4 alkyl group, or a C1-C4 haloalkyl group, A is A72, $R^{50}$, $R^{51}$, $R^{55}$, and $R^{56}$ are the same or different and represent a hydrogen atom or a C1-C3 alkyl group, and X is an oxygen atom.

A compound in which $R^1$, $R^2$, $R^4$, $R^5$, and $R^6$ are hydrogen atoms, $R^3$ is a C1-C3 alkyl group, a C3-C5 cycloalkyl group, a halogen atom, a C1-C3 haloalkyl group, a C1-C3 alkoxy group, a C1-C3 alkylthio group, a C1-C3 haloalkoxy group, or a C1-C3 haloalkylthio group, $R^7$ is a C1-C3 alkyl group, Q is Q2, n is 0, $R^{11}$, $R^{12}$, and $R^{13}$ are the same or different and represent a hydrogen atom, a halogen atom, a C1-C4 alkyl group, or a C1-C4 haloalkyl group, A is A74, $R^{50}$, $R^{51}$, $R^{55}$, and $R^{56}$ are the same or different and represent a hydrogen atom or a C1-C3 alkyl group, and X is an oxygen atom.

A compound in which $R^1$, $R^2$, $R^4$, $R^5$, and $R^6$ are hydrogen atoms, $R^3$ is a C1-C3 alkyl group, a C3-C5 cycloalkyl group, a halogen atom, a C1-C3 haloalkyl group, a C1-C3 alkoxy group, a C1-C3 alkylthio group, a C1-C3 haloalkoxy group, or a C1-C3 haloalkylthio group, $R^7$ is a C1-C3 alkyl group, Q is Q2, n is 0, $R^{11}$, $R^{12}$, and $R^{13}$ are the same or different and represent a hydrogen atom, a halogen atom, a C1-C4 alkyl group, or a C1-C4 haloalkyl group, A is A82, $R^{49}$ is a hydrogen atom, a halogen atom, or a C1-C6 alkyl group, $R^{60}$ is a hydrogen atom, a halogen atom, or a C1-C6 alkyl group, and X is an oxygen atom.

A compound in which $R^1$, $R^2$, $R^4$, $R^5$, $R^6$, and $R^9$ are hydrogen atoms, $R^3$ is a C1-C3 alkyl group, $R^7$ is a C1-C3 alkyl group, $R^{10}$ is a hydrogen atom or a C1-C4 alkyl group, Q is Q1, n is 0, $R^3$ is a C1-C4 alkyl group, A is A1, $R^{30}$, $R^{31}$, $R^{32}$, $R^{33}$, and $R^{34}$ are the same or different and represent a hydrogen atom, a halogen atom, a C1-C6 alkyl group, a C1-C6 haloalkyl group, a C1-C6 alkoxy group, or a cyano group, and X is an oxygen atom.

A compound in which $R^1$, $R^2$, $R^4$, $R^5$, $R^7$, $R^8$, $R^9$, $R^{41}$, $R^{42}$, $R^{43}$, and $R^{44}$ are hydrogen atoms, $R^3$ is a C1-C3 alkyl group, $R^7$ is a C1-C3 alkyl group, $R^{10}$ is a C1-C4 alkyl group, Q is Q1, n is 0, A is A13, m is 0, $R^{40}$ is a C1-C6 alkyl group, and X is an oxygen atom.

A compound in which $R^1$, $R^2$, $R^4$, $R^5$, $R^6$, $R^8$, $R^9$, $R^{41}$, $R^{42}$, $R^{43}$, and $R^{44}$ are hydrogen atoms, $R^3$ is a C1-C3 alkyl group, $R^7$ is a C1-C3 alkyl group, $R^{10}$ is a C1-C4 alkyl group, Q is Q1, n is 0, A is A14, m is 0, and X is an oxygen atom.

A compound in which $R^1$, $R^2$, $R^4$, $R^5$, $R^6$, $R^{12}$, $R^{13}$, $R^{30}$, $R^{32}$, $R^{33}$, and $R^{34}$ are hydrogen atoms, $R^3$ is a C1-C3 alkyl group, $R^7$ is a C1-C3 alkyl group, $R^{11}$ is a C1-C4 alkyl group, Q is Q2, n is 0, A is A14, m is 0, and X is an oxygen atom.

A compound in which $R^1$, $R^2$, $R^4$, $R^5$, and $R^6$ are hydrogen atoms, $R^3$ is a C1-C6 alkyl group, $R^7$ is a C1-C3 alkyl group optionally having one or more halogen atoms, X is an oxygen atom, and A is a C6-C10 aryl group optionally having one or more atoms or groups selected from Group $P^1$.

A compound in which $R^1$, $R^2$, $R^4$, $R^5$, and $R^6$ are hydrogen atoms, $R^3$ is a C1-C6 alkyl group, $R^7$ is a C1-C3 alkyl group optionally having one or more halogen atoms, X is an oxygen atom, Q is a 6-membered aromatic heterocyclic group having one nitrogen atom as a ring-constituent atom (provided that the heterocyclic group optionally has a C1-C4 alkyl group), and A is a phenyl group (provided that the phenyl group optionally has one or more atoms or groups selected from the group consisting of a halogen atom, a C1-C6 alkyl group, a C1-C6 haloalkyl group, a C1-C6 alkoxy group, and a cyano group).

A compound in which $R^1$, $R^2$, $R^4$, $R^5$, and $R^6$ are hydrogen atoms, $R^3$ is a C1-C6 alkyl group, $R^{11}$ is a C1-C3 alkyl group optionally having one or more halogen atoms, X is an oxygen atom, Q is Q1, and A is A1.

A compound in which $R^1$, $R^2$, $R^4$, $R^5$, and $R^6$ are hydrogen atoms, $R^3$ is a C1-C6 alkyl group, a C3-C6 cycloalkyl group, or a halogen atom, $R^7$ is a C1-C3 alkyl group optionally having one or more halogen atoms, Q is Q1, n is 0, $R^8$, $R^9$, and $R^{10}$ are the same or different and represent a hydrogen atom or a C1-C4 alkyl group, A is A1, $R^{30}$, $R^{31}$, $R^{32}$, $R^{33}$, and $R^{34}$ are the same or different and represent a hydrogen atom, a halogen atom, a C1-C6 alkyl group, a C1-C6 alkoxy group, or a cyano group, and X is an oxygen atom.

A compound in which $R^1$, $R^2$, $R^4$, $R^5$, and $R^E$ are hydrogen atoms, $R^3$ is a C1-C6 alkyl group, $R^7$ is a C1-C3 alkyl group optionally having one or more halogen atoms, Q is Q1, n is 0, $R^2$, $R^9$, and $R^{10}$ are the same or different and represent a hydrogen atom or a C1-C4 alkyl group, A is A1, $R^{30}$, $R^{31}$, $R^{32}$, $R^{33}$, and $R^{34}$ are the same or different and represent a hydrogen atom, a halogen atom, a C1-C6 alkyl group, a C1-C6 alkoxy group, or a cyano group, and X is an oxygen atom.

A compound in which $R^1$, $R^2$, $R^4$, $R^5$, and $R^6$ are hydrogen atoms, $R^3$ is a C3-C6 cycloalkyl group, $R^7$ is a C1-C3 alkyl group optionally having one or more halogen atoms, Q is Q1, n is 0, $R^3$, $R^9$, and $R^{10}$ are the same or different and represent a hydrogen atom or a C1-C4 alkyl group, A is A1, $R^{30}$, $R^{31}$, $R^{32}$, $R^{33}$, and $R^{34}$ are the same or different and represent a hydrogen atom, a halogen atom, a C1-C6 alkyl group, a C1-C6 alkoxy group, or a cyano group, and X is an oxygen atom.

A compound in which $R^1$, $R^2$, $R^4$, $R^5$, and $R^6$ are hydrogen atoms, $R^3$ is a halogen atom, $R^7$ is a C1-C3 alkyl group optionally having one or more halogen atoms, Q is Q1, n is 0, $R^8$, $R^9$, and $R^{10}$ are the same or different and represent a hydrogen atom or a C1-C4 alkyl group, A is A1, $R^{30}$, $R^{31}$, $R^{32}$, $R^{33}$, and $R^{34}$ are the same or different and represent a hydrogen atom, a halogen atom, a C1-C6 alkyl group, a C1-C6 alkoxy group, or a cyano group, and X is an oxygen atom.

The present invention includes all kinds of active isomers such as a geometrical isomer, an optical isomer, and a mixture thereof in the structural formula represented by general formula.

Next, a process for producing the present compound will be described.

The present compound can be produced, for example, by the following Production Processes.

(Production Process A)

The present compound (1) can be produced by reacting a compound represented by formula (AA1) (hereinafter referred to as the compound (AA1)) with a compound represented by formula (AA2) (hereinafter referred to as the compound (AA2)) in the presence of a base:

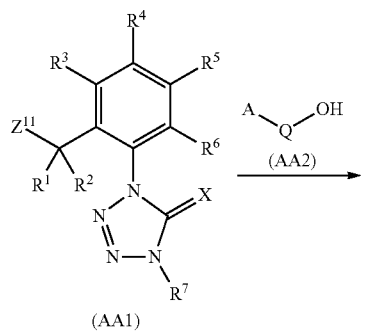

(AA1)

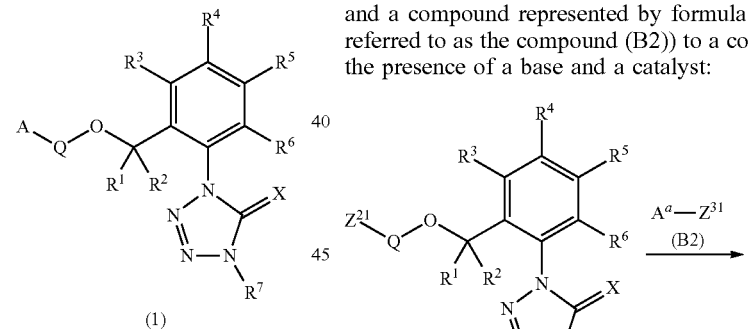

(1)

wherein $R^1$, $R^2$, $R^3$, $R^4$, $R^5$, $R^6$, $R^7$, X, A, and Q are the same as defined above, and $Z^{11}$ represents a leaving group such as a chlorine atom, a bromine atom, an iodine atom, a methanesulfonyloxy group, a trifluoromethanesulfonyloxy group, or a p-toluenesulfonyloxy group.

The reaction is usually performed in a solvent.

Examples of the solvent to be used in the reaction include hydrocarbons such as n-hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroethane, and chlorobenzene; acid amides such as N,N-dimethylformamide, 1,3-dimethyl-2-imidazolidinone, and N-methylpyrrolidone; esters such as ethyl acetate and methyl acetate; sulfoxides such as dimethyl sulfoxide; ketones such as acetone, methyl ethyl ketone, and methyl isobutyl ketone; nitriles such as acetonitrile; water; and mixtures thereof.

Examples of the base to be used in the reaction include organic bases such as triethylamine, pyridine, N-methylmorpholine, 4-dimethylaminopyridine, diisopropylethylamine, and diazabicycloundecene; alkali metal carbonates such as lithium carbonate, sodium carbonate, and potassium carbonate; alkali metal hydrogen carbonates such as sodium hydrogen carbonate and potassium hydrogen carbonate; alkali metal hydroxides such as sodium hydroxide and potassium hydroxide; alkali metal halides such as sodium fluoride, potassium fluoride, and cesium fluoride; alkali metal hydrides such as lithium hydride, sodium hydride, and potassium hydride; and alkali metal alkoxides such as sodium tert-butoxide and potassium tert-butoxide.

In the reaction, the compound (AA2) is usually used in the proportion within a range of 1 to 10 mols, and the base is usually used in the proportion within a range of 0.5 to 5 mols, based on 1 mol of the compound (AA1).

The reaction temperature of the reaction is usually within a range of −20 to 150° C. The reaction time is usually within a range of 0.1 to 24 hours.

If necessary, sodium iodide, tetrabutylammonium iodide, and the like may be added in the reaction, and these compounds are usually used in the proportion of 0.001 to 1.2 mols based on 1 mol of the compound (AA1).

After completion of the reaction, the compound (1) can be isolated by performing post-treatment operations such as extraction of the reaction mixture with an organic solvent, and drying and concentration of the organic layer. The isolated present compound can be further purified by chromatography, recrystallization, and the like.

(Production Process B)

Among the present compounds (1), a compound in which A is $A^a$ (hereinafter referred to as the compound (1-1)) can be produced by subjecting a compound represented by formula (B1) (hereinafter referred to as the compound (B1)) and a compound represented by formula (B2) (hereinafter referred to as the compound (B2)) to a coupling reaction in the presence of a base and a catalyst:

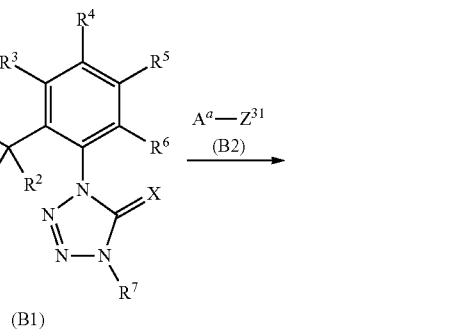

(B1)

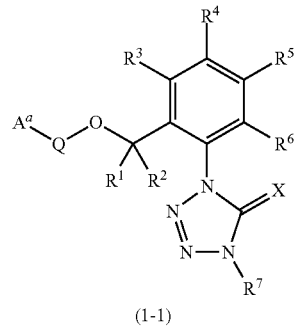

(1-1)

wherein $R^1$, $R^2$, $R^3$, $R^4$, $R^5$, $R^6$, $R^7$, X, and Q are the same as defined above, and $A^a$ represents a C6-C10 aryl group optionally having one or more atoms or groups selected from Group P¹, a 6-membered aromatic heterocyclic group having one, two, three, or four nitrogen atoms as a ring-constituent atom (provided that the heterocyclic group optionally has one or more groups or atoms selected from Group P¹), a 5-membered heterocyclic group optionally having one or more atoms or groups selected from Group P¹ (provided that the 5-membered heterocyclic group has, as a ring-constituent atom, one or more atoms selected from the group consisting of a nitrogen atom, an oxygen atom, and a sulfur atom and, when the 5-membered heterocyclic group has two or more atoms selected from the group consisting of a nitrogen atom, an oxygen atom, and a sulfur atom, the atoms may be the same or different to each other), or a C3-C10 cycloalkyl group optionally having one or more atoms or groups selected from Group P¹, $Z^{21}$ represents a chlorine atom, a bromine atom, or an iodine atom, and $Z^{31}$ represents $B(OH)_2$, an alkoxyboranyl group, or a trifluoroborate $BF_3^-K^+$.

The reaction is usually performed in a solvent.

Examples of the solvent to be used in the reaction include hydrocarbons such as n-hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroethane, and chlorobenzene; acid amides such as N,N-dimethylformamide, 1,3-dimethyl-2-imidazolidinone, and N-methylpyrrolidone; esters such as ethyl acetate and methyl acetate; sulfoxides such as dimethyl sulfoxide; ketones such as acetone, methyl ethyl ketone, and methyl isobutyl ketone; nitriles such as acetonitrile; alcohols such as methanol, ethanol, propanol, and butanol; water; and mixtures thereof.

It is possible to usually use, as the compound (B2) to be used in the reaction, commercially available compounds, or compounds produced by a known method mentioned in N. Miyaura and A. Suzuki, Chem. Rev., 1995, 95, 2457. It is possible to produce, as the compound (B2) to be used in the reaction, a boric acid ester derivative by reacting an iodine compound ($A^a$-I) or a bromo compound ($A^a$-Br) with an alkyllithium such as butyllithium, followed by a reaction with a boric acid ester. It is possible to produce a boric acid derivative by optionally hydrolyzing the boric acid ester derivative obtained by the above-mentioned reaction. It is also possible to produce a trifluoroborate $BF_3^-K^+$ by fluorinating the boric acid ester with potassium hydrogen fluoride in accordance with a known method mentioned in Molander et al. Acc. Chem. Res., 2007, 40, 275.

Examples of the catalyst to be used in the reaction include palladium(II) acetate, dichlorobis(triphenylphosphine)palladium, tetrakistriphenylphosphinepalladium(0), palladium (II) acetate/tricyclohexylphosphine, bis(diphenylphoshineferrocenyl)palladium(II) dichloride, palladium (II) acetate/dicyclohexyl(2',4',6'-triisopropylbiphenyl-2-yl)phosphine, tris(dibenzylideneacetone)dipalladium, and the like.

Examples of the base to be used in the reaction include organic bases such as triethylamine, pyridine, N-methylmorpholine, 4-dimethylaminopyridine, diisopropylethylamine, and diazabicycloundecene; alkali metal carbonates such as lithium carbonate, sodium carbonate, and potassium carbonate; alkali metal hydrogen carbonates such as sodium hydrogen carbonate and potassium hydrogen carbonate; alkali metal hydroxides such as sodium hydroxide and potassium hydroxide; alkali metal halides such as sodium fluoride, potassium fluoride, and cesium fluoride; alkali metal hydrides such as sodium hydride and potassium hydride; alkali metal phosphates such as tripotassium phosphate; and alkali metal alkoxides such as sodium methoxide, sodium ethoxide, sodium tert-butoxide, and potassium tert-butoxide.

In the reaction, the compound (B2) is usually used in the proportion within a range of 1 to 10 mols, the base is usually used in the proportion within a range of 1 to 10 mols, and the catalyst is usually used in the proportion within a range of 0.0001 to 1 mol, based on 1 mol of the compound (B1).

The reaction temperature of the reaction is usually within a range of 0 to 150° C. The reaction time of the reaction is usually within a range of 0.1 to 24 hours.

After completion of the reaction, the compound (1-1) can be isolated by performing post-treatment operations such as extraction of the reaction mixture with an organic solvent, and drying and concentration of the organic layer. The isolated present compound can be further purified by chromatography, recrystallization, and the like.

(Production Process C)

Among the present compounds (1), a compound in which A is $A^b$ (hereinafter referred to as the compound (1-2)) can be produced by subjecting the compound (B1) and a compound represented by formula (C1) (hereinafter referred to as the compound (C1)) to a coupling reaction in the presence of a base and a catalyst:

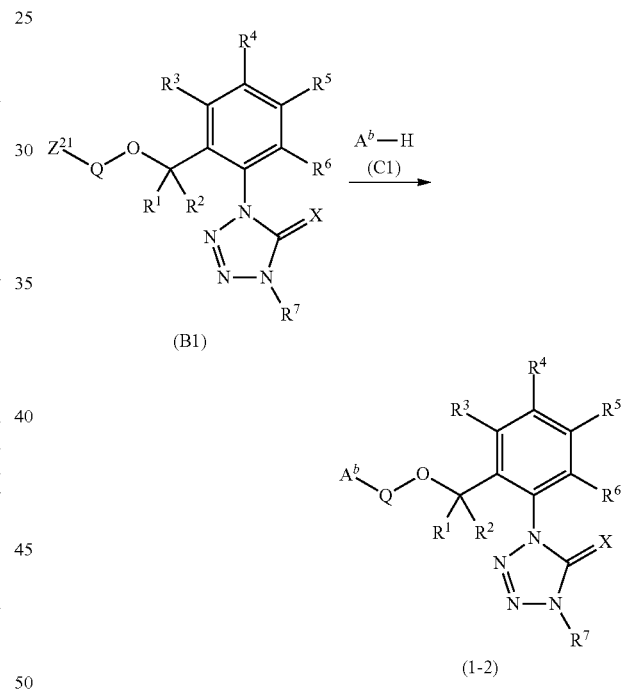

wherein $R^1$, $R^2$, $R^3$, $R^4$, $R^5$, $R^6$, $R^7$, X, Q, and $Z^{21}$ are the same as defined above, and $A^b$ represents an aliphatic C2-C9 heterocyclic group optionally having one or more atoms or groups selected from Group P¹ (provided that the aliphatic C2-C9 heterocyclic group has, as a ring-constituent atom, one or more atoms selected from the group consisting of a nitrogen atom, an oxygen atom, and a sulfur atom and, when the aliphatic C2-C9 heterocyclic group has two or more atoms selected from the group consisting of a nitrogen atom, an oxygen atom, and a sulfur atom, the atoms may be the same or different to each other, and also a carbon or nitrogen atom constituting a ring of the aliphatic C2-C9 heterocyclic group is bound to Q).

The reaction is usually performed in a solvent.

Examples of the solvent to be used in the reaction include hydrocarbons such as n-hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroethane, and chlorobenzene; acid amides such as N,N-dimethylformamide, 1,3-dimethyl-2-imidazolidinone, and N-methylpyrrolidone; esters such as ethyl acetate and methyl acetate; sulfoxides such as dimethyl sulfoxide; ketones such as acetone, methyl ethyl ketone, and methyl isobutyl ketone; nitriles such as acetonitrile; and mixtures thereof.

It is possible to usually use, as the compound (C1) to be used in the reaction, commercially available compounds. Specific examples thereof include morpholine, piperidine, piperazine, N-methylpiperazine, thiomorpholine, pyrrolidine, ethylenimine, azacyclobutane, hexamethyleneimine, and the like.

Examples of the catalyst to be used in the reaction include copper(I) iodide, copper(II) acetate, cobalt(II) chloride, palladium(II) acetate, dichlorobis(triphenylphosphine)palladium, tetrakistriphenylphosphinepalladium(0), palladium (II) acetate/triscyclohexylphosphine, bis(diphenylphoshineferrocenyl)palladium(II) dichloride, palladium (II) acetate/dicyclohexyl(2',4',6'-triisopropylbiphenyl-2-yl)phosphine, tris(dibenzylideneacetone)dipalladium, and the like.

Examples of the base to be used in the reaction include organic bases such as triethylamine, pyridine, N-methylmorpholine, 4-dimethylaminopyridine, diisopropylethylamine, and diazabicycloundecene; alkali metal carbonates such as lithium carbonate, sodium carbonate, and potassium carbonate; alkali metal hydrogen carbonates such as sodium hydrogen carbonate and potassium hydrogen carbonate; alkali metal hydroxides such as sodium hydroxide and potassium hydroxide; alkali metal halides such as sodium fluoride, potassium fluoride, and cesium fluoride; alkali metal hydrides such as lithium hydride, sodium hydride, and potassium hydride; and alkali metal alkoxides such as sodium tert-butoxide and potassium tert-butoxide.

In the reaction, the compound (C1) is usually used in the proportion within a range of 1 to 10 mols, the catalyst is usually used in the proportion within a range of 0.001 to 5 mols, and the base is usually used in the proportion within a range of 1 to 10 mols, based on 1 mol of the compound (B1).

If necessary, a ligand such as 1,10-phenanthroline or tetramethylethylenediamine may be added in the reaction, and these compounds are usually used in the proportion within a range of 0.001 to 5 mols based on 1 mol of the compound (B1).

The reaction temperature of the reaction is usually within a range of −20 to 150° C. The reaction time of the reaction is usually within a range of 0.1 to 24 hours.

After completion of the reaction, the compound (1-2) can be isolated by performing post-treatment operations such as extraction of the reaction mixture with an organic solvent, and drying and concentration of the organic layer. The isolated present compound can be further purified by chromatography, recrystallization, and the like.

(Production Process D)

The compound (1-1) can be produced by subjecting a compound represented by formula (D1) (hereinafter referred to as the compound (D1)) and a compound represented by formula (D2) (hereinafter referred to as the compound (D2)) to a coupling reaction in the presence of a base and a catalyst:

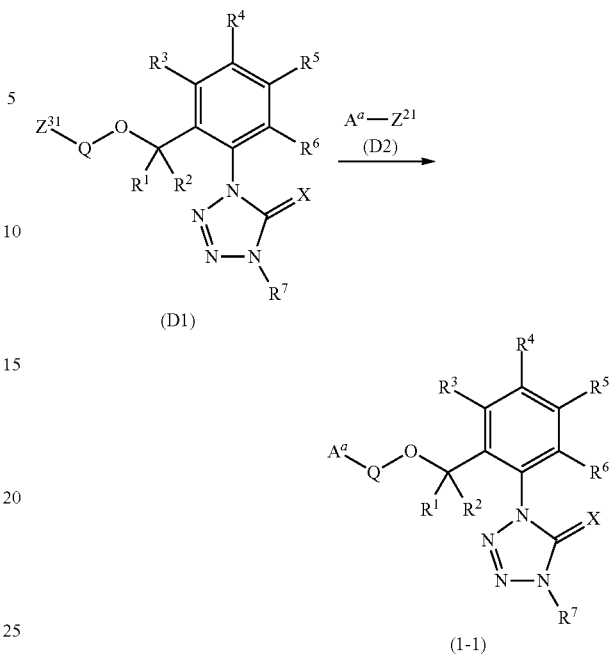

wherein symbols are the same as defined above.

The reaction is usually performed in a solvent.

Examples of the solvent to be used in the reaction include hydrocarbons such as n-hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroethane, and chlorobenzene; acid amides such as N,N-dimethylformamide, 1,3-dimethyl-2-imidazolidinone, and N-methylpyrrolidone; esters such as ethyl acetate and methyl acetate; sulfoxides such as dimethyl sulfoxide; ketones such as acetone, methyl ethyl ketone, and methyl isobutyl ketone; nitriles such as acetonitrile; alcohols such as methanol, ethanol, propanol, and butanol; water; and mixtures thereof.

Examples of the catalyst to be used in the reaction include palladium(II) acetate, dichlorobis(triphenylphosphine)palladium, tetrakistriphenylphosphinepalladium(0), palladium (II) acetate/triscyclohexylphosphine, bis(diphenylphoshineferrocenyl)palladium(II) dichloride, palladium (II) acetate/dicyclohexyl(2',4',6'-triisopropylbiphenyl-2-yl)phosphine, tris(dibenzylideneacetone)dipalladium, and the like.

Examples of the base to be used in the reaction include organic bases such as triethylamine, pyridine, N-methylmorpholine, 4-dimethylaminopyridine, diisopropylethylamine, and diazabicycloundecene; alkali metal carbonates such as lithium carbonate, sodium carbonate, and potassium carbonate; alkali metal hydrogen carbonates such as sodium hydrogen carbonate and potassium hydrogen carbonate; alkali metal hydroxides such as sodium hydroxide and potassium hydroxide; alkali metal halides such as sodium fluoride, potassium fluoride, and cesium fluoride; alkali metal hydrides such as lithium hydride, sodium hydride, and potassium hydride; alkali metal phosphates such as tripotassium phosphate; and alkali metal alkoxides such as sodium methoxide, sodium ethoxide, sodium tert-butoxide, and potassium tert-butoxide.

In the reaction, the compound (D2) is usually used in the proportion within a range of 1 to 10 mols, the base is usually used in the proportion within a range of 1 to 10 mols, and the catalyst is usually used in the proportion within a range of 0.0001 to 1 mol, based on 1 mol of the compound (D1).

The reaction temperature of the reaction is usually within a range of 0 to 150° C. The reaction time of the reaction is usually within a range of 0.1 to 24 hours.

After completion of the reaction, the compound (1-1) can be isolated by performing post-treatment operations such as extraction of the reaction mixture with an organic solvent, and drying and concentration of the organic layer. The isolated present compound can be further purified by chromatography, recrystallization, and the like.

(Production Process E)

The present compound (1) can be produced by reacting a compound represented by formula (1-3) (hereinafter referred to as the compound (1-3)) with a compound represented by formula (E1) (hereinafter referred to as the compound (E1)) in the presence of a base:

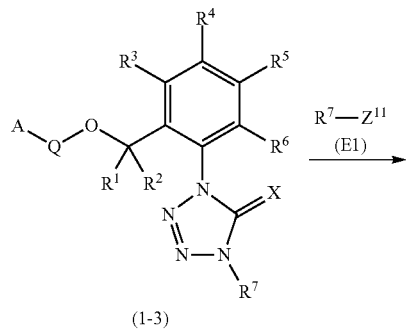

wherein symbols are the same as defined above.

The reaction is usually performed in a solvent.

Examples of the solvent to be used in the reaction include hydrocarbons such as n-hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroethane, and chlorobenzene; acid amides such as N,N-dimethylformamide, 1,3-dimethyl-2-imidazolidinone, and N-methylpyrrolidone; esters such as ethyl acetate and methyl acetate; sulfoxides such as dimethyl sulfoxide; ketones such as acetone, methyl ethyl ketone, and methyl isobutyl ketone; nitriles such as acetonitrile; water; and mixtures thereof.

It is possible to usually use, as the compound (E1) to be used in the reaction, commercially available compounds. Specific examples thereof include methyl bromide, ethyl bromide, n-propyl bromide, methyl iodide, ethyl iodide, n-propyl bromide; dialkyl sulfates such as dimethyl sulfate, diethyl sulfate, and di-n-propyl sulfate; and sulfonic acid esters such as methyl p-toluenesulfonate, ethyl p-toluenesulfonate, n-propyl p-toluenesulfonate, methyl methanesulfonate, ethyl methanesulfonate, and n-propyl methanesulfonate.

Examples of the base to be used in the reaction include organic bases such as triethylamine, pyridine, N-methylmorpholine, 4-dimethylaminopyridine, diisopropylethylamine, and diazabicycloundecene; alkali metal carbonates such as lithium carbonate, sodium carbonate, and potassium carbonate; alkali metal hydrogen carbonates such as sodium hydrogen carbonate and potassium hydrogen carbonate; alkali metal hydroxides such as sodium hydroxide and potassium hydroxide; alkali metal halides such as sodium fluoride, potassium fluoride, and cesium fluoride; alkali metal hydrides such as lithium hydride, sodium hydride, and potassium hydride; and alkali metal alkoxides such as sodium tert-butoxide and potassium tert-butoxide.

In the reaction, the compound (E1) is usually used in the proportion within a range of 1 to 10 mols, and the base is usually used in the proportion within a range of 1 to 10 mols, based on 1 mol of the compound (1-3).

The reaction temperature of the reaction is usually within a range of −20 to 150° C. The reaction time of the reaction is usually within a range of 0.1 to 24 hours.

After completion of the reaction, the present compound (1) can be isolated by performing post-treatment operations such as extraction of the reaction mixture with an organic solvent, and drying and concentration of the organic layer. The isolated present compound can be further purified by chromatography, recrystallization, and the like.

(Production Process F)

Among the present compounds (1), a compound represented by formula (1-S) in which X is a sulfur atom (hereinafter referred to as the compound (1-S)) can be produced from a compound represented by formula (1-O) in which X is an oxygen atom (hereinafter referred to as the compound (1-O)) among the present compounds (1) by a known sulfidation reaction:

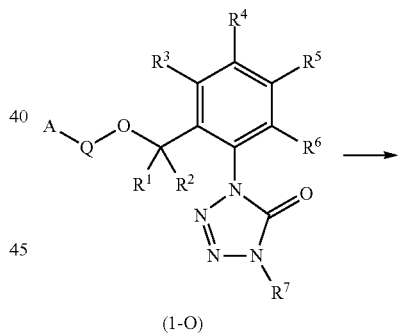

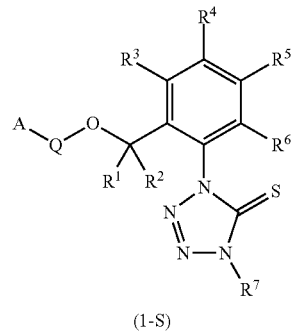

wherein symbols are the same as defined above.

The reaction is usually performed in a solvent.

Examples of the solvent to be used in the reaction include hydrocarbons such as n-hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as carbon tetrachloride, chloroform, dichloromethane, 1,2-dichloroethane, tetrachloroethane, and chlorobenzene; nitriles such as acetonitrile and propionitrile; and mixtures thereof.

Examples of the sulfurizing agent to be used in the reaction include phosphorous pentasulfide and Lawesson's reagent (2,4-Bis(4-methoxyphenyl)-1,3,2,4-dithiadiphosphetane 2,4-disulfide).

In the reaction, the sulfurizing agent is preferably used in the proportion within a range of 0.5 to 1.5 mols based on 1 mol of the compound (1-O).

The reaction temperature of the reaction is usually within a range of −20 to 150° C. The reaction time of the reaction is usually within a range of 0.1 to 24 hours.

In the reaction, if necessary, organic bases such as pyridine and trimethylamine; and inorganic bases such as alkali metal hydroxide and alkali metal carbonate may be added, and the amount of the base to be added is within a range of 0.5 to 1.5 mols based on the compound (1-O).

After completion of the reaction, the compound (1-S) can be isolated by performing post-treatment operations such as extraction of the reaction mixture with an organic solvent, and drying and concentration of the organic layer. The isolated present compound can be further purified by chromatography, recrystallization, and the like.

(Production Process G)

Among the present compounds (1), a compound represented by formula (1-4) in which $R^3$ is $R^{71}$ (hereinafter referred to as the compound (1-4)) can be produced by subjecting a compound represented by formula (G1) (hereinafter referred to as the compound (G1)) and a compound represented by formula (G21) (hereinafter referred to as the compound (G21)) to a coupling reaction in the presence of a base and a catalyst:

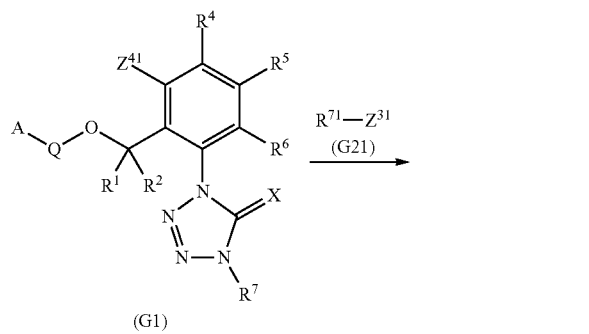

wherein $R^1$, $R^2$, $R^4$, $R^5$, $R^6$, $R^7$, X, A, Q, and $Z^{31}$ are the same as defined above, $Z^{41}$ represents a chlorine atom, a bromine atom, an iodine atom, or a trifluoromethanesulfonyloxy group, and $R^{71}$ represents a C1-C6 alkyl group, a C1-C6 haloalkyl group, a C2-C6 alkenyl group, a C2-C6 haloalkenyl group, a C3-C6 cycloalkyl group, or a C3-C6 halocycloalkyl group.

The reaction can be carried out in accordance with the reaction mentioned in Production Process B.

In accordance with the reaction mentioned in Production Process B, it is possible to produce a compound represented by formula (1-5) in which $R^4$ is $R^{72}$ (hereinafter referred to as the compound (1-5)), among the present compounds (1), by subjecting a compound represented by formula (G2) (hereinafter referred to as the compound (G2)) and a compound represented by formula (G22) (hereinafter referred to as the compound (G22)) to a coupling reaction in the presence of a base and a catalyst:

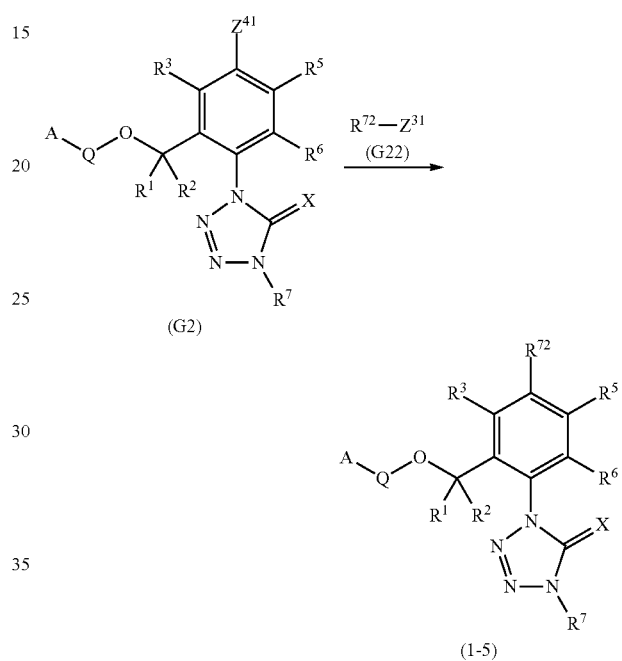

wherein $R^1$, $R^2$, $R^3$, $R^5$, $R^6$, $R^7$, X, A, Q, $Z^{31}$, and $Z^{41}$ are the same as defined above, and $R^7$ represents a C1-C3 alkyl group.

In accordance with the reaction mentioned in Production Process B, it is possible to produce a compound represented by formula (1-6) in which $R^5$ is $R^{72}$ (hereinafter referred to as the compound (1-6)) among the present compounds (1) by subjecting a compound represented by formula (G3) (hereinafter referred to as the compound (G3)) and the compound (G22) to a coupling reaction in the presence of a base and a catalyst:

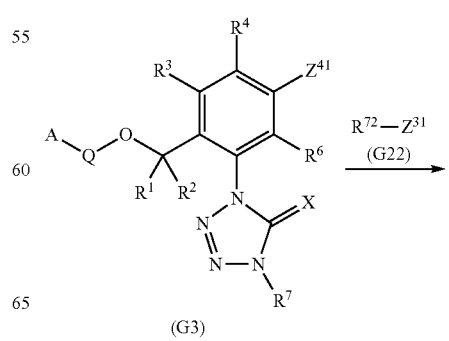

-continued

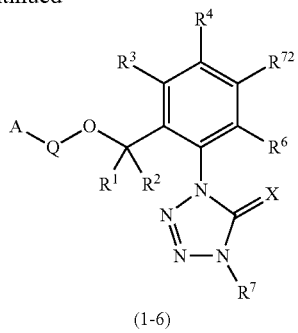

(1-6)

wherein symbols are the same as defined above.

In accordance with the reaction mentioned in Production Process B, it is possible to produce a compound represented by formula (1-7) in which $R^6$ is $R^{72}$ (hereinafter referred to as the compound (1-7)), among the present compounds (1), by subjecting a compound represented by formula (G4) formula (hereinafter referred to as the compound (G4)) and the compound (G22) to a coupling reaction in the presence of a base and a catalyst:

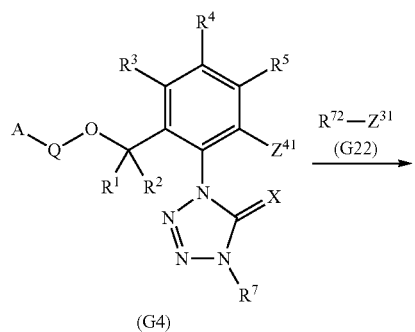

(G4)

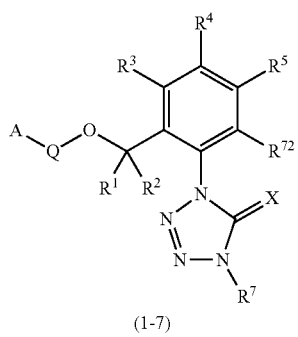

(1-7)

wherein symbols are the same as defined above.

In accordance with the reaction mentioned in Production Process B, it is possible to produce a compound in which two or more substituents selected from $R^3$, $R^4$, $R^5$, and $R^6$ are either $R^{71}$ or $R^{72}$, among the present compounds (1).

It is also possible to produce the compound (1-4), the compound (1-5), the compound (1-6), and the compound (1-7) by using other known coupling reactions in place of the coupling reaction of Production Process B.

(Production Process H)

Among the present compounds (1), a compound represented by formula (1-8) in which Q is Q1, n is 0, and $R^8$ is $R^{73}$ (hereinafter referred to as the compound (1-8)) can be produced by subjecting a compound represented by formula (H1) (hereinafter referred to as the compound (H1)) and a compound represented by formula (H21) (hereinafter referred to as the compound (H21)) to a coupling reaction in the presence of a base and a catalyst:

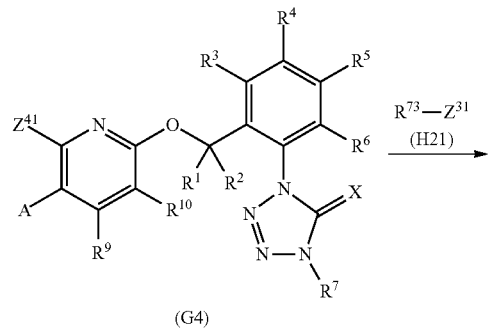

(G4)

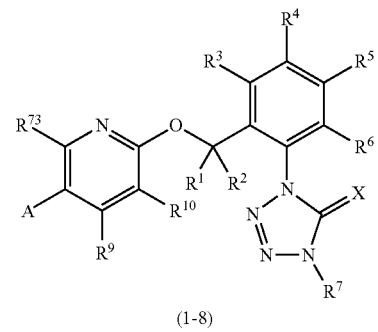

(1-8)

wherein $R^1$, $R^2$, $R^3$, $R^4$, $R^5$, $R^6$, $R^7$, $R^9$, $R^{10}$, X, A, $Z^{31}$, and $Z^{41}$ are the same as defined above, and $R^{73}$ represents a C1-C4 alkyl group, a C1-C4 haloalkyl group, a C3-C6 cycloalkyl group, or a C3-C6 halocycloalkyl group.

The reaction can be carried out in accordance with the reaction mentioned in Production Process B.

In accordance with the reaction mentioned in Production Process B, it is possible to produce a compound represented by formula (1-9) in which Q is Q1, n is 0, and $R^9$ is $R^{73}$ (hereinafter referred to as the compound (1-9)), among the present compounds (1), by subjecting a compound represented by formula (H2) (hereinafter referred to as the compound (H2)) and the compound (H21) to a coupling reaction in the presence of a base and a catalyst:

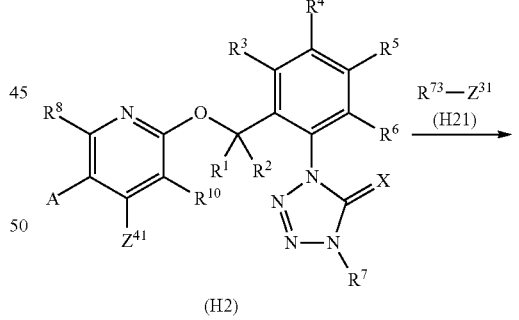

(H2)

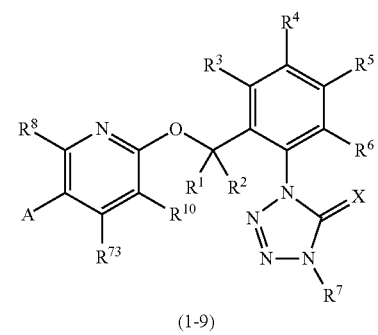

(1-9)

wherein symbols are the same as defined above.

In accordance with the reaction mentioned in Production Process B, it is possible to produce a compound represented by formula (1-10) in which Q is Q1, n is 0, and $R^{10}$ is $R^{73}$ (hereinafter referred to as the compound (1-10)), among the present compounds (1), by subjecting a compound represented by formula (H3) (hereinafter referred to as the compound (H3)) and the compound (H21) to a coupling reaction in the presence of a base and a catalyst:

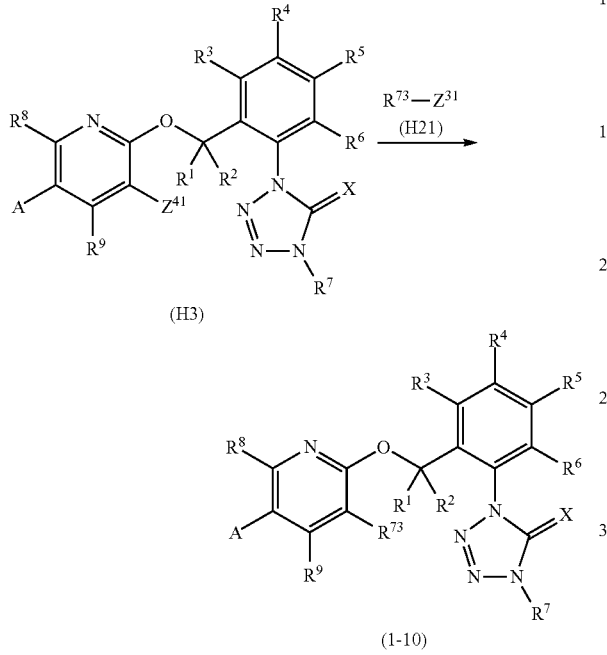

wherein symbols are the same as defined above.

In accordance with the reaction mentioned in Production Process B, it is possible to produce a compound in which Q is Q1, n is 0, and two or more substituents selected from $R^8$, $R^9$, and $R^{10}$ are $R^{73}$, among the present compounds (1).

It is also possible to produce the present compound (1) by using other known coupling reactions in place of the coupling reaction of Production Process B.

In accordance with the reaction mentioned in Production Process B, it is possible to produce a compound in which Q is Q2, n is 0, and one or more substituents selected from $R^{11}$, $R^{12}$, and $R^{13}$ are $R^{13}$, among the present compounds (1).

In accordance with the reaction mentioned in Production Process B, it is possible to produce a compound in which Q is Q3, n is 0, and one or more substituents selected from $R^{14}$ and $R^{15}$ are $R^{73}$, among the present compounds (1).

In accordance with the reaction mentioned in Production Process B, it is possible to produce a compound in which Q is Q4, n is 0, and one or more substituents selected from $R^{16}$ and $R^{17}$ are $R^{73}$, among the present compounds (1).

In accordance with the reaction mentioned in Production Process B, it is possible to produce a compound in which Q is Q5, n is 0, and one or more substituents selected from $R^{18}$ and $R^{19}$ are $R^{73}$, among the present compounds (1).

In accordance with the reaction mentioned in Production Process B, it is possible to produce a compound in which Q is Q6, n is 0, and one or more substituents selected from $R^{20}$ and $R^{21}$ are $R^{73}$, among the present compounds (1).

In accordance with the reaction mentioned in Production Process B, it is possible to produce a compound in which Q is Q7, n is 0, and $R^{22}$ is $R^{73}$, among the present compounds (1).

In accordance with the reaction mentioned in Production Process B, it is possible to produce a compound in which Q is Q8, n is 0, and $R^{23}$ is $R^{73}$, among the present compounds (1).

The process for synthesizing an intermediate compound for production will be mentioned in detail below.

(Reference Production Process A)

A compound represented by formula (XA3) (hereinafter referred to as the compound (XA3)) can be produced by reacting a compound represented by formula (XA1) (hereinafter referred to as the compound (XA1)) or a compound represented by formula (XA2) (hereinafter referred to as the compound (XA2)) with an azidation agent:

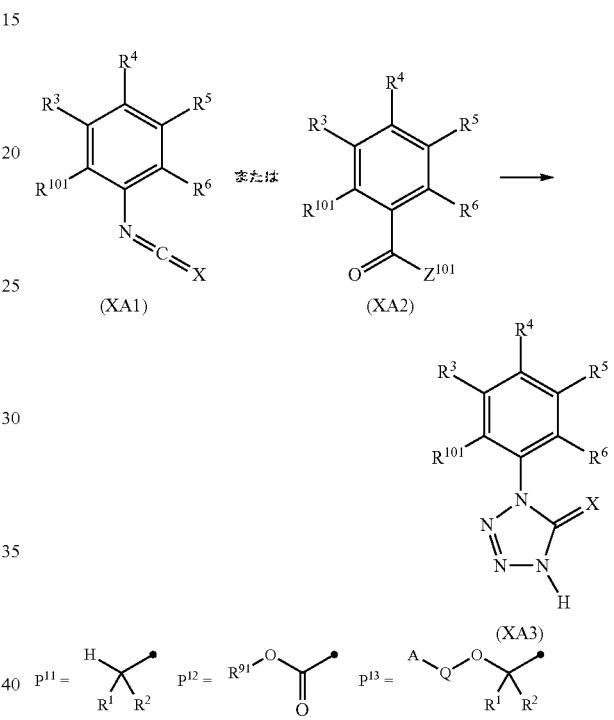

wherein $R^1$, $R^2$, $R^3$, $R^4$, $R^5$, $R^6$, X, A, and Q are the same as defined above, $R^{10}$ represents $P^{11}$, $P^{12}$, or $P^{13}$, $R^{91}$ represents a C1-C12 alkyl group, $Z^{101}$ represents a chlorine atom or bromine atom, and the symbol ● represents a binding site.

The reaction is usually performed in a solvent.

Examples of the solvent to be used in the reaction include hydrocarbons such as n-hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroethane, and chlorobenzene; acid amides such as N,N-dimethylformamide, 1,3-dimethyl-2-imidazolidinone, and N-methylpyrrolidone; esters such as ethyl acetate and methyl acetate; sulfoxides such as dimethyl sulfoxide; ketones such as acetone, methyl ethyl ketone, and methyl isobutyl ketone; nitriles such as acetonitrile; and mixtures thereof.

Examples of the azidation agent to be used in the reaction include inorganic azides such as sodium azide, barium azide, and lithium azide; and organic azides such as trimethylsilyl azide and diphenylphosphoryl azide.

In the reaction, the azidation agent is usually used in the proportion within a range of 1 to 10 mols based on 1 mol of the compound (XA1) or the compound (XA2).

The reaction temperature of the reaction is usually within a range of −20 to 150° C. The reaction time of the reaction is usually within a range of 0.1 to 24 hours.

In the reaction, if necessary, Lewis acid such as aluminum chloride or zinc chloride may be added, and these compounds are usually used in the proportion within a range of 0.05 to 5 mols based on 1 mol of the compound (XA1) or the compound (XA2).

After completion of the reaction, the compound (XA3) can be isolated by performing post-treatment operations such as extraction of the reaction mixture with an organic solvent, and drying and concentration of the organic layer. The isolated compound (XA3) can be further purified by chromatography, recrystallization, and the like.

(Reference Production Process B)

The compound (XA1) can be produced by reacting a compound represented by formula (XB1) (hereinafter referred to as the compound (XB1)) with an isocyanating agent:

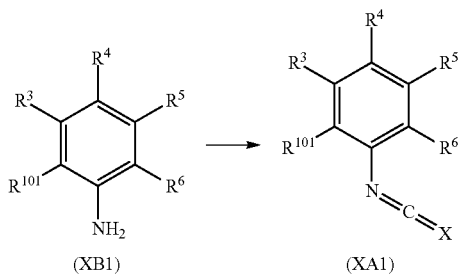

wherein symbols are the same as defined above.

The reaction is usually performed in a solvent.

Examples of the solvent to be used in the reaction include hydrocarbons such as n-hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroethane, and chlorobenzene; esters such as ethyl acetate and methyl acetate; ketones such as acetone, methyl ethyl ketone, and methyl isobutyl ketone; nitriles such as acetonitrile; and mixtures thereof.

Examples of the isocyanating agent to be used in the reaction include phosgene, diphosgene, triphosgene, thiophosgene, N,N-carbodiimidazole, and N,N-thiocarbodiimidazole.

In the reaction, the isocyanating agent is usually used in the proportion within a range of 0.34 to 10 mols based on 1 mol of the compound (XB1).

The reaction temperature of the reaction is usually within a range of −20 to 150° C. The reaction time of the reaction is usually within a range of 0.1 to 24 hours.

In the reaction, if necessary, organic bases such as triethylamine, pyridine, N-methylmorpholine, 4-dimethylaminopyridine, diisopropylethylamine, and diazabicycloundecene; alkali metal carbonates such as lithium carbonate, sodium carbonate, and potassium carbonate; and alkali metal hydrogen carbonates such as sodium hydrogen carbonate and potassium hydrogen carbonate may be added, and these compounds are usually used in the proportion within a range of 0.05 to 5 mols based on 1 mol of the compound (XB1).

After completion of the reaction, the compound (XA1) can be isolated by performing post-treatment operations such as extraction of the reaction mixture with an organic solvent, and drying and concentration of the organic layer. The isolated compound may be further purified by operations such as distillation, chromatography, and recrystallization.

(Reference Production Process C)

The compound (XA2) can be produced by reacting a compound represented by formula (XC1) (hereinafter referred to as the compound (XC1)) with a halogenating agent:

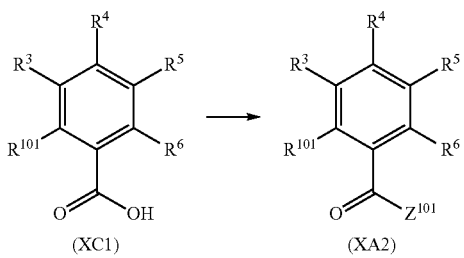

wherein symbols are the same as defined above.

The reaction is usually performed in a solvent.

Examples of the solvent to be used in the reaction include hydrocarbons such as n-hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroethane, and chlorobenzene; esters such as ethyl acetate and methyl acetate; ketones such as acetone, methyl ethyl ketone, and methyl isobutyl ketone; nitriles such as acetonitrile; and mixtures thereof.

Examples of the halogenating agent to be used in the reaction include phosphorus oxychloride, phosphorus trichloride, phosphorus pentachloride, thionyl chloride, phosphorus oxybromide, phosphorus tribromide, phosphorus pentabromide, phosphorus triiodide, oxalyl dichloride, oxalyl dibromide, triphosgene, diphosgene, phosgene, and sulfuryl chloride.

In the reaction, the halogenating agent is usually used in the proportion within a range of 1 to 10 mols based on 1 mol of the compound (XC1).

The reaction temperature of the reaction is usually within a range of −20 to 150° C. The reaction time of the reaction is usually within a range of 0.1 to 24 hours.

In the reaction, the catalyst may be added and dimethylformamide, or the like is used. The amount of the catalyst to be used is usually in the proportion within a range of 0.001 to 1 mol based on 1 mol of the compound (XC1).

In the reaction, if necessary, organic bases such as triethylamine, pyridine, N-methylmorpholine, 4-dimethylaminopyridine, diisopropylethylamine, and diazabicycloundecene; alkali metal carbonates such as lithium carbonate, sodium carbonate, and potassium carbonate; and alkali metal hydrogen carbonates such as lithium hydrogen carbonate, sodium hydrogen carbonate, potassium hydrogen carbonate, and cesium hydrogen carbonate may be added, and these compounds are usually used in the proportion within a range of 0.05 to 5 mols based on 1 mol of the compound (XC1).

After completion of the reaction, the compound (XA2) can be isolated by performing post-treatment operations such as extraction of the reaction mixture with an organic solvent, and drying and concentration of the organic layer.

The isolated present compound can be further purified by operations such as distillation, chromatography, and recrystallization.

(Reference Production Process D)

The compound (XA1) can be produced by reacting the compound (XB1) with a carbamating agent to obtain a compound represented by the following formula (XD1) (hereinafter referred to as the compound (XD1)), and then reacting the compound (XD1) with an isocyanating agent:

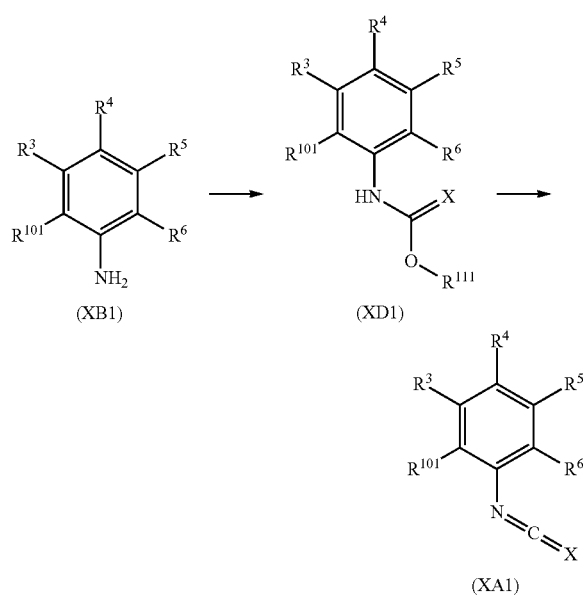

wherein $R^3$, $R^4$, $R^5$, $R^6$, $R^{101}$, and X are the same as defined above, and $R^{111}$ represents a C1-C12 alkyl group or a phenyl group.

The process for producing the compound (XD1) from the compound (XB1) will be described below.

The reaction is usually performed in a solvent.

Examples of the solvent to be used in the reaction include hydrocarbons such as n-hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroethane, and chlorobenzene; acid amides such as N,N-dimethylformamide, 1,3-dimethyl-2-imidazolidinone, and N-methylpyrrolidone; esters such as ethyl acetate and methyl acetate; sulfoxides such as dimethyl sulfoxide; ketones such as acetone, methyl ethyl ketone, and methyl isobutyl ketone; nitriles such as acetonitrile; water; and mixtures thereof.

Examples of the carbamating agent to be used in the reaction include phenyl chlorocarbonate, methyl chlorocarbonate, ethyl chlorocarbonate, n-propyl chlorocarbonate, isopropyl chlorocarbonate, n-butyl chlorocarbonate, tert-butyl chlorocarbonate, di-tert-butyl dicarbonate, dimethyl dicarbonate, diethyl dicarbonate, O-phenyl chlorothioformate, O-methyl chlorothioformate, O-ethyl chlorothioformate, and the like.

In the reaction, the carbamating agent is usually used in the proportion within a range of 1 to 10 mols based on 1 mol of the compound (XB1).

The reaction temperature of the reaction is usually within a range of −20 to 150° C. The reaction time of the reaction is usually within a range of 0.1 to 24 hours.

In the reaction, if necessary, organic bases such as triethylamine, pyridine, N-methylmorpholine, 4-dimethylaminopyridine, diisopropylethylamine, and diazabicycloundecene; alkali metal carbonates such as lithium carbonate, sodium carbonate, and potassium carbonate; and alkali metal hydrogen carbonates such as sodium hydrogen carbonate and potassium hydrogen carbonate may be added, and these compounds are usually used in the proportion within a range of 0.05 to 5 mols based on 1 mol of the compound (XB1).

After completion of the reaction, the compound (XD1) can be isolated by performing post-treatment operations such as extraction of the reaction mixture with an organic solvent, and drying and concentration of the organic layer. The isolated compound can be further purified by operations such as distillation, chromatography, and recrystallization.

The process for producing the compound (XA1) from the compound (XD1) will be described below.

The reaction is usually performed in a solvent.

Examples of the solvent to be used in the reaction include ethers such as tetrahydrofuran, dioxane, ethylene glycol dimethyl ether, and methyl tert-butyl ether; aromatic hydrocarbons such as toluene and xylene; halogenated hydrocarbons such as chloroform, 1,2-dichloroethane, and chlorobenzene; nitriles such as acetonitrile; acid amides such as N,N-dimethylformamide, 1,3-dimethyl-2-imidazolidinone, and N-methylpyrrolidone; sulfoxides such as dimethyl sulfoxide; ketones such as acetone, methyl ethyl ketone, and methyl isobutyl ketone; and mixtures thereof.

Examples of the isocyanating agent to be used in the reaction include phosphorus pentachloride, phosphorus oxychloride, diphosphorus pentaoxide, trichlorosilane, dichlorosilane, monochlorosilane, boron trichloride, 2-chloro-1,3,2-benzodioxaborole, diiodosilane, methyltrichlorosilane, dimethyldichlorosilane, chlorotrimethylsilane, and the like.

In the reaction, the isocyanating agent is usually used in the proportion within a range of 1 to 10 mols based on 1 mol of the compound (XD1).

The reaction temperature of the reaction is usually within a range of −20 to 250° C. The reaction time of the reaction is usually within a range of 0.1 to 24 hours.

In the reaction, if necessary, organic bases such as triethylamine, pyridine, N-methylmorpholine, 4-dimethylaminopyridine, diisopropylethylamine, and diazabicycloundecene; alkali metal carbonates such as lithium carbonate, sodium carbonate, and potassium carbonate; and alkali metal hydrogen carbonates such as sodium hydrogen carbonate and potassium hydrogen carbonate may be added, and these compounds are usually used in the proportion within a range of 0.05 to 5 mols based on 1 mol of the compound (XD1).

After completion of the reaction, the compound (XA1) can be isolated by performing post-treatment operations such as extraction of the reaction mixture with an organic solvent, and drying and concentration of the organic layer. The isolated present compound may be further purified by operations such as distillation, chromatography, and recrystallization.

(Reference Production Process E)

A compound represented by formula (XE2) (hereinafter referred to as the compound (XE2)) can be produced by reacting a compound represented by formula (XE1) (hereinafter referred to as the compound (XE1)) with hydrogen in the presence of a catalyst:

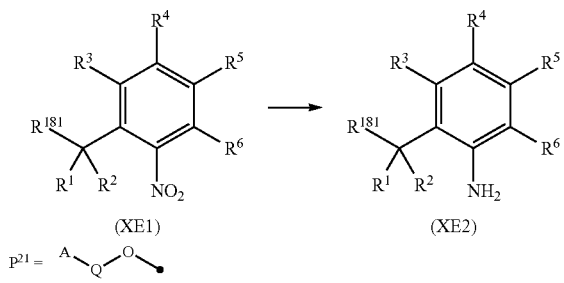

(XE1) (XE2)

$P^{21} = A\diagdown_Q\diagdown_O\bullet$ wherein $R^1$, $R^2$, $R^3$, $R^4$, $R^5$, $R^6$, A, and Q are the same as defined above, $R^{181}$ represents a hydrogen atom or $P^{21}$, and the symbol ● represents a binding site.

The reaction is usually performed in a solvent.

Examples of the solvent to be used in the reaction include alcohols such as methanol, ethanol, propanol, and butanol; esters such as ethyl acetate and butyl acetate; halogenated hydrocarbons such as chloroform, 1,2-dichloroethane, and chlorobenzene; ethers such as tetrahydrofuran, 1,4-dioxane, ethylene glycol dimethyl ether, methyl tert-butyl ether, and diisopropyl ether; hydrocarbons such as n-hexane, cyclohexane, toluene, and xylene; water; and mixtures thereof.

Examples of the catalyst to be used in the reaction include palladium-carbon (Pd/C), platinum-carbon (Pt/C), osmium-carbon (Os/C), ruthenium-carbon (Ru/C), rhodium-carbon (Rh/C), Raney nickel, and the like.

In the reaction, the catalyst is usually used in the proportion within a range of 0.0001 to 1 mol based on 1 mol of the compound (XE1).

The reaction temperature of the reaction is usually within a range of −20 to 150° C. The reaction time of the reaction is usually within a range of 0.1 to 24 hours.

After completion of the reaction, the compound (XE2) can be isolated by performing post-treatment operations such as concentration of the organic layer after filtration of the catalyst. The isolated compound may be further purified by operations such as distillation, chromatography, and recrystallization.

(Reference Production Process F)

The compound (XE2) can be produced by reacting the compound (XE1) with a reducing agent in the presence of an acid:

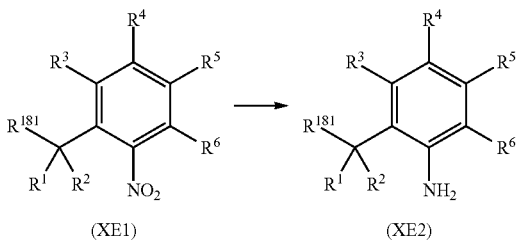

(XE1) (XE2)

wherein symbols are the same as defined above.

The reaction is usually performed in a solvent.

Examples of the solvent to be used in the reaction include aliphatic carboxylic acids such as acetic acid; alcohols such as methanol and ethanol; water; and mixtures thereof.

Examples of the reducing agent to be used in the reaction include iron, tin, and zinc.

Examples of the acid to be used in the reaction include hydrochloric acid, sulfuric acid, acetic acid, aqueous ammonium chloride solution, and the like.

In the reaction, the reducing agent is usually used in the proportion within a range of 1 to 30 mols based on 1 mol of the compound (XE1).

The reaction temperature of the reaction is usually within a range of −20 to 150° C. The reaction time of the reaction is usually within a range of 0.1 to 24 hours.

After completion of the reaction, the compound (XE2) can be isolated by performing post-treatment operations such as extraction of the reaction mixture with an organic solvent, and drying and concentration of the organic layer. The isolated compound may be further purified by operations such as distillation, chromatography, and recrystallization.

(Reference Production Process G)

A compound represented by formula (XG2) (hereinafter referred to as the compound (XG2)) can be produced by reacting a compound represented by formula (XG1) (hereinafter referred to as the compound (XG1)) with the compound (E1) in the presence of a base:

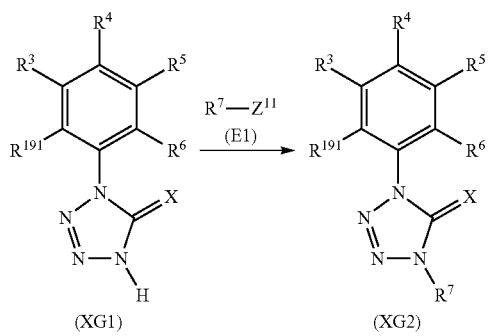

(XG1) (XG2)

wherein $R^3$, $R^4$, $R^5$, $R^6$, $R^7$, X, and $Z^{11}$ are the same as defined above, and $R^{191}$ represents $P^{11}$ or $P^{12}$.

The reaction can be carried out in accordance with the reaction mentioned in Production Process E.

(Reference Production Process H)

A compound represented by formula (XH2) (hereinafter referred to as the compound (XH2)) can be produced by reacting a compound represented by formula (XH1) (hereinafter referred to as the compound (XH1)) with a halogenating agent:

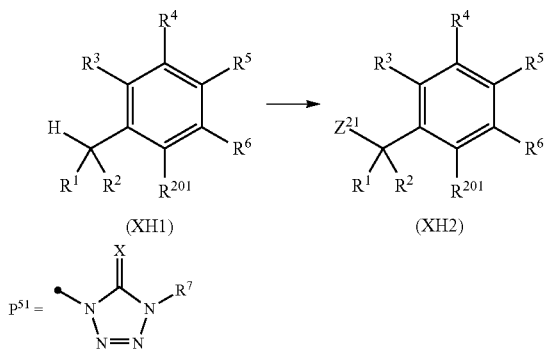

(XH1) (XH2)

wherein $R^1$, $R^2$, $R^3$, $R^4$, $R^5$, $R^6$, $R^7$, $Z^{21}$, and X are the same as defined above, $R^{201}$ represents $P^{51}$ or a nitro group, and the symbol ● represents a binding site.

The reaction is usually performed in a solvent.

Examples of the solvent to be used in the reaction include hydrocarbons such as n-hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroethane, and chlorobenzene; esters such as ethyl acetate and methyl acetate; ketones such as acetone, methyl ethyl ketone, and methyl isobutyl ketone; nitriles such as acetonitrile; and mixtures thereof.

Examples of the halogenating agent usable in the reaction include a chlorinating agent, a brominating agent, or an iodinating agent, for example, chlorine, bromine, iodine, sulfuryl chloride, N-chlorosuccinimide, N-bromosuccinimide, 1,3-dibromo-5,5-dimethylhydantoin, iodosuccinimide, tert-butyl hypochlorite, and the like.

In the reaction, a radical initiator can also be used.

Examples of the radical initiator to be used in the reaction include benzoyl peroxide, azobisisobutyronitrile (AIBN), diacyl peroxide, dialkylperoxydicarbonate, tert-alkylperoxyester, monoperoxycarbonate, di(tert-alkylperoxy)ketal, and ketone peroxide.

In the reaction, the halogenating agent is usually used in the proportion within a range of 1 to 10 mols, and the radical initiator is usually used in the proportion within a range of 0.01 to 5 mols, based on 1 mol of the compound (XH1).

The reaction temperature of the reaction is usually within a range of −20 to 150° C. The reaction time of the reaction is usually within a range of 0.1 to 24 hours.

After completion of the reaction, the compound (XH2) can be isolated by performing post-treatment operations such as extraction of the reaction mixture with an organic solvent, and drying and concentration of the organic layer. The isolated compound may be further purified by operations such as distillation, chromatography, and recrystallization.

(Reference Production Process I)

A compound represented by formula (XJ2) (hereinafter referred to as the compound (XJ2)) can be produced by reacting the compound (XH2) with a compound represented by formula (XJ1) (hereinafter referred to as the compound (XJ1)):

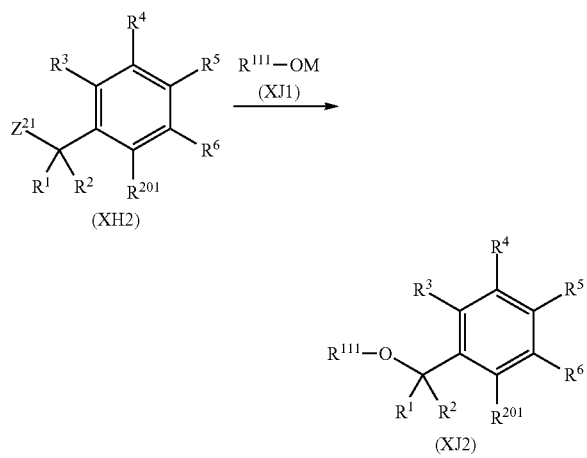

wherein $R^1$, $R^2$, $R^3$, $R^4$, $R^5$, $R^6$, $R^{201}$, $R^{111}$, and $Z^{21}$ are the same as defined above, and M represents sodium, potassium, or lithium.

The reaction is usually performed in a solvent.

Examples of the solvent to be used in the reaction include ethers such as tetrahydrofuran, 1,4-dioxane, ethylene glycol dimethyl ether, methyl tert-butyl ether, and diisopropyl ether; hydrocarbons such as n-hexane, cyclohexane, toluene, and xylene; halogenated hydrocarbons such as chloroform, 1,2-dichloroethane, and chlorobenzene; nitriles such as acetonitrile; acid amides such as N,N-dimethylformamide, 1,3-dimethyl-2-imidazolidinone, and N-methylpyrrolidone; sulfoxides such as dimethyl sulfoxide; ketones such as acetone, methyl ethyl ketone, and methyl isobutyl ketone; alcohols such as methanol, ethanol, propanol, and butanol; and mixtures thereof.

Examples of the compound (XJ1) usable in the reaction include sodium methoxide, sodium ethoxide, sodium n-propoxide, sodium n-butoxide, sodium isopropoxide, sodium sec-butoxide, sodium tert-butoxide, potassium methoxide, potassium ethoxide, potassium n-propoxide, potassium n-butoxide, potassium isopropoxide, potassium sec-butoxide, potassium tert-butoxide, and sodium phenoxide.

In the reaction, the compound (XJ1) is usually used in the proportion within a range of 1 to 10 mols based on 1 mol of the compound (XH2).

The reaction temperature of the reaction is usually within a range of −20 to 150° C. The reaction time of the reaction is usually within a range of 0.1 to 24 hours.

After completion of the reaction, the compound (XJ2) can be isolated by performing post-treatment operations such as extraction of the reaction mixture with an organic solvent, and drying and concentration of the organic layer. The isolated compound may be further purified by operations such as distillation, chromatography, and recrystallization.

(Reference Production Process J)

A compound represented by formula (XK1) (hereinafter referred to as the compound (XK1)) can be produced by reacting the compound (XH2) with water in the presence of a base:

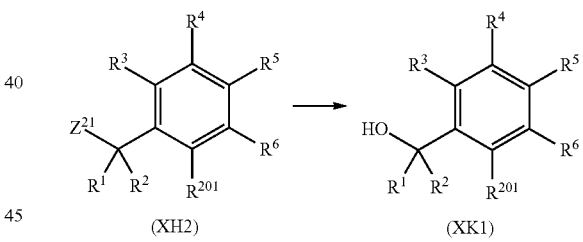

wherein symbols are the same as defined above.

The reaction is usually performed in water, or a solvent containing water.

Examples of the solvent to be used in the reaction include ethers such as tetrahydrofuran, 1,4-dioxane, ethylene glycol dimethyl ether, methyl tert-butyl ether, and diisopropyl ether; hydrocarbons such as n-hexane, cyclohexane, toluene, and xylene; halogenated hydrocarbons such as chloroform, 1,2-dichloroethane, and chlorobenzene; nitriles such as acetonitrile; acid amides such as N,N-dimethylformamide, 1,3-dimethyl-2-imidazolidinone, and N-methylpyrrolidone; sulfoxides such as dimethyl sulfoxide; ketones such as acetone, methyl ethyl ketone, and methyl isobutyl ketone; alcohols such as methanol, ethanol, propanol, and butanol; and mixtures thereof.

Examples of the base to be used in the reaction include organic bases such as triethylamine, pyridine, N-methylmorpholine, 4-dimethylaminopyridine, diisopropylethylamine, and diazabicycloundecene; metal organic acid salts such as lithium acetate, sodium formate, sodium acetate, potassium formate, and potassium acetate; metal nitrates such as silver nitrate and sodium nitrate; alkali metal carbonates such as lithium carbonate, sodium carbonate, and potassium carbonate; alkali metal hydrogen carbonates such as sodium hydrogen carbonate and potassium hydrogen carbonate; alkali metal hydroxides such as lithium hydroxide, sodium hydroxide, potassium hydroxide, and cesium hydroxide; and alkali metal alkoxides such as sodium methoxide, sodium ethoxide, sodium tert-butoxide, and potassium tert-butoxide.

In the reaction, the base is usually used in the proportion within a range of 1 to 100 mols based on 1 mol of the compound (XH2).

In the reaction, water is usually used in the proportion within a range of 1 mol to large excess based on 1 mol of the compound (XH2).

The reaction temperature of the reaction is usually within a range of −20 to 150° C. The reaction time of the reaction is usually within a range of 0.1 to 24 hours.

After completion of the reaction, the compound (XK1) can be isolated by performing post-treatment operations such as extraction of the reaction mixture with an organic solvent, and drying and concentration of the organic layer. The isolated compound may be further purified by operations such as distillation, chromatography, and recrystallization.

(Reference Production Process K)

The compound (XH2) can be produced by reacting the compound (XJ2) with a halogenating agent:

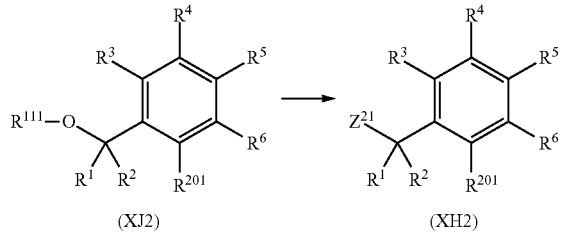

(XJ2)         (XH2)

wherein symbols are the same as defined above.

The reaction is usually performed in a solvent.

Examples of the solvent to be used in the reaction include hydrocarbons such as n-hexane, cyclohexane, toluene, and xylene; halogenated hydrocarbons such as chloroform, 1,2-dichloroethane, and chlorobenzene; ketones such as acetone, methyl ethyl ketone, and methyl isobutyl ketone; nitriles such as acetonitrile and propionitrile; organic acids such as formic acid, acetic acid, and trifluoroacetic acid; water; and mixtures thereof.

Examples of the halogenating agent to be used in the reaction include hydrochloric acid, hydrobromic acid, and hydroiodic acid.

In the reaction, the halogenating agent is usually used in the proportion of 1 mol or more based on 1 mol of the compound (XJ2).

The reaction temperature of the reaction is usually within a range of −20 to 150° C. The reaction time of the reaction is usually within a range of 0.1 to 24 hours.

After completion of the reaction, the compound (XH2) can be isolated by performing post-treatment operations such as extraction of the reaction mixture with an organic solvent, and drying and concentration of the organic layer. The isolated present compound may be further purified by operations such as distillation, chromatography, and recrystallization.

(Reference Production Process L)

The compound (XH2) can be produced by reacting the compound (XK1) with a halogenating agent:

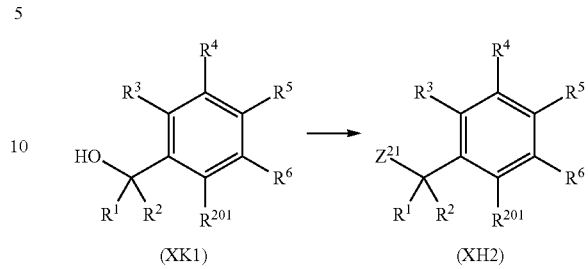

(XK1)         (XH2)

wherein symbols are the same as defined above.

The reaction is usually performed in a solvent.

Examples of the solvent to be used in the reaction include hydrocarbons such as n-hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroethane, and chlorobenzene; esters such as ethyl acetate and methyl acetate; ketones such as acetone, methyl ethyl ketone, and methyl isobutyl ketone; nitriles such as acetonitrile; organic acids such as formic acid, acetic acid, and trifluoroacetic acid; water; and mixtures thereof.

Examples of the halogenating agent to be used in the reaction include bromine, chlorine, sulfuryl chloride, hydrochloric acid, hydrobromic acid, hydroiodic acid, boron tribromide, phosphorus tribromide, trimethylsilyl chloride, trimethylsilyl bromide, trimethylsilyl iodide, thionyl chloride, thionyl bromide, phosphorus oxychloride, phosphorus trichloride, phosphorus pentachloride, thionyl chloride, phosphorus oxybromide, phosphorus pentabromide, phosphorus triiodide, oxalyl dichloride, oxalyl dibromide, acetyl chloride, carbon tetrabromide, N-bromosuccinimide, lithium chloride, sodium iodide, acetyl bromide, and the like.

In the reaction, the halogenating agent is usually used in the proportion within a range of 1 to 10 mols based on 1 mol of the compound (XK1).

In order to accelerate the reaction, additives may be added according to the halogenating agent to be used, and specific examples thereof include zinc chloride for acetyl chloride, triphenylphosphine for carbon tetrabromide, dimethyl sulfide for N-bromosuccinimide, boron trifluoride diethyl ether complex for sodium iodide, boron trifluoride diethyl ether complex for acetyl bromide, triethylamine and methanesulfonyl chloride for lithium chloride, aluminum chloride for sodium iodide, trimethylsilyl chloride for sodium iodide, and the like. Any additives are usually used in the proportion within a range of 0.01 to 5 mols based on 1 mol of the compound (XK1).

The reaction temperature of the reaction is usually within a range of −20 to 150° C. The reaction time of the reaction is usually within a range of 0.1 to 24 hours.

After completion of the reaction, the compound (XH2) can be isolated by performing post-treatment operations such as extraction of the reaction mixture with an organic solvent, and drying and concentration of the organic layer. The isolated compound may be further purified by operations such as distillation, chromatography, and recrystallization.

(Reference Production Process M)

A compound represented by formula (XM3) (hereinafter referred to as the compound (XM3)) can be produced by reacting the compound (XK1) with a compound represented by formula (XM2) (hereinafter referred to as the compound (XM2)) in the presence of a base:

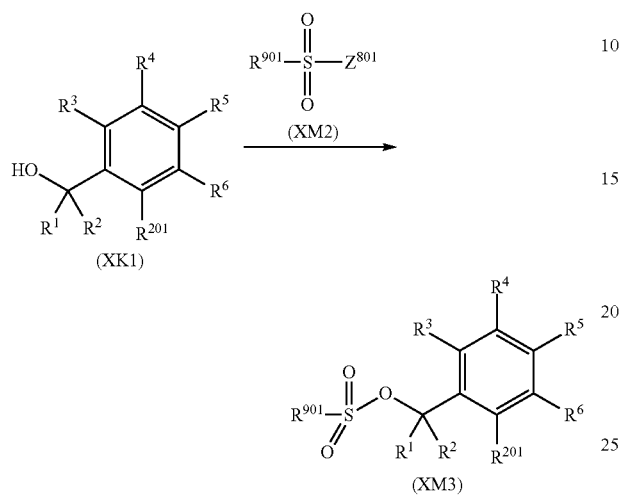

wherein $R^1$, $R^2$, $R^3$, $R^4$, $R^5$, $R^6$, and $R^{201}$ are the same as defined above, $R^{901}$ represents a C1-C6 alkyl group, a C1-C6 haloalkyl group, a C6-C16 aryl group, or a C6-C16 haloaryl group, and $Z^{801}$ represents a fluorine atom, a chlorine atom, a bromine atom, or an iodine atom.

The reaction is usually performed in a solvent.

Examples of the solvent to be used in the reaction include hydrocarbons such as n-hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroethane, and chlorobenzene; nitriles such as acetonitrile; acid amides such as N,N-dimethylformamide, 1,3-dimethyl-2-imidazolidinone, and N-methylpyrrolidone; sulfoxides such as dimethyl sulfoxide; ketones such as acetone, methyl ethyl ketone, and methyl isobutyl ketone; and mixtures thereof.

Examples of the base to be used in the reaction include organic bases such as triethylamine, pyridine, N-methylmorpholine, 4-dimethylaminopyridine, diisopropylethylamine, and diazabicycloundecene; alkali metal carbonates such as lithium carbonate, sodium carbonate, and potassium carbonate; alkali metal hydrogen carbonates such as sodium hydrogen carbonate and potassium hydrogen carbonate; alkali metal hydroxides such as sodium hydroxide and potassium hydroxide; alkali metal hydrides such as lithium hydride, sodium hydride, and potassium hydride; and alkali metal alkoxides such as sodium methoxide, sodium ethoxide, sodium tert-butoxide, and potassium tert-butoxide.

In the reaction, the compound (XM2) is usually used in the proportion within a range of 1 to 10 mols, and the base is usually used in the proportion within a range of 1 to 5 mols, based on 1 mol of the compound (XK1).

The reaction temperature of the reaction is usually within a range of −20 to 150° C. The reaction time of the reaction is usually within a range of 0.1 to 24 hours.

In the reaction, if necessary, sodium iodide, tetrabutylammonium iodide, and the like may be added, and these compounds are usually used in the proportion within a range of 0.001 to 1.2 mols based on 1 mol of the compound (XK1).

After completion of the reaction, the compound (XM3) can be isolated by performing post-treatment operations such as extraction of the reaction mixture with an organic solvent, and drying and concentration of the organic layer. The isolated compound may be further purified by operations such as distillation, chromatography, and recrystallization.

(Reference Production Process N)

A compound represented by formula (XN12) (hereinafter referred to as the compound (XN12)) can be produced by subjecting a compound represented by formula (XN11) (hereinafter referred to as the compound (XN11)) and the compound (G21) to a coupling reaction in the presence of a base and a catalyst:

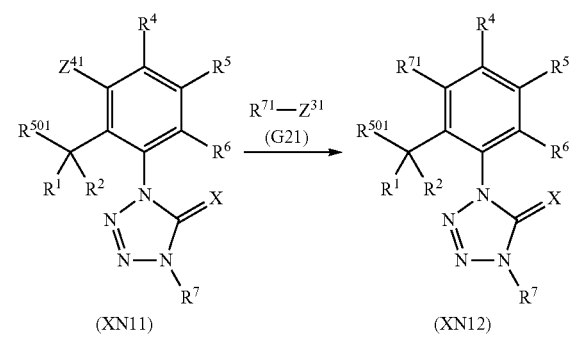

wherein $R^{501}$ represents a hydrogen atom or an $OR^{111}$ group, and $R^{111}$, $R^1$, $R^2$, $R^4$, $R^5$, $R^6$, $R^7$, $R^{71}$, X, $Z^{31}$, and $Z^{41}$ are the same as defined above.

The reaction can be carried out in accordance with the reaction mentioned in the Production Process B.

In accordance with the reaction mentioned in Production Process B, a compound represented by formula (XN22) (hereinafter referred to as the compound (XN22)) can be produced by subjecting a compound represented by formula (XN21) (hereinafter referred to as the compound (XN21)) and the compound (G22) to a coupling reaction in the presence of a base and a catalyst:

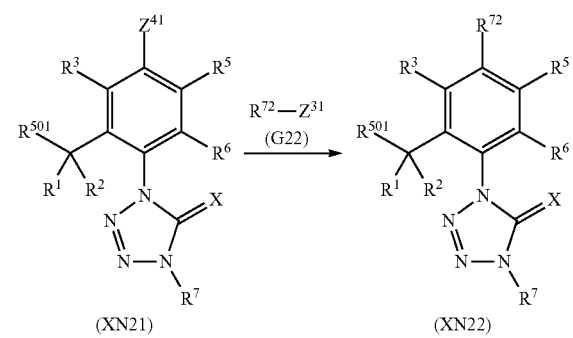

wherein symbols are the same as defined above.

In accordance with the reaction mentioned in Production Process B, a compound represented by formula (XN32) (hereinafter referred to as the compound (XN32)) can be produced by subjecting a compound represented by formula (XN31) (hereinafter referred to as the compound (XN31))

and the compound (G22) to a coupling reaction in the presence of a base and a catalyst:

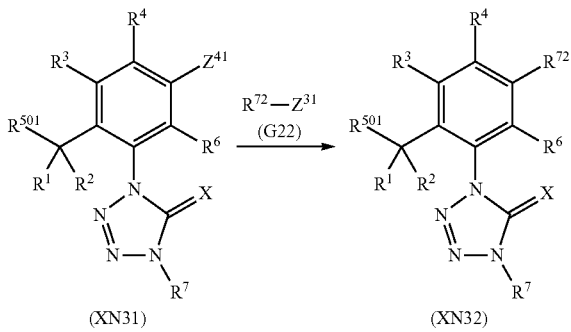

wherein symbols are the same as defined above.

In accordance with the reaction mentioned in Production Process B, a compound represented by formula (XN42) (hereinafter referred to as the compound (XN42)) can be produced by subjecting a compound represented by formula (XN41) (hereinafter referred to as the compound (XN41)) and the compound (G22) to a coupling reaction in the presence of a base and a catalyst:

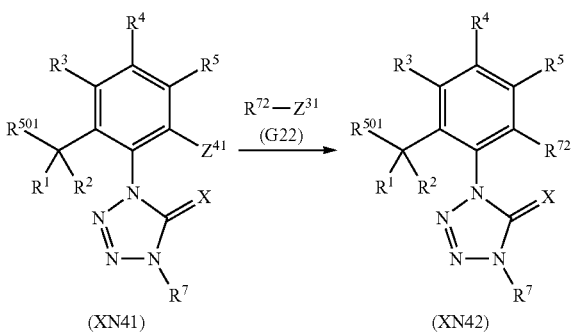

wherein symbols are the same as defined above.

In accordance with the reaction mentioned in Production Process B, it is possible to produce a compound in which two or more substituents selected from $R^3$, $R^4$, $R^5$, and $R^6$ are $R^{71}$ and/or $R^{72}$, among Group of compounds represented by formula (XN50).

It is also possible to produce the compound (XN50) by using other known coupling reactions in place of the coupling reaction of Production Process B:

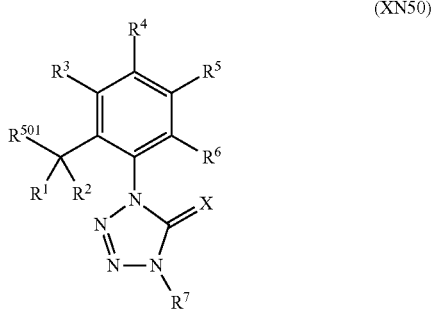

wherein symbols are the same as defined above.

(Reference Production Process O)

A compound represented by formula (XW2) (hereinafter referred to as the compound (XW2)) can be produced by reacting a compound represented by formula (XW1) (hereinafter referred to as the compound (XW1)) with a compound represented by formula (XW3) (hereinafter referred to as the compound (XW3)) in the presence of a reaction accelerator:

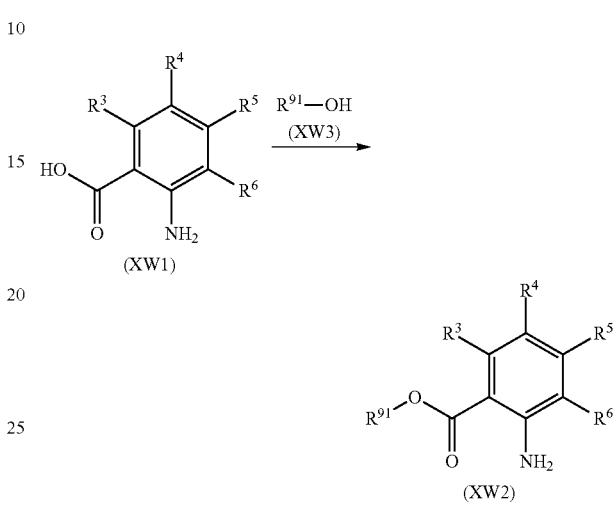

wherein symbols are the same as defined above.

The reaction is usually performed in a solvent.

Examples of the solvent to be used in the reaction include hydrocarbons such as n-hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroethane, and chlorobenzene; acid amides such as N,N-dimethylformamide, 1,3-dimethyl-2-imidazolidinone, and N-methylpyrrolidone; esters such as ethyl acetate and methyl acetate; sulfoxides such as dimethyl sulfoxide; ketones such as acetone, methyl ethyl ketone, and methyl isobutyl ketone; nitriles such as acetonitrile; and mixtures thereof, and the compound (XW3) may be used as the solvent.

Examples of the compound (XW3) usable in the reaction include methanol, ethanol, propanol, isopropanol, n-butanol, sec-butanol, t-butanol, n-pentanol, and the like.

Examples of the reaction accelerator to be used in the reaction include mineral acids such as hydrochloric acid and sulfuric acid; carbodiimides such as dicyclohexylcarbodiimide, diisopropylcarbodiimide, and N'-(3-dimethylaminopropyl)-N-ethylcarbodiimide; organic acids such as methanesulfonic acid and toluenesulfonic acid; Mitsunobu reaction reagents such as triphenylphosphine/diethyl azodicarboxylate; thionyl chloride, boron trifluoride-ethyl ether complex, and the like.

In the reaction, the reaction accelerator is usually used in the proportion within a range of 0.01 to 10 mols based on 1 mol of the compound (XW1).

In the reaction, if necessary, organic bases such as triethylamine, pyridine, N-methylmorpholine, 4-dimethylaminopyridine, diisopropylethylamine, and diazabicycloundecene; alkali metal carbonates such as lithium carbonate, sodium carbonate, and potassium carbonate; and alkali metal hydrogen carbonates such as sodium hydrogen carbonate and potassium hydrogen carbonate may be added, and these compounds are usually used in the proportion within a range of 0.001 to 5 mols based on 1 mol of the compound (XW1).

In the reaction, an excess amount of the compound (XW3) is used based on the compound (XW1).

The reaction temperature of the reaction is usually within a range of −78 to 100° C. The reaction time of the reaction is usually within a range of 0.1 to 24 hours.

After completion of the reaction, the compound (XW2) can be isolated by performing post-treatment operations such as extraction of the reaction mixture with an organic solvent, and drying and concentration of the organic layer. The isolated compound may be further purified by operations such as distillation, chromatography, and recrystallization.

(Reference Production Process P)

The compound (XW2) can be produced by reacting the compound (XW1) with a halogenating agent to obtain a compound represented by formula (XV1) (hereinafter referred to as the compound (XV1)), and then reacting the compound (XV1) with the compound (XW3):

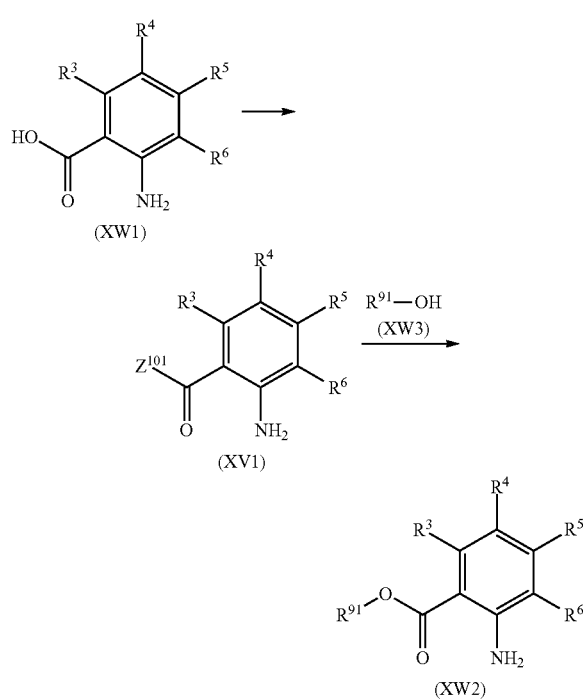

wherein symbols are the same as defined above.

The process for producing the compound (XV1) by reacting the compound (XW1) with a halogenating agent can be carried out in accordance with the reaction mentioned in Reference Production Process C.

The process for producing the compound (XW2) from the compound (XV1) will be described below.

The reaction is usually performed in a solvent.

Examples of the solvent to be used in the reaction include hydrocarbons such as n-hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroethane, and chlorobenzene; acid amides such as N,N-dimethylformamide, 1,3-dimethyl-2-imidazolidinone, and N-methylpyrrolidone; esters such as ethyl acetate and methyl acetate; sulfoxides such as dimethyl sulfoxide; ketones such as acetone, methyl ethyl ketone, and methyl isobutyl ketone; nitriles such as acetonitrile; and mixtures thereof, and the compound (XW3) may be used as the solvent.

In the reaction, an excess amount of the compound (XW3) is used based on the compound (XV1).

The reaction temperature of the reaction is usually within a range of −78 to 100° C. The reaction time of the reaction is usually within a range of 0.1 to 24 hours.

After completion of the reaction, the compound (XW2) can be isolated by performing post-treatment operations such as extraction of the reaction mixture with an organic solvent, and drying and concentration of the organic layer. The isolated compound may be further purified by operations such as distillation, chromatography, and recrystallization.

(Reference Production Process Q)

The compound (XW2) can be produced by reacting the compound (XW1) with an alkylating agent:

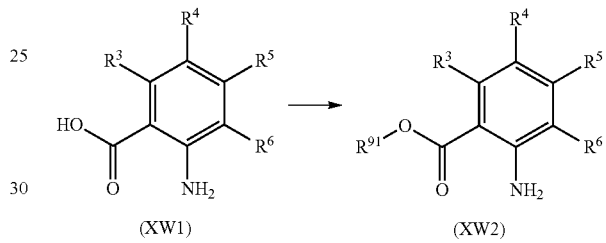

wherein symbols are the same as defined above.

The reaction is usually performed in a solvent.

Examples of the solvent to be used in the reaction include hydrocarbons such as n-hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroethane, and chlorobenzene; acid amides such as N,N-dimethylformamide, 1,3-dimethyl-2-imidazolidinone, and N-methylpyrrolidone; esters such as ethyl acetate and methyl acetate; sulfoxides such as dimethyl sulfoxide; ketones such as acetone, methyl ethyl ketone, and methyl isobutyl ketone; nitriles such as acetonitrile and propionitrile; water; and mixtures thereof.

Examples of the alkylating agent usable in the reaction include diazomethane, trimethylsilyldiazomethane, methyl bromide, ethyl bromide, n-propyl bromide, methyl iodide, ethyl iodide, n-propyl bromide; dialkyl sulfates such as dimethyl sulfate, diethyl sulfate, and di-n-propyl sulfate; and sulfonic acid esters such as methyl p-toluenesulfonate, ethyl p-toluenesulfonate, n-propyl p-toluenesulfonate, methyl methanesulfonate, ethyl methanesulfonate, and n-propyl methanesulfonate.

In the reaction, the alkylating agent is usually used in the proportion within a range of 1 to 10 mols based on 1 mol of the compound (XW1).

In the reaction, if necessary, organic bases such as triethylamine, pyridine, N-methylmorpholine, 4-dimethylaminopyridine, diisopropylethylamine, and diazabicycloundecene; alkali metal carbonates such as lithium carbonate, sodium carbonate, and potassium carbonate; alkali metal hydrogen carbonates such as sodium hydrogen carbonate and potassium hydrogen carbonate; and quaternary ammonium salts such as tetra(n-butyl)ammonium hydroxide may be added, and these compounds are usually used in the proportion within a range of 0.001 to 5 mols based on 1 mol of the compound (XW1).

The reaction temperature of the reaction is usually within a range of −78 to 100° C. The reaction time of the reaction is usually within a range of 0.1 to 24 hours.

After completion of the reaction, the compound (XW2) can be isolated by performing post-treatment operations such as extraction of the reaction mixture with an organic solvent, and drying and concentration of the organic layer. The isolated compound may be further purified by operations such as distillation, chromatography, and recrystallization.

(Reference Production Process R)

A compound represented by formula (XR2) (hereinafter referred to as the compound (XR2)) can be produced by reacting a compound represented by formula (XR1) (hereinafter referred to as the compound (XR1)) with a reducing agent:

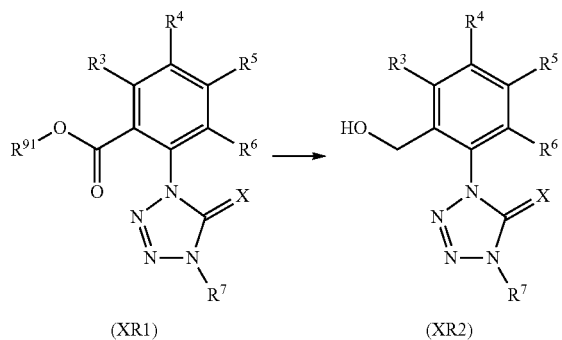

wherein symbols are the same as defined above.

The reaction is usually performed in a solvent.

Examples of the solvent to be used in the reaction include hydrocarbons such as n-hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroethane, and chlorobenzene; alcohols such as methanol, ethanol, propanol, and butanol; water; and mixtures thereof.

Examples of the reducing agent to be usable in the reaction include lithium triethylborohydride, aluminum diisobutylhydride, lithium aminoborohydride, lithium borohydride, sodium borohydride, borane, a borane dimethyl sulfide complex, and a borane tetrahydrofuran complex.

In the reaction, the reducing agent is usually used in the proportion within a range of 1 to 10 mols based on 1 mol of the compound (XR1).

The reaction temperature of the reaction is usually within a range of −78 to 100° C. The reaction time of the reaction is usually within a range of 0.1 to 24 hours.

After completion of the reaction, the compound (XR2) can be isolated by performing post-treatment operations such as extraction of the reaction mixture with an organic solvent, and drying and concentration of the organic layer. The isolated compound may be further purified by operations such as distillation, chromatography, and recrystallization.

(Reference Production Process S)

A compound represented by formula (XS2) (hereinafter referred to as the compound (XS2)) can be produced by reacting a compound represented by formula (XS1) (hereinafter referred to as the compound (XS1)) with a reducing agent:

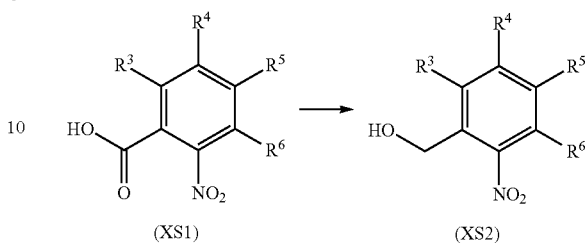

wherein symbols are the same as defined above.

The reaction is usually performed in a solvent.

Examples of the solvent to be used in the reaction include hydrocarbons such as n-hexane, cyclohexane, toluene, and xylene; ethers such as tetrahydrofuran, 1,4-dioxane, ethylene glycol dimethyl ether, methyl tert-butyl ether, and diisopropyl ether; halogenated hydrocarbons such as chloroform, 1,2-dichloroethane, and chlorobenzene; acid amides such as N,N-dimethylformamide, 1,3-dimethyl-2-imidazolidinone, and N-methylpyrrolidone; sulfoxides such as dimethyl sulfoxide; nitriles such as acetonitrile; alcohols such as methanol, ethanol, propanol, and butanol; water; and mixtures thereof.

Examples of the reducing agent to be usable in the reaction include borane, a borane tetrahydrofuran complex, and a borane dimethyl sulfide complex. It is also possible to use borane to be generated by mixing a borohydride such as sodium borohydride or potassium borohydride with an acid such as sulfuric acid, hydrochloric acid, methanesulfonic acid, or a boron trifluoride diethyl ether complex.

In the reaction, the reducing agent is usually used in the proportion within a range of 1 to 10 mols based on 1 mol of the compound (XS1).

The reaction temperature of the reaction is usually within a range from −20 to 100° C. The reaction time of the reaction is usually within a range of 0.1 to 72 hours.

After completion of the reaction, the compound (XS2) can be isolated by performing post-treatment operations such as extraction of the reaction mixture with an organic solvent, and drying and concentration of the organic layer. The isolated compound may be further purified by operations such as distillation, chromatography, and recrystallization.

(Reference Production Process T)

A compound represented by formula (XT2) (hereinafter referred to as the compound (XT2)) can be produced by reacting a compound represented by formula (XT1) (hereinafter referred to as the compound (XT1)) with the compound (AA2) in the presence of a base:

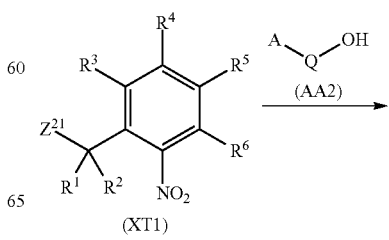

-continued

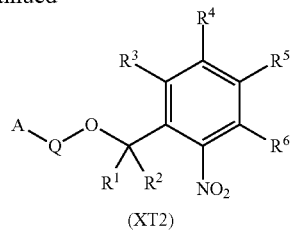

(XT2)

wherein symbols are the same as defined above.

The reaction can be carried out in accordance with the reaction mentioned in Production Process A.

(Reference Production Process U)

A compound represented by formula (XU2) (hereinafter referred to as the compound (XU2)) can be produced by subjecting a compound represented by formula (XU1) (hereinafter referred to as the compound (XU1)) and the compound (B2) to a coupling reaction in the presence of a base and a catalyst:

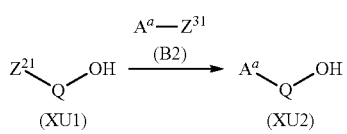

wherein symbols are the same as defined above.

The reaction can be carried out in accordance with the reaction mentioned in Production Process B.

(Reference Production Process V)

The compound (B1) can be produced by reacting a compound represented by formula (XO1) (hereinafter referred to as the compound (XO1)) with a compound represented by formula (XO2) (hereinafter referred to as the compound (XO2)) in the presence of a base:

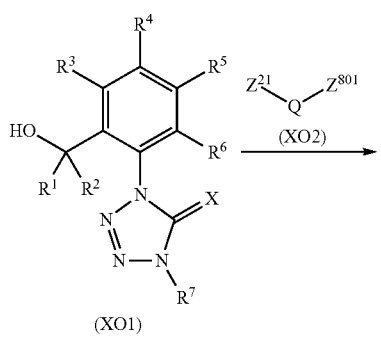

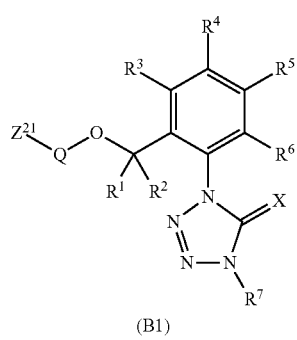

wherein symbols are the same as defined above.

The reaction can be carried out in accordance with the reaction mentioned in Production Process A.

(Reference Production Process W)

The compound (B1) can be produced by reacting the compound (AA1) with the compound (XU1) in the presence of a base:

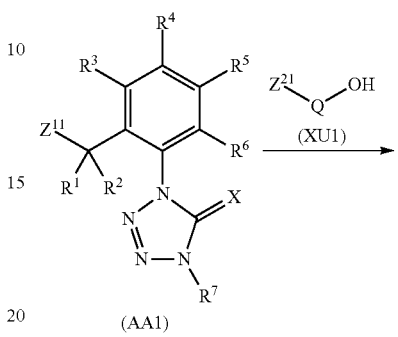

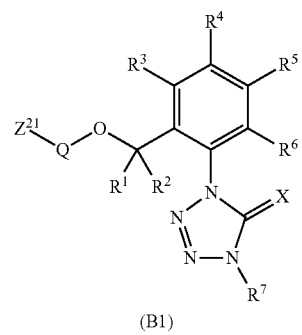

wherein symbols are the same as defined above.

The reaction can be carried out in accordance with the reaction mentioned in Production Process A.

Although a form used for the present compound may be the present compound as itself, the present compound is usually used after mixing with solid carriers, liquid carriers, surfactants, and the like, and optionally adding auxiliary agents for formulation, such as stickers, dispersers, and stabilizers to thereby formulate into wettable powders, water dispersible granules, flowables, granules, dry flowables, emulsifiable concentrates, aqueous solutions, oil solutions, smoking agents, aerosols, microcapsules, and the like. In these formulations, the present compound is usually contained within a range of 0.1 to 99%, and preferably 0.2 to 90% by weight.

Examples of the solid carriers include clays (for example, kaolin, diatomaceous earth, synthetic hydrated silicon oxide, Fubasami clay, bentonite, and acid clay), talcs or other inorganic minerals (for example, sericite, quartz powder, sulfur powder, activated charcoal, calcium carbonate, and hydrated silica) in the form of fine powders or particulates, and examples of the liquid carries include water, alcohols (for example, methanol and ethanol), ketones (for example, acetone and methyl ethyl ketone), aromatic hydrocarbons (for example, benzene, toluene, xylene, ethylbenzene, and methyl naphthalene), aliphatic hydrocarbons (for example, n-hexane, cyclohexane, and kerosene), esters (for example, ethyl acetate and butyl acetate), nitriles (for example, acetonitrile and isobutyronitrile), ethers (for example, dioxane and diisopropylether), acid amides (for example, DMF and dimethylacetamide), and halogenated hydrocarbons (for example, dichloroethane, trichloroethylene, and carbon tetrachloride).

Examples of the surfactants include alkyl sulfates, alkyl sulfonates, alkyl aryl sulfonates, alkyl aryl ethers, and polyoxyethylenated compounds thereof, polyethylene glycol ethers, polyhydric alcohol esters, and sugar alcohol derivatives.

Examples of other auxiliary agents for formulation include stickers, dispersers and stabilizers, specifically casein, gelatin, polysaccharides (for example, starch, gum arabic, cellulose derivatives, and alginic acid), lignin derivatives, bentonite, sugars, water-soluble synthetic polymers (for example, polyvinyl alcohol, polyvinylpyrrolidone, and polyacrylic acids), PAP (acidic isopropyl phosphate), BHT (2,6-di-tert-butyl-4-methylphenol), BHA (a mixture of 2-tert-butyl-4-methoxyphenol and 3-tert-butyl-4-methoxyphenol), vegetable oils, mineral oils, fatty acids or fatty acid esters thereof, and the like.

The method for applying the present compound or the present control agent is not particularly limited, as long as the applying form is a form by which the present control agent may be applied substantially, and includes, for example, an application to plants such as a foliage application; an application to area for cultivating plants such as a submerged treatment; and an application to soil such as seed disinfection.

The present compound or the present control agent can also be used as a mixture with or together with other fungicides, insecticides, acaricides, nematicides, and plant growth regulators.

Examples of these other fungicides include the followings.
(1) Azole Fungicides
such as propiconazole, prothioconazole, triadimenol, prochloraz, penconazole, tebuconazole, flusilazole, diniconazole, bromuconazole, epoxiconazole, difenoconazole, cyproconazole, metconazole, triflumizole, tetraconazole, myclobutanil, fenbuconazole, hexaconazole, fluquinconazole, triticonazole, bitertanol, imazalil, flutriafol, simeconazole, and ipconazole;
(2) Amine Fungicides
such as fenpropimorph, tridemorph, fenpropidin, and spiroxamine;
(3) Benzimidazole Fungicides
such as carbendazim, benomyl, thiabendazole, and thiophanate-methyl;
(4) Dicarboxyimide Fungicides
such as procymidone, iprodione, and vinclozolin;
(5) Anilinopyrimidine Fungicides
such as cyprodinil, pyrimethanil, and mepanipyrim;
(6) Phenylpyrrole Fungicides
such as fenpiclonil and fludioxonil;
(7) Strobilurin Fungicides
such as kresoxim-methyl, azoxystrobin, trifloxystrobin, fluoxastrobin, picoxystrobin, pyraclostrobin, dimoxystrobin, pyribencarb, metominostrobin, orysastrobin, enestrobin, pyraoxystrobin, pyrametostrobin, flufenoxystrobin, fenaminstrobin, enoxastrobin, coumoxystrobin, pyriminostrobin, triclopyricarb, and mandestrobin;
(8) Phenylamide Fungicides
such as metalaxyl, metalaxyl-M or mefenoxam, benalaxyl, and benalaxyl-M or kiralaxyl;
(9) Phenylamide Fungicides
such as dimethomorph, iprovalicarb, benthivalicarb-isopropyl, mandipropamid, and valiphenal;
(10) Carboxamide Fungicides
such as carboxin, mepronil, flutolanil, thifluzamide, furametpyr, boscalid, penthiopyrad, fluopyram, bixafen, penflufen, sedaxane, fluxapyroxad, isopyrazam, benzovindiflupyr, isofetamid, N-[2-(3,4-difluorophenyl)phenyl]-3-trifluoromethylpyrazine-2-carboxylic acid amide, and N-(1,1,3-trimethylindan-4-yl)-1-methyl-3-difluoromethylpyrazole-4-carboxylic acid amide (including a mixture of a racemic body or an enantiomer, an enantiomer of an R-form, and an enantiomer of an S-form at any ratio);
(11) Other Fungicides
such as diethofencarb; thiuram; fluazinam; mancozeb; chlorothalonil; captan; dichlofluanid; folpet; quinoxyfen; fenhexanid; fanoxadon; fenamidon; zoxamide; ethaboxam; amisulbrom; cyazofamid; metrafenone; pyriofenone; cyflufenamid; proquinazid; flusulfamide; fluopicolide; fosetyl; cymoxanil; pencycuron; tolclofos-methyl; carpropamid; diclocymet; fenoxanil; tricyclazole; pyroquilon; probenazole; isotianil; tiadinil; tebufloquin; diclomezine; kasugamycin; ferimzone; fthalide; validamycin; hydroxyisoxazole; iminoctadine acetate; isoprothiolane; oxolinic acid; oxytetracycline; streptomycin; copper oxychloride; copper hydroxide; copper hydroxide sulfate; organocopper; sulfur; ametoctradin; fenpyrazamine; oxathiapiprolin; 3-chloro-4-(2,6-difluorophenyl)-6-methyl-5-phenylpyridazine; and 3-cyano-4-(2,6-difluorophenyl)-6-methyl-5-phenylpyridazine.

Examples of these insecticides include the followings:
(1) Organophosphorus Compounds
such as acephate, Aluminium phosphide, butathiofos, cadusafos, chlorethoxyfos, chlorfenvinphos, chlorpyrifos, chlorpyrifos-methyl, cyanophos: CYAP, diazinon, DCIP (dichlorodiisopropyl ether), dichlofenthion: ECP, dichlorvos: DDVP, dimethoate, dimethylvinphos, disulfoton, EPN, ethion, ethoprophos, etrimfos, fenthion: MPP, fenitrothion: MEP, fosthiazate, formothion, Hydrogen phosphide, isofenphos, isoxathion, malathion, mesulfenfos, methidathion: DMTP, monocrotophos, naled: BRP, oxydeprofos: ESP, parathion, phosalone, phosmet: PMP, pirimiphos-methyl, pyridafenthion, quinalphos, phenthoate: PAP, profenofos, propaphos, prothiofos, pyraclorfos, salithion, sulprofos, tebupirimfos, temephos, tetrachlorvinphos, terbufos, thiometon, trichlorphon: DEP, vamidothion, phorate, and cadusafos;
(2) Carbamate Compounds
such as alanycarb, bendiocarb, benfuracarb, BPMC, carbaryl, carbofuran, carbosulfan, cloethocarb, ethiofencarb, fenobucarb, fenothiocarb, fenoxycarb, furathiocarb, isoprocarb: MIPC, metolcarb, methomyl, methiocarb, NAC, oxamyl, pirimicarb, propoxur: PHC, XMC, thiodicarb, xylylcarb, and aldicarb;
(3) Synthetic Pyrethroid Compounds
such as acrinathrin, allethrin, benfluthrin, beta-cyfluthrin, bifenthrin, cycloprothrin, cyfluthrin, cyhalothrin, cypermethrin, deltamethrin, esfenvalerate, ethofenprox, fenpropathrin, fenvalerate, flucythrinate, flufenoprox, flumethrin, fluvalinate, halfenprox, imiprothrin, permethrin, prallethrin, pyrethrins, resmethrin, sigma-cypermethrin, silafluofen, tefluthrin, tralomethrin, transfluthrin, tetramethrin, phenothrin, cyphenothrin, alpha-cypermethrin, beta-cypermethrin, theta-cypermethrin, zeta-cypermethrin, lambda-cyhalothrin, gamma-cyhalothrin, furamethrin, tau-fluvalinate, halfenprox, protrifenbute, 2,3,5,6-tetrafluoro-4-(methoxymethyl)benzyl(EZ)-(1RS,3RS;1RS,3SR)-2,2-dimethyl-3-prop-1-enylcyclopropanecarboxylate, 2,3,5,6-tetrafluoro-4-methylbenzyl(EZ)-(1RS,3RS;1RS,3SR)-2,2-dimethyl-3-prop-1-enylcyclopropanecarboxylate, and 2,3,5,6-tetrafluoro-4-(methoxymethyl)benzyl(1RS,3RS;1RS,3SR)-2,2-dimethyl-3-(2-methyl-1-propenylcyclopropanecarboxylate;

(4) Nereistoxin Compounds
such as cartap, bensultap, thiocyclam, monosultap, and bisultap;
(5) Neonicotinoid Compounds
such as imidacloprid, nitenpyram, acetamiprid, thiamethoxam, thiacloprid, dinotefuran, and clothianidin;
(6) Benzoylurea Compounds
such as chlorfluazuron, bistrifluron, diafenthiuron, diflubenzuron, fluazuron, flucycloxuron, flufenoxuron, hexaflumuron, lufenuron, novaluron, noviflumuron, teflubenzuron, triflumuron, and triazuron;
(7) Phenylpyrazole Compounds
such as acetoprole, ethiprole, fipronil, vaniliprole, pyriprole, and pyrafluprole;
(8) Bt Toxin Insecticides
such as live spores derived from and crystal toxins produced from *Bacillus thuringiesis*, and a mixture thereof;
(9) Hydrazine Compounds
such as chromafenozide, halofenozide, methoxyfenozide, and tebufenozide;
(10) Organochlorine Compounds
such as aldrin, dieldrin, dienochlor, endosulfan, and methoxychlor;
(11) Natural Insecticides
such as machine oil and nicotine-sulfate;
(12) Other Insecticides
such as avermectin-B, bromopropylate, buprofezin, chlorphenapyr, cyromazine, D-D (1,3-Dichloropropene), emamectin-benzoate, fenazaquin, flupyrazofos, hydroprene, methoprene, indoxacarb, metoxadiazone, milbemycin-A, pymetrozine, pyridalyl, pyriproxyfen, spinosad, sulfluramid, tolfenpyrad, triazamate, flubendiamide, doramectin, lepimectin, Arsenic acid, benclothiaz, Calcium cyanamide, Calcium polysulfide, chlordane, DDT, DSP, flufenerim, flonicamid, flurimfen, formetanate, metam-ammonium, metam-sodium, Methyl bromide, Potassium oleate, spiromesifen, Sulfur, metaflumizone, spirotetramat, pyrifluquinazone, spinetoram, chlorantraniliprole, cyantraniliprole, cyclaniliprole, sulfoxaflor, and flupyradifurone.

Examples of these acaricides (acaricidally active ingredients) include acequinocyl, amitraz, benzoximate, bifenaate, bromopropylate, chinomethionat, chlorobenzilate, CPCBS (chlorfenson), clofentezine, cyflumetofen, kelthane (dicofol), etoxazole, fenbutatin oxide, fenothiocarb, fenpyroximate, fluacrypyrim, fluproxyfen, hexythiazox, propargite, BPPS, polynactins, pyridaben, Pyrimidifen, tebufenpyrad, tetradifon, spirodiclofen, spiromesifen, spirotetramat, amidoflumet, and cyenopyrafen.

Examples of these nematicides (nematicidally active compounds) include DCIP, fosthiazate, levamisol hydrochloride, methyisothiocyanate, morantel tartarate, imicyafos, and fluensulfone.

Examples of these plant growth regulators include the followings:
ethephon, chlormequat-chloride, mepiquat-chloride, Gibberellin A typified by Gibberellin A3, abscisic acid, Kinetin, benzyladenine, 1,3-diphenylurea, forchlorfenuron, thidiazuron, 4-oxo-4-(2-phenylethylaminobutyric acid, methyl 5-(trifluoromethylbenzo[b]thiophene-2-carboxylate, and 5-(trifluoromethylbenzo[b]thiophene-2-carboxylic acid.

The method for applying the present compound is not particularly limited, as long as the applying form is a form by which the present compound may be applied substantially, and includes, for example, an application to plants such as a foliage application; an application to area for cultivating plants such as a submerged treatment; and an application to soil such as seed disinfection.

The application dose of the present compound varies depending on weather conditions, dosage forms, timing of application, methods of application, areas to be applied, target diseases, target crops, and the like, and is usually within a range of 1 to 500 g, and preferably 2 to 200 g, per 1,000 $m^2$ of the area to be applied. The emulsifiable concentrate, the wettable powder, or the suspension concentrate is usually applied by diluting with water. In this case, the concentration of the present compound after dilution is usually within a range of 0.0005 to 2% by weight, and preferably 0.005 to 1% by weight. The dust formulation or the granular formulation is usually applied, as itself without dilution. In the application to seeds, the amount of the present compound is usually within a range of 0.001 to 100 g, and preferably 0.01 to 50 g, per 1 kg of the seeds.

The present compound may be used as a mixture with various oils or surfactants such as mineral oils or vegetable oils. Specific examples of oils or surfactants, which can be used as a mixture with various oils or surfactants, include Nimbus (registered trademark), Assist (registered trademark), Aureo (registered trademark), Iharol (registered trademark), Silwet L-77 (registered trademark), BreakThru (registered trademark), Sundancell (registered trademark), Induce (registered trademark), Penetrator (registered trademark), AgriDex (registered trademark), Lutensol A8 (registered trademark), NP-7 (registered trademark), Triton (registered trademark), Nufilm (registered trademark), Emulgator NP7 (registered trademark), Emulad (registered trademark), TRITON X 45 (registered trademark), AGRAL 90 (registered trademark), AGROTIN (registered trademark), ARPON (registered trademark), EnSpray N (registered trademark), BANOLE (registered trademark), and the like.

In the present invention, examples of the place where the pests live include paddy fields, fields, tea gardens, orchards, non-agricultural lands, houses, nursery trays, nursery boxes, nursery soils, and nursery bed.

Also, in another embodiment, for example, the present compound can be administered to the inside (inside of the body) or the outside (body surface) of the below-mentioned vertebrate to thereby exterminate systemically or unsystematically the living things or parasites which are parasitic on the vertebrate. Examples of a method of the internal administration include oral administration, anal administration, transplantation, administration via injection subcutaneously, intramuscularly or intravenously. Examples of a method of the external administration include transdermal administration. Also, the present compound can be ingested to a livestock animal so as to exterminate sanitary insects which occur in the excrement of the animal.

When the present compound is applied to the animals such as the livestock animal and pets on which pests are parasitic, the dose varies depending on the administration method etc., and it is desirable in general to administer the present compound so that a dose of the active ingredient (the present compound or salts thereof) is generally within a range of 0.1 mg to 2,000 mg, and preferably 0.5 mg to 1,000 mg, per 1 kg of body weight of the animal.

The present compound can be used as an agent for controlling plant diseases in agricultural lands such as fields, paddy fields, lawns, and orchards. The present compound can control diseases occurred in the agricultural lands for cultivating the following "plants".

Crops: corn, rice, wheat, barley, rye, oat, sorghum, cotton, soybean, peanut, buckwheat, beet, rapeseed, sunflower, sugar cane, tobacco, and the like; Vegetables: solanaceous vegetables (for example, eggplant, tomato, pimento, pepper, and potato), cucurbitaceous vegetables (for example, cucumber, pumpkin, zucchini, water melon, and melon), cruciferous vegetables (for example, Japanese radish, white turnip, horseradish, kohlrabi, Chinese cabbage, cabbage, leaf mustard, broccoli, and cauliflower), asteraceous vegetables (for example, burdock, crown daisy, artichoke, and lettuce), liliaceous vegetables (for example, green onion, onion, garlic, and asparagus), apiaceous vegetables (for example, carrot, parsley, celery, and parsnip), chenopodiaceous vegetables (for example, spinach and Swiss chard), lamiaceous vegetables (for example, *Perilla frutescens*, mint, and basil), strawberry, sweet potato, *Dioscorea japonica, colocasia*, and the like; Flowers; Ornamental foliage plants;

Fruits: pomaceous fruits (for example, apple, pear, Japanese pear, Chinese quince, and quince), stone fruits (for example, peach, plum, nectarine, *Prunus mume*, cherry fruit, apricot, and prune), citrus fruits (for example, Citrus unshiu, orange, lemon, lime, and grapefruit), nuts (for example, chestnut, walnuts, hazelnuts, almond, pistachio, cashew nuts, and macadamia nuts), berry fruits (for example, blueberry, cranberry, blackberry, and raspberry), grape, kaki persimmon, olive, Japanese medlar, banana, coffee, date palm, coconuts, and the like;

Trees other than fruit trees: tea, mulberry, flowering plant, roadside trees (for example, ash, birch, dogwood, *Eucalyptus, Ginkgo biloba*, lilac, maple, *Quercus*, poplar, Judas tree, *Liquidambar formosana*, plane tree, *zelkova*, Japanese arborvitae, fir tree, hemlock, juniper, *Pinus, Picea*, and *Taxus cuspidate*); and the like.

The above-mentioned "plants" include genetically modified crops.

The pests which can be controlled by the present compound include plant pathogens such as filamentous fungus, as well as harmful arthropods such as harmful insects and harmful mites, and nemathelminth such as nematodes, and specifically include the following examples, but are not limited thereto.

Rice diseases: blast (*Magnaporthe grisea*), brown spot (*Cochliobolus miyabeanus*), sheath blight (*Rhizoctonia solani*), bakanae disease (*Gibberella fujikuroi*), and downy mildew (*Sclerophthora macrospora*); Wheat diseases: powdery mildew (*Erysiphe graminis*), fusarium blight (*Fusarium gaminearum, F. avenaceum, F. culmorum, Microdochium nivale*), rust (*Puccinia striiformis, P. graminis, P. recondita*), snow mould (*Micronectriella nivale*), typhulasnow blight (*Typhula* sp.), loose smut (*Ustilago tritici*), stinking smut (*Tilletia caries, T. controversa*), eyespot (*Pseudocercosporella herpotrichoides*), leaf blotch (*Septoria tritici*), glume blotch (*Stagonospora nodorum*), yellow spot (*Pyrenophora tritici*-repentis), seeding blight caused by *rhizoctonia* fungus (*Rhizoctonia solani*), and take-all disease (*Gaeumannomyces graminis*); Barly diseases: powdery mildew (*Erysiphe graminis*), fusarium blight (*Fusarium gaminearum, F. avenaceum, F. culmorum, Microdochium nivale*), rust (*Puccinia striiformis, P. graminis, P. hordei*), loose smut (*Ustilago nuda*), scald (*Rhynchosporium secalis*), net blotch (*Pyrenophora teres*), spot blotch (*Cochliobolus sativus*), leaf stripe (*Pyrenophora graminea*), *Ramularia* disease (*Ramularia collo-cygni*), and seeding blight caused by *rhizoctonia* fungus (*Rhizoctonia solani*); Corn diseases: rust (*Puccinia sorghi*), southern rust (*Puccinia polysora*), northern leaf blight (*Setosphaeria turcica*), southern leaf blight (*Cochliobolus heterostrophus*), anthracnose (*Colletotrichum graminicola*), gray leaf spot (*Cercospora zeae-maydis*), eyespot (*Kabatiella zeae*), and *phaeosphaeria* leaf spot (*Phaeosphaeria maydis*);

Cotton diseases: anthracnose (*Colletotrichum gossypii*), grey mildew (*Ramuraria areola*), and *alternaria* leaf spot (*Alternaria macrospora, A. gossypii*); Coffee diseases: rust (*Hemileia vastatrix*); Rape seed diseases: *sclerotinia* rot (*Sclerotinia sclerotiorum*), gray leaf spot (*Alternaria brassicae*), and root rot (*Phoma lingam*); Citrus diseases: melanose (*Diaporthe citri*), scab (*Elsinoe fawcetti*), and green mold (*Penicillium digitatum, P. italicum*); Apple diseases: blossom blight (*Monilinia mali*), canker (*Valsa ceratosperma*), powdery mildew (*Podosphaera leucotricha*), alternaria leaf spot (*Alternaria alternata* apple pathotype), scab (*Venturia inaequalis*), and bitter rot (*Glomerella cingulata, Colletotrichum acutatum*); Pear diseases: scab (*Venturia nashicola, V. pirina*), black spot (*Alternaria alternata* Japanese pear pathotype), and rust (*Gymnosporangium haraeanum*); Peach diseases: brown rot (*Monilinia fructicola*), scab (*Cladosporium carpophilum*), and *Phomopsis* rot (*Phomopsis* sp.); Grapes diseases: anthracnose (*Elsinoe ampelina*), ripe rot (*Glomerella cingulata, Colletotrichum acutatum*), powdery mildew (*Uncinula necator*), rust (*Phakopsora ampelopsidis*), black rot (*Guignardia bidwellii*), and downy mildew (*Plasmopara viticola*); Japanese persimmon diseases: anthracnose (*Gloeosporium kaki*) and leaf spot (*Cercospora kaki, Mycosphaerella nawae*); Diseases of gourd family: anthracnose (*Colletotrichum lagenarium*), powdery mildew (*Sphaerotheca fuliginea*), gummy stem blight (*Didymella bryoniae*), *Corynespora* leaf spot (*Corynespora cassiicola*), *fusarium* wilt (*Fusarium oxysporum*), downy mildew (*Pseudoperonospora cubensis*), *phytophthora* rot (*Phytophthora* sp.), and damping-off (*Pythium* sp.); Tomato diseases: early blight (*Alternaria solani*), leaf mold (*Cladosporium fulvum*), leaf mold (*Pseudocercospora fuligena*), and late blight (*Phytophthora infestans*); Eggplant diseases: brown spot (*Phomopsis vexans*) and powdery mildew (*Erysiphe cichoracearum*); Cruciferous vegetables diseases: alternaria leaf spot (*Alternaria japonica*), white spot (*Cercosporella brassicae*), clubroot (*Plasmodiophora brassicae*), and downy mildew (*Peronospora parasitica*); Welsh onion diseases: rust (*Puccinia allii*); Soybean diseases: purple stain (*Cercospora kikuchii*), sphaceloma scad (*Elsinoe glycines*), pod and stem blight (*Diaporthe phaseolorum* var. *sojae*), rust (*phakopsora pachyrhizi*), target spot (*Corynespora cassiicola*), anthracnose (*Colletotrithum glycines, C. truncatum*), Rhizoctonia rot (*Rhizoctonia solani*), septoria brown spot (*Septoria glycines*), and frog eye leaf spot (*Cercospora sojina*); Kindney bean diseases: anthracnose (*Colletotrichum lindemuthianum*); Peanut diseases: early leaf spot (*Cercospora personata*), brown leaf spot (*Cercospora arachidicola*), and southern blight (*Sclerotium rolfsii*); Garden pea diseases: powdery mildew (*Erysiphe pisi*); Potato diseases: early blight (*Alternaria solani*), late blight (*Phytophthora infestans*), and verticillium wilt (*verticillium albo-atrum, V. dahliae, V. nigrescens*); Strawberry diseases: powdery mildew (*Sphaerotheca humuli*); Tea diseases: net blister blight (*Exobasidium reticulatum*), white scab (*Elsinoe leucospila*), gray blight (*Pestalotiopsis* sp.), and anthracnose (*Colletotrichum theae-sinensis*); Tabacco diseases: brown spot (*Alternaria longipes*), powdery mildew (*Erysiphe cichoracearum*), anthracnose (*Colletotrichum tabacum*), downy mildew (*Peronospora tabacina*), and black shank (*Phytophthora nicotianae*); Sugar beet diseases: *cercospora* leaf spot (*Cercospora beticola*), leaf blight (*Thanatephorus cucumeris*), root rot (*Thanatephorus cucumeris*), and *aphanomyces* root rot (*Aphanomyces cochlioides*); Rose diseases: black spot (*Diplocarpon rosae*) and powdery mildew (*Sphaerotheca pannosa*); Chrysanthemum diseases: leaf blight (*Septoria chrysanthemi-indici*) and white rust (*Puccinia horiana*); Onion diseases: botrytis leaf blight (*Botrytis cinerea, B. byssoidea, B. squamosa*), gray-mold neck rot (*Botrytis allii*), and small sclerotial rot (*Botrytis squamosa*); various crops diseases: gray mold (*Botrytis cinerea*) and sclerotinia rot (*Sclerotinia sclerotiorum*); Japanese radish diseases: alternaria leaf spot (*Alternaria brassicicola*); Turfgrass diseases: dollar spot (*Sclerotinia homoeocarpa*) and brown patch and large patch (*Rhizoctonia solani*); and Banana diseases: Sigatoka disease (*Mycosphaerella fijiensis, Mycosphaerella musicola*).

Hemiptera: planthoppers (Delphacidae) such as small brown planthopper (*Laodelphax striatellus*), brown rice planthopper (*Nilaparvata lugens*), and white-backed rice planthopper (*Sogatella furcifera*); leafhoppers (Deltocephalidae) such as green rice leafhopper (*Nephotettix cincticeps*) and green rice leafhopper (*Nephotettix virescens*); aphids (Aphididae) such as cotton aphid (*Aphis gossypii*), green peach aphid (*Myzus persicae*), cabbage aphid (*Brevicoryne brassicae*), potato aphid (*Macrosiphum euphorbiae*), foxglove aphid (*Aulacorthum solani*), oat bird-cherry aphid (*Rhopalosiphum padi*), and tropical citrus aphid (*Toxoptera citricidus*); stink bugs (Pentatomidae) such as green stink bug (*Nezara antennata*), bean bug (*Riptortus clavetus*), rice bug (*Leptocorisa chinensis*), white spotted spined bug (*Eysarcoris parvus*), stink bug (*Halyomorpha mista*), and tarnished plant bug (*Lygus lineolaris*); whiteflies (Aleyrodidae) such as greenhouse whitefly (*Trialeurodes vaporariorum*) and silverleaf whitefly (*Bemisia argentifolii*); scales (Coccidae) such as Calfornia red scale (*Aonidiella aurantii*), San Jose scale (*Comstockaspis perniciosa*), citrus north scale (*Unaspis citri*), red wax scale (*Ceroplastes rubens*), and cottonycushion scale (*Icerya purchasi*); lace bugs (Tingidae); jumping plant lice (Homoptera, Psylloidea).

Lepidoptera: pyralid moths (Pyralidae) such as rice stem borer (*Chilo suppressalis*), yellow rice borer (*Tryporyza incertulas*), rice leafroller (*Cnaphalocrocis medinalis*), cotton leafroller (*Notarcha derogata*), Indian meal moth (*Plodia interpunctella*), oriental corn borer (*Ostrinia furnacalis*), cabbage webworm (*Hellula undalis*), and bluegrass webworm (*Pediasia teterrellus*); owlet moths (Noctuidae) such as common cutworm (*Spodoptera litura*), beet armyworm (*Spodoptera exigua*), armvworm (*Pseudaletia separata*), cabbage armyworm (*Mamestra brassicae*), black cutworm (*Agrotis ipsilon*), beet semi-looper (*Plusia nigrisigna*), *Thoricoplusia* spp., *Heliothis* spp., and *Helicoverpa* spp.; white butterflies (Pieridae) such as common white (*Pieris rapae*); tortricid moths (Tortricidae) such as *Adoxophyes* spp., oriental fruit moth (*Grapholita molesta*), soybean pod borer (*Leguminivora glycinivorella*), azuki bean podworm (*Matsumuraeses azukivora*), summer fruit tortrix (*Adoxophyes orana fasciata*), smaller tea tortrix (*Adoxophyes* sp.), oriental tea tortrix (*Homona magnanima*), apple tortrix (*Archips fuscocupreanus*), and codling moth (*Cydia pomonella*); leafblotch miners (Gracillariidae) such as tea leafroller (*Caloptilia theivora*), and apple leafminer (*Phyllonorycter ringoneella*); leaf miners (Gracillariidae) such as tea leafroller (*Caloptilia theivora*) and apple leafminer (*Phyllonorycter ringoneella*); codling moths (Carposimidae) such as peach fruit moth (*Carposina niponensis*); lyonetiid moths (Lyonetiidae) such as *Lyonetia* spp.; tussock moths (Lymantriidae) such as *Lymantria* spp. and *Euproctis* spp.; yponomeutid moths (Yponomeutidae) such as diamondback (*Plutella xylostella*); gelechid moths (Gelechiidae) such as pink bollworm (*Pectinophora gossypiella*) and potato tubeworm (*Phthorimaea operculella*); tiger moths and allies (Arctiidae) such as fall webworm (*Hyphantria cunea*); and tineid moths (Tineidae) such as casemaking clothes moth (*Tinea translucens*), and webbing clothes moth (*Tineola bisselliella*).

Thysanoptera: yellow citrus thrips (*Frankliniella occidentalis*), melon thrips (*Thrips palmi*), yellow tea thrips (*Scirtothrips dorsalis*), onion thrips (*Thrips tabaci*), flower thrips (*Frankliniella intonsa*), and tobacco thrips (*Frankliniella fusca*).

Diptera: houseflies (*Musca domestica*), common mosquito (*Culex pipiens pallens*), horsefly (*Tabanus trigonus*), onion maggot (*Hylemya anitqua*), seedcorn maggot (*Hylemya platura*), *Anopheles sinensis*, rice leafminer (*Agromyza oryzae*), rice leafminer (*Hydrellia griseola*), rice stem maggot (*Chlorops oryzae*), melon fly (*Dacus cucurbitae*), Meditterranean fruit fly (*Ceratitis capitata*), and legume leafminer (*Liriomyza trifolii*).

Coleoptera: twenty-eight-spotted ladybirds (*Epilachna vigintioctopunctata*), cucurbit leaf beetle (*Aulacophora femoralis*), yellow striped flea beetle (*Phyllotreta striolata*), rice leaf beetle (*Oulema oryzae*), rice curculio (*Echinocnemus squameus*), rice water weevil (*Lissorhoptrus oryzophilus*), boll weevil (*Anthonomus grandis*), azuki bean weevil (*Callosobruchus chinensis*), hunting billbug (*Sphenophorus venatus*), Japanese beetle (*Popillia japonica*), cupreous chafer (*Anomala cuprea*), corn root worms (*Diabrotica* spp.), Colorado beetle (*Leptinotarsa decemlineata*), click beetles (*Agriotes* spp.), cigarette beetle (*Lasioderma serricorne*), varied carper beetle (*Anthrenus verbasci*), red flour beetle (*Tribolium castaneum*), powder post beetle (*Lyctus brunneus*), white-spotted longicorn beetle (*Anoplophora malasiaca*), and pine shoot beetle (*Tomicus piniperda*).

Orthoptera: asiatic locusts (*Locusta migratoria*), African mole cricket (*Gryllotalpa africana*), rice grasshopper (*Oxya yezoensis*), and rice grasshopper (*Oxya japonica*).

Hymenoptera: cabbage sawflies (*Athalia rosae*), leaf-cutting ant (*Acromyrmex* spp.), and fire ant (*Solenopsis* spp.).

Nematodes: white-tip nematode (*Aphelenchoides besseyi*), strawberry bud nematode (*Nothotylenchus acris*), soybean cyst nematode (*Heterodera glycines*), southern root-knot nematode (*Meloidogyne incognita*), cobb's root-lesion nematode (*Pratylenchus penetrans*), and false root-knot nematode (*Nacobbus aberrans*).

Blattariae: German cockroach (*Blattella germanica*), smoky-brown cockroach (*Periplaneta fuliginosa*), American cockroach (*Periplaneta America*), brown cockroach (*Periplaneta brunnea*), and oriental cockroach (*Blatta orientalis*).

Acarina: Tetranychidae (for example, two-spotted spider mite (*Tetranychus urticae*), citrus red mite (*Panonychus citri*), and *Oligonychus* spp.); Eriophyidae (for example, pink citrus rust mite (*Aculops pelekassi*)); Tarsonemidae (for example, broad mite (*Polyphagotarsonemus latus*));

Tenuipalpidae; Tuckerellidae; Tuckerellidae Acaridae (for example, common grain mite (*Tyrophagus putrescentiae*)); Pyroglyphidae (for example, Americal house dust mite (*Dermatophagoides farinae*) and house dust mite (*Dermatophagoides ptrenyssnus*)); Cheyletidae (for example, cheyletid mite (*Cheyletus eruditus*), *Cheyletus malaccensis*, and *Cheyletus moorei*; and Dermanyssidae.

The formulation comprising the present compound can be used in the field relating to a treatment of livestock diseases or livestock industry, and can exterminate the living things or parasites which are parasitic on the inside and/or the outside of vertebrates such as human being, cow, sheep, pig, poultry, dog, cat, and fish, so as to maintain public health. Examples of the pests include ticks (*Ixodes* spp.) (for example, *Ixodes scapularis*), *Boophilus* spp. (for example, cattle tick (*Boophilus microplus*)), *Amblyomma* spp., *Hyalomma* spp., *Rhipicephalus* spp. (for example, kennel tick (*Rhipicephalus sanguineus*)), *Haemaphysalis* spp. (for example, *Haemaphysalis longicornis*), *dermacentor* spp., *Ornithodoros* spp. (for example, *Ornithodoros moubata*), red mite (*Dermahyssus gallinae*), ghost ant (*Ornithonyssus sylviarum*), *Sarcoptes* spp. (for example, *Sarcoptes scabiei*), *Psoroptes* spp., *Chorioptes* spp., *Demodex* spp., *Eutrombicula* spp., *Aedes* spp. (for example, Asian tiger mosquito (*Aedes albopictus*)), *Anopheles* spp., *Culex* spp., *Culicodes* spp., *Musca* spp., *Hypoderma* spp., *Gasterophilus* spp., *Haematobia* spp., *Tabanus* spp., *Simulium* spp., *Triatoma* spp., lice (*Phthiraptera*) (for example, *Damalinia* spp.), *Linognathus* spp., *Haematopinus* spp., *Ctenocephalides* spp. (for example, cat flea (*Ctenocephalides felis*)) *Xenosylla* spp., Pharaoh's ant (*monomorium pharaonis*) and nematodes (for example, hairworm (for example, *Nippostrongylus brasiliensis, Trichostrongylus axei, Trichostrongylus colubriformis*), *Trichinella* spp. (for example, *Trichinella spiriralis*), barber pole worm (*Haemonchus contortus*), *Nematodirus* spp. (for example, *Nematodirus battus*), *Ostertagia circumcincta, Cooperia* spp., *Hymenolepis nana*, and the like.

EXAMPLES

The present invention will be described in more detail below by way of Production Examples, Formulation Examples, and Test Examples, but the present invention is not limited to these Examples.

First, Production Examples will be described.

Production Example 1

A mixture of 0.39 g of 25A mentioned in Reference Production Example 25, 0.24 g of phenylboronic acid, 0.28 g of tripotassium phosphate, 0.40 ml of water, 0.02 g of [1,1'-bis(diphenylphosphino)ferrocene]palladium(II) dichloride dichloromethane adduct, and 4 ml of dimethoxyethane was stirred with heating under reflux for 4 hours. After cooling, water was poured into the reaction solution and the mixture was extracted with ethyl acetate. The organic layer was washed with water and a saturated saline solution, dried over anhydrous magnesium sulfate, and then concentrated under reduced pressure. The residue thus obtained was subjected to silica gel column chromatography to obtain 0.21 g of 1-[2-(5-phenyl-6-methyl-pyridin-2-yloxymethyl)-3-methylphenyl]-4-methyl-1,4-dihydrotetrazol-5-one (hereinafter referred to as the present compound 1).

Present Compound 1

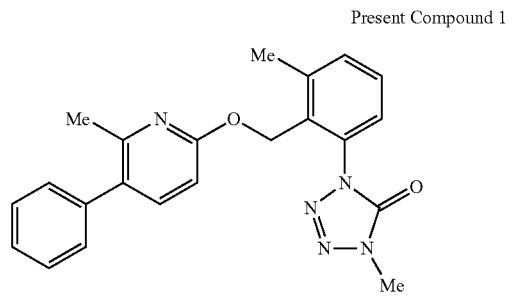 [SMILES: Cc1cccc(-n2nnn(C)c2=O)c1COc1ccc(-c2ccccc2)c(C)n1]

$^1$H-NMR (CDCl$_3$) δ:7.42-7.31 (6H, m), 7.28-7.24 (3H, m), 6.53 (1H, d, J=8.5 Hz), 5.43 (2H, s), 3.69 (3H, s), 2.59 (3H, s), 2.36 (3H, s).

According to the same reaction as in Production Example 1, the present compounds 2 to 13, and 27 to 29 were synthesized.

The structural formulas and $^1$H-NMR data thereof are shown below.

Present Compound 2

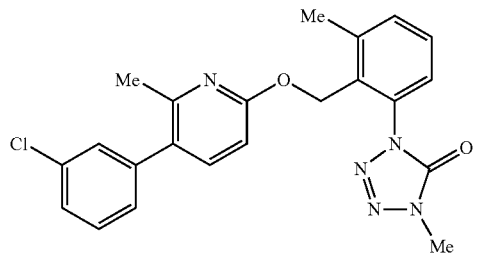

Present Compound 3

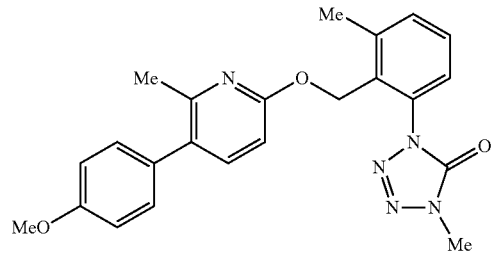

Present Compound 4

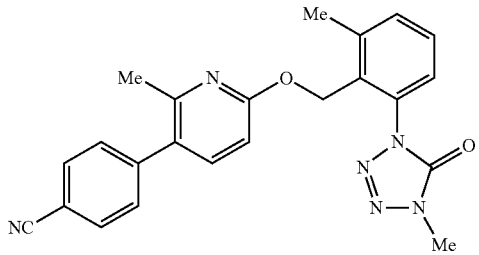

Present Compound 5

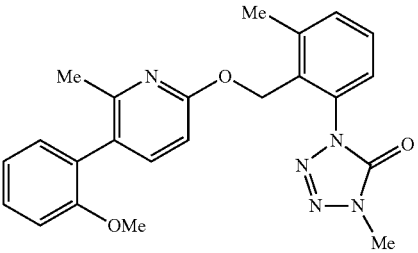

Present Compound 6

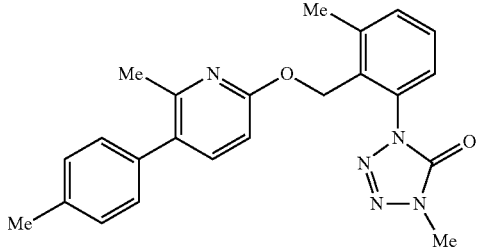

Present Compound 7
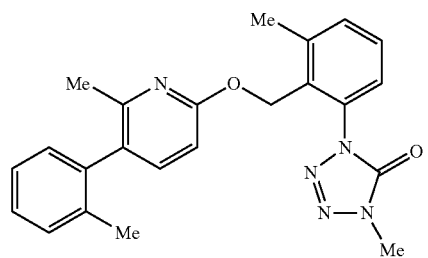
Present Compound 8
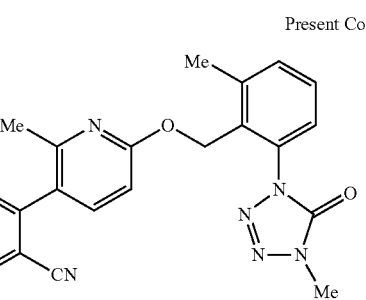
Present Compound 9
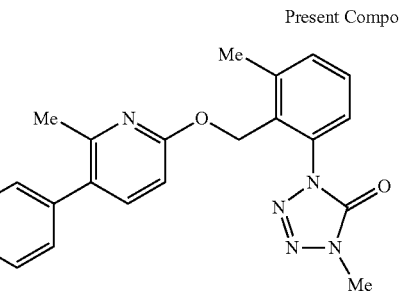
Present Compound 10
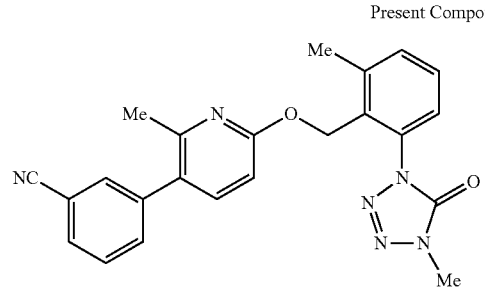
Present Compound 11
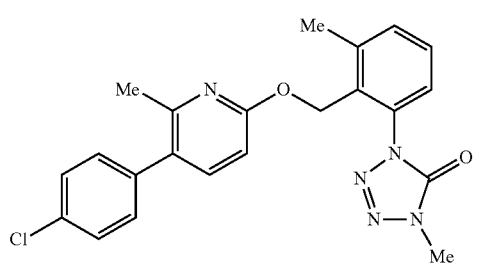
Present Compound 12
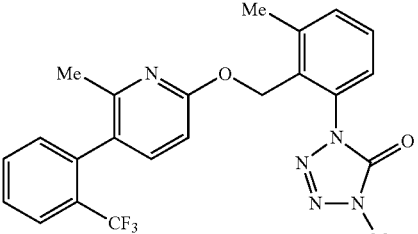
Present Compound 13
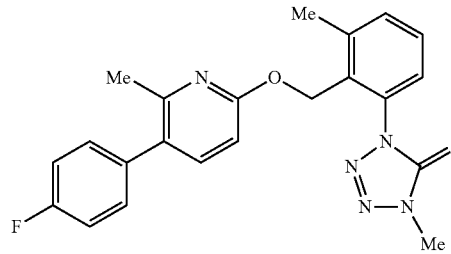
Present Compound 27
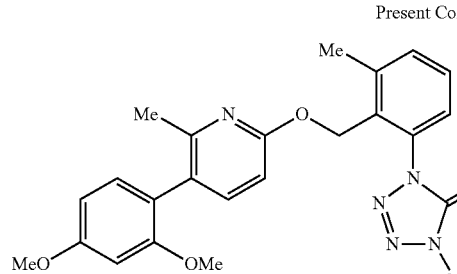
Present Compound 28
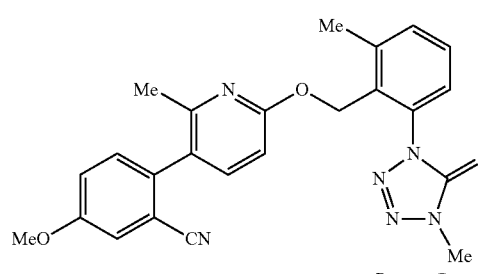
Present Compound 29
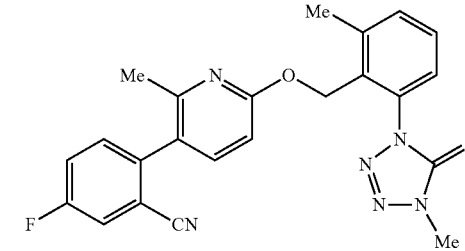
Present Compound 2
$^1$H-NMR (CDCl$_3$) δ:7.39-7.30 (5H, m), 7.27-7.23 (2H, m), 7.16-7.13 (1H, m), 6.53 (1H, d, J=8.5 Hz), 5.43 (2H, s), 3.69 (3H, s), 2.58 (3H, s), 2.35 (3H, s).
Present Compound 3
$^1$H-NMR (CDCl$_3$) δ:7.39-7.31 (4H, m), 7.26-7.23 (1H, m), 7.09 (1H, dd, J=7.5, 1.8 Hz), 6.99 (1H, td, J=7.4, 1.0

Hz), 6.95 (1H, dd, J=8.3, 0.8 Hz), 6.52 (1H, dd, J=8.4, 0.5 Hz), 5.41 (2H, s), 3.77 (3H, s), 3.67 (3H, s), 2.58 (3H, s), 2.22 (3H, s).

Present Compound 4

¹H-NMR (CDCl₃) δ:7.70 (2H, dd, J=7.0, 1.7 Hz), 7.39-7.34 (5H, m), 7.27-7.24 (1H, m), 6.56 (1H, dd, J=8.5, 0.5 Hz), 5.44 (2H, s), 3.70 (3H, s), 2.58 (3H, s), 2.34 (3H, s).

Present Compound 5

¹H-NMR (CDCl₃) δ:7.38 (2H, d, J=5.3 Hz), 7.36-7.32 (2H, m), 7.26-7.24 (1H, m), 7.10 (1H, dd, J=7.6, 1.8 Hz), 7.02-6.94 (2H, m), 6.52 (1H, d, J=8.2 Hz), 5.42 (2H, s), 3.77 (3H, s), 3.68 (3H, s), 2.58 (3H, s), 2.23 (3H, s).

Present Compound 6

¹H-NMR (CDCl₃) δ:7.40-7.35 (3H, m), 7.26-7.20 (3H, m), 7.17-7.14 (2H, m), 6.52 (1H, dd, J=8.4, 0.6 Hz), 5.43 (2H, s), 3.68 (3H, s), 2.58 (3H, s), 2.39 (3H, s), 2.36 (3H, s).

Present Compound 7

¹H-NMR (CDCl₃) δ:7.39 (2H, d, J=5.3 Hz), 7.28-7.19 (5H, m), 7.06 (1H, d, J=7.1 Hz), 6.52 (1H, dd, J=8.4, 0.6 Hz), 5.47-5.39 (2H, m), 3.69 (3H, s), 2.59 (3H, s), 2.15 (3H, s), 2.06 (3H, s).

Present Compound 8

¹H-NMR (CDCl₃) δ:7.75 (1H, d, J=7.6 Hz), 7.62 (1H, t, J=7.7 Hz), 7.45 (1H, t, J=7.7 Hz), 7.41-7.35 (3H, m), 7.33 (1H, d, J=7.8 Hz), 7.28-7.23 (1H, m), 6.58 (1H, d, J=8.2 Hz), 5.42 (2H, s), 3.69 (3H, s), 2.58 (3H, s), 2.28 (3H, s).

Present Compound 9

¹H-NMR (CDCl₃) δ:7.39-7.37 (3H, m), 7.31 (1H, t, J=7.9 Hz), 7.26-7.23 (1H, m), 6.90-6.83 (2H, m), 6.81-6.78 (1H, m), 6.52 (1H, dd, J=8.2, 0.7 Hz), 5.43 (2H, s), 3.83 (3H, s), 3.68 (3H, s), 2.58 (3H, s), 2.36 (3H, s).

Present Compound 10

¹H-NMR (CDCl₃) δ:7.65-7.61 (1H, m), 7.57-7.55 (1H, m), 7.54-7.49 (2H, m), 7.40-7.37 (2H, m), 7.34 (1H, d, J=8.2 Hz), 7.26-7.23 (1H, m), 6.55 (1H, d, J=8.5 Hz), 5.44 (2H, s), 3.70 (3H, s), 2.58 (3H, s), 2.33 (3H, s).

Present Compound 11

¹H-NMR (CDCl₃) δ:7.40-7.32 (5H, m), 7.26-7.23 (1H, m), 7.21-7.17 (2H, m), 6.52 (1H, dd, J=8.3, 0.6 Hz), 5.42 (2H, s), 3.69 (3H, s), 2.58 (3H, s), 2.33 (3H, s).

Present Compound 12

¹H-NMR (CDCl₃) δ:7.75 (1H, d, J=7.9 Hz), 7.56 (1H, t, J=7.2 Hz), 7.47 (1H, t, J=7.7 Hz), 7.39-7.36 (2H, m), 7.30-7.24 (2H, m), 7.21 (1H, d, J=7.7 Hz), 6.50 (1H, dd, J=8.4, 0.5 Hz), 5.50-5.35 (2H, m), 3.67 (3H, s), 2.58 (3H, s), 2.11 (3H, s).

Present Compound 13

¹H-NMR (CDCl₃) δ:7.39-7.33 (3H, m), 7.27-7.20 (3H, m), 7.11-7.06 (2H, m), 6.52 (1H, d, J=8.2 Hz), 5.43 (2H, s), 3.69 (3H, s), 2.58 (3H, s), 2.33 (3H, s).

Present Compound 27

¹H-NMR (CDCl₃) δ:7.43-7.39 (2H, m), 7.34 (1H, d, J=8.2 Hz), 7.29-7.26 (1H, m), 7.05-7.01 (1H, m), 6.58-6.52 (3H, m), 5.44 (2H, s), 3.88 (3H, s), 3.78 (3H, s), 3.70 (3H, s), 2.61 (3H, s), 2.25 (3H, s).

Present Compound 28

¹H-NMR (CDCl₃) δ:7.39-7.34 (3H, m), 7.28-7.20 (3H, m), 7.17-7.14 (1H, m), 6.55 (1H, d, J=8.2 Hz), 5.42 (2H, s), 3.87 (3H, s), 3.69 (3H, s), 2.57 (3H, s), 2.27 (3H, s).

Present Compound 29

¹H-NMR (CDCl₃) δ:7.46-7.43 (1H, m), 7.40-7.24 (6H, m), 6.57 (1H, dd, J=8.4, 0.6 Hz), 5.43 (2H, s), 3.69 (3H, s), 2.58 (3H, s), 2.27 (3H, s).

Production Example 2

A mixture of 0.40 g of 26A mentioned in Reference Production Example 26, 0.24 g of phenylboronic acid, 0.28 g of tripotassium phosphate, 0.40 ml of water, 0.02 g of [1,1'-bis(diphenylphosphino)ferrocene]palladium(II) dichloride dichloromethane adduct, and 4 ml of dimethoxyethane was stirred with heating under reflux for 4 hours. After cooling, water was poured into the reaction solution and the mixture was extracted with ethyl acetate. The organic layer was washed with water and a saturated saline solution, dried over anhydrous magnesium sulfate, and then concentrated under reduced pressure. The residue thus obtained was subjected to silica gel column chromatography to obtain 0.38 g of 1-[2-(5-phenyl-6-methyl-pyridin-2-yloxymethyl)-3-ethylphenyl]-4-methyl-1,4-dihydrotetrazol-5-one (hereinafter referred to as the present compound 14).

Present Compound 14

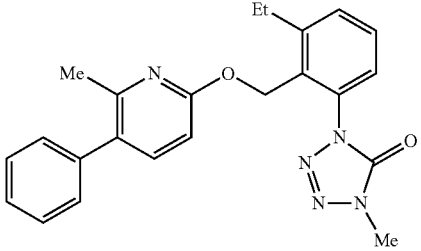

¹H-NMR (CDCl₃) δ:7.43-7.31 (7H, m), 7.27-7.22 (2H, m), 6.51 (1H, d, J=8.8 Hz), 5.43 (2H, s), 3.65 (3H, s), 2.93 (2H, q, J=7.6 Hz), 2.35 (3H, s), 1.30 (3H, t, J=7.6 Hz).

According to the same reaction as in Production Example 2, the present compounds 15 to 17 were synthesized.

The structural formulas and ¹H-NMR data thereof are shown below.

Present Compound 15

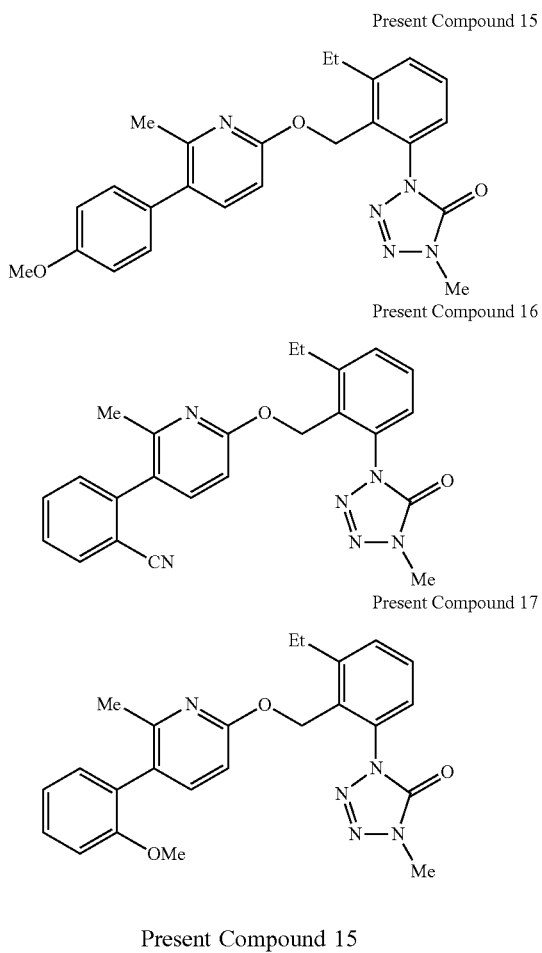

Present Compound 16

Present Compound 17

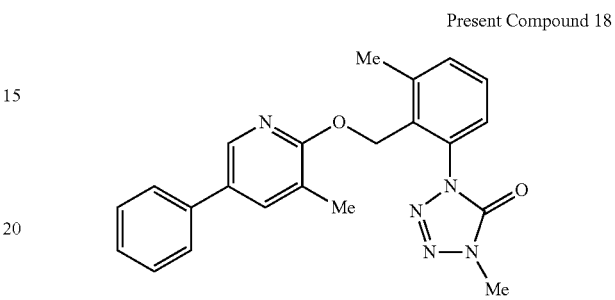

Present Compound 15

¹H-NMR (CDCl₃) δ:7.45-7.40 (2H, m), 7.35 (1H, d, J=8.4 Hz), 7.26-7.23 (1H, m), 7.18 (2H, dd, J=6.7, 2.2 Hz), 6.94 (2H, dd, J=6.7, 2.2 Hz), 6.50 (1H, d, J=8.4 Hz), 5.43 (2H, s), 3.84 (3H, s), 3.65 (3H, s), 2.94 (2H, q, J=7.6 Hz), 2.35 (3H, s), 1.30 (3H, t, J=7.6 Hz).

Present Compound 16

¹H-NMR (CDCl₃) δ:7.76 (1H, dd, J=7.7, 0.9 Hz), 7.63 (1H, td, J=7.7, 1.4 Hz), 7.49-7.42 (3H, m), 7.40-7.32 (2H, m), 7.28-7.25 (1H, m), 6.57 (1H, dd, J=8.4, 0.5 Hz), 5.44 (2H, s), 3.68 (3H, s), 2.94 (2H, q, J=7.6 Hz), 2.29 (3H, s), 1.32 (3H, t, J=7.6 Hz).

Present Compound 17

¹H-NMR (CDCl₃) δ:7.44-7.43 (2H, m), 7.37-7.31 (2H, m), 7.27-7.24 (1H, m), 7.11-7.09 (1H, m), 7.03-6.98 (1H, m), 6.96 (1H, d, J=8.5 Hz), 6.51 (1H, d, J=8.2 Hz), 5.43 (2H, s), 3.78 (3H, s), 3.65 (3H, s), 2.94 (2H, q, J=7.6 Hz), 2.24 (3H, s), 1.31 (3H, t, J=7.6 Hz)

Production Example 3

A mixture of 0.40 g of 28A mentioned in Reference Production Example 28, 0.13 g of phenylboronic acid, 0.88 g of tripotassium phosphate, 1 ml of water, 0.08 g of [1,1'-bis(diphenylphosphino)ferrocene]palladium(II) dichloride dichloromethane adduct, and 10 ml of 1,4-dioxane was stirred with heating under reflux for 5 hours. After cooling, water was poured into the reaction solution and the mixture was extracted with ethyl acetate. The organic layer was washed with water and a saturated saline solution, dried over anhydrous magnesium sulfate, and then concentrated under reduced pressure. The residue thus obtained was subjected to silica gel column chromatography to obtain 0.4 g of 1-[2-(5-phenyl-3-methyl-pyridin-2-yloxymethyl)-3-methylphenyl]-4-methyl-1,4-dihydrotetrazol-5-one (hereinafter referred to as the present compound 18).

Present Compound 18

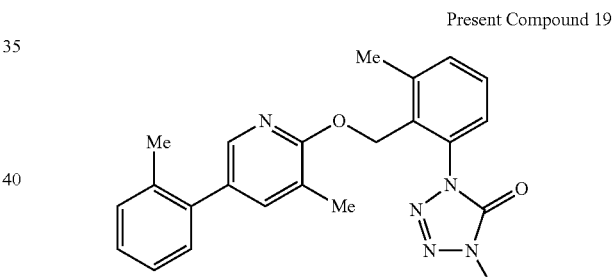

¹H-NMR (CDCl₃) δ:8.10 (1H, d, J=2.3 Hz), 7.55-7.55 (1H, m), 7.50-7.47 (2H, m), 7.44-7.37 (4H, m), 7.35-7.31 (1H, m), 7.26-7.24 (1H, m), 5.45 (2H, s), 3.68 (3H, s), 2.59 (3H, s), 2.14 (3H, s).

According to the same reaction as in Production Example 3, the present compounds 19 to 23 were synthesized.

The structural formulas and ¹H-NMR data thereof are shown below.

Present Compound 19

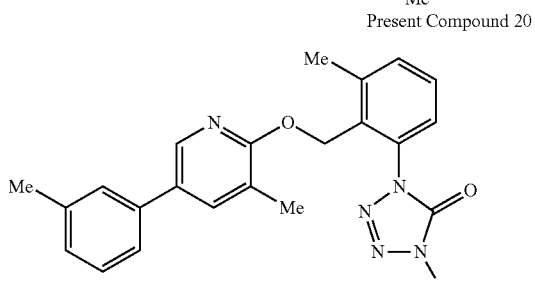

Present Compound 20

Present Compound 21

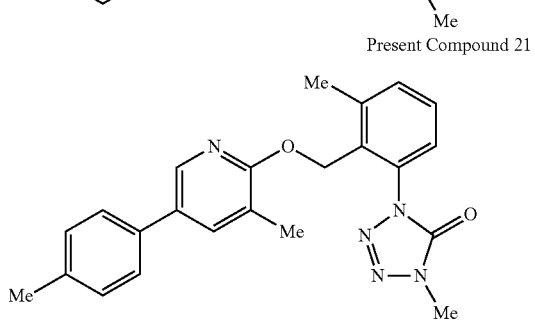

-continued

Present Compound 22

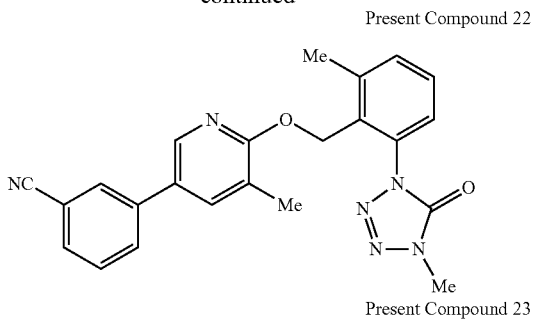

Present Compound 23

Present Compound 19

¹H-NMR (CDCl₃) δ:7.84-7.84 (1H, m), 7.40-7.38 (2H, m), 7.32-7.31 (1H, m), 7.28-7.20 (4H, m), 7.17-7.14 (1H, m), 5.46 (2H, s), 3.68 (3H, s), 2.60 (3H, s), 2.26 (3H, s), 2.12 (3H, s).

Present Compound 20

¹H-NMR (CDCl₃) δ:8.10-8.09 (1H, m), 7.55 (1H, dd, J=2.3, 0.9 Hz), 7.42-7.37 (2H, m), 7.34-7.29 (3H, m), 7.28-7.25 (1H, m), 7.17-7.14 (1H, m), 5.46 (2H, s), 3.69 (3H, s), 2.60 (3H, s), 2.41 (3H, s), 2.14 (3H, s).

Present Compound 21

¹H-NMR (CDCl₃) δ:8.08 (1H, d, J=2.3 Hz), 7.53-7.53 (1H, m), 7.39-7.36 (3H, m), 7.27-7.22 (4H, m), 5.44 (2H, s), 3.68 (3H, s), 2.59 (3H, s), 2.38 (3H, s), 2.13 (3H, s).

Present Compound 22

¹H-NMR (CDCl₃) δ:8.07-8.07 (1H, m), 7.77-7.76 (1H, m), 7.71 (1H, ddd, J=7.8, 1.8, 1.4 Hz), 7.61 (1H, dt, J=7.6, 1.4 Hz), 7.55-7.51 (2H, m), 7.40-7.38 (2H, m), 7.27-7.25 (1H, m), 5.48 (2H, s), 3.71 (3H, s), 2.60 (3H, s), 2.16 (3H, s).

Present Compound 23

¹H-NMR (CDCl₃) δ:8.76-8.76 (1H, m), 8.58 (1H, dd, J=4.8, 1.6 Hz), 8.09 (1H, t, J=1.3 Hz), 7.78 (1H, ddd, J=7.9, 2.3, 1.7 Hz), 7.55 (1H, dd, J=2.3, 0.9 Hz), 7.40-7.39 (2H, m), 7.35 (1H, ddd, J=7.9, 4.8, 0.8 Hz), 7.28-7.25 (1H, m), 5.47 (2H, s), 3.70 (3H, s), 2.60 (3H, s), 2.16 (3H, s).

Production Example 4

A mixture of 0.3 g of 32A mentioned in Reference Production Example 32, 0.09 g of phenylboronic acid, 0.65 g of tripotassium phosphate, 1 ml of water, 0.07 g of [1,1'-bis(diphenylphosphino)ferrocene]palladium(II) dichloride dichloromethane adduct, and 10 ml of 1,4-dioxane was stirred with heating under reflux for 5 hours. After cooling, water was poured into the reaction solution and the mixture was extracted with ethyl acetate. The organic layer was washed with water and a saturated saline solution, dried over anhydrous magnesium sulfate, and then concentrated under reduced pressure. The residue thus obtained was subjected to silica gel column chromatography to obtain 0.2 g of 1-[2-(6-phenyl-2-methyl-pyridin-3-yloxymethyl)-3-methylphenyl]-4-methyl-1,4-dihydrotetrazol-5-one (hereinafter referred to as the present compound 24).

Present Compound 24

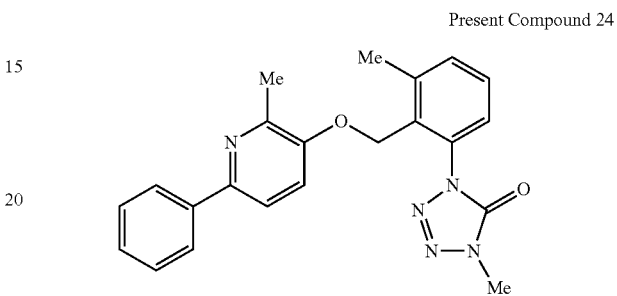

¹H-NMR (CDCl₃) δ:7.93-7.91 (2H, m), 7.50 (1H, d, J=8.5 Hz), 7.47-7.41 (4H, m), 7.36-7.30 (2H, m), 7.16 (1H, d, J=8.5 Hz), 5.09 (2H, s), 3.64 (3H, s), 2.53 (3H, s), 2.42 (3H, s).

According to the same reaction as in Production Example 4, the present compounds 25, and 60 to 61 were synthesized.

The structural formulas and ¹H-NMR data thereof are shown below.

Present Compound 25

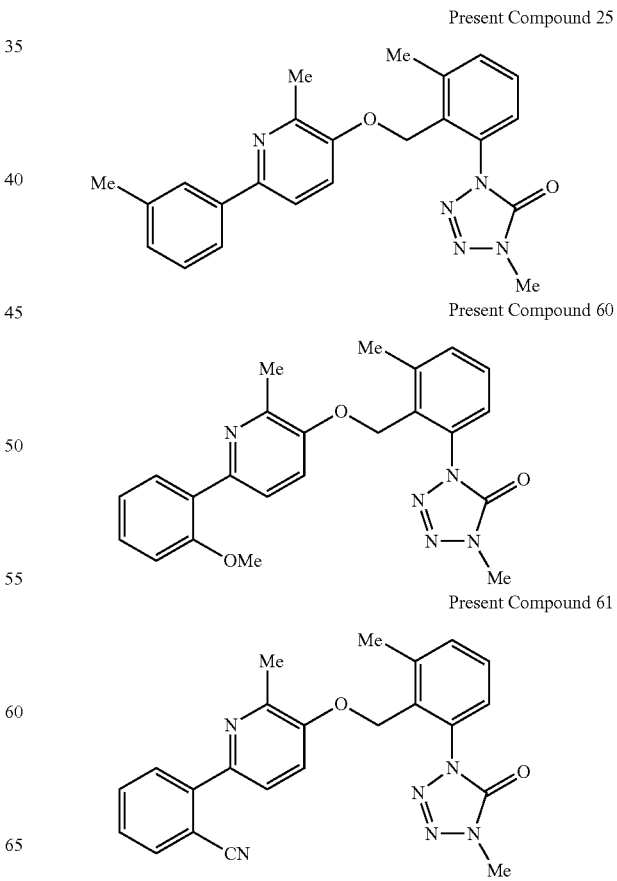

Present Compound 25

¹H-NMR (CDCl₃) δ:7.75 (1H, s), 7.67 (1H, d, J=7.8 Hz), 7.49-7.40 (3H, m), 7.33-7.29 (2H, m), 7.17-7.14 (2H, m), 5.08 (2H, s), 3.63 (3H, s), 2.52 (3H, s), 2.42 (6H, s).

Present Compound 60

¹H-NMR (CDCl₃) δ:7.74-7.70 (1H, m), 7.59 (1H, d, J=8.5 Hz), 7.49-7.41 (2H, m), 7.34-7.29 (2H, m), 7.15 (1H, d, J=8.5 Hz), 7.08-7.03 (1H, m), 6.97 (1H, dd, J=8.2, 0.9 Hz), 5.08 (2H, s), 3.85 (3H, s), 3.66 (3H, s), 2.53 (3H, s), 2.41 (3H, s).

Present Compound 61

¹H-NMR (CDCl₃) δ:7.81-7.79 (1H, m), 7.75 (1H, dd, J=7.8, 0.9 Hz), 7.64 (1H, td, J=7.8, 1.4 Hz), 7.58 (1H, d, J=8.5 Hz), 7.48-7.41 (3H, m), 7.32-7.29 (1H, m), 7.22 (1H, d, J=8.5 Hz), 5.10 (2H, s), 3.66 (3H, s), 2.53 (3H, s), 2.44 (3H, s).

Production Example 5

A mixture of 0.45 g of 29A mentioned in Reference Production Example 29, 0.18 g of 2-bromo-6-methylpyridine, 0.87 g of tripotassium phosphate, 1 ml of water, 0.08 g of [1,1'-bis(diphenylphosphino)ferrocene]palladium(II) dichloride dichloromethane adduct, and 10 ml of 1,4-dioxane was stirred with heating under reflux for 3 hours. After cooling, water was poured into the reaction solution and the mixture was extracted with ethyl acetate. The organic layer was washed with water and a saturated saline solution, dried over anhydrous magnesium sulfate, and then concentrated under reduced pressure. The residue thus obtained was subjected to silica gel column chromatography to obtain 0.39 g of 1-{2-[5-(6-methylpyridin-2-yl)-3-methylpyridin-2-yloxymethyl]-3-methylphenyl}-4-methyl-1,4-dihydro-tetrazol-5-one (hereinafter referred to as the present compound 26).

Present Compound 26

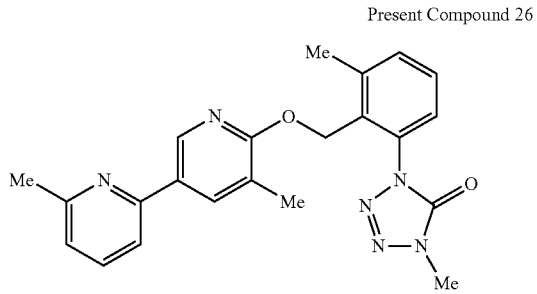 [SMILES: Cc1cccc(-c2cnc(OCc3c(C)cccc3-n3nnn(C)c3=O)c(C)c2)n1]

¹H-NMR (CDCl₃) δ:8.41-8.40 (1H, m), 8.00-8.00 (1H, m), 7.60 (1H, t, J=7.8 Hz), 7.42-7.40 (1H, m), 7.39-7.36 (1H, m), 7.26-7.23 (2H, m), 7.06 (1H, d, J=7.8 Hz), 5.47 (2H, s), 3.68 (3H, s), 2.60 (3H, s), 2.58 (3H, s), 2.14 (3H, s).

Production Example 6

A mixture of 0.42 g of 27A mentioned in Reference Production Example 27, 0.24 g of phenylboronic acid, 0.43 g of tripotassium phosphate, 1.0 ml of water, 0.03 g of [1,1'-bis(diphenylphosphino)ferrocene]palladium(II) dichloride dichloromethane adduct, and 10 ml of dimethoxyethane was stirred with heating under reflux for 5 hours. After cooling, water was poured into the reaction solution and the mixture was extracted with ethyl acetate. The organic layer was washed with water and a saturated saline solution, dried over anhydrous magnesium sulfate, and then concentrated under reduced pressure. The residue thus obtained was subjected to silica gel column chromatography to obtain 0.30 g of 1-[2-(5-phenyl-6-methyl-pyridin-2-yloxymethyl)-3-cyclopropylphenyl]-4-methyl-1,4-dihydrotetrazol-5-one (hereinafter referred to as the present compound 30).

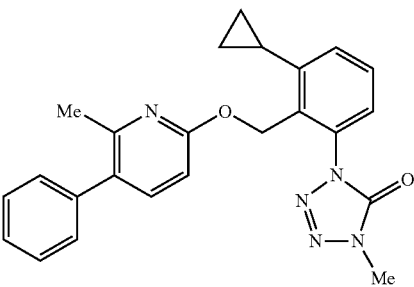 [SMILES: Cc1nc(OCc2c(C3CC3)cccc2-n2nnn(C)c2=O)ccc1-c1ccccc1]

¹H-NMR (CDCl₃) δ:7.42-7.37 (4H, m), 7.35-7.30 (1H, m), 7.28-7.23 (4H, m), 6.53 (1H, dd, J=8.4, 0.6 Hz), 5.62 (2H, s), 3.65 (3H, s), 2.36 (3H, s), 2.31-2.27 (1H, m), 1.04-0.99 (2H, m), 0.80-0.76 (2H, m).

According to the same reaction as in Production Example 6, the present compounds 31 and 32 were synthesized.

The structural formulas and ¹H-NMR data thereof are shown below.

Present Compound 31

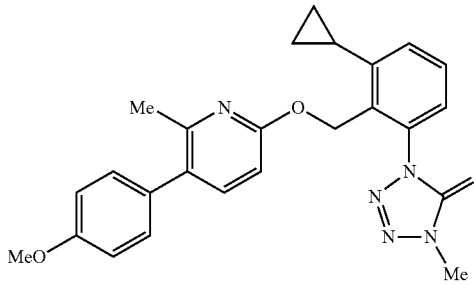

Present Compound 32

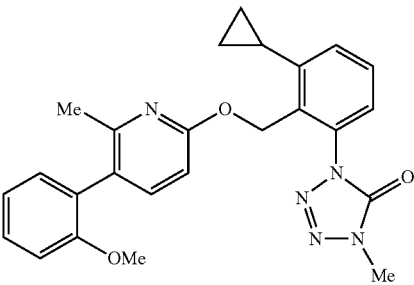

Present Compound 31

¹H-NMR (CDCl₃) δ:7.42-7.33 (2H, m), 7.25-7.17 (4H, m), 6.97-6.91 (2H, m), 6.51 (1H, d, J=8.4 Hz), 5.61 (2H, s), 3.84 (3H, s), 3.65 (3H, s), 2.35 (3H, s), 2.33-2.24 (1H, m), 1.03-1.00 (2H, m), 0.80-0.74 (2H, m).

Present Compound 32

¹H-NMR (CDCl₃) δ:7.39 (1H, t, J=7.8 Hz), 7.35-7.31 (2H, m), 7.25-7.21 (2H, m), 7.09 (1H, dd, J=7.4, 1.7 Hz), 6.99 (1H, td, J=7.4, 1.0 Hz), 6.95 (1H, d, J=8.4 Hz), 6.51 (1H, d, J=8.4 Hz), 5.60 (2H, s), 3.77 (3H, s), 3.64 (3H, s), 2.31-2.24 (1H, m), 2.23 (3H, s), 1.04-0.98 (2H, m), 0.80-0.74 (2H, m).

Production Example 7

A mixture of 0.41 g of 33A mentioned in Reference Production Example 33, 0.24 g of phenylboronic acid, 0.43 g of tripotassium phosphate, 1.0 ml of water, 0.03 g of [1,1'-bis(diphenylphosphino)ferrocene]palladium(II) dichloride dichloromethane adduct, and 10 ml of dimethoxyethane was stirred with heating under reflux for 5 hours. After cooling, water was poured into the reaction solution and the mixture was extracted with ethyl acetate. The organic layer was washed with water and a saturated saline solution, dried over anhydrous magnesium sulfate, and then concentrated under reduced pressure. The residue thus obtained was subjected to silica gel column chromatography to obtain 0.30 g of 1-[2-(5-phenyl-6-methyl-pyridin-2-yloxymethyl)-3-chlorophenyl]-4-methyl-1,4-dihydrotetrazol-5-one (hereinafter referred to as the present compound 33).

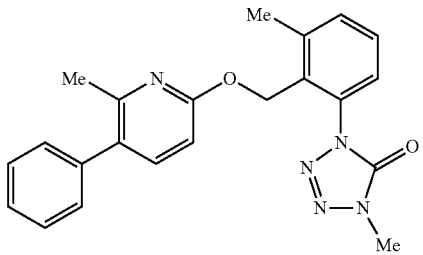 [SMILES: Cc1cccc(-n2nnn(C)c2=O)c1COc1ccc(-c2ccccc2)c(C)n1]

¹H-NMR (CDCl₃) δ:7.60 (1H, dd, J=8.0, 1.1 Hz), 7.46-7.31 (6H, m), 7.28-7.26 (2H, m), 6.50 (1H, d, J=8.2 Hz), 5.61 (2H, s), 3.66 (3H, s), 2.36 (3H, s).

According to the same reaction as in Production Example 7, the present compounds 34 and 35 were synthesized.

The structural formulas and ¹H-NMR data thereof are shown below.

Present Compound 34

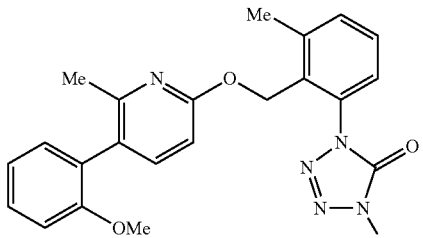

Present Compound 35

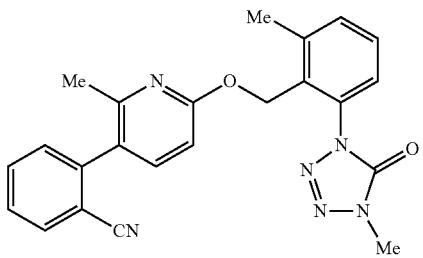

Present Compound 34

¹H-NMR (CDCl₃) δ:7.60 (1H, d, J=8.0 Hz), 7.43 (1H, t, J=8.0 Hz), 7.37-7.31 (3H, m), 7.11-7.08 (1H, m), 7.01-6.94 (2H, m), 6.49 (1H, d, J=8.2 Hz), 5.59 (2H, s), 3.77 (3H, s), 3.64 (3H, s), 2.22 (3H, s).

Present Compound 35

¹H-NMR (CDCl₃) δ:7.77-7.73 (1H, m), 7.65-7.60 (2H, m), 7.48-7.42 (2H, m), 7.41-7.36 (2H, m), 7.33 (1H, dt, J=7.8, 0.6 Hz), 6.55 (1H, dd, J=8.4, 0.6 Hz), 5.60 (2H, s), 3.67 (3H, s), 2.29 (3H, s).

Production Example 8

A mixture of 0.42 g of 35A mentioned in Reference Production Example 35, 0.45 g of 14A mentioned in Reference Production Example 14, 0.44 g of potassium carbonate, and 6.4 ml of acetonitrile was stirred with heating at 80° C. for 4 hours. Water was added to the reaction mixture and the mixture was extracted with chloroform. The organic layer was washed with a saturated saline solution, dried over anhydrous magnesium sulfate, and then concentrated under reduced pressure. The residue thus obtained was subjected to silica gel column chromatography to obtain 0.15 g of 1-[2-(3-bromo-5-phenyl-6-methyl-pyridin-2-yloxymethyl)-3-methylphenyl]-4-methyl-1,4-dihydrotetrazol-5-one (hereinafter referred to as the present compound 36).

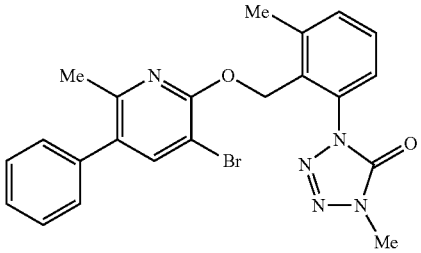 [SMILES: Cc1cccc(-n2nnn(C)c2=O)c1COc1nc(C)c(-c2ccccc2)cc1Br]

¹H-NMR (CDCl₃) δ:7.59 (1H, s), 7.42-7.31 (5H, m), 7.29-7.22 (3H, m), 5.59 (2H, s), 3.73 (3H, s), 2.67 (3H, s), 2.27 (3H, s).

Production Example 9

A mixture of 0.42 g of the present compound 5, 0.18 g of N-bromosuccinimide, and 10 ml of chloroform was stirred with heating at 60° C. for 2 hours. Water was poured into the reaction solution and the mixture was extracted with chloroform. The organic layer was washed with water and a saturated saline solution, dried over anhydrous magnesium sulfate, and then concentrated under reduced pressure. The residue thus obtained was subjected to silica gel column chromatography to obtain 0.25 g of 1-[2-{5-(5-bromo-2-methoxyphenyl)-6-methyl-pyridin-2-yloxymethyl}-3-methylphenyl]-4-methyl-1,4-dihydrotetrazol-5-one (hereinafter referred to as the present compound 37).

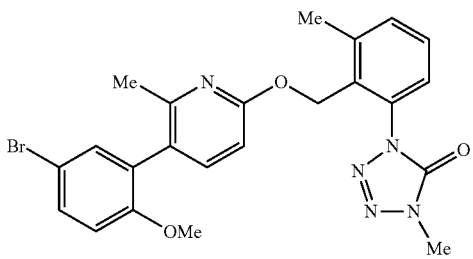 [SMILES: COc1ccc(Br)cc1-c1ccc(OCc2c(C)cccc2-n2nnn(C)c2=O)nc1C]

¹H-NMR (CDCl₃) δ:7.40-7.31 (3H, m), 7.28-7.24 (1H, m), 7.10 (1H, dd, J=7.4, 1.7 Hz), 7.02-6.98 (1H, m), 6.96 (1H, dd, J=8.2, 0.7 Hz), 6.53 (1H, dd, J=8.2, 0.7 Hz), 5.43 (2H, s), 3.77 (3H, s), 3.67 (3H, s), 2.59 (3H, s), 2.24 (3H, s).

Production Example 10

A mixture of 0.25 g of the present compound 36, 0.06 g of methylboronic acid, 0.53 g of cesium carbonate, 0.04 g of [1,1'-bis(diphenylphosphino)ferrocene]palladium(II) dichloride dichloromethane adduct, and 2 ml of dimethoxyethane was stirred with heating under reflux for 4 hours. After cooling, the reaction solution was concentrated under reduced pressure. The residue thus obtained was subjected to silica gel column chromatography to obtain 0.20 g of 1-[2-(3,6-dimethyl-5-phenylpyridin-2-yloxymethyl)-3-methylphenyl]-4-methyl-1,4-dihydrotetrazol-5-one (hereinafter referred to as the present compound 38).

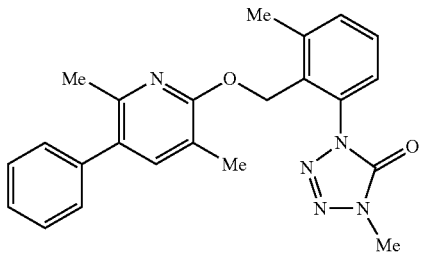 [SMILES: Cc1cc(-c2ccccc2)c(C)nc1OCc1c(C)cccc1-n1nnn(C)c1=O]

¹H-NMR (CDCl₃) δ:7.42-7.36 (4H, m), 7.33-7.29 (1H, m), 7.26-7.23 (3H, m), 7.19 (1H, s), 5.50 (2H, s), 3.69 (3H, s), 2.63 (3H, s), 2.31 (3H, s), 2.05 (3H, s).

Production Example 11

A mixture of 0.40 g of 38A mentioned in Reference Production Example 38, 0.30 g of 2-methoxyphenylboronic acid, 0.64 g of tripotassium phosphate, 0.40 ml of water, 0.02 g of [1,1'-bis(diphenylphosphino)ferrocene]palladium (II) dichloride dichloromethane adduct, and 4 ml of dimethoxyethane was stirred with heating under reflux for 4 hours. After cooling, water was poured into the reaction solution and the mixture was extracted with ethyl acetate. The organic layer was washed with water and a saturated saline solution, dried over anhydrous magnesium sulfate, and then concentrated under reduced pressure. The residue thus obtained was subjected to silica gel column chromatography to obtain 0.30 g of 1-[2-{3,6-dimethyl-5-(2-methoxyphenyl)pyridin-2-yloxymethyl}-3-methylphenyl]-4-methyl-1,4-dihydrotetrazol-5-one (hereinafter referred to as the present compound 39).

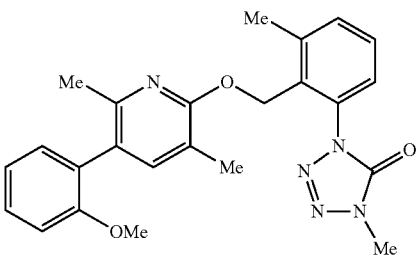 [SMILES: COc1ccccc1-c1cc(C)c(OCc2c(C)cccc2-n2nnn(C)c2=O)nc1C]

¹H-NMR (CDCl₃) δ:7.39-7.37 (2H, m), 7.36-7.31 (1H, m), 7.27-7.24 (1H, m), 7.16-7.15 (1H, m), 7.09 (1H, dd, J=7.4, 1.7 Hz), 6.99 (1H, td, J=7.4, 1.1 Hz), 6.95 (1H, dd, J=8.4, 0.8 Hz), 5.49 (2H, s), 3.78 (3H, s), 3.69 (3H, s), 2.63 (3H, s), 2.19 (3H, s), 2.04 (3H, s).

According to the same reaction as in Production Example 11, the present compounds 40 to 43 were synthesized.

The structural formulas and ¹H-NMR data thereof are shown below.

Present Compound 40

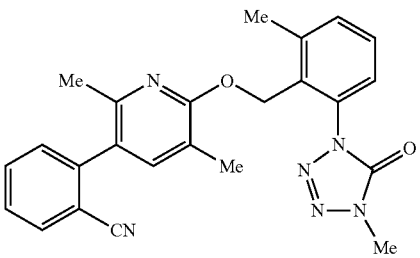

Present Compound 41

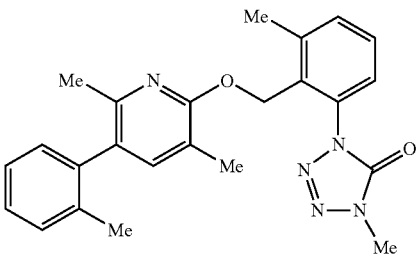

Present Compound 42

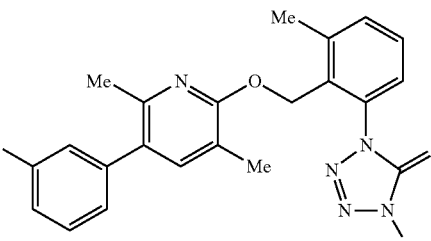

Present Compound 43

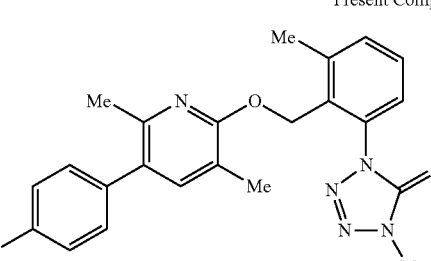

Present Compound 40

$^1$H-NMR (CDCl$_3$) δ:7.73 (1H, dd, J=7.8, 0.9 Hz), 7.61 (1H, td, J=7.7, 1.5 Hz), 7.43 (1H, td, J=7.7, 1.5 Hz), 7.40-7.37 (2H, m), 7.31 (1H, dd, J=7.8, 0.9 Hz), 7.27-7.24 (1H, m), 7.19-7.17 (1H, m), 5.49 (2H, s), 3.70 (3H, s), 2.62 (3H, s), 2.23 (3H, s), 2.06 (3H, s).

Present Compound 41

$^1$H-NMR (CDCl$_3$) δ:7.39-7.35 (2H, m), 7.25-7.16 (4H, m), 7.06 (1H, s), 7.03 (1H, d, J=7.1 Hz), 5.55-5.43 (2H, m), 3.69 (3H, s), 2.63 (3H, s), 2.09 (3H, s), 2.06 (3H, s), 2.03 (3H, s).

Present Compound 42

$^1$H-NMR (CDCl$_3$) δ:7.38-7.36 (2H, m), 7.29-7.22 (2H, m), 7.18 (1H, s), 7.14-7.11 (1H, m), 7.07-7.03 (2H, m), 5.49 (2H, s), 3.68 (3H, s), 2.62 (3H, s), 2.37 (3H, s), 2.30 (3H, s), 2.04 (3H, s).

Present Compound 43

$^1$H-NMR (CDCl$_3$) δ:7.38-7.34 (2H, m), 7.26-7.13 (6H, m), 5.49 (2H, s), 3.68 (3H, s), 2.62 (3H, s), 2.38 (3H, s), 2.31 (3H, s), 2.04 (3H, s).

Production Example 12

A mixture of 0.44 g of 39A mentioned in Reference Production Example 39, 0.11 g of 2-chloropyridine, 0.64 g of tripotassium phosphate, 0.40 ml of water, 0.02 g of [1,1'-bis(diphenylphosphino)ferrocene]palladium(II) dichloride dichloromethane adduct, and 4 ml of dimethoxyethane was stirred with heating under reflux for 4 hours. After cooling, Water was poured into the reaction solution and the mixture was extracted with chloroform. The organic layer was washed with water and a saturated saline solution, dried over anhydrous magnesium sulfate, and then concentrated under reduced pressure. The residue thus obtained was subjected to silica gel column chromatography to obtain 0.25 g of 1-[2-{6-methyl-5-(2-pyridyl)pyridin-2-yloxymethyl}-3-methylphenyl]-4-methyl-1,4-dihydrotetrazol-5-one (hereinafter referred to as the present compound 44).

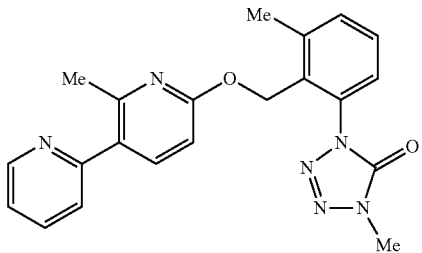 [SMILES: Cc1cccc(-n2nnn(C)c2=O)c1COc1ccc(-c2ccccn2)c(C)n1]

$^1$H-NMR (CDCl$_3$) δ:8.69-8.66 (1H, m), 7.76-7.70 (1H, m), 7.61 (1H, d, J=8.5 Hz), 7.40-7.34 (3H, m), 7.26-7.21 (2H, m), 6.56 (1H, d, J=8.5 Hz), 5.45 (2H, s), 3.68 (3H, s), 2.57 (3H, s), 2.47 (3H, s).

According to the same reaction as in Production Example 12, the present compounds 45 to 59, 65 to 68, 71 to 79, and 81 to 86 were synthesized.

The structural formulas and $^1$H-NMR data thereof are shown below.

Present Compound 45

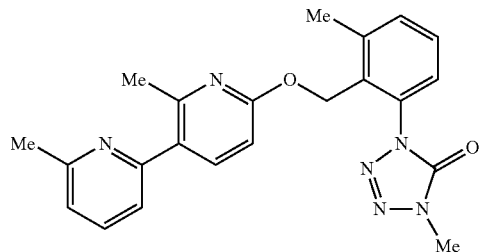

Present Compound 46

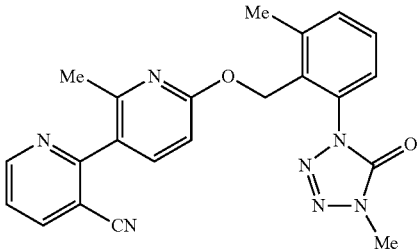

Present Compound 47

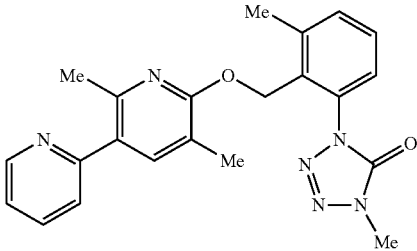

Present Compound 48

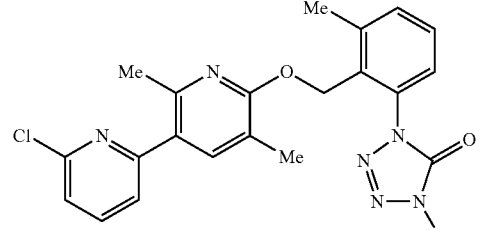

Present Compound 49

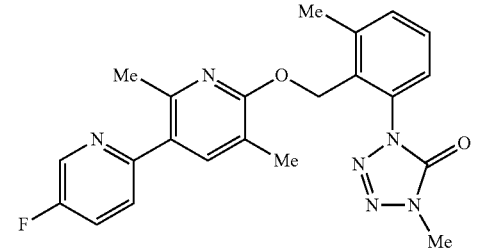

Present Compound 50
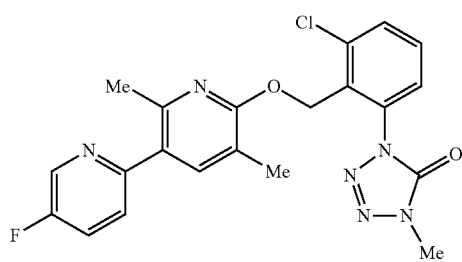
Present Compound 51
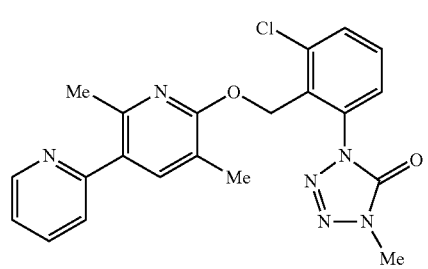
Present Compound 52
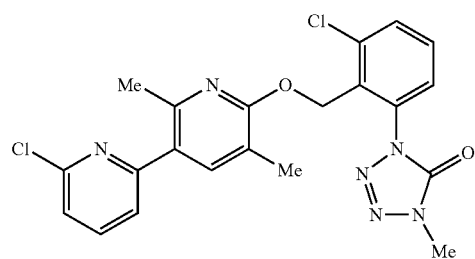
Present Compound 53
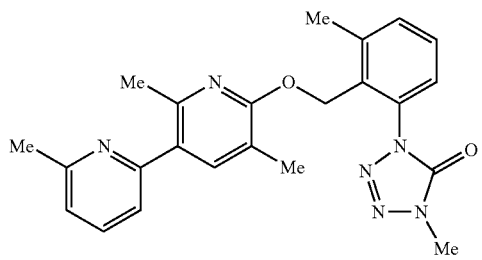
Present Compound 54
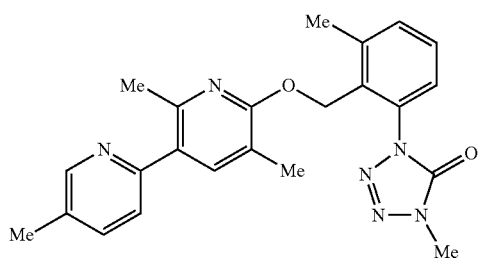
Present Compound 55
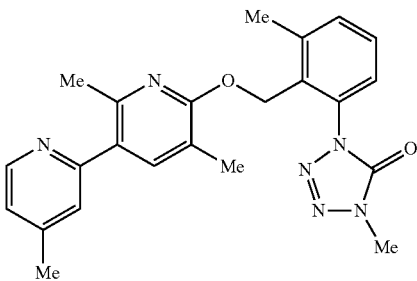
Present Compound 56
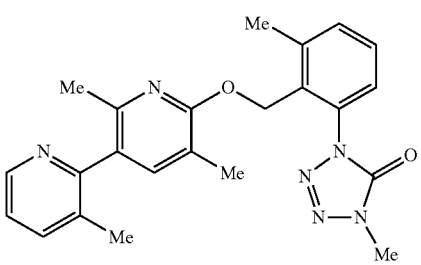
Present Compound 57
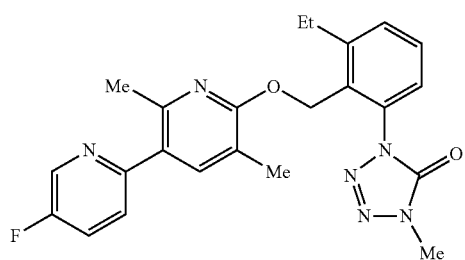
Present Compound 58
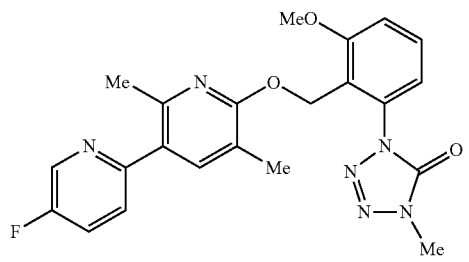
Present Compound 59
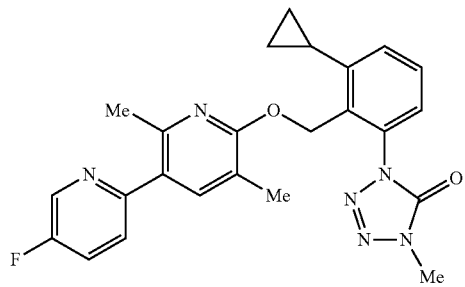

Present Compound 65
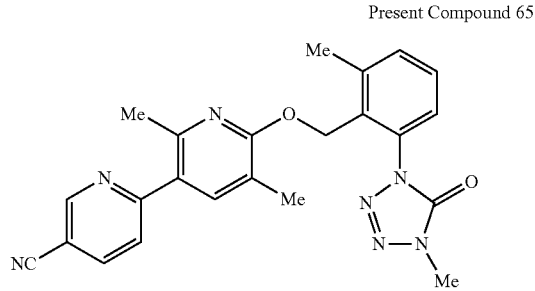
Present Compound 66
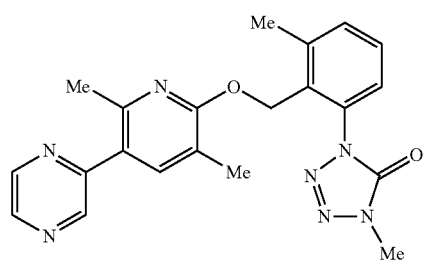
Present Compound 67
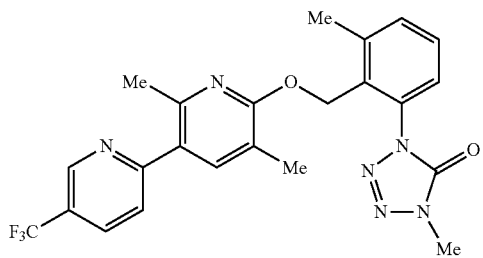
Present Compound 68
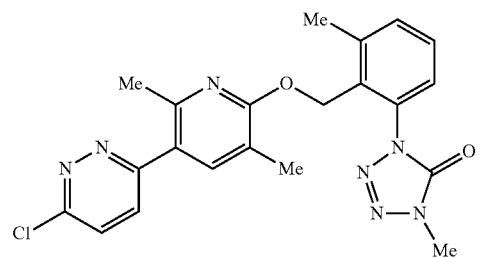
Present Compound 71
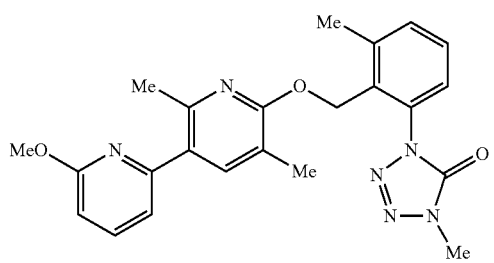
Present Compound 72
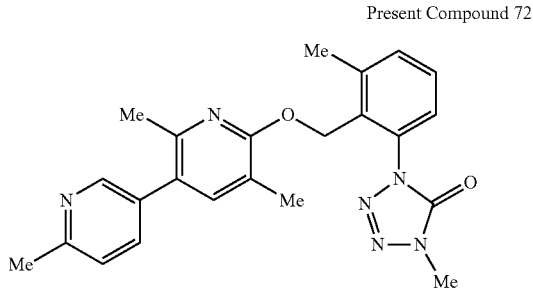
Present Compound 73
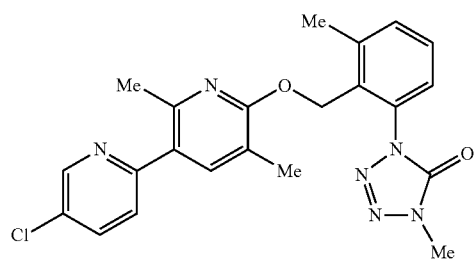
Present Compound 74
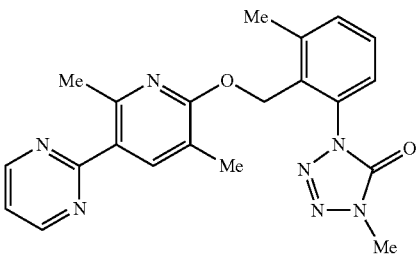
Present Compound 75
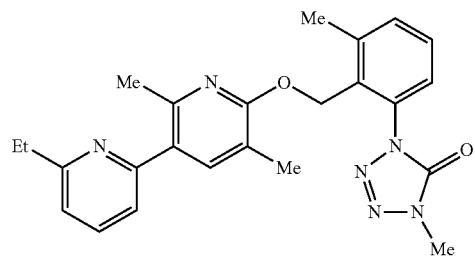
Present Compound 76
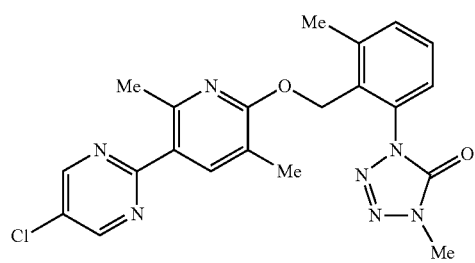

Present Compound 77

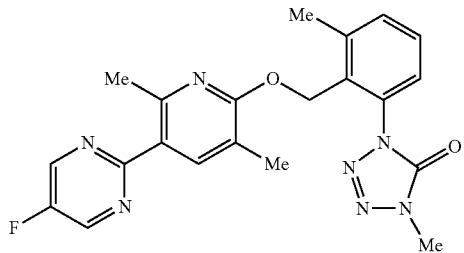

Present Compound 78

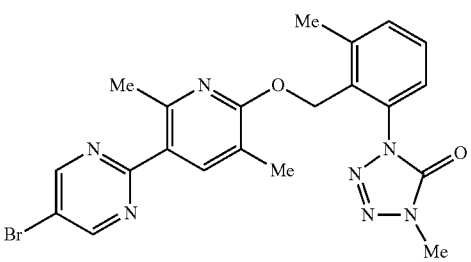

Present Compound 81

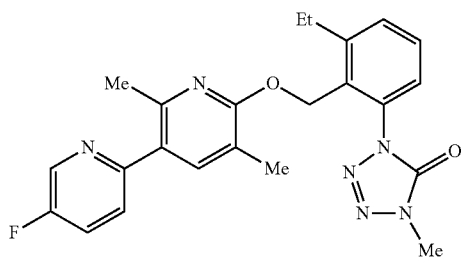

Present Compound 82

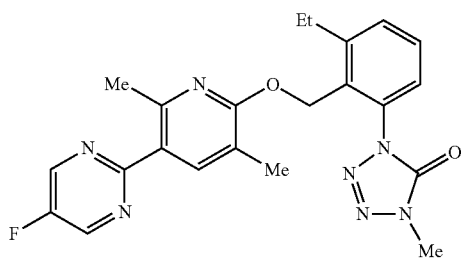

Present Compound 83

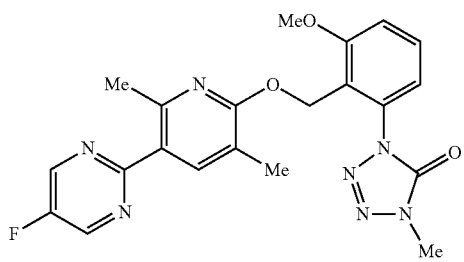

Present Compound 84

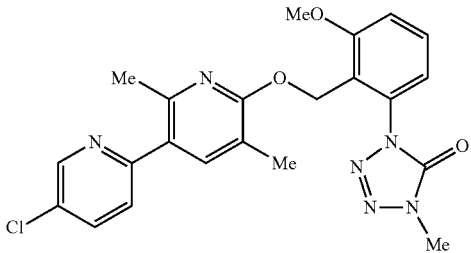

Present Compound 85

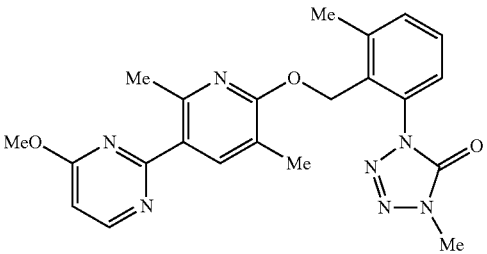

Present Compound 86

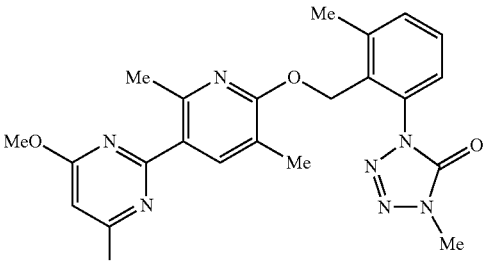

Present Compound 79

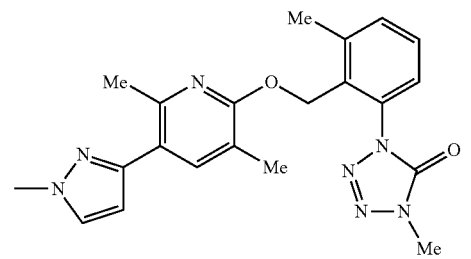

Present Compound 45

$^1$H-NMR (CDCl$_3$) δ:7.64-7.56 (2H, m), 7.40-7.35 (2H, m), 7.26-7.22 (1H, m), 7.14 (1H, d, J=7.8 Hz), 7.09 (1H, d, J=7.6 Hz), 6.55 (1H, d, J=8.2 Hz), 5.43 (2H, s), 3.69 (3H, s), 2.59 (3H, s), 2.56 (3H, s), 2.44 (3H, s).

Present Compound 46

$^1$H-NMR (CDCl$_3$) δ:8.85 (1H, dd, J=5.0, 1.8 Hz), 8.06 (1H, dd, J=7.8, 1.8 Hz), 7.56 (1H, d, J=8.5 Hz), 7.43-7.37 (3H, m), 7.28-7.24 (1H, m), 6.61 (1H, d, J=8.5 Hz), 5.44 (2H, s), 3.68 (3H, s), 2.56 (3H, s), 2.38 (3H, s).

Present Compound 47

$^1$H-NMR (CDCl$_3$) δ:8.72-8.68 (1H, m), 7.78-7.72 (1H, m), 7.48 (1H, s), 7.42-7.38 (3H, m), 7.30-7.23 (2H, m), 5.55 (2H, s), 3.72 (3H, s), 2.65 (3H, s), 2.46 (3H, s), 2.10 (3H, s).

Present Compound 48

¹H-NMR (CDCl₃) δ:7.74-7.67 (1H, m), 7.48 (1H, s), 7.43-7.38 (2H, m), 7.33-7.25 (3H, m), 5.54 (2H, s), 3.73 (3H, s), 2.63 (3H, s), 2.46 (3H, s), 2.09 (3H, s).

Present Compound 49

¹H-NMR (CDCl₃) δ:8.55 (1H, d, J=2.9 Hz), 7.50-7.44 (1H, m), 7.44 (1H, s), 7.42-7.36 (3H, m), 7.28 (1H, t, J=4.6 Hz), 5.54 (2H, s), 3.72 (3H, s), 2.64 (3H, s), 0.2.43 (3H, s), 2.10 (3H, s).

Present Compound 50

¹H-NMR (CDCl₃) δ:8.56 (1H, d, J=2.9 Hz), 7.63 (1H, dd, J=8.2, 1.4 Hz), 7.48-7.44 (3H, m), 7.41-7.37 (2H, m), 5.70 (2H, s), 3.70 (3H, s), 0.2.44 (3H, s), 2.07 (3H, s).

Present Compound 51

¹H-NMR (CDCl₃) δ:2.05 (3H, s), 2.43 (3H, s), 3.67 (3H, s), 5.68 (2H, s), 7.22 (1H, ddd, J=7.6, 4.8, 1.1 Hz), 7.34-7.37 (2H, in), 7.43 (1H, t, J=8.0 Hz), 7.45 (1H, s), 7.60 (1H, dd, J=8.0, 1.1 Hz), 7.72 (1H, td, J=7.7, 1.8 Hz), 8.67 (1H, ddd, J=5.0, 1.6, 1.1 Hz).

Present Compound 52

¹H-NMR (CDCl₃) δ:7.67 (1H, t, J=7.8 Hz), 7.61-7.57 (1H, m), 7.46-7.39 (2H, m), 7.36-7.33 (1H, m), 7.30-7.23 (2H, m), 5.66 (2H, s), 3.66 (3H, s), 2.43 (3H, s), 2.03 (3H, s).

Present Compound 53

¹H-NMR (CDCl₃) δ:7.59 (1H, t, J=7.7 Hz), 7.40 (1H, s), 7.38-7.35 (2H, m), 7.24 (1H, t, J=4.6 Hz), 7.13 (1H, d, J=7.7 Hz), 7.08 (1H, d, J=7.7 Hz), 5.49 (2H, s), 3.69 (3H, s), 2.59 (3H, s), 2.59 (3H, s), 2.39 (3H, s), 2.05 (3H, s).

Present Compound 54

¹H-NMR (CDCl₃) δ:8.50-8.48 (1H, m), 7.53-7.50 (1H, m), 7.42 (1H, s), 7.38-7.35 (2H, m), 7.26-7.21 (2H, m), 5.50 (2H, s), 3.68 (3H, s), 2.60 (3H, s), 2.40 (3H, s), 2.37 (3H, s), 2.05 (3H, s).

Present Compound 55

¹H-NMR (CDCl₃) δ:8.51 (1H, d, J=5.0 Hz), 7.41 (1H, s), 7.38-7.36 (2H, m), 7.24 (1H, t, J=4.5 Hz), 7.17-7.15 (1H, m), 7.04 (1H, d, J=4.5 Hz), 5.50 (2H, s), 3.69 (3H, s), 2.60 (3H, s), 2.41 (3H, s), 2.39 (3H, s), 2.05 (3H, s).

Present Compound 56

¹H-NMR (CDCl₃) δ:8.48 (1H, dd, J=4.7, 1.7 Hz), 7.56 (1H, d, J=6.6 Hz), 7.39-7.36 (2H, m), 7.24 (1H, t, J=4.7 Hz), 7.19-7.16 (2H, m), 5.48 (2H, s), 3.69 (3H, s), 2.60 (3H, s), 2.13 (3H, s), 2.12 (3H, s), 2.04 (3H, s).

Present Compound 57

¹H-NMR (CDCl₃) δ:8.51 (1H, d, J=2.9 Hz), 7.46-7.41 (3H, m), 7.39 (1H, s), 7.37-7.32 (1H, m), 7.25-7.22 (1H, m), 5.50 (2H, s), 3.65 (3H, s), 2.97 (2H, q, J=7.6 Hz), 2.40 (3H, s), 2.04 (3H, s), 1.29 (3H, t, J=7.6 Hz).

Present Compound 58

¹H-NMR (CDCl₃) δ:8.51 (1H, d, J=2.9 Hz), 7.47-7.40 (2H, m), 7.39-7.37 (1H, m), 7.37-7.32 (1H, m), 7.09-7.06 (1H, m), 7.03 (1H, dd, J=7.9, 1.1 Hz), 5.57 (2H, s), 3.92 (3H, s), 3.61 (3H, s), 2.41 (3H, s), 2.00 (3H, s).

Present Compound 59

¹H-NMR (CDCl₃) δ:8.51 (1H, d, J=2.7 Hz), 7.46-7.33 (4H, m), 7.27-7.19 (2H, m), 5.68 (2H, s), 3.66 (3H, s), 2.40 (3H, s), 2.37-2.27 (1H, m), 2.06 (3H, s), 1.03-0.99 (2H, m), 0.79-0.75 (2H, m).

Present Compound 65

¹H-NMR (CDCl₃) δ:8.93 (1H, d, J=2.1 Hz), 7.98 (1H, dd, J=8.3, 2.1 Hz), 7.50 (1H, d, J=8.3 Hz), 7.48 (1H, s), 7.39 (1H, d, J=1.4 Hz), 7.37 (1H, s), 7.27-7.23 (1H, m), 5.52 (2H, s), 3.69 (3H, s), 2.61 (3H, s), 2.45 (3H, s), 2.08 (3H, s).

Present Compound 66

¹H-NMR (CDCl₃) δ:8.67 (1H, t, J=2.0 Hz), 8.63 (1H, q, J=2.0 Hz), 8.49 (1H, t, J=2.5 Hz), 7.47 (1H, s), 7.40-7.35 (2H, m), 7.26-7.23 (1H, m), 5.52 (2H, s), 3.69 (3H, s), 2.61 (3H, s), 2.46 (3H, s), 2.08 (3H, s).

Present Compound 67

¹H-NMR (CDCl₃) δ:8.92 (1H, s), 7.94 (1H, dd, J=8.2, 2.1 Hz), 7.49 (1H, d, J=8.2 Hz), 7.47 (1H, s), 7.38-7.34 (2H, m), 7.24 (1H, t, J=4.7 Hz), 5.53 (2H, s), 3.69 (3H, s), 2.61 (3H, s), 2.44 (3H, s), 2.08 (3H, s).

Present Compound 68

¹H-NMR (CDCl₃) δ:7.54 (1H, d, J=8.9 Hz), 7.50 (1H, d, J=8.9 Hz), 7.48 (1H, s), 7.39-7.36 (2H, m), 7.24 (1H, t, J=4.6 Hz), 5.53 (2H, s), 3.69 (3H, s), 2.61 (3H, s), 2.43 (3H, s), 2.08 (3H, s).

Present Compound 71

¹H-NMR (CDCl₃) δ:7.59 (1H, t, J=8.0 Hz), 7.44 (1H, s), 7.37 (1H, d, J=4.6 Hz), 7.37 (1H, d, J=4.6 Hz), 7.24 (1H, t, J=4.6 Hz), 6.92 (1H, d, J=7.2 Hz), 6.66 (1H, d, J=8.2 Hz), 5.50 (2H, s), 3.94 (3H, s), 3.69 (3H, s), 2.61 (3H, s), 2.48 (3H, s), 2.06 (3H, s).

Present Compound 72

¹H-NMR (CDCl₃) δ:8.40 (1H, d, J=2.4 Hz), 7.47 (1H, dd, J=7.8, 2.4 Hz), 7.37 (1H, d, J=4.9 Hz), 7.37 (1H, d, J=4.9 Hz), 7.24 (1H, t, J=4.9 Hz), 7.18 (1H, d, J=7.8 Hz), 7.16 (1H, s), 5.50 (2H, s), 3.69 (3H, s), 2.62 (3H, s), 2.59 (3H, s), 2.30 (3H, s), 2.05 (3H, s).

Present Compound 73

¹H-NMR (CDCl₃) δ:8.61 (1H, d, J=2.5 Hz), 7.69 (1H, dd, J=8.2, 2.5 Hz), 7.41 (1H, s), 7.37 (2H, d, J=4.8 Hz), 7.31 (1H, d, J=8.2 Hz), 7.24 (1H, t, J=4.8 Hz), 5.51 (2H, s), 3.68 (3H, s), 2.60 (3H, s), 2.41 (3H, s), 2.05 (3H, s).

Present Compound 74

$^1$H-NMR (CDCl$_3$) δ:8.80 (2H, d, J=4.8 Hz), 7.91 (1H, s), 7.37 (2H, d, J=4.5 Hz), 7.24 (1H, t, J=4.6 Hz), 7.16 (1H, t, J=4.8 Hz), 5.54 (2H, s), 3.68 (3H, s), 2.65 (3H, s), 2.60 (3H, s), 2.08 (3H, s).

Present Compound 75

$^1$H-NMR (CDCl$_3$) δ:7.61 (1H, t, J=7.7 Hz), 7.41 (1H, s), 7.36 (2H, d, J=4.7 Hz), 7.23 (1H, t, J=4.7 Hz), 7.14 (1H, d, J=7.7 Hz), 7.08 (1H, d, J=7.7 Hz), 5.50 (2H, s), 3.68 (3H, s), 2.85 (2H, q, J=7.6 Hz), 2.60 (3H, s), 2.41 (3H, s), 2.06 (3H, s), 1.33 (3H, t, J=7.6 Hz).

Present Compound 76

$^1$H-NMR (CDCl$_3$) δ:8.73 (2H, s), 7.93 (1H, d, J=0.5 Hz), 7.37 (2H, d, J=5.0 Hz), 7.24 (1H, t, J=5.0 Hz), 5.54 (2H, s), 3.67 (3H, s), 2.64 (3H, s), 2.60 (3H, s), 2.08 (3H, s).

Present Compound 77

$^1$H-NMR (CDCl$_3$) δ:8.65 (2H, s), 7.88 (1H, s), 7.37 (2H, d, J=4.8 Hz), 7.24 (1H, t, J=4.8 Hz), 5.53 (2H, s), 3.68 (3H, s), 2.62 (3H, s), 2.60 (3H, s), 2.08 (3H, s).

Present Compound 78

$^1$H-NMR (CDCl$_3$) δ:8.82 (2H, s), 7.93 (1H, s), 7.37 (2H, d, J=4.8 Hz), 7.24 (1H, t, J=4.8 Hz), 5.54 (2H, s), 3.67 (3H, s), 2.64 (3H, s), 2.60 (3H, s), 2.08 (3H, s).

Present Compound 79

$^1$H-NMR (CDCl$_3$) δ:7.54 (1H, s), 7.38-7.35 (3H, m), 7.25-7.22 (2H, in), 6.32 (1H, d, J=2.3 Hz), 5.49 (2H, s), 3.94 (3H, s), 3.67 (3H, s), 2.60 (3H, s), 2.49 (3H, s), 2.04 (3H, s).

Present Compound 81

$^1$H-NMR (CDCl$_3$) δ:8.60 (1H, d, J=2.5 Hz), 7.67 (1H, dd, J=8.4, 2.5 Hz), 7.43-7.38 (3H, m), 7.29 (1H, d, J=8.4 Hz), 7.22 (1H, dd, J=5.8, 3.4 Hz), 5.49 (2H, s), 3.63 (3H, s), 2.95 (2H, q, J=7.6 Hz), 2.40 (3H, s), 2.03 (3H, s), 1.28 (3H, t, J=7.6 Hz).

Present Compound 82

$^1$H-NMR (CDCl$_3$) δ:8.65 (2H, s), 7.88 (1H, s), 7.44-7.41 (2H, m), 7.26-7.23 (1H, m), 5.54 (2H, s), 3.64 (3H, d, J=0.5 Hz), 2.97 (2H, q, J=7.7 Hz), 2.63 (3H, s), 2.07 (3H, s), 1.30 (3H, t, J=7.7 Hz).

Present Compound 83

$^1$H-NMR (CDCl$_3$) δ:8.65 (2H, s), 7.87 (1H, s), 7.45 (1H, t, J=8.1 Hz), 7.09 (1H, d, J=8.2 Hz), 7.04 (1H, d, J=8.0 Hz), 5.62 (2H, s), 3.94 (3H, s), 3.60 (3H, s), 2.64 (3H, s), 2.04 (3H, s).

Present Compound 84

$^1$H-NMR (CDCl$_3$) δ:8.62 (1H, d, J=2.5 Hz), 7.69 (1H, dd, J=8.4, 2.5 Hz), 7.45 (1H, t, J=8.4 Hz), 7.41 (1H, s), 7.32 (1H, d, J=8.4 Hz), 7.08 (1H, d, J=8.4 Hz), 7.04 (1H, d, J=8.4 Hz), 5.58 (2H, s), 3.94 (3H, s), 3.62 (3H, s), 2.43 (3H, s), 2.01 (3H, s).

Present Compound 85

$^1$H-NMR (CDCl$_3$) δ:8.48 (1H, dd, J=5.8, 0.8 Hz), 7.97 (1H, s), 7.37 (2H, d, J=4.6 Hz), 7.24 (1H, t, J=4.6 Hz), 6.59 (1H, dd, J=5.8, 0.8 Hz), 5.53 (2H, s), 4.02 (3H, s), 3.67 (3H, s), 2.70 (3H, s), 2.60 (3H, s), 2.08 (3H, s).

Present Compound 86

$^1$H-NMR (CDCl$_3$) δ:8.05 (1H, s), 7.38 (2H, d, J=4.7 Hz), 7.24 (1H, t, J=4.7 Hz), 5.94 (1H, s), 5.54 (2H, s), 3.99 (6H, s), 3.68 (3H, s), 2.75 (3H, s), 2.61 (3H, s), 2.09 (3H, s).

Production Example 13

A mixture of 0.39 g of 32A mentioned in Reference Production Example 32, 0.12 g of 2-cyanophenol, 0.02 g of copper iodide, 0.06 g of N-butylimidazole, 0.28 g of potassium carbonate, and 2 mL of toluene was stirred at 120° C. for 8 hours. The reaction solution was poured into water and the mixture was extracted with chloroform. The organic layer was washed with water and a saturated saline solution, dried over anhydrous magnesium sulfate, and then concentrated under reduced pressure. The residue thus obtained was subjected to silica gel column chromatography to obtain 0.13 g of 1-[2-{2-methyl-6-(2-cyanophenoxy)pyridin-3-yloxymethyl}-3-methylphenyl]-4-methyl-1,4-dihydrotetrazol-5-one (hereinafter referred to as the present compound 62).

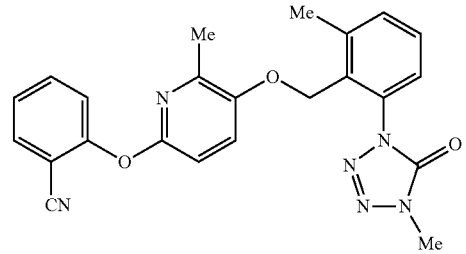 [SMILES: Cc1cccc(-n2nnn(C)c2=O)c1COc1ccc(Oc2ccccc2C#N)nc1C]

$^1$H-NMR (CDCl$_3$) δ:7.64 (1H, dd, J=7.7, 1.8 Hz), 7.55-7.49 (1H, m), 7.47-7.39 (2H, m), 7.31-7.27 (1H, m), 7.23-7.15 (2H, m), 7.12 (1H, dd, J=8.4, 0.5 Hz), 6.81 (1H, d, J=8.6 Hz), 5.03 (2H, s), 3.66 (3H, s), 2.52 (3H, s), 2.22 (3H, s).

Production Example 14

A mixture of 0.44 g of 45A mentioned in Reference Production Example 45, 0.09 g of phenol, 0.02 g of copper iodide, 0.06 g of N-butylimidazole, 0.28 g of potassium carbonate, and 2 mL of toluene was stirred at 120° C. for 16 hours. The reaction solution was poured into water and the mixture was extracted with chloroform. The organic layer was washed with water and a saturated saline solution, dried over anhydrous magnesium sulfate, and then concentrated under reduced pressure. The residue thus obtained was subjected to silica gel column chromatography to obtain 0.15 g of 1-[2-{5-phenoxypyridin-3-yloxymethyl}-3-methylphenyl]-4-methyl-1,4-dihydrotetrazol-5-one (hereinafter referred to as the present compound 63).

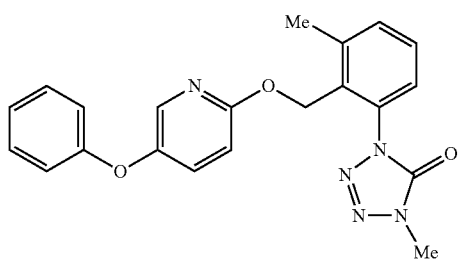 [SMILES: Cc1cccc(-n2nnn(C)c2=O)c1COc1ccc(Oc2ccccc2)cn1]

1H-NMR (CDCl$_3$) δ:7.86 (1H, d, J=3.0 Hz), 7.43-7.37 (2H, m), 7.35-7.29 (2H, m), 7.28-7.24 (2H, m), 7.11-7.05 (1H, m), 6.95-6.93 (2H, m), 6.66 (1H, d, J=8.9 Hz), 5.35 (2H, s), 3.68 (3H, s), 2.56 (3H, s).

According to the same reaction as in Production Example 14, the present compound 64 was synthesized.

The structural formula and $^1$H-NMR data of the thus obtained compound are shown below.

Present Compound 64

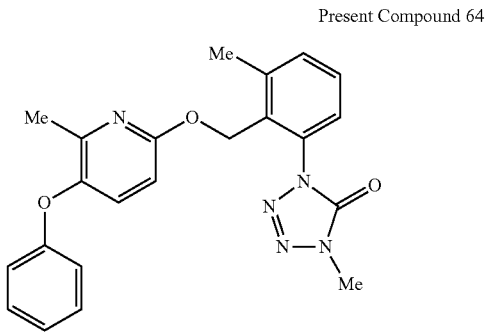 [SMILES: Cc1cccc(-n2nnn(C)c2=O)c1COc1ccc(Oc2ccccc2)c(C)n1]

$^1$H-NMR (CDCl$_3$) δ:7.57 (1H, d, J=8.5 Hz), 7.39-7.36 (3H, m), 7.31-7.27 (1H, m), 7.17 (1H, d, J=8.7 Hz), 7.05-7.00 (1H, m), 6.84-6.82 (2H, m), 6.48 (1H, dd, J=8.7, 0.5 Hz), 5.38 (2H, s), 3.68 (3H, s), 2.57 (3H, s), 2.29 (3H, s).

Production Example 15

A mixture of 0.41 g of 46A mentioned in Reference Production Example 46, 0.15 g of 2-methoxyphenylboronic acid, 0.64 g of tripotassium phosphate, 0.40 ml of water, 0.02 g of [1,1'-bis(diphenylphosphino)ferrocene]palladium (II) dichloride dichloromethane adduct, and 4 ml of dimethoxyethane was stirred with heating under reflux for 4 hours. After cooling, water was poured into the reaction solution and the mixture was extracted with ethyl acetate.

The organic layer was washed with water and a saturated saline solution, dried over anhydrous magnesium sulfate, and then concentrated under reduced pressure. The residue thus obtained was subjected to silica gel column chromatography to obtain 0.20 g of 1-[2-{5-(2-methoxyphenyl)-6-methyl-pyridin-2-yloxymethyl}-3-methoxyphenyl]-4-methyl-1,4-dihydrotetrazol-5-one (hereinafter referred to as the present compound 69).

Present Compound 69

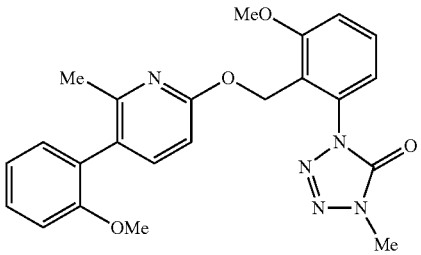

$^1$H-NMR (CDCl$_3$) δ:7.45 (1H, t, J=8.2 Hz), 7.39-7.30 (2H, m), 7.11-6.94 (5H, m), 6.48 (1H, d, J=8.4 Hz), 5.50 (2H, s), 3.93 (3H, s), 3.77 (3H, s), 3.62 (3H, s), 2.23 (3H, s).

According to the same reaction as in Production Example 15, the present compound 70 was synthesized.

The structural formula and $^1$H-NMR data of the thus obtained compound are shown below.

Present Compound 70

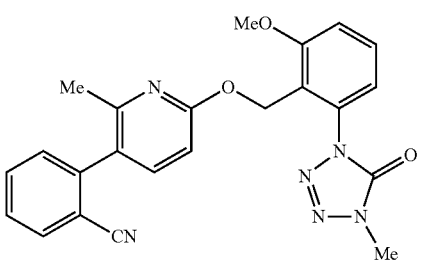

$^1$H-NMR (CDCl$_3$) δ:7.77-7.74 (1H, m), 7.66-7.60 (1H, m), 7.50-7.43 (2H, m), 7.38-7.35 (1H, m), 7.35-7.32 (1H, m), 7.10 (1H, d, J=8.4 Hz), 7.06 (1H, d, J=7.9 Hz), 6.55 (1H, d, J=8.4 Hz), 5.50 (2H, s), 3.93 (3H, s), 3.64 (3H, s), 2.29 (3H, s).

Production Example 16

A mixture of 0.45 g of 44A of Reference Production Example 44, 0.16 g of 3-methylpyrazole, 0.55 g of copper (II) acetate, 0.32 g of pyridine, 0.53 g of Molecular Sieves 4 Å, and 4 ml of acetonitrile was stirred with heating under reflux for 12 hours. After cooling, water was poured into the reaction solution and the mixture was extracted with ethyl acetate. The organic layer was washed with water and a saturated saline solution, dried over anhydrous magnesium sulfate, and then concentrated under reduced pressure. The residue thus obtained was subjected to silica gel column chromatography to obtain 0.30 g of 1-[2-{2,6-dimethyl-5-(3-methylpyrazol-1-yl)pyridin-2-yloxymethyl}-3-methylphenyl]-4-methyl-1,4-dihydrotetrazol-5-one (hereinafter referred to as the present compound 69).

Present Compound 80

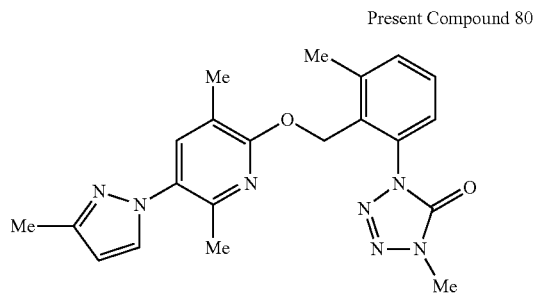 [SMILES: Cc1ccn(-c2cc(C)c(OCc3c(C)cccc3-n3nnn(C)c3=O)nc2C)n1]

$^1$H-NMR (CDCl$_3$) δ:7.38-7.36 (3H, m), 7.30 (1H, s), 7.25-7.22 (1H, m), 6.18 (1H, d, J=2.3 Hz), 5.47 (2H, s), 3.69 (3H, s), 2.59 (3H, s), 2.34 (3H, s), 2.22 (3H, s), 2.03 (3H, s).

Production Example 17

A mixture of 0.41 g of the present compound 79, 0.27 g of N-chlorosuccinimide, and 8 ml of chloroform was stirred with heating under reflux for 8 hours. After cooling, water was poured into the reaction solution and the mixture was extracted with ethyl acetate. The organic layer was washed with water and a saturated saline solution, dried over anhydrous magnesium sulfate, and then concentrated under reduced pressure. The residue thus obtained was subjected to silica gel column chromatography to obtain 0.07 g of 1-[2-{3,6-dimethyl-5-(4-chloro-1-methylpyrazol-3-yl)pyridin-2-yloxymethyl}-3-methylphenyl]-4-methyl-1,4-dihydrotetrazol-5-one (hereinafter referred to as the present compound 69).

Present Compound 87

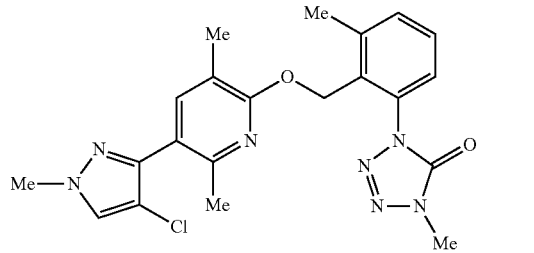

$^1$H-NMR (CDCl$_3$) δ:7.42 (1H, s), 7.39-7.36 (2H, m), 7.31 (1H, s), 7.26-7.22 (1H, m), 5.49 (2H, s), 3.90 (3H, s), 3.67 (3H, s), 2.59 (3H, s), 2.35 (3H, s), 2.04 (3H, s).

Production Example 18

A mixture of 0.42 g of the present compound 3, 0.49 g of Lawesson's reagent (2,4-Bis(4-methoxyphenyl)-1,3,2,4-dithiadiphosphetane 2,4-disulfide), 0.01 g of triethylamine, and 10 mL of toluene was stirred with heating under reflux for 8 hours, and then concentrated under reduced pressure. The residue thus obtained was subjected to silica gel column chromatography to obtain 0.10 g of 1-[2-{6-methyl-5-(4-methoxyphenyl)pyridin-2-yloxymethyl}-3-methylphenyl]-4-methyl-1,4-dihydrotetrazole-5-thione (hereinafter referred to as the present compound 88).

Present Compound 88

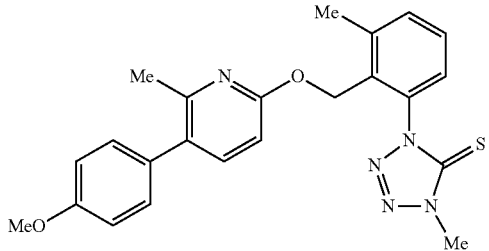

$^1$H-NMR (CDCl$_3$) δ:7.42 (1H, d, J=6.9 Hz), 7.38-7.34 (1H, m), 7.32 (1H, d, J=8.0 Hz), 7.24-7.21 (2H, m), 7.20-7.17 (1H, m), 7.00-6.95 (3H, m), 4.48 (2H, s), 3.91 (3H, s), 3.86 (3H, s), 2.55 (3H, s), 2.48 (3H, s).

With respect to the production of intermediates for the production of the above-mentioned present compounds, Reference Production Example are shown below.

Reference Production Example 1

Under ice cooling, 21.9 g of anhydrous aluminum chloride was added to 250 ml of N,N-dimethylformamide, followed by stirring for 15 minutes. To this was added 10.7 g of sodium azide and, after stirring for 15 minutes, 25.0 g of 1-chloro-3-isocyanato-2-methylbenzene was added and the mixture was heated at 80° C. for 5 hours. After cooling, the reaction solution was added in a mixture of 35 g of sodium nitrite, 2 L of water, and 500 g of ice while stirring. The mixture was acidified with 10% hydrochloric acid and then extracted with ethyl acetate. The organic layer was washed with water and a saturated saline solution, dried over anhydrous magnesium sulfate, and then concentrated under reduced pressure to obtain 17.0 g of 1-(2-methyl-3-chlorophenyl)-1,4-dihydrotetrazol-5-one (hereinafter referred to as 1A).

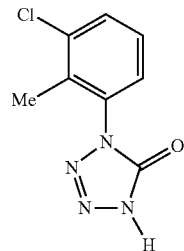

$^1$H-NMR (CDCl$_3$) δ (ppm): 2.32 (3H, s), 7.28-7.36 (2H, m), 7.57 (1H, dd, J=6.8, 2.2 Hz), 13.08 (1H, s).

Reference Production Example 2

To a mixture of 10.00 g of 1A mentioned in Reference Production Example 1 and 100 mL of N,N-dimethylformamide, 2.30 g of 60% sodium hydride was added under ice cooling. The temperature of the mixture was raised to room temperature, followed by stirring for 1 hour. To the reaction mixture, 3.2 ml of methyl iodide was added under ice cooling. The temperature of the mixture was raised to room temperature, followed by stirring for 14 hours. Water was poured into the reaction mixture and the mixture was extracted with ethyl acetate. The organic layer was washed with 10% hydrochloric acid, water, and a saturated saline solution, dried over anhydrous magnesium sulfate, and then concentrated under reduced pressure. The residue thus obtained was subjected to silica gel column chromatography to obtain 1.56 g of 1-(2-methyl-3-chlorophenyl)-4-methyl-1,4-dihydrotetrazol-5-one (hereinafter referred to as 2A).

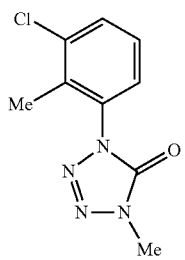

$^1$H-NMR (CDCl$_3$) δ (ppm): 2.30 (3H, s), 3.73 (3H, s), 7.27 (1H, d, J=2.7 Hz), 7.28 (1H, d, J=7.1 Hz), 7.52 (1H, dd, J=2.7, 6.8 Hz).

Reference Production Example 3

A mixture of 1.56 g of 2A mentioned in Reference Production Example 2, 0.34 g of 1,1'-azobis(cyclohexane-1-carbonitrile), 1.42 g of N-bromosuccinimide, and 30 ml of chlorobenzene was stirred with heating under reflux for 5 hours. After cooling, water was poured into the reaction solution and the mixture was extracted with ethyl acetate. The organic layer was washed with water and a saturated saline solution, dried over anhydrous magnesium sulfate, and then concentrated under reduced pressure. The residue thus obtained was subjected to silica gel column chromatography to obtain 1.94 g of 1-(2-bromomethyl-3-chlorophenyl)-4-methyl-1,4-dihydrotetrazol-5-one (hereinafter referred to as 3A).

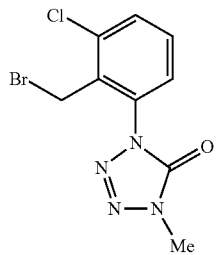

$^1$H-NMR (CDCl$_3$) δ (ppm): 3.76 (3H, s), 4.69 (2H, s), 7.35 (1H, dd, J=1.2, 8.1 Hz), 7.43 (1H, t, J=8.1 Hz), 7.58 (1H, dd, J=1.2, 8.1 Hz).

Reference Production Example 4

A mixture of 15.0 g of 3-amino-1-methoxy-2-methylbenzene, 48.7 g of triphosgene, and 350 ml of toluene was stirred with heating under reflux for 3 hours. The reaction mixture allowed to cool was concentrated under reduced pressure to obtain 17.0 g of 1-methoxy-3-isocyanato-2-methylbenzene (hereinafter referred to as 4A).

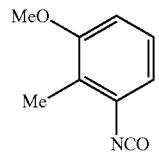

$^1$H-NMR (CDCl$_3$) δ (ppm): 2.19 (3H, s), 3.82 (3H, s), 6.69 (1H, d, J=8.2 Hz), 6.72 (1H, dd, J=0.5, 8.0 Hz), 7.09 (1H, t, J=8.2 Hz).

Reference Production Example 5

Under ice cooling, 16.0 g of anhydrous aluminum chloride was added to 180 mL of N,N-dimethylformamide, followed by stirring for 15 minutes. To this was added 7.8 g of sodium azide and, after stirring for 15 minutes, 17.0 g of 4A mentioned in Reference Production Example 4 was added and the mixture was heated at 80° C. for 4.5 hours. After cooling, the reaction solution was added in a mixture of 25 g of sodium nitrite, 2 L of water, and 500 g of ice while stirring. The mixture was acidified with 10% hydrochloric acid and then extracted with ethyl acetate. The organic layer was washed with water and a saturated saline solution, dried over anhydrous magnesium sulfate, and then concentrated under reduced pressure to obtain 16.2 g of 1-(2-methyl-3-methoxyphenyl)-1,4-dihydrotetrazol-5-one (hereinafter referred to as 5A).

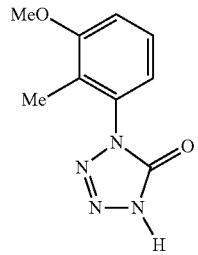 [SMILES: COc1cccc(-n2nn[nH]c2=O)c1C]

$^1$H-NMR (DMSO-d$_6$) δ (ppm): 1.99 (3H, s), 3.87 (3H, s), 7.01 (1H, d, J=8.1 Hz), 7.17 (1H, d, J=8.1 Hz), 7.36 (1H, t, J=8.3 Hz), 14.63 (1H, s).

Reference Production Example 6

To a mixture of 10.00 g of 5A mentioned in Reference Production Example 5 and 100 mL of N,N-dimethylformamide, 2.47 g of 60% sodium hydride was added under ice cooling. The temperature of the mixture was raised to room temperature, followed by stirring for 1 hour. To the reaction mixture, 3.5 mL of methyl iodide was added under ice cooling. The temperature of the mixture was raised to room temperature, followed by stirring for 14 hours. Water was poured into the reaction mixture and the mixture was extracted with ethyl acetate. The organic layer was washed with 10% hydrochloric acid, water, and a saturated saline solution, dried over anhydrous magnesium sulfate, and then concentrated under reduced pressure. The residue thus obtained was subjected to silica gel column chromatography to obtain 2.19 g of 1-(2-methyl-3-methoxyphenyl)-4-methyl-1,4-dihydrotetrazol-5-one (hereinafter referred to as 6A).

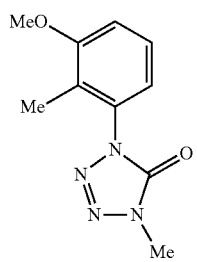 [SMILES: COc1cccc(-n2nnn(C)c2=O)c1C]

¹H-NMR (CDCl₃) δ (ppm): 2.11 (3H, s), 3.72 (3H, s), 3.88 (3H, s), 6.95 (1H, d, J=8.2 Hz), 6.98 (1H, d, J=8.5 Hz), 7.29 (1H, t, J=8.2 Hz)

Reference Production Example 7

A mixture of 2.19 g of 6A mentioned in Reference Production Example 6, 0.52 g of 1,1'-azobis(cyclohexane-1-carbonitrile), 2.16 g of N-bromosuccinimide, and 40 mL of chlorobenzene was stirred with heating under reflux for 5 hours. After cooling, water was poured into the reaction solution and the mixture was extracted with ethyl acetate. The organic layer was washed with water and a saturated saline solution, dried over anhydrous magnesium sulfate, and then concentrated under reduced pressure. The residue thus obtained was subjected to silica gel column chromatography to obtain 2.36 g of 1-(2-bromomethyl-3-methoxyphenyl)-4-methyl-1,4-dihydrotetrazol-5-one (hereinafter referred to as 7A).

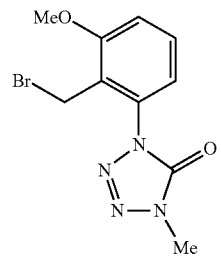

¹H-NMR (CDCl₃) δ (ppm): 3.74 (3H, s), 3.96 (3H, s), 4.93 (2H, s), 7.02 (1H, dd, J=1.0, 8.5 Hz), 7.04 (1H, d, J=9.0 Hz), 7.43 (1H, t, J=8.1 Hz).

Reference Production Example 8

A mixture of 25.0 g of 1-bromo-2-methyl-3-aminobenzene, 60.0 g of triphosgene, and 400 ml of toluene was stirred with heating under reflux for 3 hours. The reaction mixture allowed to cool was concentrated under reduced pressure to obtain 30.3 g of 1-bromo-3-isocyanato-2-methylbenzene (hereinafter referred to as 8A).

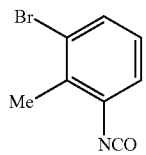

¹H-NMR (CDCl₃) δ (ppm): 2.42 (3H, s), 7.00 (1H, dt, J=0.5, 8.0 Hz), 7.05 (1H, dd, J=1.7, 8.0 Hz), 7.39 (1H, dd, 1.5, 7.7 Hz).

Reference Production Example 9

Under ice cooling, 19.7 g of anhydrous aluminum chloride was added to 220 ml of N,N-dimethylformamide, followed by stirring for 15 minutes. To this was added 9.6 g of sodium azide and, after stirring for 15 minutes, 30.3 g of 8A mentioned in Reference Production Example 8 was added and the mixture was heated at 80° C. for 5 hours. After cooling, the reaction solution was added in a mixture of 33 g of sodium nitrite, 2 L of water, and 500 g of ice while stirring. The mixture was acidified with 10% hydrochloric acid and then extracted with ethyl acetate. The organic layer was washed with water and a saturated saline solution, dried over anhydrous magnesium sulfate, and then concentrated under reduced pressure to obtain 31.4 g of 1-(2-methyl-3-bromophenyl)-1,4-dihydrotetrazol-5-one (hereinafter referred to as 9A).

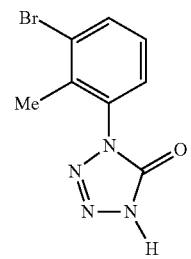

¹H-NMR (DMSO-d₆) δ (ppm): 2.22 (3H, s), 7.34 (1H, t, J=7.2 Hz), 7.49 (1H, dd, J=8.2, 1.1 Hz), 7.82 (1H, dd, J=8.0, 1.0 Hz), 14.72 (1H, s).

Reference Production Example 10

To a mixture of 31.4 g of 9A mentioned in Reference Production Example 9 and 250 mL of N,N-dimethylformamide, 5.90 g of 60% sodium hydride was added under ice cooling. The temperature of the mixture was raised to room temperature, followed by stirring for 1 hour. To the reaction mixture, 8.4 mL of methyl iodide was added under ice cooling. The temperature of the mixture was raised to room temperature, followed by stirring for 14 hours. Water was poured into the reaction mixture and the mixture was extracted with ethyl acetate. The organic layer was washed with 10% hydrochloric acid, water, and a saturated saline solution, dried over anhydrous magnesium sulfate, and then concentrated under reduced pressure. The residue thus obtained was subjected to silica gel column chromatography to obtain 8.47 g of 1-(2-methyl-3-bromophenyl)-4-methyl-1,4-dihydrotetrazol-5-one (hereinafter referred to as 10A)

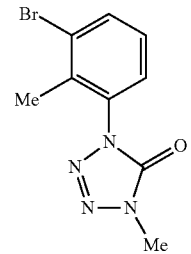

¹H-NMR (CDCl₃) δ (ppm): 2.33 (3H, s), 3.73 (3H, s), 7.21 (1H, dt, J=0.5, 7.8 Hz), 7.30 (1H, dd, J=1.0, 8.0 Hz), 7.71 (1H, dd, J=1.2, 8.3 Hz).

Reference Production Example 11

A mixture of 8.47 g of 10A mentioned in Reference Production Example 10, 1.54 g of 1,1'-azobis(cyclohexane-1-carbonitrile), 6.44 g of N-bromosuccinimide, and 125 ml of chlorobenzene was stirred with heating under reflux for 5 hours. After cooling, water was poured into the reaction solution and the mixture was extracted with ethyl acetate. The organic layer was washed with water and a saturated saline solution, dried over anhydrous magnesium sulfate, and then concentrated under reduced pressure. The residue thus obtained was subjected to silica gel column chromatography to obtain 7.52 g of 1-(2-bromomethyl-3-bromophenyl)-4-methyl-1,4-dihydrotetrazol-5-one (hereinafter referred to as 11A).

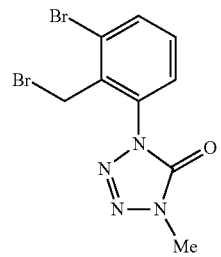

$^{1}$H-NMR (CDCl$_3$) δ (ppm): 3.76 (3H, s), 4.71 (2H, s), 7.34 (1H, t, J=7.8 Hz), 7.38 (1H, dd, J=8.0, 1.7 Hz), 7.77 (1H, dd, J=7.8, 1.7 Hz).

Reference Production Example 12

A mixture of 45.0 g of 11A mentioned in Reference Production Example 11, 37.4 g of sodium methoxide, and 600 mL of tetrahydrofuran was stirred at room temperature for 3 hours. A saturated sodium bicarbonate solution was poured into the reaction mixture and the mixture was extracted with ethyl acetate. The organic layer was washed with a saturated sodium bicarbonate solution, dried over anhydrous sodium sulfate, and then concentrated under reduced pressure to obtain 36.2 g of 1-(2-methoxymethyl-3-bromophenyl)-4-methyl-1,4-dihydrotetrazol-5-one (hereinafter referred to as 12A).

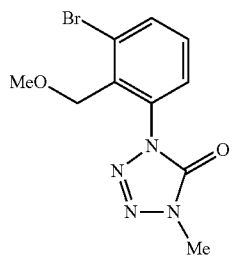 [SMILES: COCc1c(Br)cccc1-n1nnn(C)c1=O]

$^{1}$H-NMR (CDCl$_3$) δ (ppm): 3.23 (3H, s), 3.72 (3H, s), 4.67 (2H, s), 7.33 (1H, t, J=7.8 Hz), 7.38 (1H, dd, J=1.2, 8.1 Hz), 7.76 (1H, dd, J=1.5, 7.8 Hz).

Reference Production Example 13

A mixture of 36.2 g of 12A mentioned in Reference Production Example 12, 23.2 g of methylboronic acid, 66.7 g of cesium fluoride, 10.6 g of [1,1'-bis(diphenylphosphino)ferrocene]palladium(II) dichloride dichloromethane adduct, and 500 ml of dioxane was stirred at 90° C. for 5.5 hours. After cooling, the reaction mixture was filtered and the filtrate was concentrated under reduced pressure. The residue thus obtained was subjected to silica gel column chromatography to obtain 25.6 g of 1-(2-methoxymethyl-3-methylphenyl)-4-methyl-1,4-dihydrotetrazol-5-one (hereinafter referred to as 13A).

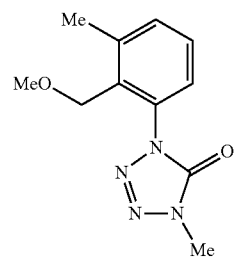 [SMILES: COCc1c(C)cccc1-n1nnn(C)c1=O]

$^{1}$H-NMR (CDCl$_3$) δ (ppm): 2.48 (3H, s), 3.23 (3H, s), 3.72 (3H, s), 4.42 (2H, s), 7.21 (1H, t, J=5.1 Hz), 7.35 (2H, d, J=4.8 Hz).

Reference Production Example 14

A mixture of 25.6 g of 13A mentioned in Reference Production Example 13, 50 ml of acetic acid, and 50 ml of a 25% hydrogen bromide-acetic acid solution was stirred at 65° C. for 1 hour. A saturated saline solution was poured into the reaction mixture and the mixture was extracted with ethyl acetate. The organic layer was washed with a saturated sodium bicarbonate solution, dried over anhydrous sodium sulfate, and then concentrated under reduced pressure to obtain 27.9 g of 1-(2-bromomethyl-3-methylphenyl)-4-methyl-1,4-dihydrotetrazol-5-one (hereinafter referred to as 14A).

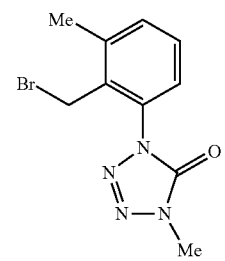

$^{1}$H-NMR (CDCl$_3$) δ (ppm): 2.51 (3H, s), 3.75 (3H, s), 4.51 (2H, s), 7.22-7.24 (1H, m), 7.36-7.39 (2H, m).

Reference Production Example 15

A mixture of 30.1 g of 12A mentioned in Reference Production Example 12, 12.9 g of cyclopropylboronic acid, 46.2 g of cesium fluoride, 8.2 g of [1,1'-bis(diphenylphosphino)ferrocene]palladium(II) dichloride dichloromethane adduct, and 680 ml of dioxane was stirred at 90° C. for 4 hours. After cooling, the reaction mixture was filtered and the filtrate was concentrated under reduced pressure. The residue thus obtained was subjected to silica gel column chromatography to obtain 26.0 g of 1-(2-methoxymethyl-3-cyclopropylphenyl)-4-methyl-1,4-dihydrotetrazol-5-one (hereinafter referred to as 15A).

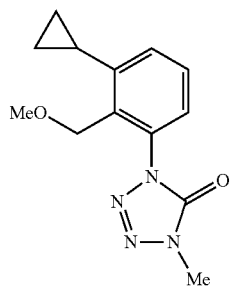 [SMILES: COCc1c(C2CC2)cccc1-n1nnn(C)c1=O]

$^1$H-NMR (CDCl$_3$) δ (ppm): 7.36 (1H, t, J=8.0 Hz), 7.20 (2H, d, J=8.0 Hz), 4.64 (2H, s), 3.72 (3H, s), 3.24 (3H, s), 2.20-2.13 (1H, m), 1.04-1.00 (2H, m), 0.76-0.72 (2H, m).

Reference Production Example 16

A mixture of 26.0 g of 15A mentioned in Reference Production Example 15, 40 ml of acetic acid, and 40 ml of a 25% hydrogen bromide-acetic acid solution was stirred at 65° C. for 2 hours. A saturated saline solution was poured into the reaction mixture and the mixture was extracted with ethyl acetate. The organic layer was washed with a saturated sodium bicarbonate solution, dried over anhydrous sodium sulfate, and then concentrated under reduced pressure to obtain 30.8 g of 1-(2-bromomethyl-3-cyclopropylphenyl)-4-methyl-1,4-dihydrotetrazol-5-one (hereinafter referred to as 16A).

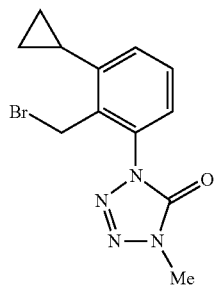

$^1$H-NMR (CDCl$_3$) δ (ppm): 7.38 (1H, t, J=7.8 Hz), 7.26-7.22 (2H, m), 4.77 (2H, s), 3.75 (3H, s), 2.16-2.09 (1H, m), 1.10-1.06 (2H, m), 0.82-0.78 (2H, m).

Reference Production Example 17

A mixture of 29.8 g of 12A mentioned in Reference Production Example 12, 35.2 g of tributylvinyltin, 11.6 g of tetrakistriphenylphosphinepalladium, and 500 ml of toluene was stirred with heating under reflux for 14 hours. After cooling, an aqueous saturated ammonium chloride solution was poured into the reaction solution and the mixture was extracted with ethyl acetate. The organic layer was washed with water and a saturated saline solution, dried over anhydrous magnesium sulfate, and then concentrated under reduced pressure. The residue thus obtained was subjected to silica gel column chromatography to obtain 19.7 g of 1-(2-methoxymethyl-3-ethenylphenyl)-4-methyl-1,4-dihydrotetrazol-5-one (hereinafter referred to as 17A)

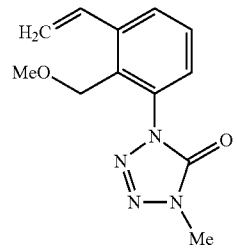 [SMILES: C=Cc1cccc(-n2nnn(C)c2=O)c1COC]

$^1$H-NMR (CDCl$_3$) δ (ppm): 7.67 (1H, dd, J=7.8, 1.3 Hz), 7.44 (1H, t, J=7.8 Hz), 7.29 (1H, dd, J=7.8, 1.3 Hz), 7.11 (1H, dd, J=17.4, 11.1 Hz), 5.72 (1H, dd, J=17.4, 1.3 Hz), 5.44 (1H, dd, J=11.1, 1.3 Hz), 4.45 (2H, s), 3.72 (3H, s), 3.23 (3H, s).

Reference Production Example 18

A mixture of 19.7 g of 17A mentioned in Reference Production Example 17, 3.02 g of a palladium-fibroin complex, and 1 L of methanol was stirred in a hydrogen atmosphere at room temperature for 11 hours. The reaction mixture was filtered and the filtrate was concentrated under reduced pressure. The residue thus obtained was subjected to silica gel column chromatography to obtain 19.3 g of 1-(2-methoxymethyl-3-ethylphenyl)-4-methyl-1,4-dihydrotetrazol-5-one (hereinafter referred to as 18A).

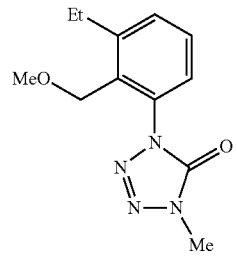 [SMILES: CCc1cccc(-n2nnn(C)c2=O)c1COC]

$^1$H-NMR (CDCl$_3$) δ (ppm): 7.42-7.38 (2H, m), 7.23-7.20 (1H, m), 4.44 (2H, s), 3.72 (3H, s), 3.22 (3H, s), 2.82 (2H, q, J=7.6 Hz), 1.27 (3H, t, J=7.6 Hz).

Reference Production Example 19

A mixture of 19.3 g of 18A mentioned in Reference Production Example 18, 40 ml of acetic acid, and 40 ml of a 25% hydrogen bromide-acetic acid solution was stirred at 65° C. for 1.5 hours. A saturated saline solution was poured into the reaction mixture and the mixture was extracted with ethyl acetate. The organic layer was washed with a saturated sodium bicarbonate solution, dried over anhydrous sodium sulfate, and then concentrated under reduced pressure to obtain 23.3 g of 1-(2-bromomethyl-3-ethylphenyl)-4-methyl-1,4-dihydrotetrazol-5-one (hereinafter referred to as 19A).

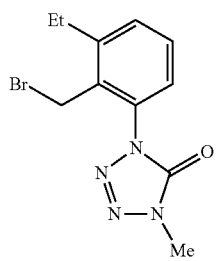

$^1$H-NMR (CDCl$_3$) δ (ppm): 7.44-7.37 (2H, m), 7.23 (1H, dd, J=7.1, 2.0 Hz), 4.56 (2H, s), 3.75 (3H, s), 2.85 (2H, q, J=7.6 Hz), 1.33 (3H, t, J=7.6 Hz).

Reference Production Example 20

Under ice cooling, a mixture of 7.00 g of 14A mentioned in Reference Production Example 14, 9.90 g of calcium carbonate, 80 ml of dioxane, and 80 ml of water was stirred with heating under reflux for 7 hours. After cooling, water was poured into the reaction solution and the mixture was extracted with ethyl acetate. The organic layer was washed with water and a saturated saline solution, dried over anhydrous magnesium sulfate, and then concentrated under reduced pressure to obtain 4.68 g of 1-(2-hydroxymethyl-3-methylphenyl)-4-methyl-1,4-dihydrotetrazol-5-one (hereinafter referred to as 20A).

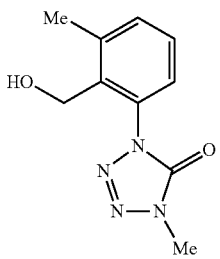 [SMILES: Cc1cccc(-n2nnn(C)c2=O)c1CO]

$^1$H-NMR (CDCl$_3$) δ (ppm): 7.39-7.34 (2H, m), 7.23-7.18 (1H, m), 4.48 (2H, d, J=7.1 Hz), 3.75 (3H, s), 2.56 (3H, s).

Reference Production Example 21

Under ice cooling, a mixture of 3.00 g of 19A mentioned in Reference Production Example 19, 4.00 g of calcium carbonate, 50 ml of dioxane, and 50 ml of water was stirred with heating under reflux for 6 hours. After cooling, water was poured into the reaction solution and the mixture was extracted with ethyl acetate. The organic layer was washed with water and a saturated saline solution, dried over anhydrous magnesium sulfate, and then concentrated under reduced pressure to obtain 2.58 g of 1-(2-hydroxymethyl-3-ethylphenyl)-4-methyl-1,4-dihydrotetrazol-5-one (hereinafter referred to as 21A).

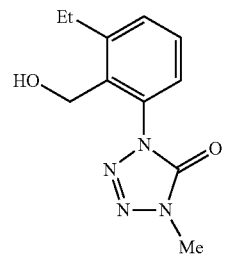

$^1$H-NMR (CDCl$_3$) δ (ppm): 7.44-7.39 (2H, m), 7.23-7.19 (1H, m), 4.49 (2H, d, J=7.2 Hz), 3.75 (3H, s), 2.93 (2H, q, J=7.6 Hz), 1.31 (3H, t, J=7.6 Hz).

Reference Production Example 22

Under ice cooling, a mixture of 3.00 g of 16A mentioned in Reference Production Example 16, 3.90 g of calcium carbonate, 50 ml of dioxane, and 50 ml of water was stirred with heating under reflux for 6 hours. After cooling, water was poured into the reaction solution and the mixture was extracted with ethyl acetate. The organic layer was washed with water and a saturated saline solution, dried over anhydrous magnesium sulfate, and then concentrated under reduced pressure to obtain 2.72 g of 1-(2-hydroxymethyl-3-cyclopropylphenyl)-4-methyl-1,4-dihydrotetrazol-5-one (hereinafter referred to as 22A).

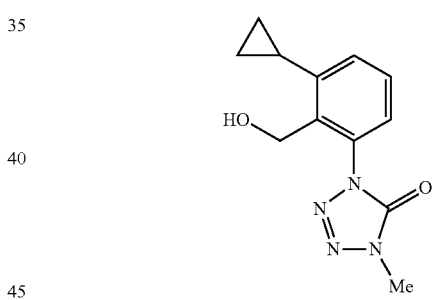

$^1$H-NMR (CDCl$_3$) δ (ppm): 7.38 (1H, t, J=7.8 Hz), 7.20 (1H, d, J=8.0 Hz), 7.16 (1H, d, J=7.7 Hz), 4.68 (2H, d, J=7.0 Hz), 3.76 (3H, s), 2.39-2.32 (1H, m), 1.10-1.05 (2H, m), 0.79-0.75 (2H, m).

Reference Production Example 23

Under ice cooling, a mixture of 3.00 g of 7A mentioned in Reference Production Example 7, 4.02 g of calcium carbonate, 50 ml of dioxane, and 50 ml of water was stirred with heating under reflux for 5 hours. After cooling, water was poured into the reaction solution and the mixture was extracted with ethyl acetate. The organic layer was washed with water and a saturated saline solution, dried over anhydrous magnesium sulfate, and then concentrated under reduced pressure to obtain 1.70 g of 1-(2-hydroxymethyl-3-methoxyphenyl)-4-methyl-1,4-dihydrotetrazol-5-one (hereinafter referred to as 23A).

119

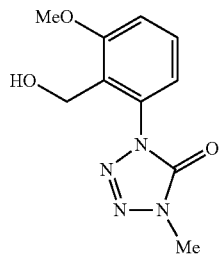 [SMILES: COc1cccc(-n2nnn(C)c2=O)c1CO]

¹H-NMR (CDCl₃) δ (ppm): 7.44 (1H, t, J=8.2 Hz), 7.07 (1H, d, J=8.5 Hz), 7.01 (1H, d, J=8.0 Hz), 4.55 (2H, d, J=7.0 Hz), 3.95 (3H, s), 3.74 (3H, s).

Reference Production Example 24

Under ice cooling, a mixture of 4.87 g of 3A mentioned in Reference Production Example 3, 6.42 g of calcium carbonate, 50 ml of dioxane, and 50 ml of water was stirred with heating under reflux for 7 hours. After cooling, water was poured into the reaction solution and the mixture was extracted with ethyl acetate. The organic layer was washed with water and a saturated saline solution, dried over anhydrous magnesium sulfate, and then concentrated under reduced pressure to obtain 2.00 g of 1-(2-hydroxymethyl-3-chlorophenyl)-4-methyl-1,4-dihydrotetrazol-5-one (hereinafter referred to as 24A).

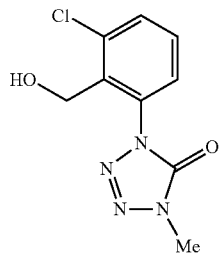 [SMILES: Cn1nnn(-c2cccc(Cl)c2CO)c1=O]

¹H-NMR (CDCl₃) δ (ppm): 7.61 (1H, dd, J=8.0, 1.1 Hz), 7.43 (1H, t, J=8.0 Hz), 7.34 (1H, dd, J=8.0, 1.1 Hz), 4.64 (2H, d, J=7.3 Hz), 3.76 (3H, s).

Reference Production Example 25

A mixture of 5.56 g of 14A mentioned in Reference Production Example 14, 3.76 g of 3-bromo-6-hydroxy-2-methylpyridine, 5.53 g of potassium carbonate, and 80 ml of acetonitrile was stirred with heating at 80° C. for 4 hours. Water was added to the reaction mixture and the mixture was extracted with chloroform. The organic layer was washed with a saturated saline solution, dried over anhydrous magnesium sulfate, and then concentrated under reduced pressure to obtain 4.51 g of 1-[2-(5-bromo-6-methyl-pyridin-2-yloxymethyl)-3-methylphenyl]-4-methyl-1,4-dihydrotetrazol-5-one (hereinafter referred to as 25A).

120

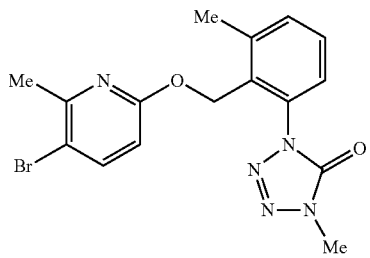 [SMILES: Cc1cccc(-n2nnn(C)c2=O)c1COc1ccc(Br)c(C)n1]

¹H-NMR (CDCl₃) δ:7.57 (1H, d, J=8.5 Hz), 7.39-7.35 (2H, m), 7.25-7.21 (1H, m), 6.37 (1H, dd, J=8.6, 0.6 Hz), 5.35 (2H, s), 3.67 (3H, s), 2.54 (3H, s), 2.49 (3H, s).

Reference Production Example 26

A mixture of 1.59 g of 19A mentioned in Reference Production Example 19, 1.05 g of 3-bromo-6-hydroxy-2-methylpyridine, 1.55 g of potassium carbonate, and 22 ml of acetonitrile was stirred with heating at 80° C. for 4 hours. Water was added to the reaction mixture and the mixture was extracted with chloroform. The organic layer was washed with a saturated saline solution, dried over anhydrous magnesium sulfate, and then concentrated under reduced pressure to obtain 2.04 g of 1-[2-(5-bromo-6-methyl-pyridin-2-yloxymethyl)-3-ethylphenyl]-4-methyl-1,4-dihydrotetrazol-5-one (hereinafter referred to as 26A).

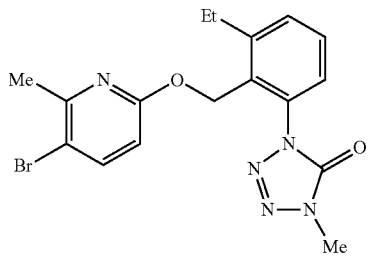 [SMILES: CCc1cccc(-n2nnn(C)c2=O)c1COc1ccc(Br)c(C)n1]

¹H-NMR (CDCl₃) δ:7.57 (1H, d, J=8.5 Hz), 7.45-7.39 (2H, m), 7.26-7.21 (1H, m), 6.36 (1H, d, J=8.7 Hz), 5.36 (2H, s), 3.65 (3H, s), 2.89 (2H, q, J=7.6 Hz), 2.49 (3H, s), 1.28 (3H, t, J=7.6 Hz).

Reference Production Example 27

A mixture of 1.64 g of 16A mentioned in Reference Production Example 16, 1.00 g of 3-bromo-6-hydroxy-2-methylpyridine, 1.47 g of potassium carbonate, and 21 ml of acetonitrile was stirred with heating at 80° C. for 4 hours. Water was added to the reaction mixture and the mixture was extracted with chloroform. The organic layer was washed with a saturated saline solution, dried over anhydrous magnesium sulfate, and then concentrated under reduced pressure to obtain 2.04 g of 1-[2-(5-bromo-6-methyl-pyridin-2-yloxymethyl)-3-cyclopropylphenyl]-4-methyl-1,4-dihydrotetrazol-5-one (hereinafter referred to as 27A).

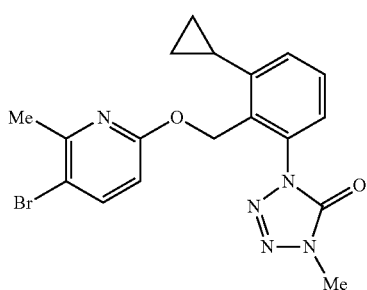 [SMILES: Cc1nc(OCc2c(C3CC3)cccc2-n2nnn(C)c2=O)ccc1Br]

¹H-NMR (CDCl₃) δ:7.60 (1H, d, J=8.6 Hz), 7.42 (1H, t, J=7.9 Hz), 7.28-7.24 (2H, m), 6.40 (1H, dd, J=8.6, 0.6 Hz), 5.58 (2H, s), 3.68 (3H, s), 2.53 (3H, s), 2.27-2.22 (1H, m), 1.06-1.00 (2H, m), 0.82-0.76 (2H, m).

Reference Production Example 28

To a mixture of 1.7 g of 20A mentioned in Reference Production Example 20 and 50 ml of N,N-dimethylformamide, 0.42 g of 55% sodium hydride was added at room temperature, followed by stirring for 1 hour. To the reaction mixture, 2 g of 2,5-dibromo-3-methylpyridine was added, followed by stirring for 4 hours. Water was added to the reaction mixture and the mixture was extracted with ethyl acetate. The organic layer was washed with a saturated saline solution, dried over anhydrous magnesium sulfate, concentrated under reduced pressure, and then subjected to silica gel column chromatography to obtain 1.5 g of 1-[2-(5-bromo-3-methyl-pyridin-2-yloxymethyl)-3-methylphenyl]-4-methyl-1,4-dihydrotetrazol-5-one (hereinafter referred to as 28A).

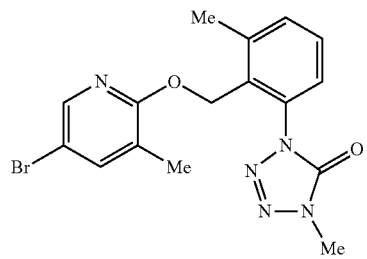 [SMILES: Cc1cc(Br)cnc1OCc1c(C)cccc1-n1nnn(C)c1=O]

¹H-NMR (CDCl₃) δ:7.90 (1H, d, J=2.3 Hz), 7.43 (1H, dd, J=1.6, 0.7 Hz), 7.40-7.35 (2H, m), 7.24 (1H, dd, J=6.5, 2.6 Hz), 5.37 (2H, s), 3.69 (3H, s), 2.55 (3H, s), 2.06 (3H, s).

Reference Production Example 29

A mixture of 1.2 g of 28A mentioned in Reference Production Example 28, 0.94 g of bis(pinacolato)diboron, 0.91 g of potassium acetate, 0.25 g of [1,1'-bis(diphenylphosphino)ferrocene]palladium(II) dichloride dichloromethane adduct, and 30 ml of dimethyl sulfoxide was stirred in a nitrogen atmosphere at 80° C. for 8 hours. Water was poured into the reaction mixture and the mixture was extracted with ethyl acetate. The organic layer was washed with water and a saturated saline solution, dried over anhydrous magnesium sulfate, and then concentrated under reduced pressure. The residue thus obtained was subjected to silica gel column chromatography to obtain 0.9 g of 1-methyl-4-{3-methyl-2-[3-methyl-5-(4,4,5,5-tetramethyl-[1,3,2]dioxaborolan-2-yl)-pyridin-2-yloxymethyl]-phenyl}-1,4-dihydro-tetrazol-5-one (hereinafter referred to as 29A).

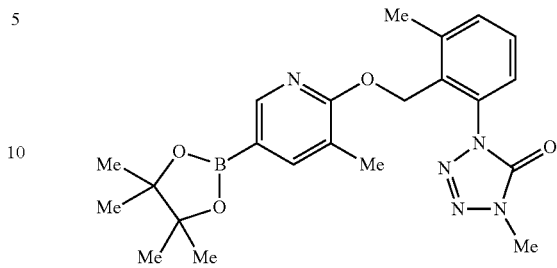

¹H-NMR (CDCl₃) δ:8.26 (1H, d, J=1.4 Hz), 7.68-7.67 (1H, m), 7.36-7.35 (2H, m), 7.24-7.21 (1H, m), 5.44 (2H, s), 3.67 (3H, s), 2.55 (3H, s), 2.04 (3H, s), 1.31 (12H, s).

Reference Production Example 30

A mixture of 5 g of 3-hydroxy-2-methylpyridine, 17.1 g of N-bromo-succinimide, and 70 ml of acetonitrile was stirred at room temperature for 2 hours. The solvent was distilled off under reduced pressure and the mixture was extracted with ethyl acetate. The organic layer was washed with water and a saturated saline solution, dried over anhydrous magnesium sulfate, and then concentrated under reduced pressure. The residue thus obtained was subjected to silica gel column chromatography to obtain 10.8 g of 2,4-dibromo-3-hydroxy-6-methylpyridine (hereinafter referred to as 30A).

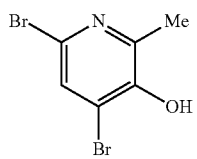

¹H-NMR (CDCl₃) δ:7.46 (1H, d, J=0.7 Hz), 5.55 (1H, s), 2.53 (3H, s).

Reference Production Example 31

To a mixture of 10.8 g of 2,4-dibromo-3-hydroxy-6-methylpyridine 30A mentioned in Reference Production Example 30 and 150 ml of tetrahydrofuran, 50.6 ml of a 1.64M n-butyllithium-hexane solution was added at −78° C., followed by stirring for 2 hours. After pouring 100 ml of water into the mixture, the mixture was acidified by adding 10% hydrochloric acid and extracted with ethyl acetate. The organic layer was washed with water and a saturated saline solution, dried over anhydrous magnesium sulfate, and then concentrated under reduced pressure. The residue thus obtained was washed with hexane, dried under reduced pressure to obtain 6.2 g of 2-bromo-5-hydroxy-6-methylpyridine (hereinafter referred to as 31A).

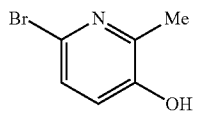

¹H-NMR (DMSO-D₆) δ:10.12 (1H, s), 7.24 (1H, d, J=8.5 Hz), 7.08 (1H, d, J=8.5 Hz), 2.28 (3H, s).

Reference Production Example 32

A mixture of 3.7 g of 14A mentioned in Reference Production Example 14, 2.5 g of 2-bromo-5-hydroxy-6-methylpyridine mentioned in Reference Production Example 31, 2.4 g of potassium carbonate, and 70 ml of acetonitrile was stirred with heating under reflux for 8 hours. The reaction mixture was filtered and the filtrate was concentrated under reduced pressure, and then the residue thus obtained was washed with hexane to obtain 3.7 g of 1-[2-(6-bromo-2-methyl-pyridin-3-yloxymethyl)-3-methylphenyl]-4-methyl-1,4-dihydrotetrazol-5-one (hereinafter referred to as 32A).

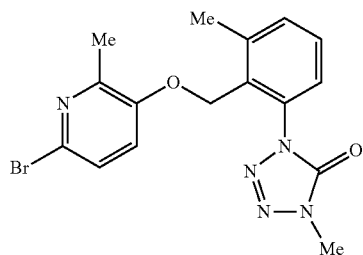 [SMILES: Cc1cccc(-n2nnn(C)c2=O)c1COc1ccc(Br)nc1C]

$^1$H-NMR (CDCl$_3$) δ:7.47-7.41 (2H, m), 7.30 (1H, dd, J=7.4, 1.7 Hz), 7.23 (1H, d, J=8.5 Hz), 6.99 (1H, d, J=8.7 Hz), 5.02 (2H, s), 3.65 (3H, s), 2.49 (3H, s), 2.32 (3H, s).

Reference Production Example 33

A mixture of 3.04 g of 3A mentioned in Reference Production Example 3, 1.88 g of 3-bromo-6-hydroxy-2-methylpyridine, 2.76 g of potassium carbonate, and 22 ml of acetonitrile was stirred with heating at 80° C. for 4 hours. Water was added to the reaction mixture and the mixture was extracted with chloroform. The organic layer was washed with a saturated saline solution, dried over anhydrous magnesium sulfate, and then concentrated under reduced pressure to obtain 3.70 g of 1-[2-(5-bromo-6-methyl-pyridin-2-yloxymethyl)-3-chlorophenyl]-4-methyl-1,4-dihydrotetrazol-5-on e (hereinafter referred to as 33A).

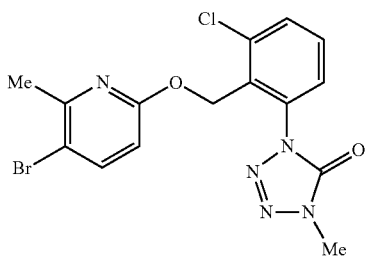

$^1$H-NMR (CDCl$_3$) δ:7.60-7.56 (2H, m), 7.43 (1H, t, J=8.0 Hz), 7.37-7.33 (1H, m), 6.35 (1H, d, J=8.5 Hz), 5.53 (2H, s), 3.65 (3H, s), 2.49 (3H, s).

Reference Production Example 34

A mixture of 0.94 g of 3-bromo-6-hydroxy-2-methylpyridine, 0.91 g of phenylboronic acid, 3.18 g of tripotassium phosphate, 2.0 ml of water, 0.08 g of [1,1'-bis(diphenylphosphino)ferrocene]palladium(II) dichloride dichloromethane adduct, and 20 ml of dimethoxyethane was stirred with heating under reflux for 4 hours. After cooling, the reaction solution was concentrated under reduced pressure. The residue thus obtained was subjected to silica gel column chromatography to obtain 0.30 g of 6-hydroxy-2-methyl-3-phenylpyridine (hereinafter referred to as 34A).

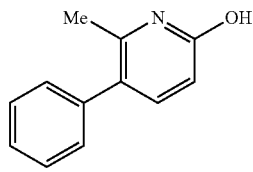 [SMILES: Cc1nc(O)ccc1-c1ccccc1]

$^1$H-NMR (CDCl$_3$) δ:7.46-7.39 (3H, m), 7.37-7.32 (1H, m), 7.28-7.26 (2H, m), 6.51 (1H, d, J=9.2 Hz), 2.38 (3H, s).

Reference Production Example 35

A mixture of 0.30 g of 34A mentioned in Reference Production Example 34, 0.29 g of N-bromosuccinimide, and 16 ml of chloroform was stirred at room temperature for 2 hours, and then the reaction solution was concentrated under reduced pressure. The residue thus obtained was subjected to silica gel column chromatography to obtain 0.43 g of 5-bromo-6-hydroxy-2-methyl-3-phenylpyridine (hereinafter referred to as 35A).

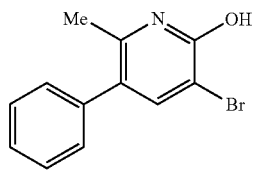 [SMILES: Cc1nc(O)c(Br)cc1-c1ccccc1]

$^1$H-NMR (CDCl$_3$) δ:7.82 (1H, s), 7.46-7.40 (2H, m), 7.38-7.35 (1H, m), 7.28-7.24 (2H, m), 2.39 (3H, s).

Reference Production Example 36

A mixture of 2.83 g of 14A mentioned in Reference Production Example 14, 1.88 g of 3-bromo-2-hydroxy-6-methylpyridine, 2.76 g of potassium carbonate, and 40 ml of acetonitrile was stirred with heating at 80° C. for 4 hours. Water was added to the reaction mixture and the mixture was extracted with chloroform. The organic layer was washed with a saturated saline solution, dried over anhydrous magnesium sulfate, and then concentrated under reduced pressure to obtain 4.08 g of 1-[2-(3-bromo-6-methyl-pyridin-2-yloxymethyl)-3-methylphenyl]-4-methyl-1,4-dihydrotetrazol-5-one (hereinafter referred to as 36A).

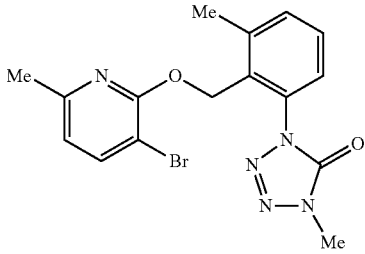 [SMILES: Cc1ccc(Br)c(OCc2c(C)cccc2-n2nnn(C)c2=O)n1]

$^1$H-NMR (CDCl$_3$) δ:7.56 (1H, d, J=7.6 Hz), 7.36-7.32 (2H, m), 7.26-7.22 (1H, m), 6.55 (1H, d, J=7.8 Hz), 5.53 (2H, s), 3.71 (3H, s), 2.63 (3H, s), 2.30 (3H, s).

Reference Production Example 37

A mixture of 3.90 g of 36A mentioned in Reference Production Example 36, 1.20 g of methylboronic acid, 9.77 g of cesium carbonate, 0.82 g of [1,1'-bis(diphenylphosphino)ferrocene]palladium(II) dichloride dichloromethane adduct, and 40 ml of dimethoxyethane was stirred with heating under reflux for 4 hours. After cooling, water was poured into the reaction solution and the mixture was extracted with ethyl acetate. The organic layer was washed with water and a saturated saline solution, dried over anhydrous magnesium sulfate, and then concentrated under reduced pressure. The residue thus obtained was subjected to silica gel column chromatography to obtain 2.38 g of 1-[2-(3,5-dimethyl-pyridin-2-yloxymethyl)-3-methylphenyl]-4-methyl-1,4-dihydrotetrazol-5-one (hereinafter referred to as 37A).

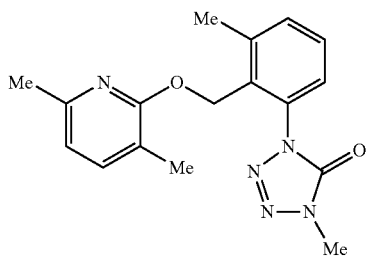 [SMILES: Cc1ccc(C)c(OCc2c(C)cccc2-n2nnn(C)c2=O)n1]

$^1$H-NMR (CDCl$_3$) δ:7.37-7.34 (2H, m), 7.24-7.21 (1H, m), 7.19 (1H, d, J=7.3 Hz), 6.57 (1H, d, J=7.1 Hz), 5.44 (2H, s), 3.67 (3H, s), 2.59 (3H, s), 2.33 (3H, s), 2.00 (3H, s).

Reference Production Example 38

A mixture of 2.25 g of 37A mentioned in Reference Production Example 37, 1.35 g of N-bromosuccinimide, and 35 ml of chloroform was stirred at room temperature for 2 hours. Water was poured into the reaction solution and the mixture was extracted with chloroform. The organic layer was washed with water and a saturated saline solution, dried over anhydrous magnesium sulfate, and then concentrated under reduced pressure. The residue thus obtained was subjected to silica gel column chromatography to obtain 2.27 g of 1-[2-(3,6-dimethyl-5-bromopyridin-2-yloxymethyl)-3-methylphenyl]-4-methyl-1,4-dihydrotetrazol-5-one (hereinafter referred to as 38A).

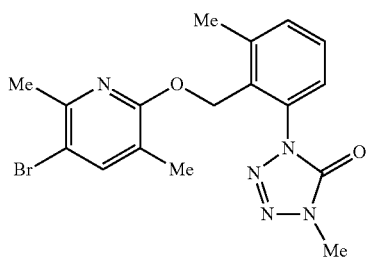 [SMILES: Cc1cc(Br)c(C)nc1OCc1c(C)cccc1-n1nnn(C)c1=O]

$^1$H-NMR (CDCl$_3$) δ: 7.40 (1H, s), 7.39-7.35 (2H, m), 7.25-7.21 (1H, m), 5.41 (2H, s), 3.68 (3H, s), 2.58 (3H, s), 2.44 (3H, s), 2.00 (3H, s).

Reference Production Example 39

A mixture of 1.78 g of 25A mentioned in Reference Production Example 25, 1.27 g of bis(pinacolato)diboron, 1.35 g of potassium acetate, 0.11 g of [1,1'-bis(diphenylphosphino)ferrocene]palladium(II) dichloride dichloromethane adduct, and 15 ml of dimethyl sulfoxide was stirred in a nitrogen atmosphere at 80° C. for 10 hours. Water was poured into the reaction mixture and the mixture was extracted with chloroform. The organic layer was washed with water and a saturated saline solution, dried over anhydrous magnesium sulfate, and then concentrated under reduced pressure. The residue thus obtained was subjected to silica gel column chromatography to obtain 0.97 g of 1-methyl-4-{2-[6-methyl-5-(4,4,5,5-tetramethyl-1,3,2-dioxaborolan-2-yl)-pyridin-2-yloxymethyl]-3-methylphenyl}-1,4-dihydro-tetrazol-5-one (hereinafter referred to as 39A).

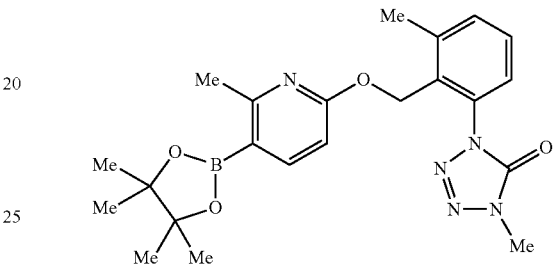

$^1$H-NMR (CDCl$_3$) δ:7.85 (1H, d, J=8.2 Hz), 7.37-7.34 (2H, m), 7.25-7.21 (1H, m), 6.41 (1H, d, J=8.2 Hz), 5.42 (2H, s), 3.66 (3H, s), 2.59 (3H, s), 2.54 (3H, s), 1.32 (12H, s).

Reference Production Example 40

To a mixture of 50.0 g of 2-hydroxy-6-methylnicotinic acid and 500 ml tetrahydrofuran, 18.6 g of lithium aluminum hydride was added in a nitrogen atmosphere at 70° C. for 1 hour. To the reaction mixture, 19 ml of water was added dropwise under ice cooling, followed by stirring at 0° C. for 1 hour. Furthermore, 16 ml of an aqueous 15% sodium oxide solution was added dropwise, followed by stirring at room temperature for 1 hour. The reaction mixture was filtered through Cerite and the filtrate was concentrated under reduced pressure to obtain 38.0 g of 2-hydroxy-3-hydroxymethyl-6-methylpyridine (hereinafter referred to as 40A).

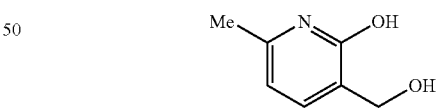

$^1$H-NMR (DMSO-D$_6$) δ:6.82 (1H, d, J=6.8 Hz), 5.83 (1H, d, J=6.8 Hz), 4.25 (2H, s), 2.06 (3H, s).

Reference Production Example 41

A mixture of 38.0 g of 40A mentioned in Reference Production Example 40, 28.79 g of 10% palladium-carbon, and 190 ml of acetic acid was stirred in a hydrogen atmosphere under 0.4 Mpa at room temperature for 48 hours. The reaction mixture was filtered through Cerite and the filtrate was concentrated under reduced pressure to obtain 33.6 g of 2-hydroxy-3,6-dimethylpyridine (hereinafter referred to as 41A).

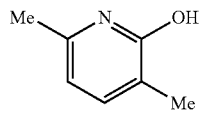

¹H-NMR (DMSO-D₆) δ:7.19 (1H, dd, J=6.8, 0.9 Hz), 5.89 (1H, dd, J=6.8, 0.7 Hz), 2.14 (3H, s), 1.92 (3H, s).

Reference Production Example 42

To a mixture of 1.34 g of 41A mentioned in Reference Production Example 41 and 11 ml of acetic acid, a mixture of 1.73 g of bromine and 4.6 ml of acetic acid was added dropwise, followed by stirring at room temperature for 1 hour. The pH of the reaction mixture was adjusted to 6 by adding sodium hydrogen carbonate, and the solid thus obtained was washed with water to obtain 33.6 g of 5-bromo-2-hydroxy-3,6-dimethylpyridine (hereinafter referred to as 42A).

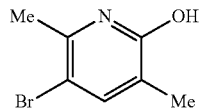

¹H-NMR (DMSO-D) δ:7.42 (1H, s), 2.22 (3H, s), 1.94 (3H, s).

Reference Production Example 43

A mixture of 2.61 g of 14A mentioned in Reference Production Example 14, 1.86 g of 42A mentioned in Reference Production Example 42, 2.54 g of potassium carbonate, and 20 ml of acetonitrile was stirred with heating at 80° C. for 4 hours. Water was added to the reaction mixture and the mixture was extracted with chloroform. The organic layer was washed with a saturated saline solution, dried over anhydrous magnesium sulfate, and then concentrated under reduced pressure to obtain 4.58 g of 38A mentioned in Reference Production Example 38.

Reference Production Example 44

A mixture of 2.00 g of 38A mentioned in Reference Production Example 38, 1.63 g of bis(pinacolato)diboron, 1.46 g of potassium acetate, 0.12 g of [1,1'-bis(diphenylphosphino)ferrocene]palladium(II) dichloride dichloromethane adduct, and 30 ml of dimethyl sulfoxide was stirred in a nitrogen atmosphere at 80° C. for 10 hours. Water was poured into the reaction mixture and the mixture was extracted with chloroform. The organic layer was washed with water and a saturated saline solution, dried over anhydrous magnesium sulfate, and then concentrated under reduced pressure. The residue thus obtained was subjected to silica gel column chromatography to obtain 2.04 g of 1-methyl-4-{2-[3,6-dimethyl-5-(4,4,5,5-tetramethyl-1,3,2-dioxa borolan-2-yl)-pyridin-2-yloxymethyl]-3-methylphenyl}-1,4-dihydro-tetrazol-5-one (hereinafter referred to as 44A).

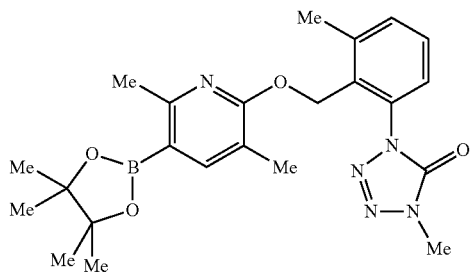 [SMILES: Cc1cc(B2OC(C)(C)C(C)(C)O2)c(C)nc1OCc1c(C)cccc1-n1nnn(C)c1=O]

¹H-NMR (CDCl₃) δ:7.68 (1H, s), 7.41-7.38 (2H, m), 7.28-7.24 (1H, m), 5.53 (2H, s), 3.71 (3H, s), 2.62 (3H, s), 2.59 (3H, s), 2.03 (3H, s), 1.36 (12H, s).

Reference Production Example 45

To a mixture of 4.36 g of sodium hydride and 20 ml of tetrahydrofuran, 2.20 g of 20A mentioned in Reference Production Example 20 and 2.37 g of 2,5-dibromopyridine were added, followed by stirring at room temperature for 8 hours. Water was added to the reaction mixture and the mixture was extracted with chloroform. The organic layer was washed with a saturated saline solution, dried over anhydrous magnesium sulfate, and then concentrated under reduced pressure to obtain 3.65 g of 1-[2-(5-bromopyridin-2-yloxymethyl)-3-methylphenyl]-4-methyl-1,4-dihydrotetrazol-5-one (hereinafter referred to as 45A).

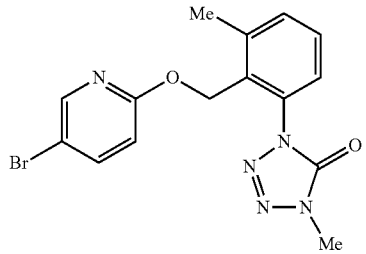 [SMILES: Cc1cccc(-n2nnn(C)c2=O)c1COc1ccc(Br)cn1]

¹H-NMR (CDCl₃) δ:8.09 (1H, dd, J=2.5, 0.7 Hz), 7.59 (1H, dd, J=8.7, 2.5 Hz), 7.43-7.35 (2H, m), 7.24 (1H, dd, J=6.8, 2.5 Hz), 6.57 (1H, dd, J=8.7, 0.7 Hz), 5.33 (2H, s), 3.69 (3H, s), 2.53 (3H, s).

Reference Production Example 46

A mixture of 0.60 g of 7A mentioned in Reference Production Example 7, 0.38 g of 3-bromo-6-hydroxy-2-methylpyridine, 0.55 g of potassium carbonate, and 8 ml of acetonitrile was stirred with heating at 80° C. for 4 hours. Water was added to the reaction mixture and the mixture was extracted with chloroform. The organic layer was washed with a saturated saline solution, dried over anhydrous magnesium sulfate, and then concentrated under reduced pressure to obtain 0.80 g of 1-[2-(5-bromo-6-methyl-pyridin-2-yloxymethyl)-3-methoxyphenyl]-4-methyl-1,4-dihydrotetrazol-5-one (hereinafter referred to as 46A).

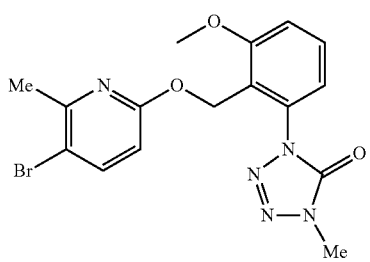 [SMILES: COc1cccc(-n2nnn(C)c2=O)c1COc1ccc(Br)c(C)n1]
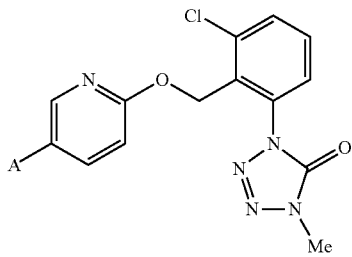
(EPA5)
$^1$H-NMR (CDCl$_3$) δ:7.55 (1H, d, J=8.5 Hz), 7.46 (1H, t, J=8.2 Hz), 7.08 (1H, dd, J=8.5, 0.7 Hz), 7.05-7.01 (1H, m), 6.34 (1H, dd, J=8.6, 0.6 Hz), 5.43 (2H, s), 3.92 (3H, s), 3.62 (3H, s), 2.50 (3H, s).
In accordance with the process mentioned above, it is possible to obtain compounds EPA1-001 to EPI12-1305.
The compounds EPA1-001 to EPI12-1305 are tetrazolinone compounds represented by the following formulas:
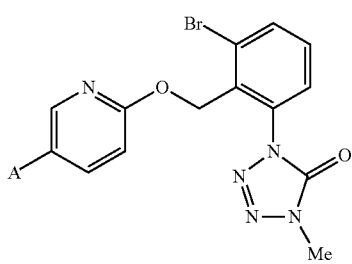
(EPA6)
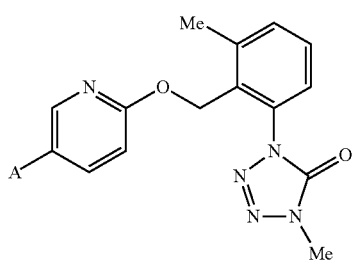
(EPA1)
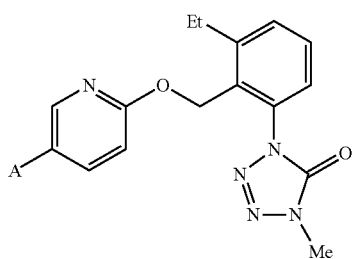
(EPA2)
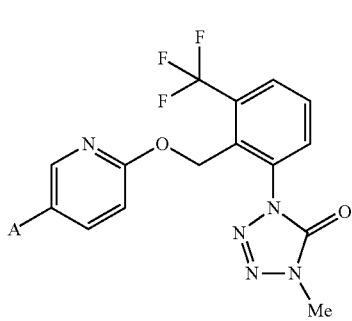
(EPA7)
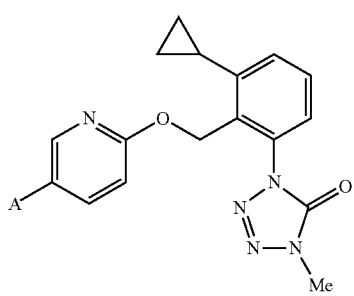
(EPA3)
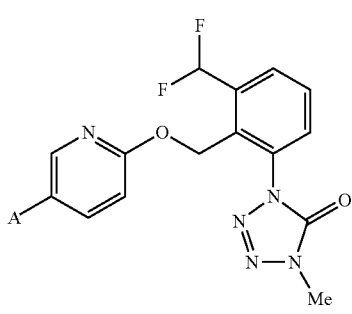
(EPA8)
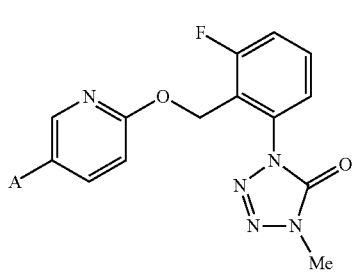
(EPA4)
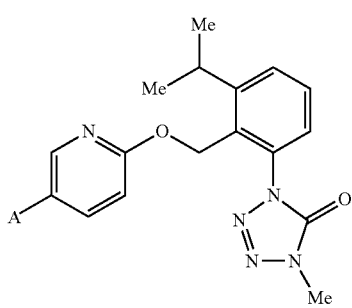
(EPA9)

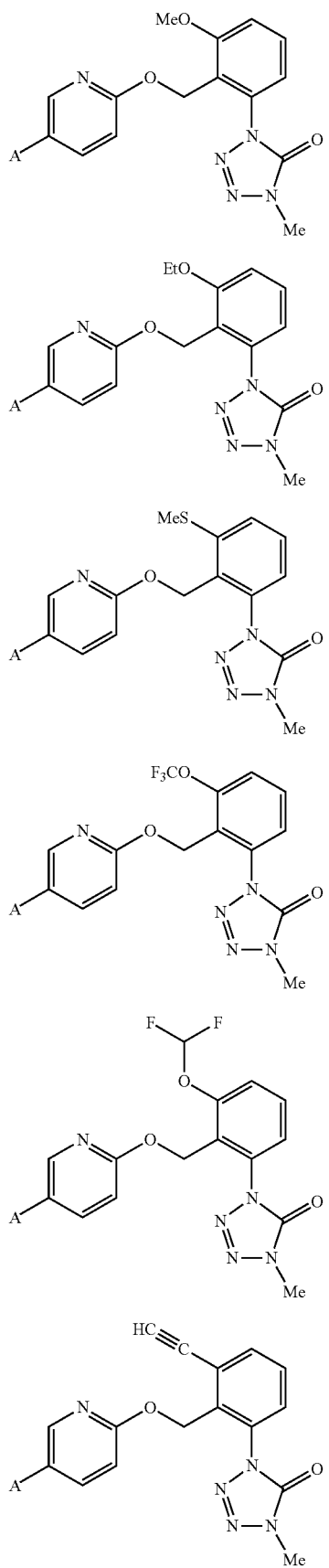
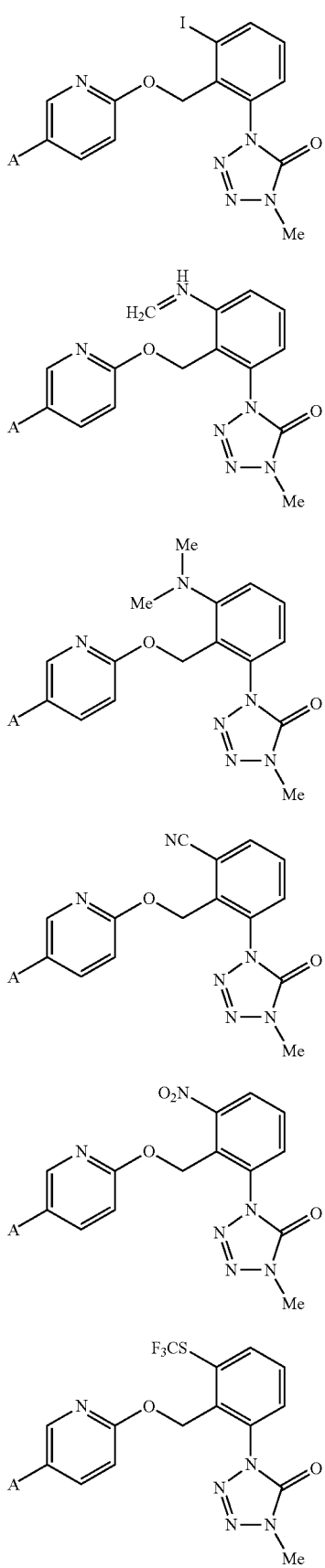

(EPA22) 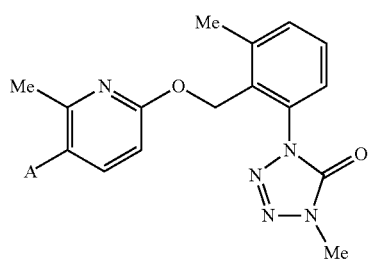
(EPA23) 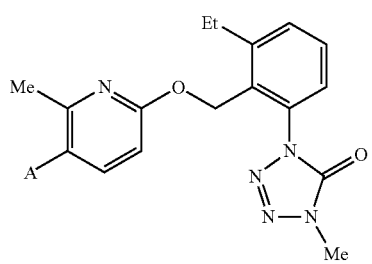
(EPA24) 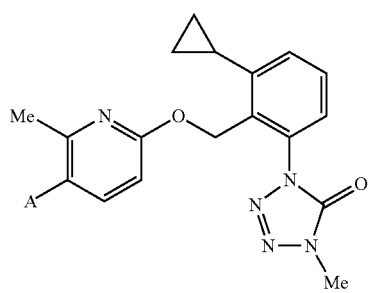
(EPA25) 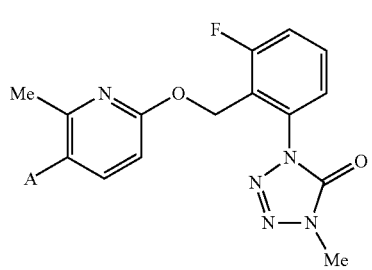
(EPA26) 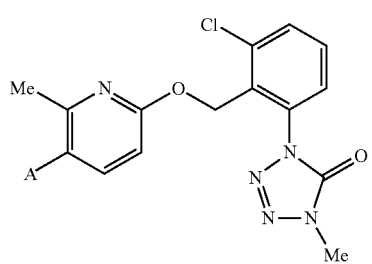
(EPA27) 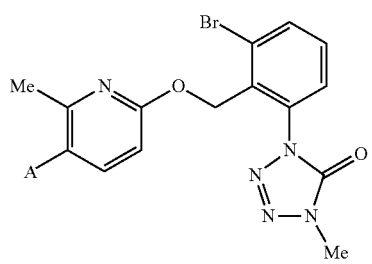
(EPA28) 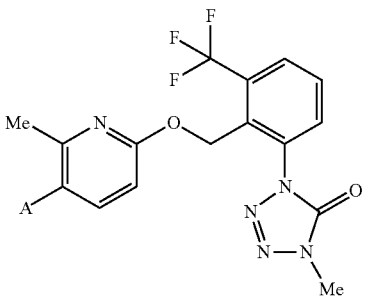
(EPA29) 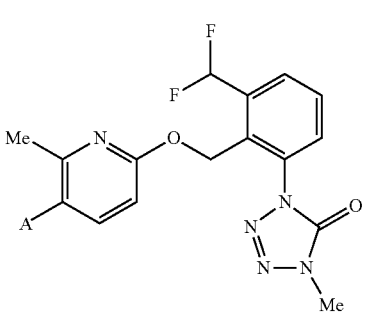
(EPA30) 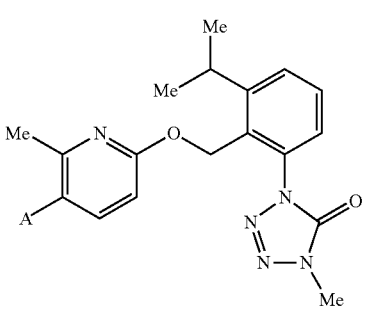
(EPA31) 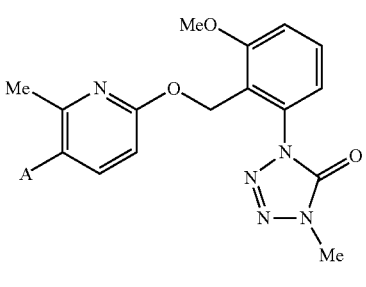
(EPA32) 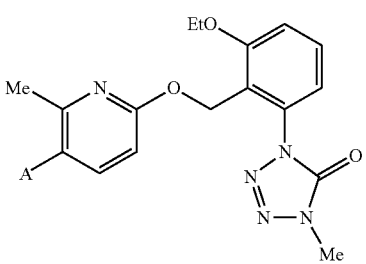

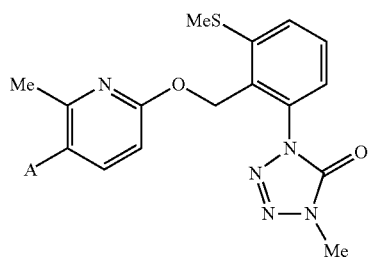 (EPA33)
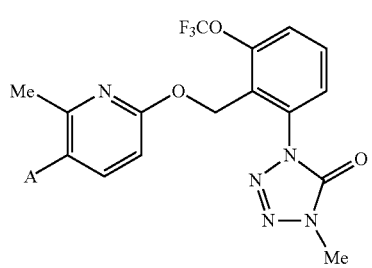 (EPA34)
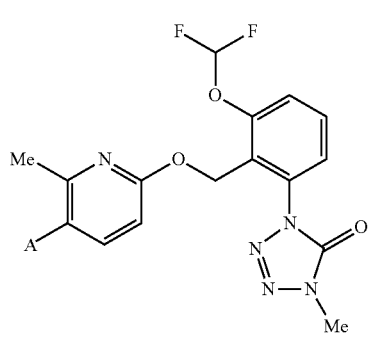 (EPA35)
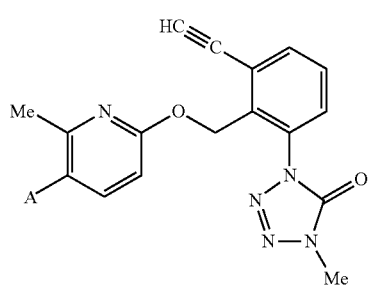 (EPA36)
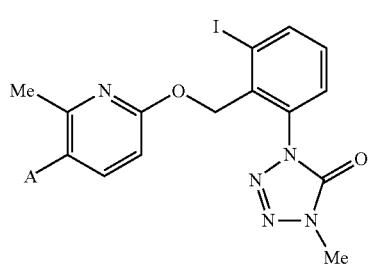 (EPA37)
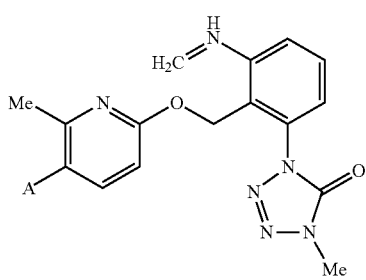 (EPA38)
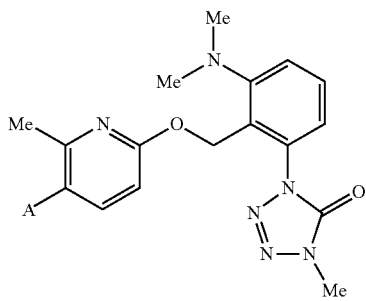 (EPA39)
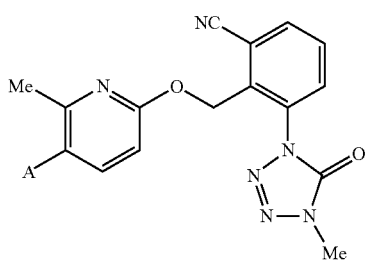 (EPA40)
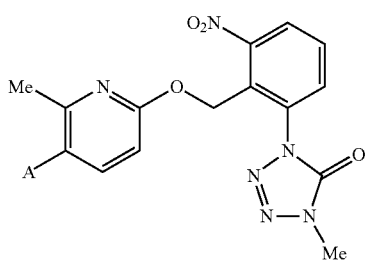 (EPA41)
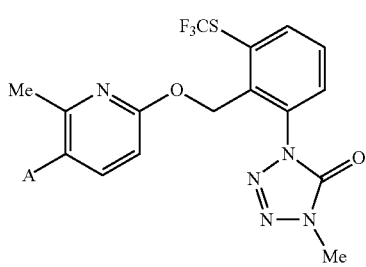 (EPA42)
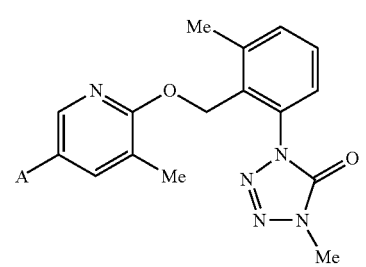 (EPA43)

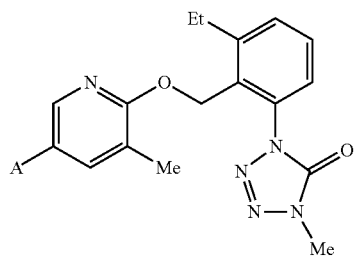 (EPA44)
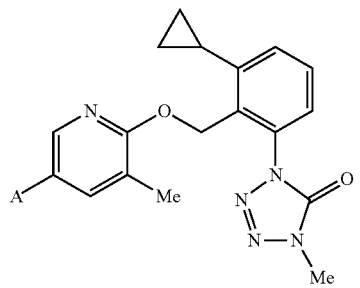 (EPA45)
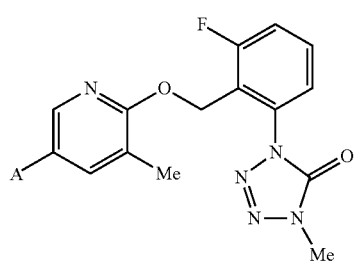 (EPA46)
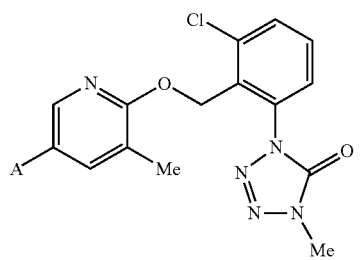 (EPA47)
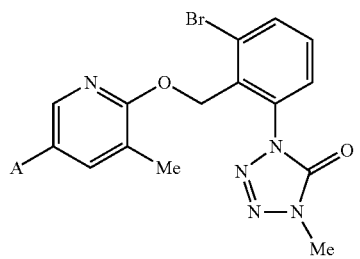 (EPA48)
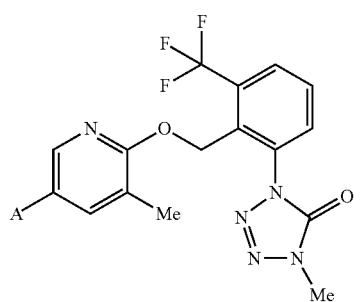 (EPA49)
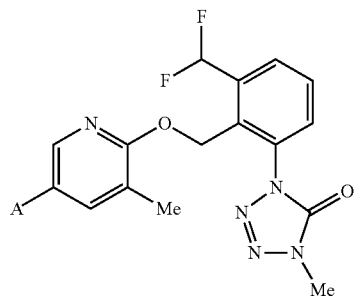 (EPA50)
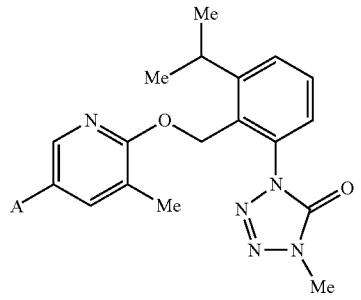 (EPA51)
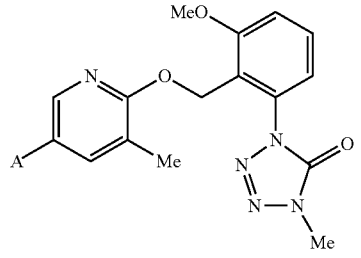 (EPA52)
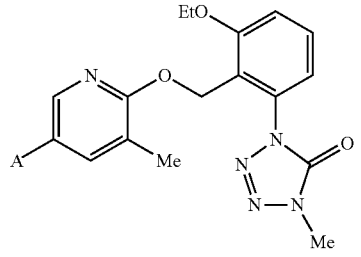 (EPA53)
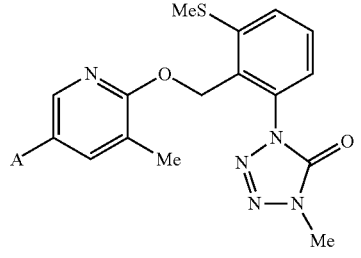 (EPA54)
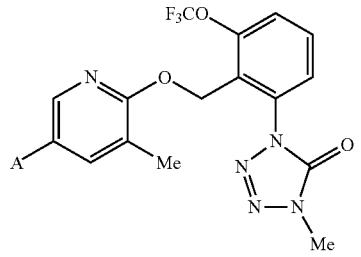 (EPA55)

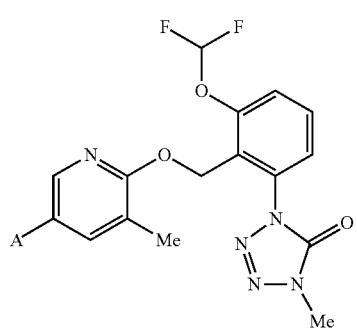
(EPA56)
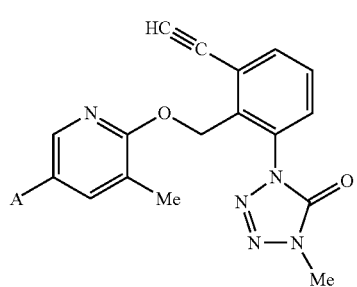
(EPA57)
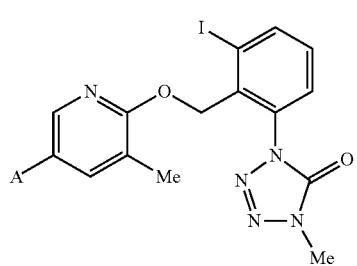
(EPA58)
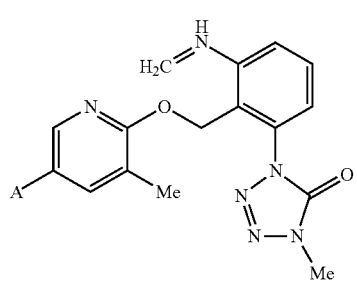
(EPA59)
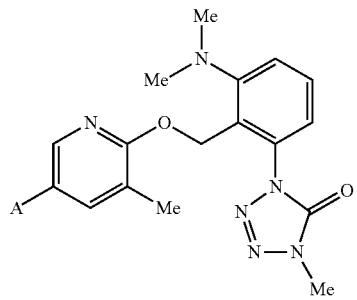
(EPA60)
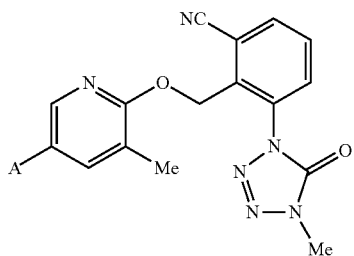
(EPA61)
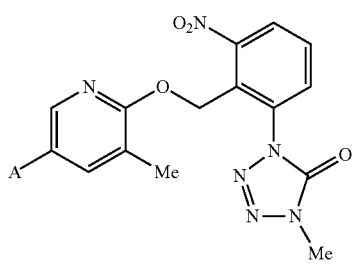
(EPA62)
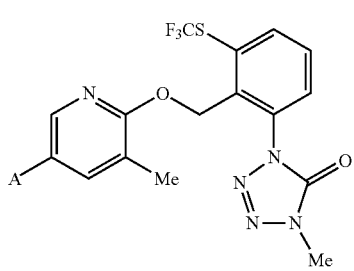
(EPA63)
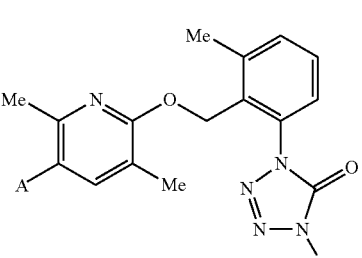
(EPA64)
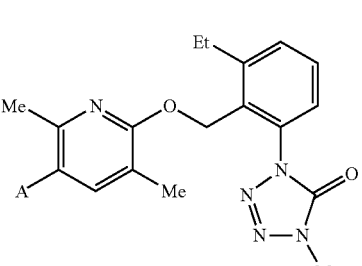
(EPA65)
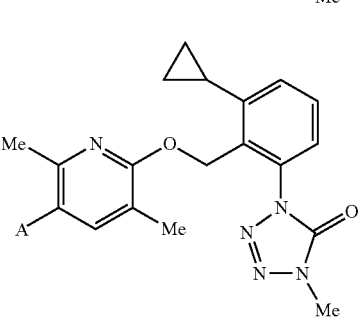
(EPA66)

-continued
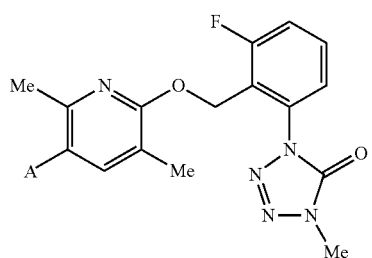 (EPA67)
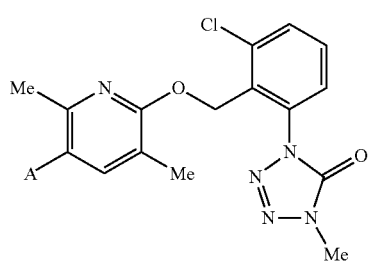 (EPA68)
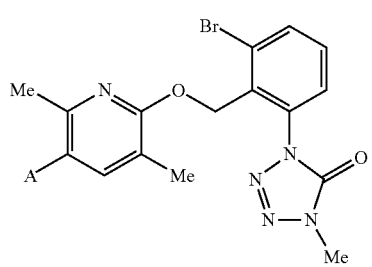 (EPA69)
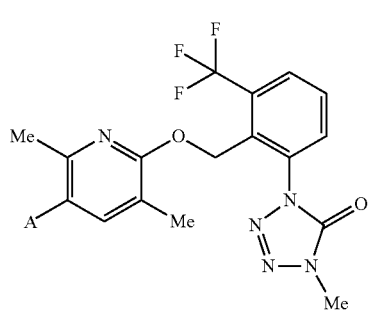 (EPA70)
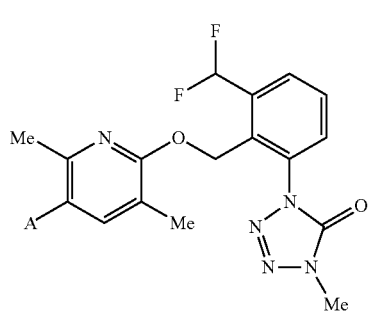 (EPA71)
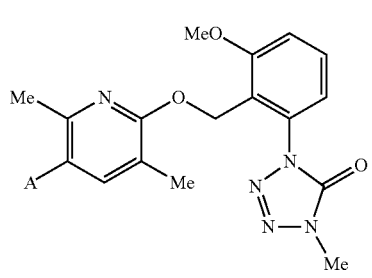 (EPA72)
-continued
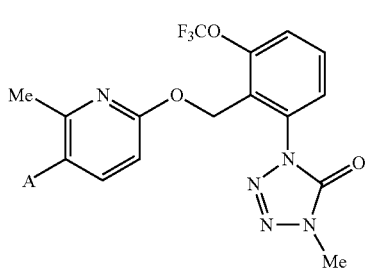 (EPA73)
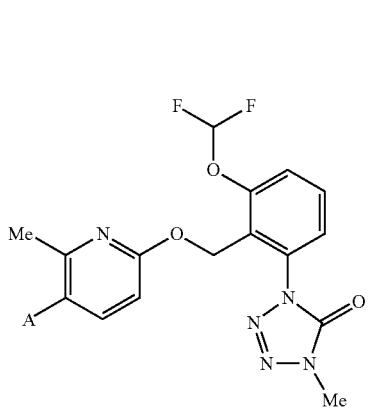 (EPA74)
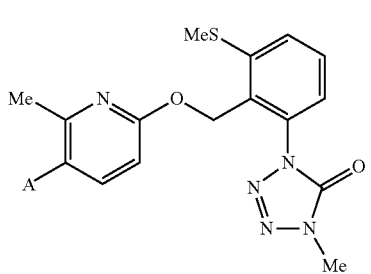 (EPA75)
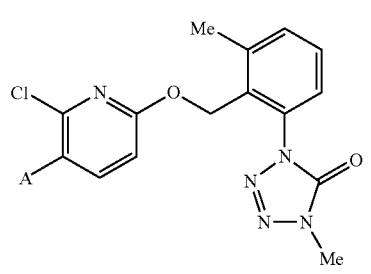 (EPA76)
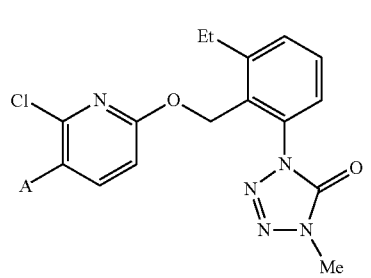 (EPA77)

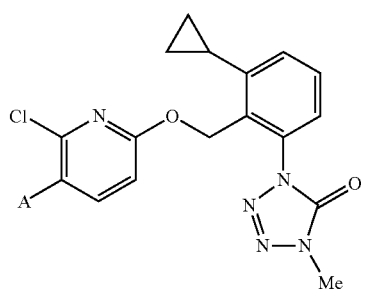 (EPA78)
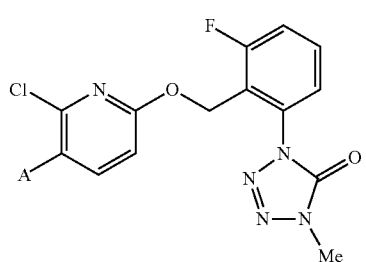 (EPA79)
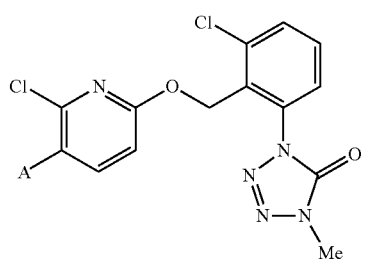 (EPA80)
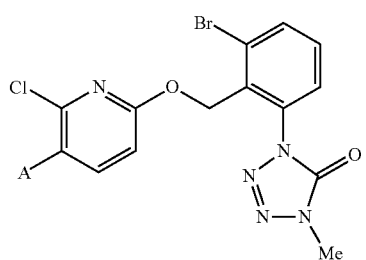 (EPA81)
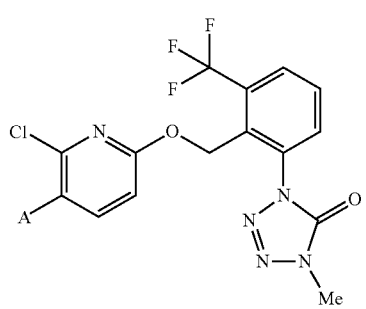 (EPA82)
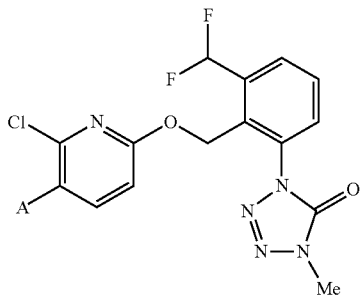 (EPA83)
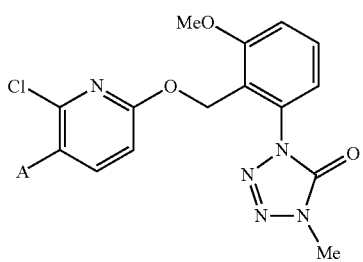 (EPA84)
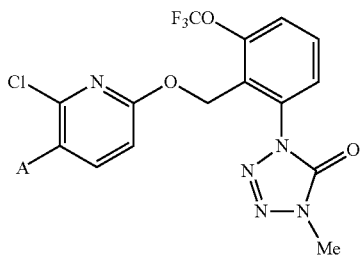 (EPA85)
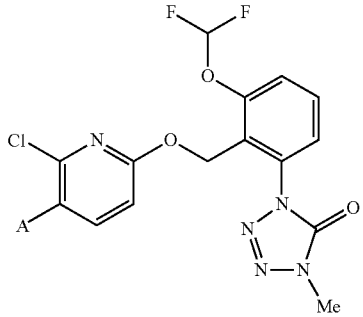 (EPA86)
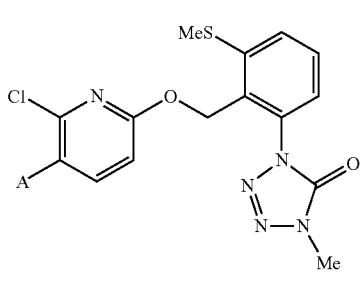 (EPA87)

(EPA88)
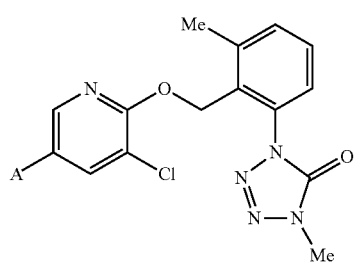
(EPA89)
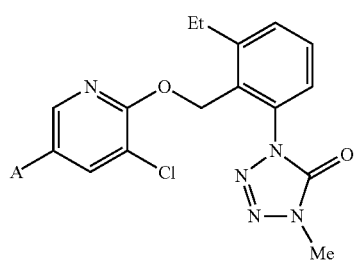
(EPA90)
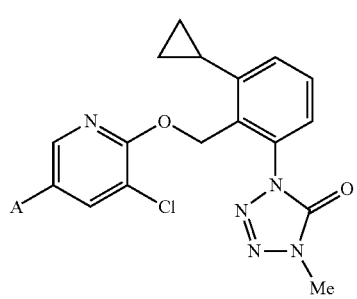
(EPA91)
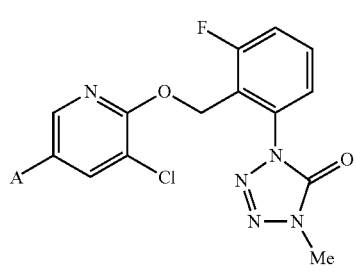
(EPA92)
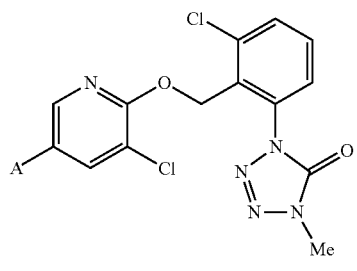
(EPA93)
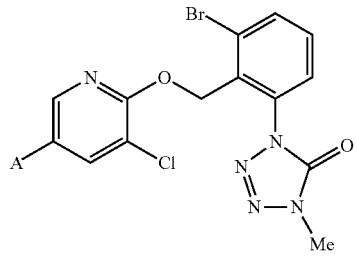
(EPA94)
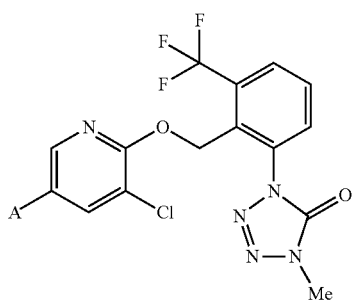
(EPA95)
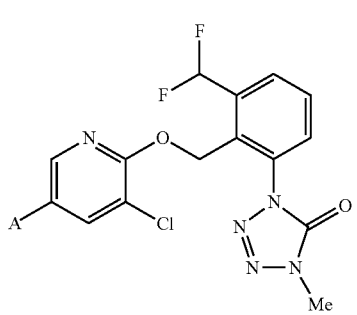
(EPA96)
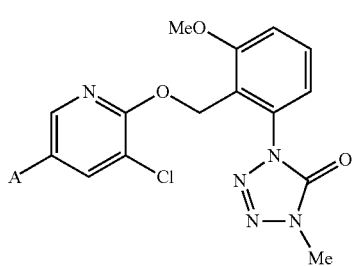
(EPA97)
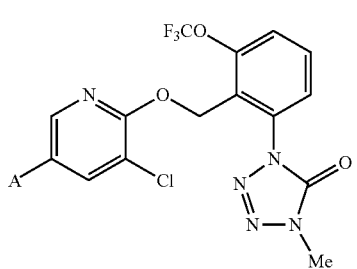
(EPA98)
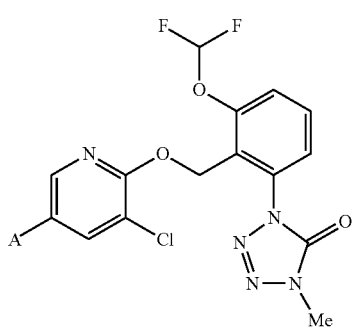

-continued (EPA99)
(EPA100)
(EPA101)
(EPA102)
(EPA103)
(EPA104)

-continued (EPA105)
(EPA106)
(EPA107)
(EPA108)
(EPA109)

-continued
(EPA110)
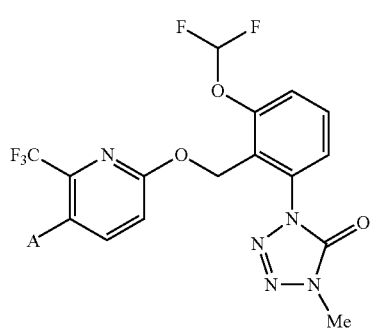
(EPA111)
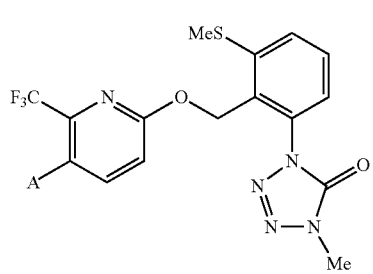
(EPA112)
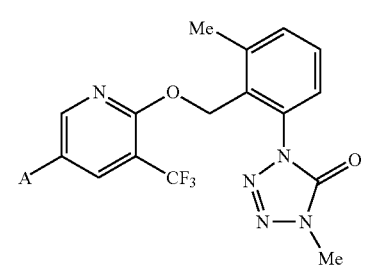
(EPA113)
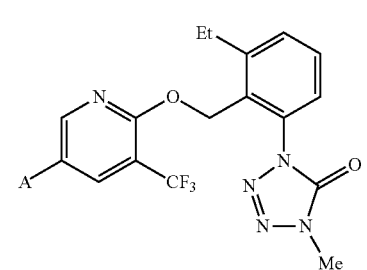
(EPA114)
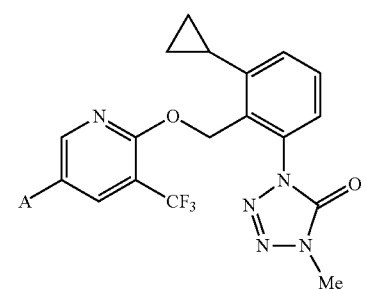
-continued
(EPA115)
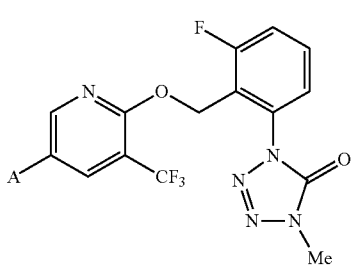
(EPA116)
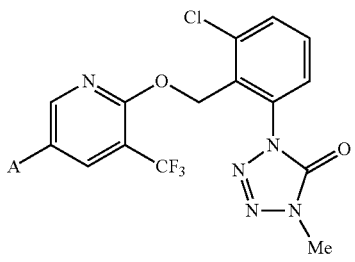
(EPA117)
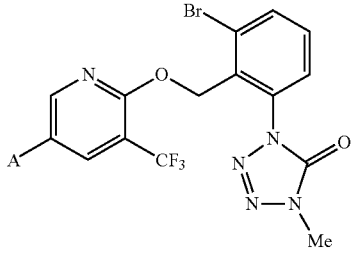
(EPA118)
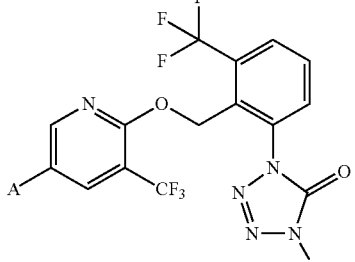
(EPA119)
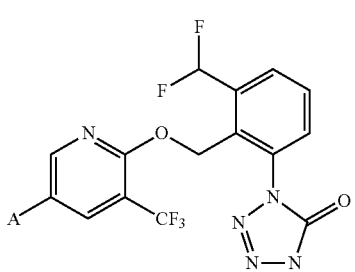
(EPA120)
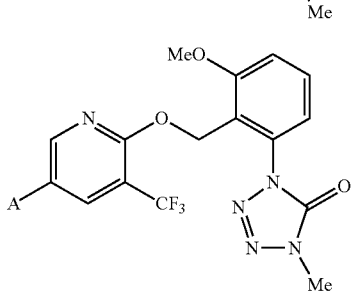

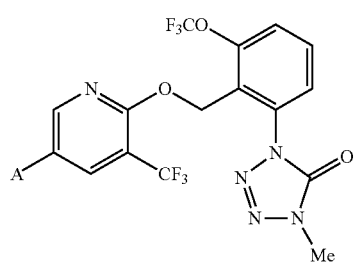
(EPA121)
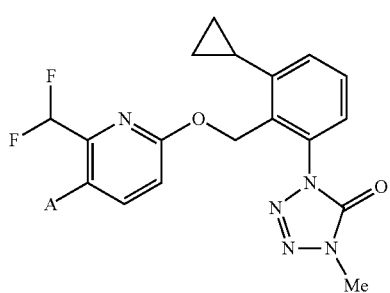
(EPA126)
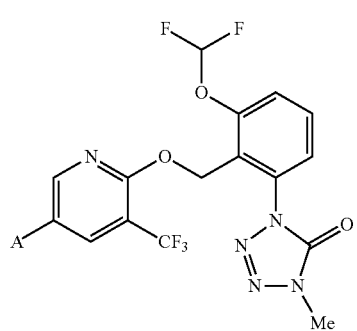
(EPA122)
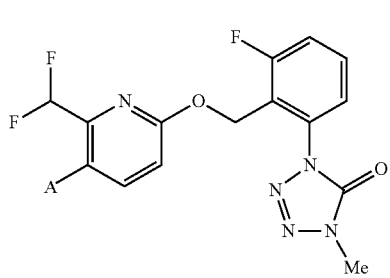
(EPA127)
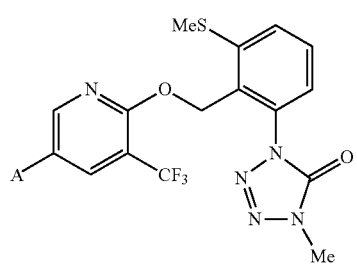
(EPA123)
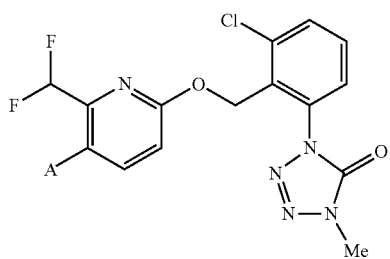
(EPA128)
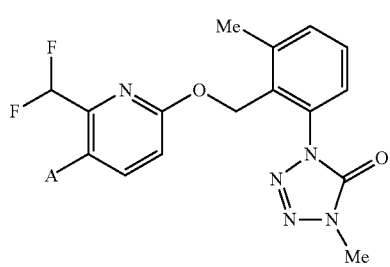
(EPA124)
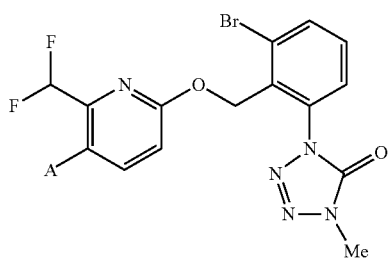
(EPA129)
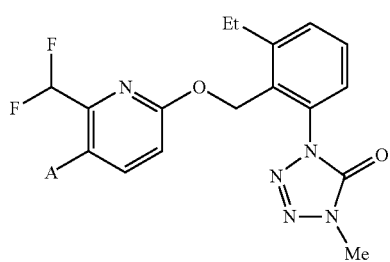
(EPA125)
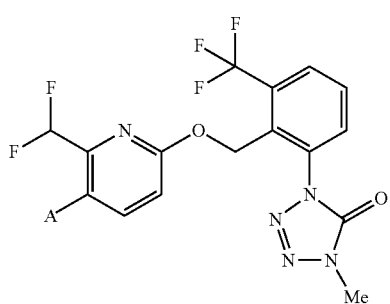
(EPA130)

153
-continued
(EPA131)
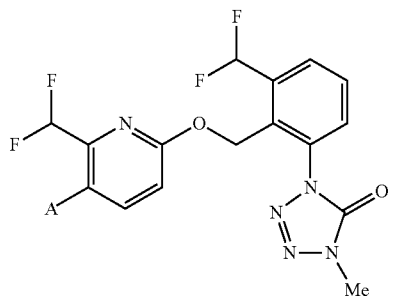
(EPA132)
(EPA133)
(EPA134)
(EPA135)
154
-continued
(EPA136)
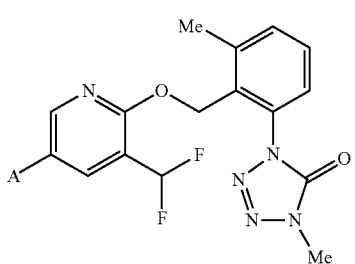
(EPA137)
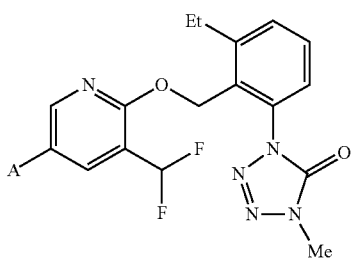
(EPA138)
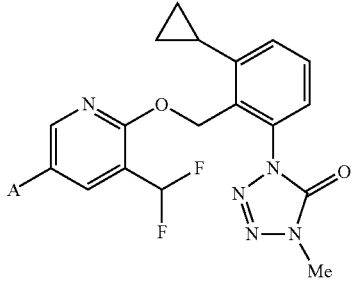
(EPA139)
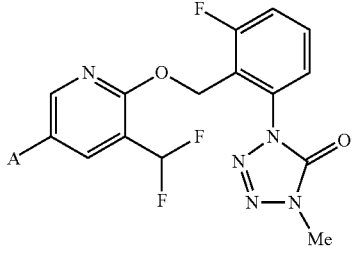
(EPA140)
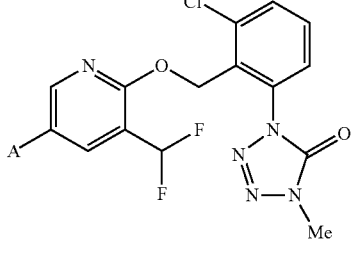
(EPA141)
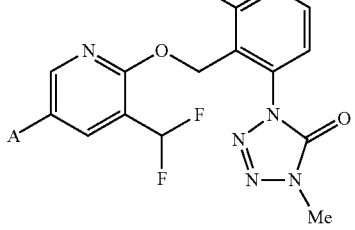

(EPA142)
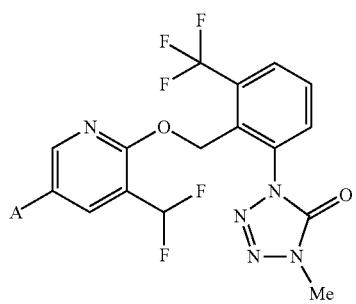
(EPA143)
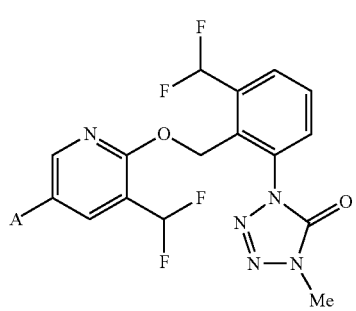
(EPA144)
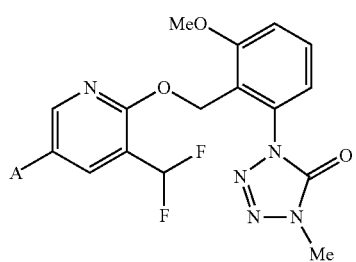
(EPA145)
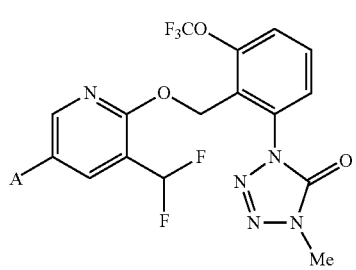
(EPA146)
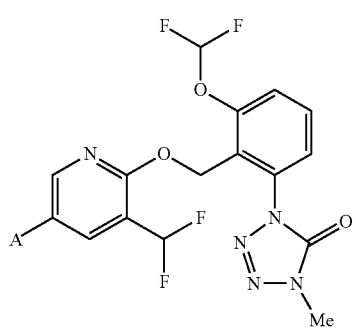
(EPA147)
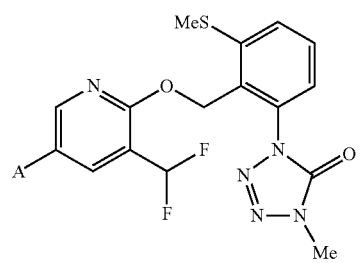
(EPA148)
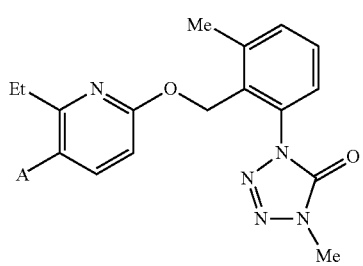
(EPA149)
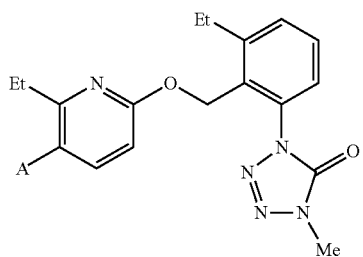
(EPA150)
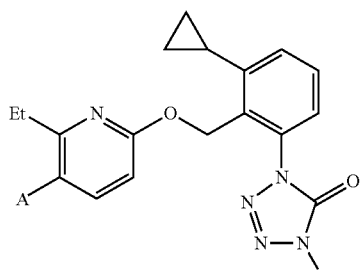
(EPA151)
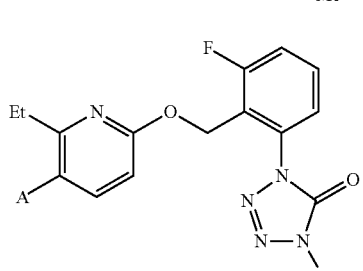
(EPA152)
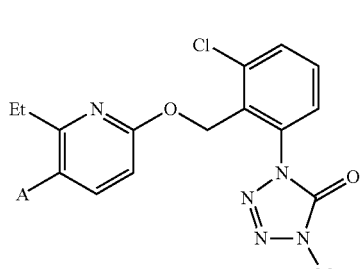

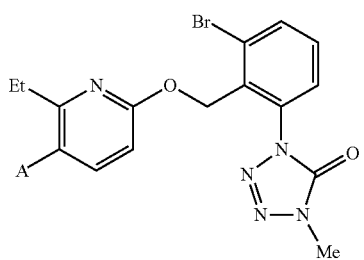
(EPA153)
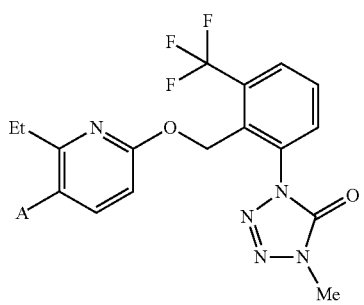
(EPA154)
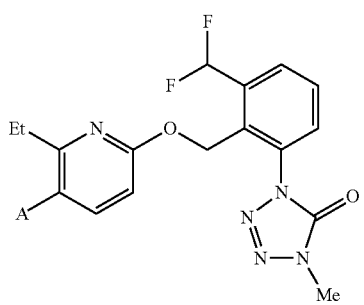
(EPA155)
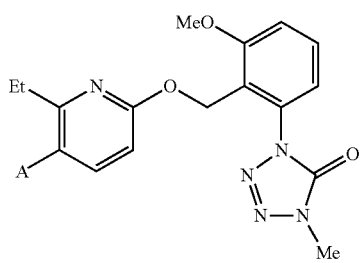
(EPA156)
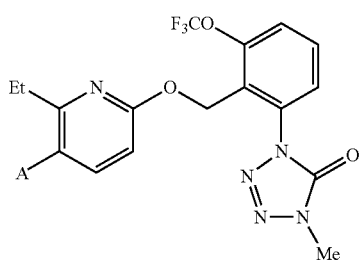
(EPA157)
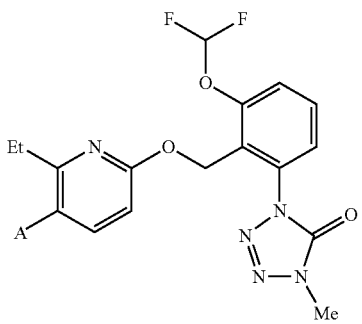
(EPA158)
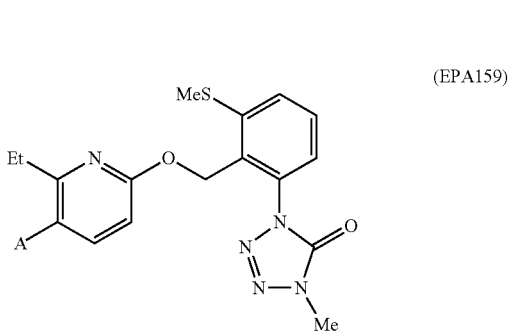
(EPA159)
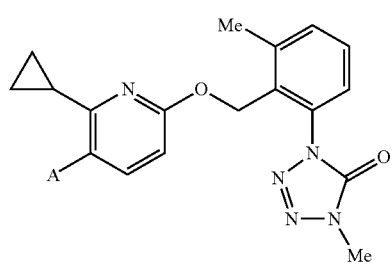
(EPA160)
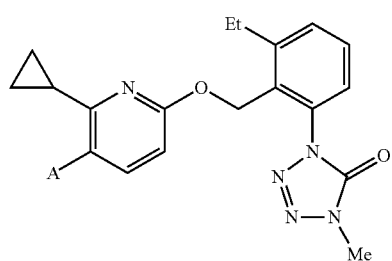
(EPA161)
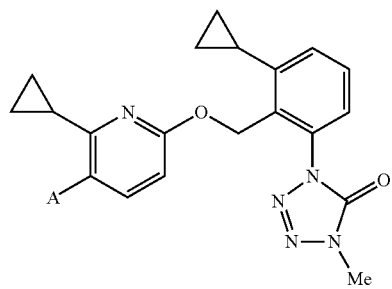
(EPA162)

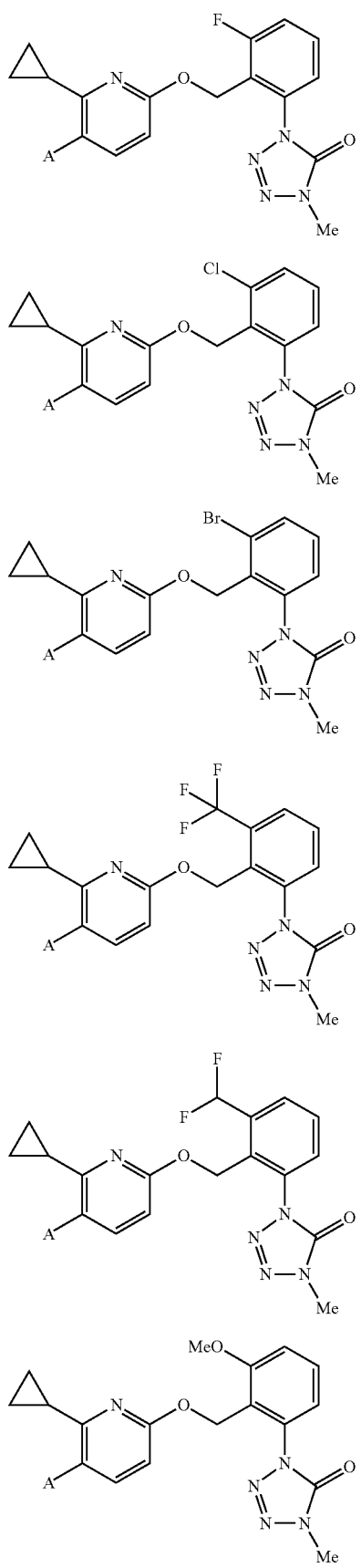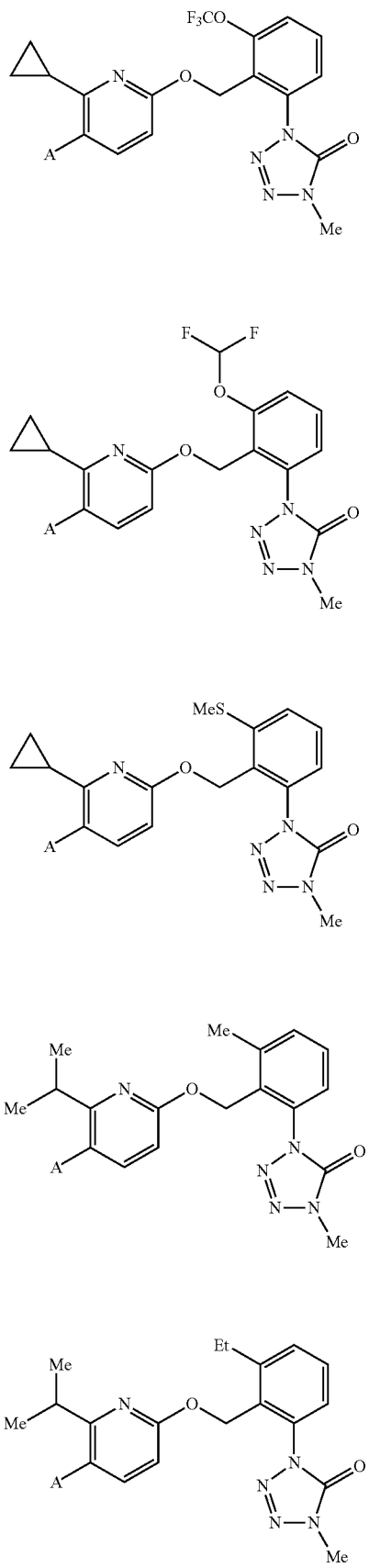

-continued
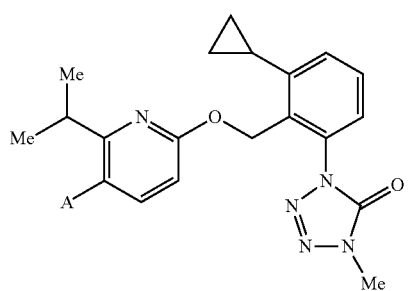
(EPA174)
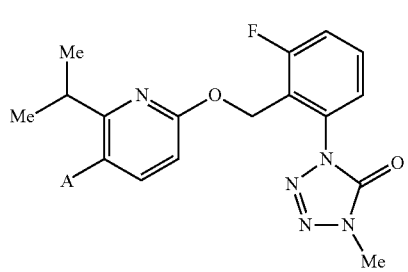
(EPA175)
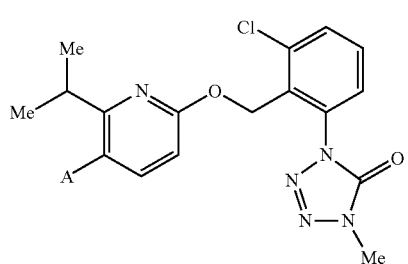
(EPA176)
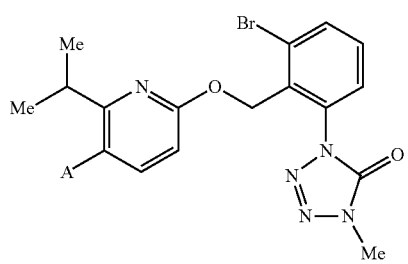
(EPA177)
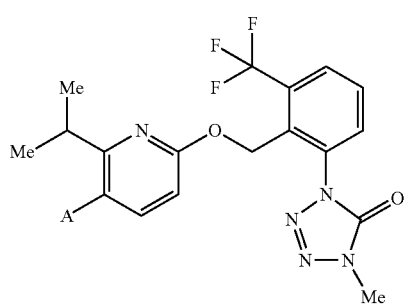
(EPA178)
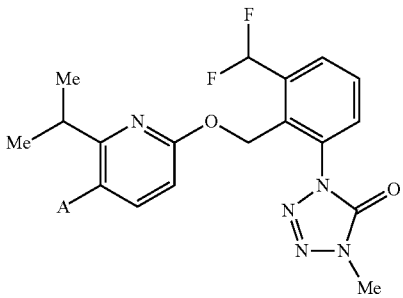
(EPA179)
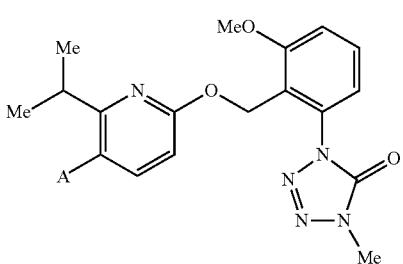
(EPA180)
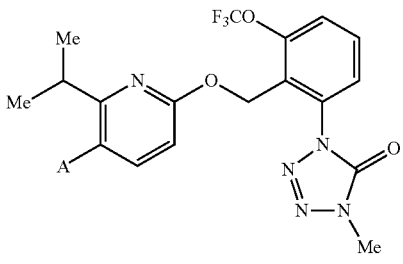
(EPA181)
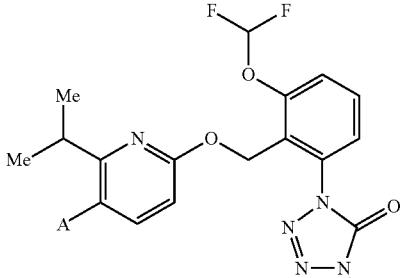
(EPA182)
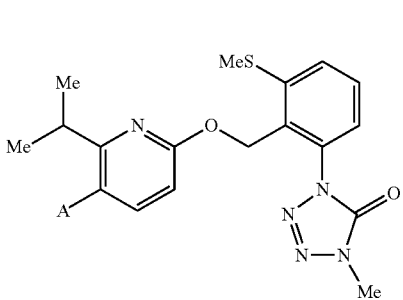
(EPA183)

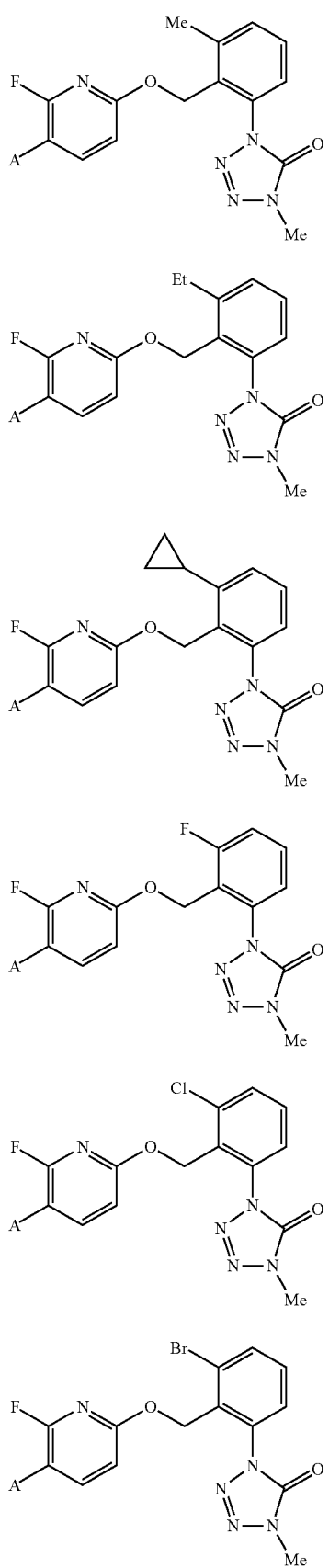
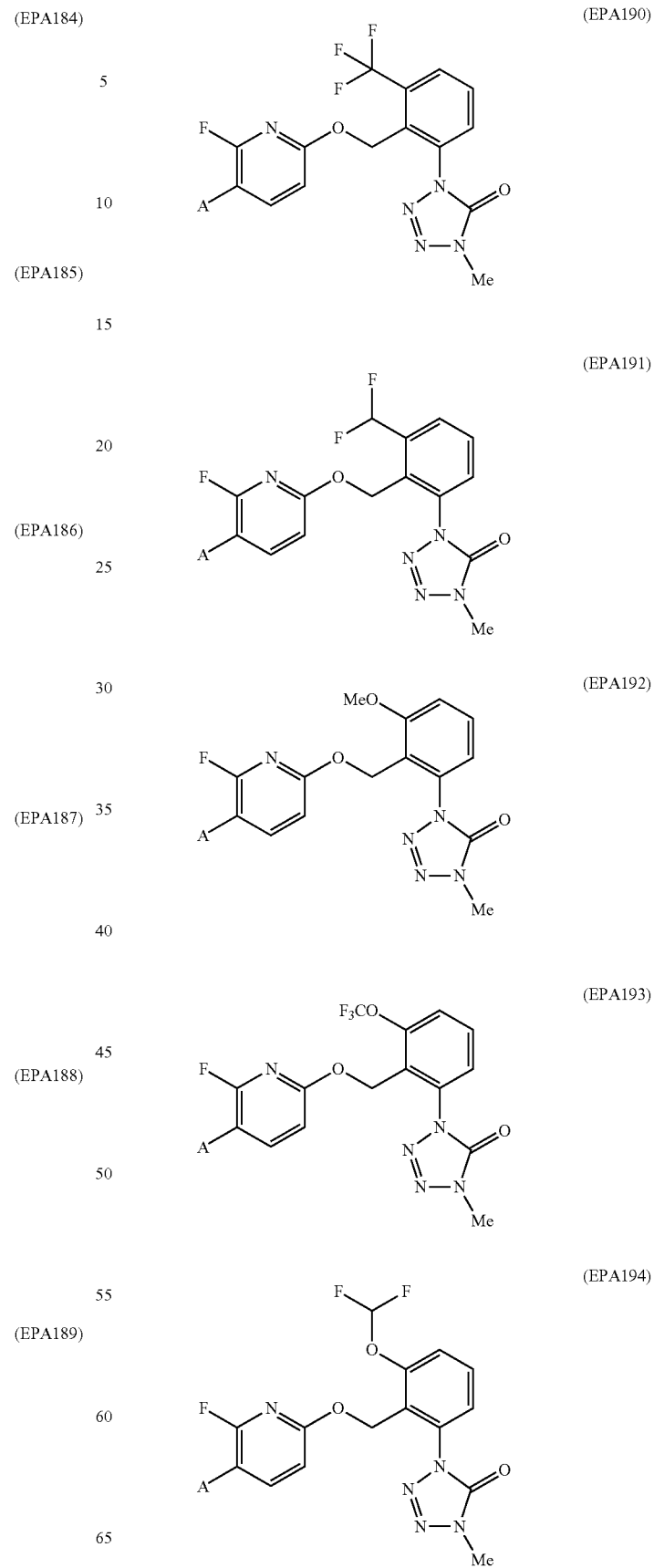

| | |
|---|---|
| 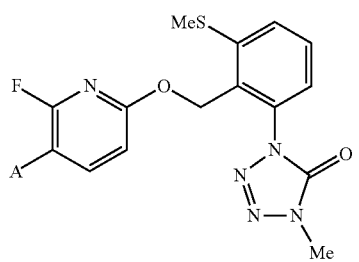 (EPA195) | 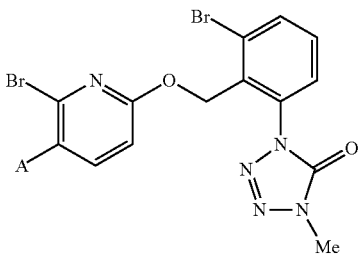 (EPA201) |
| 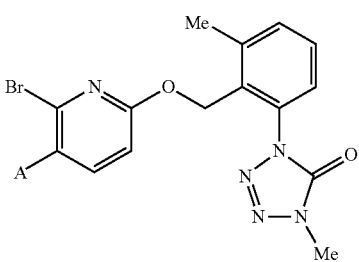 (EPA196) | 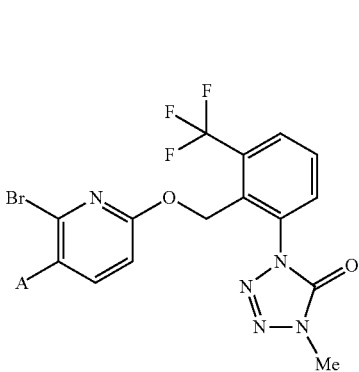 (EPA202) |
| 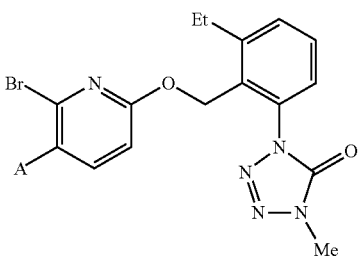 (EPA197) | |
| 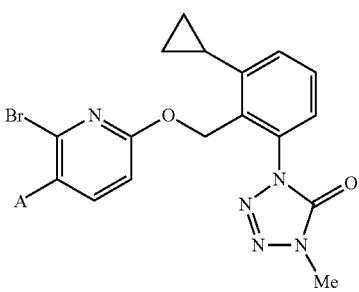 (EPA198) | 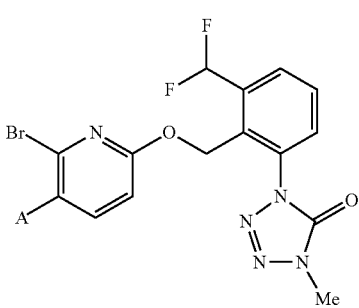 (EPA203) |
| 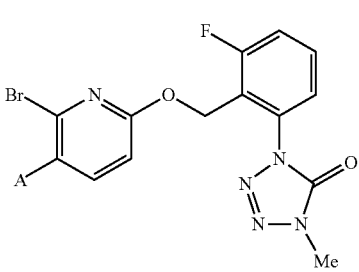 (EPA199) | 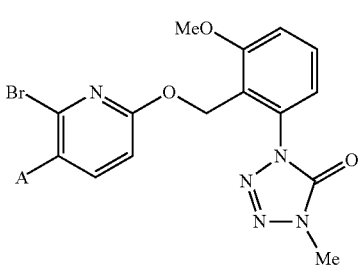 (EPA204) |
| 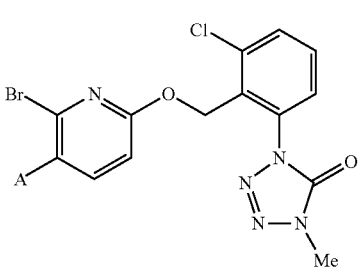 (EPA200) | 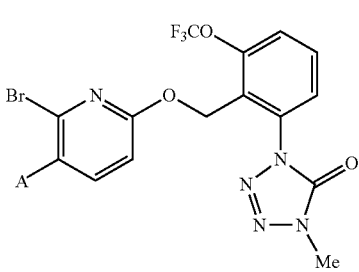 (EPA205) |

-continued
(EPA206)
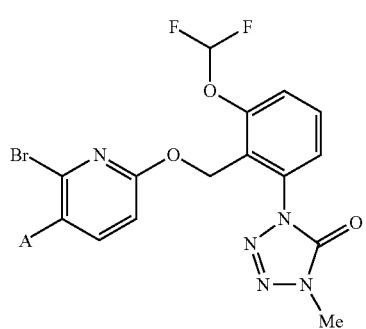
(EPA207)
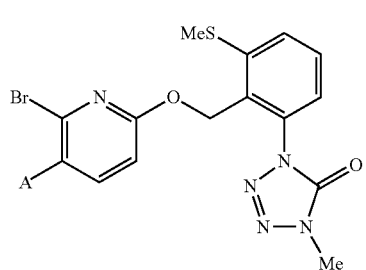
(EPA208)
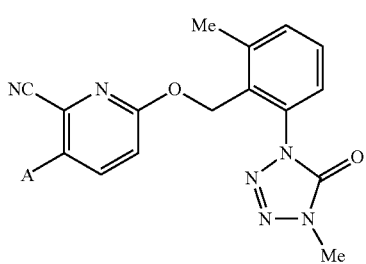
(EPA209)
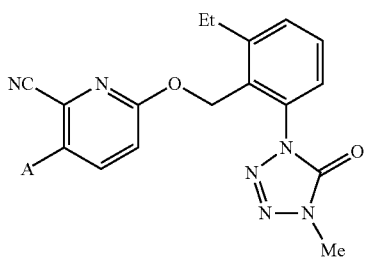
(EPA210)
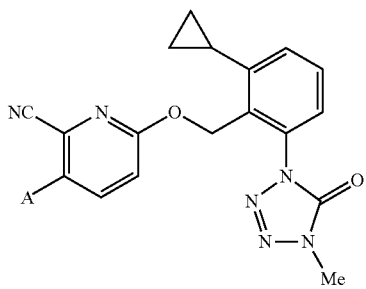
-continued
(EPA211)
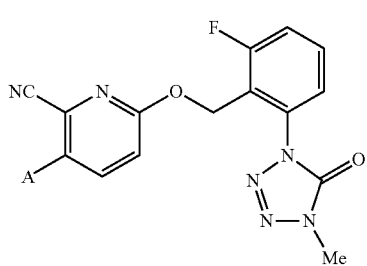
(EPA212)
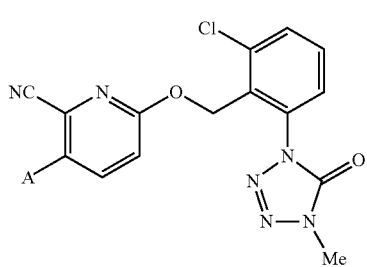
(EPA213)
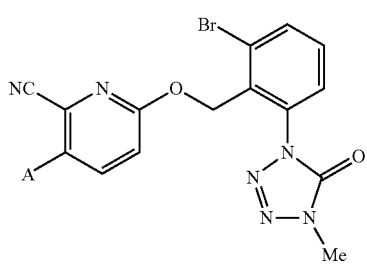
(EPA214)
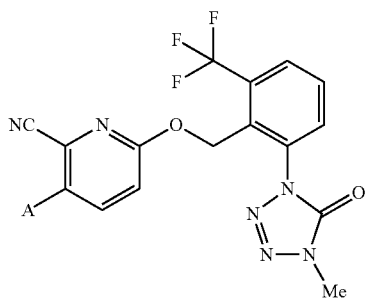
(EPA215)
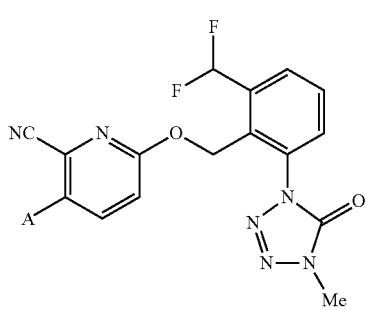
(EPA216)
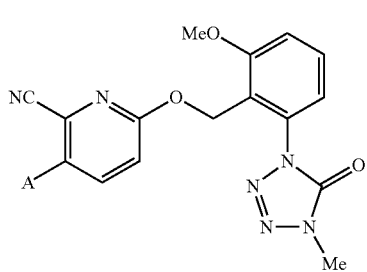

-continued
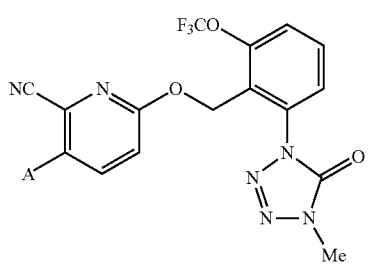
(EPA217)
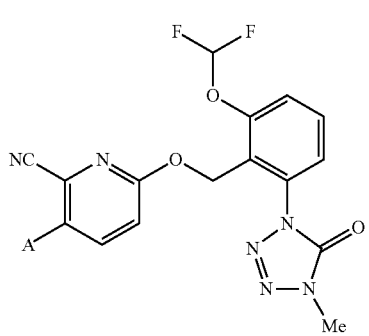
(EPA218)
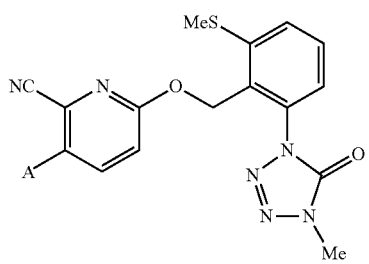
(EPA219)
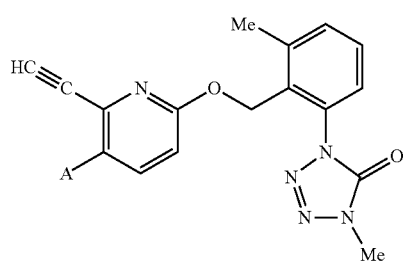
(EPA220)
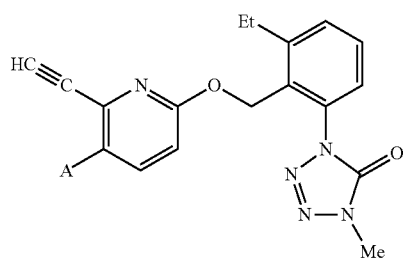
(EPA221)
-continued
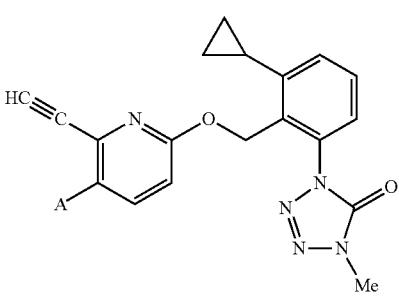
(EPA222)
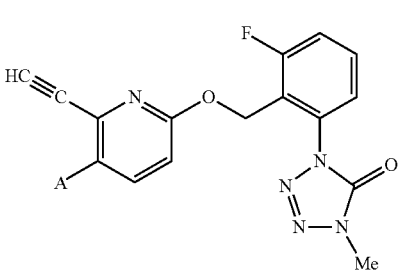
(EPA223)
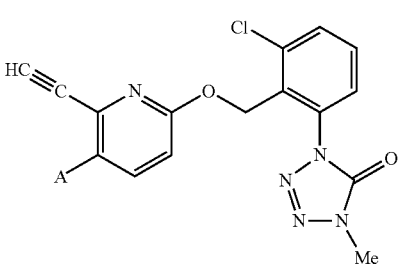
(EPA224)
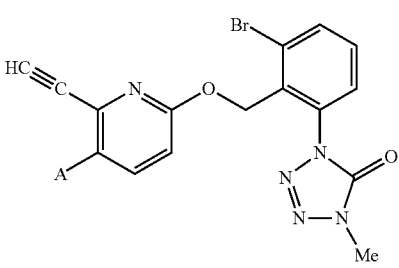
(EPA225)
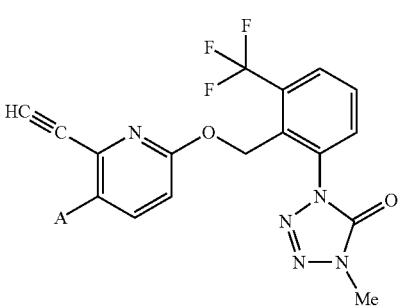
(EPA226)

-continued
(EPA227)
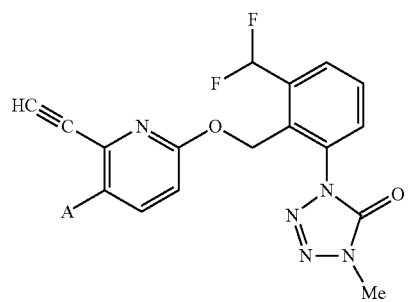
(EPA228)
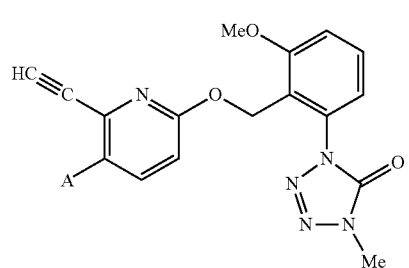
(EPA229)

(EPA230)
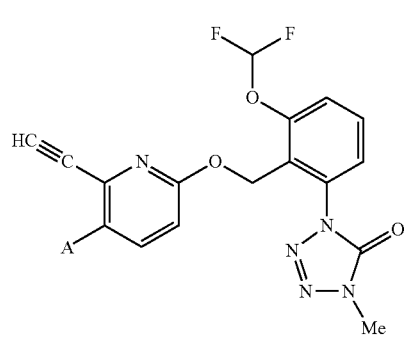
(EPA231)
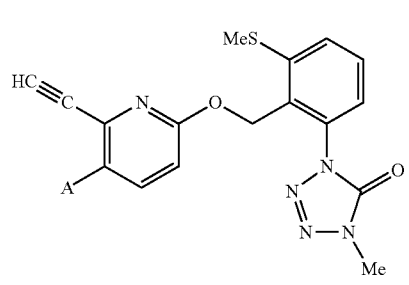
-continued
(EPA232)
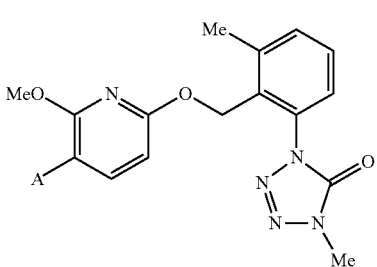
(EPA233)
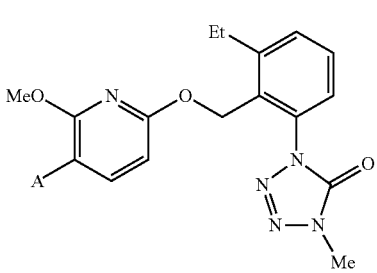
(EPA234)

(EPA235)
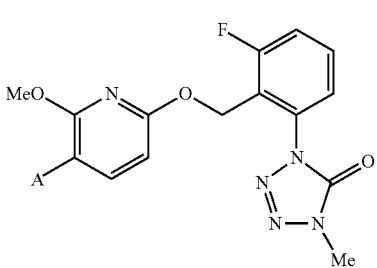
(EPA236)
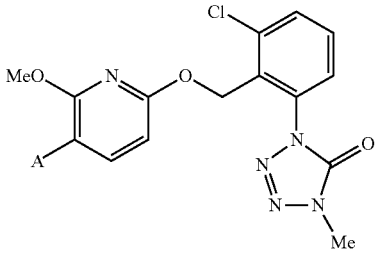
(EPA237)
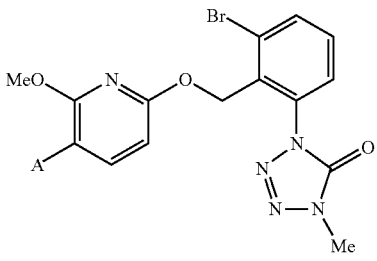

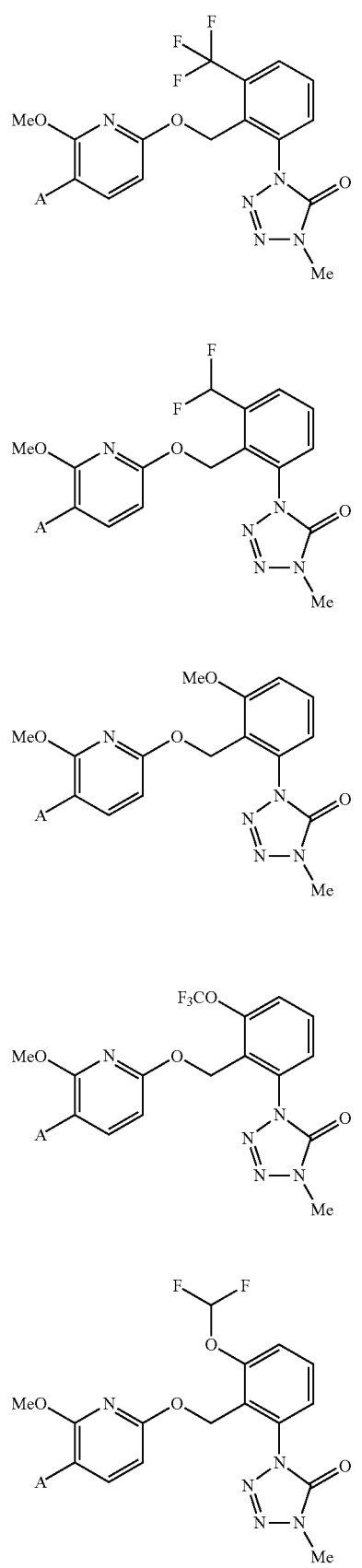
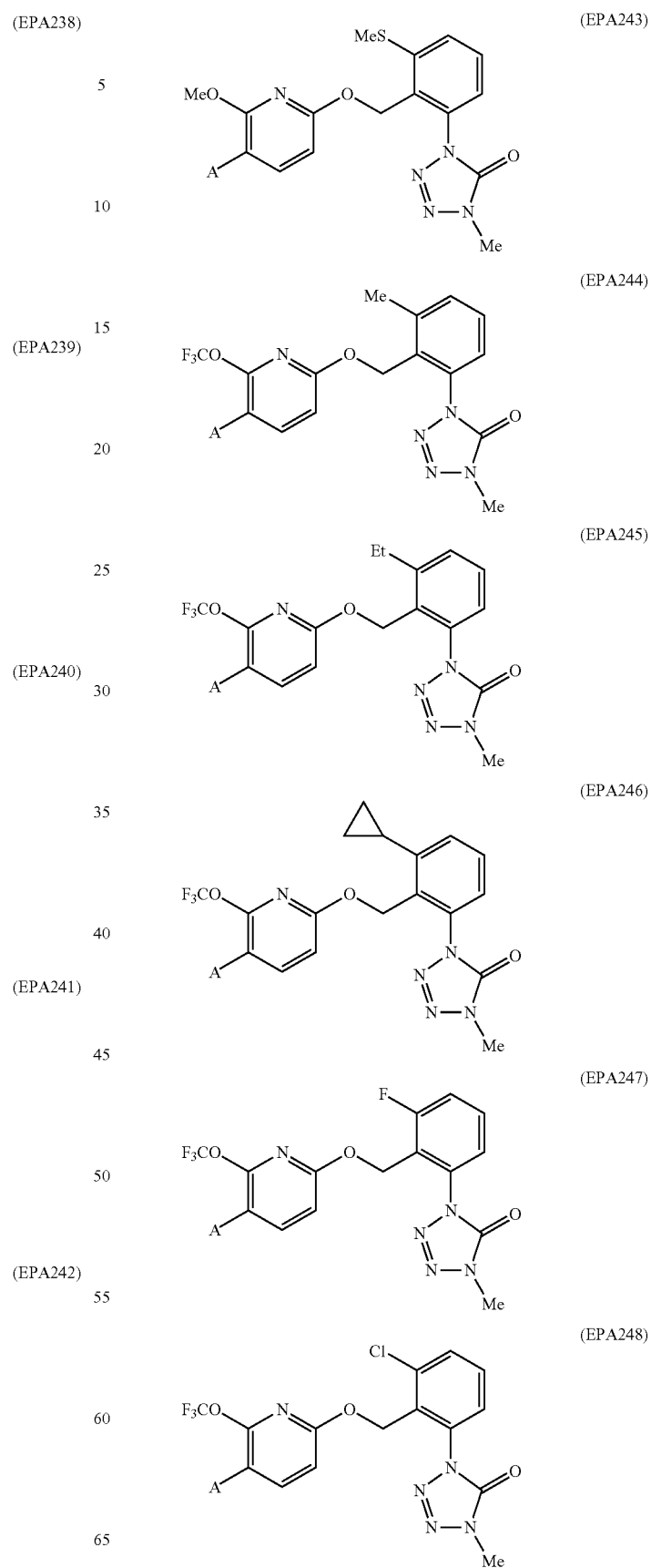

-continued
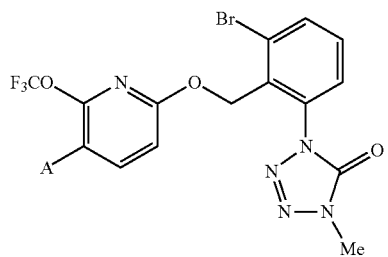
(EPA249)
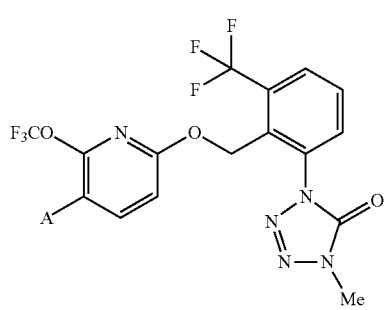
(EPA250)
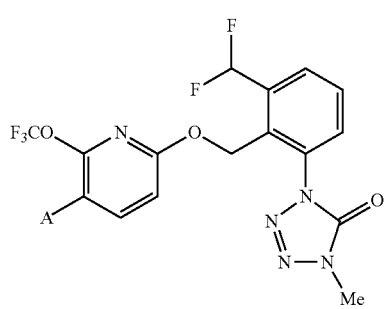
(EPA251)
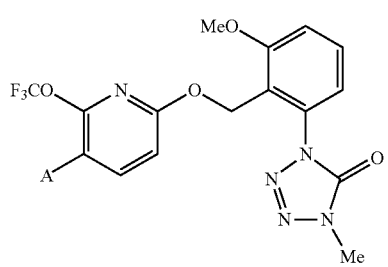
(EPA252)
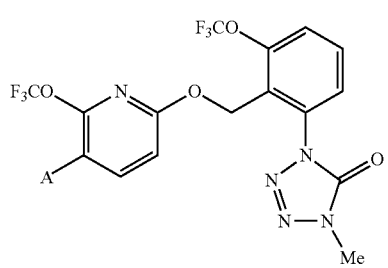
(EPA253)
-continued
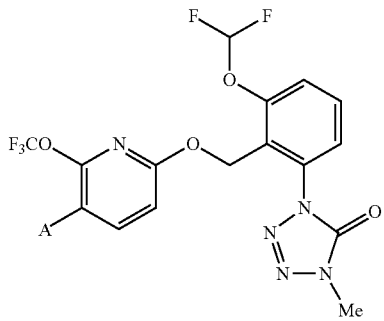
(EPA254)
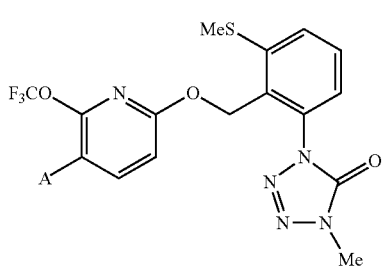
(EPA255)
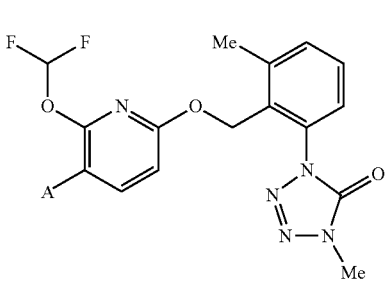
(EPA256)
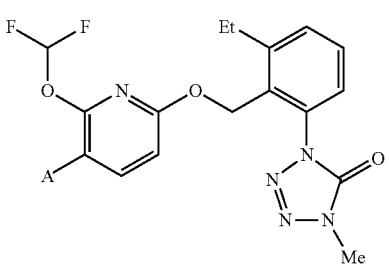
(EPA257)
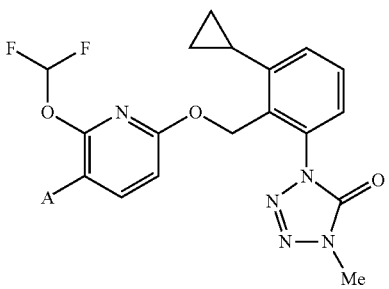
(EPA258)

-continued
(EPA259)
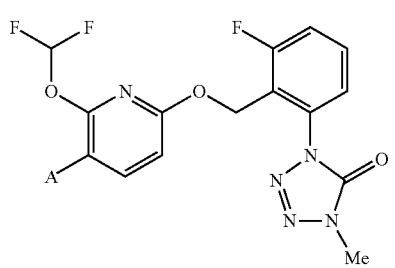
(EPA260)
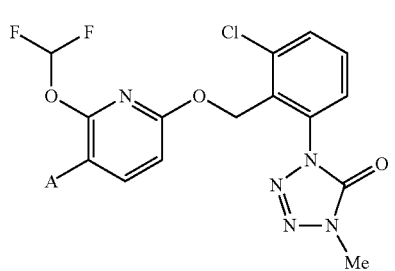
(EPA261)
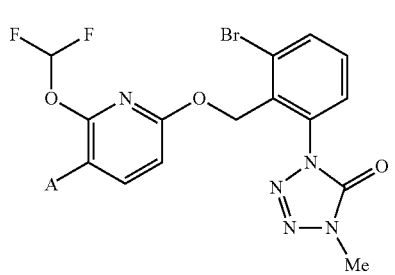
(EPA262)
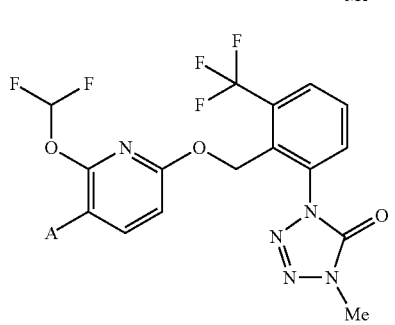
(EPA263)
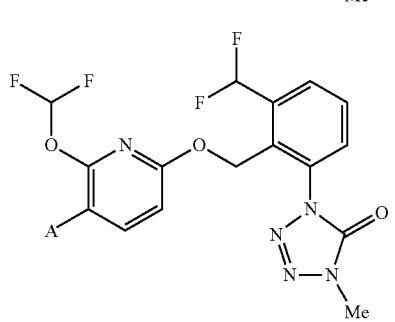
(EPA264)
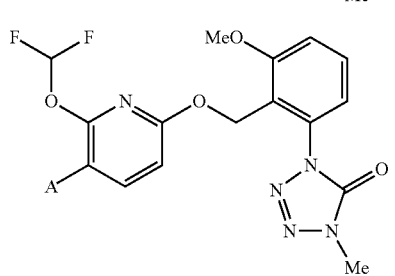
-continued
(EPA265)
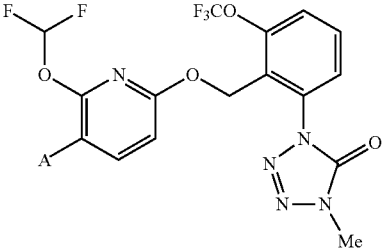
(EPA266)
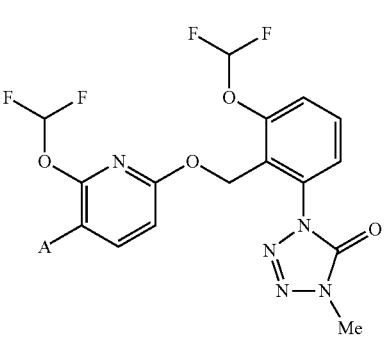
(EPA267)
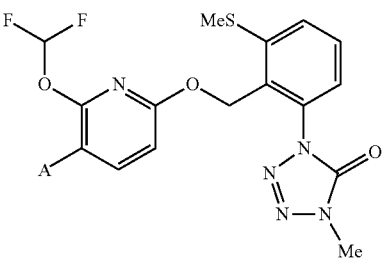
(EPA268)
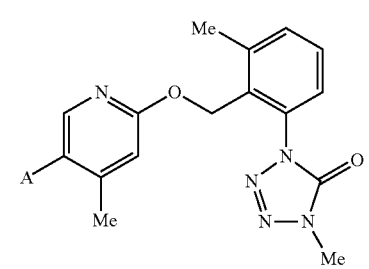
(EPA269)
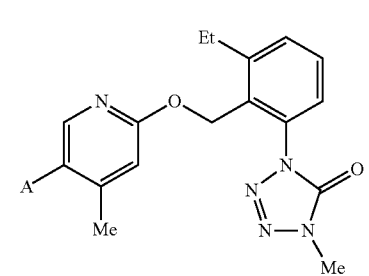

-continued (EPA270)
(EPA271)
(EPA272)
(EPA273)
(EPA274)

(EPA275)
(EPA276)
(EPA277)
(EPA278)
(EPA279)

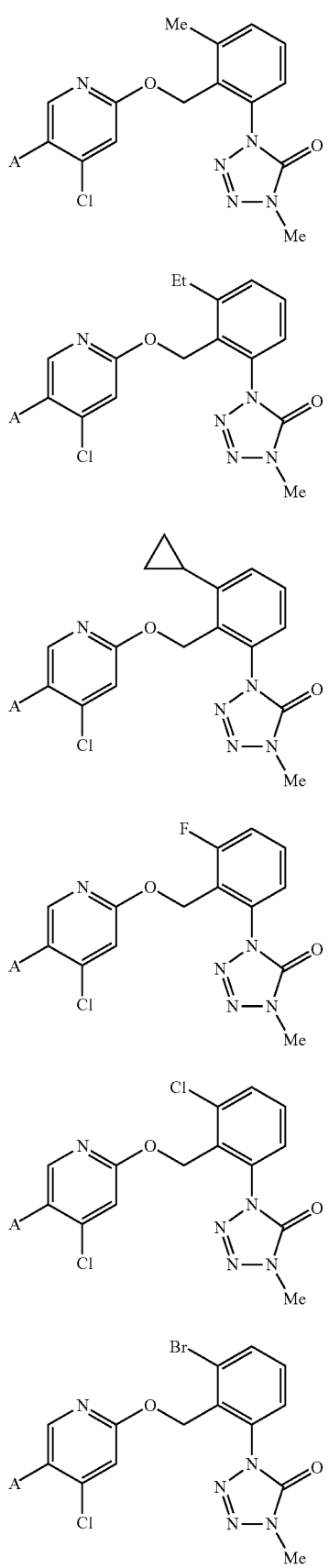
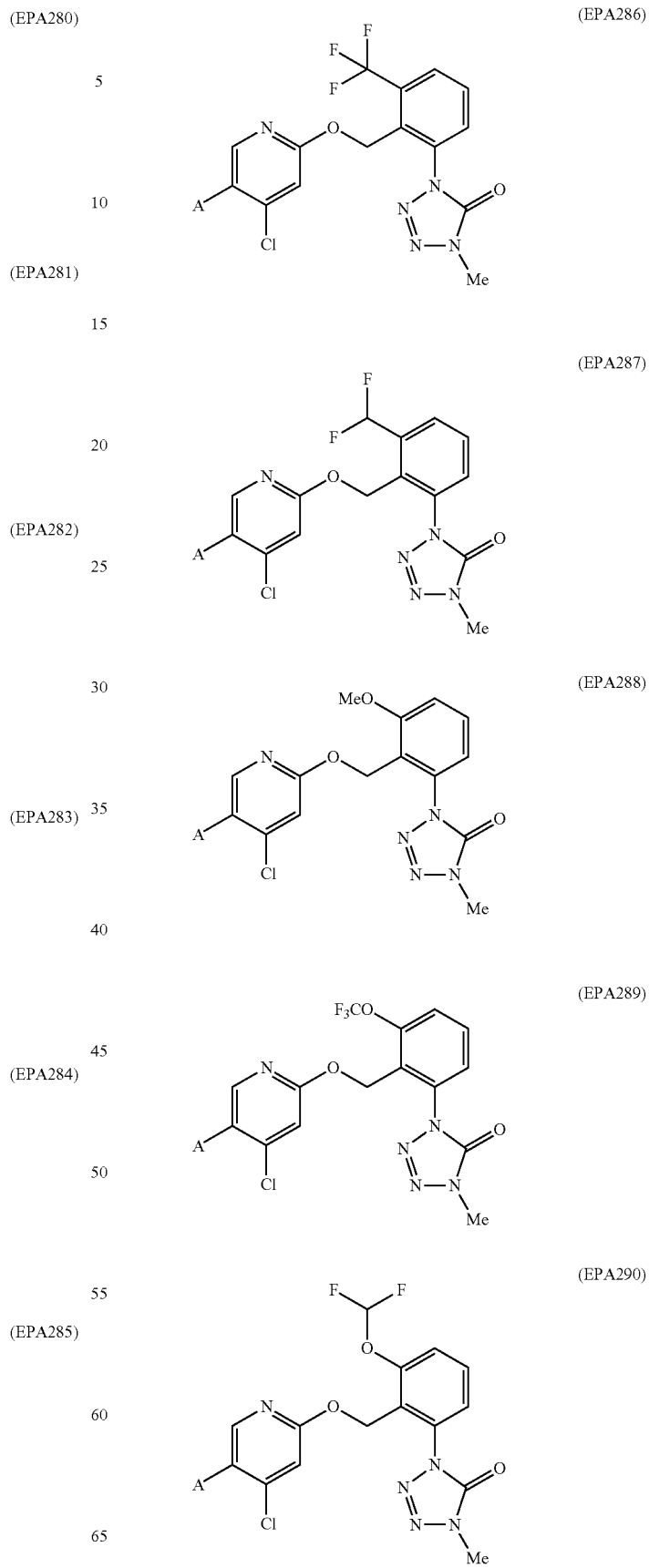

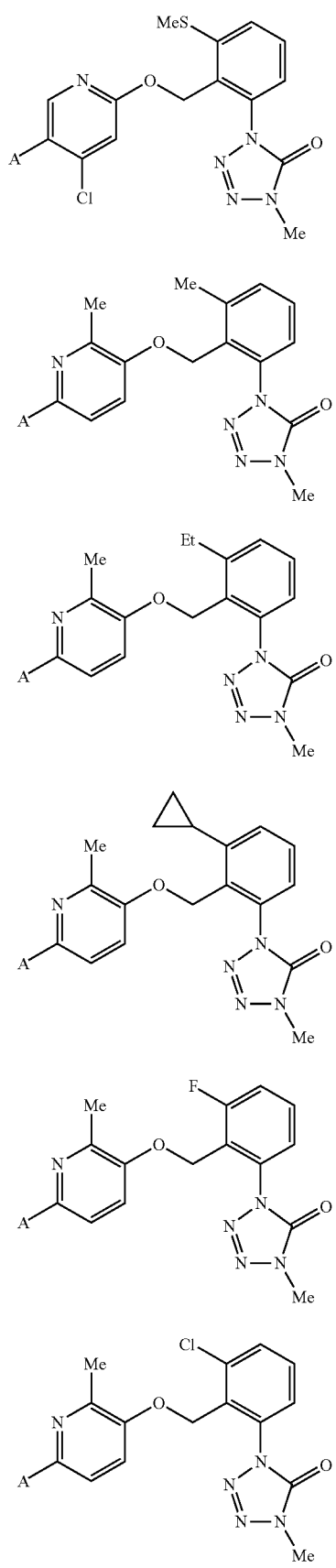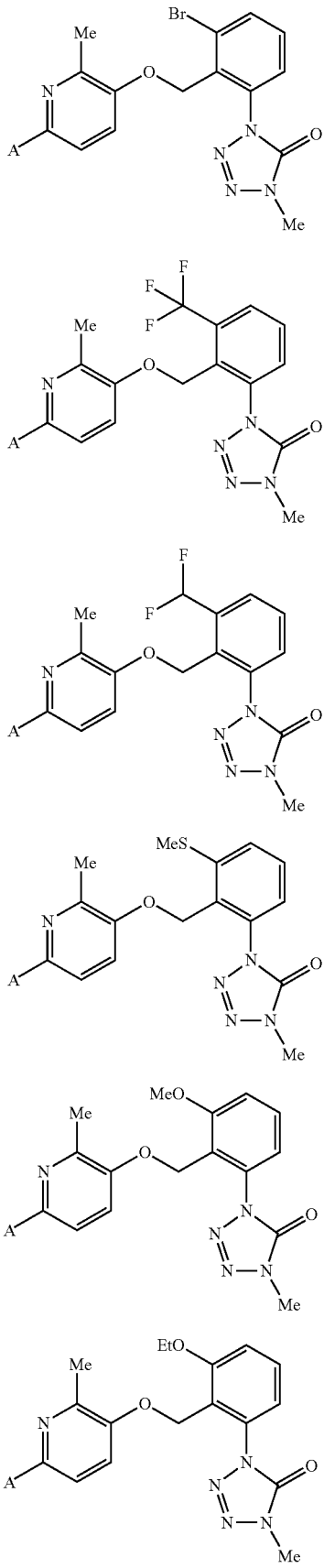

(EPB12)
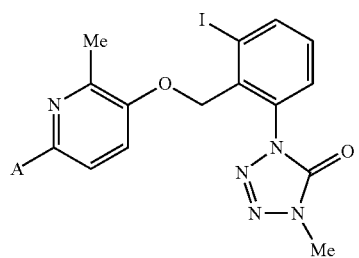
(EPB13)
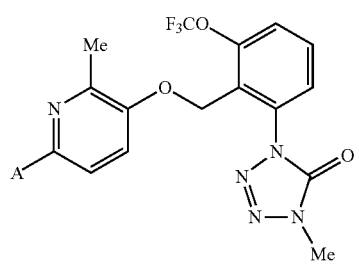
(EPB14)
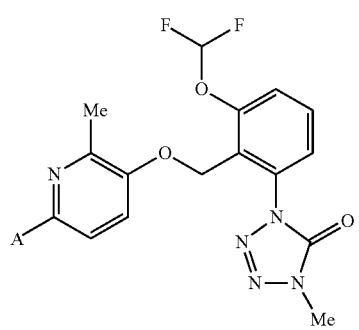
(EPB15)
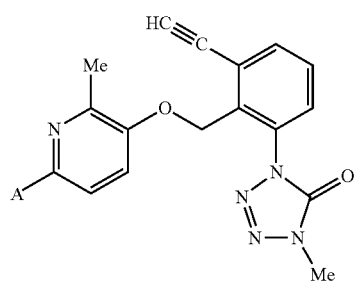
(EPB16)
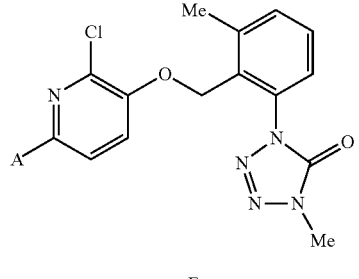
(EPB17)
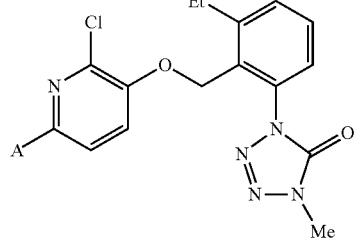
(EPB18)
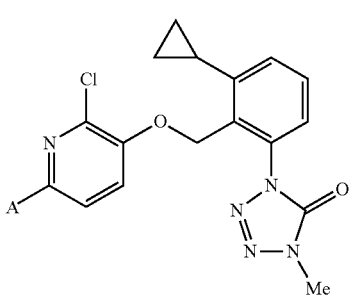
(EPB19)
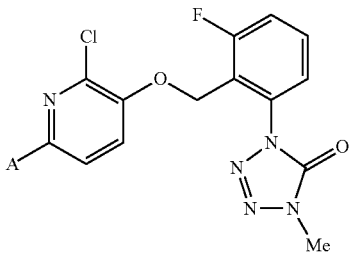
(EPB20)
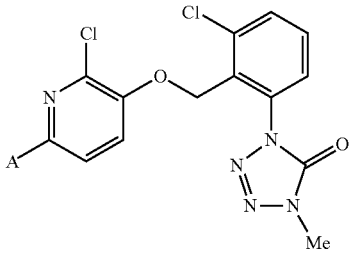
(EPB21)
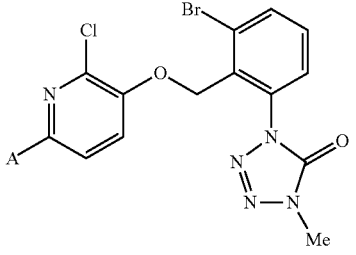
(EPB22)
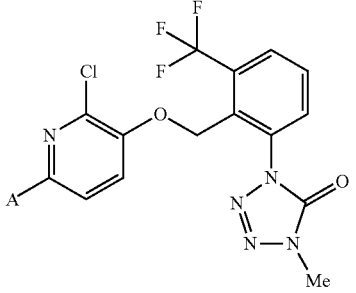

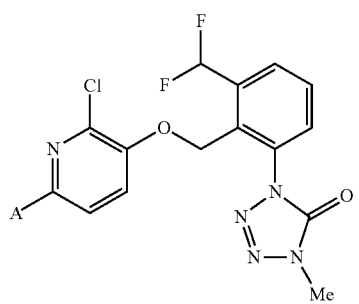
(EPB23)
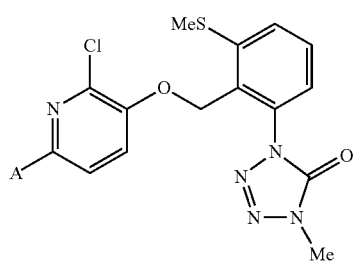
(EPB24)
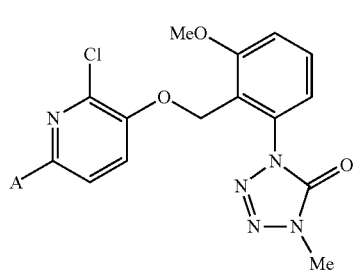
(EPB25)
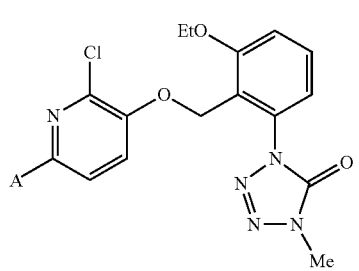
(EPB26)
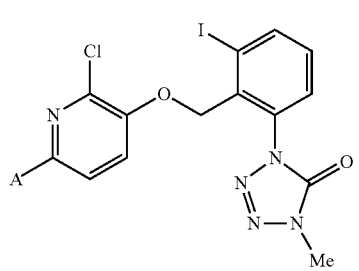
(EPB27)
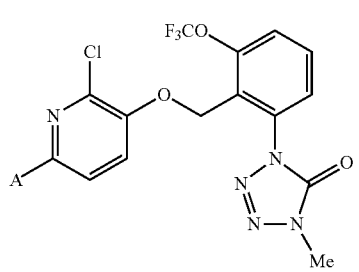
(EPB28)
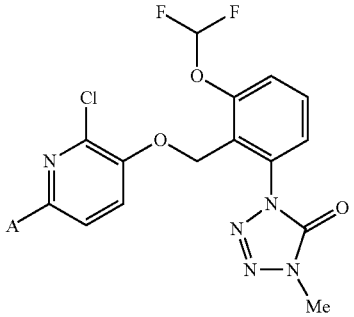
(EPB29)
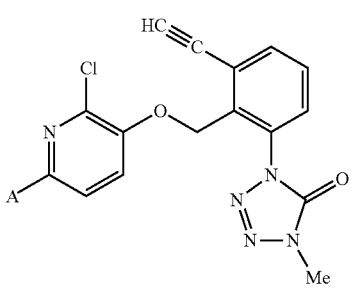
(EPB30)
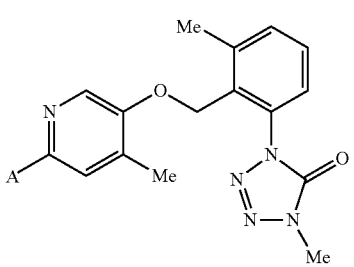
(EPB31)
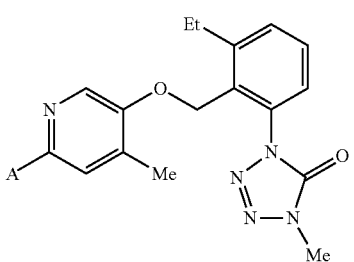
(EPB32)
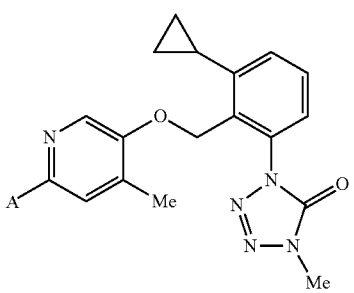
(EPB33)

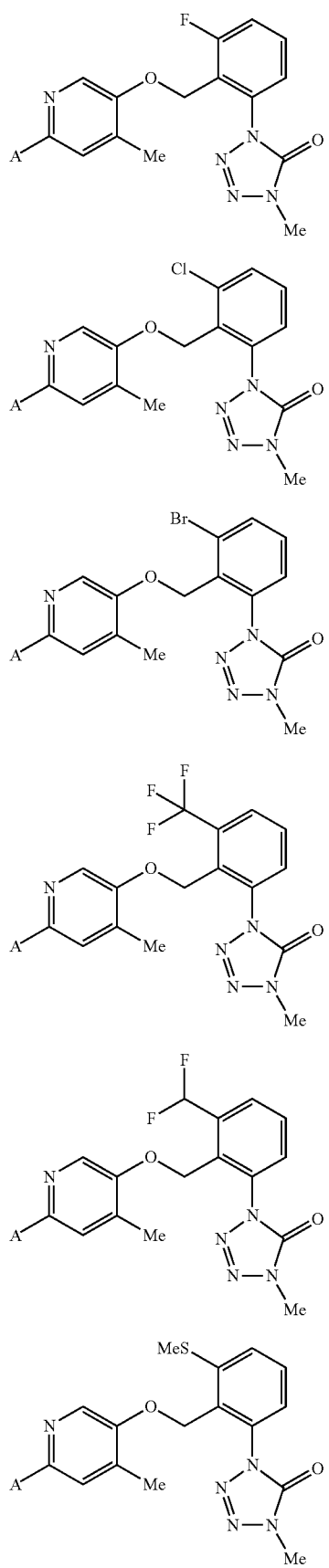
(EPB34)
(EPB35)
(EPB36)
(EPB37)
(EPB38)
(EPB39)
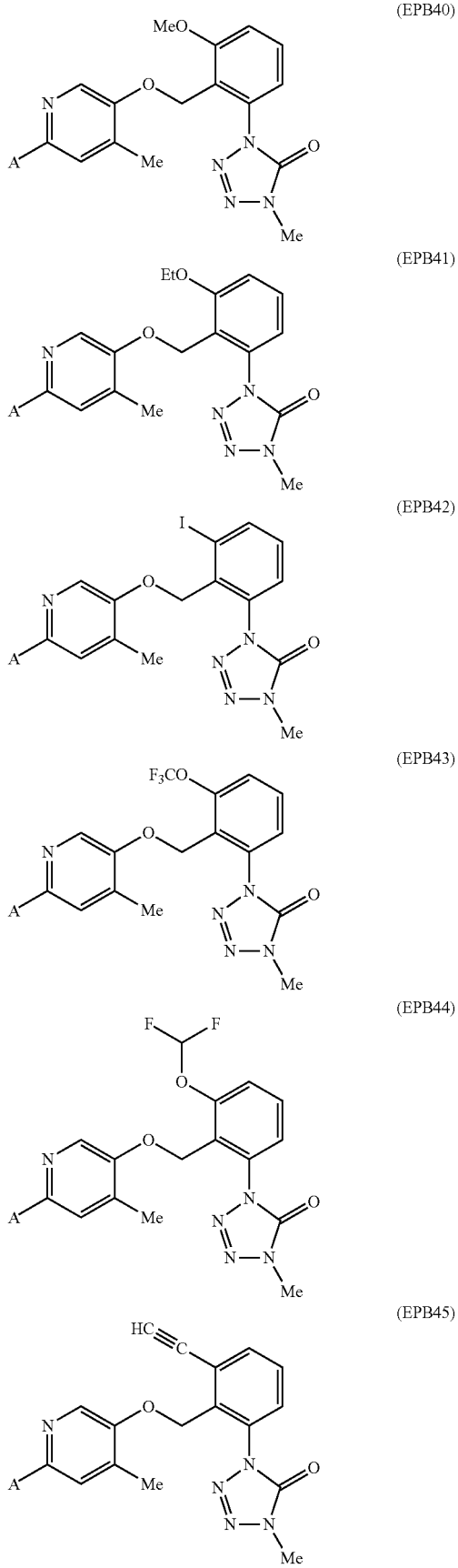
(EPB40)
(EPB41)
(EPB42)
(EPB43)
(EPB44)
(EPB45)

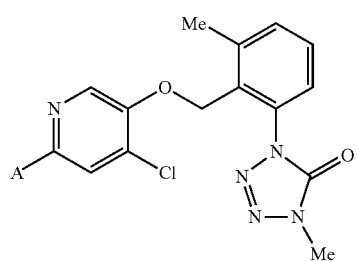
(EPB46)
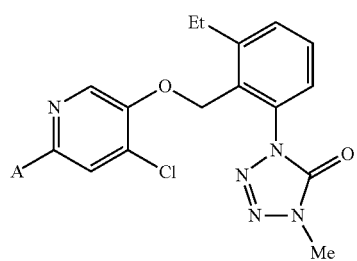
(EPB47)
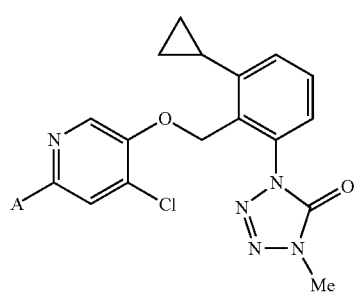
(EPB48)
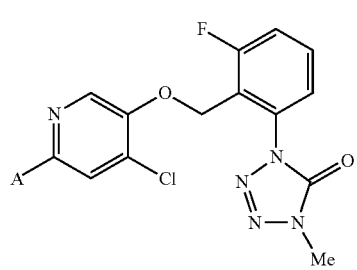
(EPB49)
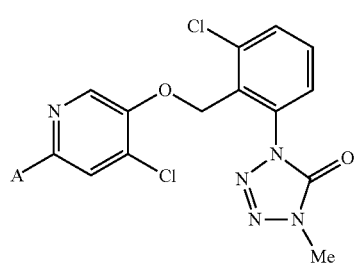
(EPB50)
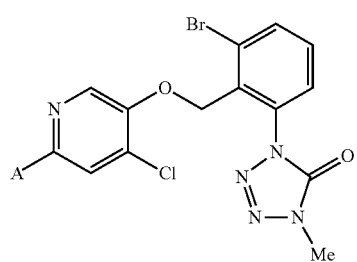
(EPB51)
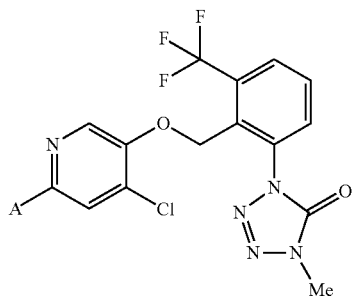
(EPB52)
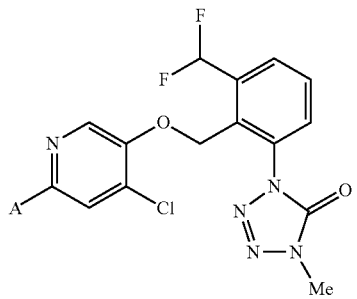
(EPB53)
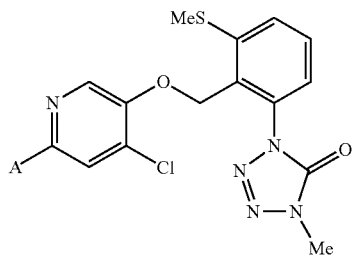
(EPB54)
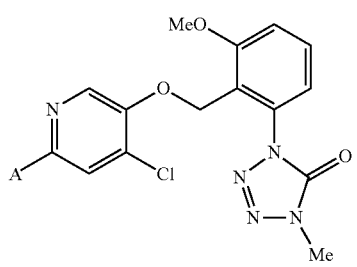
(EPB55)
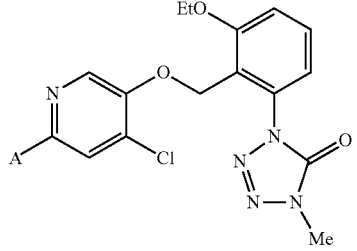
(EPB56)
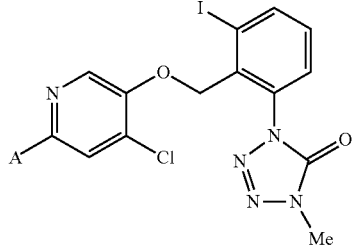
(EPB57)

193
-continued
(EPB58)
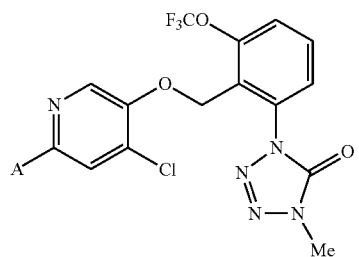
(EPB59)
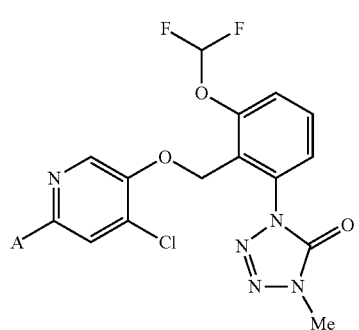
(EPB60)
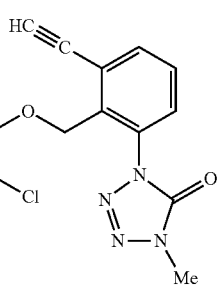
(EPC1)
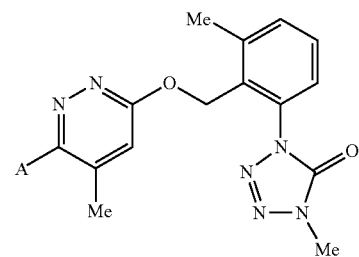
(EPC2)
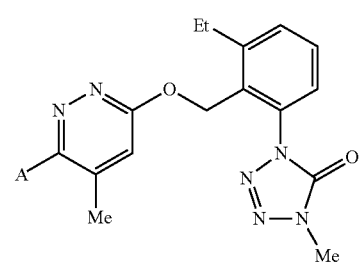
194
-continued
(EPC3)
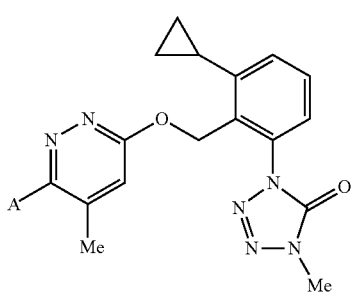
(EPC4)
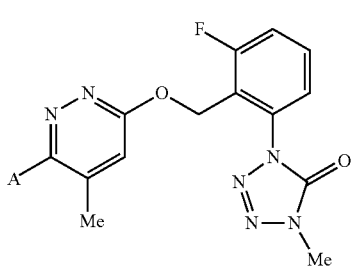
(EPC5)
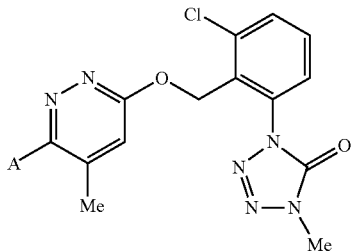
(EPC6)
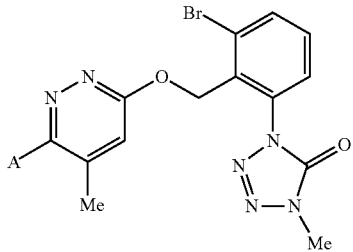
(EPC7)
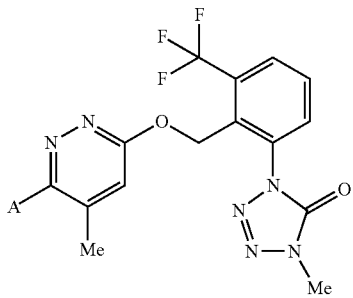

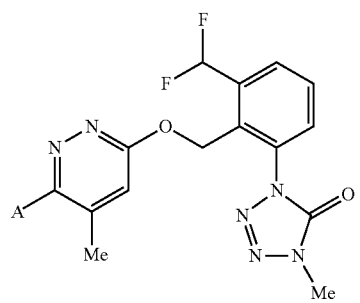 (EPC8)
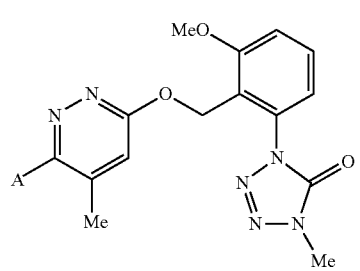 (EPC9)
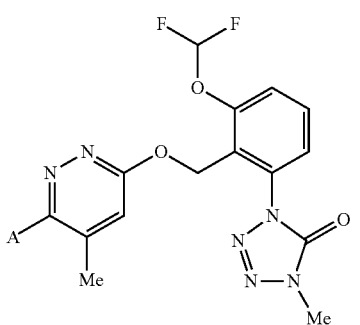 (EPC10)
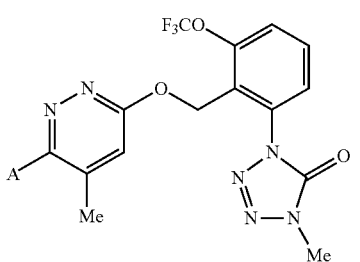 (EPC11)
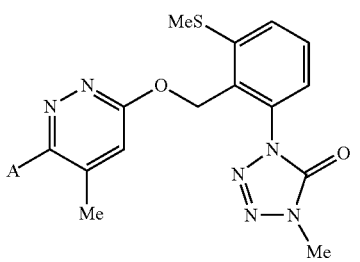 (EPC12)
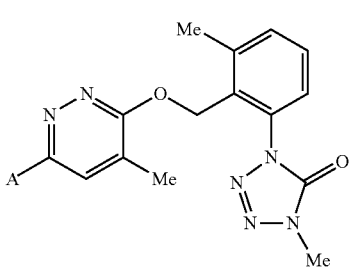 (EPC13)
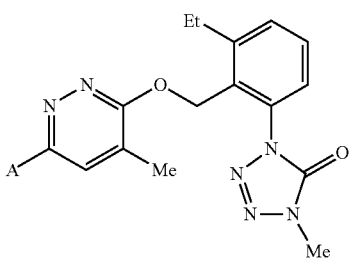 (EPC14)
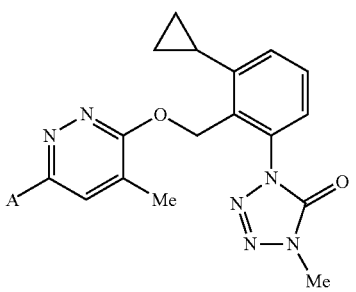 (EPC15)
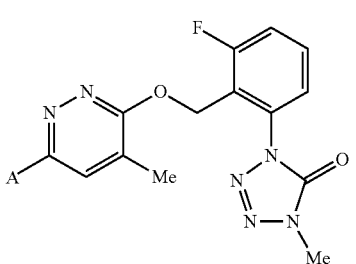 (EPC16)
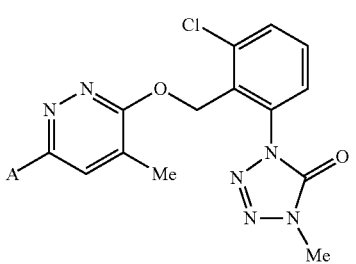 (EPC17)
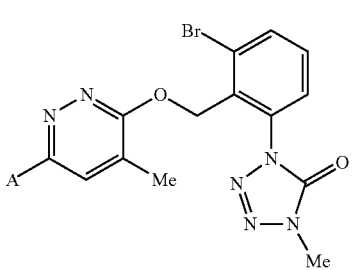 (EPC18)

(EPC19)
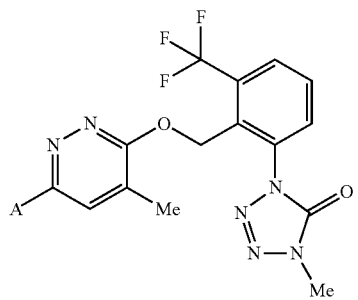
(EPC20)
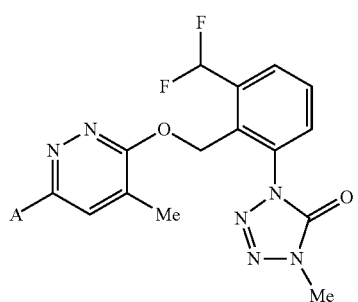
(EPC21)
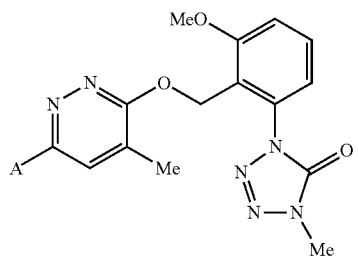
(EPC22)
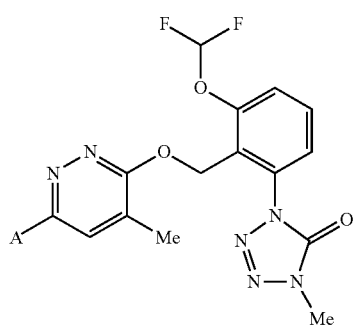
(EPC23)
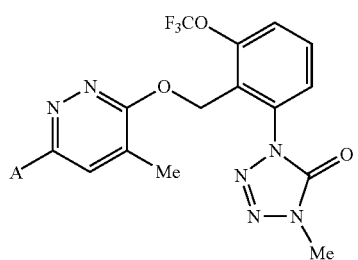
(EPC24)
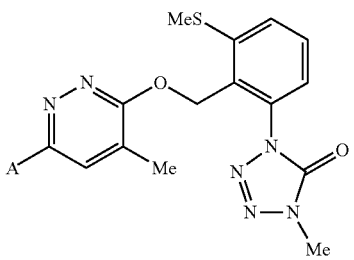
(EPD1)
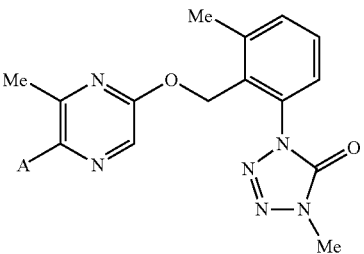
(EPD2)
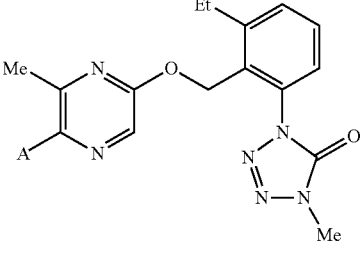
(EPD3)
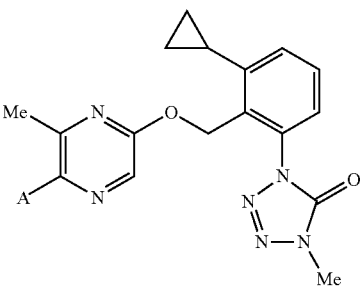
(EPD4)
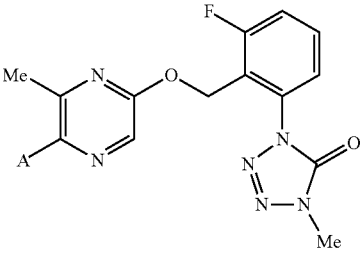
(EPD5)
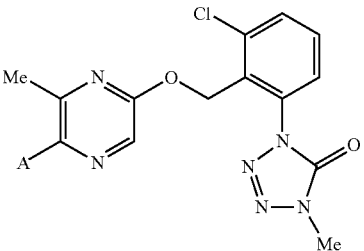

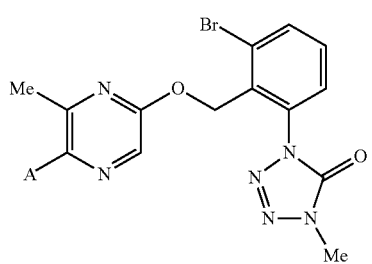
(EPD6)
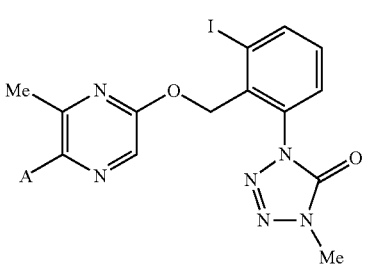
(EPD12)
(EPD7)
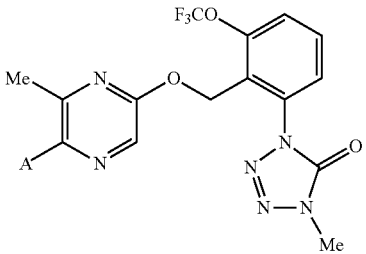
(EPD13)
(EPD8)
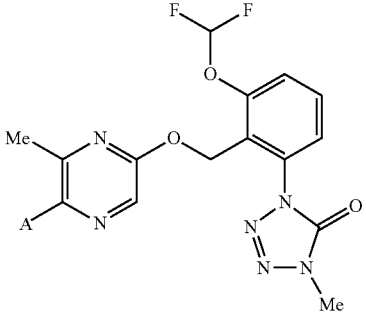
(EPD14)
(EPD9)
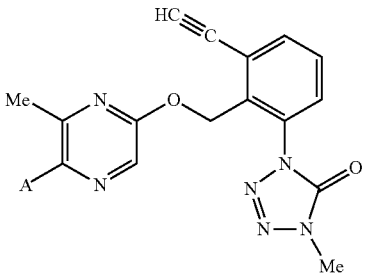
(EPD15)
(EPD10)
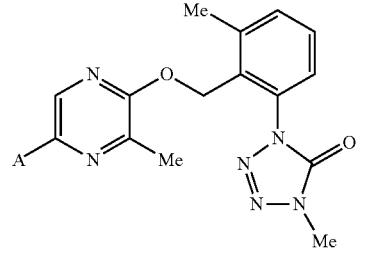
(EPD16)
(EPD11)
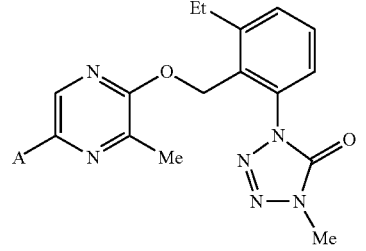
(EPD17)

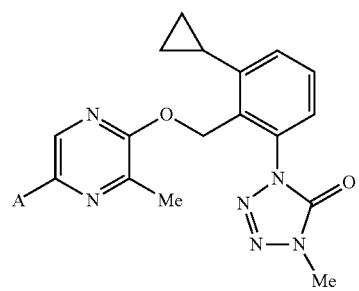
(EPD18)
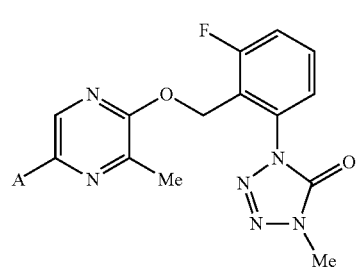
(EPD19)
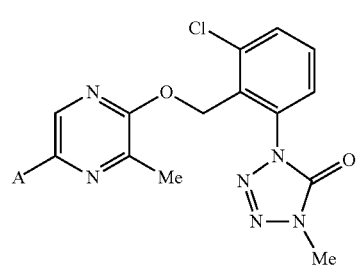
(EPD20)
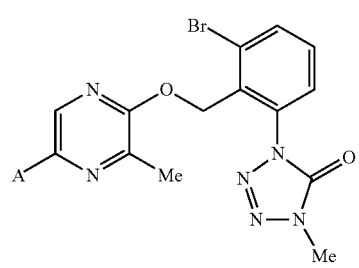
(EPD21)
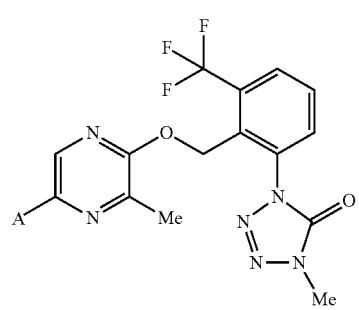
(EPD22)
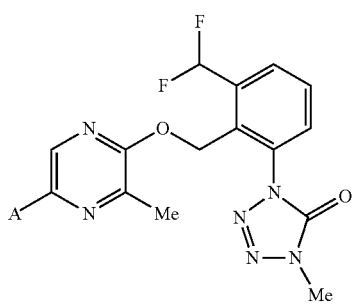
(EPD23)
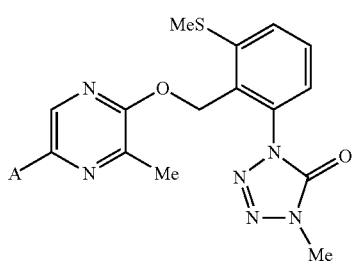
(EPD24)
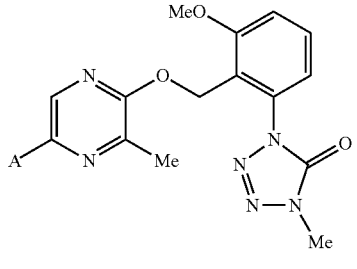
(EPD25)
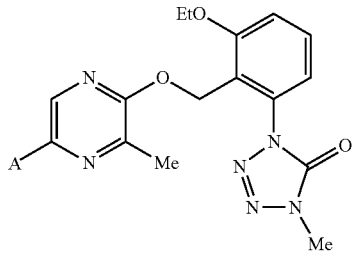
(EPD26)
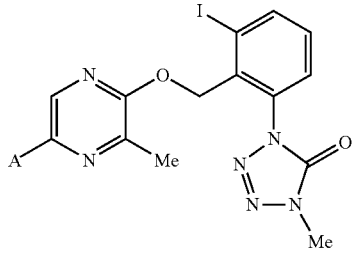
(EPD27)
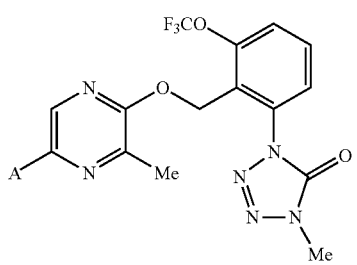
(EPD28)

203
-continued
(EPD29)
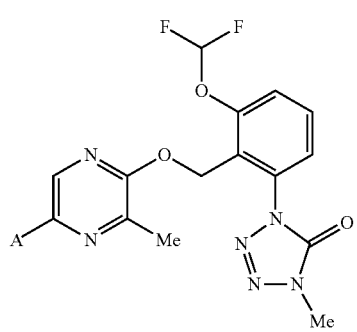
(EPD30)
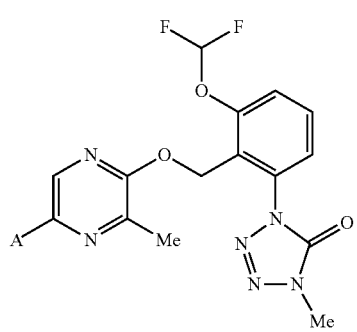
(EPE1)
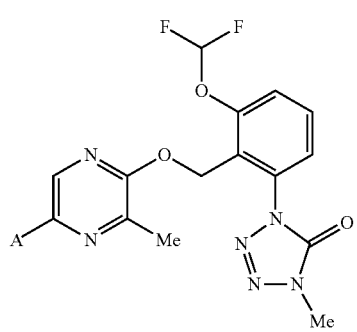
(EPE2)
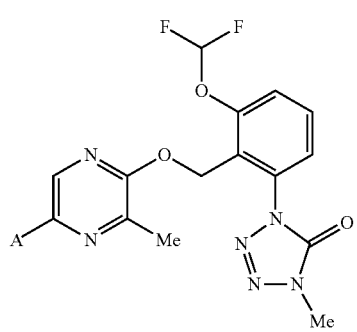
(EPE3)
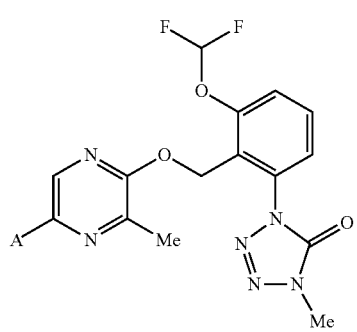
204
-continued
(EPE4)
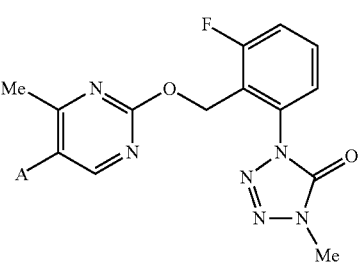
(EPE5)
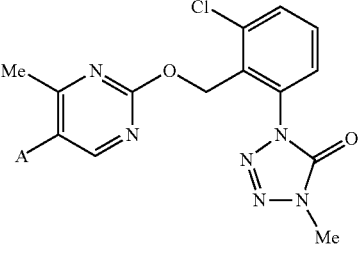
(EPE6)
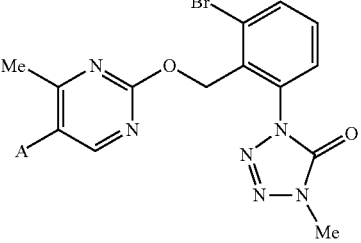
(EPE7)
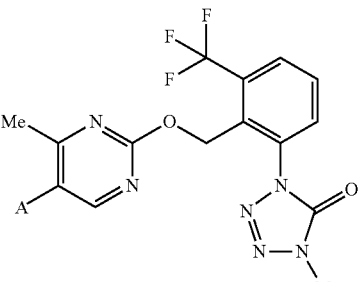
(EPE8)
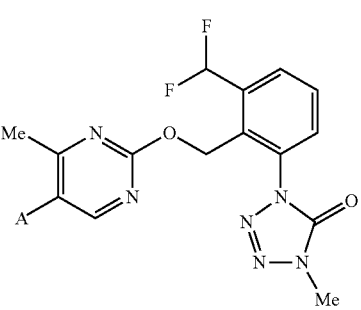
(EPE9)
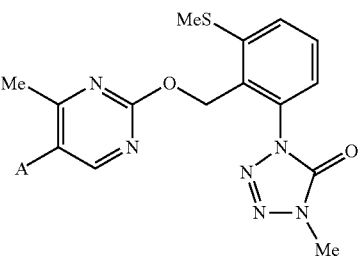

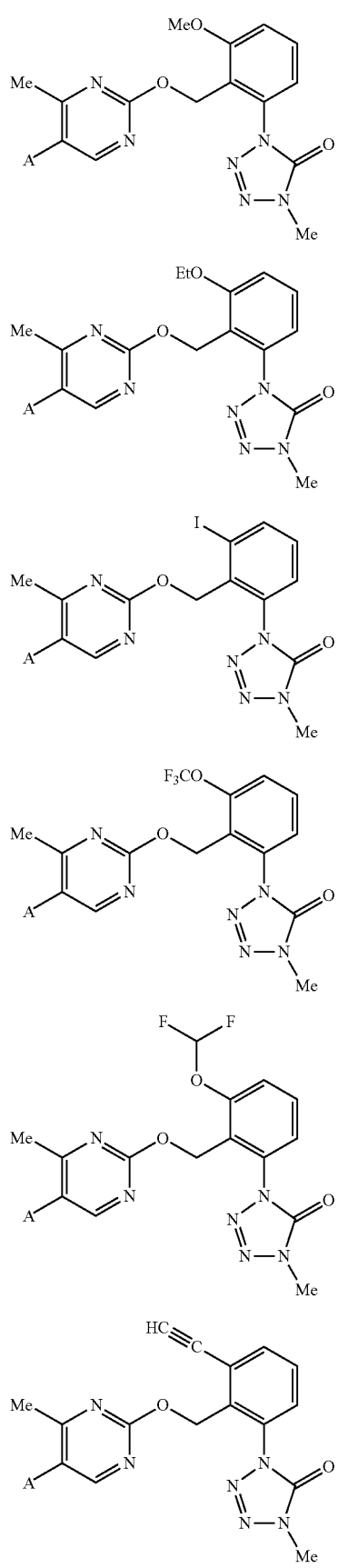
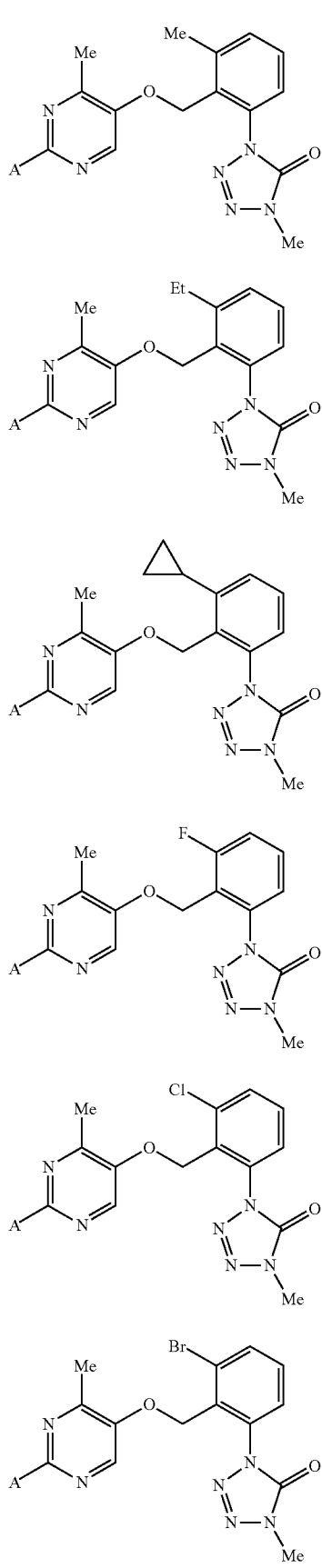

207
-continued
(EPF7)
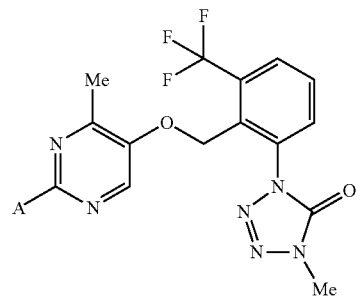
(EPF8)
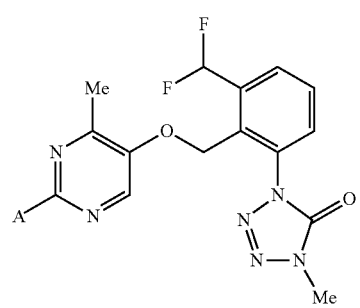
(EPF9)
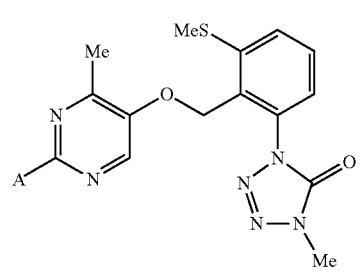
(EPF10)
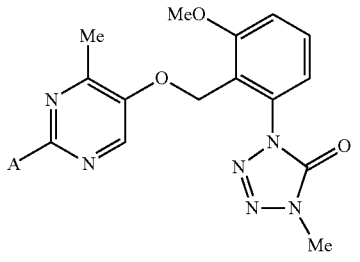
(EPF11)
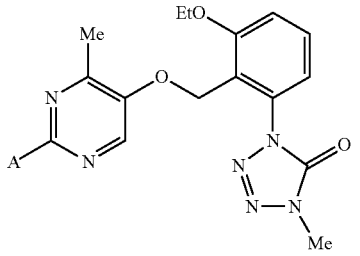
(EPF12)
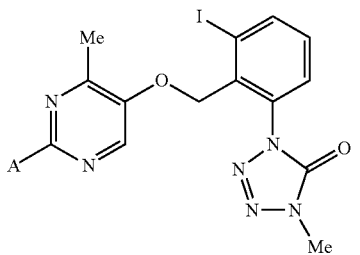
208
-continued
(EPF13)
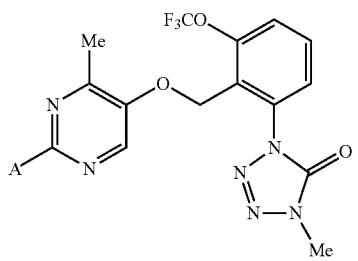
(EPF14)
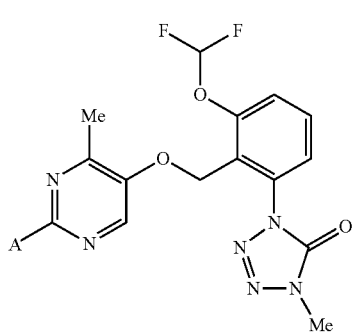
(EPF15)
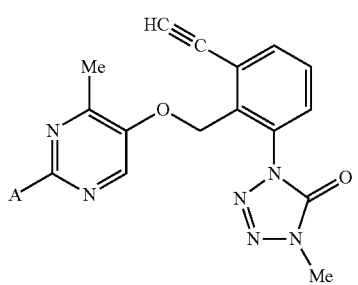
(EPG1)
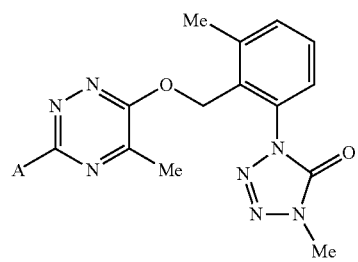
(EPG2)
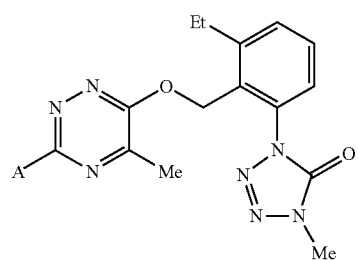

-continued (EPG3)

(EPG4)

(EPG5)

(EPG6)

(EPG7)

-continued (EPG8)

(EPG9)

(EPG10)

(EPG11)

(EPG12)

211
-continued
(EPH1)
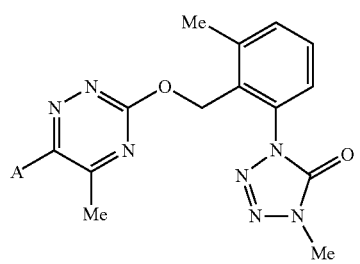
(EPH2)
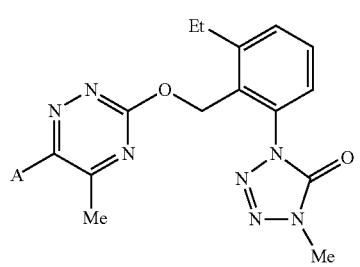
(EPH3)
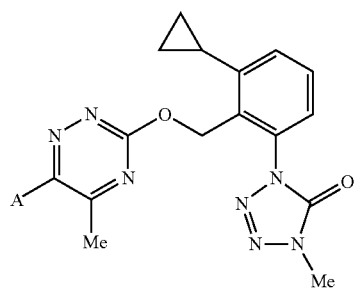
(EPH4)
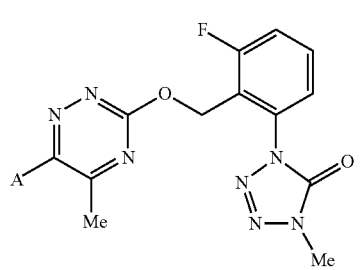
(EPH5)
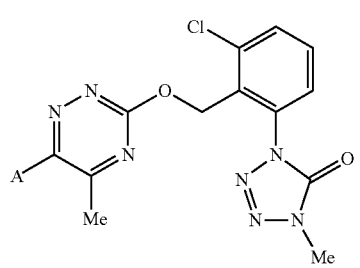
(EPH6)
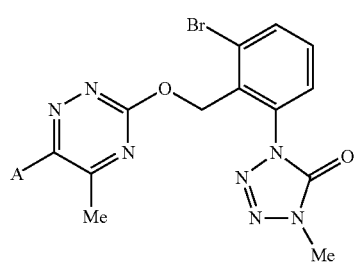
212
-continued
(EPH7)
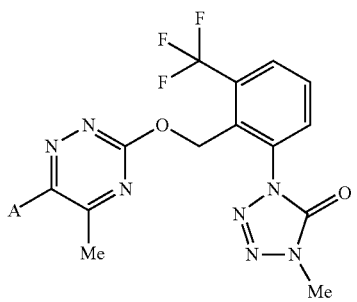
(EPH8)
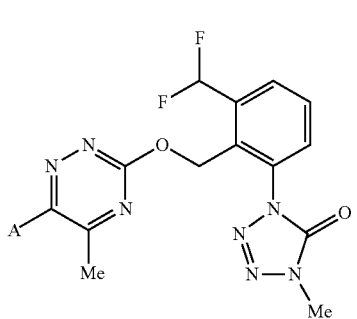
(EPH9)
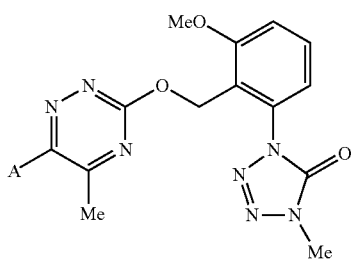
(EPH10)
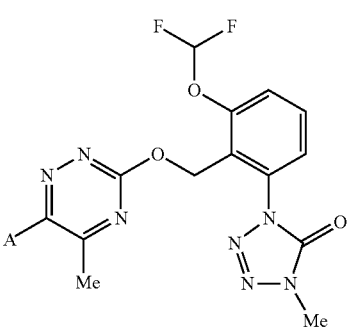
(EPH11)
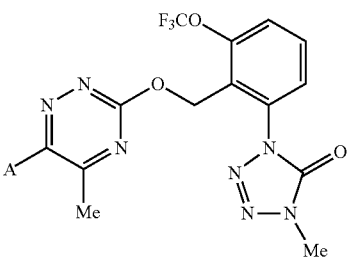

213
-continued (EPH12)
(EPI1)
(EPI2)
(EPI3)
(EPI4)
(EPI5)

214
-continued (EPI6)
(EPI7)
(EPI8)
(EPI9)
(EPI10)

(EPI11)
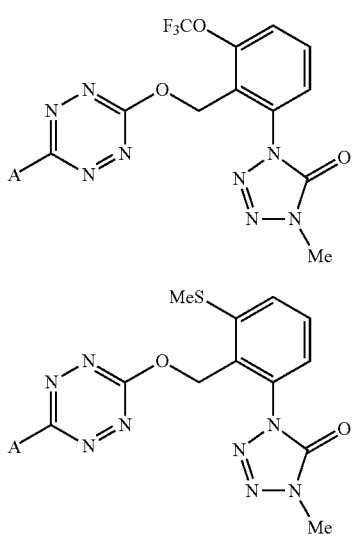

(EPI12)
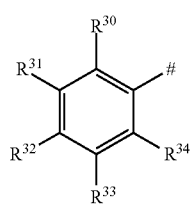

wherein A is a substituent corresponding to each of substituent numbers 1 to 1305.

Substituents in Case where A is A1:

(A1)
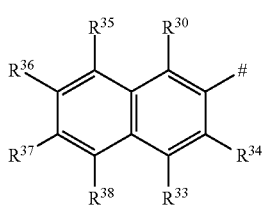

are shown below.

[substituent numbers, $R^{30}$, $R^{31}$, $R^{32}$, $R^{33}$, $R^{34}$]=[1, H, H, H, H, H], [2, Me, H, H, H, H], [3, H, Me, H, H, H], [4, H, H, Me, H, H], [5, Et, H, H, H, H], [6, H, Et, H, H, H], [7, H, H, Et, H, H], [8, cyclopropyl, H, H, H, H], [9, H, cyclopropyl, H, H, H], [10, H, H, cyclopropyl, H, H], [11, F, H, H, H, H], [12, H, F, H, H, H], [13, H, H, F, H, H], [14, Cl, H, H, H, H], [15, H, Cl, H, H, H], [16, H, H, Cl, H, H], [17, Br, H, H, H, H], [18, H, Br, H, H, H], [19, H, H, Br, H, H], [20, CN, H, H, H, H], [21, H, CN, H, H, H], [22, H, H, CN, H, H], [23, OMe, H, H, H, H], [24, H, OMe, H, H, H], [25, H, H, OMe, H, H], [26, OEt, H, H, H, H], [27, H, OEt, H, H, H], [28, H, H, OEt, H, H], [29, CF$_3$, H, H, H, H], [30, H, CF$_3$, H, H, H], [31, H, H, CF$_3$, H, H], [32, CHF$_2$, H, H, H, H], [33, H, CHF$_2$, H, H, H], [34, H, H, CHF$_2$, H, H], [35, Me, Me, H, H, H], [36, Me, H, Me, H, H], [37, Me, H, H, Me, H], [38, Me, H, H, H, Me], [39, Cl, Cl, H, H, H], [40, Cl, H, Cl, H, H], [41, Cl, H, H, Cl, H], [42, Cl, H, H, H, Cl], [43, H, Me, Me, H, H], [44, H, Me, H, Me, H], [45, H, Me, H, H, Me], [46, H, Cl, Cl, H, H], [47, H, Cl, H, Cl, H], [48, H, Cl, H, H, Cl], Substituents in Case where A is A2:

(A2)
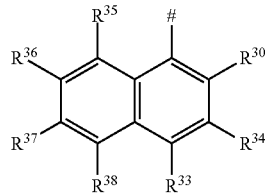

are shown below.

[substituent numbers, $R^{30}$, $R^{33}$, $R^{34}$, $R^{35}$, $R^{36}$, $R^{37}$, $R^{38}$]=[49, H, H, H, H, H, H, H], Substituents in Case where A is A3:

(A3)
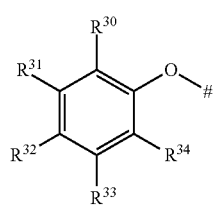

are shown below.

[substituent numbers, $R^{30}$, $R^{33}$, $R^{34}$, $R^{35}$, $R^{36}$, $R^{37}$, $R^{31}$]=[50, H, H, H, H, H, H, H], Substituents in Case where A is A4:

(A4)
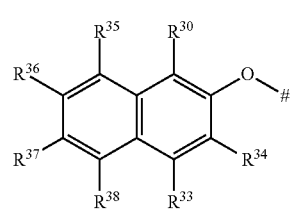

are shown below.

[substituent numbers, $R^{30}$, $R^{31}$, $R^{32}$, $R^{33}$, $R^{34}$]=[51, H, H, H, H, H], [52, Me, H, H, H, H], [53, H, Me, H, H, H], [54, H, H, Me, H, H], [55, Et, H, H, H, H], [56, H, Et, H, H, H], [57, H, H, Et, H, H], [58, cyclopropyl, H, H, H, H], [59, H, cyclopropyl, H, H, H], [60, H, H, cyclopropyl, H, H], [61, F, H, H, H, H], [62, H, F, H, H, H], [63, H, H, F, H, H], [64, Cl, H, H, H, H], [65, H, Cl, H, H, H], [66, H, H, Cl, H, H], [67, Br, H, H, H, H], [68, H, Br, H, H, H], [69, H, H, Br, H, H], [70, CN, H, H, H, H], [71, H, CN, H, H, H], [72, H, H, CN, H, H], [73, OMe, H, H, H, H], [74, H, OMe, H, H, H], [75, H, H, OMe, H, H], [76, OEt, H, H, H, H], [77, H, OEt, H, H, H], [78, H, H, OEt, H, H], [79, CF$_3$, H, H, H, H], [80, H, CF$_3$, H, H, H], [81, H, H, CF$_3$, H, H], [82, CHF$_2$, H, H, H, H], [83, H, CHF$_2$, H, H, H], [84, H, H, CHF$_2$, H, H], [85, Me, Me, H, H, H], [86, Me, H, Me, H, H], [87, Me, H, H, Me, H], [88, Me, H, H, H, Me], [89, Cl, Cl, H, H, H], [90, Cl, H, Cl, H, H], [91, Cl, H, H, Cl, H], [92, Cl, H, H, H, Cl], [93, H, Me, Me, H, H], [94, H, Me, H, Me, H], [95, H, Me, H, H, Me], [96, H, Cl, Cl, H, H], [97, H, Cl, H, Cl, H], [98, H, Cl, H, H, Cl], Substituents in Case where A is A5:

(A5)

are shown below.

[substituent numbers, $R^{30}$, $R^{33}$, $R^{34}$, $R^{35}$, $R^{36}$, $R^{37}$, $R^{38}$]= [99, H, H, H, H, H, H, H], [1261, Me, H, H, H, H, H, H], [1262, H, Me, H, H, H, H, H], [1263, H, H, Me, H, H, H, H], [1264, OMe, H, H, H, H, H, H], [1265, CN, H, H, H, H, H, H], [1266, H, Et, H, H, H, H, H], Substituents in Case where A is A6:

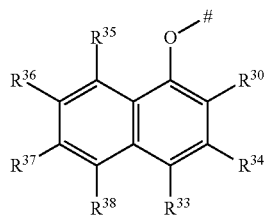

(A6)

are shown below.
[substituent numbers, $R^{30}$, $R^{33}$, $R^{34}$, $R^{35}$, $R^{36}$, $R^{37}$, $R^{38}$], [100, H, H, H, H, H, H, H], Substituents in Case where A is A7:

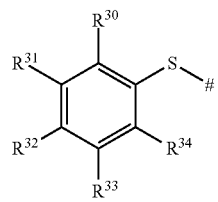

(A7)

are shown below.
[substituent numbers, $R^{30}$, $R^{31}$, $R^{32}$, $R^{33}$, $R^{34}$]=[101, H, H, H, H, H], [102, Me, H, H, H, H], [103, H, Me, H, H, H], [104, H, H, Me, H, H], [105, Et, H, H, H, H], [106, H, Et, H, H, H], [107, H, H, Et, H, H], [108, cyclopropyl, H, H, H, H], [109, H, cyclopropyl, H, H, H], [110, H, H, cyclopropyl, H, H], [111, F, H, H, H, H], [112, H, F, H, H, H], [113, H, H, F, H, H], [114, Cl, H, H, H, H], [115, H, Cl, H, H, H], [116, H, H, Cl, H, H], [117, Br, H, H, H, H], [118, H, Br, H, H, H], [119, H, H, Br, H, H], [120, CN, H, H, H, H], [121, H, CN, H, H, H], [122, H, H, CN, H, H], [123, OMe, H, H, H, H], [124, H, OMe, H, H, H], [125, H, H, OMe, H, H], [126, OEt, H, H, H, H], [127, H, OEt, H, H, H], [128, H, H, OEt, H, H], [129, $CF_3$, H, H, H, H], [130, H, $CF_3$, H, H, H], [131, H, H, $CF_3$, H, H], [132, $CHF_2$, H, H, H, H], [133, H, $CHF_2$, H, H, H], [134, H, H, $CHF_2$, H, H], Substituents in Case where A is A8:

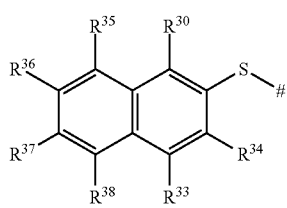

(A8)

are shown below.
[substituent numbers, $R^{30}$, $R^{33}$, $R^{34}$, $R^{35}$, $R^{36}$, $R^{37}$, $R^{38}$]= [135, H, H, H, H, H, H, H], Substituents in Case where A is A9:

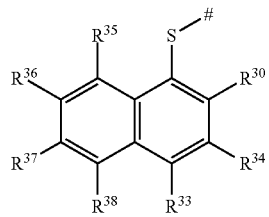

(A9)

are shown below.
[substituent numbers, $R^{30}$, $R^{33}$, $R^{34}$, $R^{35}$, $R^{36}$, $R^{37}$, $R^{38}$]= [136, H, H, H, H, H, H, H], Substituents in Case where A is A10:

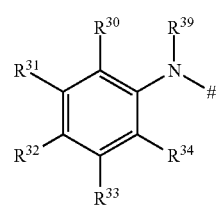

(A10)

are shown below.
[substituent numbers, $R^{30}$, $R^{31}$, $R^{32}$, $R^{33}$, $R^{34}$, $R^{39}$]=[137, H, H, H, H, H, Me], [138, Me, H, H, H, H, Me], [139, H, Me, H, H, H, Me], [140, H, H, Me, H, H, Me], [141, Et, H, H, H, H, Me], [142, H, Et, H, H, H, Me], [143, H, H, Et, H, H, Me], [144, cyclopropyl, H, H, H, H, Me], [145, H, cyclopropyl, H, H, H, Me], [146, H, H, cyclopropyl, H, H, Me], [147, F, H, H, H, H, Me], [148, H, F, H, H, H, Me], [149, H, H, F, H, H, Me], [150, Cl, H, H, H, H, Me], [151, H, Cl, H, H, H, Me], [152, H, H, Cl, H, H, Me], [153, Br, H, H, H, H, Me], [154, H, Br, H, H, H, Me], [155, H, H, Br, H, H, Me], [156, CN, H, H, H, H, Me], [157, H, CN, H, H, H, Me], [158, H, H, CN, H, H, Me], [159, OMe, H, H, H, H, Me], [160, H, OMe, H, H, H, Me], [161, H, H, OMe, H, H, Me], [162, OEt, H, H, H, H, Me], [163, H, OEt, H, H, H, Me], [164, H, H, OEt, H, H, Me], [165, $CF_3$, H, H, H, H, Me], [166, H, $CF_3$, H, H, H, Me], [167, H, H, $CF_3$, H, H, Me], [168, $CHF_2$, H, H, H, H, Me], [169, H, $CHF_2$, H, H, H, Me], [170, H, H, $CHF_2$, H, H, Me], Substituents in case where A is A11:

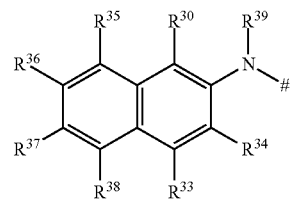

(A11)

are shown below.
[substituent numbers, $R^{30}$, $R^{33}$, $R^{34}$, $R^{35}$, $R^{36}$, $R^{37}$, $R^{38}$, $R^{39}$]=[171, H, H, H, H, H, H, H, Me], Substituents in Case where A is A12:

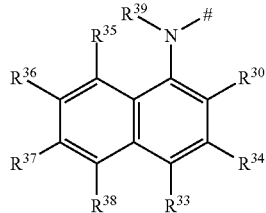
(A12)

are shown below.
[substituent numbers, $R^{30}$, $R^3$, $R^{34}$, $R^{35}$, $R^{36}$, $R^{37}$, $R^{38}$, $R^{39}$]=[172, H, H, H, H, H, H, H, Me], Substituents in Case where A is A13:

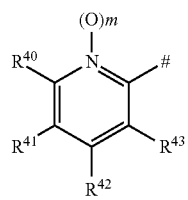
(A13)

are shown below.
[substituent numbers, m, $R^{40}$, $R^{41}$, $R^{42}$, $R^{43}$]=[173, 0, H, H, H, H], [174, 0, Me, H, H, H], [175, 0, H, Me, H, H], [176, 0, H, H, Me, H], [177, 0, H, H, H, Me], [178, 0, Et, H, H, H], [179, 0, H, Et, H, H], [180, 0, H, H, Et, H], [181, 0, H, H, H, Et], [182, 0, cyclopropyl, H, H, H], [183, 0, H, cyclopropyl, H, H], [184, 0, H, H, cyclopropyl, H], [185, 0, H, H, H, cyclopropyl], [186, 0, F, H, H, H], [187, 0, H, F, H, H], [188, 0, H, H, F, H], [189, 0, H, H, H, F], [190, 0, Cl, H, H, H], [191, 0, H, Cl, H, H], [192, 0, H, H, Cl, H], [193, 0, H, H, H, Cl], [194, 0, Br, H, H, H], [195, 0, H, Br, H, H], [196, 0, H, H, Br, H], [197, 0, H, H, H, Br], [198, 0, CN, H, H, H], [199, 0, H, CN, H, H], [200, 0, H, H, CN, H], [201, 0, H, H, H, CN], [202, 0, OMe, H, H, H], [203, 0, H, OMe, H, H], [204, 0, H, H, OMe, H], [205, 0, H, H, H, OMe], [206, 0, OEt, H, H, H], [207, 0, H, OEt, H, H], [208, 0, H, H, OEt, H], [209, 0, H, H, H, OEt], [210, 0, $CF_3$, H, H, H], [211, 0, H, $CF_3$, H, H], [212, 0, H, H, $CF_3$, H], [213, 0, H, H, H, $CF_3$], [214, 0, $CHF_2$, H, H, H], [215, 0, H, $CHF_2$, H, H], [216, 0, H, H, $CHF_2$, H], [217, 0, H, H, H, $CHF_2$], [218, 0, Me, Me, H, H], [219, 0, Me, H, Me, H], [220, 0, Me, H, H, Me], [221, 0, Me, H, H, H], [222, 0, CN, Me, H, H], [223, 0, CN, H, Me, H], [224, 0, Cl, Cl, H, H], [225, 0, Cl, H, Cl, H], [226, 0, Cl, H, H, Cl], [227, 0, Cl, H, H, H], [228, 0, H, Me, Me, H], [229, 0, H, Me, H, Me], [230, 0, H, Me, H, H], [231, 0, H, Cl, Cl, H], [232, 0, H, Cl, H, Cl], [233, 0, H, Cl, H, H], [234, A13, 1, H, H, H, H], [235, 1, Me, H, H, H], [236, 1, H, Me, H, H], [237, 1, Et, H, H, H], [238, 1, Cl, H, H, H], [239, 1, H, Cl, H, H], Substituents in Case where A is A14:

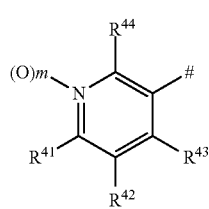
(A14)

are shown below.
[substituent numbers, m, $R^{41}$, $R^{42}$, $R^{43}$, $R^{44}$]=[240, 0, H, H, H, H], [241, 0, Me, H, H, H], [242, 0, H, Me, H, H], [243, 0, H, H, Me, H], [244, 0, H, H, H, Me], [245, 0, Et, H, H, H], [246, 0, H, Et, H, H], [247, 0, H, H, Et, H], [248, 0, H, H, H, Et], [249, 0, cyclopropyl, H, H, H], [250, 0, H, cyclopropyl, H, H], [251, 0, H, H, cyclopropyl, H], [252, 0, H, H, H, cyclopropyl], [253, 0, F, H, H, H], [254, 0, H, F, H, H], [255, 0, H, H, F, H], [256, 0, H, H, H, F], [257, 0, Cl, H, H, H], [258, 0, H, Cl, H, H], [259, 0, H, H, Cl, H], [260, 0, H, H, H, Cl], [261, 0, Br, H, H, H], [262, 0, H, Br, H, H], [263, 0, H, H, Br, H], [264, 0, H, H, H, Br], [265, 0, CN, H, H, H], [266, 0, H, CN, H, H], [267, 0, H, H, CN, H], [268, 0, H, H, H, CN], [269, 0, OMe, H, H, H], [270, 0, H, OMe, H, H], [271, 0, H, H, OMe, H], [272, 0, H, H, H, OMe], [273, 0, OEt, H, H, H], [274, 0, H, OEt, H, H], [275, 0, H, H, OEt, H], [276, 0, H, H, H, OEt], [277, 0, $CF_3$, H, H, H], [278, 0, H, $CF_3$, H, H], [279, 0, H, H, $CF_3$, H], [280, 0, H, H, H, $CF_3$], [281, 0, $CHF_2$, H, H, H], [282, 0, H, $CHF_2$, H, H], [283, 0, H, H, $CHF_2$, H], [284, 0, H, H, H, $CHF_2$], [285, 0, Me, Me, H, H], [286, 0, Me, H, Me, H], [287, 0, Me, H, H, Me], [288, 0, Me, H, H, H], [289, 0, CN, Me, H, H], [290, 0, CN, H, Me, H], [291, 0, Cl, Cl, H, H], [292, 0, Cl, H, Cl, H], [293, 0, Cl, H, H, Cl], [294, 0, Cl, H, H, H], [295, 0, H, Me, Me, H], [296, 0, H, Me, H, Me], [297, 0, H, Me, H, H], [298, 0, H, Cl, Cl, H], [299, 0, H, Cl, H, Cl], [300, 0, H, Cl, H, H], [301, 1, H, H, H, H], [302, 1, Me, H, H, H], [303, 1, H, Me, H, H], [304, 1, Et, H, H, H], [305, 1, Cl, H, H, H], [306, 1, H, Cl, H, H], Substituents in Case where A is A15:

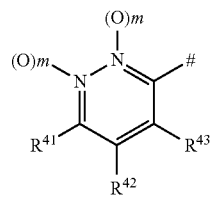
(A15)

are shown below.
[substituent numbers, m, $R^{41}$, $R^{42}$, $R^{43}$]=[307, 0, H, H, H], [308, 0, Me, H, H], [309, 0, H, Me, H], [310, 0, H, H, Me], [311, 0, Et, H, H], [312, 0, H, Et, H], [313, 0, H, H, Et], [314, 0, cyclopropyl, H, H], [315, 0, H, cyclopropyl, H], [316, 0, H, H, cyclopropyl], [317, 0, F, H, H], [318, 0, H, F, H], [319, 0, H, H, F], [320, 0, Cl, H, H], [321, 0, H, Cl, H], [322, 0, H, H, Cl], [323, 0, Br, H, H], [324, 0, H, Br, H], [325, 0, H, H, Br], [326, 0, CN, H, H], [327, 0, H, CN, H], [328, 0, H, H, CN], [329, 0, OMe, H, H], [330, 0, H, OMe, H], [331, 0, H, H, OMe], [332, 0, OEt, H, H], [333, 0, H, OEt, H], [334, 0, H, H, OEt], [335, 0, $CF_3$, H, H], [336, 0, H, $CF_3$, H], [337, 0, H, H, $CF_3$], [338, 0, $CHF_2$, H, H], [339, 0, H, $CHF_2$, H], [340, 0, H, H, $CHF_2$], [341, 0, Me, Me, H], [342, 0, Me, H, Me], [343, 0, CN, Me, H], [344, 0, CN, H, Me], [345, 0, Cl, Cl, H], [346, 0, Cl, H, Cl], [347, 0, H, Me, Me], [348, 0, H, Cl, Cl], Substituents in Case where A is A16:

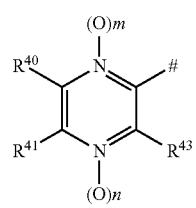
(A16)

are shown below.

[substituent numbers, m, $R^{40}$, $R^{41}$, $R^{43}$]=[349, 0, H, H, H], [350, 0, Me, H, H], [351, 0, H, Me, H], [352, 0, H, H, Me], [353, 0, Et, H, H], [354, 0, H, Et, H], [355, 0, H, H, Et], [356, 0, cyclopropyl, H, H], [357, 0, H, cyclopropyl, H], [358, 0, H, H, cyclopropyl], [359, 0, F, H, H], [360, 0, H, F, H], [361, 0, H, H, F], [362, 0, Cl, H, H], [363, 0, H, Cl, H], [364, 0, H, H, Cl], [365, 0, Br, H, H], [366, 0, H, Br, H], [367, 0, H, H, Br], [368, 0, CN, H, H], [369, 0, H, CN, H], [370, 0, H, H, CN], [371, 0, OMe, H, H], [372, 0, H, OMe, H], [373, 0, H, H, OMe], [374, 0, OEt, H, H], [375, 0, H, OEt, H], [376, 0, H, H, OEt], [377, 0, $CF_3$, H, H], [378, 0, H, $CF_3$, H], [379, 0, H, H, $CF_3$], [380, 0, $CHF_2$, H, H], [381, 0, H, $CHF_2$, H], [382, 0, H, H, $CHF_2$], [383, 0, Me, Me, H], [384, 0, Me, H, Me], [385, 0, CN, Me, H], [386, 0, CN, H, Me], [387, 0, Cl, Cl, H], [388, 0, Cl, H, Cl], [389, 0, H, Me, Me], [390, 0, H, Cl, Cl], Substituents in Case where A is A17:

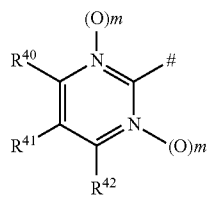

(A17)

are shown below.

[substituent numbers, m, $R^{40}$, $R^{41}$, $R^{42}$]=[391, 0, H, H, H], [392, 0, Me, H, H], [393, 0, H, Me, H], [394, 0, H, H, Me], [395, 0, Et, H, H], [396, 0, H, Et, H], [397, 0, H, H, Et], [398, 0, cyclopropyl, H, H], [399, 0, H, cyclopropyl, H], [400, 0, H, H, cyclopropyl], [401, 0, F, H, H], [402, 0, H, F, H], [403, 0, H, H, F], [404, 0, Cl, H, H], [405, 0, H, Cl, H], [406, 0, H, H, Cl], [407, 0, Br, H, H], [408, 0, H, Br, H], [409, 0, H, H, Br], [410, 0, CN, H, H], [411, 0, H, CN, H], [412, 0, H, H, CN], [413, 0, OMe, H, H], [414, 0, H, OMe, H], [415, 0, H, H, OMe], [416, 0, OEt, H, H], [417, 0, H, OEt, H], [418, 0, H, H, OEt], [419, 0, $CF_3$, H, H], [420, 0, H, $CF_3$, H], [421, 0, H, H, $CF_3$], [422, 0, $CHF_2$, H, H], [423, 0, H, $CHF_2$, H], [424, 0, H, H, $CHF_2$], [425, 0, Me, Me, H], [426, 0, Me, H, Me], [427, 0, CN, Me, H], [428, 0, CN, H, Me], [429, 0, Cl, Cl, H], [430, 0, Cl, H, Cl], [431, 0, H, Me, Me], [432, 0, H, Cl, Cl], Substituents in Case where A is A18:

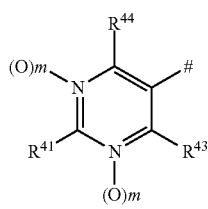

(A18)

are shown below.

[substituent numbers, m, $R^{41}$, $R^{43}$, $R^{44}$]=[433, 0, H, H, H], [434, 0, H, H, Me], [435, 0, Me, H, H], [436, 0, H, Me, H], [437, 0, H, H, Et], [438, 0, Et, H, H], [439, 0, H, Et, H], [440, 0, H, H, cyclopropyl], [441, 0, cyclopropyl, H, H], [442, 0, H, cyclopropyl, H], [443, 0, H, H, F], [444, 0, F, H, H], [445, 0, H, F, H], [446, 0, H, H, Cl], [447, 0, Cl, H, H], [448, 0, H, Cl, H], [449, 0, H, H, Br], [450, 0, Br, H, H], [451, 0, H, Br, H], [452, 0, H, H, CN], [453, 0, CN, H, H], [454, 0, H, CN, H], [455, 0, H, H, OMe], [456, 0, OMe, H, H], [457, 0, H, OMe, H], [458, 0, H, H, OEt], [459, 0, OEt, H, H], [460, 0, H, Oft, H], [461, 0, H, H, $CF_3$], [462, 0, $CF_3$, H, H], [463, 0, H, $CF_3$, H], [464, 0, H, H, $CHF_2$], [465, 0, $CHF_2$, H, H], [466, 0, H, $CHF_2$, H], [467, 0, Me, H, Me], [468, 0, H, Me, Me], [469, 0, Me, H, CN], [470, 0, H, Me, CN], [471, 0, Cl, H, Cl], [472, 0, H, Cl, Cl], [473, 0, Me, Me, H], [474, 0, Cl, Cl, H], Substituents in Case where A is A19:

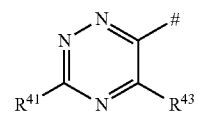

(A19)

are shown below.

[substituent numbers, $R^{41}$, $R^{43}$]=[475, H, H], [476, Me, H], [477, H, Me], [478, Et, H], [479, H, Et], [480, cyclopropyl, H], [481, H, cyclopropyl], [482, F, H], [483, H, F], [484, Cl, H], [485, H, Cl], [486, Br, H], [487, H, Br], [488, CN, H], [489, H, CN], [490, OMe, H], [491, H, OMe], [492, OEt, H], [493, H, OEt], [494, $CF_3$, H], [495, H, $CF_3$], [496, $CHF_2$, H], [497, H, $CHF_2$], [498, Me, Me], [499, Cl, Cl], Substituents in Case where A is A20:

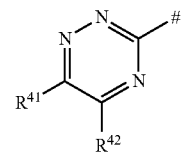

(A20)

are shown below.

[substituent numbers, $R^{41}$, $R^{42}$]=[500, H, H], [501, Me, H], [502, H, Me], [503, Et, H], [504, H, Et], [505, cyclopropyl, H], [506, H, cyclopropyl], [507, F, H], [508, H, F], [509, Cl, H], [510, H, Cl], [511, Br, H], [512, H, Br], [513, CN, H], [514, H, CN], [515, OMe, H], [516, H, OMe], [517, OEt, H], [518, H, OEt], [519, $CF_3$, H], [520, H, $CF_3$], [521, $CHF_2$, H], [522, H, $CHF_2$], [523, Me, Me], [524, Cl, Cl], Substituents in Case where A is A21:

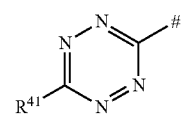

(A21)

are shown below.

[substituent numbers, $R^{41}$]=[525, H], [526, Me], [527, A21, H], [528, Et], [529, H], [530, cyclopropyl], [531, H], [532, F], [533, H], [534, Cl], [535, H], [536, Br], [537, H], [538, CN], [539, H], [540, OMe], [541, H], [542, OEt], [543, H], [544, $CF_3$], [545, H], [546, $CHF_2$], [547, H], [548, Me], [549, Cl], Substituents in Case where A is A25:

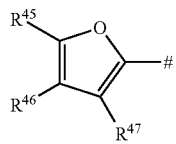

are shown below.
[substituent numbers, $R^{45}$, $R^{46}$, $R^{47}$]=[550, H, H, H], [551, Me, H, H], Substituents in Case where A is A27:

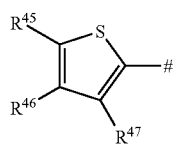

are shown below.
[substituent numbers, $R^{45}$, $R^{46}$, $R^{47}$]=[552, H, H, H], [553, Me, H, H], [554, H, Me, H], Substituents in Case where A is A28:

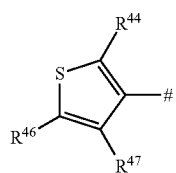

are shown below.
[substituent numbers, $R^{44}$, $R^{46}$, $R^{47}$]=[555, H, H, H], [556, H, Me, H], Substituents in Case where A is A29:

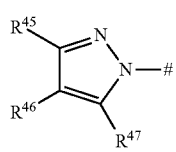

are shown below.
[substituent numbers, $R^{45}$, $R^{46}$, $R^{47}$]=[557, H, H, H], [558, Me, H, H], [559, H, Me, H], [560, H, H, Me], [561, Et, H, H], [562, H, Et, H], [563, H, H, Et], [564, cyclopropyl, H, H], [565, H, cyclopropyl, H], [566, H, H, cyclopropyl], [567, F, H, H], [568, H, F, H], [569, H, H, F], [570, Cl, H, H], [571, H, Cl, H], [572, H, H, Cl], [573, Br, H, H], [574, H, Br, H], [575, H, H, Br], [576, CN, H, H], [577, H, CN, H], [578, H, H, CN], [579, OMe, H, H], [580, H, OMe, H], [581, H, H, OMe], [582, OEt, H, H], [583, H, OEt, H], [584, H, H, OEt], [585, $CF_3$, H, H], [586, H, $CF_3$, H], [587, H, H, $CF_3$], [588, $CHF_2$, H, H], [589, H, $CHF_2$, H], [590, H, H, $CHF_2$], [591, Me, Me, H], [592, Me, H, Me], [593, Me, Me, Me], [594, Et, H, Et], [595, Me, Et, Me], [596, Me, F, Me], [597, Me, Cl, Me], [598, Me, Br, Me], [599, Me, $CF_3$, Me], [600, Me, $CHF_2$, Me], [601, Me, OMe, Me], [602, Me, OEt, Me], [603, Me, SMe, Me], [604, Me, SEt, Me], [605, Me, $OCF_3$, Me], [606, Me, $OCHF_2$, Me], [607, Me, CN, Me], [608, Et, H, Me], [609, Et, Et, Me], [610, Et, F, Me], [611, Et, Cl, Me], [612, Et, Br, Me], [613, Et, $CF_3$, Me], [614, Et, $CHF_2$, Me], [615, Et, OMe, Me], [616, Et, OEt, Me], [617, Et, SMe, Me], [618, Et, SEt, Me], [619, Et, $OCF_3$, Me], [620, Et, $OCHF_2$, Me], [621, Et, CN, Me], [622, Et, F, Et], [623, Et, Cl, Et], [624, Et, Br, Et], [625, Et, $CF_3$, Et], [626, Et, $CHF_2$, Et], [627, Et, OMe, Et], [628, Et, OEt, Et], [629, Et, SMe, Et], [630, Et, SEt, Et], [631, Et, $OCF_3$, Et], [632, Et, $OCHF_2$, Et], [633, Et, CN, Et], [634, $CHF_2$, H, Me], [635, $CHF_2$, Me, Me], [636, $CHF_2$, Et, Me], [637, $CHF_2$, F, Me], [638, $CHF_2$, Cl, Me], [639, $CHF_2$, Br, Me], [640, $CHF_2$, $CF_3$, Me], [641, $CHF_2$, $CHF_2$, Me], [642, $CHF_2$, OMe, Me], [643, $CHF_2$, OEt, Me], [644, $CHF_2$, SMe, Me], [645, $CHF_2$, SEt, Me], [646, $CHF_2$, $OCF_3$, Me], [647, $CHF_2$, $OCHF_2$, Me], [648, $CHF_2$, CN, Me], Substituents in Case where A is A30:

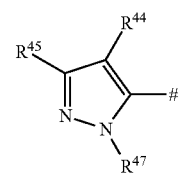

are shown below.
[substituent numbers, $R^{44}$, $R^{45}$, $R^{47}$]=[649, H, H, H], [650, Me, H, H], [651, H, Me, H], [652, H, H, Me], [653, Et, H, H], [654, H, Et, H], [655, H, H, Et], [656, cyclopropyl, H, H], [657, H, cyclopropyl, H], [658, H, H, cyclopropyl], [659, F, H, H], [660, H, F, H], [661, H, H, F], [662, Cl, H, H], [663, H, Cl, H], [664, Br, H, H], [665, H, Br, H], [666, CN, H, H], [667, H, CN, H], [668, H, H, CN], [669, OMe, H, H], [670, H, OMe, H], [671, H, OEt, H], [672, H, OEt, H], [673, $CF_3$, H, H], [674, H, $CF_3$, H], [675, H, H, $CF_3$], [676, $CHF_2$, H, H], [677, H, $CHF_2$, H], [678, H, H, $CHF_2$], [679, Me, Me, H], [680, Me, H, Me], [681, Me, Me, Me], [682, Et, H, Et], [683, Me, Et, Me], [684, Me, F, Me], [685, Me, Cl, Me], [686, Me, Br, Me], [687, Me, $CF_3$, Me], [688, Me, $CHF_2$, Me], [689, Me, OMe, Me], [690, Me, OEt, Me], [691, Me, SMe, Me], [692, Me, SEt, Me], [693, Me, $OCF_3$, Me], [694, Me, $OCHF_2$, Me], [695, Me, CN, Me], [696, Et, H, Me], [697, Et, Et, Me], [698, Et, F, Me], [699, Et, Cl, Me], [700, Et, Br, Me], [701, Et, $CF_3$, Me], [702, Et, $CHF_2$, Me], [703, Et, OMe, Me], [704, Et, OEt, Me], [705, Et, SMe, Me], [706, Et, SEt, Me], [707, Et, $OCF_3$, Me], [708, Et, $OCHF_2$, Me], [709, Et, CN, Me], [710, Et, F, Et], [711, Et, Cl, Et], [712, Et, Br, Et], [713, Et, $CF_3$, Et], [714, Et, $CHF_2$, Et], [715, Et, OMe, Et], [716, Et, OEt, Et], [717, Et, SMe, Et], [718, Et, SEt, Et], [719, Et, $OCF_3$, Et], [720, Et, $OCHF_2$, Et], [721, Et, CN, Et], [722, $CHF_2$, H, Me], [723, $CHF_2$, Me, Me], [724, $CHF_2$, Et, Me], [725, $CHF_2$, F, Me], [726, $CHF_2$, Cl, Me], [727, $CHF_2$, Br, Me], [728, $CHF_2$, $CF_3$, Me], [729, $CHF_2$, $CHF_2$, Me], [730, $CHF_2$, OMe, Me], [731, $CHF_2$, OEt, Me], [732, $CHF_2$, SMe, Me], [733, $CHF_2$, SEt, Me], [734, $CHF_2$, $OCF_3$, Me], [735, $CHF_2$, $OCHF_2$, Me], [736, $CHF_2$, CN, Me], Substituents in Case where A is A31:

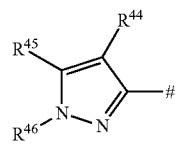
(A31)

are shown below.

[substituent numbers, $R^{44}$, $R^{45}$, $R^{46}$]=[737, H, H, H], [738, Me, H, H], [739, H, Me, H], [740, H, H, Me], [741, Et, H, H], [742, H, Et, H], [743, H, H, Et], [744, cyclopropyl, H, H], [745, H, cyclopropyl, H], [746, H, H, cyclopropyl], [747, F, H, H], [748, H, F, H], [749, H, H, F], [750, Cl, H, H], [751, H, Cl, H], [752, Br, H, H], [753, H, Br, H], [754, CN, H, H], [755, H, CN, H], [756, H, H, CN], [757, OMe, H, H], [758, H, OMe, H], [759, OEt, H, H], [760, H, OEt, H], [761, $CF_3$, H, H], [762, H, $CF_3$, H], [763, H, H, $CF_3$], [764, $CHF_2$, H, H], [765, H, $CHF_2$, H], [766, H, H, $CHF_2$], [767, Me, Me, H], [768, Me, H, Me], [769, Me, H, Et], [770, Me, H, 2-propyn-1-yl], [771, Me, Me, Me], [772, Me, Me, Et], [773, Me, Me, 2-propyn-1-yl], [774, Et, H, Et], [775, Me, Et, Me], [776, Me, Et, Et], [777, Me, Et, 2-propyn-1-yl], [778, Me, F, Me], [779, Me, F, Et], [780, Me, F, 2-propyn-1-yl], [781, Me, Cl, Me], [782, Me, Cl, Et], [783, Me, Cl, 2-propyn-1-yl], [784, Me, Br, Me], [785, Me, Br, Et], [786, Me, Br, 2-propyn-1-yl], [787, Me, $CF_3$, Me], [788, Me, $CF_3$, Et], [789, Me, $CF_3$, 2-propyn-1-yl], [790, Me, $CHF_2$, Me], [791, Me, $CHF_2$, Et], [792, Me, $CHF_2$, 2-propyn-1-yl], [793, Me, OMe, Me], [794, Me, OMe, Et], [795, Me, OMe, 2-propyn-1-yl], [796, Me, OEt, Me], [797, Me, OEt, Et], [798, Me, OEt, 2-propyn-1-yl], [799, Me, SMe, Me], [800, Me, SMe, Et], [801, Me, SMe, 2-propyn-1-yl], [802, Me, SEt, Me], [803, Me, SEt, Et], [804, Me, SEt, 2-propyn-1-yl], [805, Me, $OCF_3$, Me], [806, Me, $OCF_3$, Et], [807, Me, $OCF_3$, 2-propyn-1-yl], [808, Me, $OCHF_2$, Me], [809, Me, $OCHF_2$, Et], [810, Me, $OCHF_2$, 2-propyn-1-yl], [811, Me, CN, Me], [812, Me, CN, Et], [813, Me, CN, 2-propyn-1-yl], [814, Et, H, Me], [815, Et, Et, Me], [816, Et, F, Me], [817, Et, Cl, Me], [818, Et, Br, Me], [819, Et, $CF_3$, Me], [820, Et, $CHF_2$, Me], [821, Et, OMe, Me], [822, Et, OEt, Me], [823, Et, SMe, Me], [824, Et, SEt, Me], [825, Et, $OCF_3$, Me], [826, Et, $OCHF_2$, Me], [827, Et, CN, Me], [828, Et, F, Et], [829, Et, Cl, Et], [830, Et, Br, Et], [831, Et, $CF_3$, Et], [832, Et, $CHF_2$, Et], [833, Et, OMe, Et], [834, Et, OEt, Et], [835, Et, SMe, Et], [836, Et, SEt, Et], [837, Et, $OCF_3$, Et], [838, Et, $OCHF_2$, Et], [839, Et, CN, Et], [840, $CHF_2$, H, Me], [841, $CHF_2$, Me, Me], [842, $CHF_2$, Et, Me], [843, $CHF_2$, F, Me], [844, $CHF_2$, Cl, Me], [845, $CHF_2$, Br, Me], [846, $CHF_2$, $CF_3$, Me], [847, $CHF_2$, $CHF_2$, Me], [848, $CHF_2$, OMe, Me], [849, $CHF_2$, OEt, Me], [850, $CHF_2$, SMe, Me], [851, $CHF_2$, SEt, Me], [852, $CHF_2$, $OCF_3$, Me], [853, $CHF_2$, $OCHF_2$, Me], [854, $CHF_2$, CN, Me], [855, Me, H, 2-butyn-1-yl], [856, Me, Me, 2-butyn-1-yl], [857, Me, Et, 2-butyn-1-yl], [858, Me, F, 2-butyn-1-yl], [859, Me, Cl, 2-butyn-1-yl], [860, Me, Br, 2-butyn-1-yl], [861, Me, $CF_3$, 2-butyn-1-yl], [862, Me, $CHF_2$, 2-butyn-1-yl], [863, Me, OMe, 2-butyn-1-yl], [864, Me, OEt, 2-butyn-1-yl], [865, Me, SMe, 2-butyn-1-yl], [866, Me, SEt, 2-butyn-1-yl], [867, Me, $OCF_3$, 2-butyn-1-yl], [868, Me, $OCHF_2$, 2-butyn-1-yl], [869, Me, CN, 2-butyn-1-yl], [870, Me, H, 2,2,2-trifluoroethyl], [871, Me, Me, 2,2,2-trifluoroethyl], [872, Me, Et, 2,2,2-trifluoroethyl], [873, Me, F, 2,2,2-trifluoroethyl], [874, Me, Cl, 2,2,2-trifluoroethyl], [875, Me, Br, 2,2,2-trifluoroethyl], [876, Me, $CF_3$, 2,2,2-trifluoroethyl], [877, Me, $CHF_2$, 2,2,2-trifluoroethyl], [878, Me, OMe, 2,2,2-trifluoroethyl], [879, Me, OEt, 2,2,2-trifluoroethyl], [880, Me, SMe, 2,2,2-trifluoroethyl], [881, Me, SEt, 2,2,2-trifluoroethyl], [882, Me, $OCF_3$, 2,2,2-trifluoroethyl], [883, Me, $OCHF_2$, 2,2,2-trifluoroethyl], [884, Me, CN, 2,2,2-trifluoroethyl], [885, Me, H, 2,2-difluoroethyl], [886, Me, Me, 2,2-difluoroethyl], [887, Me, Et, 2,2-difluoroethyl], [888, Me, F, 2,2-difluoroethyl], [889, Me, Cl, 2,2-difluoroethyl], [890, Me, Br, 2,2-difluoroethyl], [891, Me, $CF_3$, 2,2-difluoroethyl], [892, Me, $CHF_2$, 2,2-difluoroethyl], [893, Me, OMe, 2,2-difluoroethyl], [894, Me, OEt, 2,2-difluoroethyl], [895, Me, SMe, 2,2-difluoroethyl], [896, Me, SEt, 2,2-difluoroethyl], [897, Me, $OCF_3$, 2,2-difluoroethyl], [898, Me, $OCHF_2$, 2,2-difluoroethyl], [899, Me, CN, 2,2-difluoroethyl], [900, Me, H, cyclopropylmethyl], [901, Me, Me, cyclopropylmethyl], [902, Me, Et, cyclopropylmethyl], [903, Me, F, cyclopropylmethyl], [904, Me, Cl, cyclopropylmethyl], [905, Me, Br, cyclopropylmethyl], [906, Me, $CF_3$, cyclopropylmethyl], [907, Me, $CHF_2$, cyclopropylmethyl], [908, Me, OMe, cyclopropylmethyl], [909, Me, OEt, cyclopropylmethyl], [910, Me, SMe, cyclopropylmethyl], [911, Me, SEt, cyclopropylmethyl], [912, Me, $OCF_3$, cyclopropylmethyl], [913, Me, $OCHF_2$, cyclopropylmethyl], [914, Me, CN, cyclopropylmethyl], Substituents in Case where A is A32:

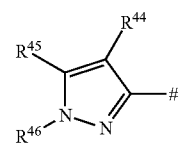
(A31)

are shown below.

[substituent numbers, $R^{44}$, $R^{46}$, $R^{47}$]=[915, H, Me, H], [916, Me, Me, H], [917, H, Me, Me], [918, Me, Me, Me], Substituents in Case where A is A33:

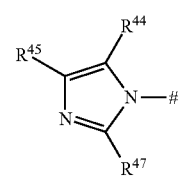
(A33)

are shown below.

[substituent numbers, $R^{44}$, $R^{45}$, $R^{47}$]=[919, H, H, H], [920, H, Me, H], [921, Me, Me, Me], Substituents in Case where A is A34:

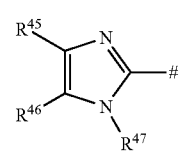
(A34)

are shown below.

[substituent numbers, $R^{45}$, $R^{46}$, $R^{47}$]=[922, H, H, H], [923, Me, H, H], [924, Me, Me, Me], [925, Cl, Cl, Me], [926, Me, Cl, Me], [927, Me, CN, Me], [928, Me, F, Me], Substituents in Case where A is A35:

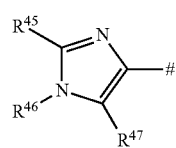
(A35)

are shown below.
[substituent numbers, $R^{45}$, $R^4$, $R^{47}$]=[929, H, H, H], [930, Me, Me, H], [931, Me, Me, Me], [932, Cl, Me, Me], [933, Me, Me, Cl], [934, Me, Et, Me], [935, Cl, Et, Me], [936, Me, Et, Cl], [937, CN, Me, Me], [938, CN, Me, Cl], Substituents in Case where A is A36:

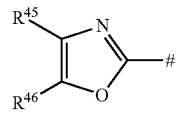
(A36)

are shown below.
[substituent numbers, $R^{45}$, $R^{46}$]=[939, H, H], [940, Me, H], [941, H, Me], [942, Me, Me], [943, Cl, Me], [944, Me, Cl], [945, Et, Me], [946, Et, Cl], [947, CN, Me], [948, Me, CN], [949, OMe, H], [950, OMe, Me], [951, OMe, Cl], Substituents in Case where A is A37:

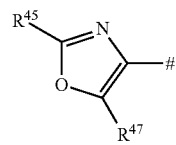
(A37)

are shown below.
[substituent numbers, $R^{45}$, $R^{47}$]=[952, H, H], [953, Me, H], [954, H, Me], [955, Me, Me], [956, Cl, Me], [957, Me, Cl], [958, Et, Me], [959, Et, Cl], [960, CN, Me], [961, Me, CN], [962, OMe, H], [963, OMe, Me], [964, OMe, Cl], Substituents in Case where A is A38:

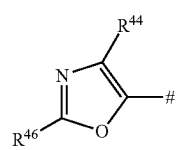
(A38)

are shown below.
[substituent numbers, $R^{44}$, $R^{46}$]=[965, H, H], [966, Me, H], [967, H, Me], Substituents in Case where A is A39:

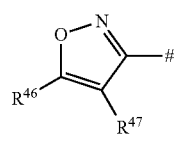
(A39)

are shown below.
[substituent numbers, $R^{46}$, $R^{47}$], [968, H, H], [969, Me, H], [970, H, Me], A substituent in case where A is A40:

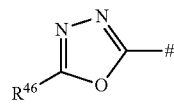
(A40)

is shown below.
[substituent number, $R^{46}$]=[971, H], [972, Me],

A substituents in case where A is A41:

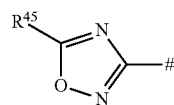
(A41)

is shown below.
[substituent number, $R^{45}$]=[973, H], [974, Me],

A substituent in case where A is A42:

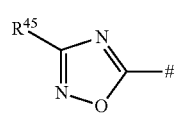
(A42)

is shown below.
[substituent number, $R^{45}$]=[975, H], [976, Me],

Substituents in Case where A is A43:

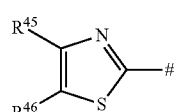
(A43)

are shown below.
[substituent numbers, $R^{45}$, $R^{46}$]=[977, H, H], [978, Me, H], [979, H, Me], [980, Me, Me], [981, Cl, Me], [982, Me, Cl], [983, Et, Me], [984, Et, Cl], [985, CN, Me], [986, Me, CN], [987, OMe, H], [988, OMe, Me], [989, OMe, Cl], [990, H, OMe], [991, Me, OMe], [992, Cl, OMe], [993, $CF_3$, H], [994, $CF_3$, Me], [995, $CF_3$, Cl], [996, H, $CF_3$], [997, Me, $CF_3$], [998, Cl, $CF_3$], [999, $CHF_2$, H], [1000, $CHF_2$, Me], [1001, $CHF_2$, Cl], [1002, H, $CHF_2$], [1003, Me, $CHF_2$], [1004, Cl, $CHF_2$], Substituents in Case where A is A44:

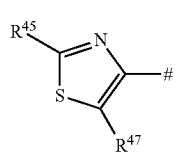
(A44)

are shown below.

[substituent numbers, $R^{45}$, $R^{47}$]=[1005, H, H], [1006, Me, H], [1007, H, Me], [1008, Me, Me], [1009, Cl, Me], [1010, Me, Cl], [1011, Et, Me], [1012, Et, Cl], [1013, CN, Me], [1014, Me, CN], [1015, OMe, H], [1016, OMe, Me], [1017, OMe, Cl], [1018, H, OMe], [1019, Me, OMe], [1020, Cl, OMe], [1021, $CF_3$, H], [1022, $CF_3$, Me], [1023, $CF_3$, Cl], [1024, H, $CF_3$], [1025, Me, $CF_3$], [1026, Cl, $CF_3$], [1027, $CHF_2$, H], [1028, $CHF_2$, Me], [1029, $CHF_2$, Cl], [1030, H, $CHF_2$], [1031, Me, $CHF_2$], [1032, Cl, $CHF_2$], Substituents in Case where A is A45:

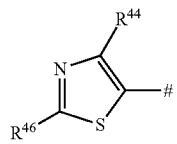
(A45)

are shown below.

[substituent numbers, $R^{44}$, $R^{46}$]=[1033, H, H], [1034, H, Me], [1035, Me, H], [1036, Me, Me], [1037, Me, Cl], [1038, Cl, Me], [1039, Me, Et], [1040, Cl, Et], [1041, Me, CN], [1042, CN, Me], [1043, H, OMe], [1044, Me, OMe], [1045, Cl, OMe], [1046, OMe, H], [1047, OMe, Me], [1048, OMe, Cl], [1049, H, $CF_3$], [1050, Me, $CF_3$], [1051, Cl, $CF_3$], [1052, $CF_3$, H], [1053, $CF_3$, Me], [1054, $CF_3$, Cl], [1055, H, $CHF_2$], [1056, Me, $CHF_2$], [1057, Cl, $CHF_2$], [1058, $CHF_2$, H], [1059, $CHF_2$, Me], [1060, $CHF_2$, Cl], Substituents in Case where A is A46:

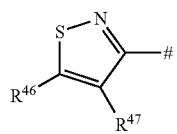
(A46)

are shown below.

[substituent numbers, $R^{46}$, $R^{47}$]=[1061, H, H], [1062, Me, H], [1063, H, Me], [1064, Me, Me], [1065, Cl, Me], [1066, Me, Cl], [1067, Et, Me], [1068, Et, Cl], [1069, CN, Me], [1070, Me, CN], [1071, OMe, H], [1072, OMe, Me], [1073, OMe, Cl], [1074, H, OMe], [1075, Me, OMe], [1076, Cl, OMe], [1077, $CF_3$, H], [1078, $CF_3$, Me], [1079, $CF_3$, Cl], [1080, H, $CF_3$], [1081, Me, $CF_3$], [1082, Cl, $CF_3$], [1083, $CHF_2$, H], [1084, $CHF_2$, Me], [1085, $CHF_2$, Cl], [1086, H, $CHF_2$], [1087, Me, $CHF_2$], [1088, Cl, $CHF_2$], A substituent in case where A is A47:

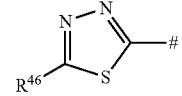
(A47)

is shown below.

[substituent number, $R^{46}$]=[1089, H], [1090, Me],

A substituent in case where A is A48:

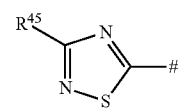
(A48)

is shown below.

[substituent number, $R^{45}$]=[1091, H], [1092, Me], [1093, Et], [1094, Cl], [1095, OMe], [1096, OEt], [1097, $CF_3$], [1098, $CHF_2$], [1099, CN], [1100, SMe], A substituent in case where A is A49:

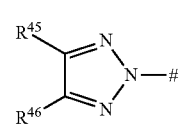
(A49)

is shown below.

[substituent number, $R^{45}$]=[1101, H], [1102, Me], [1103, Et], [1104, Cl], [1105, OMe], [1106, OEt], [1107, $CF_3$], [1108, $CHF_2$], [1109, CN], [1110, SMe], Substituents in Case where A is A50:

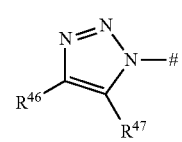
(A50)

are shown below.

[substituent numbers, $R^{45}$, $R^{46}$]=[1111, H, H], [1112, Me, H], [1113, Me, Me], [1114, Cl, Me], [1115, Et, Me], [1116, Et, Cl], [1117, CN, Me], [1118, OMe, H], [1119, OMe, Me], [1120, OMe, Cl], [1121, $CF_3$, H], [1122, $CF_3$, Me], [1123, $CF_3$, Cl], [1124, $CHF_2$, H], [1125, $CHF_2$, Me], [1126, $CHF_2$, Cl], [1127, C1, Cl], [1128, CN, CN], [1129, $CF_3$, $CF_3$], [1130, $CHF_2$, $CHF_2$], Substituents in Case where A is A51:

(A51)

are shown below.

[substituent numbers, $R^{46}$, $R^{47}$]=[1131, H, H], [1132, Me, H], [1133, Me, Me], [1134, Cl, Me], [1135, Et, Me], [1136, Et, Cl], [1137, CN, Me], [1138, OMe, H], [1139, OMe, Me], [1140, OMe, Cl], [1141, CF$_3$, H], [1142, CF$_3$, Me], [1143, CF$_3$, Cl], [1144, CHF$_2$, H], [1145, CHF$_2$, Me], [1146, CHF$_2$, Cl], [1147, Cl, Cl], [1148, CN, CN], [1149, CF$_3$, CF$_3$], [1150, CHF$_2$, CHF$_2$], A substituent in case where A is A52:

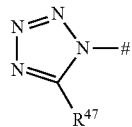
(A52)

is shown below.
[substituent number, R$^{47}$]=[1151, H], [1152, Me],

A substituent in case where A is A53:

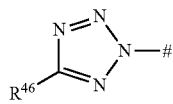
(A53)

is shown below.
[substituent number, R$^{46}$]=[1153, H], [1154, Me],

Substituents in Case where A is A59:

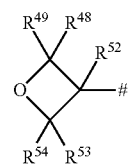
(A59)

are shown below.
[substituent numbers, R$^{48}$, R$^{49}$, R$^{52}$, R$^{53}$, R$^{54}$]=[1155, H, H, H, H, H], Substituents in Case where A is A61:

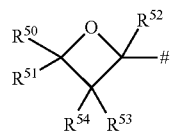
(A61)

Are shown below.
[substituent numbers, R$^{50}$, R$^{51}$, R$^{52}$, R$^{53}$, R$^{54}$]=[1156, H, H, H, H, H], Substituents in Case where A is A63:

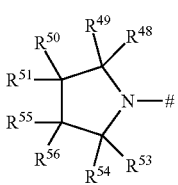
(A63)

are shown below.
[substituent numbers, R$^{48}$, R$^{49}$, R$^{50}$, R$^{51}$, R$^{53}$, R$^{54}$, R$^{55}$, R$^{56}$]=[1157, H, H, H, H, H, H, H, H], Substituents in Case where A is A65:

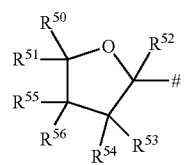
(A65)

are shown below.
[substituent numbers, R$^{50}$, R$^{51}$, R$^{52}$, R$^{53}$, R$^{54}$, R$^{55}$, R$^{56}$]=[1158, H, H, H, H, H, H, H], Substituents in Case where A is A69:

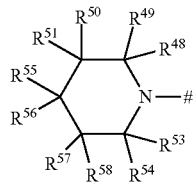
(A69)

are shown below.
[substituent numbers, R$^{48}$, R$^{49}$, R$^{50}$, R$^{51}$, R$^{53}$, R$^{54}$, R$^{55}$, R$^{56}$, R$^{57}$, R$^{58}$]=[1159, H, H, H, H, H, H, H, H, H, H], Substituents in Case where A is A70:

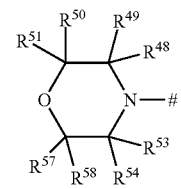
(A70)

are shown below.
[substituent numbers, R$^{46}$, R$^{49}$, R$^{50}$, R$^{51}$, R$^{53}$, R$^{54}$, R$^{57}$, R$^{58}$]=[1160, H, H, H, H, H, H, H, H], Substituents in Case where A is A71:

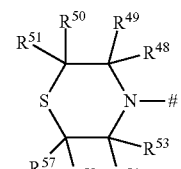
(A71)

are shown below.
[substituent numbers, R$^{48}$, R$^{49}$, R$^{50}$, R$^5$, R$^{53}$, R$^{54}$, R$^{57}$, R$^{58}$]=[1161, H, H, H, H, H, H, H, H], Substituents in Case where A is A72:

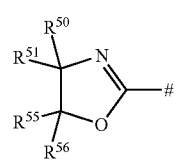
(A72)

are shown below.

[substituent numbers, $R^{50}$, $R^{51}$, $R^{55}$, $R^{56}$]=[1162, H, H, H, H], [1163, Me, H, H, H], [1164, Me, Me, H, H], [1165, H, H, H, Me], [1166, H, H, Me, Me], [1167, F, F, H, H], Substituents in Case where A is A73:

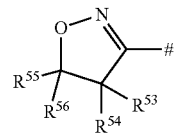
(A73)

are shown below.

[substituent numbers, $R^{53}$, $R^{54}$, $R^{5'}$, $R^{\$6}$]=[1168, H, H, H, H], [1169, H, H, Me, H], [1170, H, H, Me, Me], [1171, H, Me, H, H], [1172, Me, Me, H, H], Substituents in Case where A is A74:

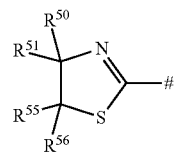
(A74)

are shown below.

[substituent numbers, $R^{50}$, $R^{51}$, $R^{55}$, $R^{56}$]=[1173, H, H, H, H], [1174, Me, H, H, H], [1175, Me, Me, H, H], [1176, H, H, H, Me], [1177, H, H, Me, Me], [1178, F, F, H, H], Substituents in Case where A is A75:

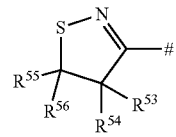
(A75)

are shown below.

[substituent numbers, $R^{53}$, $R^{54}$, $R^{55}$, $R^{16}$]=[1179, H, H, H, H], [1180, H, H, Me, H], [1181, H, H, Me, Me], [1182, H, Me, H, H], [1183, Me, Me, H, H], Substituents in Case where A is A76:

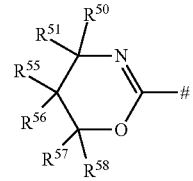
(A76)

are shown below.

[substituent numbers, $R^{50}$, $R^{51}$, $R^{55}$, $R^{56}$, $R^{57}$, $R^{18}$]=[1184, H, H, H, H, H, H], [1185, Me, H, H, H, H, H], [1186, Me, Me, H, H, H, H], [1187, H, H, Me, Me, H, H], [1188, Me, Me, H, H, Me, Me], Substituents in Case where A is A77:

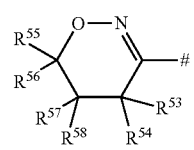
(A77)

are shown below.

[substituent numbers, $R^{53}$, $R^{54}$, $R^{55}$, $R^{56}$, $R^{57}$, $R^{58}$]=[1189, H, H, H, H, H, H], [1190, Me, H, Me, Me, H, H], Substituents in Case where A is A78:

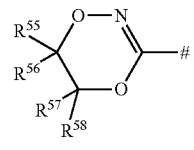
(A78)

are shown below.

[substituent numbers, $R^{55}$, $R^{56}$, $R^{57}$, $R^{58}$]=[1191, H, H, H, H], [1192, Me, H, H, H], [1193, Me, Me, H, H], [1194, Me, Me, Me, Me], [1195, Me, H, Me, H], Substituents in Case where A is A79:

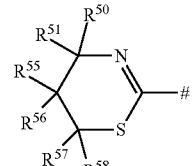
(A79)

are shown below.

[substituent numbers, $R^{50}$, $R^{51}$, $R^{55}$, $R^{56}$, $R^{57}$, $R^{58}$]=[1196, H, H, H, H, H, H], [1197, Me, H, H, H, H, H], [1198, Me, Me, H, H, H, H], [1199, H, H, Me, Me, H, H], [1200, Me, Me, H, H, Me, Me], Substituents in Case where A is A80:

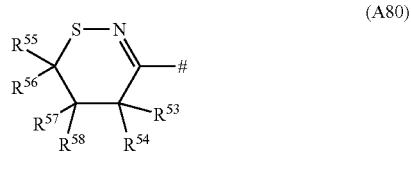
(A80)

are shown below.

[substituent numbers, $R^5$, $R^{54}$, $R^{55}$, $R^{56}$, $R^{57}$, $R^{58}$]=[1201, H, H, H, H, H, H], [1202, Me, H, Me, Me, H, H], Substituents in Case where A is A81:

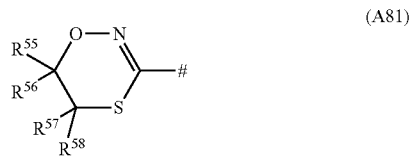
(A81)

are shown below.

[substituent numbers, $R^{55}$, $R^{56}$, $R^{57}$, $R^{58}$], [1203, H, H, H, H], [1204, Me, Me, H, H], Substituents in Case where A is A82:

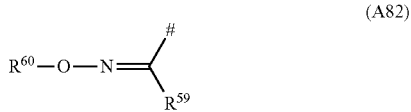
(A82)

are shown below.

[substituent numbers, $R^5$, $R^6$]=[1205, H, H], [1206, H, H], [1207, H, Me], [1208, H, Et], [1209, H, Pr], [1210, H, Bu], [1211, H, cyclopropyl], [1212, H, $CF_3$], [1213, H, 2,2,2-trifluoroethyl], [1214, H, 2,2-difluoroethyl], [1215, Me, H], [1216, Me, Me], [1217, Me, Et], [1218, Me, Pr], [1219, Me, Bu], [1220, Me, cyclopropyl], [1221, Me, $CF_3$], [1222, Me, 2,2,2-trifluoroethyl], [1223, Me, 2,2-difluoroethyl], [1224, Et, H], [1225, Et, Me], [1226, Et, Et], [1227, Et, Pr], [1228, Et, Bu], [1229, Et, cyclopropyl], [1230, Et, $CF_3$], [1231, Et, 2,2,2-trifluoroethyl], [1232, Et, 2,2-difluoroethyl], [1233, cyclopropyl, H], [1234, cyclopropyl, Me], [1235, cyclopropyl, Et], [1236, cyclopropyl, Pr], [1237, cyclopropyl, Bu], [1238, cyclopropyl, cyclopropyl], [1239, cyclopropyl, $CF_3$], [1240, cyclopropyl, 2,2,2-trifluoroethyl], [1241, cyclopropyl, 2,2-difluoroethyl], [1242, $CF_3$, H], [1243, $CF_3$, Me], [1244, $CF_3$, Et], [1245, $CF_3$, Pr], [1246, $CF_3$, Bu], [1247, $CF_3$, cyclopropyl], [1248, $CF_3$, $CF_3$], [1249, $CF_3$, 2,2,2-trifluoroethyl], [1250, $CF_3$, 2,2-difluoroethyl], [1251, $CHF_2$, H], [1252, $CHF_2$, Me], [1253, $CHF_2$, Et], [1254, $CHF_2$, Pr], [1255, $CHF_2$, Bu], [1256, $CHF_2$, cyclopropyl], [1257, $CHF_2$, $CF_3$], [1258, $CHF_2$, 2,2,2-trifluoroethyl], [1259, $CHF_2$, 2,2-difluoroethyl], [1260, $CHF_2$, $CHF_2$]

Substituents in Case where A is A83:

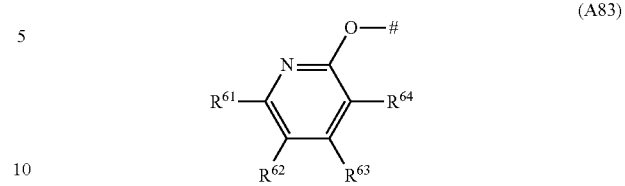
(A83)

are shown below.

[substituent numbers, $R^{61}$, $R^{62}$, $R^{63}$, $R^{64}$], [1267, H, H, H, H], [1268, H, F, H, H], [1269, H, H, F, H], [1270, H, H, H, F], [1271, Cl, H, H, H], [1272, H, Cl, H, H], [1273, H, H, Cl, H], [1274, H, H, H, Cl], [1275, Me, H, H, H], [1276, H, Me, H, H], [1277, H, H, Me, H], [1278, H, H, H, Me], [1279, OMe, H, H, H], [1280, H, OMe, H, H], [1281, H, H, OMe, H], [1282, H, H, H, OMe], [1283, $CF_3$, H, H, H], [1284, H, $CF_3$, H, H], [1285, H, H, $CF_3$, H], [1286, H, H, H, $CF_3$], Substituents in Case where A is A84:

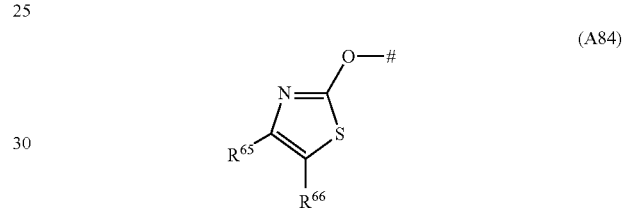
(A84)

are shown below.

[substituent numbers, $R^{66}$, $R^{65}$], [1287, H, H], [1288, Me, H], [1289, H, Me], [1289, Me, Me], Substituents in Case where A is A85:

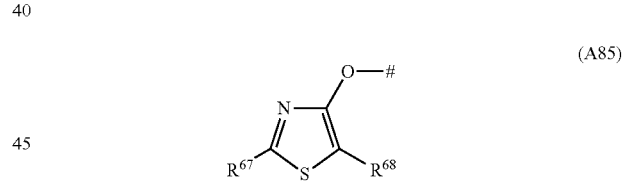
(A85)

are shown below.

[substituent numbers, $R^{67}$, $R^{68}$], [1290, H, H], [1291, Me, H], [1292, H, Me], [1293, Me, Me], Substituents in Case where A is A86:

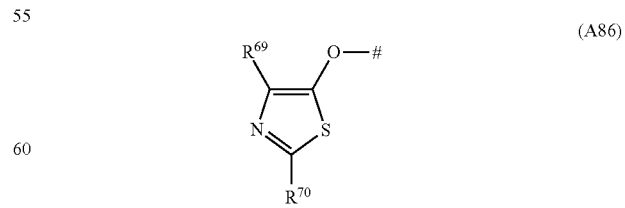
(A86)

are shown below.

[substituent numbers, $R^{69}$, $R^{70}$], [1294, H, H], [1295, Me, H], [1296, H, Me], [1297, Me, Me], Substituents in Case where A is A87:

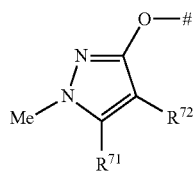
(A87)

are shown below.
[substituent numbers, $R^{11}$, $R^{72}$], [1298, H, H], [1299, Me, H], [1300, H, Me], [1301, Me, Me], Substituents in Case where A is A88:

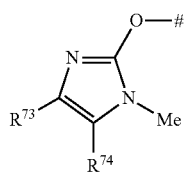
(A88)

are shown below.
[substituent numbers, $R^{73}$, $R^{74}$], [1302, H, H], [1303, Me, H], [1304, H, Me], [1305, Me, Me]

In accordance with the process mentioned above, it is possible to obtain compounds QEPA1-001 to QEPF60-1305.

The compounds QEPA1-001 to QEPF60-1305 are tetrazolinone compounds represented by the following formulas:

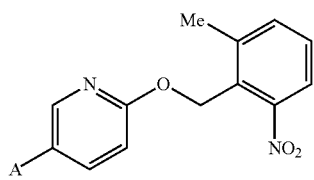
(QEPA1)

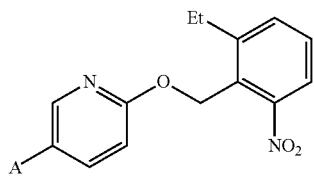
(QEPA2)

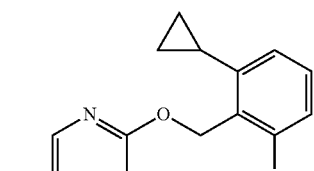
(QEPA3)

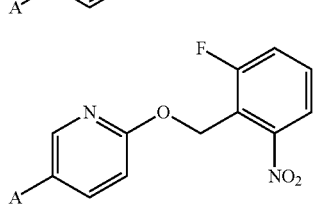
(QEPA4)

(QEPA5)

(QEPA6)

(QEPA7)

(QEPA8)

(QEPA9)

(QEPA10)

(QEPA11)

(QEPA12)

(QEPA13) 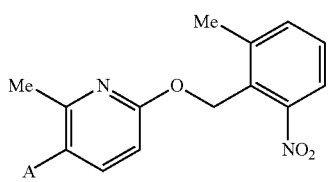
(QEPA14) 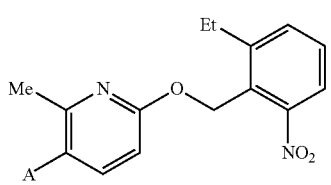
(QEPA15) 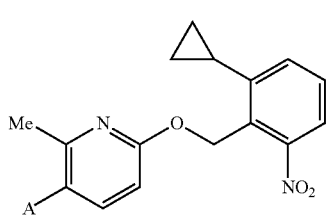
(QEPA16) 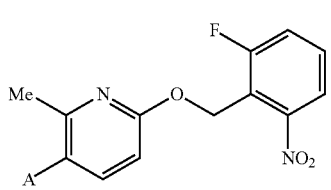
(QEPA17) 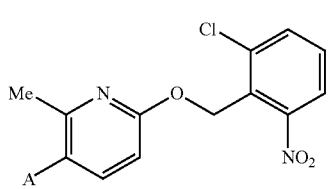
(QEPA18) 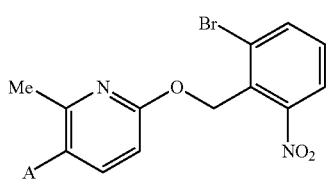
(QEPA19) 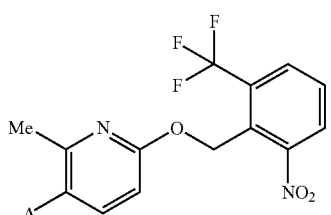
(QEPA20) 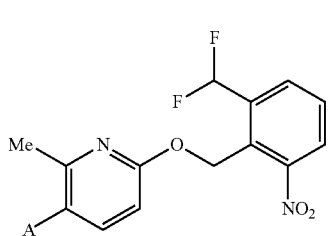
(QEPA21) 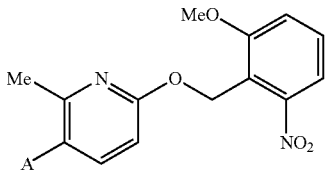
(QEPA22) 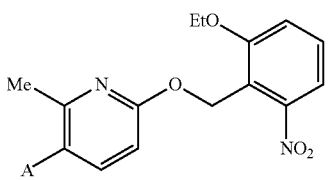
(QEPA23) 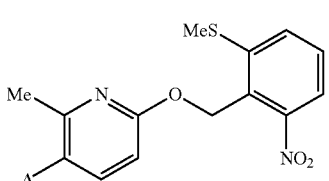
(QEPA24) 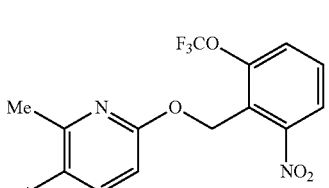
(QEPA25) 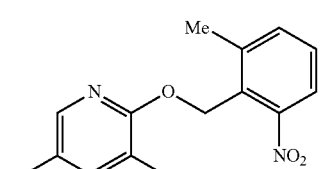
(QEPA26) 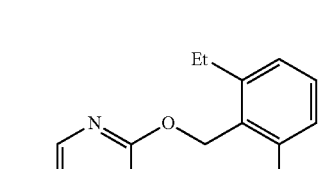
(QEPA27) 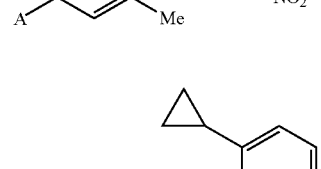
(QEPA28) 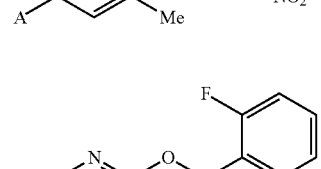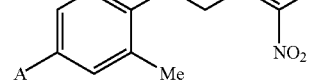

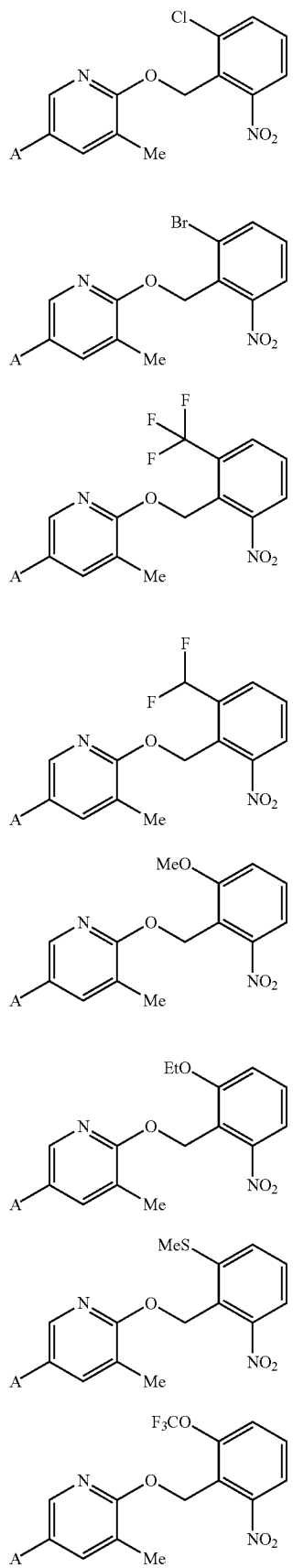
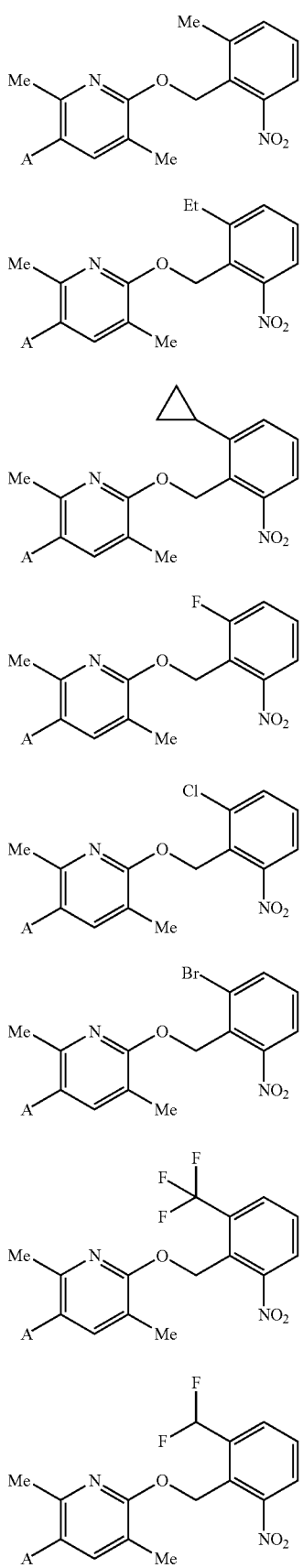

243
-continued
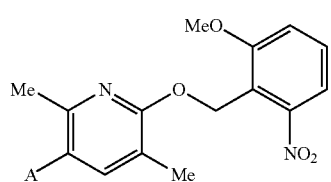 (QEPA45)
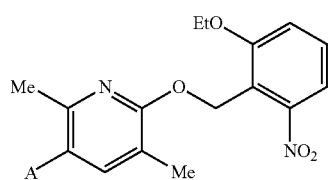 (QEPA46)
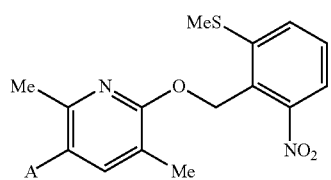 (QEPA47)
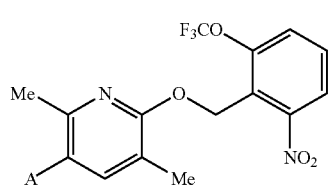 (QEPA48)
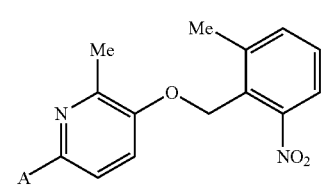 (QEPA49)
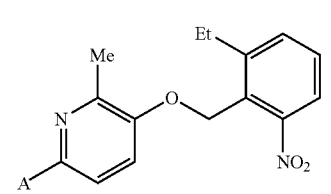 (QEPA50)
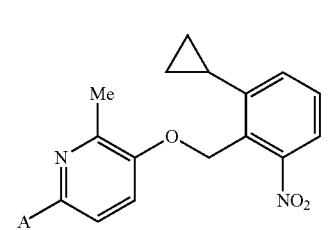 (QEPA51)
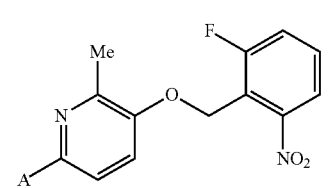 (QEPA52)
244
-continued
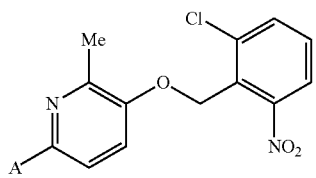 (QEPA53)
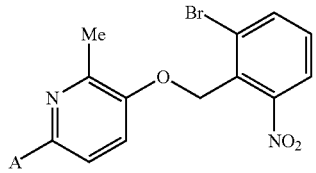 (QEPA54)
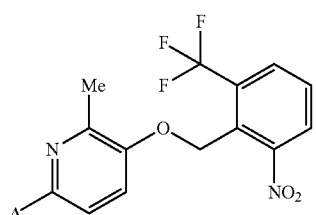 (QEPA55)
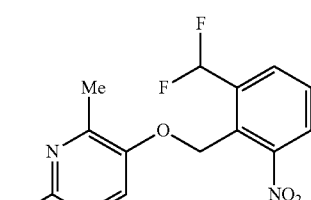 (QEPA56)
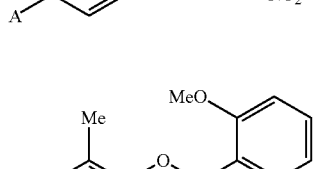 (QEPA57)
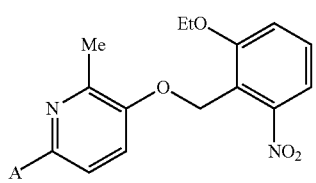 (QEPA58)
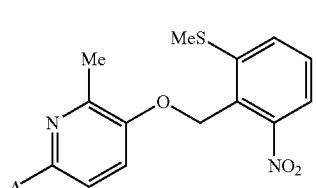 (QEPA59)
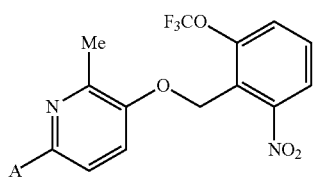 (QEPA60)

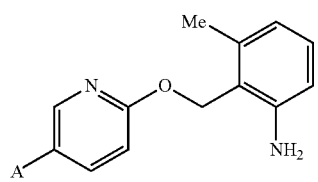 (QEPB1)
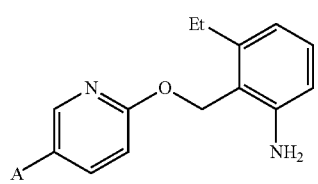 (QEPB2)
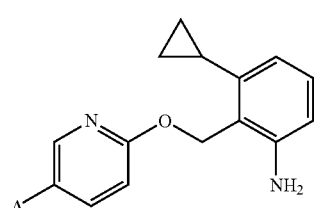 (QEPB3)
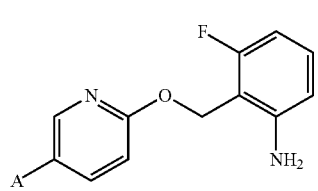 (QEPB4)
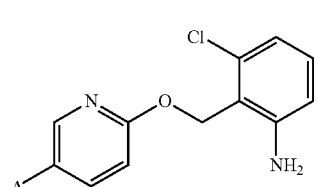 (QEPB5)
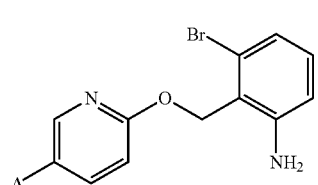 (QEPB6)
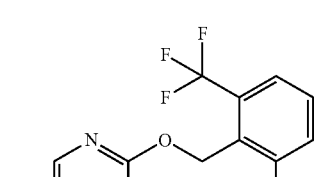 (QEPB7)
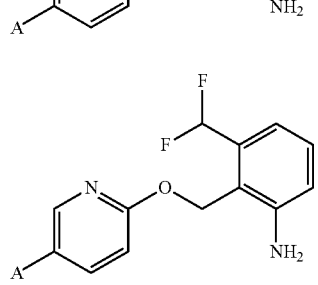 (QEPB8)
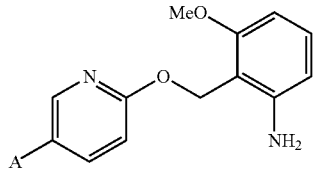 (QEPB9)
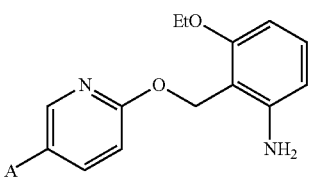 (QEPB10)
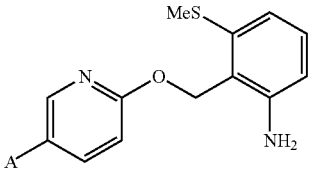 (QEPB11)
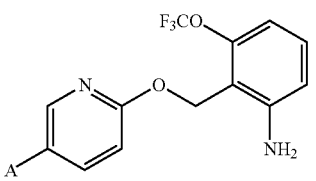 (QEPB12)
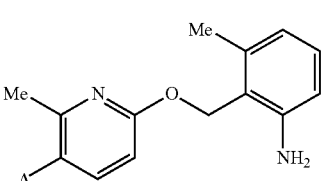 (QEPB13)
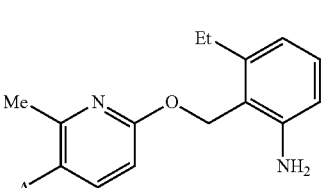 (QEPB14)
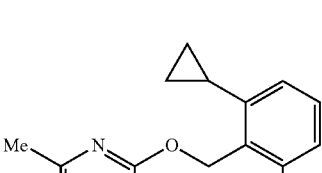 (QEPB15)
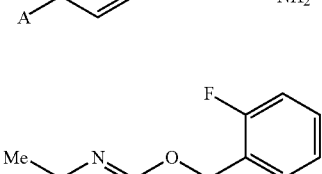 (QEPB16)
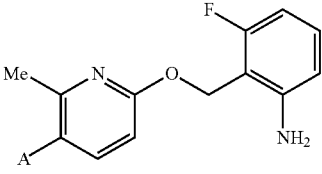

247
-continued
(QEPB17)
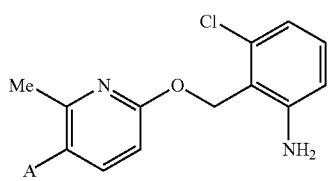
(QEPB18)
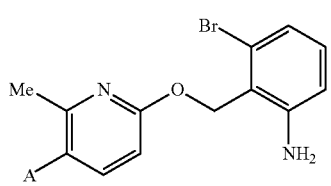
(QEPB19)
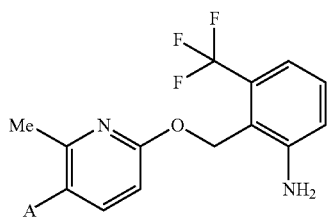
(QEPB20)
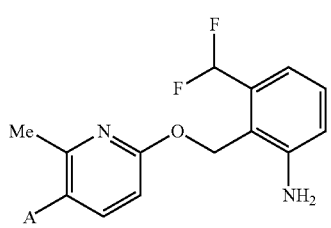
(QEPB21)
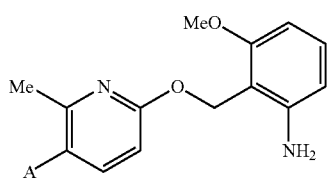
(QEPB22)
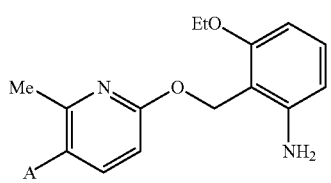
(QEPB23)
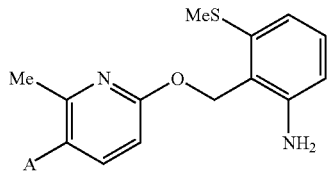
(QEPB24)
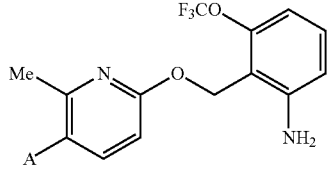
248
-continued
(QEPB25)
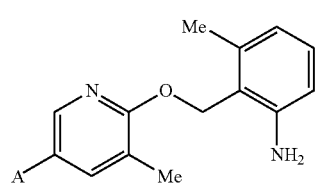
(QEPB26)
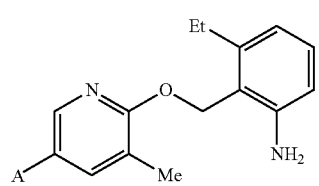
(QEPB27)
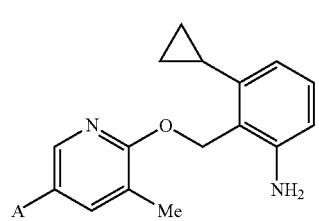
(QEPB28)
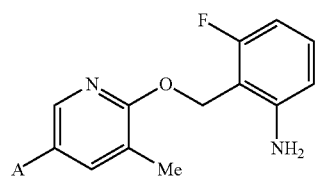
(QEPB29)
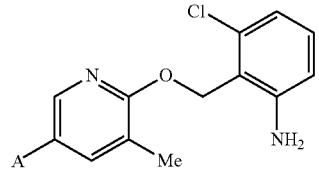
(QEPB30)
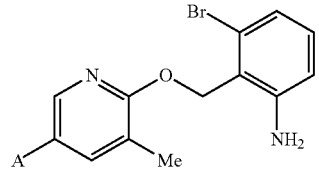
(QEPB31)
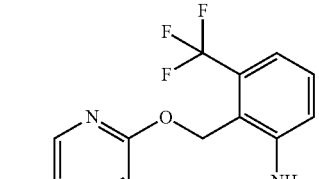
(QEPB32)
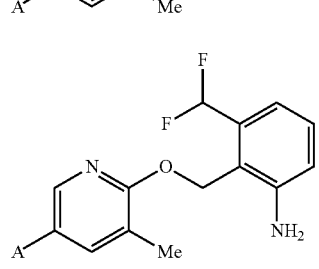

-continued
(QEPB33)
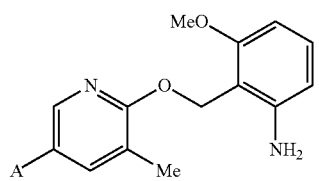
(QEPB34)
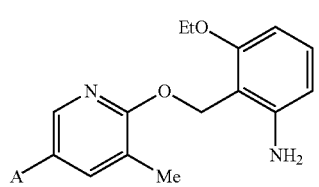
(QEPB35)
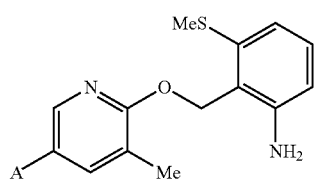
(QEPB36)
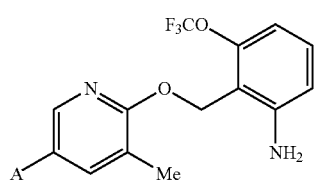
(QEPB37)
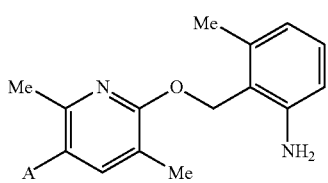
(QEPB38)
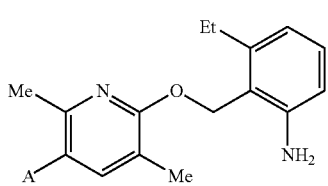
(QEPB39)
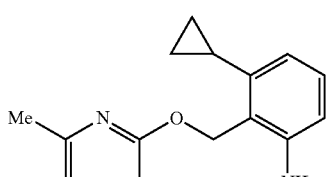
(QEPB40)
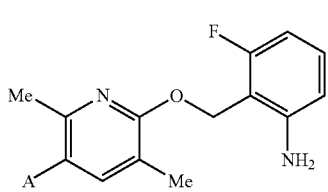
-continued
(QEPB41)
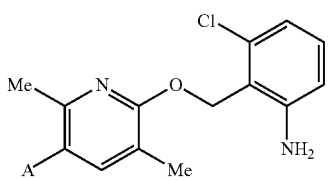
(QEPB42)
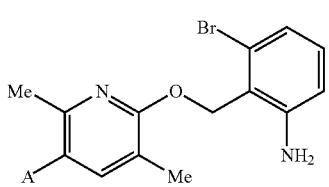
(QEPB43)
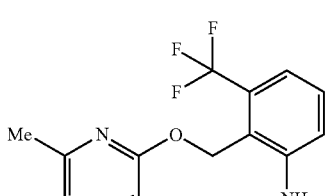
(QEPB44)
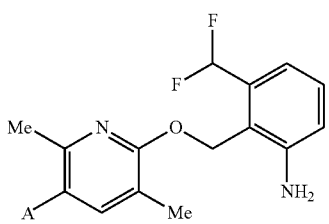
(QEPB45)
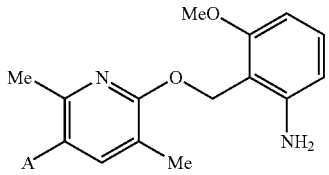
(QEPB46)
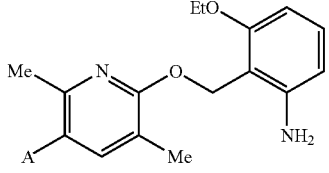
(QEPB47)
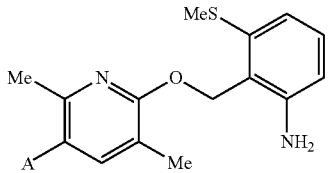
(QEPB48)
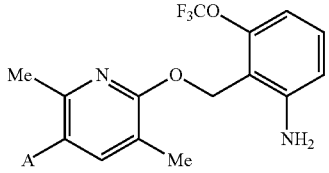

| | |
|---|---|
| (QEPB49) 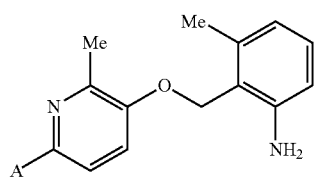 | (QEPB57) 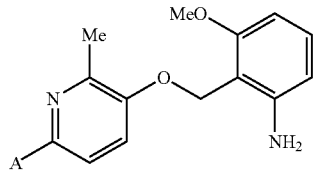 |
| (QEPB50) 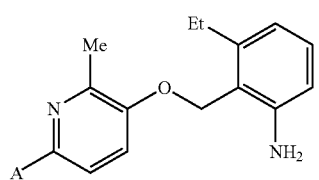 | (QEPB58) 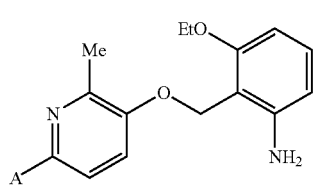 |
| (QEPB51) 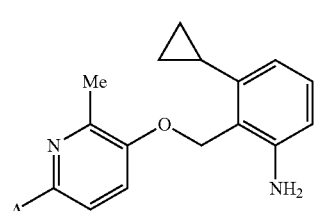 | (QEPB59) 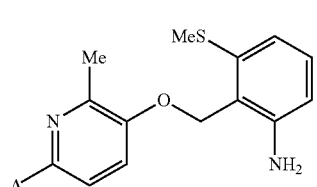 |
| (QEPB52) 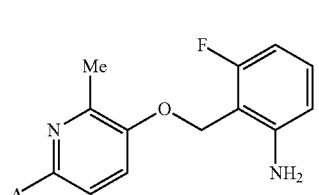 | (QEPB52) 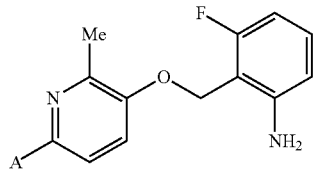 |
| (QEPB53) 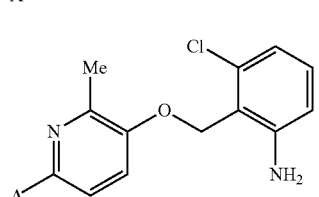 | (QEPB53) 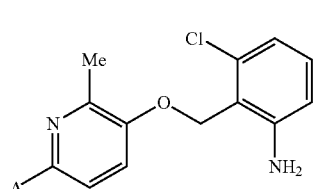 |
| (QEPB54) 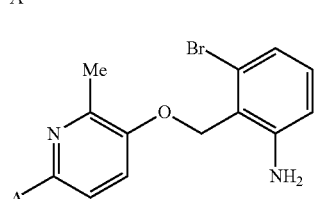 | (QEPB54) 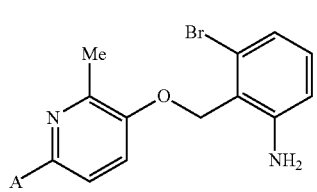 |
| (QEPB55) 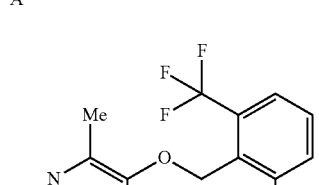 | (QEPB55) 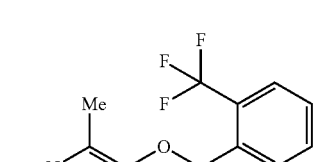 |
| (QEPB56) 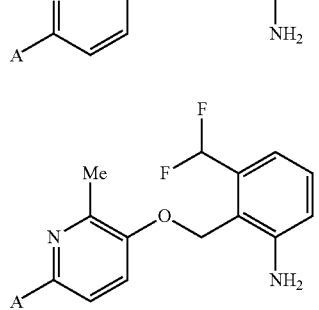 | (QEPB56) 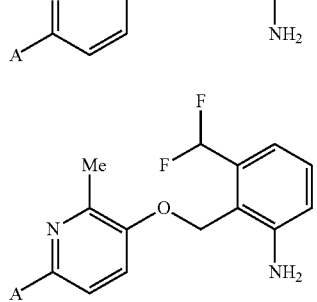 |

253
-continued
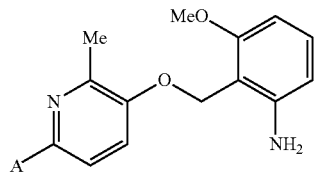 (QEPB57)
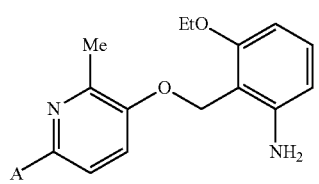 (QEPB58)
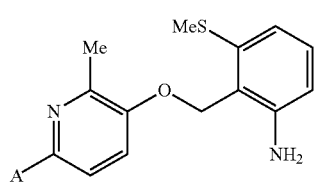 (QEPB59)
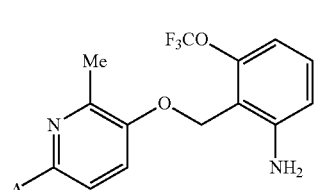 (QEPB60)
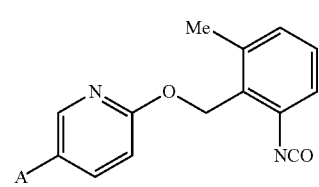 (QEPC1)
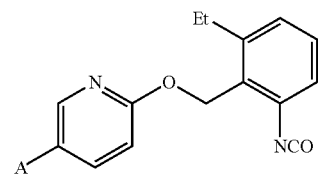 (QEPC2)
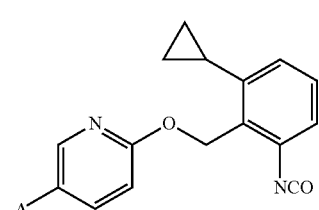 (QEPC3)
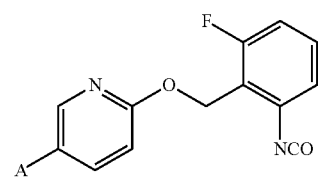 (QEPC4)
254
-continued
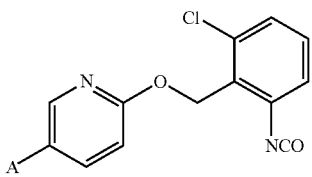 (QEPC5)
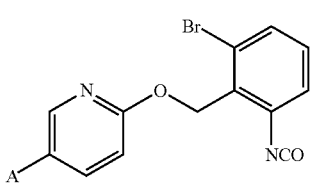 (QEPC6)
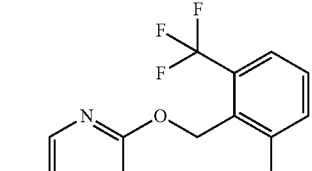 (QEPC7)
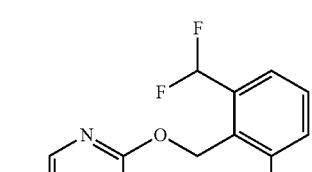 (QEPC8)
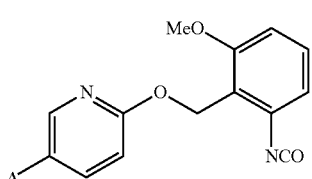 (QEPC9)
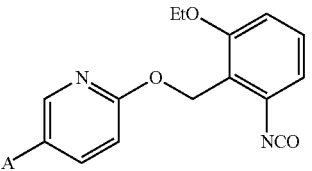 (QEPC10)
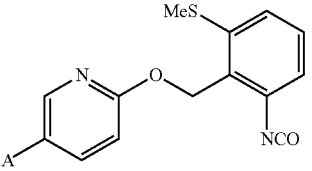 (QEPC11)
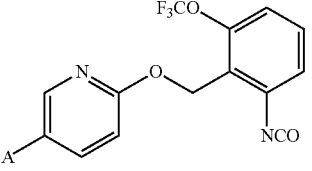 (QEPC12)

-continued (QEPC13)
(QEPC14)
(QEPC15)
(QEPC16)
(QEPC17)
(QEPC18)
(QEPC19)
(QEPC20)
(QEPC21)
(QEPC22)
(QEPC23)
(QEPC24)
(QEPC25)
(QEPC26)
(QEPC27)
(QEPC28)

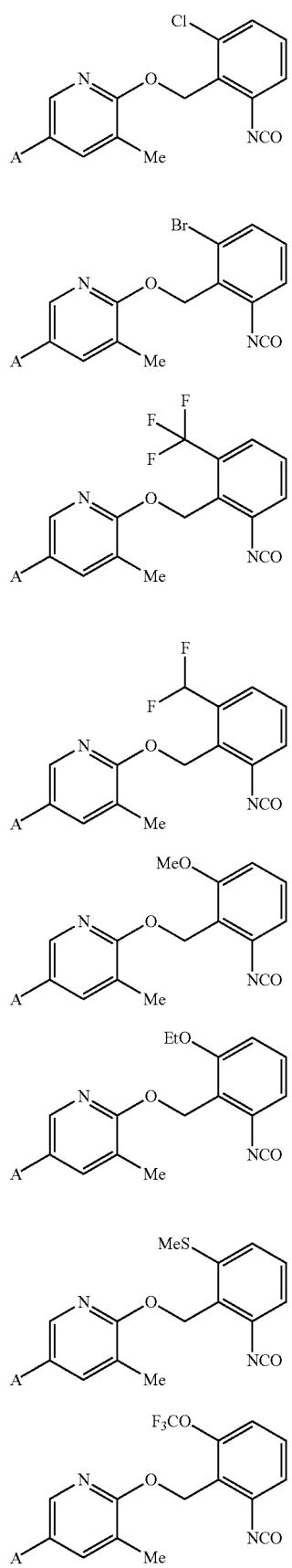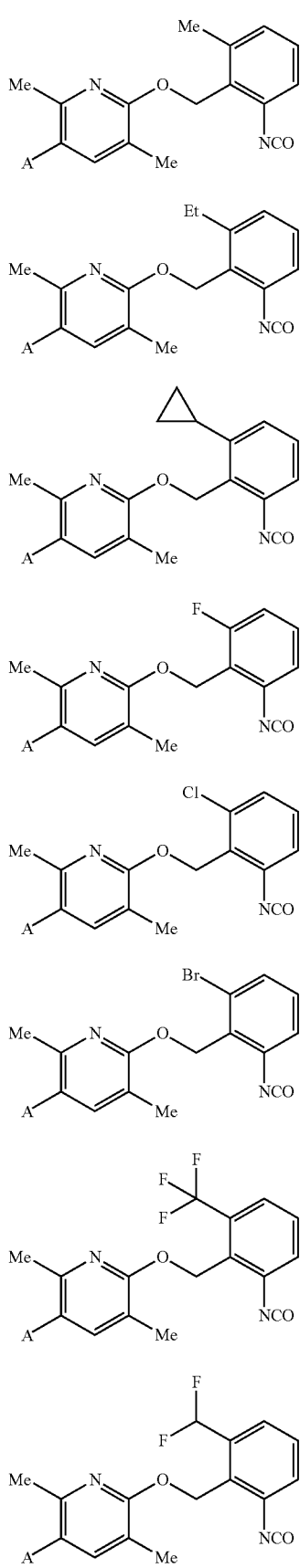

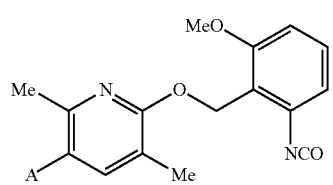
(QEPC45)
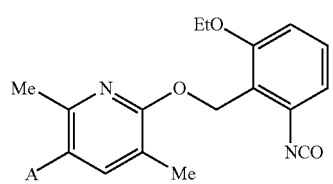
(QEPC46)
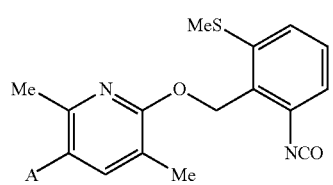
(QEPC47)
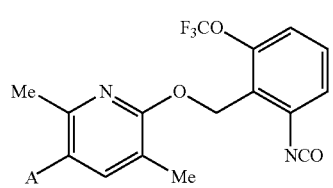
(QEPC48)
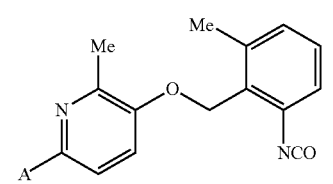
(QEPC49)
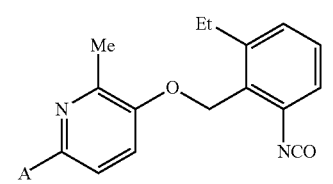
(QEPC50)
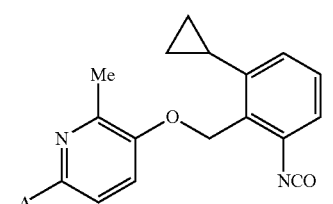
(QEPC51)
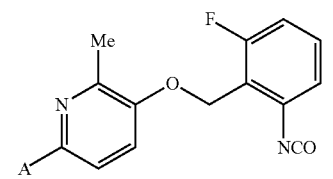
(QEPC52)
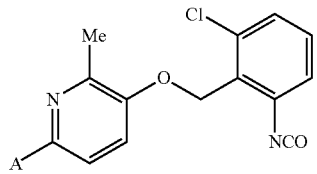
(QEPC53)
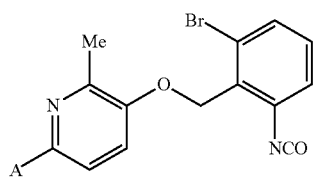
(QEPC54)
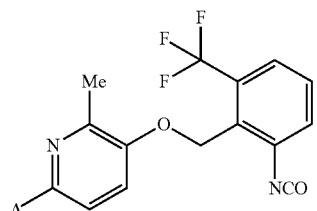
(QEPC55)
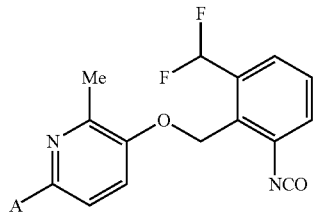
(QEPC56)
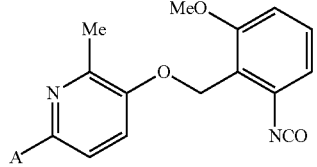
(QEPC57)
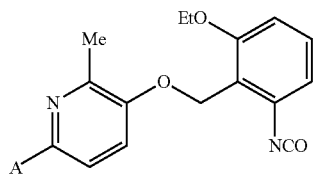
(QEPC58)
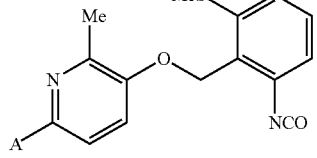
(QEPC59)
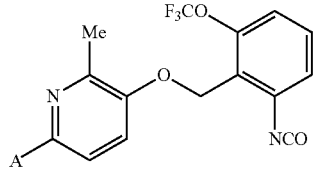
(QEPC60)

-continued
(QEPD1)
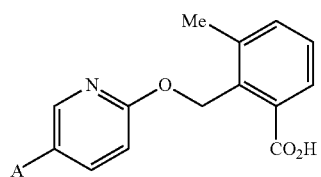
(QEPD2)
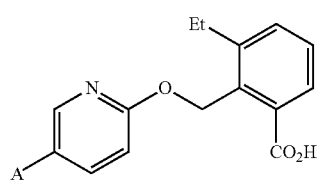
(QEPD3)
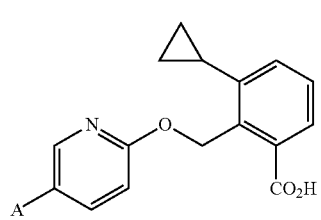
(QEPD4)
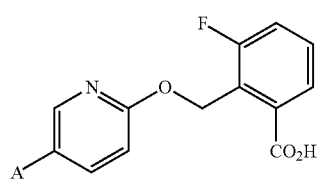
(QEPD5)
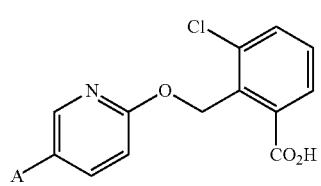
(QEPD6)
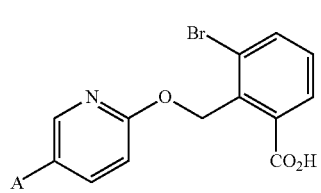
(QEPD7)
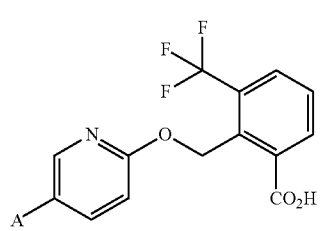
(QEPD8)
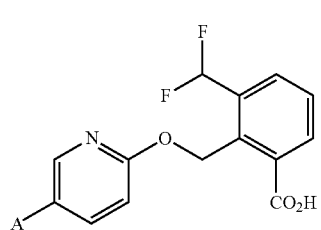
-continued
(QEPD9)
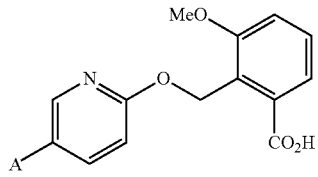
(QEPD10)
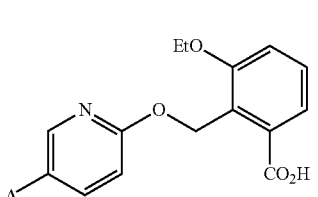
(QEPD11)
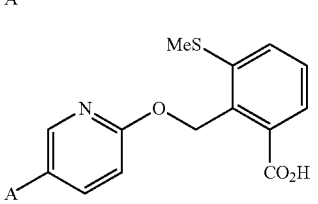
(QEPD12)
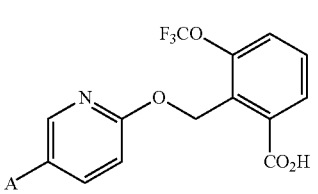
(QEPD13)
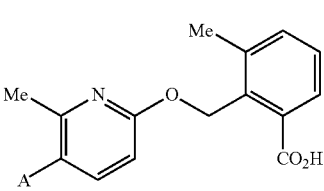
(QEPD14)
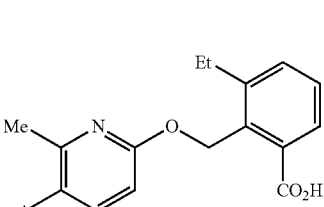
(QEPD15)
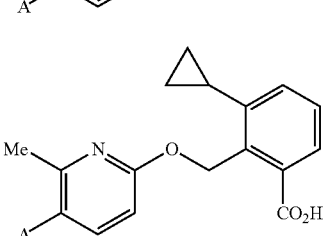
(QEPD16)
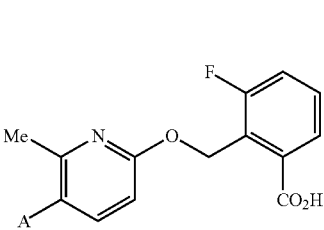

(QEPD17)
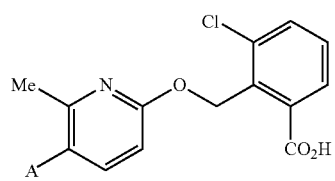
(QEPD18)
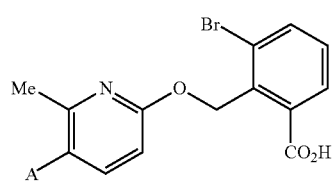
(QEPD19)
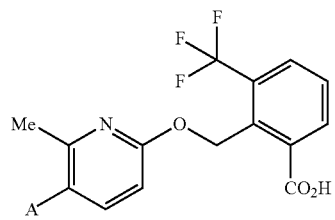
(QEPD20)
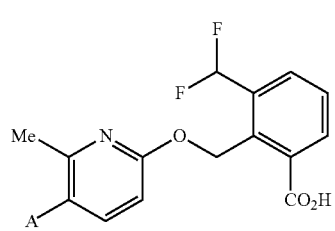
(QEPD21)
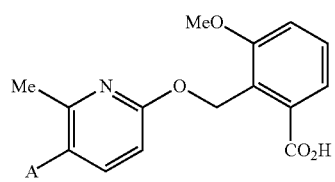
(QEPD22)
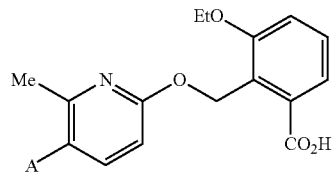
(QEPD23)
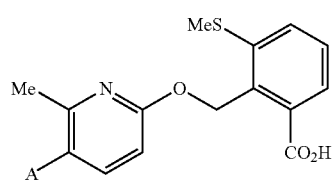
(QEPD24)
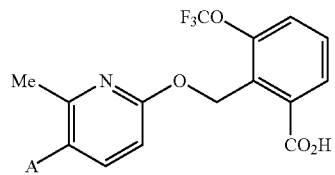
(QEPD25)
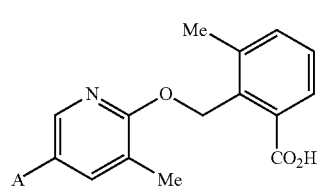
(QEPD26)
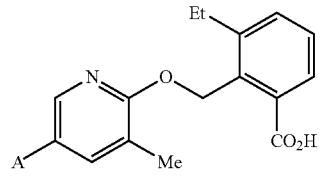
(QEPD27)
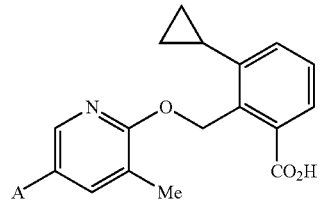
(QEPD28)
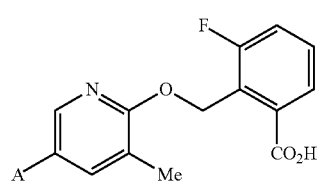
(QEPD29)
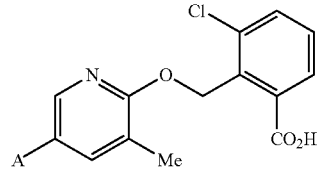
(QEPD30)
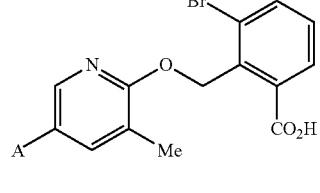
(QEPD31)
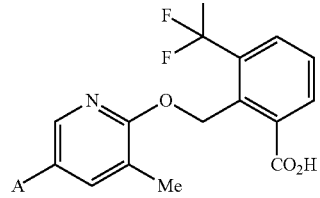
(QEPD32)
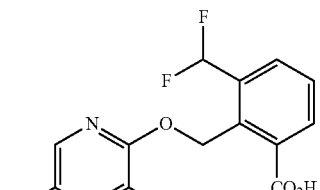

(QEPD33) 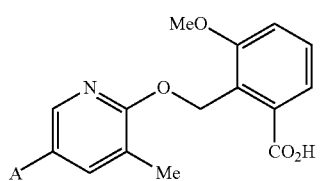
(QEPD34) 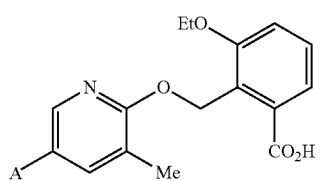
(QEPD35) 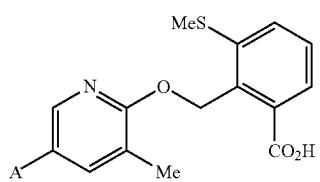
(QEPD36) 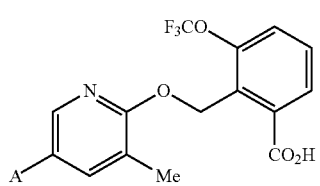
(QEPD37) 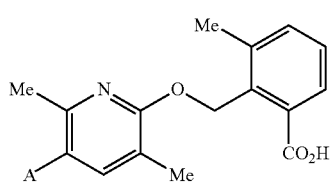
(QEPD38) 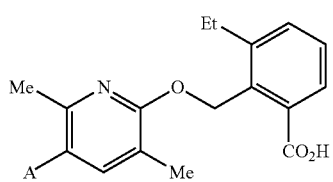
(QEPD39) 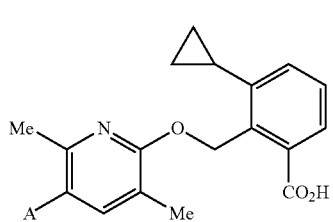
(QEPD40) 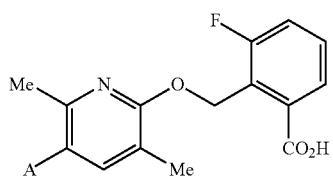
(QEPD41) 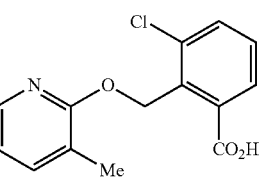
(QEPD42) 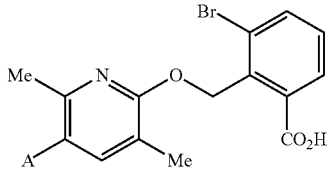
(QEPD43) 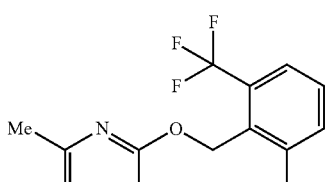
(QEPD44) 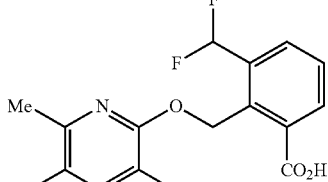
(QEPD45) 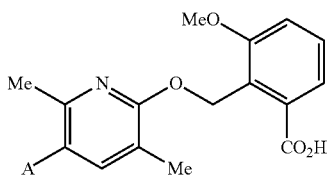
(QEPD46) 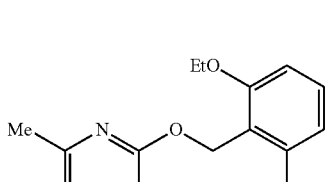
(QEPD47) 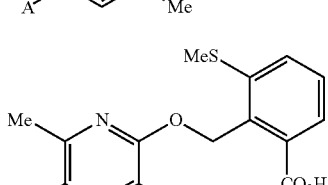
(QEPD48) 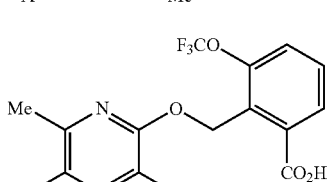

(QEPD49) 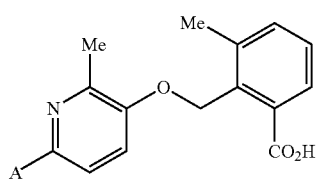
(QEPD50) 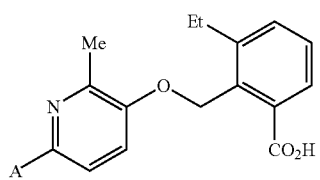
(QEPD51) 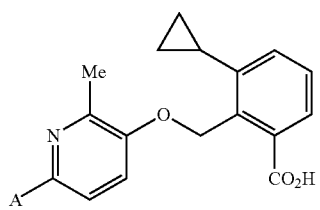
(QEPD52) 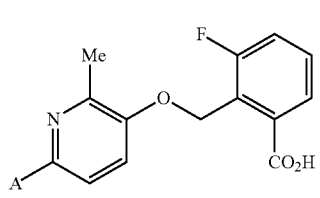
(QEPD53) 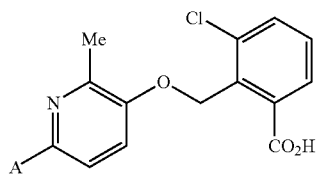
(QEPD54) 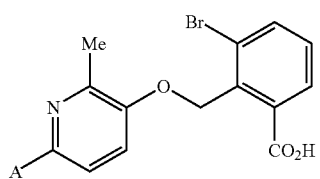
(QEPD55) 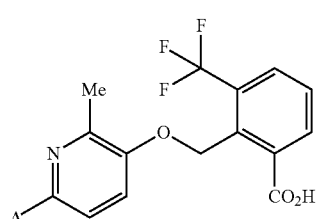
(QEPD56) 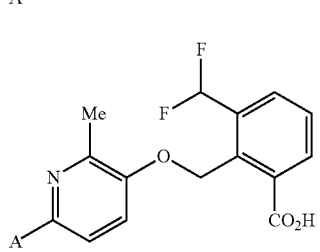
(QEPD57) 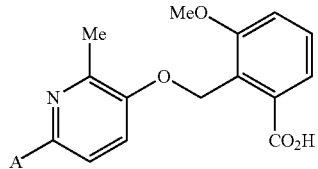
(QEPD58) 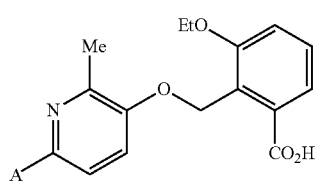
(QEPD59) 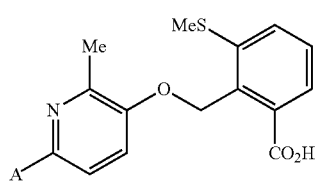
(QEPD60) 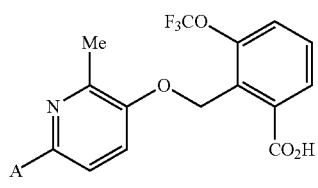
(QEPE1) 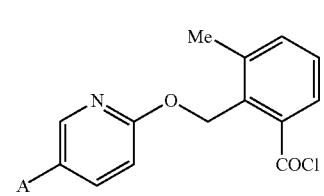
(QEPE2) 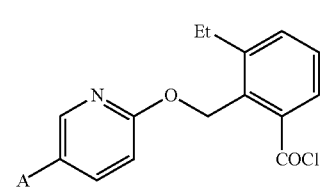
(QEPE3) 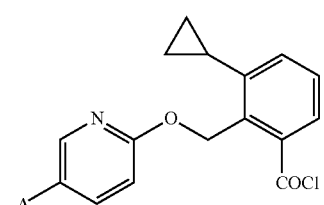
(QEPE4) 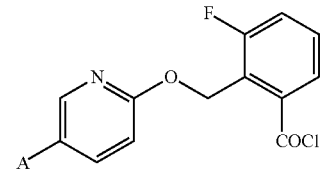

| 269 -continued | 270 -continued |
|---|---|
| 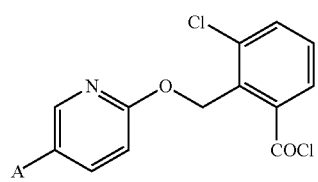 (QEPE5) | 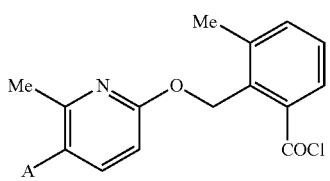 (QEPE13) |
| 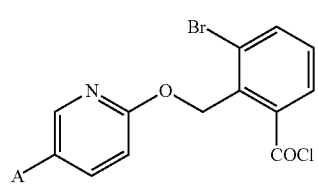 (QEPE6) | 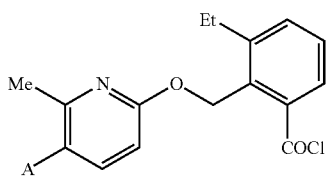 (QEPE14) |
| 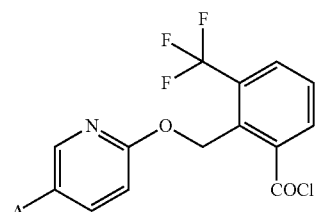 (QEPE7) | 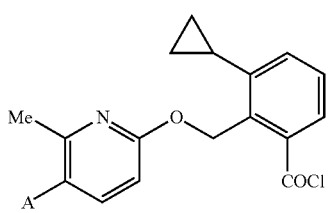 (QEPE15) |
| 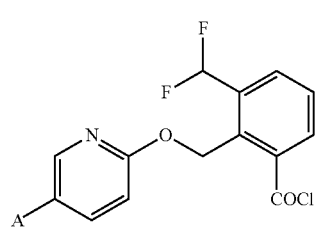 (QEPE8) | 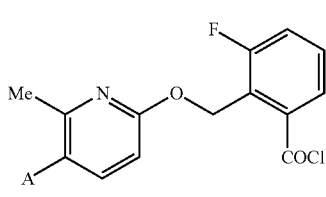 (QEPE16) |
| 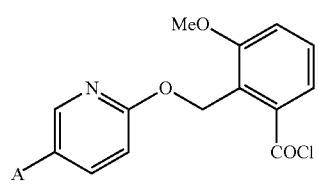 (QEPE9) | 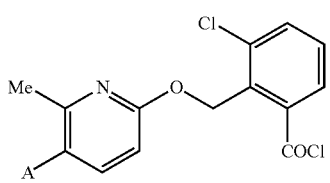 (QEPE17) |
| 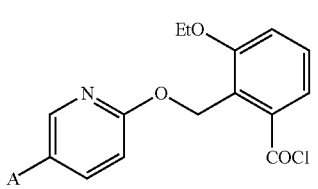 (QEPE10) | 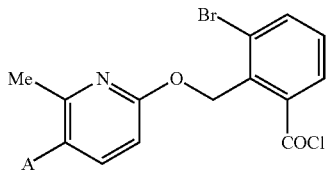 (QEPE18) |
| 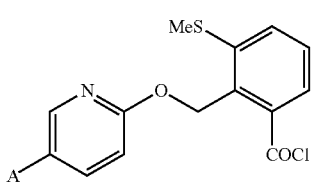 (QEPE11) | 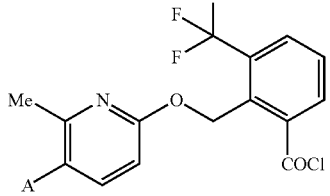 (QEPE19) |
| 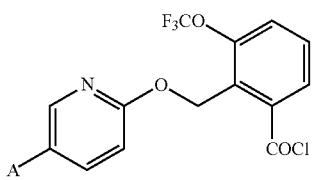 (QEPE12) | 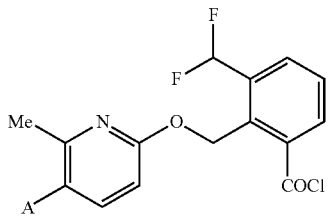 (QEPE20) |

(QEPE21), (QEPE22), (QEPE23), (QEPE24), (QEPE25), (QEPE26), (QEPE27), (QEPE28), (QEPE29), (QEPE30), (QEPE31), (QEPE32), (QEPE33), (QEPE34), (QEPE35), (QEPE36)

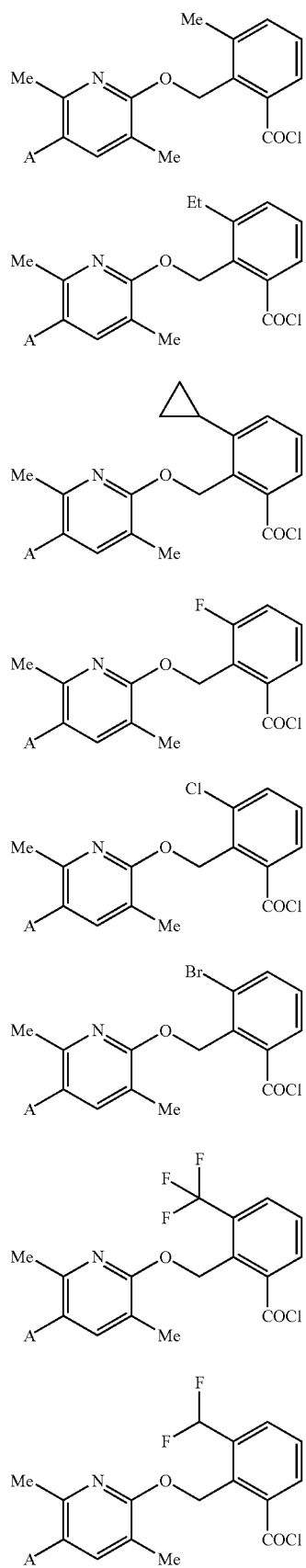
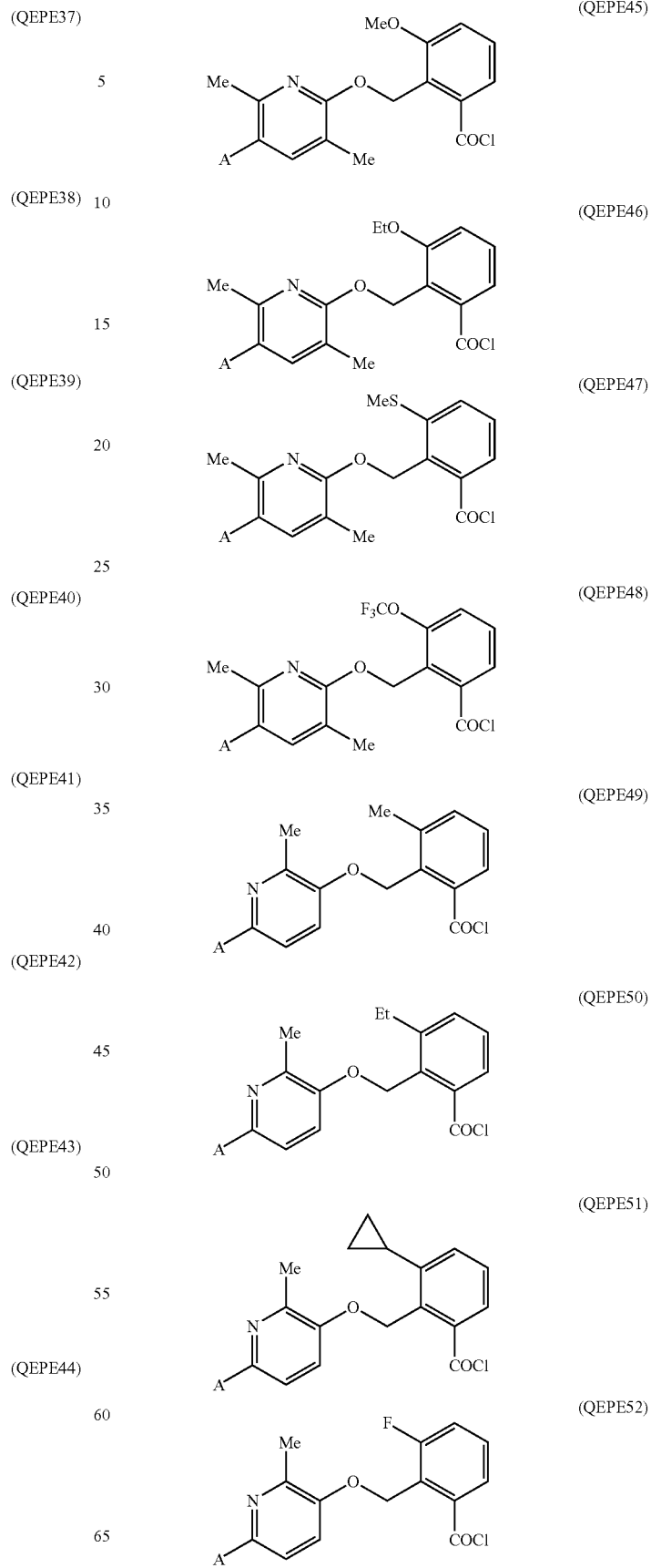

275 -continued
(QEPE53)
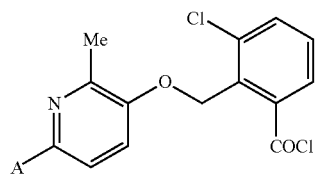
(QEPE54)
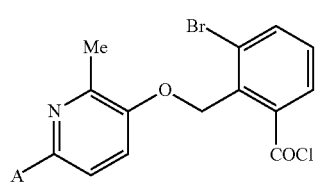
(QEPE55)
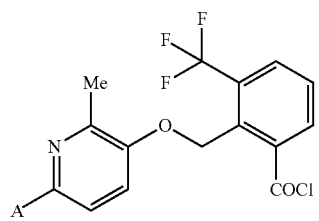
(QEPE56)
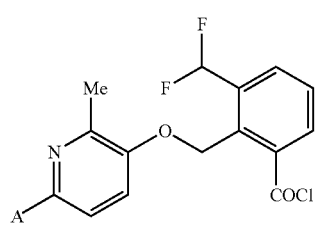
(QEPE57)
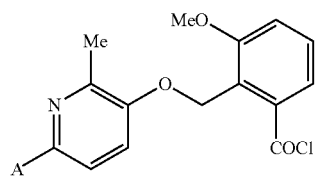
(QEPE58)
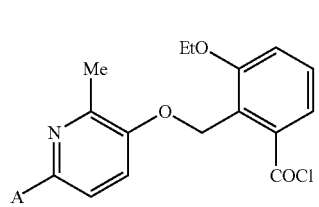
(QEPE59)
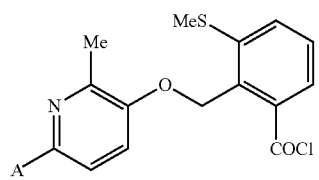
(QEPE60)
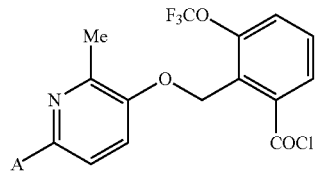
276 -continued
(QEPF1)
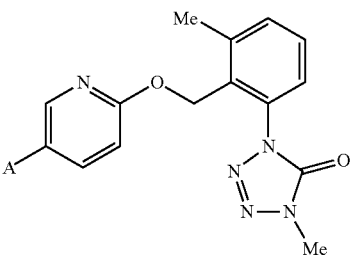
(QEPF2)
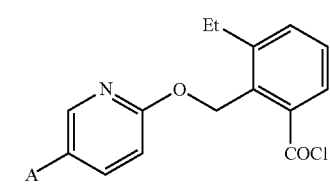
(QEPF3)
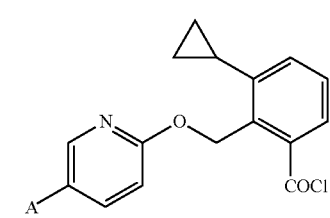
(QEPE4)
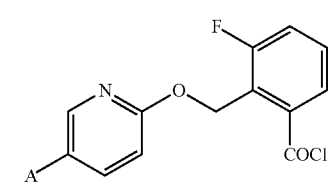
(QEPE5)
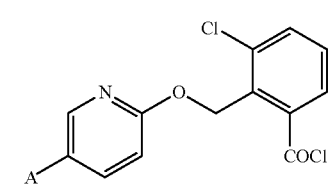
(QEPE6)
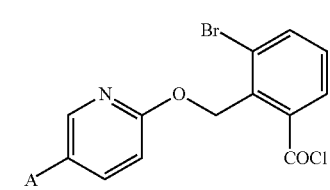
(QEPE7)
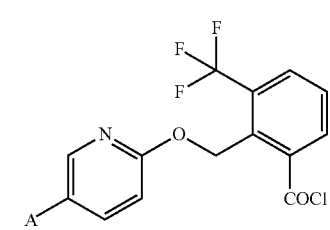

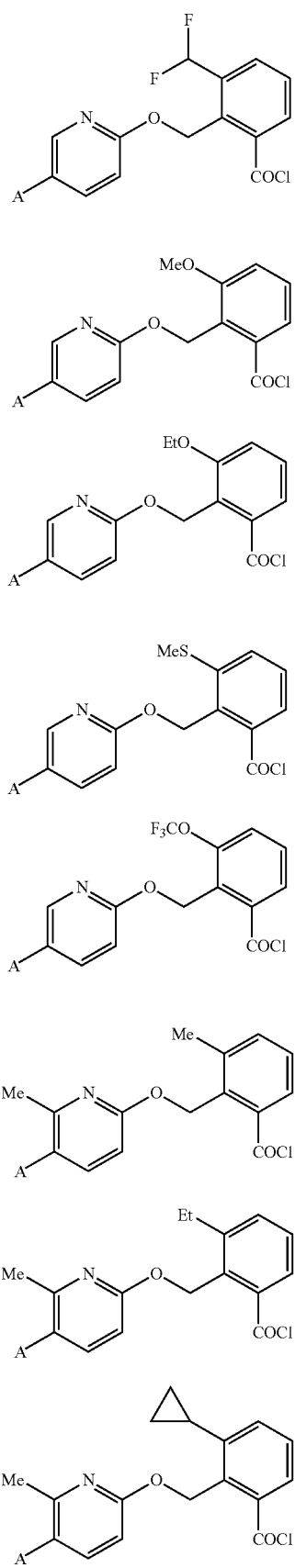
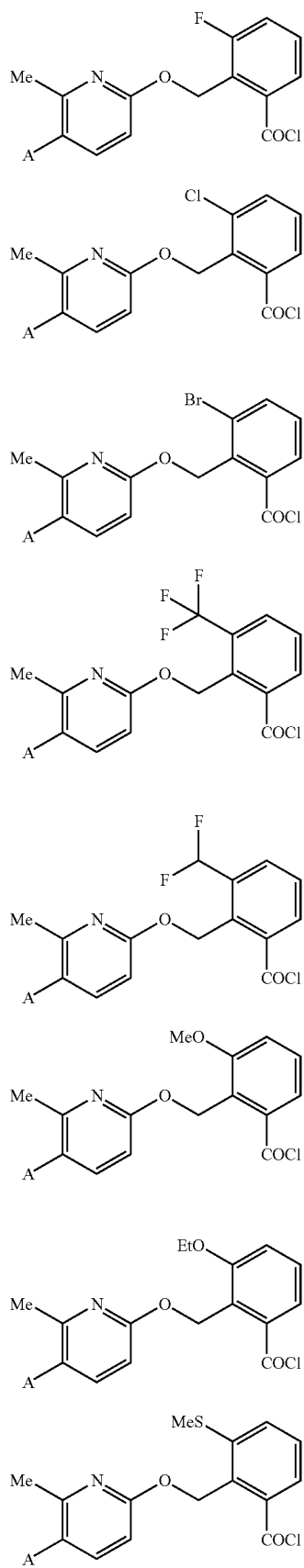

-continued (QEPE24)
(QEPE25)
(QEPE26)
(QEPE27)
(QEPE28)
(QEPE29)
(QEPE30)
(QEPE31)
(QEPE32)
(QEPE33)
(QEPE34)
(QEPE35)
(QEPE36)
(QEPE37)
(QEPE38)
(QEPE39)

281
-continued (QEPE40)
(QEPE41)
(QEPE42)
(QEPE43)
(QEPE44)
(QEPE45)
(QEPE46)
(QEPE47)

282
-continued (QEPE48)
(QEPE49)
(QEPE50)
(QEPE51)
(QEPE52)
(QEPE53)
(QEPE54)
(QEPE55)

(QEPE56) 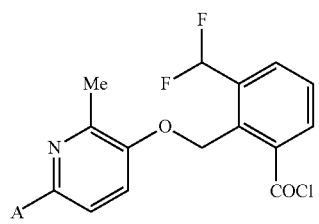
(QEPE57) 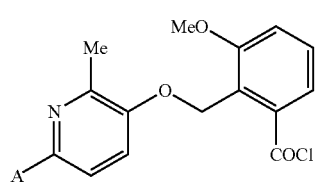
(QEPE58) 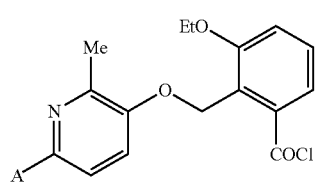
(QEPE59) 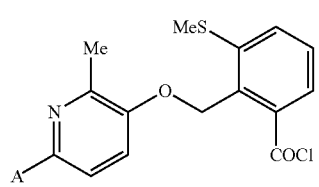
(QEPE60) 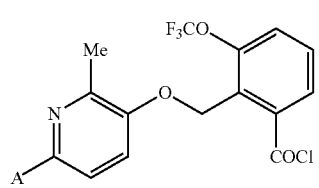
(QEPF1) 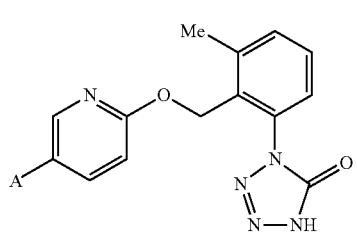
(QEPF2) 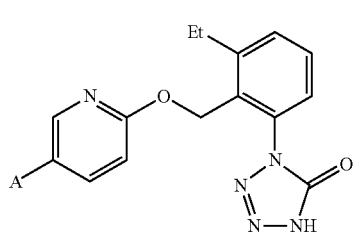
(QEPF3) 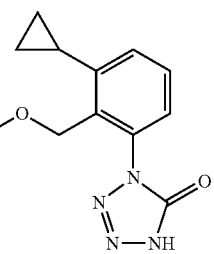
(QEPF4) 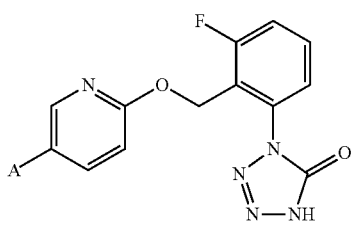
(QEPF5) 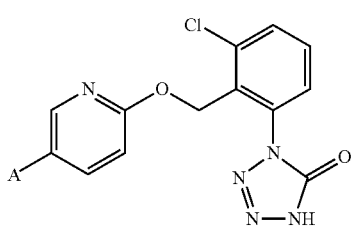
(QEPF6) 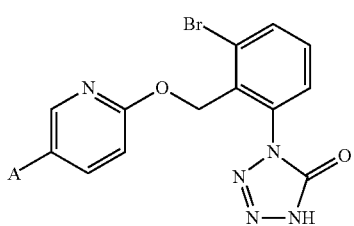
(QEPF7) 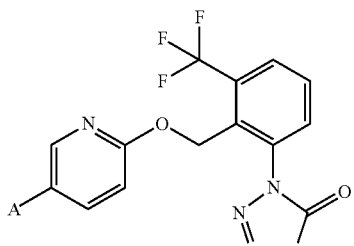
(QEPF8) 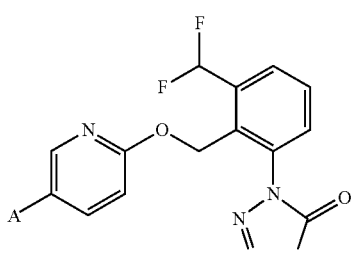

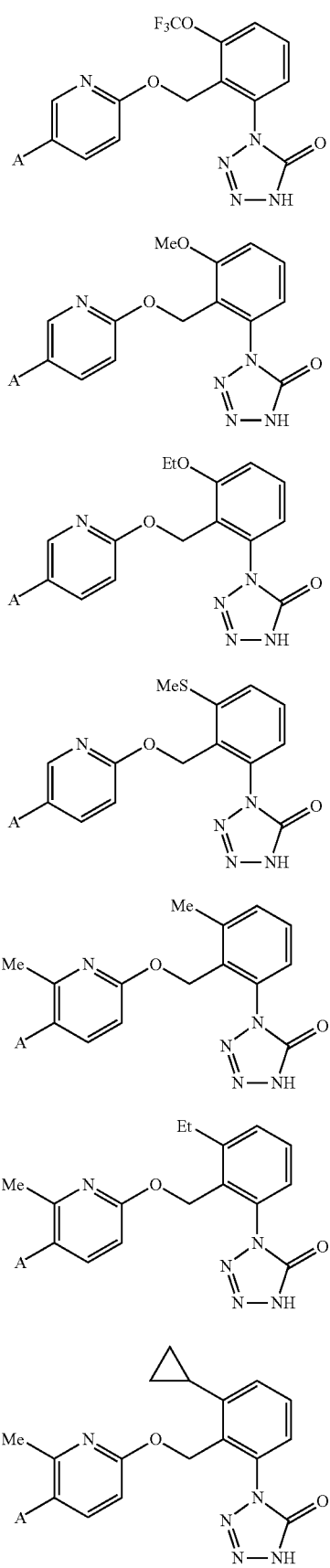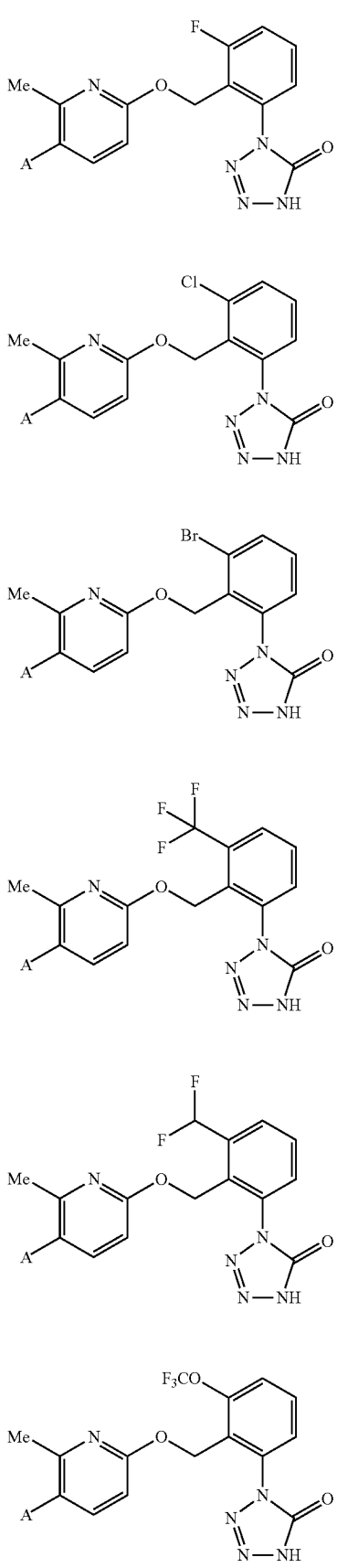

287
-continued
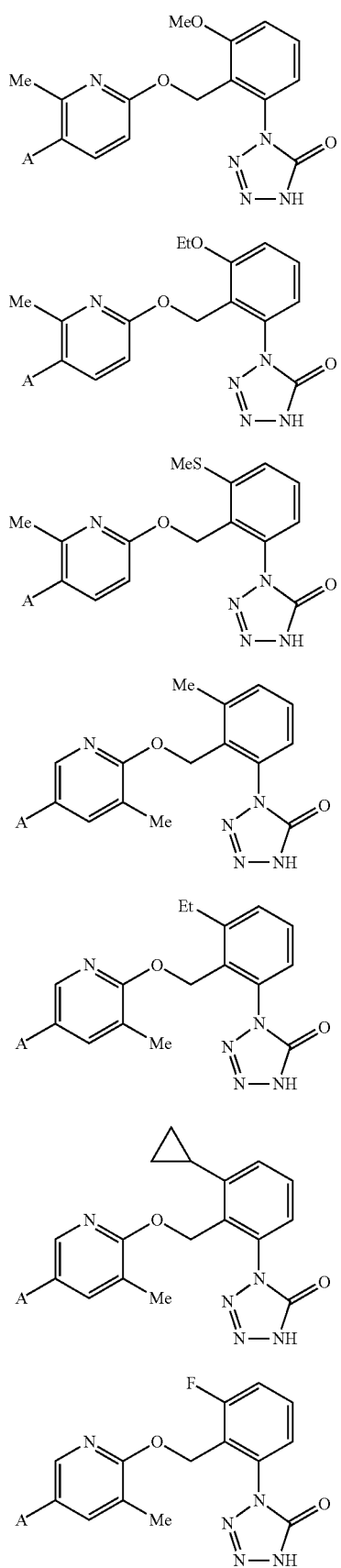
(QEPF22)
(QEPF23)
(QEPF24)
(QEPF25)
(QEPF26)
(QEPF27)
(QEPF28)
288
-continued
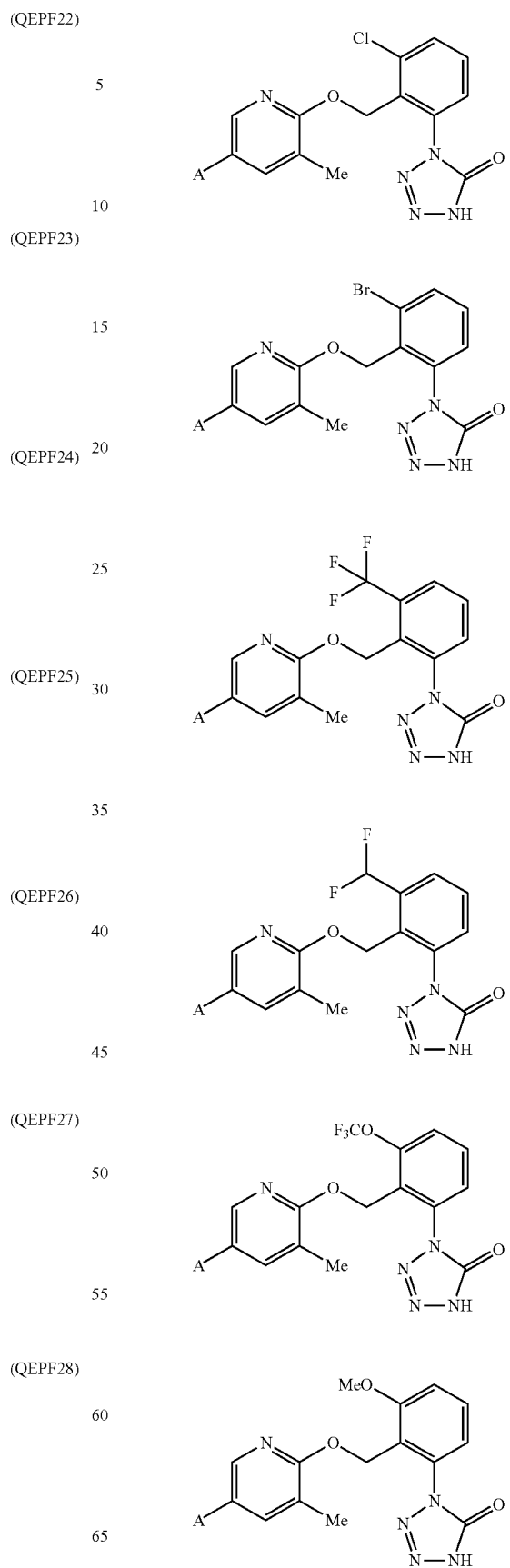
(QEPF29)
(QEPF30)
(QEPF31)
(QEPF32)
(QEPF33)
(QEPF34)

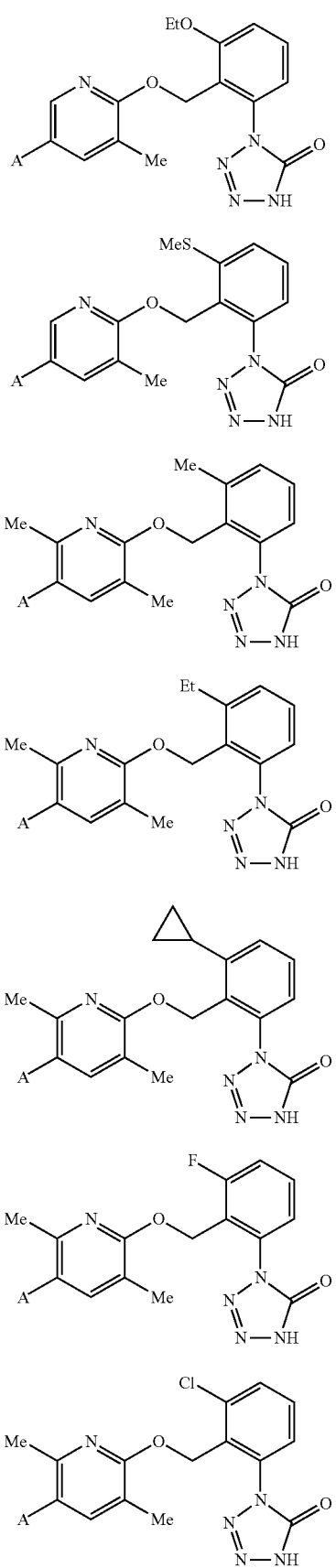
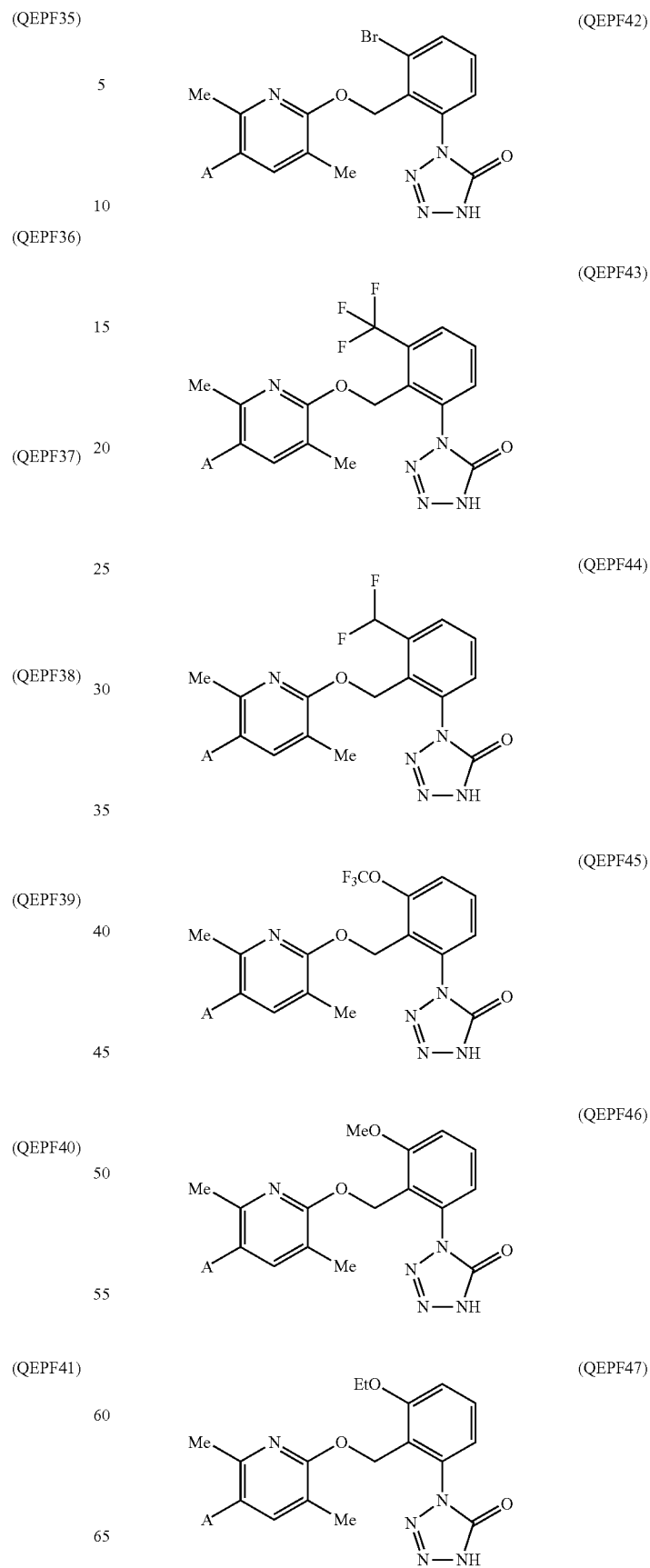

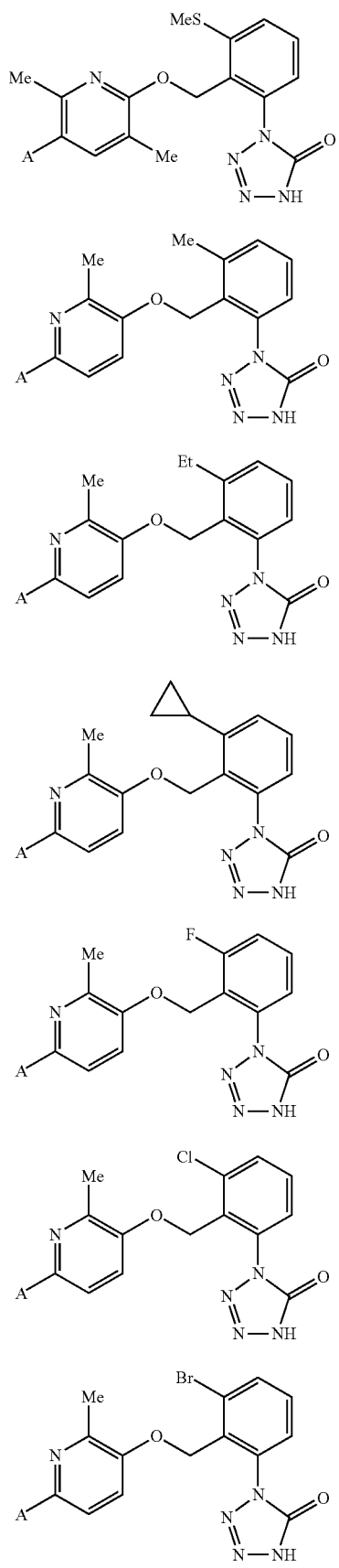
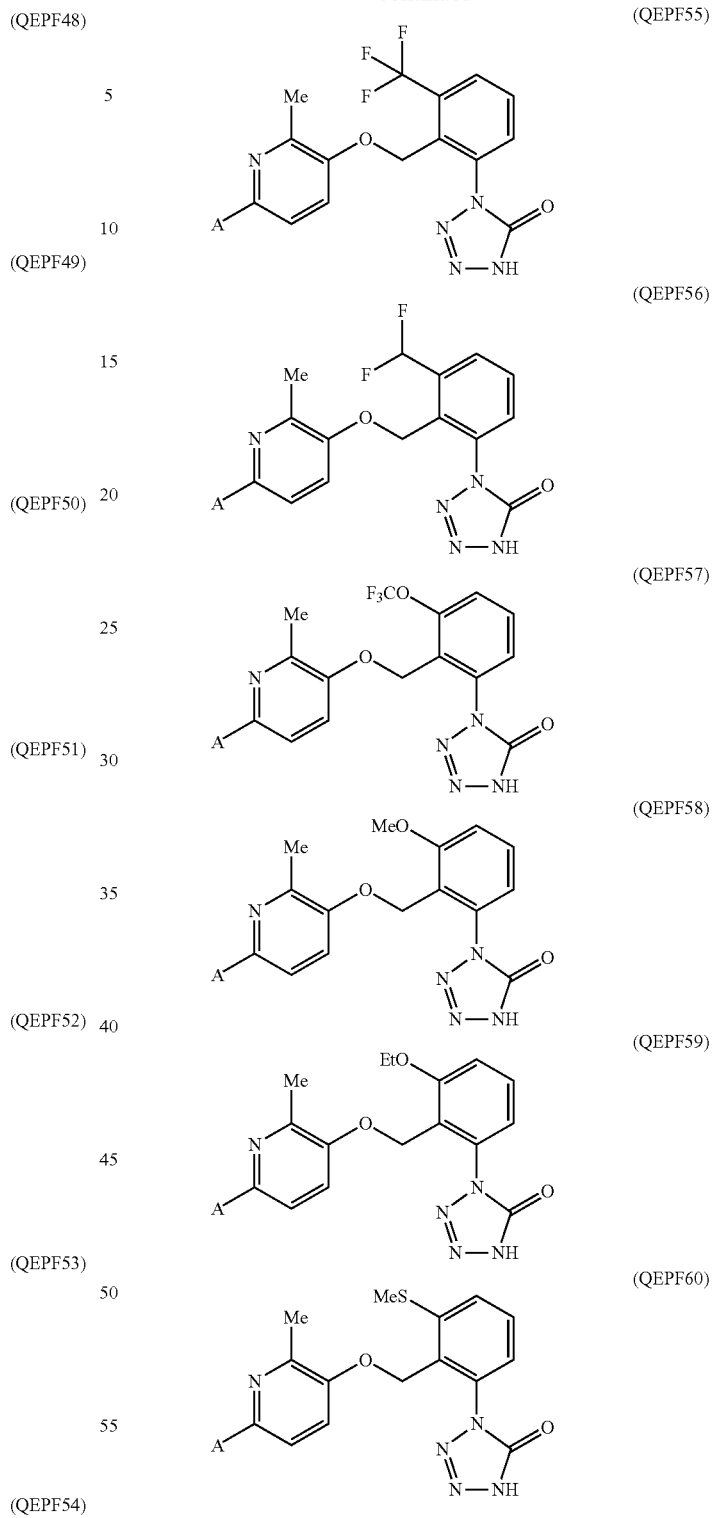

wherein A is a substituent corresponding to each of substituent numbers 1 to 1260.

In accordance with the process mentioned above, it is possible to obtain compounds TA-L001 to TX-L036.

The compounds TA-L001 to TX-L036 represent aromatic compounds shown below [wherein $A_1$ and $A_2$ represent any one of the following substituent numbers L001 to L036]. In the following [substituent numbers: $A_1$, $A_2$], F represents a fluorine atom, Cl represents a chlorine atom, Br represents a bromine atom, Me represents a methyl group, Et represents an ethyl group, Cy represents a cyclopropyl group, OMe represents a methoxy group, OEt represents an ethoxy group, CF3 represents a trifluoromethyl group, CF2H represents a difluoromethyl group, OCF3 represents a trifluoromethoxy group, SMe represents a methylthio group, B(OH)2 represents a borono group, and BY represents a 4,4,5,5-tetramethyl-1,3,2-dioxaborolan-2-yl group.

The compounds TA-L001 to TX-L036 are compounds represented by the following formulas:

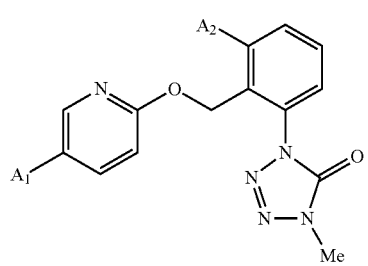
(TA)

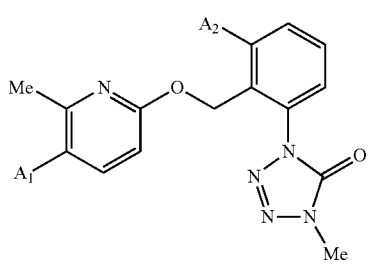
(TB)

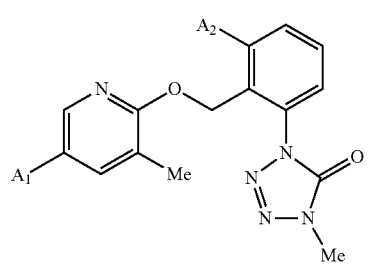
(TC)

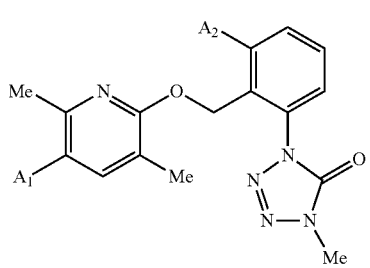
(TD)

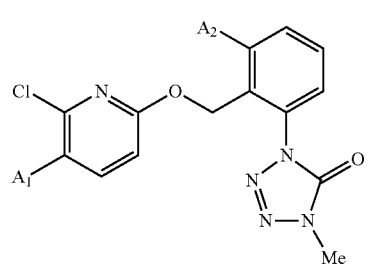
(TE)

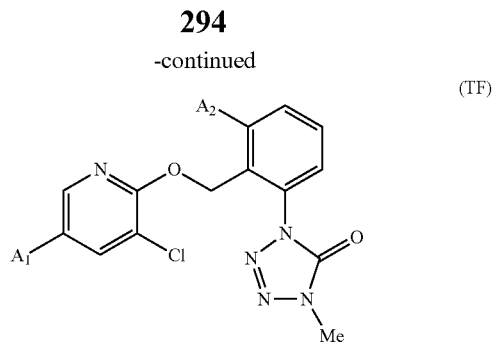
(TF)

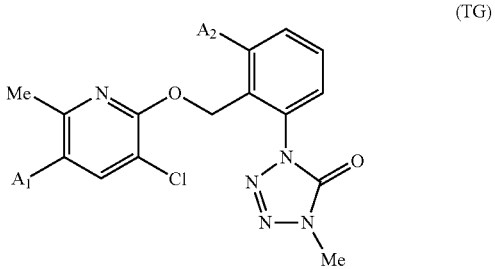
(TG)

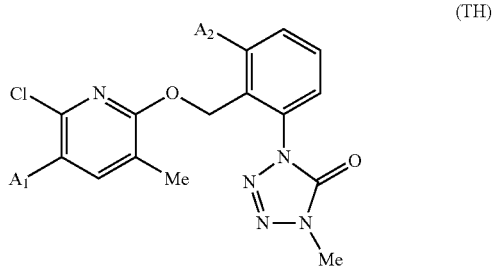
(TH)

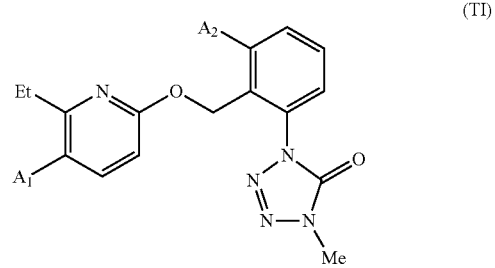
(TI)

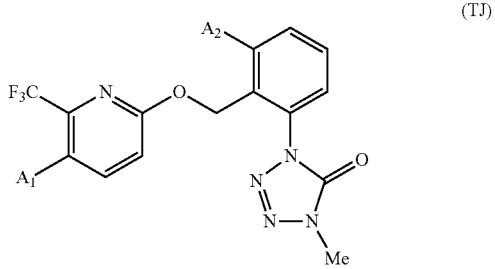
(TJ)

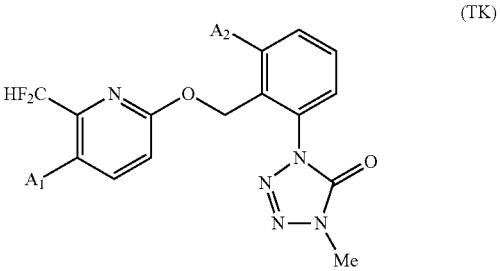
(TK)

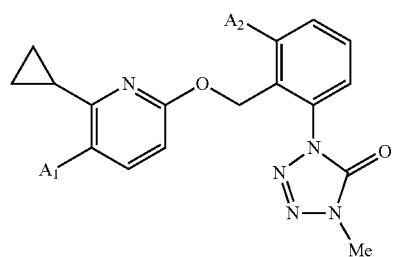 (TL)
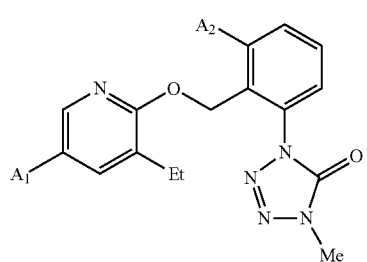 (TM)
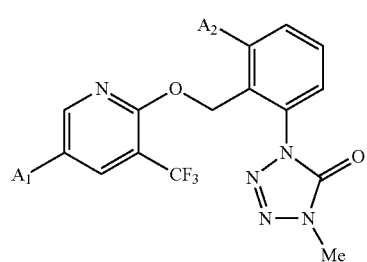 (TN)
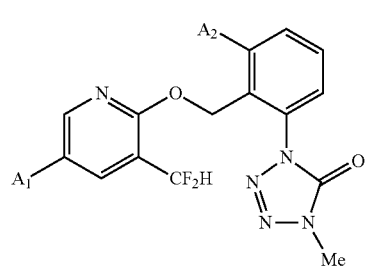 (TO)
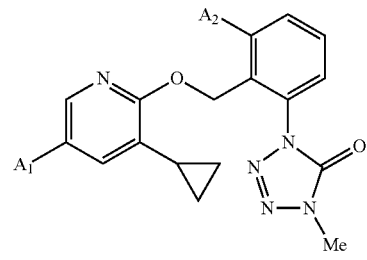 (TP)
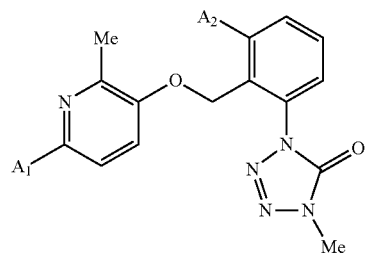 (TQ)
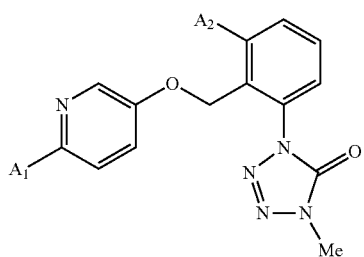 (TQ)
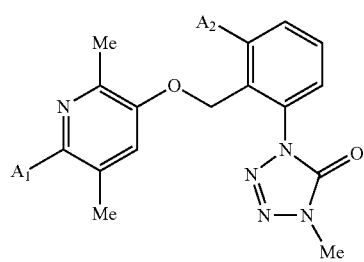 (TS)
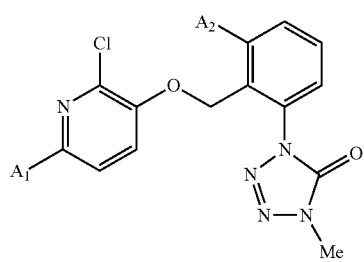 (TT)
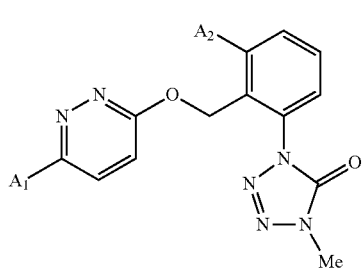 (TU)
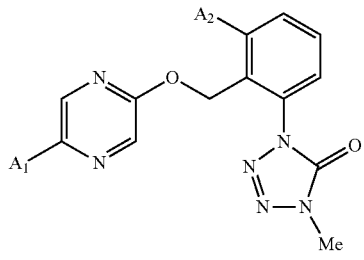 (TV)
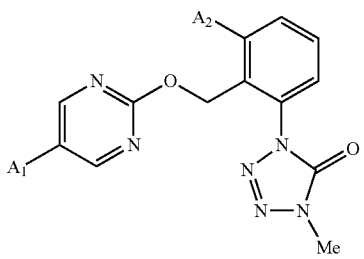 (TW)

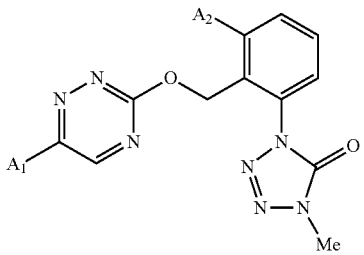

(TX)

[substituent numbers: $A_1$, $A_2$], [L001:Br, F], [L002:Br, Cl], [L003:Br, Br], [L004:Br, Me], [L005:Br, Et], [L006:Br, Cy], [L007:Br, OMe], [L008:Br, OEt], [L009:Br, CF3], [L010:Br, CF2H], [L011:Br, OCF3], [L012:Br, SMe], [L013:B(OH)2, F], [L014:B(OH)2, Cl], [L015:B(OH)2, Br], [L016:B(OH)2, Me], [L017:B(OH)2, Et], [L018:B(OH)2, Cy], [L019:B(OH)2, OMe], [L020:B(OH)2, OEt], [L021:B(OH)2, CF3], [L022:B(OH)2, CF2H], [L023:B(OH)2, OCF3], [L024:B(OH)2, SMe], [L025:BY, F], [L026:BY, Cl], [L027:BY, Br], [L028:BY, Me], [L029:BY, Et], [L030:BY, Cy], [L031:BY, OMe], [L032:BY, OEt], [L033:BY, CF3], [L034:BY, CF2H], [L035:BY, OCF3], [L036:BY, SMe]

For example, TA-L001 is a compound represented by formula (TA) in which substituent number is L001, having the following structure.

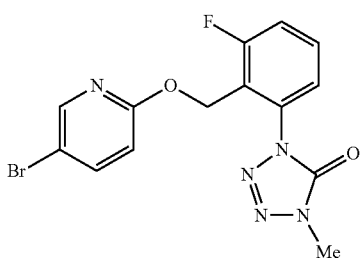

(TA-L001)

Examples of the present pest control agent include the followings:
a pest control composition comprising any one of the present compounds 1 to 88 and prothioconazole at a ratio of 0.1:1; a pest control composition comprising any one of the present compounds 1 to 88 and prothioconazole at a ratio of 1:1; a pest control composition comprising any one of the present compounds 1 to 88 and prothioconazole at a ratio of 10:1; a pest control composition comprising any one of the present compounds 1 to 88 and bromuconazole at a ratio of 0.1:1; a pest control composition comprising any one of the present compounds 1 to 88 and bromuconazole at a ratio of 1:1; a pest control composition comprising any one of the present compounds 1 to 88 and bromuconazole at a ratio of 10:1; a pest control composition comprising any one of the present compounds 1 to 88 and metconazole at a ratio of 0.1:1; a pest control composition comprising any one of the present compounds 1 to 88 and metconazole at a ratio of 1:1; a pest control composition comprising any one of the present compounds 1 to 88 and metconazole at a ratio of 10:1; a pest control composition comprising any one of the present compounds 1 to 88 and tebuconazole at a ratio of 0.1:1; a pest control composition comprising any one of the present compounds 1 to 88 and tebuconazole at a ratio of 1:1; a pest control composition comprising any one of the present compounds 1 to 88 and tebuconazole at a ratio of 10:1; a pest control composition comprising any one of the present compounds 1 to 88 and tetraconazole at a ratio of 0.1:1; a pest control composition comprising any one of the present compounds 1 to 88 and tetraconazole at a ratio of 1:1; a pest control composition comprising any one of the present compounds 1 to 88 and tetraconazole at a ratio of 10:1; a pest control composition comprising any one of the present compounds 1 to 88 and cyproconazole at a ratio of 0.1:1; a pest control composition comprising any one of the present compounds 1 to 88 and cyproconazole at a ratio of 1:1; a pest control composition comprising any one of the present compounds 1 to 88 and cyproconazole at a ratio of 10:1; a pest control composition comprising any one of the present compounds 1 to 88 and flusilazol at a ratio of 0.1:1; a pest control composition comprising any one of the present compounds 1 to 88 and flusilazol at a ratio of 1:1; a pest control composition comprising any one of the present compounds 1 to 88 and flusilazol at a ratio of 10:1;
a pest control composition comprising any one of the present compounds 1 to 88 and prochloraz at a ratio of 0.1:1; a pest control composition comprising any one of the present compounds 1 to 88 and prochloraz at a ratio of 1:1; a pest control composition comprising any one of the present compounds 1 to 88 and prochloraz at a ratio of 10:1; a pest control composition comprising any one of the present compounds 1 to 88 and imazalil at a ratio of 0.1:1; a pest control composition comprising any one of the present compounds 1 to 88 and imazalil at a ratio of 1:1; a pest control composition comprising any one of the present compounds 1 to 88 and imazalil at a ratio of 10:1; a pest control composition comprising any one of the present compounds 1 to 88 and epoxiconazole at a ratio of 0.1:1; a pest control composition comprising any one of the present compounds 1 to 88 and epoxiconazole at a ratio of 1:1; a pest control composition comprising any one of the present compounds 1 to 88 and epoxiconazole at a ratio of 10:1; a pest control composition comprising any one of the present compounds 1 to 88 and propiconazole at a ratio of 0.1:1; a pest control composition comprising any one of the present compounds 1 to 88 and propiconazole at a ratio of 1:1; a pest control composition comprising any one of the present compounds 1 to 88 and propiconazole at a ratio of 10:1; a pest control composition comprising any one of the present compounds 1 to 88 and difenoconazole at a ratio of 0.1:1; a pest control composition comprising any one of the present compounds 1 to 88 and difenoconazole at a ratio of 1:1; a pest control composition comprising any one of the present compounds 1 to 88 and difenoconazole at a ratio of 10:1; a pest control composition comprising any one of the present compounds 1 to 88 and myclobutanil at a ratio of 0.1:1; a pest control composition comprising any one of the present compounds 1 to 88 and myclobutanil at a ratio of 1:1; a pest control composition comprising any one of the present compounds 1 to 88 and myclobutanil at a ratio of 10:1; a pest control composition comprising any one of the present compounds 1 to 88 and triadimenol at a ratio of 0.1:1; a pest control composition comprising any one of the present compounds 1 to 88 and triadimenol at a ratio of 1:1; a pest control composition comprising any one of the present compounds 1 to 88 and triadimenol at a ratio of 10:1;
a pest control composition comprising any one of the present compounds 1 to 88 and triadimefon at a ratio of 0.1:1; a pest control composition comprising any one of the present compounds 1 to 88 and triadimefon at a ratio of 1:1; a pest control composition comprising any one of the present compounds 1 to 88 and triadimefon at a ratio of 10:1; a pest control composition comprising any one of the present compounds 1 to 88 and fluquinconazole at a ratio of 0.1:1; a pest control composition comprising any one of the present compounds 1 to 88 and fluquinconazole at a ratio of 1:1; a pest control composition comprising any one of the present compounds 1 to 88 and fluquinconazole at a ratio of 10:1; a pest control composition comprising any one of the present compounds 1 to 88 and triticonazole at a ratio of 0.1:1; a pest control composition comprising any one of the present compounds 1 to 88 and triticonazole at a ratio of 1:1; a pest control composition comprising any one of the present compounds 1 to 88 and triticonazole at a ratio of 10:1; a pest control composition comprising any one of the present compounds 1 to 88 and ipconazole at a ratio of 0.1:1; a pest control composition comprising any one of the present compounds 1 to 88 and ipconazole at a ratio of 1:1; a pest control composition comprising any one of the present compounds 1 to 88 and ipconazole at a ratio of 10:1; a pest control composition comprising any one of the present compounds 1 to 88 and triflumizol at a ratio of 0.1:1; a pest control composition comprising any one of the present compounds 1 to 88 and triflumizol at a ratio of 1:1; a pest control composition comprising any one of the present compounds 1 to 88 and triflumizol at a ratio of 10:1; a pest control composition comprising any one of the present compounds 1 to 88 and fenbuconazole at a ratio of 0.1:1; a pest control composition comprising any one of the present compounds 1 to 88 and fenbuconazole at a ratio of 1:1; a pest control composition comprising any one of the present compounds 1 to 88 and fenbuconazole at a ratio of 10:1; a pest control composition comprising any one of the present compounds 1 to 88 and hexaconazole at a ratio of 0.1:1; a pest control composition comprising any one of the present compounds 1 to 88 and hexaconazole at a ratio of 1:1; a pest control composition comprising any one of the present compounds 1 to 88 and hexaconazole at a ratio of 10:1; a pest compounds 1 to 88 and bitertanol at a ratio of 0.1:1; a pest control composition comprising any one of the present compounds 1 to 88 and bitertanol at a ratio of 1:1; a pest control composition comprising any one of the present compounds 1 to 88 and bitertanol at a ratio of 10:1; a pest control composition comprising any one of the present compounds 1 to 88 and flutriafol at a ratio of 0.1:1; a pest control composition comprising any one of the present compounds 1 to 88 and flutriafol at a ratio of 1:1; a pest control composition comprising any one of the present compounds 1 to 88 and flutriafol at a ratio of 10:1; a pest control composition comprising any one of the present compounds 1 to 88 and simeconazole at a ratio of 0.1:1; a pest control composition comprising any one of the present compounds 1 to 88 and simeconazole at a ratio of 1:1; a pest control composition comprising any one of the present compounds 1 to 88 and simeconazole at a ratio of 10:1; a pest control composition comprising any one of the present compounds 1 to 88 and imibenconazole at a ratio of 0.1:1; a pest control composition comprising any one of the present compounds 1 to 88 and imibenconazole at a ratio of 1:1; a pest control composition comprising any one of the present compounds 1 to 88 and imibenconazole at a ratio of 10:1; a pest control composition comprising any one of the present compounds 1 to 88 and oxpoconazole at a ratio of 0.1:1; a pest control composition comprising any one of the present compounds 1 to 88 and oxpoconazole at a ratio of 1:1; a pest control composition comprising any one of the present compounds 1 to 88 and oxpoconazole at a ratio of 10:1; a pest compounds 1 to 88 and azoxystrobin at a ratio of 0.1:1; a pest control composition comprising any one of the present compounds 1 to 88 and azoxystrobin at a ratio of 1:1; a pest control composition comprising any one of the present compounds 1 to 88 and azoxystrobin at a ratio of 10:1; a pest control composition comprising any one of the present compounds 1 to 88 and pyraclostrobin at a ratio of 0.1:1; a pest control composition comprising any one of the present compounds 1 to 88 and pyraclostrobin at a ratio of 1:1; a pest control composition comprising any one of the present compounds 1 to 88 and pyraclostrobin at a ratio of 10:1; a pest control composition comprising any one of the present compounds 1 to 88 and picoxystrobin at a ratio of 0.1:1; a pest control composition comprising any one of the present compounds 1 to 88 and picoxystrobin at a ratio of 1:1; a pest control composition comprising any one of the present compounds 1 to 88 and picoxystrobin at a ratio of 10:1; a pest control composition comprising any one of the present compounds 1 to 88 and fluoxastrobin at a ratio of 0.1:1; a pest control composition comprising any one of the present compounds 1 to 88 and fluoxastrobin at a ratio of 1:1; a pest control composition comprising any one of the present compounds 1 to 88 and fluoxastrobin at a ratio of 10:1; a pest control composition comprising any one of the present compounds 1 to 88 and trifloxystrobin at a ratio of 0.1:1; a pest control composition comprising any one of the present compounds 1 to 88 and trifloxystrobin at a ratio of 1:1; a pest control composition comprising any one of the present compounds 1 to 88 and trifloxystrobin at a ratio of 10:1; a pest control composition comprising any one of the present compounds 1 to 88 and mandestrobin at a ratio of 0.1:1; a pest control composition comprising any one of the present compounds 1 to 88 and mandestrobin at a ratio of 1:1; a pest control composition comprising any one of the present compounds 1 to 88 and mandestrobin at a ratio of 10:1; a pest control composition comprising any one of the present compounds 1 to 88 and kresoxim-methyl at a ratio of 0.1:1; a pest control composition comprising any one of the present compounds 1 to 88 and kresoxim-methyl at a ratio of 1:1; a pest control composition comprising any one of the present compounds 1 to 88 and kresoxim-methyl at a ratio of 10:1; a pest control composition comprising any one of the present compounds 1 to 88 and dimoxystrobin at a ratio of 0.1:1; a pest control composition comprising any one of the present compounds 1 to 88 and dimoxystrobin at a ratio of 1:1; a pest control composition comprising any one of the present compounds 1 to 88 and dimoxystrobin at a ratio of 10:1; a pest control composition comprising any one of the present compounds 1 to 88 and pyribencarb at a ratio of 0.1:1; a pest control composition comprising any one of the present compounds 1 to 88 and pyribencarb at a ratio of 1:1; a pest control composition comprising any one of the present compounds 1 to 88 and pyribencarb at a ratio of 10:1; a pest control composition comprising any one of the present compounds 1 to 88 and famoxadon at a ratio of 0.1:1; a pest control composition comprising any one of the present compounds 1 to 88 and famoxadon at a ratio of 1:1; a pest control composition comprising any one of the present compounds 1 to 88 and famoxadon at a ratio of 10:1; a pest control composition comprising any one of the present compounds 1 to 88 and fenamidone at a ratio of 0.1:1; a pest control composition comprising any one of the present compounds 1 to 88 and fenamidone at a ratio of 1:1; a pest control composition comprising any one of the present compounds 1 to 88 and fenamidone at a ratio of 10:1; a pest control composition comprising any one of the present compounds 1 to 88 and metominostrobin at a ratio of 0.1:1; a pest control composition comprising any one of the present compounds 1 to 88 and metominostrobin at a ratio of 1:1; a pest control composition comprising any one of the present compounds 1 to 88 and metominostrobin at a ratio of 10:1;

a pest control composition comprising any one of the present compounds 1 to 88 and orysastrobin at a ratio of 0.1:1; a pest control composition comprising any one of the present compounds 1 to 88 and orysastrobin at a ratio of 1:1; a pest control composition comprising any one of the present compounds 1 to 88 and orysastrobin at a ratio of 10:1; a pest control composition comprising any one of the present compounds 1 to 88 and enestrobin at a ratio of 0.1:1; a pest control composition comprising any one of the present compounds 1 to 88 and enestrobin at a ratio of 1:1;
a pest control composition comprising any one of the present compounds 1 to 88 and enestrobin at a ratio of 10:1; a pest control composition comprising any one of the present compounds 1 to 88 and pyraoxystrobin at a ratio of 0.1:1; a pest control composition comprising any one of the present compounds 1 to 88 and pyraoxystrobin at a ratio of 1:1; a pest control composition comprising any one of the present compounds 1 to 88 and pyraoxystrobin at a ratio of 10:1; a pest control composition comprising any one of the present compounds 1 to 88 and pyrametostrobin at a ratio of 0.1:1; a pest control composition comprising any one of the present compounds 1 to 88 and pyrametostrobin at a ratio of 1:1; a pest control composition comprising any one of the present compounds 1 to 88 and pyrametostrobin at a ratio of 10:1;
a pest control composition comprising any one of the present compounds 1 to 88 and fenaminstrobin at a ratio of 0.1:1; a pest control composition comprising any one of the present compounds 1 to 88 and fenaminstrobin at a ratio of 1:1; a pest control composition comprising any one of the present compounds 1 to 88 and fenaminstrobin at a ratio of 10:1; a pest control composition comprising any one of the present compounds 1 to 88 and enoxastrobin at a ratio of 0.1:1; a pest control composition comprising any one of the present compounds 1 to 88 and enoxastrobin at a ratio of 1:1; a pest control composition comprising any one of the present compounds 1 to 88 and enoxastrobin at a ratio of 10:1; a pest control composition comprising any one of the present compounds 1 to 88 and coumoxystrobin at a ratio of 0.1:1; a pest control composition comprising any one of the present compounds 1 to 88 and coumoxystrobin at a ratio of 1:1; a pest control composition comprising any one of the present compounds 1 to 88 and coumoxystrobin at a ratio of 10:1; a pest control composition comprising any one of the present compounds 1 to 88 and triclopyricarb at a ratio of 0.1:1; a pest control composition comprising any one of the present compounds 1 to 88 and triclopyricarb at a ratio of 1:1;
a pest control composition comprising any one of the present compounds 1 to 88 and triclopyricarb at a ratio of 10:1; a pest control composition comprising any one of the present compounds 1 to 88 and bixafen at a ratio of 0.1:1; a pest control composition comprising any one of the present compounds 1 to 88 and bixafen at a ratio of 1:1; a pest control composition comprising any one of the present compounds 1 to 88 and bixafen at a ratio of 10:1; a pest control composition comprising any one of the present compounds 1 to 88 and isopyrazam at a ratio of 0.1:1; a pest control composition comprising any one of the present compounds 1 to 88 and isopyrazam at a ratio of 1:1; a pest control composition comprising any one of the present compounds 1 to 88 and isopyrazam at a ratio of 10:1; a pest control composition comprising any one of the present compounds 1 to 88 and fluopyram at a ratio of 0.1:1; a pest control composition comprising any one of the present compounds 1 to 88 and fluopyram at a ratio of 1:1; a pest control composition comprising any one of the present compounds 1 to 88 and fluopyram at a ratio of 10:1; a pest control composition comprising any one of the present compounds 1 to 88 and penthiopyrad at a ratio of 0.1:1; a pest control composition comprising any one of the present compounds 1 to 88 and penthiopyrad at a ratio of 1:1; a pest control composition comprising any one of the present compounds 1 to 88 and penthiopyrad at a ratio of 10:1; a pest control composition comprising any one of the present compounds 1 to 88 and benzovindiflupyr at a ratio of 0.1:1; a compounds 1 to 88 and benzovindiflupyr at a ratio of 1:1; a pest control composition comprising any one of the present compounds 1 to 88 and benzovindiflupyr at a ratio of 10:1; a pest control composition comprising any one of the present compounds 1 to 88 and fluxapyroxad at a ratio of 0.1:1; a pest control composition comprising any one of the present compounds 1 to 88 and fluxapyroxad at a ratio of 1:1; a pest control composition comprising any one of the present compounds 1 to 88 and fluxapyroxad at a ratio of 10:1; a pest control composition comprising any one of the present compounds 1 to 88 and boscalid at a ratio of 0.1:1;
a pest control composition comprising any one of the present compounds 1 to 88 and boscalid at a ratio of 1:1; a pest control composition comprising any one of the present compounds 1 to 88 and boscalid at a ratio of 10:1; a pest control composition comprising any one of the present compounds 1 to 88 and sedaxane at a ratio of 0.1:1; a pest control composition comprising any one of the present compounds 1 to 88 and sedaxane at a ratio of 1:1; a pest control composition comprising any one of the present compounds 1 to 88 and sedaxane at a ratio of 10:1; a pest control composition comprising any one of the present compounds 1 to 88 and penflufen at a ratio of 0.1:1; a pest control composition comprising any one of the present compounds 1 to 88 and penflufen at a ratio of 1:1; a pest control composition comprising any one of the present compounds 1 to 88 and penflufen at a ratio of 10:1; a pest control composition comprising any one of the present compounds 1 to 88 and carboxin at a ratio of 0.1:1; a pest control composition comprising any one of the present compounds 1 to 88 and carboxin at a ratio of 1:1; a pest control composition comprising any one of the present compounds 1 to 88 and carboxin at a ratio of 10:1; a pest control composition comprising any one of the present compounds 1 to 88 and mepronil at a ratio of 0.1:1; a pest control composition comprising any one of the present compounds 1 to 88 and mepronil at a ratio of 1:1; a pest control composition comprising any one of the present compounds 1 to 88 and mepronil at a ratio of 10:1; a pest control composition comprising any one of the present compounds 1 to 88 and flutolanil at a ratio of 0.1:1; a pest control composition comprising any one of the present compounds 1 to 88 and flutolanil at a ratio of 1:1; a pest control composition comprising any one of the present compounds 1 to 88 and flutolanil at a ratio of 10:1; a pest control composition comprising any one of the present compounds 1 to 88 and thifluzamide at a ratio of 0.1:1; a pest control composition comprising any one of the present compounds 1 to 88 and thifluzamide at a ratio of 1:1; a pest control composition comprising any one of the present compounds 1 to 88 and thifluzamide at a ratio of 10:1;
a pest control composition comprising any one of the present compounds 1 to 88 and furametpyr at a ratio of 0.1:1; a pest control composition comprising any one of the present compounds 1 to 88 and furametpyr at a ratio of 1:1; a pest control composition comprising any one of the present compounds 1 to 88 and furametpyr at a ratio of 10:1; a pest control composition comprising any one of the present compounds 1 to 88 and isofetamid at a ratio of 0.1:1; a pest control composition comprising any one of the present compounds 1 to 88 and isofetamid at a ratio of 1:1; a pest control composition comprising any one of the present compounds 1 to 88 and isofetamid at a ratio of 10:1; a pest control composition comprising any one of the present compounds 1 to 88 and N-[2-(3,4-difluorophenyl)phenyl]-3-trifluoromethylpyrazine-2-carboxylic acid amide at a ratio of 0.1:1; a pest control composition comprising any one of the present compounds 1 to 88 and N-[2-(3,4-difluorophenyl)phenyl]-3-trifluoromethylpyrazine-2-carboxylic acid amide at a ratio of 1:1; a pest control composition comprising any one of the present compounds 1 to 88 and N-[2-(3,4-difluorophenyl)phenyl]-3-trifluoromethylpyrazine-2-carboxylic acid amide at a ratio of 10:1; a pest control composition comprising any one of the present compounds 1 to 88 and (R)-(−)-N-(1,1,3-trimethylindan-4-yl)-1-methyl-3-difluoromethylpyrazole-4-carboxylic acid amide at a ratio of 0.1:1; a pest control composition comprising any one of the present compounds 1 to 88 and (R)-(−)-N-(1,1,3-trimethylindan-4-yl)-1-methyl-3-difluoromethylpyrazole-4-carboxylic acid amide at a ratio of 1:1; a pest control composition comprising any one of the present compounds 1 to 88 and (R)-(−)-N-(1,1,3-trimethylindan-4-yl)-1-methyl-3-difluoromethylpyrazole-4-carboxylic acid amide at a ratio of 10:1; a pest control composition comprising any one of the present compounds 1 to 88 and 3-chloro-4-(2,6-difluorophenyl)-6-methyl-5-phenylpyridazine at a ratio of 0.1:1; a pest control composition comprising any one of the present compounds 1 to 88 and 3-chloro-4-(2,6-difluorophenyl)-6-methyl-5-phenylpyridazine at a ratio of 1:1; a pest control composition comprising any one of the present compounds 1 to 88 and 3-chloro-4-(2,6-difluorophenyl)-6-methyl-5-phenylpyridazine at a ratio of 10:1; a pest control composition comprising any one of the present compounds 1 to 88 and 3-cyano-4-(2,6-difluorophenyl)-6-methyl-5-phenylpyridazine at a ratio of 0.1:1; a pest control composition comprising any one of the present compounds 1 to 88 and 3-cyano-4-(2,6-difluorophenyl)-6-methyl-5-phenylpyridazine at a ratio of 1:1; a pest control composition comprising any one of the present compounds 1 to 88 and 3-cyano-4-(2,6-difluorophenyl)-6-methyl-5-phenylpyridazine at a ratio of 10:1; a pest control composition comprising any one of the present compounds 1 to 88 and fenpropimorph at a ratio of 0.1:1; a pest control composition comprising any one of the present compounds 1 to 88 and fenpropimorph at a ratio of 1:1; a pest control composition comprising any one of the present compounds 1 to 88 and fenpropimorph at a ratio of 10:1; a pest control composition comprising any one of the present compounds 1 to 88 and fenpropidin at a ratio of 0.1:1; a pest control composition comprising any one of the present compounds 1 to 88 and fenpropidin at a ratio of 1:1; a pest control composition comprising any one of the present compounds 1 to 88 and fenpropidin at a ratio of 10:1; a pest control composition comprising any one of the present compounds 1 to 88 and spiroxamine at a ratio of 0.1:1; a pest control composition comprising any one of the present compounds 1 to 88 and spiroxamine at a ratio of 1:1; a pest control composition comprising any one of the present compounds 1 to 88 and spiroxamine at a ratio of 10:1; a pest control composition comprising any one of the present compounds 1 to 88 and tridemorph at a ratio of 0.1:1; a pest control composition comprising any one of the present compounds 1 to 88 and tridemorph at a ratio of 1:1; a pest control composition comprising any one of the present compounds 1 to 88 and tridemorph at a ratio of 10:1; a pest control composition comprising any one of the present compounds 1 to 88 and cyprodinil at a ratio of 0.1:1; a pest control composition comprising any one of the present compounds 1 to 88 and cyprodinil at a ratio of 1:1; a pest control composition comprising any one of the present compounds 1 to 88 and cyprodinil at a ratio of 10:1; a pest control composition comprising any one of the present compounds 1 to 88 and pyrimethanil at a ratio of 0.1:1; a pest control composition comprising any one of the present compounds 1 to 88 and pyrimethanil at a ratio of 1:1; a pest control composition comprising any one of the present compounds 1 to 88 and pyrimethanil at a ratio of 10:1; a pest control composition comprising any one of the present compounds 1 to 88 and mepanipyrim at a ratio of 0.1:1; a pest control composition comprising any one of the present compounds 1 to 88 and mepanipyrim at a ratio of 1:1; a pest control composition comprising any one of the present compounds 1 to 88 and mepanipyrim at a ratio of 10:1; a pest control composition comprising any one of the present compounds 1 to 88 and fenpiclonil at a ratio of 0.1:1; a pest control composition comprising any one of the present compounds 1 to 88 and fenpiclonil at a ratio of 1:1; a pest control composition comprising any one of the present compounds 1 to 88 and fenpiclonil at a ratio of 10:1; a pest control composition comprising any one of the present compounds 1 to 88 and fludioxonil at a ratio of 0.1:1; a pest control composition comprising any one of the present compounds 1 to 88 and fludioxonil at a ratio of 1:1; a pest control composition comprising any one of the present compounds 1 to 88 and fludioxonil at a ratio of 10:1; a pest control composition comprising any one of the present compounds 1 to 88 and procymidone at a ratio of 0.1:1; a pest control composition comprising any one of the present compounds 1 to 88 and procymidone at a ratio of 1:1; a pest control composition comprising any one of the present compounds 1 to 88 and procymidone at a ratio of 10:1; a pest control composition comprising any one of the present compounds 1 to 88 and iprodione at a ratio of 0.1:1; a pest control composition comprising any one of the present compounds 1 to 88 and iprodione at a ratio of 1:1; a pest control composition comprising any one of the present compounds 1 to 88 and iprodione at a ratio of 10:1; a pest control composition comprising any one of the present compounds 1 to 88 and vinclozolin at a ratio of 0.1:1; a pest control composition comprising any one of the present compounds 1 to 88 and vinclozolin at a ratio of 1:1; a pest control composition comprising any one of the present compounds 1 to 88 and vinclozolin at a ratio of 10:1; a pest control composition comprising any one of the present compounds 1 to 88 and benomyl at a ratio of 0.1:1; a pest control composition comprising any one of the present compounds 1 to 88 and benomyl at a ratio of 1:1; a pest control composition comprising any one of the present compounds 1 to 88 and benomyl at a ratio of 10:1; a pest control composition comprising any one of the present compounds 1 to 88 and thiophanate-methyl at a ratio of 0.1:1; a pest control composition comprising any one of the present compounds 1 to 88 and thiophanate-methyl at a ratio of 1:1; a pest control composition comprising any one of the present compounds 1 to 88 and thiophanate-methyl at a ratio of 10:1; a pest control composition comprising any one of the present compounds 1 to 88 and carbendazim at a ratio of 0.1:1; a pest control composition comprising any one of the present compounds 1 to 88 and carbendazim at a ratio of 1:1; a pest control composition comprising any one of the present compounds 1 to 88 and carbendazim at a ratio of 10:1; a pest control composition comprising any one of the present compounds 1 to 88 and diethofencarb at a ratio of 0.1:1; a pest control composition comprising any one of the present compounds 1 to 88 and diethofencarb at a ratio of 1:1; a pest control composition comprising any one of the present compounds 1 to 88 and diethofencarb at a ratio of 10:1; a pest control composition comprising any one of the present compounds 1 to 88 and metalaxyl at a ratio of 0.1:1; a pest control composition comprising any one of the present compounds 1 to 88 and metalaxyl at a ratio of 1:1; a pest control composition comprising any one of the present compounds 1 to 88 and metalaxyl at a ratio of 10:1;

a pest control composition comprising any one of the present compounds 1 to 88 and metalaxyl-M (mefenoxam) at a ratio of 0.1:1; a pest control composition comprising any one of the present compounds 1 to 88 and metalaxyl-M (mefenoxam) at a ratio of 1:1; a pest control composition comprising any one of the present compounds 1 to 88 and metalaxyl-M (mefenoxam) at a ratio of 10:1; a pest control composition comprising any one of the present compounds 1 to 88 and benalaxyl at a ratio of 0.1:1; a pest control composition comprising any one of the present compounds 1 to 88 and benalaxyl at a ratio of 1:1; a pest control composition comprising any one of the present compounds 1 to 88 and benalaxyl at a ratio of 10:1; a pest control composition comprising any one of the present compounds 1 to 88 and benalaxyl-M (kiralaxyl) at a ratio of 0.1:1; a pest control composition comprising any one of the present compounds 1 to 88 and benalaxyl-M (kiralaxyl) at a ratio of 1:1; a pest control composition comprising any one of the present compounds 1 to 88 and benalaxyl-M (kiralaxyl) at a ratio of 10:1; a pest control composition comprising any one of the present compounds 1 to 88 and dimethomorph at a ratio of 0.1:1; a pest control composition comprising any one of the present compounds 1 to 88 and dimethomorph at a ratio of 1:1; a pest control composition comprising any one of the present compounds 1 to 88 and dimethomorph at a ratio of 10:1; a pest control composition comprising any one of the present compounds 1 to 88 and iprovalicarb at a ratio of 0.1:1; a pest compounds 1 to 88 and iprovalicarb at a ratio of 1:1; a pest control composition comprising any one of the present compounds 1 to 88 and iprovalicarb at a ratio of 10:1; a pest control composition comprising any one of the present compounds 1 to 88 and benthivalicarb-isopropyl at a ratio of 0.1:1; a pest control composition comprising any one of the present compounds 1 to 88 and benthivalicarb-isopropyl at a ratio of 1:1; a pest control composition comprising any one of the present compounds 1 to 88 and benthivalicarb-isopropyl at a ratio of 10:1; a pest control composition comprising any one of the present compounds 1 to 88 and mandipropamid at a ratio of 0.1:1;

a pest control composition comprising any one of the present compounds 1 to 88 and mandipropamid at a ratio of 1:1; a pest control composition comprising any one of the present compounds 1 to 88 and mandipropamid at a ratio of 10:1; a pest control composition comprising any one of the present compounds 1 to 88 and valifenalate at a ratio of 0.1:1; a pest control composition comprising any one of the present compounds 1 to 88 and valifenalate at a ratio of 1:1; a pest control composition comprising any one of the present compounds 1 to 88 and valifenalate at a ratio of 10:1; a pest control composition comprising any one of the present compounds 1 to 88 and cymoxanil at a ratio of 0.1:1; a pest control composition comprising any one of the present compounds 1 to 88 and cymoxanil at a ratio of 1:1; a pest control composition comprising any one of the present compounds 1 to 88 and cymoxanil at a ratio of 10:1; a pest compounds 1 to 88 and fluopicolide at a ratio of 0.1:1; a pest control composition comprising any one of the present compounds 1 to 88 and fluopicolide at a ratio of 1:1; a pest control composition comprising any one of the present compounds 1 to 88 and fluopicolide at a ratio of 10:1; a pest control composition comprising any one of the present compounds 1 to 88 and cyazofamid at a ratio of 0.1:1; a pest control composition comprising any one of the present compounds 1 to 88 and cyazofamid at a ratio of 1:1; a pest control composition comprising any one of the present compounds 1 to 88 and cyazofamid at a ratio of 10:1; a pest control composition comprising any one of the present compounds 1 to 88 and amisulbrom at a ratio of 0.1:1; a pest control composition comprising any one of the present compounds 1 to 88 and amisulbrom at a ratio of 1:1; a pest control composition comprising any one of the present compounds 1 to 88 and amisulbrom at a ratio of 10:1; a pest control composition comprising any one of the present compounds 1 to 88 and ametoctradin at a ratio of 0.1:1; a pest control composition comprising any one of the present compounds 1 to 88 and ametoctradin at a ratio of 1:1;

a pest control composition comprising any one of the present compounds 1 to 88 and ametoctradin at a ratio of 10:1; a pest control composition comprising any one of the present compounds 1 to 88 and ethaboxam at a ratio of 0.1:1; a pest control composition comprising any one of the present compounds 1 to 88 and ethaboxam at a ratio of 1:1; a pest control composition comprising any one of the present compounds 1 to 88 and ethaboxam at a ratio of 10:1; a pest control composition comprising any one of the present compounds 1 to 88 and zoxamide at a ratio of 0.1:1; a pest control composition comprising any one of the present compounds 1 to 88 and zoxamide at a ratio of 1:1; a pest control composition comprising any one of the present compounds 1 to 88 and zoxamide at a ratio of 10:1; a pest control composition comprising any one of the present compounds 1 to 88 and oxathiapiprolin at a ratio of 1:1; a pest control composition comprising any one of the present compounds 1 to 88 and oxathiapiprolin at a ratio of 10:1; a pest control composition comprising any one of the present compounds 1 to 88 and oxathiapiprolin at a ratio of 50:1; a pest control composition comprising any one of the present compounds 1 to 88 and picarbutrazox at a ratio of 0.1:1; a pest control composition comprising any one of the present compounds 1 to 88 and picarbutrazox at a ratio of 1:1; a pest control composition comprising any one of the present compounds 1 to 88 and picarbutrazox at a ratio of 10:1; a pest control composition comprising any one of the present compounds 1 to 88 and fosetyl aluminum at a ratio of 0.01:1; a pest control composition comprising any one of the present compounds 1 to 88 and fosetyl aluminum at a ratio of 0.1:1; a pest control composition comprising any one of the present compounds 1 to 88 and fosetyl aluminum at a ratio of 1:1; a pest control composition comprising any one of the present compounds 1 to 88 and a potassium salt of phosphorous acid at a ratio of 0.01:1; a pest control composition comprising any one of the present compounds 1 to 88 and a potassium salt of phosphorous acid at a ratio of 0.1:1; a pest control composition comprising any one of the present compounds 1 to 88 and a potassium salt of phosphorous acid at a ratio of 1:1; a pest control composition comprising any one of the present compounds 1 to 88 and propamocarb hydrochloride at a ratio of 0.01:1;

a pest control composition comprising any one of the present compounds 1 to 88 and propamocarb hydrochloride at a ratio of 0.1:1; a pest control composition comprising any one of the present compounds 1 to 88 and propamocarb hydrochloride at a ratio of 1:1; a pest control composition comprising any one of the present compounds 1 to 88 and fenpyrazamine at a ratio of 0.1:1; a pest control composition comprising any one of the present compounds 1 to 88 and fenpyrazamine at a ratio of 1:1; a pest control composition comprising any one of the present compounds 1 to 88 and fenpyrazamine at a ratio of 10:1; a pest control composition comprising any one of the present compounds 1 to 88 and fenhexanid at a ratio of 0.1:1; a pest control composition comprising any one of the present compounds 1 to 88 and fenhexanid at a ratio of 1:1; a pest control composition comprising any one of the present compounds 1 to 88 and fenhexanid at a ratio of 10:1; a pest control composition comprising any one of the present compounds 1 to 88 and fluazinam at a ratio of 0.1:1; a pest control composition comprising any one of the present compounds 1 to 88 and fluazinam at a ratio of 1:1; a pest control composition comprising any one of the present compounds 1 to 88 and fluazinam at a ratio of 10:1; a pest control composition comprising any one of the present compounds 1 to 88 and flusulfamide at a ratio of 0.1:1; a pest compounds 1 to 88 and flusulfamide at a ratio of 1:1; a pest control composition comprising any one of the present compounds 1 to 88 and flusulfamide at a ratio of 10:1; a pest control composition comprising any one of the present compounds 1 to 88 and ferimzone at a ratio of 0.1:1; a pest control composition comprising any one of the present compounds 1 to 88 and ferimzone at a ratio of 1:1; a pest control composition comprising any one of the present compounds 1 to 88 and ferimzone at a ratio of 10:1; a pest control composition comprising any one of the present compounds 1 to 88 and quinoxyfen at a ratio of 0.1:1; a pest control composition comprising any one of the present compounds 1 to 88 and quinoxyfen at a ratio of 1:1;
a pest control composition comprising any one of the present compounds 1 to 88 and quinoxyfen at a ratio of 10:1; a pest control composition comprising any one of the present compounds 1 to 88 and metrafenone at a ratio of 0.1:1; a pest control composition comprising any one of the present compounds 1 to 88 and metrafenone at a ratio of 1:1; a pest control composition comprising any one of the present compounds 1 to 88 and metrafenone at a ratio of 10:1; a pest control composition comprising any one of the present compounds 1 to 88 and pyriofenone at a ratio of 0.1:1; a pest control composition comprising any one of the present compounds 1 to 88 and pyriofenone at a ratio of 1:1; a pest control composition comprising any one of the present compounds 1 to 88 and pyriofenone at a ratio of 10:1; a pest control composition comprising any one of the present compounds 1 to 88 and proquinazid at a ratio of 0.1:1; a pest control composition comprising any one of the present compounds 1 to 88 and proquinazid at a ratio of 1:1; a pest control composition comprising any one of the present compounds 1 to 88 and proquinazid at a ratio of 10:1; a pest control composition comprising any one of the present compounds 1 to 88 and cyflufenamid at a ratio of 0.1:1; a pest control composition comprising any one of the present compounds 1 to 88 and cyflufenamid at a ratio of 1:1; a pest control composition comprising any one of the present compounds 1 to 88 and cyflufenamid at a ratio of 10:1; a pest control composition comprising any one of the present compounds 1 to 88 and tolclofos-methyl at a ratio of 0.01:1; a pest control composition comprising any one of the present compounds 1 to 88 and tolclofos-methyl at a ratio of 0.1:1; a pest control composition comprising any one of the present compounds 1 to 88 and tolclofos-methyl at a ratio of 1:1; a pest control composition comprising any one of the present compounds 1 to 88 and laminarin at a ratio of 0.1:1; a pest control composition comprising any one of the present compounds 1 to 88 and laminarin at a ratio of 1:1; a pest control composition comprising any one of the present compounds 1 to 88 and laminarin at a ratio of 10:1; a pest control composition comprising any one of the present compounds 1 to 88 and pencycuron at a ratio of 0.1:1;
a pest control composition comprising any one of the present compounds 1 to 88 and pencycuron at a ratio of 1:1; a pest control composition comprising any one of the present compounds 1 to 88 and pencycuron at a ratio of 10:1; a pest compounds 1 to 88 and carpropamid at a ratio of 0.1:1; a pest control composition comprising any one of the present compounds 1 to 88 and carpropamid at a ratio of 1:1; a pest control composition comprising any one of the present compounds 1 to 88 and carpropamid at a ratio of 10:1; a pest control composition comprising any one of the present compounds 1 to 88 and diclocymet at a ratio of 0.1:1; a pest control composition comprising any one of the present compounds 1 to 88 and diclocymet at a ratio of 1:1; a pest control composition comprising any one of the present compounds 1 to 88 and diclocymet at a ratio of 10:1; a pest control composition comprising any one of the present compounds 1 to 88 and tricyclazole at a ratio of 0.1:1; a pest control composition comprising any one of the present compounds 1 to 88 and tricyclazole at a ratio of 1:1; a pest control composition comprising any one of the present compounds 1 to 88 and tricyclazole at a ratio of 10:1; a pest control composition comprising any one of the present compounds 1 to 88 and pyroquilon at a ratio of 0.1:1; a pest control composition comprising any one of the present compounds 1 to 88 and pyroquilon at a ratio of 1:1; a pest control composition comprising any one of the present compounds 1 to 88 and pyroquilon at a ratio of 10:1; a pest control composition comprising any one of the present compounds 1 to 88 and fthalide at a ratio of 0.1:1; a pest control composition comprising any one of the present compounds 1 to 88 and fthalide at a ratio of 1:1; a pest control composition comprising any one of the present compounds 1 to 88 and fthalide at a ratio of 10:1; a pest compounds 1 to 88 and probenazole at a ratio of 0.1:1; a pest control composition comprising any one of the present compounds 1 to 88 and probenazole at a ratio of 1:1; a pest control composition comprising any one of the present compounds 1 to 88 and probenazole at a ratio of 10:1; a pest control composition comprising any one of the present compounds 1 to 88 and isotianil at a ratio of 0.1:1;
a pest control composition comprising any one of the present compounds 1 to 88 and isotianil at a ratio of 1:1; a pest control composition comprising any one of the present compounds 1 to 88 and isotianil at a ratio of 10:1; a pest control composition comprising any one of the present compounds 1 to 88 and tiadinil at a ratio of 0.1:1; a pest control composition comprising any one of the present compounds 1 to 88 and tiadinil at a ratio of 1:1; a pest control composition comprising any one of the present compounds 1 to 88 and tiadinil at a ratio of 10:1; a pest control composition comprising any one of the present compounds 1 to 88 and tebufloquin at a ratio of 0.1:1; a pest control composition comprising any one of the present compounds 1 to 88 and tebufloquin at a ratio of 1:1; a pest control composition comprising any one of the present compounds 1 to 88 and tebufloquin at a ratio of 10:1; a pest control composition comprising any one of the present compounds 1 to 88 and tolprocarb at a ratio of 0.1:1; a pest control composition comprising any one of the present compounds 1 to 88 and tolprocarb at a ratio of 1:1; a pest control composition comprising any one of the present compounds 1 to 88 and tolprocarb at a ratio of 10:1; a pest control composition comprising any one of the present compounds 1 to 88 and diclomezine at a ratio of 0.1:1; a pest control composition comprising any one of the present compounds 1 to 88 and diclomezine at a ratio of 1:1; a pest control composition comprising any one of the present compounds 1 to 88 and diclomezine at a ratio of 10:1; a pest control composition comprising any one of the present compounds 1 to 88 and validamycin at a ratio of 0.1:1; a pest control composition comprising any one of the present compounds 1 to 88 and validamycin at a ratio of 1:1; a pest control composition comprising any one of the present compounds 1 to 88 and validamycin at a ratio of 10:1; a pest control composition comprising any one of the present compounds 1 to 88 and isoprothiolane at a ratio of 0.1:1; a pest control composition comprising any one of the present compounds 1 to 88 and isoprothiolane at a ratio of 1:1; a pest control composition comprising any one of the present compounds 1 to 88 and isoprothiolane at a ratio of 10:1; a pest control composition comprising any one of the present compounds 1 to 88 and hydroxyisoxazole at a ratio of 0.1:1; a pest control composition comprising any one of the present compounds 1 to 88 and hydroxyisoxazole at a ratio of 1:1; a pest control composition comprising any one of the present compounds 1 to 88 and hydroxyisoxazole at a ratio of 10:1; a pest control composition comprising any one of the present compounds 1 to 88 and kasugamycin at a ratio of 0.1:1; a pest control composition comprising any one of the present compounds 1 to 88 and kasugamycin at a ratio of 1:1; a pest compounds 1 to 88 and kasugamycin at a ratio of 10:1; a pest control composition comprising any one of the present compounds 1 to 88 and streptomycin at a ratio of 0.1:1; a pest control composition comprising any one of the present compounds 1 to 88 and streptomycin at a ratio of 1:1; a pest control composition comprising any one of the present compounds 1 to 88 and streptomycin at a ratio of 10:1; a pest control composition comprising any one of the present compounds 1 to 88 and oxolinic acid at a ratio of 0.1:1; a pest control composition comprising any one of the present compounds 1 to 88 and oxolinic acid at a ratio of 1:1; a pest control composition comprising any one of the present compounds 1 to 88 and oxolinic acid at a ratio of 10:1; a pest control composition comprising any one of the present compounds 1 to 88 and tetracycline at a ratio of 0.1:1; a pest control composition comprising any one of the present compounds 1 to 88 and tetracycline at a ratio of 1:1; a pest control composition comprising any one of the present compounds 1 to 88 and tetracycline at a ratio of 10:1; a pest control composition comprising any one of the present compounds 1 to 88 and oxytetracycline at a ratio of 0.1:1; a pest control composition comprising any one of the present compounds 1 to 88 and oxytetracycline at a ratio of 1:1; a pest control composition comprising any one of the present compounds 1 to 88 and oxytetracycline at a ratio of 10:1; a pest control composition comprising any one of the present compounds 1 to 88 and silthiofam at a ratio of 0.01:1; a pest control composition comprising any one of the present compounds 1 to 88 and silthiofam at a ratio of 0.1:1; a pest control composition comprising any one of the present compounds 1 to 88 and silthiofam at a ratio of 1:1; a pest control composition comprising any one of the present compounds 1 to 88 and chlorothalonil at a ratio of 0.01:1; a pest control composition comprising any one of the present compounds 1 to 88 and chlorothalonil at a ratio of 0.1:1; a pest control composition comprising any one of the present compounds 1 to 88 and chlorothalonil at a ratio of 1:1; a pest control composition comprising any one of the present compounds 1 to 88 and mancozeb at a ratio of 0.01:1; a pest control composition comprising any one of the present compounds 1 to 88 and mancozeb at a ratio of 0.1:1; a pest control composition comprising any one of the present compounds 1 to 88 and mancozeb at a ratio of 1:1; a pest control composition comprising any one of the present compounds 1 to 88 and folpet at a ratio of 0.01:1; a pest control composition comprising any one of the present compounds 1 to 88 and folpet at a ratio of 0.1:1; a pest control composition comprising any one of the present compounds 1 to 88 and folpet at a ratio of 1:1; a pest control composition comprising any one of the present compounds 1 to 88 and captan at a ratio of 0.01:1; a pest control composition comprising any one of the present compounds 1 to 88 and captan at a ratio of 0.1:1; a pest control composition comprising any one of the present compounds 1 to 88 and captan at a ratio of 1:1; a pest control composition comprising any one of the present compounds 1 to 88 and thiuram at a ratio of 0.01:1; a pest control composition comprising any one of the present compounds 1 to 88 and thiuram at a ratio of 0.1:1; a pest compounds 1 to 88 and thiuram at a ratio of 1:1; a pest control composition comprising any one of the present compounds 1 to 88 and metiram at a ratio of 0.01:1; a pest control composition comprising any one of the present compounds 1 to 88 and metiram at a ratio of 0.1:1; a pest control composition comprising any one of the present compounds 1 to 88 and metiram at a ratio of 1:1; a pest control composition comprising any one of the present compounds 1 to 88 and maneb at a ratio of 0.01:1;
a pest control composition comprising any one of the present compounds 1 to 88 and maneb at a ratio of 0.1:1; a pest control composition comprising any one of the present compounds 1 to 88 and maneb at a ratio of 1:1; a pest control composition comprising any one of the present compounds 1 to 88 and iminoctadine acetate at a ratio of 0.1:1; a pest control composition comprising any one of the present compounds 1 to 88 and iminoctadine acetate at a ratio of 1:1; a pest control composition comprising any one of the present compounds 1 to 88 and iminoctadine acetate at a ratio of 10:1; a pest control composition comprising any one of the present compounds 1 to 88 and sulfur at a ratio of 0.01:1; a pest control composition comprising any one of the present compounds 1 to 88 and sulfur at a ratio of 0.1:1; a pest control composition comprising any one of the present compounds 1 to 88 and sulfur at a ratio of 1:1; a pest control composition comprising any one of the present compounds 1 to 88 and copper oxychloride at a ratio of 0.01:1; a pest control composition comprising any one of the present compounds 1 to 88 and copper oxychloride at a ratio of 0.1:1; a pest control composition comprising any one of the present compounds 1 to 88 and copper oxychloride at a ratio of 1:1; a pest control composition comprising any one of the present compounds 1 to 88 and copper hydroxide at a ratio of 0.01:1; a pest control composition comprising any one of the present compounds 1 to 88 and copper hydroxide at a ratio of 0.1:1; a pest control composition comprising any one of the present compounds 1 to 88 and copper hydroxide at a ratio of 1:1; a pest control composition comprising any one of the present compounds 1 to 88 and copper hydroxide sulfate at a ratio of 0.01:1; a pest control composition comprising any one of the present compounds 1 to 88 and copper hydroxide sulfate at a ratio of 0.1:1; a pest control composition comprising any one of the present compounds 1 to 88 and copper hydroxide sulfate at a ratio of 1:1; a pest control composition comprising any one of the present compounds 1 to 88 and Bordeaux mixture at a ratio of 0.01:1; a pest control composition comprising any one of the present compounds 1 to 88 and Bordeaux mixture at a ratio of 0.1:1; a pest control composition comprising any one of the present compounds 1 to 88 and Bordeaux mixture at a ratio of 1:1;
a pest control composition comprising any one of the present compounds 1 to 88 and (3S,6S,7R,8R)-3-{[(3-hydroxy-4-methoxy-2-pyridinyl)carbonyl]amino}-6-methyl-4,9-dioxo-8-(phenylmethyl)-1,5-dioxonan-7-yl 2-methylpropanoate at a ratio of 0.1:1; a pest control composition comprising any one of the present compounds 1 to 88 and (3S,6S,7R,8R)-3-{[(3-hydroxy-4-methoxy-2-pyridinyl)carbonyl]amino}-6-methyl-4,9-dioxo-8-(phenylmethyl)-1,5-dioxonan-7-yl 2-methylpropanoate at a ratio of 1:1; a pest control composition comprising any one of the present compounds 1 to 88 and (3S,6S,7R,8R)-3-{[(3-hydroxy-4-methoxy-2-pyridinyl)carbonyl]amino}-6-methyl-4,9-dioxo-8-(phenylmethyl)-1,5-dioxonan-7-yl 2-methylpropanoate at a ratio of 10:1; a pest control composition comprising any one of the present compounds 1 to 88 and {[4-methoxy-2-({[(3S,7R,8R,9S)-9-methyl-8-(2-methyl-1-oxopropoxy)-2,6-dioxo-7-(phenylmethyl)-1,5-dioxonan-3-yl]amino}carbonyl)-3-pyridinyl]oxy}methyl 2-methylpropanoate at a ratio of 0.1:1; a pest control composition comprising any one of the present compounds 1 to 88 and carboxamide; {[4-methoxy-2-({[(3S,7R,8R,9S)-9-methyl-8-(2-methyl-1-oxopropoxy)-2,6-dioxo-7-(phenylmethyl)-1,5-dioxonan-3-yl]amino}carbonyl)-3-pyridinyl]oxy}methyl 2-methylpropanoate at a ratio of 1:1; a pest control composition comprising any one of the present compounds 1 to 88 and carboxamide; {[4-methoxy-2-({[(3S,7R,8R,9S)-9-methyl-8-(2-methyl-1-oxopropoxy)-2,6-dioxo-7-(phenylmethyl)-1,5-dioxonan-3-yl]amino}carbonyl)-3-pyridinyl]oxy}methyl 2-methylpropanoate at a ratio of 10:1;
a pest control composition comprising any one of the present compounds 1 to 88 and N'-[4-({3-[(4-chlorophenyl)methyl]-1,2,4-thiadiazol-5-yl}oxy)-2,5-dimethylphenyl]-N-ethyl-N-methylmethaneimidamide at a ratio of 0.1:1; a pest control composition comprising any one of the present compounds 1 to 88 and N'-[4-({3-[(4-chlorophenyl)methyl]-1,2,4-thiadiazol-5-yl}oxy)-2,5-dimethylphenyl]-N-ethyl-N-methylmethaneimidamide at a ratio of 1:1; a pest control composition comprising any one of the present compounds 1 to 88 and N'-[4-({3-[(4-chlorophenyl)methyl]-1,2,4-thiadiazol-5-yl}oxy)-2,5-dimethylphenyl]-N-ethyl-N-methylmethaneimidamide at a ratio of 10:1; a pest control composition comprising any one of the present compounds 1 to 88 and 2,6-dimethyl-1H,5H-[1,4]dithiino[2,3-c:5,6-c']dipyrrole-1,3,5,7(2H,6H)-tetrone at a ratio of 0.01:1; a pest control composition comprising any one of the present compounds 1 to 88 and 2,6-dimethyl-1H,5H-[1,4]dithiino[2,3-c:5,6-c']dipyrrole-1,3,5,7(2H,6H)-tetrone at a ratio of 0.1:1; a pest control composition comprising any one of the present compounds 1 to 88 and 2,6-dimethyl-1H,5H-[1,4]dithiino[2,3-c:5,6-c']dipyrrole-1,3,5,7(2H,6H)-tetrone at a ratio of 1:1; a pest control composition comprising any one of the present compounds 1 to 88 and 3-(4,4-difluoro-3,3-dimethyl-3,4-dihydroisoquinolin-1-yl)quino line at a ratio of 0.1:1; a pest control composition comprising any one of the present compounds 1 to 88 and 3-(4,4-difluoro-3,3-dimethyl-3,4-dihydroisoquinolin-1-yl)quinoline at a ratio of 1:1;
a pest control composition comprising any one of the present compounds 1 to 88 and 3-(4,4-difluoro-3,3-dimethyl-3,4-dihydroisoquinolin-1-yl)quinoline at a ratio of 10:1; a pest control composition comprising any one of the present compounds 1 to 88 and 3-(5-fluoro-3,3,4,4-tetramethyl-3,4-dihydroisoquinolin-1-yl)quinoline at a ratio of 0.1:1;
a pest control composition comprising any one of the present compounds 1 to 88 and 3-(5-fluoro-3,3,4,4-tetramethyl-3,4-dihydroisoquinolin-1-yl)quinoline at a ratio of 1:1; a pest control composition comprising any one of the present compounds 1 to 88 and 3-(5-fluoro-3,3,4,4-tetramethyl-3,4-dihydroisoquinolin-1-yl)quinoline at a ratio of 10:1; a pest control composition comprising any one of the present compounds 1 to 88 and 3-(4,4,5-trifluoro-3,3-dimethyl-3,4-dihydroisoquinolin-1-yl)quinoline at a ratio of 0.1:1; a pest control composition comprising any one of the present compounds 1 to 88 and 3-(4,4,5-trifluoro-3,3-dimethyl-3,4-dihydroisoquinolin-1-yl)quinoline at a ratio of 1:1; a pest control composition comprising any one of the present compounds 1 to 88 and 3-(4,4,5-trifluoro-3,3-dimethyl-3,4-dihydroisoquinolin-1-yl)quinoline at a ratio of 10:1; a pest control composition comprising any one of the present compounds 1 to 88 and [3-(4-chloro-2-fluorophenyl)-5-(2,4-difluorophenyl)-1,2-oxazol-4-yl](pyridin-3-yl)methanol at a ratio of 0.1:1; a pest control composition comprising any one of the present compounds 1 to 88 and [3-(4-chloro-2-fluorophenyl)-5-(2,4-difluorophenyl)-1,2-oxazol-4-yl](pyridin-3-yl)methanol at a ratio of 1:1; a pest control composition comprising any one of the present compounds 1 to 88 and [3-(4-chloro-2-fluorophenyl)-5-(2,4-difluorophenyl)-1,2-oxazol-4-yl](pyridin-3-yl)methanol at a ratio of 10:1; a pest control composition comprising any one of the present compounds 1 to 88 and s-[3-(4-chloro-2-fluorophenyl)-5-(2,4-difluorophenyl)-1,2-oxazol-4-yl](pyridin-3-yl)methanol at a ratio of 0.1:1;
a pest control composition comprising any one of the present compounds 1 to 88 and (S)-[3-(4-chloro-2-fluorophenyl)-5-(2,4-difluorophenyl)-1,2-oxazol-4-yl](pyridin-3-yl)methanol at a ratio of 1:1; a pest control composition comprising any one of the present compounds 1 to 88 and (S)-[3-(4-chloro-2-fluorophenyl)-5-(2,4-difluorophenyl)-1,2-oxazol-4-yl](pyridin-3-yl)methanol at a ratio of 10:1; a pest control composition comprising any one of the present compounds 1 to 88 and (R)-[3-(4-chloro-2-fluorophenyl)-5-(2,4-difluorophenyl)-1,2-oxazol-4-yl](pyridin-3-yl)methanol at a ratio of 0.1:1; a pest control composition comprising any one of the present compounds 1 to 88 and (R)-[3-(4-chloro-2-fluorophenyl)-5-(2,4-difluorophenyl)-1,2-oxazol-4-yl](pyridin-3-yl)methanol at a ratio of 1:1; a pest control composition comprising any one of the present compounds 1 to 88 and (R)-[3-(4-chloro-2-fluorophenyl)-5-(2,4-difluorophenyl)-1,2-oxazol-4-yl](pyridin-3-yl)methanol at a ratio of 10:1; a pest control composition comprising any one of the present compounds 1 to 88 and 2-{[3-(2-chlorophenyl)-2-(2,4-difluorophenyl)oxiran-2-yl]methyl}-2,4-dihydro-3H-1,2,4-triazole-3-thione at a ratio of 0.1:1; a pest control composition comprising any one of the present compounds 1 to 88 and 2-{[3-(2-chlorophenyl)-2-(2,4-difluorophenyl)oxiran-2-yl]methyl}-2,4-dihydro-3H-1,2,4-triazole-3-thione at a ratio of 1:1; a pest control composition comprising any one of the present compounds 1 to 88 and 2-{[3-(2-chlorophenyl)-2-(2,4-difluorophenyl)oxiran-2-yl]methyl}-2,4-dihydro-3H-1,2,4-triazole-3-thione at a ratio of 10:1; a pest control composition comprising any one of the present compounds 1 to 88 and 2-{[rel-(2R,3S)-3-(2-chlorophenyl)-2-(2,4-difluorophenyl)oxiran-2-yl]methyl}-2,4-dihydro-3H-1,2,4-triazole-3-thione at a ratio of 0.1:1;
a pest control composition comprising any one of the present compounds 1 to 88 and 2-{[rel-(2R,3S)-3-(2-chlorophenyl)-2-(2,4-difluorophenyl)oxiran-2-yl]methyl}-2,4-dihydro-3H-1,2,4-triazole-3-thione at a ratio of 1:1; a pest control composition comprising any one of the present compounds 1 to 88 and 2-{[rel-(2R,3S)-3-(2-chlorophenyl)-2-(2,4-difluorophenyl)oxiran-2-yl]methyl}-2,4-dihydro-3H-1,2,4-triazole-3-thione at a ratio of 10:1; a pest control composition comprising any one of the present compounds 1 to 88 and 2-{[rel-(2R,3R)-3-(2-chlorophenyl)-2-(2,4-difluorophenyl)oxiran-2-yl]methyl}-2,4-dihydro-3H-1,2,4-triazole-3-thione at a ratio of 0.1:1; a pest control composition comprising any one of the present compounds 1 to 88 and 2-{[rel-(2R,3R)-3-(2-chlorophenyl)-2-(2,4-difluorophenyl)oxiran-2-yl]methyl}-2,4-dihydro-3H-1,2,4-triazole-3-thione at a ratio of 1:1; a pest control composition comprising any one of the present compounds 1 to 88 and 2-{[rel-(2R,3R)-3-(2-chlorophenyl)-2-(2,4-difluorophenyl)oxiran-2-yl]methyl}-2,4-dihydro-3H-1,2,4-triazole-3-thione at a ratio of 10:1; a pest control composition comprising any one of the present compounds 1 to 88 and 2-{[(2R,3S)-3-(2-chlorophenyl)-2-(2,4-difluorophenyl)oxiran-2-yl]methyl}-2,4-dihydro-3H-1,2,4-triazole-3-thione at a ratio of 0.1:1; a pest control composition comprising any one of the present compounds 1 to 88 and 2-{[(2R,3S)-3-(2-chlorophenyl)-2-(2,4-difluorophenyl)oxiran-2-yl]methyl}-2,4-dihydro-3H-1,2,4-triazole-3-thione at a ratio of 1:1; a pest control composition comprising any one of the present compounds 1 to 88 and 2-{[(2R,3S)-3-(2-chlorophenyl)-2-(2,4-difluorophenyl)oxiran-2-yl]methyl}-2,4-dihydro-3H-1,2,4-triazole-3-thione at a ratio of 10:1;

a pest control composition comprising any one of the present compounds 1 to 88 and 2-{[(2S,3R)-3-(2-chlorophenyl)-2-(2,4-difluorophenyl)oxiran-2-yl]methyl}-2,4-dihydro-3H-1,2,4-triazole-3-thione at a ratio of 0.1:1; a pest control composition comprising any one of the present compounds 1 to 88 and 2-{[(2S,3R)-3-(2-chlorophenyl)-2-(2,4-difluorophenyl)oxiran-2-yl]methyl}-2,4-dihydro-3H-1,2,4-triazole-3-thione at a ratio of 1:1; a pest control composition comprising any one of the present compounds 1 to 88 and 2-{[(2S,3R)-3-(2-chlorophenyl)-2-(2,4-difluorophenyl)oxiran-2-yl]methyl}-2,4-dihydro-3H-1,2,4-triazole-3-thione at a ratio of 10:1; a pest control composition comprising any one of the present compounds 1 to 88 and 2-{[(2R,3R)-3-(2-chlorophenyl)-2-(2,4-difluorophenyl)oxiran-2-yl]methyl}-2,4-dihydro-3H-1,2,4-triazole-3-thione at a ratio of 0.1:1; a pest control composition comprising any one of the present compounds 1 to 88 and 2-{[(2R,3R)-3-(2-chlorophenyl)-2-(2,4-difluorophenyl)oxiran-2-yl]methyl}-2,4-dihydro-3H-1,2,4-triazole-3-thione at a ratio of 1:1; a pest control composition comprising any one of the present compounds 1 to 88 and 2-{[(2R,3R)-3-(2-chlorophenyl)-2-(2,4-difluorophenyl)oxiran-2-yl]methyl}-2,4-dihydro-3H-1,2,4-triazole-3-thione at a ratio of 10:1; a pest control composition comprising any one of the present compounds 1 to 88 and 2-{[(2S,3S)-3-(2-chlorophenyl)-2-(2,4-difluorophenyl)oxiran-2-yl]methyl}-2,4-dihydro-3H-1,2,4-triazole-3-thione at a ratio of 0.1:1;

a pest control composition comprising any one of the present compounds 1 to 88 and 2-{[(2S,3S)-3-(2-chlorophenyl)-2-(2,4-difluorophenyl)oxiran-2-yl]methyl}-2,4-dihydro-3H-1,2,4-triazole-3-thione at a ratio of 1:1; a pest control composition comprising any one of the present compounds 1 to 88 and 2-{[(2S,3S)-3-(2-chlorophenyl)-2-(2,4-difluorophenyl)oxiran-2-yl]methyl}-2,4-dihydro-3H-1,2,4-triazole-3-thione at a ratio of 10:1; a pest control composition comprising any one of the present compounds 1 to 88 and 1-{[3-(2-chlorophenyl)-2-(2,4-difluorophenyl)oxiran-2-yl]methyl}-1H-1,2,4-triazole-5-thiol at a ratio of 0.1:1; a pest control composition comprising any one of the present compounds 1 to 88 and 1-{[3-(2-chlorophenyl)-2-(2,4-difluorophenyl)oxiran-2-yl]methyl}-1H-1,2,4-triazole-5-thiol at a ratio of 1:1; a pest control composition comprising any one of the present compounds 1 to 88 and 1-{[3-(2-chlorophenyl)-2-(2,4-difluorophenyl)oxiran-2-yl]methyl}-1H-1,2,4-triazole-5-thiol at a ratio of 10:1; a pest control composition comprising any one of the present compounds 1 to 88 and 1-{[rel-(2R,3S)-3-(2-chlorophenyl)-2-(2,4-difluorophenyl)oxiran-2-yl]methyl}-1H-1,2,4-triazole-5-thiol at a ratio of 0.1:1; a pest control composition comprising any one of the present compounds 1 to 88 and 1-{[rel-(2R,3S)-3-(2-chlorophenyl)-2-(2,4-difluorophenyl)oxiran-2-yl]methyl}-1H-1,2,4-triazole-5-thiol at a ratio of 1:1; a pest control composition comprising any one of the present compounds 1 to 88 and 1-{[rel-(2R,3S)-3-(2-chlorophenyl)-2-(2,4-difluorophenyl)oxiran-2-yl]methyl}-1H-1,2,4-triazole-5-thiol at a ratio of 10:1; a pest control composition comprising any one of the present compounds 1 to 88 and 1-{[rel-(2R,3R)-3-(2-chlorophenyl)-2-(2,4-difluorophenyl)oxiran-2-yl]methyl}-1H-1,2,4-triazole-5-thiol at a ratio of 0.1:1;

a pest control composition comprising any one of the present compounds 1 to 88 and 1-{[rel-(2R,3R)-3-(2-chlorophenyl)-2-(2,4-difluorophenyl)oxiran-2-yl]methyl}-1H-1,2,4-triazole-5-thiol at a ratio of 1:1; a pest control composition comprising any one of the present compounds 1 to 88 and 1-{[rel-(2R,3R)-3-(2-chlorophenyl)-2-(2,4-difluorophenyl)oxiran-2-yl]methyl}-1H-1,2,4-triazole-5-thiol at a ratio of 10:1; a compounds 1 to 88 and 1-{[(2R,3S)-3-(2-chlorophenyl)-2-(2,4-difluorophenyl)oxiran-2-yl]methyl}-1H-1,2,4-triazole-5-thiol at a ratio of 0.1:1; a pest control composition comprising any one of the present compounds 1 to 88 and 1-{[(2R,3S)-3-(2-chlorophenyl)-2-(2,4-difluorophenyl)oxiran-2-yl]methyl}-1H-1,2,4-triazole-5-thiol at a ratio of 1:1; a pest control composition comprising any one of the present compounds 1 to 88 and 1-{[(2S,3R)-3-(2-chlorophenyl)-2-(2,4-difluorophenyl)oxiran-2-yl]methyl}-1H-1,2,4-triazole-5-thiol at a ratio of 10:1; a pest control composition comprising any one of the present compounds 1 to 88 and 1-{[(2S,3R)-3-(2-chlorophenyl)-2-(2,4-difluorophenyl)oxiran-2-yl]methyl}-1H-1,2,4-triazole-5-thiol at a ratio of 0.1:1; a pest control composition comprising any one of the present compounds 1 to 88 and 1-{[(2S,3R)-3-(2-chlorophenyl)-2-(2,4-difluorophenyl)oxiran-2-yl]methyl}-1H-1,2,4-triazole-5-thiol at a ratio of 1:1; a pest control composition comprising any one of the present compounds 1 to 88 and 1-{[(2S,3R)-3-(2-chlorophenyl)-2-(2,4-difluorophenyl)oxiran-2-yl]methyl}-1H-1,2,4-triazole-5-thiol at a ratio of 10:1; a pest control composition comprising any one of the present compounds 1 to 88 and 1-{[(2R,3R)-3-(2-chlorophenyl)-2-(2,4-difluorophenyl)oxiran-2-yl]methyl}-1H-1,2,4-triazole-5-thiol at a ratio of 0.1:1; a pest control composition comprising any one of the present compounds 1 to 88 and 1-{[(2R,3R)-3-(2-chlorophenyl)-2-(2,4-difluorophenyl)oxiran-2-yl]methyl}-1H-1,2,4-triazole-5-thiol at a ratio of 1:1; a pest control composition comprising any one of the present compounds 1 to 88 and 1-{[(2R,3R)-3-(2-chlorophenyl)-2-(2,4-difluorophenyl)oxiran-2-yl]methyl}-1H-1,2,4-triazole-5-thiol at a ratio of 10:1; a pest control composition comprising any one of the present compounds 1 to 88 and 1-{[(2S,3S)-3-(2-chlorophenyl)-2-(2,4-difluorophenyl)oxiran-2-yl]methyl}-1H-1,2,4-triazole-5-thiol at a ratio of 0.1:1; a pest control composition comprising any one of the present compounds 1 to 88 and 1-{[(2S,3S)-3-(2-chlorophenyl)-2-(2,4-difluorophenyl)oxiran-2-yl]methyl}-1H-1,2,4-triazole-5-thiol at a ratio of 1:1; a pest control composition comprising any one of the present compounds 1 to 88 and 1-{[(2S,3S)-3-(2-chlorophenyl)-2-(2,4-difluorophenyl)oxiran-2-yl]methyl}-1H-1,2,4-triazole-5-thiol at a ratio of 10:1; a pest control composition comprising any one of the present compounds 1 to 88 and 1-{[3-(2-chlorophenyl)-2-(2,4-difluorophenyl)oxiran-2-yl]methy l}-1H-1,2,4-triazol-5-yl thiocyanate at a ratio of 0.1:1; a pest control composition comprising any one of the present compounds 1 to 88 and 1-{[3-(2-chlorophenyl)-2-(2,4-difluorophenyl)oxiran-2-yl]methyl}-1H-1,2,4-triazol-5-yl thiocyanate at a ratio of 1:1; a pest control composition comprising any one of the present compounds 1 to 88 and 1-{[3-(2-chlorophenyl)-2-(2,4-difluorophenyl)oxiran-2-yl]methyl}-1H-1,2,4-triazol-5-yl thiocyanate at a ratio of 10:1; a pest control composition comprising any one of the present compounds 1 to 88 and 1-{[rel-(2R,3S)-3-(2-chlorophenyl)-2-(2,4-difluorophenyl)oxiran-2-yl]methyl}-1H-1,2,4-triazol-5-yl thiocyanate at a ratio of 0.1:1; a pest control composition comprising any one of the present compounds 1 to 88 and 1-{[rel-(2R,3S)-3-(2-chlorophenyl)-2-(2,4-difluorophenyl)oxiran-2-yl]methyl}-1H-1,2,4-triazol-5-yl thiocyanate at a ratio of 1:1; a pest control composition comprising any one of the present compounds 1 to 88 and 1-{[rel-(2R,3S)-3-(2-chlorophenyl)-2-(2,4-difluorophenyl)oxiran-2-yl]methyl}-1H-1,2,4-triazol-5-yl thiocyanate at a ratio of 10:1; a pest control composition comprising any one of the present compounds 1 to 88 and 1-{[rel-(2R,3R)-3-(2-chlorophenyl)-2-(2,4-difluorophenyl)oxiran-2-yl]methyl}-1H-1,2,4-triazol-5-yl thiocyanate at a ratio of 0.1:1; a pest control composition comprising any one of the present compounds 1 to 88 and 1-{[rel-(2R,3R)-3-(2-chlorophenyl)-2-(2,4-difluorophenyl)oxiran-2-yl]methyl}-1H-1,2,4-triazol-5-yl thiocyanate at a ratio of 1:1; a pest control composition comprising any one of the present compounds 1 to 88 and 1-{[rel-(2R,3R)-3-(2-chlorophenyl)-2-(2,4-difluorophenyl)oxiran-2-yl]methyl}-1H-1,2,4-triazol-5-yl thiocyanate at a ratio of 10:1; a pest control composition comprising any one of the present compounds 1 to 88 and 1-{[(2R,3S)-3-(2-chlorophenyl)-2-(2,4-difluorophenyl)oxiran-2-yl]methyl}-1H-1,2,4-triazol-5-yl thiocyanate at a ratio of 0.1:1; a pest control composition comprising any one of the present compounds 1 to 88 and 1-{[(2R,3S)-3-(2-chlorophenyl)-2-(2,4-difluorophenyl)oxiran-2-yl]methyl}-1H-1,2,4-triazol-5-yl thiocyanate at a ratio of 1:1; a pest control composition comprising any one of the present compounds 1 to 88 and 1-{[(2R,3S)-3-(2-chlorophenyl)-2-(2,4-difluorophenyl)oxiran-2-yl]methyl}-1H-1,2,4-triazol-5-yl thiocyanate at a ratio of 10:1; a pest control composition comprising any one of the present compounds 1 to 88 and 1-{[(2S,3R)-3-(2-chlorophenyl)-2-(2,4-difluorophenyl)oxiran-2-yl]methyl}-1H-1,2,4-triazol-5-ylthiocyanate at a ratio of 0.1:1; a pest control composition comprising any one of the present compounds 1 to 88 and 1-{[(2S,3R)-3-(2-chlorophenyl)-2-(2,4-difluorophenyl)oxiran-2-yl]methyl}-1H-1,2,4-triazol-5-yl thiocyanate at a ratio of 1:1; a pest control composition comprising any one of the present compounds 1 to 88 and 1-{[(2S,3R)-3-(2-chlorophenyl)-2-(2,4-difluorophenyl)oxiran-2-yl]methyl}-1H-1,2,4-triazol-5-yl thiocyanate at a ratio of 10:1; a pest control composition comprising any one of the present compounds 1 to 88 and 1-{[(2R,3R)-3-(2-chlorophenyl)-2-(2,4-difluorophenyl)oxiran-2-yl]methyl}-1H-1,2,4-triazol-5-yl thiocyanate at a ratio of 0.1:1; a pest control composition comprising any one of the present compounds 1 to 88 and 1-{[(2R,3R)-3-(2-chlorophenyl)-2-(2,4-difluorophenyl)oxiran-2-yl]methyl}-1H-1,2,4-triazol-5-yl thiocyanate at a ratio of 1:1; a pest control composition comprising any one of the present compounds 1 to 88 and 1-{[(2R,3R)-3-(2-chlorophenyl)-2-(2,4-difluorophenyl)oxiran-2-yl]methyl}-1H-1,2,4-triazol-5-yl thiocyanate at a ratio of 10:1; a pest control composition comprising any one of the present compounds 1 to 88 and 1-{[(2S,3S)-3-(2-chlorophenyl)-2-(2,4-difluorophenyl)oxiran-2-yl]methyl}-1H-1,2,4-triazol-5-yl thiocyanate at a ratio of 0.1:1;
a pest control composition comprising any one of the present compounds 1 to 88 and 1-{[(2S,3S)-3-(2-chlorophenyl)-2-(2,4-difluorophenyl)oxiran-2-yl]methyl}-1H-1,2,4-triazol-5-yl thiocyanate at a ratio of 1:1; a pest control composition comprising any one of the present compounds 1 to 88 and 1-{[(2S,3S)-3-(2-chlorophenyl)-2-(2,4-difluorophenyl)oxiran-2-yl]methyl}-1H-1,2,4-triazol-5-ylthiocyanate at a ratio of 10:1; a pest control composition comprising any one of the present compounds 1 to 88 and 5-(4-chlorobenzyl)-2-chloromethyl-2-methyl-1-(1H-1,2,4-triazol-1-ylmethyl)cyclopentanol at a ratio of 0.1:1; a pest control composition comprising any one of the present compounds 1 to 88 and 5-(4-chlorobenzyl)-2-chloromethyl-2-methyl-1-(1H-1,2,4-triazol-1-ylmethyl)cyclopentanol at a ratio of 1:1; a pest control composition comprising any one of the present compounds 1 to 88 and 5-(4-chlorobenzyl)-2-chloromethyl-2-methyl-1-(1H-1,2,4-triazol-1-ylmethyl)cyclopentanol at a ratio of 10:1; a pest control composition comprising any one of the present compounds 1 to 88 and (1RS,2SR,5SR)-5-(4-chlorobenzyl)-2-chloromethyl-2-methyl-1-(1H-1,2,4-triazol-1-ylmethyl)cyclopentanol at a ratio of 0.1:1; a pest control composition comprising any one of the present compounds 1 to 88 and (1RS,2SR,5SR)-5-(4-chlorobenzyl)-2-chloromethyl-2-methyl-1-(1H-1,2,4-triazol-1-ylmethyl)cyclopentanol at a ratio of 1:1; a pest control composition comprising any one of the present compounds 1 to 88 and (1RS,2SR,5SR)-5-(4-chlorobenzyl)-2-chloromethyl-2-methyl-1-(1H-1,2,4-triazol-1-ylmethyl)cyclopentanol at a ratio of 10:1;
a pest control composition comprising any one of the present compounds 1 to 88 and (1RS,2RS,5RS)-2-chloromethyl-5-(4-fluorobenzyl)-2-methyl-1-(1H-1,2,4-triazol-1-ylmethyl)cyclopentanol at a ratio of 0.1:1; a pest control composition comprising any one of the present compounds 1 to 88 and (1RS,2RS,5RS)-2-chloromethyl-5-(4-fluorobenzyl)-2-methyl-1-(1H-1,2,4-triazol-1-ylmethyl)cyclopentanol at a ratio of 1:1; a pest control composition comprising any one of the present compounds 1 to 88 and (1RS,2RS,5RS)-2-chloromethyl-5-(4-fluorobenzyl)-2-methyl-1-(1H-1,2,4-triazol-1-ylmethyl)cyclopentanol at a ratio of 10:1; a pest control composition comprising any one of the present compounds 1 to 88 and (1RS,2RS,5SR)-2-chloromethyl-5-(4-fluorobenzyl)-2-methyl-1-(1H-1,2,4-triazol-1-ylmethyl)cyclopentanol at a ratio of 0.1:1; a pest control composition comprising any one of the present compounds 1 to 88 and (1RS,2RS,5SR)-2-chloromethyl-5-(4-fluorobenzyl)-2-methyl-1-(1H-1,2,4-triazol-1-ylmethyl)cyclopentanol at a ratio of 1:1; a pest control composition comprising any one of the present compounds 1 to 88 and (1RS,2RS,5SR)-2-chloromethyl-5-(4-fluorobenzyl)-2-methyl-1-(1H-1,2,4-triazol-1-ylmethyl)cyclopentanol at a ratio of 10:1; a pest control composition comprising any one of the present compounds 1 to 88 and (1RS,2SR,5RS)-2-chloromethyl-5-(4-fluorobenzyl)-2-methyl-1-(1H-1,2,4-triazol-1-ylmethyl)cyclopentanol at a ratio of 0.1:1; a pest control composition comprising any one of the present compounds 1 to 88 and (1RS,2SR,5RS)-2-chloromethyl-5-(4-fluorobenzyl)-2-methyl-1-(1H-1,2,4-triazol-1-ylmethyl)cyclopentanol at a ratio of 1:1; a pest control composition comprising any one of the present compounds 1 to 88 and (1RS,2SR,5RS)-2-chloromethyl-5-(4-fluorobenzyl)-2-methyl-1-(1H-1,2,4-triazol-1-ylmethyl)cyclopentanol at a ratio of 10:1;
a pest control composition comprising any one of the present compounds 1 to 88 and (1R,2S,5S)-2-chloromethyl-5-(4-fluorobenzyl)-2-methyl-1-(1H-1, 2,4-triazol-1-ylmethyl)cyclopentanol at a ratio of 0.1:1; a pest control composition comprising any one of the present compounds 1 to 88 and (1R,2S,5S)-2-chloromethyl-5-(4-fluorobenzyl)-2-methyl-1-(1H-1, 2,4-triazol-1-ylmethyl)cyclopentanol at a ratio of 1:1; a pest control composition comprising any one of the present compounds 1 to 88 and (1R,2S,5S)-2-chloromethyl-5-(4-fluorobenzyl)-2-methyl-1-(1H-1, 2,4-triazol-1-ylmethyl)cyclopentanol at a ratio of 10:1; a pest control composition comprising any one of the present compounds 1 to 88 and (1S,2R,5R)-2-chloromethyl-5-(4-fluorobenzyl)-2-methyl-1-(1H-1, 2,4-triazol-1-ylmethyl)cyclopentanol at a ratio of 0.1:1; a pest control composition comprising any one of the present compounds 1 to 88 and (1S,2R,5R)-2-chloromethyl-5-(4-fluorobenzyl)-2-methyl-1-(1H-1, 2,4-triazol-1-ylmethyl)cyclopentanol at a ratio of 1:1; a pest control composition comprising any one of the present compounds 1 to 88 and (1S,2R,5R)-2-chloromethyl-5-(4-fluorobenzyl)-2-methyl-1-(1H-1,2,4-triazol-1-ylmethyl)cyclopentanol at a ratio of 10:1; a pest control composition comprising any one of the present compounds 1 to 88 and (1R,2R,5R)-2-chloromethyl-5-(4-fluorobenzyl)-2-methyl-1-(1H-1,2,4-triazol-1-ylmethyl)cyclopentanol at a ratio of 0.1:1; a pest control composition comprising any one of the present compounds 1 to 88 and (1R,2R,5R)-2-chloromethyl-5-(4-fluorobenzyl)-2-methyl-1-(1H-1,2,4-triazol-1-ylmethyl)cyclopentanol at a ratio of 1:1;

a pest control composition comprising any one of the present compounds 1 to 88 and (1R,2R,5R)-2-chloromethyl-5-(4-fluorobenzyl)-2-methyl-1-(1H-1,2,4-triazol-1-ylmethyl)cyclopentanol at a ratio of 10:1; a pest control composition comprising any one of the present compounds 1 to 88 and (1S,2S,5S)-2-chloromethyl-5-(4-fluorobenzyl)-2-methyl-1-(1H-1,2,4-triazol-1-ylmethyl)cyclopentanol at a ratio of 0.1:1; a pest control composition comprising any one of the present compounds 1 to 88 and (1S,2S,5S)-2-chloromethyl-5-(4-fluorobenzyl)-2-methyl-1-(1H-1,2,4-triazol-1-ylmethyl)cyclopentanol at a ratio of 1:1; a pest control composition comprising any one of the present compounds 1 to 88 and (1S,2S,5S)-2-chloromethyl-5-(4-fluorobenzyl)-2-methyl-1-(1H-1,2,4-triazol-1-ylmethyl)cyclopentanol at a ratio of 10:1; a pest control composition comprising any one of the present compounds 1 to 88 and (1R,2R,5S)-2-chloromethyl-5-(4-fluorobenzyl)-2-methyl-1-(1H-1,2,4-triazol-1-ylmethyl)cyclopentanol at a ratio of 0.1:1; a pest control composition comprising any one of the present compounds 1 to 88 and (1R,2R,5S)-2-chloromethyl-5-(4-fluorobenzyl)-2-methyl-1-(1H-1,2,4-triazol-1-ylmethyl)cyclopentanol at a ratio of 1:1; a pest control composition comprising any one of the present compounds 1 to 88 and (1R,2R,5S)-2-chloromethyl-5-(4-fluorobenzyl)-2-methyl-1-(1H-1,2,4-triazol-1-ylmethyl)cyclopentanol at a ratio of 10:1; a pest control composition comprising any one of the present compounds 1 to 88 and (1S,2S,5R)-2-chloromethyl-5-(4-fluorobenzyl)-2-methyl-1-(1H-1,2,4-triazol-1-ylmethyl)cyclopentanol at a ratio of 0.1:1; a pest control composition comprising any one of the present compounds 1 to 88 and (1S,2S,5R)-2-chloromethyl-5-(4-fluorobenzyl)-2-methyl-1-(1H-1,2,4-triazol-1-ylmethyl)cyclopentanol at a ratio of 1:1; a pest control composition comprising any one of the present compounds 1 to 88 and (1S,2S,5R)-2-chloromethyl-5-(4-fluorobenzyl)-2-methyl-1-(1H-1,2,4-triazol-1-ylmethyl)cyclopentanol at a ratio of 10:1; a pest control composition comprising any one of the present compounds 1 to 88 and (1R,2S,5R)-2-chloromethyl-5-(4-fluorobenzyl)-2-methyl-1-(1H-1,2,4-triazol-1-ylmethyl)cyclopentanol at a ratio of 0.1:1; a pest control composition comprising any one of the present compounds 1 to 88 and (1R,2S,5R)-2-chloromethyl-5-(4-fluorobenzyl)-2-methyl-1-(1H-1,2,4-triazol-1-ylmethyl)cyclopentanol at a ratio of 1:1; a pest control composition comprising any one of the present compounds 1 to 88 and (1R,2S,5R)-2-chloromethyl-5-(4-fluorobenzyl)-2-methyl-1-(1H-1,2,4-triazol-1-ylmethyl)cyclopentanol at a ratio of 10:1; a pest control composition comprising any one of the present compounds 1 to 88 and (1S,2R,5S)-2-chloromethyl-5-(4-fluorobenzyl)-2-methyl-1-(1H-1,2,4-triazol-1-ylmethyl)cyclopentanol at a ratio of 0.1:1; a pest control composition comprising any one of the present compounds 1 to 88 and (1S,2R,5S)-2-chloromethyl-5-(4-fluorobenzyl)-2-methyl-1-(1H-1,2,4-triazol-1-ylmethyl)cyclopentanol at a ratio of 1:1; a pest control composition comprising any one of the present compounds 1 to 88 and (1S,2R,5S)-2-chloromethyl-5-(4-fluorobenzyl)-2-methyl-1-(1H-1,2,4-triazol-1-ylmethyl)cyclopentanol at a ratio of 10:1; a pest control composition comprising any one of the present compounds 1 to 88 and 2-chloromethyl-5-(4-fluorobenzyl)-2-methyl-1-(1H-1,2,4-triazol-1-ylmethyl)cyclopentanol at a ratio of 0.1:1; a pest control composition comprising any one of the present compounds 1 to 88 and 2-chloromethyl-5-(4-fluorobenzyl)-2-methyl-1-(1H-1,2,4-triazol-1-ylmethyl)cyclopentanol at a ratio of 1:1;

a pest control composition comprising any one of the present compounds 1 to 88 and 2-chloromethyl-5-(4-fluorobenzyl)-2-methyl-1-(1H-1,2,4-triazol-1-ylmethyl)cyclopentanol at a ratio of 10:1; a pest control composition comprising any one of the present compounds 1 to 88 and (1RS,2SR,5SR)-2-chloromethyl-5-(4-fluorobenzyl)-2-methyl-1-(1H-1,2,4-triazol-1-ylmethyl)cyclopentanol at a ratio of 0.1:1; a pest control composition comprising any one of the present compounds 1 to 88 and (1RS,2SR,5SR)-2-chloromethyl-5-(4-fluorobenzyl)-2-methyl-1-(1H-1,2,4-triazol-1-ylmethyl)cyclopentanol at a ratio of 1:1; a pest control composition comprising any one of the present compounds 1 to 88 and (1RS,2SR,5SR)-2-chloromethyl-5-(4-fluorobenzyl)-2-methyl-1-(1H-1,2,4-triazol-1-ylmethyl)cyclopentanol at a ratio of 10:1; a pest control composition comprising any one of the present compounds 1 to 88 and (1RS,2RS,5RS)-2-chloromethyl-5-(4-fluorobenzyl)-2-methyl-1-(1H-1,2,4-triazol-1-ylmethyl)cyclopentanol at a ratio of 0.1:1; a pest control composition comprising any one of the present compounds 1 to 88 and (1RS,2RS,5RS)-2-chloromethyl-5-(4-fluorobenzyl)-2-methyl-1-(1H-1,2,4-triazol-1-ylmethyl)cyclopentanol at a ratio of 1:1; a pest control composition comprising any one of the present compounds 1 to 88 and (1RS,2RS,5RS)-2-chloromethyl-5-(4-fluorobenzyl)-2-methyl-1-(1H-1,2,4-triazol-1-ylmethyl)cyclopentanol at a ratio of 10:1; a pest control composition comprising any one of the present compounds 1 to 88 and (1RS,2RS,5SR)-2-chloromethyl-5-(4-fluorobenzyl)-2-methyl-1-(1H-1,2,4-triazol-1-ylmethyl)cyclopentanol at a ratio of 0.1:1;

a pest control composition comprising any one of the present compounds 1 to 88 and (1RS,2RS,5SR)-2-chloromethyl-5-(4-fluorobenzyl)-2-methyl-1-(1H-1,2,4-triazol-1-ylmethyl)cyclopentanol at a ratio of 1:1; a pest control composition comprising any one of the present compounds 1 to 88 and (1RS,2RS,5SR)-2-chloromethyl-5-(4-fluorobenzyl)-2-methyl-1-(1H-1,2,4-triazol-1-ylmethyl)cyclopentanol at a ratio of 10:1; a pest control composition comprising any one of the present compounds 1 to 88 and (1RS,2SR,5RS)-2-chloromethyl-5-(4-fluorobenzyl)-2-methyl-1-(1H-1,2,4-triazol-1-ylmethyl)cyclopentanol at a ratio of 0.1:1; a pest control composition comprising any one of the present compounds 1 to 88 and (1RS,2SR,5RS)-2-chloromethyl-5-(4-fluorobenzyl)-2-methyl-1-(1H-1,2,4-triazol-1-ylmethyl)cyclopentanol at a ratio of 1:1; a pest control composition comprising any one of the present compounds 1 to 88 and (1RS,2SR,5RS)-2-chloromethyl-5-(4-fluorobenzyl)-2- methyl-1-(1H-1,2,4-triazol-1-ylmethyl)cyclopentanol at a ratio of 10:1; a compounds 1 to 88 and (1R,2S,5S)-2-chloromethyl-5-(4-fluorobenzyl)-2-methyl-1-(1H-1,2,4-triazol-1-ylmethyl)cyclopentanol at a ratio of 0.1:1; a pest control composition comprising any one of the present compounds 1 to 88 and (1R,2S,5S)-2-chloromethyl-5-(4-fluorobenzyl)-2-methyl-1-(1H-1,2,4-triazol-1-ylmethyl)cyclopentanol at a ratio of 1:1; a pest control composition comprising any one of the present compounds 1 to 88 and (1R,2S,5S)-2-chloromethyl-5-(4-fluorobenzyl)-2-methyl-1-(1H-1,2,4-triazol-1-ylmethyl)cyclopentanol at a ratio of 10:1;

a pest control composition comprising any one of the present compounds 1 to 88 and (1S,2R,5R)-2-chloromethyl-5-(4-fluorobenzyl)-2-methyl-1-(1H-1,2,4-triazol-1-ylmethyl)cyclopentanol at a ratio of 0.1:1; a pest control composition comprising any one of the present compounds 1 to 88 and (1S,2R,5R)-2-chloromethyl-5-(4-fluorobenzyl)-2-methyl-1-(1H-1,2,4-triazol-1-ylmethyl)cyclopentanol at a ratio of 1:1; a pest control composition comprising any one of the present compounds 1 to 88 and (1S,2R,5R)-2-chloromethyl-5-(4-fluorobenzyl)-2-methyl-1-(1H-1,2,4-triazol-1-ylmethyl)cyclopentanol at a ratio of 10:1; a pest control composition comprising any one of the present compounds 1 to 88 and (1R,2R,5R)-2-chloromethyl-5-(4-fluorobenzyl)-2-methyl-1-(1H-1,2,4-triazol-1-ylmethyl)cyclopentanol at a ratio of 0.1:1; a pest control composition comprising any one of the present compounds 1 to 88 and (1R,2R,5R)-2-chloromethyl-5-(4-fluorobenzyl)-2-methyl-1-(1H-1,2,4-triazol-1-ylmethyl)cyclopentanol at a ratio of 1:1; a pest control composition comprising any one of the present compounds 1 to 88 and (1R,2R,5R)-2-chloromethyl-5-(4-fluorobenzyl)-2-methyl-1-(1H-1,2,4-triazol-1-ylmethyl)cyclopentanol at a ratio of 10:1; a pest control composition comprising any one of the present compounds 1 to 88 and (1S,2S,5S)-2-chloromethyl-5-(4-fluorobenzyl)-2-methyl-1-(1H-1,2,4-triazol-1-ylmethyl)cyclopentanol at a ratio of 0.1:1; a pest control composition comprising any one of the present compounds 1 to 88 and (1S,2S,5S)-2-chloromethyl-5-(4-fluorobenzyl)-2-methyl-1-(1H-1,2,4-triazol-1-ylmethyl)cyclopentanol at a ratio of 1:1; a pest control composition comprising any one of the present compounds 1 to 88 and (1S,2S,5S)-2-chloromethyl-5-(4-fluorobenzyl)-2-methyl-1-(1H-1,2,4-triazol-1-ylmethyl)cyclopentanol at a ratio of 10:1;

a pest control composition comprising any one of the present compounds 1 to 88 and (1R,2R,5S)-2-chloromethyl-5-(4-fluorobenzyl)-2-methyl-1-(1H-1,2,4-triazol-1-ylmethyl)cyclopentanol at a ratio of 0.1:1; a pest control composition comprising any one of the present compounds 1 to 88 and (1R,2R,5S)-2-chloromethyl-5-(4-fluorobenzyl)-2-methyl-1-(1H-1,2,4-triazol-1-ylmethyl)cyclopentanol at a ratio of 1:1; a pest control composition comprising any one of the present compounds 1 to 88 and (1R,2R,5S)-2-chloromethyl-5-(4-fluorobenzyl)-2-methyl-1-(1H-1,2,4-triazol-1-ylmethyl)cyclopentanol at a ratio of 10:1; a pest control composition comprising any one of the present compounds 1 to 88 and (1S,2S,5R)-2-chloromethyl-5-(4-fluorobenzyl)-2-methyl-1-(1H-1,2,4-triazol-1-ylmethyl)cyclopentanol at a ratio of 0.1:1; a pest control composition comprising any one of the present compounds 1 to 88 and (1S,2S,5R)-2-chloromethyl-5-(4-fluorobenzyl)-2-methyl-1-(1H-1,2,4-triazol-1-ylmethyl)cyclopentanol at a ratio of 1:1; a pest control composition comprising any one of the present compounds 1 to 88 and (1S,2S,5R)-2-chloromethyl-5-(4-fluorobenzyl)-2-methyl-1-(1H-1,2,4-triazol-1-ylmethyl)cyclopentanol at a ratio of 10:1; a pest control composition comprising any one of the present compounds 1 to 88 and (1R,2S,5R)-2-chloromethyl-5-(4-fluorobenzyl)-2-methyl-1-(1H-1,2,4-triazol-1-ylmethyl)cyclopentanol at a ratio of 0.1:1; a pest control composition comprising any one of the present compounds 1 to 88 and (1R,2S,5R)-2-chloromethyl-5-(4-fluorobenzyl)-2-methyl-1-(1H-1,2,4-triazol-1-ylmethyl)cyclopentanol at a ratio of 1:1;

a pest control composition comprising any one of the present compounds 1 to 88 and (1R,2S,5R)-2-chloromethyl-5-(4-fluorobenzyl)-2-methyl-1-(1H-1,2,4-triazol-1-ylmethyl)cyclopentanol at a ratio of 10:1; a pest control composition comprising any one of the present compounds 1 to 88 and (1S,2R,5S)-2-chloromethyl-5-(4-fluorobenzyl)-2-methyl-1-(1H-1,2,4-triazol-1-ylmethyl)cyclopentanol at a ratio of 0.1:1; a pest control composition comprising any one of the present compounds 1 to 88 and (1S,2R,5S)-2-chloromethyl-5-(4-fluorobenzyl)-2-methyl-1-(1H-1,2,4-triazol-1-ylmethyl)cyclopentanol at a ratio of 1:1; a pest control composition comprising any one of the present compounds 1 to 88 and (1S,2R,5S)-2-chloromethyl-5-(4-fluorobenzyl)-2-methyl-1-(1H-1,2,4-triazol-1-ylmethyl)cyclopentanol at a ratio of 10:1;

a pest control composition comprising any one of the present compounds 1 to 88 and 5-amino-4-(2-chloro-4-fluorophenyl)-N-(2,6-difluorophenyl)-1,3-dimethyl-1H-pyrazole at a ratio of 0.1:1; a pest control composition comprising any one of the present compounds 1 to 88 and 5-amino-4-(2-chloro-4-fluorophenyl)-N-(2,6-difluorophenyl)-1,3-dimethyl-1H-pyrazole at a ratio of 1:1; a pest control composition comprising any one of the present compounds 1 to 88 and 5-amino-4-(2-chloro-4-fluorophenyl)-N-(2,6-difluorophenyl)-1,3-dimethyl-1H-pyrazole at a ratio of 10:1; a pest control composition comprising any one of the present compounds 1 to 88 and 5-amino-4-(2-bromo-4-fluorophenyl)-N-(2,6-difluorophenyl)-1,3-dimethyl-1H-pyrazole at a ratio of 0.1:1; a pest control composition comprising any one of the present compounds 1 to 88 and 5-amino-4-(2-bromo-4-fluorophenyl)-N-(2,6-difluorophenyl)-1,3-dimethyl-1H-pyrazole at a ratio of 1:1; a pest control composition comprising any one of the present compounds 1 to 88 and 5-amino-4-(2-bromo-4-fluorophenyl)-N-(2,6-difluorophenyl)-1,3-dimethyl-1H-pyrazole at a ratio of 10:1;

a pest control composition comprising any one of the present compounds 1 to 88 and 5-amino-4-(2-chloro-4-fluorophenyl)-N-(2-chloro-6-fluorophenyl)-1,3-dimethyl-1H-pyrazole at a ratio of 0.1:1; a pest control composition comprising any one of the present compounds 1 to 88 and 5-amino-4-(2-chloro-4-fluorophenyl)-N-(2-chloro-6-fluorophenyl)-1,3-dimethyl-1H-pyrazole at a ratio of 1:1; a pest control composition comprising any one of the present compounds 1 to 88 and 5-amino-4-(2-chloro-4-fluorophenyl)-N-(2-chloro-6-fluorophenyl)-1,3-dimethyl-1H-pyrazole at a ratio of 10:1; a pest control composition comprising any one of the present compounds 1 to 88 and 5-amino-4-(2-bromo-4-fluorophenyl)-N-(2-chloro-6-fluorophenyl)-1,3-dimethyl-1H-pyrazole at a ratio of 0.1:1; a pest control composition comprising any one of the present compounds 1 to 88 and 5-amino-4-(2-bromo-4-fluorophenyl)-N-(2-chloro-6-fluorophenyl)-1,3-dimethyl-1H-pyrazole at a ratio of 1:1; a pest control composition comprising any one of the present compounds 1 to 88 and 5-amino-4-(2-bromo-4-fluorophenyl)-N-(2-chloro-6-fluorophenyl)-1,3-dimethyl-1H-pyrazole at a ratio of 10:1;

a pest control composition comprising any one of the present compounds 1 to 88 and 5-amino-4-(2-chloro-4-fluorophenyl)-N-(2,6-difluoro-4-methylphenyl)-1,3-dimethyl-1H-pyrazole at a ratio of 0.1:1; a pest control composition comprising any one of the present compounds 1 to 88 and 5-amino-4-(2-chloro-4-fluorophenyl)-N-(2,6-difluoro-4-methylphenyl)-1,3-dimethyl-1H-pyrazole at a ratio of 1:1; a pest control composition comprising any one of the present compounds 1 to 88 and 5-amino-4-(2-chloro-4-fluorophenyl)-N-(2,6-difluoro-4-methylphenyl)-1,3-dimethyl-1H-pyrazole at a ratio of 10:1;

a pest control composition comprising any one of the present compounds 1 to 88 and 5-amino-4-(2-bromo-4-fluorophenyl)-N-(2,6-difluoro-4-methylphenyl)-1,3-dimethyl-1H-pyrazole at a ratio of 0.1:1; a pest control composition comprising any one of the present compounds 1 to 88 and 5-amino-4-(2-bromo-4-fluorophenyl)-N-(2,6-difluoro-4-methylphenyl)-1,3-dimethyl-1H-pyrazole at a ratio of 1:1; a pest control composition comprising any one of the present compounds 1 to 88 and 5-amino-4-(2-bromo-4-fluorophenyl)-N-(2,6-difluoro-4-methylphenyl)-1,3-dimethyl-1H-pyrazole at a ratio of 10:1;

a pest control composition comprising any one of the present compounds 1 to 88 and 5-amino-N-(2-chloro-6-fluoro-4-methylphenyl)-4-(2-chloro-4-fluorophenyl)-1,3-dimethyl-1H-pyrazole at a ratio of 0.1:1; a pest control composition comprising any one of the present compounds 1 to 88 and 5-amino-N-(2-chloro-6-fluoro-4-methylphenyl)-4-(2-chloro-4-fluorophenyl)-1,3-dimethyl-1H-pyrazole at a ratio of 1:1; a pest control composition comprising any one of the present compounds 1 to 88 and 5-amino-N-(2-chloro-6-fluoro-4-methylphenyl)-4-(2-chloro-4-fluorophenyl)-1,3-dimethyl-1H-pyrazole at a ratio of 10:1;

a pest control composition comprising any one of the present compounds 1 to 88 and 5-amino-4-(2-bromo-4-fluorophenyl)-N-(2-chloro-6-fluoro-4-methylphenyl)-1,3-dimethyl-1H-pyrazole at a ratio of 0.1:1; a pest control composition comprising any one of the present compounds 1 to 88 and 5-amino-4-(2-bromo-4-fluorophenyl)-N-(2-chloro-6-fluoro-4-methylphenyl)-1,3-dimethyl-1H-pyrazole at a ratio of 1:1; a pest control composition comprising any one of the present compounds 1 to 88 and 5-amino-4-(2-bromo-4-fluorophenyl)-N-(2-chloro-6-fluoro-4-methylphenyl)-1,3-dimethyl-1H-pyrazole at a ratio of 10:1;

a pest control composition comprising any one of the present compounds 1 to 88 and 9-fluoro-2,3-dihydro-2,2-dimethyl-5-(quinolin-3-yl)-1,4-benzoxazepine at a ratio of 0.1:1; a pest control composition comprising any one of the present compounds 1 to 88 and 9-fluoro-2,3-dihydro-2,2-dimethyl-5-(quinolin-3-yl)-1,4-benzoxazepine at a ratio of 1:1; a pest control composition comprising any one of the present compounds 1 to 88 and 9-fluoro-2,3-dihydro-2,2-dimethyl-5-(quinolin-3-yl)-1,4-benzoxazepine at a ratio of 10:1; a pest control composition comprising any one of the present compounds 1 to 88 and N-cyclopropyl-3-(difluoromethyl)-5-fluoro-N-(2-isopropylbenzyl)-1-methyl-1H-pyrazole-4-carboxamide at a ratio of 0.1:1; a pest control composition comprising any one of the present compounds 1 to 88 and N-cyclopropyl-3-(difluoromethyl)-5-fluoro-N-(2-isopropylbenzyl)-1-methyl-1H-pyrazole-4-carboxamide at a ratio of 1:1; a pest control composition comprising any one of the present compounds 1 to 88 and N-cyclopropyl-3-(difluoromethyl)-5-fluoro-N-(2-isopropylbenzyl)-1-methyl-1H-pyrazole-4-carboxamide at a ratio of 10:1; a pest control composition comprising any one of the present compounds 1 to 88 and N-cyclopropyl-3-(difluoromethyl)-5-fluoro-N-(5-chloro-2-isopropylbenzyl)-1-methyl-1H-pyrazole-4-carboxamide at a ratio of 0.1:1; a pest control composition comprising any one of the present compounds 1 to 88 and N-cyclopropyl-3-(difluoromethyl)-5-fluoro-N-(5-chloro-2-isopropylbenzyl)-1-methyl-1H-pyrazole-4-carboxamide at a ratio of 1:1; a pest control composition comprising any one of the present compounds 1 to 88 and N-cyclopropyl-3-(difluoromethyl)-5-fluoro-N-(5-chloro-2-isopropylbenzyl)-1-methyl-1H-pyrazole-4-carboxamide at a ratio of 10:1; a pest control composition comprising any one of the present compounds 1 to 88 and N-[1-(2,4-dichlorophenyl)-1-methoxypropan-2-yl]-3-difluoromethyl-1-methyl-1H-pyrazole-4-carboxamide at a ratio of 0.1:1;

a pest control composition comprising any one of the present compounds 1 to 88 and N-[1-(2,4-dichlorophenyl)-1-methoxypropan-2-yl]-3-difluoromethyl-1-methyl-1H-pyrazole-4-carboxamide at a ratio of 1:1; a pest control composition comprising any one of the present compounds 1 to 88 and N-[1-(2,4-dichlorophenyl)-1-methoxypropan-2-yl]-3-difluoromethyl-1-methyl-1H-pyrazole-4-carboxamide at a ratio of 10:1; a pest control composition comprising any one of the present compounds 1 to 88 and N-[(1R,2R)1-(2,4-dichlorophenyl)-1-methoxypropan-2-yl]-3-difluoromethyl-1-methyl-1H-pyrazole-4-carboxamide at a ratio of 0.1:1; a pest control composition comprising any one of the present compounds 1 to 88 and N-[(1R,2R)1-(2,4-dichlorophenyl)-1-methoxypropan-2-yl]-3-difluoromethyl-1-methyl-1H-pyrazole-4-carboxamide at a ratio of 1:1; a pest control composition comprising any one of the present compounds 1 to 88 and N-[(1R,2R)1-(2,4-dichlorophenyl)-1-methoxypropan-2-yl]-3-difluoromethyl-1-methyl-1H-pyrazole-4-carboxamide at a ratio of 10:1; a pest control composition comprising any one of the present compounds 1 to 88 and N-[(1R,2S)1-(2,4-dichlorophenyl)-1-methoxypropan-2-yl]-3-difluoromethyl-1-methyl-1H-pyrazole-4-carboxamide at a ratio of 0.1:1; a pest control composition comprising any one of the present compounds 1 to 88 and N-[(1R,2S)1-(2,4-dichlorophenyl)-1-methoxypropan-2-yl]-3-difluoromethyl-1-methyl-1H-pyrazole-4-carboxamide at a ratio of 1:1; a pest control composition comprising any one of the present compounds 1 to 88 and N-[(1R,2S)1-(2,4-dichlorophenyl)-1-methoxypropan-2-yl]-3-difluoromethyl-1-methyl-1H-pyrazole-4-carboxamide at a ratio of 10:1; a pest control composition comprising any one of the present compounds 1 to 88 and N-[(1S,2R)1-(2,4-dichlorophenyl)-1-methoxypropan-2-yl]-3-difluoromethyl-1-methyl-1H-pyrazole-4-carboxamide at a ratio of 0.1:1;

a pest control composition comprising any one of the present compounds 1 to 88 and N-[(1S,2R) 1-(2,4-dichlorophenyl)-1-methoxypropan-2-yl]-3-difluoromethyl-1-methyl-1H-pyrazole-4-carboxamide at a ratio of 1:1; a pest control composition comprising any one of the present compounds 1 to 88 and N-[(1S,2R) 1-(2,4-dichlorophenyl)-1-methoxypropan-2-yl]-3-difluoromethyl-1-methyl-1H-pyrazole-4-carboxamide at a ratio of 10:1; a pest control composition comprising any one of the present compounds 1 to 88 and N-[(1S,2S)1-(2,4-dichlorophenyl)-1-methoxypropan-2-yl]-3-difluoromethyl-1-methyl-1H-pyrazole-4-carboxamide at a ratio of 0.1:1; a pest control composition comprising any one of the present compounds 1 to 88 and N-[(1S,2S)1-(2,4-dichlorophenyl)-1-methoxypropan-2-yl]-3-difluoromethyl-1-methyl-1H-pyrazole-4-carboxamide at a ratio of 1:1; a pest control composition comprising any one of the present compounds 1 to 88 and N-[(1S,2S)1-(2,4-dichlorophenyl)-1-methoxypropan-2-yl]-3-difluoromethyl-1-methyl-1H-pyrazole-4-carboxamide at a ratio of 10:1; a pest control composition comprising any one of the present compounds 1 to 88 and rel-N-[(1R,2R)1-(2,4-dichlorophenyl)-1-methoxypropan-2-yl]-3-difluoromethyl-1-methyl-1H-pyrazole-4-carboxamide at a ratio of 0.1:1; a pest control composition comprising any one of the present compounds 1 to 88 and rel-N-[(1R,2R)1-(2,4-dichlorophenyl)-1-methoxypropan-2-yl]-3-difluoromethyl-1-methyl-1H-pyrazole-4-carboxamide at a ratio of 1:1; a pest control composition comprising any one of the present compounds 1 to 88 and rel-N-[(1R,2R)1-(2,4-dichlorophenyl)-1-methoxypropan-2-yl]-3-difluoromethyl-1-methyl-1H-pyrazole-4-carboxamide at a ratio of 10:1;

a pest control composition comprising any one of the present compounds 1 to 88 and rel-N-[(1R,2S)1-(2,4-dichlorophenyl)-1-methoxypropan-2-yl]-3-difluoromethyl-1-methyl-1H-pyrazole-4-carboxamide at a ratio of 0.1:1; a pest control composition comprising any one of the present compounds 1 to 88 and rel-N-[(1R,2S)1-(2,4-dichlorophenyl)-1-methoxypropan-2-yl]-3-difluoromethyl-1-methyl-1H-pyrazole-4-carboxamide at a ratio of 1:1; a pest control composition comprising any one of the present compounds 1 to 88 and rel-N-[(1R,2S)1-(2,4-dichlorophenyl)-1-methoxypropan-2-yl]-3-difluoromethyl-1-methyl-1H-pyrazole-4-carboxamide at a ratio of 10:1; a pest control composition comprising any one of the present compounds 1 to 88 and N-[(1R,2RS)1-(2,4-dichlorophenyl)-1-methoxypropan-2-yl]-3-difluoromethyl-1-methyl-1H-pyrazole-4-carboxamide at a ratio of 0.1:1; a pest control composition comprising any one of the present compounds 1 to 88 and N-[(1R,2RS)1-(2,4-dichlorophenyl)-1-methoxypropan-2-yl]-3-difluoromethyl-1-methyl-1H-pyrazole-4-carboxamide at a ratio of 1:1; a pest control composition comprising any one of the present compounds 1 to 88 and N-[(1R,2RS)1-(2,4-dichlorophenyl)-1-methoxypropan-2-yl]-3-difluoromethyl-1-methyl-1H-pyrazole-4-carboxamide at a ratio of 10:1; a pest control composition comprising any one of the present compounds 1 to 88 and N-[(1S,2RS)1-(2,4-dichlorophenyl)-1-methoxypropan-2-yl]-3-difluoromethyl-1-methyl-1H-pyrazole-4-carboxamide at a ratio of 0.1:1; a pest control composition comprising any one of the present compounds 1 to 88 and N-[(1S,2RS)1-(2,4-dichlorophenyl)-1-methoxypropan-2-yl]-3-difluoromethyl-1-methyl-1H-pyrazole-4-carboxamide at a ratio of 1:1;

a pest control composition comprising any one of the present compounds 1 to 88 and N-[(1S,2RS)1-(2,4-dichlorophenyl)-1-methoxypropan-2-yl]-3-difluoromethyl-1-methyl-1H-pyrazole-4-carboxamide at a ratio of 10:1; a pest control composition comprising any one of the present compounds 1 to 88 and N-[(1RS,2R)1-(2,4-dichlorophenyl)-1-methoxypropan-2-yl]-3-difluoromethyl-1-methyl-1H-pyrazole-4-carboxamide at a ratio of 0.1:1; a pest control composition comprising any one of the present compounds 1 to 88 and N-[(1RS,2R)1-(2,4-dichlorophenyl)-1-methoxypropan-2-yl]-3-difluoromethyl-1-methyl-1H-pyrazole-4-carboxamide at a ratio of 1:1; a pest control composition comprising any one of the present compounds 1 to 88 and N-[(1RS,2R)1-(2,4-dichlorophenyl)-1-methoxypropan-2-yl]-3-difluoromethyl-1-methyl-1H-pyrazole-4-carboxamide at a ratio of 10:1; a pest control composition comprising any one of the present compounds 1 to 88 and N-[(1RS,2S)1-(2,4-dichlorophenyl)-1-methoxypropan-2-yl]-3-difluoromethyl-1-methyl-1H-pyrazole-4-carboxamide at a ratio of 0.1:1; a pest control composition comprising any one of the present compounds 1 to 88 and N-[(1RS,2S)1-(2,4-dichlorophenyl)-1-methoxypropan-2-yl]-3-difluoromethyl-1-methyl-1H-pyrazole-4-carboxamide at a ratio of 1:1; a pest control composition comprising any one of the present compounds 1 to 88 and N-[(1RS,2S)1-(2,4-dichlorophenyl)-1-methoxypropan-2-yl]-3-difluoromethyl-1-methyl-1H-pyrazole-4-carboxamide at a ratio of 10:1;

a pest control composition comprising any one of the present compounds 1 to 88 and 3-difluoromethyl-N-methoxy-1-methyl-N-[1-methyl-2-(2,4,6-trichlorophenyl)ethyl]pyrazole-4-carboxamide at a ratio of 0.1:1; a pest control composition comprising any one of the present compounds 1 to 88 and 3-difluoromethyl-N-methoxy-1-methyl-N-[1-methyl-2-(2,4,6-trichlorophenyl)ethyl]pyrazole-4-carboxamide at a ratio of 1:1; a pest control composition comprising any one of the present compounds 1 to 88 and 3-difluoromethyl-N-methoxy-1-methyl-N-[1-methyl-2-(2,4,6-trichlorophenyl)ethyl]pyrazole-4-carboxamide at a ratio of 10:1; a pest control composition comprising any one of the present compounds 1 to 88 and 3-difluoromethyl-N-methoxy-1-methyl-N-[(1R)-1-methyl-2-(2,4,6-trichlorophenyl)ethyl]pyrazole-4-carboxamide at a ratio of 0.1:1; a pest control composition comprising any one of the present compounds 1 to 88 and 3-difluoromethyl-N-methoxy-1-methyl-N-[(1R)-1-methyl-2-(2,4,6-trichlorophenyl)ethyl]pyrazole-4-carboxamide at a ratio of 1:1; a pest control composition comprising any one of the present compounds 1 to 88 and 3-difluoromethyl-N-methoxy-1-methyl-N-[(1R)-1-methyl-2-(2,4,6-trichlorophenyl)ethyl]pyrazole-4-carboxamide at a ratio of 10:1; a pest control composition comprising any one of the present compounds 1 to 88 and 3-difluoromethyl-N-methoxy-1-methyl-N-[(1S)-1-methyl-2-(2,4,6-trichlorophenyl)ethyl]pyrazole-4-carboxamide at a ratio of 0.1:1; a pest control composition comprising any one of the present compounds 1 to 88 and 3-difluoromethyl-N-methoxy-1-methyl-N-[(1S)-1-methyl-2-(2,4,6-trichlorophenyl)ethyl]pyrazole-4-carboxamide at a ratio of 1:1; a pest control composition comprising any one of the present compounds 1 to 88 and 3-difluoromethyl-N-methoxy-1-methyl-N-[(1S)-1-methyl-2-(2,4,6-trichlorophenyl)ethyl]pyrazole-4-carboxamide at a ratio of 10:1;

a pest control composition comprising any one of the present compounds 1 to 88 and 3-butyn-1-yl N-{6-[({(Z)-[(1-methyl-1H-tetrazol-5-yl)phenylmethylene]amino}oxy)methyl]-2-pyridinyl}carbamate at a ratio of 0.1:1; a pest control composition comprising any one of the present compounds 1 to 88 and 3-butyn-1-yl N-{6-[({(Z)-[(1-methyl-1H-tetrazol-5-yl)phenylmethylene]amino}oxy)methyl]-2-pyridinyl}carbamate at a ratio of 1:1; a pest control composition comprising any one of the present compounds 1 to 88 and 3-butyn-1-yl N-{6-[({(Z)-[(1-methyl-1H-tetrazol-5-yl)phenylmethylene]amino}oxy)methyl]-2-pyridinyl}carbamate at a ratio of 10:1; a pest control composition comprising any one of the present compounds 1 to 88 and 5-fluoro-2-[(4-methylphenyl)methoxy]-4-pyrimidineamine at a ratio of 0.1:1; a pest control composition comprising any one of the present compounds 1 to 88 and 5-fluoro-2-[(4-methylphenyl)methoxy]-4-pyrimidineamine at a ratio of 1:1; a pest control composition comprising any one of the present compounds 1 to 88 and 5-fluoro-2-[(4-methylphenyl)methoxy]-4-pyrimidineamine at a ratio of 10:1; a pest control composition comprising any one of the present compounds 1 to 88 and 2-[6-(3-fluoro-4-methoxyphenyl)-5-methylpyridin-2-yl]quinazoline at a ratio of 0.1:1; a pest control composition comprising any one of the present compounds 1 to 88 and 2-[6-(3-fluoro-4-methoxyphenyl)-5-methylpyridin-2-yl]quinazoline at a ratio of 1:1; a pest control composition comprising any one of the present compounds 1 to 88 and 2-[6-(3-fluoro-4-methoxyphenyl)-5-methylpyridin-2-yl]quinazoline at a ratio of 10:1; a pest control composition comprising any one of the present compounds 1 to 88 and azaconazole; a pest control composition comprising any one of the present compounds 1 to 88 and diniconazole-M; a pest control composition comprising any one of the present compounds 1 to 88 and etaconazole; a pest control composition comprising any one of the present compounds 1 to 88 and uniconazole; a pest control composition comprising any one of the present compounds 1 to 88 and (S)-(+)-N-(1,1,3-trimethylindan-4-yl)-1-methyl-3-difluoromethylpyrazole-4-carboxylic acid amide; a pest control composition comprising any one of the present compounds 1 to 88 and benodanil; a pest control composition comprising any one of the present compounds 1 to 88 and fenfuram; a pest control composition comprising any one of the present compounds 1 to 88 and oxycarboxin;

a pest control composition comprising any one of the present compounds 1 to 88 and dodemorph; a pest control composition comprising any one of the present compounds 1 to 88 and piperalin; a pest control composition comprising any one of the present compounds 1 to 88 and thiabendazole; a pest control composition comprising any one of the present compounds 1 to 88 and fuberidazole; a pest control composition comprising any one of the present compounds 1 to 88 and thiophanate; a pest control composition comprising any one of the present compounds 1 to 88 and furalaxyl; a pest control composition comprising any one of the present compounds 1 to 88 and ofurace; a pest control composition comprising any one of the present compounds 1 to 88 and oxadixyl; a pest control composition comprising any one of the present compounds 1 to 88 and flumorph; a pest control composition comprising any one of the present compounds 1 to 88 and dichlofluanid; a pest compounds 1 to 88 and fenoxanil; a pest control composition comprising any one of the present compounds 1 to 88 and acibenzolar-S-methyl; a pest control composition comprising any one of the present compounds 1 to 88 and anilazine; a pest control composition comprising any one of the present compounds 1 to 88 and bethoxazine; a pest control composition comprising any one of the present compounds 1 to 88 and binapacryl; a pest control composition comprising any one of the present compounds 1 to 88 and biphenyl; a pest control composition comprising any one of the present compounds 1 to 88 and blasticidin S; a pest control composition comprising any one of the present compounds 1 to 88 and bupirimate; a pest control composition comprising any one of the present compounds 1 to 88 and captafol; a pest control composition comprising any one of the present compounds 1 to 88 and chloroneb; a pest control composition comprising any one of the present compounds 1 to 88 and dichloran; a pest control composition comprising any one of the present compounds 1 to 88 and diflumetorim; a pest control composition comprising any one of the present compounds 1 to 88 and dimethirimol; a pest control composition comprising any one of the present compounds 1 to 88 and dinocap; a pest control composition comprising any one of the present compounds 1 to 88 and dithianon;

a pest control composition comprising any one of the present compounds 1 to 88 and dodine; a pest control composition comprising any one of the present compounds 1 to 88 and edifenphos; a pest control composition comprising any one of the present compounds 1 to 88 and ethirimol; a pest control composition comprising any one of the present compounds 1 to 88 and etridiazol; a pest control composition comprising any one of the present compounds 1 to 88 and fenarimol; a pest control composition comprising any one of the present compounds 1 to 88 and fentin acetate; a pest control composition comprising any one of the present compounds 1 to 88 and fentin hydroxide; a pest control composition comprising any one of the present compounds 1 to 88 and ferbam; a pest control composition comprising any one of the present compounds 1 to 88 and fluoroimide; a pest control composition comprising any one of the present compounds 1 to 88 and flutianil; a pest control composition comprising any one of the present compounds 1 to 88 and furmecyclox; a pest control composition comprising any one of the present compounds 1 to 88 and iodocarb; a pest control composition comprising any one of the present compounds 1 to 88 and iprobenfos; a pest control composition comprising any one of the present compounds 1 to 88 and meptyldinocap; a pest control composition comprising any one of the present compounds 1 to 88 and methasulfocarb; a pest control composition comprising any one of the present compounds 1 to 88 and metiram; a pest control composition comprising any one of the present compounds 1 to 88 and naftifine; a pest control composition comprising any one of the present compounds 1 to 88 and nuarimol; a pest control composition comprising any one of the present compounds 1 to 88 and octhilinone; a pest control composition comprising any one of the present compounds 1 to 88 and pefurazoate; a pest control composition comprising any one of the present compounds 1 to 88 and phosphorous acid; a compounds 1 to 88 and a sodium salt of phosphorous acid; a pest control composition comprising any one of the present compounds 1 to 88 and an ammonium salt of phosphorous acid; a pest control composition comprising any one of the present compounds 1 to 88 and polyoxin;

a pest control composition comprising any one of the present compounds 1 to 88 and propineb; a pest control composition comprising any one of the present compounds 1 to 88 and prothiocarb; a pest control composition comprising any one of the present compounds 1 to 88 and pyrazophos; a pest control composition comprising any one of the present compounds 1 to 88 and pyributicarb; a pest control composition comprising any one of the present compounds 1 to 88 and pyrifenox; a pest control composition comprising any one of the present compounds 1 to 88 and pyrrolnitrin; a pest control composition comprising any one of the present compounds 1 to 88 and PCNB; a pest control composition comprising any one of the present compounds 1 to 88 and TCNB; a pest control composition comprising any one of the present compounds 1 to 88 and tecloftalam; a pest control composition comprising any one of the present compounds 1 to 88 and terbinafine; a pest control composition comprising any one of the present compounds 1 to 88 and tolylfluanid; a pest control composition comprising any one of the present compounds 1 to 88 and triarimol; a pest control composition comprising any one of the present compounds 1 to 88 and triazoxide; a pest control composition comprising any one of the present compounds 1 to 88 and triforine; a pest control composition comprising any one of the present compounds 1 to 88 and trimoprhamide; a pest control composition comprising any one of the present compounds 1 to 88 and zineb; a pest control composition comprising any one of the present compounds 1 to 88 and ziram; a pest control composition comprising any one of the present compounds 1 to 88 and acephate at a ratio of 1:1; a pest control composition comprising any one of the present compounds 1 to 88 and acephate at a ratio of 1:10; a pest control composition comprising any one of the present compounds 1 to 88 and acephate at a ratio of 1:50; a pest control composition comprising any one of the present compounds 1 to 88 and azamethiphos at a ratio of 1:1; a pest control composition comprising any one of the present compounds 1 to 88 and azamethiphos at a ratio of 1:10; a pest control composition comprising any one of the present compounds 1 to 88 and azamethiphos at a ratio of 1:50; a pest control composition comprising any one of the present compounds 1 to 88 and azinphos-ethyl at a ratio of 1:1; a pest control composition comprising any one of the present compounds 1 to 88 and azinphos-ethyl at a ratio of 1:10; a pest control composition comprising any one of the present compounds 1 to 88 and azinphos-ethyl at a ratio of 1:50; a pest control composition comprising any one of the present compounds 1 to 88 and azinphos-methyl at a ratio of 1:1; a pest control composition comprising any one of the present compounds 1 to 88 and azinphos-methyl at a ratio of 1:10; a pest control composition comprising any one of the present compounds 1 to 88 and azinphos-methyl at a ratio of 1:50; a pest control composition comprising any one of the present compounds 1 to 88 and cadusafos at a ratio of 1:1; a pest control composition comprising any one of the present compounds 1 to 88 and cadusafos at a ratio of 1:10; a pest control composition comprising any one of the present compounds 1 to 88 and cadusafos at a ratio of 1:50; a pest control composition comprising any one of the present compounds 1 to 88 and chlorethoxyfos at a ratio of 1:1; a pest control composition comprising any one of the present compounds 1 to 88 and chlorethoxyfos at a ratio of 1:10; a pest control composition comprising any one of the present compounds 1 to 88 and chlorethoxyfos at a ratio of 1:50; a pest control composition comprising any one of the present compounds 1 to 88 and chlorfenvinphos at a ratio of 1:1; a pest control composition comprising any one of the present compounds 1 to 88 and chlorfenvinphos at a ratio of 1:10; a pest control composition comprising any one of the present compounds 1 to 88 and chlorfenvinphos at a ratio of 1:50; a pest control composition comprising any one of the present compounds 1 to 88 and chlormephos at a ratio of 1:1; a pest control composition comprising any one of the present compounds 1 to 88 and chlormephos at a ratio of 1:10; a pest control composition comprising any one of the present compounds 1 to 88 and chlormephos at a ratio of 1:50; a pest control composition comprising any one of the present compounds 1 to 88 and chlorpyrifos at a ratio of 1:1; a pest control composition comprising any one of the present compounds 1 to 88 and chlorpyrifos at a ratio of 1:10; a pest control composition comprising any one of the present compounds 1 to 88 and chlorpyrifos at a ratio of 1:50; a pest compounds 1 to 88 and chlorpyrifos-methyl at a ratio of 1:1; a pest control composition comprising any one of the present compounds 1 to 88 and chlorpyrifos-methyl at a ratio of 1:10; a pest control composition comprising any one of the present compounds 1 to 88 and chlorpyrifos-methyl at a ratio of 1:50; a pest control composition comprising any one of the present compounds 1 to 88 and coumaphos at a ratio of 1:1; a pest control composition comprising any one of the present compounds 1 to 88 and coumaphos at a ratio of 1:10; a pest control composition comprising any one of the present compounds 1 to 88 and coumaphos at a ratio of 1:50; a pest control composition comprising any one of the present compounds 1 to 88 and cyanophos at a ratio of 1:1; a pest control composition comprising any one of the present compounds 1 to 88 and cyanophos at a ratio of 1:10; a pest control composition comprising any one of the present compounds 1 to 88 and cyanophos at a ratio of 1:50; a pest control composition comprising any one of the present compounds 1 to 88 and demeton-S-methyl at a ratio of 1:1; a pest control composition comprising any one of the present compounds 1 to 88 and demeton-S-methyl at a ratio of 1:10; a pest control composition comprising any one of the present compounds 1 to 88 and demeton-S-methyl at a ratio of 1:50; a pest control composition comprising any one of the present compounds 1 to 88 and diazinon at a ratio of 1:1; a pest control composition comprising any one of the present compounds 1 to 88 and diazinon at a ratio of 1:10; a pest control composition comprising any one of the present compounds 1 to 88 and diazinon at a ratio of 1:50; a pest compounds 1 to 88 and dichlorvos at a ratio of 1:1; a pest control composition comprising any one of the present compounds 1 to 88 and dichlorvos at a ratio of 1:10; a pest control composition comprising any one of the present compounds 1 to 88 and dichlorvos at a ratio of 1:50;
a pest control composition comprising any one of the present compounds 1 to 88 and dicrotophos at a ratio of 1:1; a pest control composition comprising any one of the present compounds 1 to 88 and dicrotophos at a ratio of 1:10; a pest control composition comprising any one of the present compounds 1 to 88 and dicrotophos at a ratio of 1:50; a pest control composition comprising any one of the present compounds 1 to 88 and dimethoate at a ratio of 1:1; a pest control composition comprising any one of the present compounds 1 to 88 and dimethoate at a ratio of 1:10; a pest control composition comprising any one of the present compounds 1 to 88 and dimethoate at a ratio of 1:50; a pest control composition comprising any one of the present compounds 1 to 88 and dimethylvinphos at a ratio of 1:1; a pest control composition comprising any one of the present compounds 1 to 88 and dimethylvinphos at a ratio of 1:10; a pest control composition comprising any one of the present compounds 1 to 88 and dimethylvinphos at a ratio of 1:50; a pest control composition comprising any one of the present compounds 1 to 88 and disulfoton at a ratio of 1:1; a pest control composition comprising any one of the present compounds 1 to 88 and disulfoton at a ratio of 1:10; a pest control composition comprising any one of the present compounds 1 to 88 and disulfoton at a ratio of 1:50; a pest control composition comprising any one of the present compounds 1 to 88 and EPN at a ratio of 1:1; a pest control composition comprising any one of the present compounds 1 to 88 and EPN at a ratio of 1:10; a pest control composition comprising any one of the present compounds 1 to 88 and EPN at a ratio of 1:50; a pest control composition comprising any one of the present compounds 1 to 88 and ethion at a ratio of 1:1; a pest control composition comprising any one of the present compounds 1 to 88 and ethion at a ratio of 1:10; a pest control composition comprising any one of the present compounds 1 to 88 and ethion at a ratio of 1:50; a pest control composition comprising any one of the present compounds 1 to 88 and ethoprophos at a ratio of 1:1; a pest control composition comprising any one of the present compounds 1 to 88 and ethoprophos at a ratio of 1:10; a pest control composition comprising any one of the present compounds 1 to 88 and ethoprophos at a ratio of 1:50; a pest control composition comprising any one of the present compounds 1 to 88 and famphur at a ratio of 1:1; a pest control composition comprising any one of the present compounds 1 to 88 and famphur at a ratio of 1:10; a pest control composition comprising any one of the present compounds 1 to 88 and famphur at a ratio of 1:50; a pest control composition comprising any one of the present compounds 1 to 88 and fenamiphos at a ratio of 1:1; a pest control composition comprising any one of the present compounds 1 to 88 and fenamiphos at a ratio of 1:10; a pest control composition comprising any one of the present compounds 1 to 88 and fenamiphos at a ratio of 1:50; a pest control composition comprising any one of the present compounds 1 to 88 and fenitrothion at a ratio of 1:1; a pest control composition comprising any one of the present compounds 1 to 88 and fenitrothion at a ratio of 1:10; a pest control composition comprising any one of the present compounds 1 to 88 and fenitrothion at a ratio of 1:50; a pest control composition comprising any one of the present compounds 1 to 88 and fenthion at a ratio of 1:1; a pest control composition comprising any one of the present compounds 1 to 88 and fenthion at a ratio of 1:10; a pest control composition comprising any one of the present compounds 1 to 88 and fenthion at a ratio of 1:50; a pest control composition comprising any one of the present compounds 1 to 88 and heptenophos at a ratio of 1:1; a pest control composition comprising any one of the present compounds 1 to 88 and heptenophos at a ratio of 1:10; a pest control composition comprising any one of the present compounds 1 to 88 and heptenophos at a ratio of 1:50; a pest control composition comprising any one of the present compounds 1 to 88 and isofenphos at a ratio of 1:1; a pest control composition comprising any one of the present compounds 1 to 88 and isofenphos at a ratio of 1:10; a pest control composition comprising any one of the present compounds 1 to 88 and isofenphos at a ratio of 1:50; a pest control composition comprising any one of the present compounds 1 to 88 and isocarbophos at a ratio of 1:1; a pest control composition comprising any one of the present compounds 1 to 88 and isocarbophos at a ratio of 1:10; a pest compounds 1 to 88 and isocarbophos at a ratio of 1:50; a pest control composition comprising any one of the present compounds 1 to 88 and isoxathion at a ratio of 1:1; a pest control composition comprising any one of the present compounds 1 to 88 and isoxathion at a ratio of 1:10; a pest control composition comprising any one of the present compounds 1 to 88 and isoxathion at a ratio of 1:50; a pest control composition comprising any one of the present compounds 1 to 88 and malathion at a ratio of 1:1; a pest control composition comprising any one of the present compounds 1 to 88 and malathion at a ratio of 1:10; a pest control composition comprising any one of the present compounds 1 to 88 and malathion at a ratio of 1:50; a pest control composition comprising any one of the present compounds 1 to 88 and mecarbam at a ratio of 1:1; a pest control composition comprising any one of the present compounds 1 to 88 and mecarbam at a ratio of 1:10; a pest control composition comprising any one of the present compounds 1 to 88 and mecarbam at a ratio of 1:50; a pest control composition comprising any one of the present compounds 1 to 88 and methamidophos at a ratio of 1:1; a pest control composition comprising any one of the present compounds 1 to 88 and methamidophos at a ratio of 1:10; a pest control composition comprising any one of the present compounds 1 to 88 and methamidophos at a ratio of 1:50; a pest control composition comprising any one of the present compounds 1 to 88 and methidathion at a ratio of 1:1; a pest control composition comprising any one of the present compounds 1 to 88 and methidathion at a ratio of 1:10; a pest compounds 1 to 88 and methidathion at a ratio of 1:50; a pest control composition comprising any one of the present compounds 1 to 88 and mevinphos at a ratio of 1:1; a pest control composition comprising any one of the present compounds 1 to 88 and mevinphos at a ratio of 1:10; a pest control composition comprising any one of the present compounds 1 to 88 and mevinphos at a ratio of 1:50; a pest control composition comprising any one of the present compounds 1 to 88 and monocrotophos at a ratio of 1:1; a pest control composition comprising any one of the present compounds 1 to 88 and monocrotophos at a ratio of 1:10; a pest control composition comprising any one of the present compounds 1 to 88 and monocrotophos at a ratio of 1:50; a pest control composition comprising any one of the present compounds 1 to 88 and naled at a ratio of 1:1; a pest control composition comprising any one of the present compounds 1 to 88 and naled at a ratio of 1:10; a pest control composition comprising any one of the present compounds 1 to 88 and naled at a ratio of 1:50; a pest control composition comprising any one of the present compounds 1 to 88 and omethoate at a ratio of 1:1; a pest control composition comprising any one of the present compounds 1 to 88 and omethoate at a ratio of 1:10; a pest control composition comprising any one of the present compounds 1 to 88 and omethoate at a ratio of 1:50; a pest control composition comprising any one of the present compounds 1 to 88 and oxydemeton-methyl at a ratio of 1:1; a pest control composition comprising any one of the present compounds 1 to 88 and oxydemeton-methyl at a ratio of 1:10; a compounds 1 to 88 and oxydemeton-methyl at a ratio of 1:50; a pest control composition comprising any one of the present compounds 1 to 88 and parathion at a ratio of 1:1; a pest control composition comprising any one of the present compounds 1 to 88 and parathion at a ratio of 1:10; a pest control composition comprising any one of the present compounds 1 to 88 and parathion at a ratio of 1:50; a pest control composition comprising any one of the present compounds 1 to 88 and methylparathion at a ratio of 1:1; a pest control composition comprising any one of the present compounds 1 to 88 and methylparathion at a ratio of 1:10; a pest control composition comprising any one of the present compounds 1 to 88 and methylparathion at a ratio of 1:50; a pest control composition comprising any one of the present compounds 1 to 88 and phenthoate at a ratio of 1:1; a pest control composition comprising any one of the present compounds 1 to 88 and phenthoate at a ratio of 1:10; a pest control composition comprising any one of the present compounds 1 to 88 and phenthoate at a ratio of 1:50; a pest control composition comprising any one of the present compounds 1 to 88 and phorate at a ratio of 1:1; a pest control composition comprising any one of the present compounds 1 to 88 and phorate at a ratio of 1:10; a pest control composition comprising any one of the present compounds 1 to 88 and phorate at a ratio of 1:50; a pest control composition comprising any one of the present compounds 1 to 88 and phosalone at a ratio of 1:1; a pest control composition comprising any one of the present compounds 1 to 88 and phosalone at a ratio of 1:10; a pest control composition comprising any one of the present compounds 1 to 88 and phosalone at a ratio of 1:50; a pest control composition comprising any one of the present compounds 1 to 88 and phosmet at a ratio of 1:1; a pest control composition comprising any one of the present compounds 1 to 88 and phosmet at a ratio of 1:10; a pest control composition comprising any one of the present compounds 1 to 88 and phosmet at a ratio of 1:50; a pest control composition comprising any one of the present compounds 1 to 88 and phosphamidon at a ratio of 1:1; a pest control composition comprising any one of the present compounds 1 to 88 and phosphamidon at a ratio of 1:10; a pest control composition comprising any one of the present compounds 1 to 88 and phosphamidon at a ratio of 1:50; a pest control composition comprising any one of the present compounds 1 to 88 and phoxim at a ratio of 1:1; a pest control composition comprising any one of the present compounds 1 to 88 and phoxim at a ratio of 1:10; a pest control composition comprising any one of the present compounds 1 to 88 and phoxim at a ratio of 1:50; a pest control composition comprising any one of the present compounds 1 to 88 and pirimiphos-methyl at a ratio of 1:1; a pest control composition comprising any one of the present compounds 1 to 88 and pirimiphos-methyl at a ratio of 1:10; a pest control composition comprising any one of the present compounds 1 to 88 and pirimiphos-methyl at a ratio of 1:50; a pest control composition comprising any one of the present compounds 1 to 88 and profenofos at a ratio of 1:1; a pest compounds 1 to 88 and profenofos at a ratio of 1:10; a pest control composition comprising any one of the present compounds 1 to 88 and profenofos at a ratio of 1:50; a pest control composition comprising any one of the present compounds 1 to 88 and propetamphos at a ratio of 1:1; a pest control composition comprising any one of the present compounds 1 to 88 and propetamphos at a ratio of 1:10; a pest control composition comprising any one of the present compounds 1 to 88 and propetamphos at a ratio of 1:50; a pest control composition comprising any one of the present compounds 1 to 88 and prothiofos at a ratio of 1:1; a pest control composition comprising any one of the present compounds 1 to 88 and prothiofos at a ratio of 1:10; a pest control composition comprising any one of the present compounds 1 to 88 and prothiofos at a ratio of 1:50; a pest control composition comprising any one of the present compounds 1 to 88 and pyraclofos at a ratio of 1:1; a pest control composition comprising any one of the present compounds 1 to 88 and pyraclofos at a ratio of 1:10; a pest control composition comprising any one of the present compounds 1 to 88 and pyraclofos at a ratio of 1:50; a pest control composition comprising any one of the present compounds 1 to 88 and pyridaphenthion at a ratio of 1:1; a pest control composition comprising any one of the present compounds 1 to 88 and pyridaphenthion at a ratio of 1:10; a pest control composition comprising any one of the present compounds 1 to 88 and pyridaphenthion at a ratio of 1:50; a pest control composition comprising any one of the present compounds 1 to 88 and quinalphos at a ratio of 1:1; a pest compounds 1 to 88 and quinalphos at a ratio of 1:10; a pest control composition comprising any one of the present compounds 1 to 88 and quinalphos at a ratio of 1:50; a pest control composition comprising any one of the present compounds 1 to 88 and sulfotep at a ratio of 1:1; a pest control composition comprising any one of the present compounds 1 to 88 and sulfotep at a ratio of 1:10; a pest control composition comprising any one of the present compounds 1 to 88 and sulfotep at a ratio of 1:50; a pest control composition comprising any one of the present compounds 1 to 88 and tebupirimfos at a ratio of 1:1;
a pest control composition comprising any one of the present compounds 1 to 88 and tebupirimfos at a ratio of 1:10; a pest control composition comprising any one of the present compounds 1 to 88 and tebupirimfos at a ratio of 1:50; a pest control composition comprising any one of the present compounds 1 to 88 and temephos at a ratio of 1:1; a pest control composition comprising any one of the present compounds 1 to 88 and temephos at a ratio of 1:10; a pest control composition comprising any one of the present compounds 1 to 88 and temephos at a ratio of 1:50; a pest control composition comprising any one of the present compounds 1 to 88 and terbufos at a ratio of 1:1; a pest control composition comprising any one of the present compounds 1 to 88 and terbufos at a ratio of 1:10; a pest control composition comprising any one of the present compounds 1 to 88 and terbufos at a ratio of 1:50; a pest control composition comprising any one of the present compounds 1 to 88 and tetrachlorvinphos at a ratio of 1:1; a pest control composition comprising any one of the present compounds 1 to 88 and tetrachlorvinphos at a ratio of 1:10; a pest control composition comprising any one of the present compounds 1 to 88 and tetrachlorvinphos at a ratio of 1:50; a pest control composition comprising any one of the present compounds 1 to 88 and thiometon at a ratio of 1:1; a pest control composition comprising any one of the present compounds 1 to 88 and thiometon at a ratio of 1:10; a pest control composition comprising any one of the present compounds 1 to 88 and thiometon at a ratio of 1:50; a pest control composition comprising any one of the present compounds 1 to 88 and triazophos at a ratio of 1:1; a pest control composition comprising any one of the present compounds 1 to 88 and triazophos at a ratio of 1:10; a pest control composition comprising any one of the present compounds 1 to 88 and triazophos at a ratio of 1:50; a pest control composition comprising any one of the present compounds 1 to 88 and trichlorfon at a ratio of 1:1; a pest control composition comprising any one of the present compounds 1 to 88 and trichlorfon at a ratio of 1:10; a pest control composition comprising any one of the present compounds 1 to 88 and trichlorfon at a ratio of 1:50;
a pest control composition comprising any one of the present compounds 1 to 88 and vamidothion at a ratio of 1:1; a pest control composition comprising any one of the present compounds 1 to 88 and vamidothion at a ratio of 1:10; a pest control composition comprising any one of the present compounds 1 to 88 and vamidothion at a ratio of 1:50; a pest compounds 1 to 88 and alanycarb at a ratio of 1:1; a pest control composition comprising any one of the present compounds 1 to 88 and alanycarb at a ratio of 1:10; a pest control composition comprising any one of the present compounds 1 to 88 and alanycarb at a ratio of 1:50; a pest control composition comprising any one of the present compounds 1 to 88 and aldicarb at a ratio of 1:1; a pest control composition comprising any one of the present compounds 1 to 88 and aldicarb at a ratio of 1:10; a pest control composition comprising any one of the present compounds 1 to 88 and aldicarb at a ratio of 1:50; a pest control composition comprising any one of the present compounds 1 to 88 and bendiocarb at a ratio of 1:1; a pest control composition comprising any one of the present compounds 1 to 88 and bendiocarb at a ratio of 1:10; a pest control composition comprising any one of the present compounds 1 to 88 and bendiocarb at a ratio of 1:50; a pest control composition comprising any one of the present compounds 1 to 88 and benfuracarb at a ratio of 1:1; a pest control composition comprising any one of the present compounds 1 to 88 and benfuracarb at a ratio of 1:10; a pest control composition comprising any one of the present compounds 1 to 88 and benfuracarb at a ratio of 1:50; a pest control composition comprising any one of the present compounds 1 to 88 and butocarboxim at a ratio of 1:1; a pest control composition comprising any one of the present compounds 1 to 88 and butocarboxim at a ratio of 1:10; a pest control composition comprising any one of the present compounds 1 to 88 and butocarboxim at a ratio of 1:50; a pest compounds 1 to 88 and butoxycarboxim at a ratio of 1:1; a pest control composition comprising any one of the present compounds 1 to 88 and butoxycarboxim at a ratio of 1:10; a pest control composition comprising any one of the present compounds 1 to 88 and butoxycarboxim at a ratio of 1:50;
a pest control composition comprising any one of the present compounds 1 to 88 and carbaryl at a ratio of 1:1; a pest control composition comprising any one of the present compounds 1 to 88 and carbaryl at a ratio of 1:10; a pest control composition comprising any one of the present compounds 1 to 88 and carbaryl at a ratio of 1:50; a pest control composition comprising any one of the present compounds 1 to 88 and carbofuran at a ratio of 1:1; a pest control composition comprising any one of the present compounds 1 to 88 and carbofuran at a ratio of 1:10; a pest control composition comprising any one of the present compounds 1 to 88 and carbofuran at a ratio of 1:50; a pest control composition comprising any one of the present compounds 1 to 88 and carbosulfan at a ratio of 1:1; a pest control composition comprising any one of the present compounds 1 to 88 and carbosulfan at a ratio of 1:10; a pest control composition comprising any one of the present compounds 1 to 88 and carbosulfan at a ratio of 1:50; a pest control composition comprising any one of the present compounds 1 to 88 and ethiofencarb at a ratio of 1:1; a pest control composition comprising any one of the present compounds 1 to 88 and ethiofencarb at a ratio of 1:10; a pest control composition comprising any one of the present compounds 1 to 88 and ethiofencarb at a ratio of 1:50; a pest control composition comprising any one of the present compounds 1 to 88 and fenobucarb at a ratio of 1:1; a pest control composition comprising any one of the present compounds 1 to 88 and fenobucarb at a ratio of 1:10; a pest control composition comprising any one of the present compounds 1 to 88 and fenobucarb at a ratio of 1:50; a pest control composition comprising any one of the present compounds 1 to 88 and formetanate at a ratio of 1:1; a pest control composition comprising any one of the present compounds 1 to 88 and formetanate at a ratio of 1:10; a pest control composition comprising any one of the present compounds 1 to 88 and formetanate at a ratio of 1:50; a pest control composition comprising any one of the present compounds 1 to 88 and furathiocarb at a ratio of 1:1;
a pest control composition comprising any one of the present compounds 1 to 88 and furathiocarb at a ratio of 1:10; a pest control composition comprising any one of the present compounds 1 to 88 and furathiocarb at a ratio of 1:50; a pest control composition comprising any one of the present compounds 1 to 88 and isoprocarb at a ratio of 1:1; a pest control composition comprising any one of the present compounds 1 to 88 and isoprocarb at a ratio of 1:10; a pest control composition comprising any one of the present compounds 1 to 88 and isoprocarb at a ratio of 1:50; a pest control composition comprising any one of the present compounds 1 to 88 and methiocarb at a ratio of 1:1; a pest control composition comprising any one of the present compounds 1 to 88 and methiocarb at a ratio of 1:10; a pest compounds 1 to 88 and methiocarb at a ratio of 1:50; a pest control composition comprising any one of the present compounds 1 to 88 and methomyl at a ratio of 1:1; a pest control composition comprising any one of the present compounds 1 to 88 and methomyl at a ratio of 1:10; a pest control composition comprising any one of the present compounds 1 to 88 and methomyl at a ratio of 1:50; a pest control composition comprising any one of the present compounds 1 to 88 and metolcarb at a ratio of 1:1; a pest control composition comprising any one of the present compounds 1 to 88 and metolcarb at a ratio of 1:10; a pest control composition comprising any one of the present compounds 1 to 88 and metolcarb at a ratio of 1:50; a pest control composition comprising any one of the present compounds 1 to 88 and oxamyl at a ratio of 1:1; a pest control composition comprising any one of the present compounds 1 to 88 and oxamyl at a ratio of 1:10; a pest control composition comprising any one of the present compounds 1 to 88 and oxamyl at a ratio of 1:50; a pest control composition comprising any one of the present compounds 1 to 88 and pirimicarb at a ratio of 1:1;
a pest control composition comprising any one of the present compounds 1 to 88 and pirimicarb at a ratio of 1:10; a pest control composition comprising any one of the present compounds 1 to 88 and pirimicarb at a ratio of 1:50; a pest control composition comprising any one of the present compounds 1 to 88 and propoxur at a ratio of 1:1; a pest control composition comprising any one of the present compounds 1 to 88 and propoxur at a ratio of 1:10; a pest control composition comprising any one of the present compounds 1 to 88 and propoxur at a ratio of 1:50; a pest control composition comprising any one of the present compounds 1 to 88 and thiodicarb at a ratio of 1:1; a pest control composition comprising any one of the present compounds 1 to 88 and thiodicarb at a ratio of 1:10; a pest control composition comprising any one of the present compounds 1 to 88 and thiodicarb at a ratio of 1:50; a pest control composition comprising any one of the present compounds 1 to 88 and thiofanox at a ratio of 1:1; a pest control composition comprising any one of the present compounds 1 to 88 and thiofanox at a ratio of 1:10; a pest control composition comprising any one of the present compounds 1 to 88 and thiofanox at a ratio of 1:50; a pest control composition comprising any one of the present compounds 1 to 88 and triazamate at a ratio of 1:1; a pest control composition comprising any one of the present compounds 1 to 88 and triazamate at a ratio of 1:10; a pest control composition comprising any one of the present compounds 1 to 88 and triazamate at a ratio of 1:50; a pest control composition comprising any one of the present compounds 1 to 88 and trimethacarb at a ratio of 1:1; a pest control composition comprising any one of the present compounds 1 to 88 and trimethacarb at a ratio of 1:10; a pest control composition comprising any one of the present compounds 1 to 88 and trimethacarb at a ratio of 1:50; a pest control composition comprising any one of the present compounds 1 to 88 and XMC at a ratio of 1:1; a pest control composition comprising any one of the present compounds 1 to 88 and XMC at a ratio of 1:10; a pest control composition comprising any one of the present compounds 1 to 88 and XMC at a ratio of 1:50;
a pest control composition comprising any one of the present compounds 1 to 88 and xylylcarb at a ratio of 1:1; a pest control composition comprising any one of the present compounds 1 to 88 and xylylcarb at a ratio of 1:10; a pest control composition comprising any one of the present compounds 1 to 88 and xylylcarb at a ratio of 1:50; a pest control composition comprising any one of the present compounds 1 to 88 and acrinathrin at a ratio of 0.1:1; a pest control composition comprising any one of the present compounds 1 to 88 and acrinathrin at a ratio of 1:1; a pest control composition comprising any one of the present compounds 1 to 88 and acrinathrin at a ratio of 1:10; a pest control composition comprising any one of the present compounds 1 to 88 and allethrin at a ratio of 0.1:1; a pest control composition comprising any one of the present compounds 1 to 88 and allethrin at a ratio of 1:1; a pest control composition comprising any one of the present compounds 1 to 88 and allethrin at a ratio of 1:10; a pest control composition comprising any one of the present compounds 1 to 88 and bifenthrin at a ratio of 0.1:1; a pest control composition comprising any one of the present compounds 1 to 88 and bifenthrin at a ratio of 1:1; a pest control composition comprising any one of the present compounds 1 to 88 and bifenthrin at a ratio of 1:10; a pest control composition comprising any one of the present compounds 1 to 88 and bioallethrin at a ratio of 0.1:1; a pest compounds 1 to 88 and bioallethrin at a ratio of 1:1; a pest control composition comprising any one of the present compounds 1 to 88 and bioallethrin at a ratio of 1:10; a pest control composition comprising any one of the present compounds 1 to 88 and bioresmethrin at a ratio of 0.1:1; a pest control composition comprising any one of the present compounds 1 to 88 and bioresmethrin at a ratio of 1:1; a pest control composition comprising any one of the present compounds 1 to 88 and bioresmethrin at a ratio of 1:10; a pest control composition comprising any one of the present compounds 1 to 88 and cycloprothrin at a ratio of 0.1:1; a pest control composition comprising any one of the present compounds 1 to 88 and cycloprothrin at a ratio of 1:1; a pest control composition comprising any one of the present compounds 1 to 88 and cycloprothrin at a ratio of 1:10;
a pest control composition comprising any one of the present compounds 1 to 88 and cyfluthrin at a ratio of 0.1:1; a pest control composition comprising any one of the present compounds 1 to 88 and cyfluthrin at a ratio of 1:1; a pest control composition comprising any one of the present compounds 1 to 88 and cyfluthrin at a ratio of 1:10; a pest control composition comprising any one of the present compounds 1 to 88 and beta-cyfluthrin at a ratio of 0.1:1; a pest control composition comprising any one of the present compounds 1 to 88 and beta-cyfluthrin at a ratio of 1:1; a pest control composition comprising any one of the present compounds 1 to 88 and beta-cyfluthrin at a ratio of 1:10; a pest control composition comprising any one of the present compounds 1 to 88 and cyhalothrin at a ratio of 0.1:1; a pest control composition comprising any one of the present compounds 1 to 88 and cyhalothrin at a ratio of 1:1; a pest control composition comprising any one of the present compounds 1 to 88 and cyhalothrin at a ratio of 1:10; a pest control composition comprising any one of the present compounds 1 to 88 and gamma-cyhalothrin at a ratio of 0.1:1; a pest control composition comprising any one of the present compounds 1 to 88 and gamma-cyhalothrin at a ratio of 1:1; a pest control composition comprising any one of the present compounds 1 to 88 and gamma-cyhalothrin at a ratio of 1:10; a pest control composition comprising any one of the present compounds 1 to 88 and lambda-cyhalothrin at a ratio of 0.1:1; a pest control composition comprising any one of the present compounds 1 to 88 and lambda-cyhalothrin at a ratio of 1:1; a pest control composition comprising any one of the present compounds 1 to 88 and lambda-cyhalothrin at a ratio of 1:10; a pest control composition comprising any one of the present compounds 1 to 88 and cypermethrin at a ratio of 0.1:1; a pest control composition comprising any one of the present compounds 1 to 88 and cypermethrin at a ratio of 1:1; a pest control composition comprising any one of the present compounds 1 to 88 and cypermethrin at a ratio of 1:10; a pest control composition comprising any one of the present compounds 1 to 88 and alpha-cypermethrin at a ratio of 0.1:1;
a pest control composition comprising any one of the present compounds 1 to 88 and alpha-cypermethrin at a ratio of 1:1; a pest control composition comprising any one of the present compounds 1 to 88 and alpha-cypermethrin at a ratio of 1:10; a compounds 1 to 88 and beta-cypermethrin at a ratio of 0.1:1; a pest control composition comprising any one of the present compounds 1 to 88 and beta-cypermethrin at a ratio of 1:1; a pest control composition comprising any one of the present compounds 1 to 88 and beta-cypermethrin at a ratio of 1:10; a pest control composition comprising any one of the present compounds 1 to 88 and theta-cypermethrin at a ratio of 0.1:1; a pest control composition comprising any one of the present compounds 1 to 88 and theta-cypermethrin at a ratio of 1:1; a pest control composition comprising any one of the present compounds 1 to 88 and theta-cypermethrin at a ratio of 1:10; a pest control composition comprising any one of the present compounds 1 to 88 and zeta-cypermethrin at a ratio of 0.1:1; a pest control composition comprising any one of the present compounds 1 to 88 and zeta-cypermethrin at a ratio of 1:1; a pest control composition comprising any one of the present compounds 1 to 88 and zeta-cypermethrin at a ratio of 1:10; a pest control composition comprising any one of the present compounds 1 to 88 and cyphenothrin at a ratio of 0.1:1; a pest control composition comprising any one of the present compounds 1 to 88 and cyphenothrin at a ratio of 1:1; a pest control composition comprising any one of the present compounds 1 to 88 and cyphenothrin at a ratio of 1:10; a pest control composition comprising any one of the present compounds 1 to 88 and deltamethrin at a ratio of 0.1:1; a pest control composition comprising any one of the present compounds 1 to 88 and deltamethrin at a ratio of 1:1; a pest control composition comprising any one of the present compounds 1 to 88 and deltamethrin at a ratio of 1:10; a pest compounds 1 to 88 and empenthrin at a ratio of 0.1:1; a pest control composition comprising any one of the present compounds 1 to 88 and empenthrin at a ratio of 1:1; a pest control composition comprising any one of the present compounds 1 to 88 and empenthrin at a ratio of 1:10;
a pest control composition comprising any one of the present compounds 1 to 88 and esfenvalerate at a ratio of 0.1:1; a pest control composition comprising any one of the present compounds 1 to 88 and esfenvalerate at a ratio of 1:1; a pest control composition comprising any one of the present compounds 1 to 88 and esfenvalerate at a ratio of 1:10; a pest control composition comprising any one of the present compounds 1 to 88 and etofenprox at a ratio of 0.1:1; a pest control composition comprising any one of the present compounds 1 to 88 and etofenprox at a ratio of 1:1; a pest control composition comprising any one of the present compounds 1 to 88 and etofenprox at a ratio of 1:10; a pest control composition comprising any one of the present compounds 1 to 88 and fenpropathrin at a ratio of 0.1:1; a pest control composition comprising any one of the present compounds 1 to 88 and fenpropathrin at a ratio of 1:1; a pest control composition comprising any one of the present compounds 1 to 88 and fenpropathrin at a ratio of 1:10; a pest control composition comprising any one of the present compounds 1 to 88 and fenvalerate at a ratio of 0.1:1; a pest control composition comprising any one of the present compounds 1 to 88 and fenvalerate at a ratio of 1:1; a pest control composition comprising any one of the present compounds 1 to 88 and fenvalerate at a ratio of 1:10; a pest control composition comprising any one of the present compounds 1 to 88 and flucythrinate at a ratio of 0.1:1; a pest control composition comprising any one of the present compounds 1 to 88 and flucythrinate at a ratio of 1:1; a pest control composition comprising any one of the present compounds 1 to 88 and flucythrinate at a ratio of 1:10; a pest control composition comprising any one of the present compounds 1 to 88 and flumethrin at a ratio of 0.1:1; a pest control composition comprising any one of the present compounds 1 to 88 and flumethrin at a ratio of 1:1; a pest control composition comprising any one of the present compounds 1 to 88 and flumethrin at a ratio of 1:10; a pest control composition comprising any one of the present compounds 1 to 88 and fluvalinate at a ratio of 0.1:1; a pest control composition comprising any one of the present compounds 1 to 88 and fluvalinate at a ratio of 1:1; a pest control composition comprising any one of the present compounds 1 to 88 and fluvalinate at a ratio of 1:10; a pest control composition comprising any one of the present compounds 1 to 88 and tau-fluvalinate at a ratio of 0.1:1;
a pest control composition comprising any one of the present compounds 1 to 88 and tau-fluvalinate at a ratio of 1:1; a pest control composition comprising any one of the present compounds 1 to 88 and tau-fluvalinate at a ratio of 1:10; a pest control composition comprising any one of the present compounds 1 to 88 and halfenprox at a ratio of 0.1:1; a pest control composition comprising any one of the present compounds 1 to 88 and halfenprox at a ratio of 1:1; a pest compounds 1 to 88 and halfenprox at a ratio of 1:10; a pest control composition comprising any one of the present compounds 1 to 88 and heptafluthrin at a ratio of 0.1:1; a pest control composition comprising any one of the present compounds 1 to 88 and heptafluthrin at a ratio of 1:1; a pest control composition comprising any one of the present compounds 1 to 88 and heptafluthrin at a ratio of 1:10; a pest control composition comprising any one of the present compounds 1 to 88 and imiprothrin at a ratio of 0.1:1; a pest control composition comprising any one of the present compounds 1 to 88 and imiprothrin at a ratio of 1:1; a pest control composition comprising any one of the present compounds 1 to 88 and imiprothrin at a ratio of 1:10; a pest control composition comprising any one of the present compounds 1 to 88 and kadethrin at a ratio of 0.1:1; a pest control composition comprising any one of the present compounds 1 to 88 and kadethrin at a ratio of 1:1; a pest control composition comprising any one of the present compounds 1 to 88 and kadethrin at a ratio of 1:10; a pest control composition comprising any one of the present compounds 1 to 88 and meperfluthrin at a ratio of 0.1:1; a pest control composition comprising any one of the present compounds 1 to 88 and meperfluthrin at a ratio of 1:1; a pest control composition comprising any one of the present compounds 1 to 88 and meperfluthrin at a ratio of 1:10; a pest control composition comprising any one of the present compounds 1 to 88 and momfluorothrin at a ratio of 0.1:1; a pest control composition comprising any one of the present compounds 1 to 88 and momfluorothrin at a ratio of 1:1; a pest control composition comprising any one of the present compounds 1 to 88 and momfluorothrin at a ratio of 1:10; a pest control composition comprising any one of the present compounds 1 to 88 and permethrin at a ratio of 0.1:1; a pest control composition comprising any one of the present compounds 1 to 88 and permethrin at a ratio of 1:1; a pest control composition comprising any one of the present compounds 1 to 88 and permethrin at a ratio of 1:10; a pest control composition comprising any one of the present compounds 1 to 88 and phenothrin at a ratio of 0.1:1; a pest control composition comprising any one of the present compounds 1 to 88 and phenothrin at a ratio of 1:1; a pest control composition comprising any one of the present compounds 1 to 88 and phenothrin at a ratio of 1:10; a pest control composition comprising any one of the present compounds 1 to 88 and prallethrin at a ratio of 0.1:1; a pest control composition comprising any one of the present compounds 1 to 88 and prallethrin at a ratio of 1:1; a pest control composition comprising any one of the present compounds 1 to 88 and prallethrin at a ratio of 1:10; a pest control composition comprising any one of the present compounds 1 to 88 and pyrethrins at a ratio of 0.1:1; a pest control composition comprising any one of the present compounds 1 to 88 and pyrethrins at a ratio of 1:1; a pest control composition comprising any one of the present compounds 1 to 88 and pyrethrins at a ratio of 1:10; a pest control composition comprising any one of the present compounds 1 to 88 and resmethrin at a ratio of 0.1:1; a pest control composition comprising any one of the present compounds 1 to 88 and resmethrin at a ratio of 1:1; a pest control composition comprising any one of the present compounds 1 to 88 and resmethrin at a ratio of 1:10; a pest control composition comprising any one of the present compounds 1 to 88 and silafluofen at a ratio of 0.1:1; a pest control composition comprising any one of the present compounds 1 to 88 and silafluofen at a ratio of 1:1; a pest control composition comprising any one of the present compounds 1 to 88 and silafluofen at a ratio of 1:10; a pest control composition comprising any one of the present compounds 1 to 88 and tefluthrin at a ratio of 0.1:1; a pest control composition comprising any one of the present compounds 1 to 88 and tefluthrin at a ratio of 1:1; a pest control composition comprising any one of the present compounds 1 to 88 and tefluthrin at a ratio of 1:10; a pest control composition comprising any one of the present compounds 1 to 88 and tetramethrin at a ratio of 0.1:1; a pest control composition comprising any one of the present compounds 1 to 88 and tetramethrin at a ratio of 1:1; a pest control composition comprising any one of the present compounds 1 to 88 and tetramethrin at a ratio of 1:10; a pest control composition comprising any one of the present compounds 1 to 88 and tetramethylfluthrin at a ratio of 0.1:1; a pest control composition comprising any one of the present compounds 1 to 88 and tetramethylfluthrin at a ratio of 1:1; a pest control composition comprising any one of the present compounds 1 to 88 and tetramethylfluthrin at a ratio of 1:10; a pest control composition comprising any one of the present compounds 1 to 88 and tralomethrin at a ratio of 0.1:1; a pest compounds 1 to 88 and tralomethrin at a ratio of 1:1; a pest control composition comprising any one of the present compounds 1 to 88 and tralomethrin at a ratio of 1:10; a pest control composition comprising any one of the present compounds 1 to 88 and transfluthrin at a ratio of 0.1:1; a pest control composition comprising any one of the present compounds 1 to 88 and transfluthrin at a ratio of 1:1; a pest control composition comprising any one of the present compounds 1 to 88 and transfluthrin at a ratio of 1:10; a pest control composition comprising any one of the present compounds 1 to 88 and bensultap at a ratio of 1:1; a pest control composition comprising any one of the present compounds 1 to 88 and bensultap at a ratio of 1:10; a pest control composition comprising any one of the present compounds 1 to 88 and bensultap at a ratio of 1:50; a pest control composition comprising any one of the present compounds 1 to 88 and cartap at a ratio of 1:1; a pest control composition comprising any one of the present compounds 1 to 88 and cartap at a ratio of 1:10; a pest control composition comprising any one of the present compounds 1 to 88 and cartap at a ratio of 1:50; a pest control composition comprising any one of the present compounds 1 to 88 and cartap hydrochloride at a ratio of 1:1; a pest control composition comprising any one of the present compounds 1 to 88 and cartap hydrochloride at a ratio of 1:10; a pest control composition comprising any one of the present compounds 1 to 88 and cartap hydrochloride at a ratio of 1:50; a pest control composition comprising any one of the present compounds 1 to 88 and thiocyclam at a ratio of 1:1; a pest control composition comprising any one of the present compounds 1 to 88 and thiocyclam at a ratio of 1:10; a pest control composition comprising any one of the present compounds 1 to 88 and thiocyclam at a ratio of 1:50; a pest control composition comprising any one of the present compounds 1 to 88 and bisultap at a ratio of 1:1; a pest control composition comprising any one of the present compounds 1 to 88 and bisultap at a ratio of 1:10; a pest control composition comprising any one of the present compounds 1 to 88 and bisultap at a ratio of 1:50; a pest control composition comprising any one of the present compounds 1 to 88 and monosultap at a ratio of 1:1; a pest control composition comprising any one of the present compounds 1 to 88 and monosultap at a ratio of 1:10; a pest control composition comprising any one of the present compounds 1 to 88 and monosultap at a ratio of 1:50; a pest control composition comprising any one of the present compounds 1 to 88 and acetamiprid at a ratio of 1:1; a pest control composition comprising any one of the present compounds 1 to 88 and acetamiprid at a ratio of 1:10; a pest control composition comprising any one of the present compounds 1 to 88 and acetamiprid at a ratio of 1:50; a pest control composition comprising any one of the present compounds 1 to 88 and clothianidin at a ratio of 1:1; a pest control composition comprising any one of the present compounds 1 to 88 and clothianidin at a ratio of 1:10; a pest control composition comprising any one of the present compounds 1 to 88 and clothianidin at a ratio of 1:50;
a pest control composition comprising any one of the present compounds 1 to 88 and imidacloprid at a ratio of 1:1; a pest control composition comprising any one of the present compounds 1 to 88 and imidacloprid at a ratio of 1:10; a pest control composition comprising any one of the present compounds 1 to 88 and imidacloprid at a ratio of 1:50; a pest control composition comprising any one of the present compounds 1 to 88 and thiamethoxam at a ratio of 1:1; a pest control composition comprising any one of the present compounds 1 to 88 and thiamethoxam at a ratio of 1:10; a pest control composition comprising any one of the present compounds 1 to 88 and thiamethoxam at a ratio of 1:50; a pest control composition comprising any one of the present compounds 1 to 88 and dinotefuran at a ratio of 1:1; a pest control composition comprising any one of the present compounds 1 to 88 and dinotefuran at a ratio of 1:10; a pest control composition comprising any one of the present compounds 1 to 88 and dinotefuran at a ratio of 1:50; a pest control composition comprising any one of the present compounds 1 to 88 and sulfoxaflor at a ratio of 1:1; a pest control composition comprising any one of the present compounds 1 to 88 and sulfoxaflor at a ratio of 1:10; a pest control composition comprising any one of the present compounds 1 to 88 and sulfoxaflor at a ratio of 1:50; a pest control composition comprising any one of the present compounds 1 to 88 and flupyradifurone at a ratio of 1:1; a pest control composition comprising any one of the present compounds 1 to 88 and flupyradifurone at a ratio of 1:10; a pest control composition comprising any one of the present compounds 1 to 88 and flupyradifurone at a ratio of 1:50; a compounds 1 to 88 and nitenpyram at a ratio of 1:1; a pest control composition comprising any one of the present compounds 1 to 88 and nitenpyram at a ratio of 1:10; a pest control composition comprising any one of the present compounds 1 to 88 and nitenpyram at a ratio of 1:50; a pest control composition comprising any one of the present compounds 1 to 88 and thiacloprid at a ratio of 1:1;
a pest control composition comprising any one of the present compounds 1 to 88 and thiacloprid at a ratio of 1:10; a pest control composition comprising any one of the present compounds 1 to 88 and thiacloprid at a ratio of 1:50; a pest control composition comprising any one of the present compounds 1 to 88 and bistrifluron at a ratio of 0.1:1; a pest control composition comprising any one of the present compounds 1 to 88 and bistrifluron at a ratio of 1:1; a pest control composition comprising any one of the present compounds 1 to 88 and bistrifluron at a ratio of 1:10; a pest control composition comprising any one of the present compounds 1 to 88 and chlorfluazuron at a ratio of 0.1:1; a pest control composition comprising any one of the present compounds 1 to 88 and chlorfluazuron at a ratio of 1:1; a pest control composition comprising any one of the present compounds 1 to 88 and chlorfluazuron at a ratio of 1:10; a pest control composition comprising any one of the present compounds 1 to 88 and diflubenzuron at a ratio of 0.1:1; a pest control composition comprising any one of the present compounds 1 to 88 and diflubenzuron at a ratio of 1:1; a pest control composition comprising any one of the present compounds 1 to 88 and diflubenzuron at a ratio of 1:10; a pest control composition comprising any one of the present compounds 1 to 88 and flucycloxuron at a ratio of 0.1:1; a pest control composition comprising any one of the present compounds 1 to 88 and flucycloxuron at a ratio of 1:1; a pest control composition comprising any one of the present compounds 1 to 88 and flucycloxuron at a ratio of 1:10; a pest control composition comprising any one of the present compounds 1 to 88 and flufenoxuron at a ratio of 0.1:1; a pest control composition comprising any one of the present compounds 1 to 88 and flufenoxuron at a ratio of 1:1; a pest control composition comprising any one of the present compounds 1 to 88 and flufenoxuron at a ratio of 1:10; a pest control composition comprising any one of the present compounds 1 to 88 and hexaflumuron at a ratio of 0.1:1; a pest control composition comprising any one of the present compounds 1 to 88 and hexaflumuron at a ratio of 1:1; a pest control composition comprising any one of the present compounds 1 to 88 and hexaflumuron at a ratio of 1:10;
a pest control composition comprising any one of the present compounds 1 to 88 and lufenuron at a ratio of 0.1:1; a pest control composition comprising any one of the present compounds 1 to 88 and lufenuron at a ratio of 1:1; a pest control composition comprising any one of the present compounds 1 to 88 and lufenuron at a ratio of 1:10; a pest control composition comprising any one of the present compounds 1 to 88 and novaluron at a ratio of 0.1:1; a pest control composition comprising any one of the present compounds 1 to 88 and novaluron at a ratio of 1:1; a pest compounds 1 to 88 and novaluron at a ratio of 1:10; a pest control composition comprising any one of the present compounds 1 to 88 and noviflumuron at a ratio of 0.1:1; a pest control composition comprising any one of the present compounds 1 to 88 and noviflumuron at a ratio of 1:1; a pest control composition comprising any one of the present compounds 1 to 88 and noviflumuron at a ratio of 1:10; a pest control composition comprising any one of the present compounds 1 to 88 and teflubenzuron at a ratio of 0.1:1; a pest control composition comprising any one of the present compounds 1 to 88 and teflubenzuron at a ratio of 1:1; a pest control composition comprising any one of the present compounds 1 to 88 and teflubenzuron at a ratio of 1:10; a pest control composition comprising any one of the present compounds 1 to 88 and triflumuron at a ratio of 0.1:1; a pest control composition comprising any one of the present compounds 1 to 88 and triflumuron at a ratio of 1:1; a pest control composition comprising any one of the present compounds 1 to 88 and triflumuron at a ratio of 1:10; a pest control composition comprising any one of the present compounds 1 to 88 and ethiprole at a ratio of 1:1; a pest control composition comprising any one of the present compounds 1 to 88 and ethiprole at a ratio of 1:10; a pest control composition comprising any one of the present compounds 1 to 88 and ethiprole at a ratio of 1:50; a pest control composition comprising any one of the present compounds 1 to 88 and fipronil at a ratio of 1:1; a pest control composition comprising any one of the present compounds 1 to 88 and fipronil at a ratio of 1:10;
a pest control composition comprising any one of the present compounds 1 to 88 and fipronil at a ratio of 1:50; a pest control composition comprising any one of the present compounds 1 to 88 and flufiprole at a ratio of 1:1; a pest control composition comprising any one of the present compounds 1 to 88 and flufiprole at a ratio of 1:10; a pest control composition comprising any one of the present compounds 1 to 88 and flufiprole at a ratio of 1:50; a pest control composition comprising any one of the present compounds 1 to 88 and chromafenozide at a ratio of 0.1:1; a pest control composition comprising any one of the present compounds 1 to 88 and chromafenozide at a ratio of 1:1; a pest control composition comprising any one of the present compounds 1 to 88 and chromafenozide at a ratio of 1:10; a pest control composition comprising any one of the present compounds 1 to 88 and halofenozide at a ratio of 0.1:1; a pest control composition comprising any one of the present compounds 1 to 88 and halofenozide at a ratio of 1:1; a pest control composition comprising any one of the present compounds 1 to 88 and halofenozide at a ratio of 1:10; a pest control composition comprising any one of the present compounds 1 to 88 and methoxyfenozide at a ratio of 0.1:1; a pest control composition comprising any one of the present compounds 1 to 88 and methoxyfenozide at a ratio of 1:1; a pest control composition comprising any one of the present compounds 1 to 88 and methoxyfenozide at a ratio of 1:10; a pest control composition comprising any one of the present compounds 1 to 88 and tebufenozide at a ratio of 0.1:1; a pest control composition comprising any one of the present compounds 1 to 88 and tebufenozide at a ratio of 1:1; a pest control composition comprising any one of the present compounds 1 to 88 and tebufenozide at a ratio of 1:10; a pest control composition comprising any one of the present compounds 1 to 88 and chlordane at a ratio of 1:1; a pest control composition comprising any one of the present compounds 1 to 88 and chlordane at a ratio of 1:10; a pest control composition comprising any one of the present compounds 1 to 88 and chlordane at a ratio of 1:50; a pest control composition comprising any one of the present compounds 1 to 88 and endosulfan at a ratio of 1:1; a pest control composition comprising any one of the present compounds 1 to 88 and endosulfan at a ratio of 1:10; a pest control composition comprising any one of the present compounds 1 to 88 and endosulfan at a ratio of 1:50; a pest control composition comprising any one of the present compounds 1 to 88 and alpha-endosulfan at a ratio of 1:1; a pest control composition comprising any one of the present compounds 1 to 88 and alpha-endosulfan at a ratio of 1:10; a pest control composition comprising any one of the present compounds 1 to 88 and alpha-endosulfan at a ratio of 1:50; a pest control composition comprising any one of the present compounds 1 to 88 and chlorantraniliprole at a ratio of 1:0.1; a pest control composition comprising any one of the present compounds 1 to 88 and chlorantraniliprole at a ratio of 1:1; a pest control composition comprising any one of the present compounds 1 to 88 and chlorantraniliprole at a ratio of 1:10; a pest control composition comprising any one of the present compounds 1 to 88 and chlorantraniliprole at a ratio of 1:50; a pest control composition comprising any one of the present compounds 1 to 88 and cyantraniliprole at a ratio of 1:0.1; a pest control composition comprising any one of the present compounds 1 to 88 and cyantraniliprole at a ratio of 1:1; a pest control composition comprising any one of the present compounds 1 to 88 and cyantraniliprole at a ratio of 1:10; a pest control composition comprising any one of the present compounds 1 to 88 and cyantraniliprole at a ratio of 1:50; a pest control composition comprising any one of the present compounds 1 to 88 and cycloniliprole at a ratio of 1:0.1; a pest control composition comprising any one of the present compounds 1 to 88 and cycloniliprole at a ratio of 1:1; a pest control composition comprising any one of the present compounds 1 to 88 and cycloniliprole at a ratio of 1:10; a pest control composition comprising any one of the present compounds 1 to 88 and cycloniliprole at a ratio of 1:50;

a pest control composition comprising any one of the present compounds 1 to 88 and flubendiamide at a ratio of 1:0.1; a pest control composition comprising any one of the present compounds 1 to 88 and flubendiamide at a ratio of 1:1; a pest control composition comprising any one of the present compounds 1 to 88 and flubendiamide at a ratio of 1:10; a pest control composition comprising any one of the present compounds 1 to 88 and flubendiamide at a ratio of 1:50; a pest control composition comprising any one of the present compounds 1 to 88 and tetraniliprole at a ratio of 1:0.1; a pest control composition comprising any one of the present compounds 1 to 88 and tetraniliprole at a ratio of 1:1; a pest control composition comprising any one of the present compounds 1 to 88 and tetraniliprole at a ratio of 1:10; a pest control composition comprising any one of the present compounds 1 to 88 and tetraniliprole at a ratio of 1:50; a pest control composition comprising any one of the present compounds 1 to 88 and *Bacillus thuringiensis* var. *aizawai* at a ratio of 1:1; a pest control composition comprising any one of the present compounds 1 to 88 and *Bacillus thuringiensis* var. *aizawai* at a ratio of 1:10; a pest control composition comprising any one of the present compounds 1 to 88 and *Bacillus thuringiensis* var. *aizawai* at a ratio of 1:50; a pest control composition comprising any one of the present compounds 1 to 88 and *Bacillus thuringiensis* var. *kurstaki* at a ratio of 1:1; a pest control composition comprising any one of the present compounds 1 to 88 and *Bacillus thuringiensis* var. *kurstaki* at a ratio of 1:10; a pest control composition comprising any one of the present compounds 1 to 88 and *Bacillus thuringiensis* var. *kurstaki* at a ratio of 1:50; a pest control composition comprising any one of the present compounds 1 to 88 and *Bacillus thuringiensis* var. *israelensis* at a ratio of 1:1; a pest control composition comprising any one of the present compounds 1 to 88 and *Bacillus thuringiensis* var. *israelensis* at a ratio of 1:10; a pest control composition comprising any one of the present compounds 1 to 88 and *Bacillus thuringiensis* var. *israelensis* at a ratio of 1:50;

a pest control composition comprising any one of the present compounds 1 to 88 and *Bacillus thuringiensis* var. *tenebriosis* at a ratio of 1:1; a pest control composition comprising any one of the present compounds 1 to 88 and *Bacillus thuringiensis* var. *tenebriosis* at a ratio of 1:10; a pest control composition comprising any one of the present compounds 1 to 88 and *Bacillus thuringiensis* var. *tenebriosis* at a ratio of 1:50; a pest control composition comprising any one of the present compounds 1 to 88 and *Bacillus* films at a ratio of 1:1; a pest control composition comprising any one of the present compounds 1 to 88 and *Bacillus* films at a ratio of 1:10; a pest control composition comprising any one of the present compounds 1 to 88 and *Bacillus* films at a ratio of 1:50; a pest control composition comprising any one of the present compounds 1 to 88 and *Bacillus sphaericus* at a ratio of 1:1; a pest control composition comprising any one of the present compounds 1 to 88 and *Bacillus sphaericus* at a ratio of 1:10; a pest control composition comprising any one of the present compounds 1 to 88 and *Bacillus sphaericus* at a ratio of 1:50; a pest control composition comprising any one of the present compounds 1 to 88 and *Beauveria bassiana* at a ratio of 1:1; a pest control composition comprising any one of the present compounds 1 to 88 and *Beauveria bassiana* at a ratio of 1:10; a pest control composition comprising any one of the present compounds 1 to 88 and *Beauveria bassiana* at a ratio of 1:50; a pest control composition comprising any one of the present compounds 1 to 88 and *Beauveria Brongniartii* at a ratio of 1:1; a pest control composition comprising any one of the present compounds 1 to 88 and *Beauveria Brongniartii* at a ratio of 1:10; a pest control composition comprising any one of the present compounds 1 to 88 and *Beauveria Brongniartii* at a ratio of 1:50; a pest control composition comprising any one of the present compounds 1 to 88 and *Paecilomyces fumosoroseus* at a ratio of 1:1; a pest control composition comprising any one of the present compounds 1 to 88 and *Paecilomyces fumosoroseus* at a ratio of 1:10; a pest control composition comprising any one of the present compounds 1 to 88 and *Paecilomyces fumosoroseus* at a ratio of 1:50;

a pest control composition comprising any one of the present compounds 1 to 88 and *Paecilomyces lilacinus* at a ratio of 1:1; a pest control composition comprising any one of the present compounds 1 to 88 and *Paecilomyces lilacinus* at a ratio of 1:10; a pest control composition comprising any one of the present compounds 1 to 88 and *Paecilomyces lilacinus* at a ratio of 1:50; a pest control composition comprising any one of the present compounds 1 to 88 and *Paecilomyces tenuipes* at a ratio of 1:1; a pest control composition comprising any one of the present compounds 1 to 88 and *Paecilomyces tenuipes* at a ratio of 1:10; a pest control composition comprising any one of the present compounds 1 to 88 and *Paecilomyces tenuipes* at a ratio of 1:50; a pest control composition comprising any one of the present compounds 1 to 88 and *Trichoderma harzianum* at a ratio of 1:1; a pest control composition comprising any one of the present compounds 1 to 88 and *Trichoderma harzianum* at a ratio of 1:10; a pest control composition comprising any one of the present compounds 1 to 88 and *Trichoderma harzianum* at a ratio of 1:50; a pest control composition comprising any one of the present compounds 1 to 88 and *Verticillium lecanii* at a ratio of 1:1; a pest control composition comprising any one of the present compounds 1 to 88 and *Verticillium lecanii* at a ratio of 1:10; a pest control composition comprising any one of the present compounds 1 to 88 and *Verticillium lecanii* at a ratio of 1:50; a pest control composition comprising any one of the present compounds 1 to 88 and *Pasteuria penetrans* at a ratio of 1:1; a pest control composition comprising any one of the present compounds 1 to 88 and *Pasteuria penetrans* at a ratio of 1:10; a pest control composition comprising any one of the present compounds 1 to 88 and *Pasteuria penetrans* at a ratio of 1:50; a pest control composition comprising any one of the present compounds 1 to 88 and dazomet at a ratio of 1:1; a pest control composition comprising any one of the present compounds 1 to 88 and dazomet at a ratio of 1:10; a pest control composition comprising any one of the present compounds 1 to 88 and dazomet at a ratio of 1:50; a pest control composition comprising any one of the present compounds 1 to 88 and fluensulfone at a ratio of 1:1;

a pest control composition comprising any one of the present compounds 1 to 88 and fluensulfone at a ratio of 1:10; a pest control composition comprising any one of the present compounds 1 to 88 and fluensulfone at a ratio of 1:50; a pest control composition comprising any one of the present compounds 1 to 88 and fosthiazate at a ratio of 1:1; a pest control composition comprising any one of the present compounds 1 to 88 and fosthiazate at a ratio of 1:10; a pest control composition comprising any one of the present compounds 1 to 88 and fosthiazate at a ratio of 1:50; a pest control composition comprising any one of the present compounds 1 to 88 and imicyafos at a ratio of 1:1; a pest control composition comprising any one of the present compounds 1 to 88 and imicyafos at a ratio of 1:10; a pest control composition comprising any one of the present compounds 1 to 88 and imicyafos at a ratio of 1:50; a pest control composition comprising any one of the present compounds 1 to 88 and metam at a ratio of 1:1; a pest control composition comprising any one of the present compounds 1 to 88 and metam at a ratio of 1:10; a pest control composition comprising any one of the present compounds 1 to 88 and metam at a ratio of 1:50; a pest control composition comprising any one of the present compounds 1 to 88 and tartar emetic at a ratio of 1:1; a pest control composition comprising any one of the present compounds 1 to 88 and tartar emetic at a ratio of 1:10; a pest control composition comprising any one of the present compounds 1 to 88 and tartar emetic at a ratio of 1:50; a pest control composition comprising any one of the present compounds 1 to 88 and tioxazafen at a ratio of 1:1; a pest control composition comprising any one of the present compounds 1 to 88 and tioxazafen at a ratio of 1:10; a pest control composition comprising any one of the present compounds 1 to 88 and tioxazafen at a ratio of 1:50; a pest control composition comprising any one of the present compounds 1 to 88 and *Arthrobotrys dactyloydes* at a ratio of 1:1; a pest control composition comprising any one of the present compounds 1 to 88 and *Arthrobotrys dactyloydes* at a ratio of 1:10; a pest control composition comprising any one of the present compounds 1 to 88 and *Arthrobotrys dactyloydes* at a ratio of 1:50;

a pest control composition comprising any one of the present compounds 1 to 88 and *Bacillus megaterium* at a ratio of 1:1; a pest control composition comprising any one of the present compounds 1 to 88 and *Bacillus megaterium* at a ratio of 1:10; a pest control composition comprising any one of the present compounds 1 to 88 and *Bacillus megaterium* at a ratio of 1:50; a pest control composition comprising any one of the present compounds 1 to 88 and *Hirsutella rhossiliensis* at a ratio of 1:1; a pest control composition comprising any one of the present compounds 1 to 88 and *Hirsutella rhossiliensis* at a ratio of 1:10; a pest control composition comprising any one of the present compounds 1 to 88 and *Hirsutella rhossiliensis* at a ratio of 1:50; a pest control composition comprising any one of the present compounds 1 to 88 and *Hirsutella minnesotensis* at a ratio of 1:1; a pest control composition comprising any one of the present compounds 1 to 88 and *Hirsutella minnesotensis* at a ratio of 1:10; a pest control composition comprising any one of the present compounds 1 to 88 and *Hirsutella minnesotensis* at a ratio of 1:50; a pest control composition comprising any one of the present compounds 1 to 88 and *Monacrosporium phymatopagum* at a ratio of 1:1; a pest control composition comprising any one of the present compounds 1 to 88 and *Monacrosporium phymatopagum* at a ratio of 1:10; a pest control composition comprising any one of the present compounds 1 to 88 and *Monacrosporium phymatopagum* at a ratio of 1:50; a pest control composition comprising any one of the present compounds 1 to 88 and *Pasteuria nishizawae* at a ratio of 1:1; a pest control composition comprising any one of the present compounds 1 to 88 and *Pasteuria nishizawae* at a ratio of 1:10; a pest control composition comprising any one of the present compounds 1 to 88 and *Pasteuria nishizawae* at a ratio of 1:50; a pest control composition comprising any one of the present compounds 1 to 88 and *Pasteuria usgae* at a ratio of 1:1; a pest control composition comprising any one of the present compounds 1 to 88 and *Pasteuria usgae* at a ratio of 1:10; a pest control composition comprising any one of the present compounds 1 to 88 and *Pasteuria usgae* at a ratio of 1:50; a pest control composition comprising any one of the present compounds 1 to 88 and *Verticillium chlamydosporium* at a ratio of 1:1; a pest control composition comprising any one of the present compounds 1 to 88 and *Verticillium chlamydosporium* at a ratio of 1:10; a pest control composition comprising any one of the present compounds 1 to 88 and *Verticillium chlamydosporium* at a ratio of 1:50; a pest control composition comprising any one of the present compounds 1 to 88 and Harpin protein at a ratio of 1:1; a pest control composition comprising any one of the present compounds 1 to 88 and Harpin protein at a ratio of 1:10; a pest control composition comprising any one of the present compounds 1 to 88 and Harpin protein at a ratio of 1:50; a pest control composition comprising any one of the present compounds 1 to 88 and 6-bromo-N-{[2-chloro-5-(trifluoromethyl)phenyl]sulfonyl}-imidazo[1,2-a]pyrimidine-2-carboxamide at a ratio of 1:1; a pest control composition comprising any one of the present compounds 1 to 88 and 6-bromo-N-{[2-chloro-5-(trifluoromethyl)phenyl]sulfonyl}-imidazo[1,2-a]pyrimidine-2-carboxamide at a ratio of 1:10; a pest control composition comprising any one of the present compounds 1 to 88 and 6-bromo-N-{[2-chloro-5-(trifluoromethyl)phenyl]sulfonyl}-imidazo[1,2-a]pyrimidine-2-carboxamide at a ratio of 1:50; a pest control composition comprising any one of the present compounds 1 to 88 and 8-chloro-N-[(2-chloro-5-methoxyphenyl)sulfonyl]-6-(trifluoromethyl)-imidazo[1,2-a]pyridine-2-carboxamide at a ratio of 1:1; a pest control composition comprising any one of the present compounds 1 to 88 and 8-chloro-N-[(2-chloro-5-methoxyphenyl)sulfonyl]-6-(trifluoromethyl)-imidazo[1,2-a]pyridine-2-carboxamide at a ratio of 1:10; a pest control composition comprising any one of the present compounds 1 to 88 and 8-chloro-N-[(2-chloro-5-methoxyphenyl)sulfonyl]-6-(trifluoromethyl)-imidazo[1,2-a]pyridine-2-carboxamide at a ratio of 1:50;

a pest control composition comprising any one of the present compounds 1 to 88 and acequinocyl at a ratio of 0.1:1; a pest control composition comprising any one of the present compounds 1 to 88 and acequinocyl at a ratio of 1:1; a pest control composition comprising any one of the present compounds 1 to 88 and acequinocyl at a ratio of 1:10; a pest control composition comprising any one of the present compounds 1 to 88 and amitraz at a ratio of 0.1:1; a pest control composition comprising any one of the present compounds 1 to 88 and amitraz at a ratio of 1:1; a pest control composition comprising any one of the present compounds 1 to 88 and amitraz at a ratio of 1:10; a pest control composition comprising any one of the present compounds 1 to 88 and benzoximate at a ratio of 0.1:1; a pest control composition comprising any one of the present compounds 1 to 88 and benzoximate at a ratio of 1:1; a pest control composition comprising any one of the present compounds 1 to 88 and benzoximate at a ratio of 1:10; a pest control composition comprising any one of the present compounds 1 to 88 and bifenazate at a ratio of 0.1:1; a pest control composition comprising any one of the present compounds 1 to 88 and bifenazate at a ratio of 1:1; a pest control composition comprising any one of the present compounds 1 to 88 and bifenazate at a ratio of 1:10; a pest control composition comprising any one of the present compounds 1 to 88 and bromopropylate at a ratio of 0.1:1; a pest control composition comprising any one of the present compounds 1 to 88 and bromopropylate at a ratio of 1:1; a pest control composition comprising any one of the present compounds 1 to 88 and bromopropylate at a ratio of 1:10; a pest control composition comprising any one of the present compounds 1 to 88 and chinomethionat at a ratio of 0.1:1; a pest control composition comprising any one of the present compounds 1 to 88 and chinomethionat at a ratio of 1:1; a pest control composition comprising any one of the present compounds 1 to 88 and chinomethionat at a ratio of 1:10; a pest control composition comprising any one of the present compounds 1 to 88 and clofentezine at a ratio of 0.1:1;

a pest control composition comprising any one of the present compounds 1 to 88 and clofentezine at a ratio of 1:1; a pest control composition comprising any one of the present compounds 1 to 88 and clofentezine at a ratio of 1:10; a pest control composition comprising any one of the present compounds 1 to 88 and cyenopyrafen at a ratio of 0.1:1; a pest control composition comprising any one of the present compounds 1 to 88 and cyenopyrafen at a ratio of 1:1; a pest control composition comprising any one of the present compounds 1 to 88 and cyenopyrafen at a ratio of 1:10; a pest compounds 1 to 88 and cyflumetofen at a ratio of 0.1:1; a pest control composition comprising any one of the present compounds 1 to 88 and cyflumetofen at a ratio of 1:1; a pest control composition comprising any one of the present compounds 1 to 88 and cyflumetofen at a ratio of 1:10; a pest control composition comprising any one of the present compounds 1 to 88 and cyhexatin at a ratio of 0.1:1; a pest control composition comprising any one of the present compounds 1 to 88 and cyhexatin at a ratio of 1:1; a pest control composition comprising any one of the present compounds 1 to 88 and cyhexatin at a ratio of 1:10; a pest control composition comprising any one of the present compounds 1 to 88 and dicofol at a ratio of 0.1:1; a pest control composition comprising any one of the present compounds 1 to 88 and dicofol at a ratio of 1:1; a pest control composition comprising any one of the present compounds 1 to 88 and dicofol at a ratio of 1:10; a pest control composition comprising any one of the present compounds 1 to 88 and etoxazole at a ratio of 0.1:1; a pest control composition comprising any one of the present compounds 1 to 88 and etoxazole at a ratio of 1:1; a pest control composition comprising any one of the present compounds 1 to 88 and etoxazole at a ratio of 1:10; a pest control composition comprising any one of the present compounds 1 to 88 and fenazaquin at a ratio of 0.1:1; a pest control composition comprising any one of the present compounds 1 to 88 and fenazaquin at a ratio of 1:1;

a pest control composition comprising any one of the present compounds 1 to 88 and fenazaquin at a ratio of 1:10; a pest control composition comprising any one of the present compounds 1 to 88 and fenbutatin oxide at a ratio of 0.1:1; a pest control composition comprising any one of the present compounds 1 to 88 and fenbutatin oxide at a ratio of 1:1; a pest control composition comprising any one of the present compounds 1 to 88 and fenbutatin oxide at a ratio of 1:10; a pest control composition comprising any one of the present compounds 1 to 88 and fenpyroximate at a ratio of 0.1:1; a pest control composition comprising any one of the present compounds 1 to 88 and fenpyroximate at a ratio of 1:1; a pest control composition comprising any one of the present compounds 1 to 88 and fenpyroximate at a ratio of 1:10; a pest control composition comprising any one of the present compounds 1 to 88 and fluacrypyrim at a ratio of 0.1:1; a pest control composition comprising any one of the present compounds 1 to 88 and fluacrypyrim at a ratio of 1:1; a pest control composition comprising any one of the present compounds 1 to 88 and fluacrypyrim at a ratio of 1:10; a pest control composition comprising any one of the present compounds 1 to 88 and fluazuron at a ratio of 0.1:1; a pest control composition comprising any one of the present compounds 1 to 88 and fluazuron at a ratio of 1:1; a pest control composition comprising any one of the present compounds 1 to 88 and fluazuron at a ratio of 1:10; a pest control composition comprising any one of the present compounds 1 to 88 and flufenoxystrobin at a ratio of 0.1:1; a pest control composition comprising any one of the present compounds 1 to 88 and flufenoxystrobin at a ratio of 1:1; a pest control composition comprising any one of the present compounds 1 to 88 and flufenoxystrobin at a ratio of 1:10; a pest control composition comprising any one of the present compounds 1 to 88 and hexythiazox at a ratio of 0.1:1; a pest control composition comprising any one of the present compounds 1 to 88 and hexythiazox at a ratio of 1:1; a pest control composition comprising any one of the present compounds 1 to 88 and hexythiazox at a ratio of 1:10;

a pest control composition comprising any one of the present compounds 1 to 88 and propargite at a ratio of 0.1:1; a pest control composition comprising any one of the present compounds 1 to 88 and propargite at a ratio of 1:1; a pest control composition comprising any one of the present compounds 1 to 88 and propargite at a ratio of 1:10; a pest control composition comprising any one of the present compounds 1 to 88 and pyflubumide at a ratio of 0.1:1; a pest control composition comprising any one of the present compounds 1 to 88 and pyflubumide at a ratio of 1:1; a pest control composition comprising any one of the present compounds 1 to 88 and pyflubumide at a ratio of 1:10; a pest control composition comprising any one of the present compounds 1 to 88 and pyridaben at a ratio of 0.1:1; a pest control composition comprising any one of the present compounds 1 to 88 and pyridaben at a ratio of 1:1; a pest control composition comprising any one of the present compounds 1 to 88 and pyridaben at a ratio of 1:10; a pest control composition comprising any one of the present compounds 1 to 88 and Pyrimidifen at a ratio of 0.1:1; a pest control composition comprising any one of the present compounds 1 to 88 and Pyrimidifen at a ratio of 1:1; a pest compounds 1 to 88 and Pyrimidifen at a ratio of 1:10; a pest control composition comprising any one of the present compounds 1 to 88 and pyriminostrobin at a ratio of 0.1:1; a pest control composition comprising any one of the present compounds 1 to 88 and pyriminostrobin at a ratio of 1:1; a pest control composition comprising any one of the present compounds 1 to 88 and pyriminostrobin at a ratio of 1:10; a pest control composition comprising any one of the present compounds 1 to 88 and spirodiclofen at a ratio of 0.1:1; a pest control composition comprising any one of the present compounds 1 to 88 and spirodiclofen at a ratio of 1:1; a pest control composition comprising any one of the present compounds 1 to 88 and spirodiclofen at a ratio of 1:10; a pest control composition comprising any one of the present compounds 1 to 88 and spiromesifen at a ratio of 0.1:1; a pest control composition comprising any one of the present compounds 1 to 88 and spiromesifen at a ratio of 1:1; a pest control composition comprising any one of the present compounds 1 to 88 and spiromesifen at a ratio of 1:10;

a pest control composition comprising any one of the present compounds 1 to 88 and tebufenpyrad at a ratio of 0.1:1; a pest control composition comprising any one of the present compounds 1 to 88 and tebufenpyrad at a ratio of 1:1; a pest control composition comprising any one of the present compounds 1 to 88 and tebufenpyrad at a ratio of 1:10; a pest control composition comprising any one of the present compounds 1 to 88 and tetradifon at a ratio of 0.1:1; a pest control composition comprising any one of the present compounds 1 to 88 and tetradifon at a ratio of 1:1; a pest control composition comprising any one of the present compounds 1 to 88 and tetradifon at a ratio of 1:10; a pest control composition comprising any one of the present compounds 1 to 88 and abamectin at a ratio of 1:1; a pest control composition comprising any one of the present compounds 1 to 88 and abamectin at a ratio of 1:10; a pest control composition comprising any one of the present compounds 1 to 88 and abamectin at a ratio of 1:50; a pest control composition comprising any one of the present compounds 1 to 88 and emamectin benzoate at a ratio of 1:1; a pest control composition comprising any one of the present compounds 1 to 88 and emamectin benzoate at a ratio of 1:10; a pest control composition comprising any one of the present compounds 1 to 88 and emamectin benzoate at a ratio of 1:50; a pest control composition comprising any one of the present compounds 1 to 88 and lepimectin at a ratio of 1:1; a pest control composition comprising any one of the present compounds 1 to 88 and lepimectin at a ratio of 1:10; a pest control composition comprising any one of the present compounds 1 to 88 and lepimectin at a ratio of 1:50; a pest control composition comprising any one of the present compounds 1 to 88 and milbemectin at a ratio of 1:1; a pest control composition comprising any one of the present compounds 1 to 88 and milbemectin at a ratio of 1:10; a pest control composition comprising any one of the present compounds 1 to 88 and milbemectin at a ratio of 1:50; a pest control composition comprising any one of the present compounds 1 to 88 and spinetoram at a ratio of 1:1; a pest control composition comprising any one of the present compounds 1 to 88 and spinetoram at a ratio of 1:10; a pest control composition comprising any one of the present compounds 1 to 88 and spinetoram at a ratio of 1:50; a pest control composition comprising any one of the present compounds 1 to 88 and spinosad at a ratio of 1:1; a pest control composition comprising any one of the present compounds 1 to 88 and spinosad at a ratio of 1:10; a pest control composition comprising any one of the present compounds 1 to 88 and spinosad at a ratio of 1:50; a pest control composition comprising any one of the present compounds 1 to 88 and afidopyropen at a ratio of 1:1; a pest control composition comprising any one of the present compounds 1 to 88 and afidopyropen at a ratio of 1:10; a pest control composition comprising any one of the present compounds 1 to 88 and afidopyropen at a ratio of 1:50; a pest control composition comprising any one of the present compounds 1 to 88 and aluminum phoshide at a ratio of 1:1; a pest control composition comprising any one of the present compounds 1 to 88 and aluminum phoshide at a ratio of 1:10; a pest control composition comprising any one of the present compounds 1 to 88 and aluminum phoshide at a ratio of 1:50; a pest control composition comprising any one of the present compounds 1 to 88 and calcium phosphide at a ratio of 1:1; a pest control composition comprising any one of the present compounds 1 to 88 and calcium phosphide at a ratio of 1:10; a pest control composition comprising any one of the present compounds 1 to 88 and calcium phosphide at a ratio of 1:50; a pest control composition comprising any one of the present compounds 1 to 88 and hydrogen phosphide at a ratio of 1:1; a compounds 1 to 88 and hydrogen phosphide at a ratio of 1:10; a pest control composition comprising any one of the present compounds 1 to 88 and hydrogen phosphide at a ratio of 1:50; a pest control composition comprising any one of the present compounds 1 to 88 and zinc phosphide at a ratio of 1:1; a pest control composition comprising any one of the present compounds 1 to 88 and zinc phosphide at a ratio of 1:10; a pest control composition comprising any one of the present compounds 1 to 88 and zinc phosphide at a ratio of 1:50;

a pest control composition comprising any one of the present compounds 1 to 88 and azadirachtin at a ratio of 1:1; a pest control composition comprising any one of the present compounds 1 to 88 and azadirachtin at a ratio of 1:10; a pest control composition comprising any one of the present compounds 1 to 88 and azadirachtin at a ratio of 1:50; a pest control composition comprising any one of the present compounds 1 to 88 and buprofezin at a ratio of 1:1; a pest control composition comprising any one of the present compounds 1 to 88 and buprofezin at a ratio of 1:10; a pest control composition comprising any one of the present compounds 1 to 88 and buprofezin at a ratio of 1:50; a pest control composition comprising any one of the present compounds 1 to 88 and chlorfenapyr at a ratio of 1:1; a pest control composition comprising any one of the present compounds 1 to 88 and chlorfenapyr at a ratio of 1:10; a pest control composition comprising any one of the present compounds 1 to 88 and chlorfenapyr at a ratio of 1:50; a pest control composition comprising any one of the present compounds 1 to 88 and chloropicrin at a ratio of 1:1; a pest control composition comprising any one of the present compounds 1 to 88 and chloropicrin at a ratio of 1:10; a pest control composition comprising any one of the present compounds 1 to 88 and chloropicrin at a ratio of 1:50; a pest control composition comprising any one of the present compounds 1 to 88 and cyromazine at a ratio of 1:1; a pest control composition comprising any one of the present compounds 1 to 88 and cyromazine at a ratio of 1:10; a pest control composition comprising any one of the present compounds 1 to 88 and cyromazine at a ratio of 1:50; a pest control composition comprising any one of the present compounds 1 to 88 and diafenthiuron at a ratio of 1:1; a pest control composition comprising any one of the present compounds 1 to 88 and diafenthiuron at a ratio of 1:10; a pest control composition comprising any one of the present compounds 1 to 88 and diafenthiuron at a ratio of 1:50; a pest control composition comprising any one of the present compounds 1 to 88 and DNOC at a ratio of 1:1; a pest control composition comprising any one of the present compounds 1 to 88 and DNOC at a ratio of 1:10; a pest control composition comprising any one of the present compounds 1 to 88 and DNOC at a ratio of 1:50; a pest control composition comprising any one of the present compounds 1 to 88 and fenoxycarb at a ratio of 1:1; a pest control composition comprising any one of the present compounds 1 to 88 and fenoxycarb at a ratio of 1:10; a pest control composition comprising any one of the present compounds 1 to 88 and fenoxycarb at a ratio of 1:50; a pest control composition comprising any one of the present compounds 1 to 88 and flometoquin at a ratio of 1:1; a pest control composition comprising any one of the present compounds 1 to 88 and flometoquin at a ratio of 1:10; a pest control composition comprising any one of the present compounds 1 to 88 and flometoquin at a ratio of 1:50; a pest control composition comprising any one of the present compounds 1 to 88 and flonicamid at a ratio of 1:1; a pest control composition comprising any one of the present compounds 1 to 88 and flonicamid at a ratio of 1:10; a pest control composition comprising any one of the present compounds 1 to 88 and flonicamid at a ratio of 1:50; a pest control composition comprising any one of the present compounds 1 to 88 and hydramethylnon at a ratio of 1:1; a pest control composition comprising any one of the present compounds 1 to 88 and hydramethylnon at a ratio of 1:10; a pest control composition comprising any one of the present compounds 1 to 88 and hydramethylnon at a ratio of 1:50; a pest control composition comprising any one of the present compounds 1 to 88 and hydroprene at a ratio of 1:1; a pest control composition comprising any one of the present compounds 1 to 88 and hydroprene at a ratio of 1:10; a pest control composition comprising any one of the present compounds 1 to 88 and hydroprene at a ratio of 1:50; a pest control composition comprising any one of the present compounds 1 to 88 and indoxacarb at a ratio of 1:1; a pest control composition comprising any one of the present compounds 1 to 88 and indoxacarb at a ratio of 1:10; a pest control composition comprising any one of the present compounds 1 to 88 and indoxacarb at a ratio of 1:50; a pest control composition comprising any one of the present compounds 1 to 88 and kinoprene at a ratio of 1:1;
a pest control composition comprising any one of the present compounds 1 to 88 and kinoprene at a ratio of 1:10; a pest control composition comprising any one of the present compounds 1 to 88 and kinoprene at a ratio of 1:50; a pest control composition comprising any one of the present compounds 1 to 88 and metaflumizone at a ratio of 1:1; a pest control composition comprising any one of the present compounds 1 to 88 and metaflumizone at a ratio of 1:10; a pest control composition comprising any one of the present compounds 1 to 88 and metaflumizone at a ratio of 1:50; a pest control composition comprising any one of the present compounds 1 to 88 and methoprene at a ratio of 1:1; a pest control composition comprising any one of the present compounds 1 to 88 and methoprene at a ratio of 1:10; a pest control composition comprising any one of the present compounds 1 to 88 and methoprene at a ratio of 1:50; a pest control composition comprising any one of the present compounds 1 to 88 and methoxychlor at a ratio of 1:1; a pest control composition comprising any one of the present compounds 1 to 88 and methoxychlor at a ratio of 1:10; a pest control composition comprising any one of the present compounds 1 to 88 and methoxychlor at a ratio of 1:50; a pest control composition comprising any one of the present compounds 1 to 88 and methyl bromide at a ratio of 1:1; a pest control composition comprising any one of the present compounds 1 to 88 and methyl bromide at a ratio of 1:10; a pest control composition comprising any one of the present compounds 1 to 88 and methyl bromide at a ratio of 1:50; a pest control composition comprising any one of the present compounds 1 to 88 and metoxadiazone at a ratio of 1:1; a pest control composition comprising any one of the present compounds 1 to 88 and metoxadiazone at a ratio of 1:10; a pest control composition comprising any one of the present compounds 1 to 88 and metoxadiazone at a ratio of 1:50; a pest control composition comprising any one of the present compounds 1 to 88 and pymetrozine at a ratio of 1:1; a pest control composition comprising any one of the present compounds 1 to 88 and pymetrozine at a ratio of 1:10; a pest control composition comprising any one of the present compounds 1 to 88 and pymetrozine at a ratio of 1:50; a pest control composition comprising any one of the present compounds 1 to 88 and pyrazophos at a ratio of 1:1;
a pest control composition comprising any one of the present compounds 1 to 88 and pyrazophos at a ratio of 1:10; a pest control composition comprising any one of the present compounds 1 to 88 and pyrazophos at a ratio of 1:50; a pest control composition comprising any one of the present compounds 1 to 88 and pyridalyl at a ratio of 1:1; a pest control composition comprising any one of the present compounds 1 to 88 and pyridalyl at a ratio of 1:10; a pest control composition comprising any one of the present compounds 1 to 88 and pyridalyl at a ratio of 1:50; a pest control composition comprising any one of the present compounds 1 to 88 and pyrifluquinazone at a ratio of 1:1; a pest control composition comprising any one of the present compounds 1 to 88 and pyrifluquinazone at a ratio of 1:10; a compounds 1 to 88 and pyrifluquinazone at a ratio of 1:50;

a pest control composition comprising any one of the present compounds 1 to 88 and pyriproxyfen at a ratio of 1:1; a pest control composition comprising any one of the present compounds 1 to 88 and pyriproxyfen at a ratio of 1:10; a pest control composition comprising any one of the present compounds 1 to 88 and pyriproxyfen at a ratio of 1:50; a pest control composition comprising any one of the present compounds 1 to 88 and sodium aluminum fluoride at a ratio of 1:1; a pest control composition comprising any one of the present compounds 1 to 88 and sodium aluminum fluoride at a ratio of 1:10; a pest control composition comprising any one of the present compounds 1 to 88 and sodium aluminum fluoride at a ratio of 1:50; a pest control composition comprising any one of the present compounds 1 to 88 and spirotetramat at a ratio of 1:1; a pest control composition comprising any one of the present compounds 1 to 88 and spirotetramat at a ratio of 1:10; a pest control composition comprising any one of the present compounds 1 to 88 and spirotetramat at a ratio of 1:50; a pest control composition comprising any one of the present compounds 1 to 88 and sulfluramid at a ratio of 1:1; a pest control composition comprising any one of the present compounds 1 to 88 and sulfluramid at a ratio of 1:10;

a pest control composition comprising any one of the present compounds 1 to 88 and sulfluramid at a ratio of 1:50; a pest control composition comprising any one of the present compounds 1 to 88 and sulfuryl fluoride at a ratio of 1:1; a pest control composition comprising any one of the present compounds 1 to 88 and sulfuryl fluoride at a ratio of 1:10; a pest control composition comprising any one of the present compounds 1 to 88 and sulfuryl fluoride at a ratio of 1:50; a pest control composition comprising any one of the present compounds 1 to 88 and tolfenpyrad at a ratio of 1:1; a pest control composition comprising any one of the present compounds 1 to 88 and tolfenpyrad at a ratio of 1:10; a pest control composition comprising any one of the present compounds 1 to 88 and tolfenpyrad at a ratio of 1:50; a pest control composition comprising any one of the present compounds 1 to 88 and triflumezopyrim at a ratio of 1:1; a pest control composition comprising any one of the present compounds 1 to 88 and triflumezopyrim at a ratio of 1:10; a pest control composition comprising any one of the present compounds 1 to 88 and triflumezopyrim at a ratio of 1:50; a pest control composition comprising any one of the present compounds 1 to 88 and 4-oxo-4-(2-phenylethyl)aminobutyric acid at a ratio of 5:1; a pest control composition comprising any one of the present compounds 1 to 88 and 4-oxo-4-(2-phenylethyl)aminobutyric acid at a ratio of 1:10; a pest control composition comprising any one of the present compounds 1 to 88 and 4-oxo-4-(2-phenylethyl)aminobutyric acid at a ratio of 1:50; a pest control composition comprising any one of the present compounds 1 to 88 and methyl 5-(trifluoromethyl)benzo[b]thiophene-2-carboxylate at a ratio of 5:1; a pest control composition comprising any one of the present compounds 1 to 88 and methyl 5-(trifluoromethyl)benzo[b]thiophene-2-carboxylate at a ratio of 1:10; a pest control composition comprising any one of the present compounds 1 to 88 and methyl 5-(trifluoromethyl)benzo[b]thiophene-2-carboxylate at a ratio of 1:50;

a pest control composition comprising any one of the present compounds 1 to 88 and 5-(trifluoromethyl)benzo[b]thiophene-2-carboxylic acid at a ratio of 5:1; a pest control composition comprising any one of the present compounds 1 to 88 and 5-(trifluoromethyl)benzo[b]thiophene-2-carboxylic acid at a ratio of 1:10; a pest control composition comprising any one of the present compounds 1 to 88 and 5-(trifluoromethyl)benzo[b]thiophene-2-carboxylic acid at a ratio of 1:50; a pest control composition comprising any one of the present compounds 1 to 88 and 2,4-D at a ratio of 0.1:1; a pest control composition comprising any one of the present compounds 1 to 88 and 2,4-D at a ratio of 1:1; a pest control composition comprising any one of the present compounds 1 to 88 and 2,4-D at a ratio of 1:20; a pest control composition comprising any one of the present compounds 1 to 88 and 2,4-DB at a ratio of 0.1:1; a pest control composition comprising any one of the present compounds 1 to 88 and 2,4-DB at a ratio of 1:1; a pest control composition comprising any one of the present compounds 1 to 88 and 2,4-DB at a ratio of 1:20; a pest control composition comprising any one of the present compounds 1 to 88 and acetochlor at a ratio of 0.1:1; a pest control composition comprising any one of the present compounds 1 to 88 and acetochlor at a ratio of 1:1; a pest control composition comprising any one of the present compounds 1 to 88 and acetochlor at a ratio of 1:20; a pest control composition comprising any one of the present compounds 1 to 88 and acifluorfen at a ratio of 0.1:1; a pest control composition comprising any one of the present compounds 1 to 88 and acifluorfen at a ratio of 1:1; a pest control composition comprising any one of the present compounds 1 to 88 and acifluorfen at a ratio of 1:20; a pest control composition comprising any one of the present compounds 1 to 88 and alachlor at a ratio of 0.1:1; a pest control composition comprising any one of the present compounds 1 to 88 and alachlor at a ratio of 1:1; a pest control composition comprising any one of the present compounds 1 to 88 and alachlor at a ratio of 1:20; a pest control composition comprising any one of the present compounds 1 to 88 and ametryn at a ratio of 0.1:1; a pest control composition comprising any one of the present compounds 1 to 88 and ametryn at a ratio of 1:1; a pest control composition comprising any one of the present compounds 1 to 88 and ametryn at a ratio of 1:20;

a pest control composition comprising any one of the present compounds 1 to 88 and amicarbazone at a ratio of 0.1:1; a pest control composition comprising any one of the present compounds 1 to 88 and amicarbazone at a ratio of 1:1; a pest control composition comprising any one of the present compounds 1 to 88 and amicarbazone at a ratio of 1:20; a pest control composition comprising any one of the present compounds 1 to 88 and aminopyralid at a ratio of 0.1:1; a pest control composition comprising any one of the present compounds 1 to 88 and aminopyralid at a ratio of 1:1; a pest control composition comprising any one of the present compounds 1 to 88 and aminopyralid at a ratio of 1:20; a pest control composition comprising any one of the present compounds 1 to 88 and atrazine at a ratio of 0.1:1; a pest control composition comprising any one of the present compounds 1 to 88 and atrazine at a ratio of 1:1; a pest control composition comprising any one of the present compounds 1 to 88 and atrazine at a ratio of 1:20; a pest control composition comprising any one of the present compounds 1 to 88 and benefin at a ratio of 0.1:1; a pest control composition comprising any one of the present compounds 1 to 88 and benefin at a ratio of 1:1; a pest control composition comprising any one of the present compounds 1 to 88 and benefin at a ratio of 1:20; a pest control composition comprising any one of the present compounds 1 to 88 and bentazon at a ratio of 0.1:1; a pest control composition comprising any one of the present compounds 1 to 88 and bentazon at a ratio of 1:1; a pest control composition comprising any one of the present compounds 1 to 88 and bentazon at a ratio of 1:20; a pest control composition comprising any one of the present compounds 1 to 88 and bromoxynil at a ratio of 0.1:1; a pest control composition comprising any one of the present compounds 1 to 88 and bromoxynil at a ratio of 1:1; a pest control composition comprising any one of the present compounds 1 to 88 and bromoxynil at a ratio of 1:20; a pest control composition comprising any one of the present compounds 1 to 88 and carfentrazone at a ratio of 0.1:1; a pest control composition comprising any one of the present compounds 1 to 88 and carfentrazone at a ratio of 1:1; a pest control composition comprising any one of the present compounds 1 to 88 and carfentrazone at a ratio of 1:20; a pest control composition comprising any one of the present compounds 1 to 88 and carfentrazone-ethyl at a ratio of 0.1:1; a pest control composition comprising any one of the present compounds 1 to 88 and carfentrazone-ethyl at a ratio of 1:1; a pest control composition comprising any one of the present compounds 1 to 88 and carfentrazone-ethyl at a ratio of 1:20; a pest control composition comprising any one of the present compounds 1 to 88 and chloransulam at a ratio of 0.1:1; a pest control composition comprising any one of the present compounds 1 to 88 and chloransulam at a ratio of 1:1; a pest control composition comprising any one of the present compounds 1 to 88 and chloransulam at a ratio of 1:20; a pest control composition comprising any one of the present compounds 1 to 88 and chlorimuron at a ratio of 0.1:1; a pest control composition comprising any one of the present compounds 1 to 88 and chlorimuron at a ratio of 1:1; a pest control composition comprising any one of the present compounds 1 to 88 and chlorimuron at a ratio of 1:20; a pest control composition comprising any one of the present compounds 1 to 88 and chlorimuron-ethyl at a ratio of 0.1:1; a pest control composition comprising any one of the present compounds 1 to 88 and chlorimuron-ethyl at a ratio of 1:1; a pest control composition comprising any one of the present compounds 1 to 88 and chlorimuron-ethyl at a ratio of 1:20; a pest control composition comprising any one of the present compounds 1 to 88 and chloridazon at a ratio of 0.1:1; a pest control composition comprising any one of the present compounds 1 to 88 and chloridazon at a ratio of 1:1; a pest control composition comprising any one of the present compounds 1 to 88 and chloridazon at a ratio of 1:20; a pest control composition comprising any one of the present compounds 1 to 88 and clethodim at a ratio of 0.1:1; a pest control composition comprising any one of the present compounds 1 to 88 and clethodim at a ratio of 1:1; a pest control composition comprising any one of the present compounds 1 to 88 and clethodim at a ratio of 1:20; a pest control composition comprising any one of the present compounds 1 to 88 and clodinafop at a ratio of 0.1:1; a pest control composition comprising any one of the present compounds 1 to 88 and clodinafop at a ratio of 1:1; a pest control composition comprising any one of the present compounds 1 to 88 and clodinafop at a ratio of 1:20; a pest control composition comprising any one of the present compounds 1 to 88 and clomazone at a ratio of 0.1:1; a pest control composition comprising any one of the present compounds 1 to 88 and clomazone at a ratio of 1:1; a pest control composition comprising any one of the present compounds 1 to 88 and clomazone at a ratio of 1:20; a pest control composition comprising any one of the present compounds 1 to 88 and clopyralid at a ratio of 0.1:1; a pest control composition comprising any one of the present compounds 1 to 88 and clopyralid at a ratio of 1:1; a pest control composition comprising any one of the present compounds 1 to 88 and clopyralid at a ratio of 1:20; a pest control composition comprising any one of the present compounds 1 to 88 and cloransulam-methyl at a ratio of 0.1:1; a pest control composition comprising any one of the present compounds 1 to 88 and cloransulam-methyl at a ratio of 1:1; a compounds 1 to 88 and cloransulam-methyl at a ratio of 1:20; a pest control composition comprising any one of the present compounds 1 to 88 and desmedipham at a ratio of 0.1:1; a pest control composition comprising any one of the present compounds 1 to 88 and desmedipham at a ratio of 1:1; a pest control composition comprising any one of the present compounds 1 to 88 and desmedipham at a ratio of 1:20; a pest control composition comprising any one of the present compounds 1 to 88 and dicamba at a ratio of 0.1:1; a pest control composition comprising any one of the present compounds 1 to 88 and dicamba at a ratio of 1:1; a pest control composition comprising any one of the present compounds 1 to 88 and dicamba at a ratio of 1:20; a pest control composition comprising any one of the present compounds 1 to 88 and diclofop at a ratio of 0.1:1; a pest control composition comprising any one of the present compounds 1 to 88 and diclofop at a ratio of 1:1; a pest control composition comprising any one of the present compounds 1 to 88 and diclofop at a ratio of 1:20; a pest control composition comprising any one of the present compounds 1 to 88 and diclosulam at a ratio of 0.1:1; a pest control composition comprising any one of the present compounds 1 to 88 and diclosulam at a ratio of 1:1; a pest control composition comprising any one of the present compounds 1 to 88 and diclosulam at a ratio of 1:20; a pest control composition comprising any one of the present compounds 1 to 88 and diufenzopyr at a ratio of 0.1:1; a pest control composition comprising any one of the present compounds 1 to 88 and diufenzopyr at a ratio of 1:1; a pest control composition comprising any one of the present compounds 1 to 88 and diufenzopyr at a ratio of 1:20; a pest control composition comprising any one of the present compounds 1 to 88 and dimethenamid at a ratio of 0.1:1; a pest control composition comprising any one of the present compounds 1 to 88 and dimethenamid at a ratio of 1:1; a pest control composition comprising any one of the present compounds 1 to 88 and dimethenamid at a ratio of 1:20; a pest control composition comprising any one of the present compounds 1 to 88 and diquat at a ratio of 0.1:1; a pest control composition comprising any one of the present compounds 1 to 88 and diquat at a ratio of 1:1; a pest control composition comprising any one of the present compounds 1 to 88 and diquat at a ratio of 1:20; a pest control composition comprising any one of the present compounds 1 to 88 and diuron at a ratio of 0.1:1; a pest control composition comprising any one of the present compounds 1 to 88 and diuron at a ratio of 1:1; a pest control composition comprising any one of the present compounds 1 to 88 and diuron at a ratio of 1:20; a pest control composition comprising any one of the present compounds 1 to 88 and EPTC at a ratio of 0.1:1; a pest control composition comprising any one of the present compounds 1 to 88 and EPTC at a ratio of 1:1; a pest control composition comprising any one of the present compounds 1 to 88 and EPTC at a ratio of 1:20;

a pest control composition comprising any one of the present compounds 1 to 88 and ethalfluralin at a ratio of 0.1:1; a pest control composition comprising any one of the present compounds 1 to 88 and ethalfluralin at a ratio of 1:1; a pest control composition comprising any one of the present compounds 1 to 88 and ethalfluralin at a ratio of 1:20; a pest control composition comprising any one of the present compounds 1 to 88 and ethofumesate at a ratio of 0.1:1; a pest control composition comprising any one of the present compounds 1 to 88 and ethofumesate at a ratio of 1:1; a pest control composition comprising any one of the present compounds 1 to 88 and ethofumesate at a ratio of 1:20; a pest control composition comprising any one of the present compounds 1 to 88 and fenoxaprop at a ratio of 0.1:1; a pest control composition comprising any one of the present compounds 1 to 88 and fenoxaprop at a ratio of 1:1; a pest control composition comprising any one of the present compounds 1 to 88 and fenoxaprop at a ratio of 1:20; a pest control composition comprising any one of the present compounds 1 to 88 and fenoxaprop-P-ethyl at a ratio of 0.1:1; a pest control composition comprising any one of the present compounds 1 to 88 and fenoxaprop-P-ethyl at a ratio of 1:1; a pest control composition comprising any one of the present compounds 1 to 88 and fenoxaprop-P-ethyl at a ratio of 1:20; a pest control composition comprising any one of the present compounds 1 to 88 and florasulam at a ratio of 0.1:1; a pest control composition comprising any one of the present compounds 1 to 88 and florasulam at a ratio of 1:1; a pest control composition comprising any one of the present compounds 1 to 88 and florasulam at a ratio of 1:20; a pest control composition comprising any one of the present compounds 1 to 88 and fluazifop-P-butyl at a ratio of 0.1:1; a pest control composition comprising any one of the present compounds 1 to 88 and fluazifop-P-butyl at a ratio of 1:1; a pest control composition comprising any one of the present compounds 1 to 88 and fluazifop-P-butyl at a ratio of 1:20; a pest control composition comprising any one of the present compounds 1 to 88 and flufenacet at a ratio of 0.1:1; a pest control composition comprising any one of the present compounds 1 to 88 and flufenacet at a ratio of 1:1;
a pest control composition comprising any one of the present compounds 1 to 88 and flufenacet at a ratio of 1:20; a pest control composition comprising any one of the present compounds 1 to 88 and flumetsulam at a ratio of 0.1:1; a pest control composition comprising any one of the present compounds 1 to 88 and flumetsulam at a ratio of 1:1; a pest control composition comprising any one of the present compounds 1 to 88 and flumetsulam at a ratio of 1:20; a pest control composition comprising any one of the present compounds 1 to 88 and flumiclorac at a ratio of 0.1:1; a pest control composition comprising any one of the present compounds 1 to 88 and flumiclorac at a ratio of 1:1; a pest control composition comprising any one of the present compounds 1 to 88 and flumiclorac at a ratio of 1:20; a pest control composition comprising any one of the present compounds 1 to 88 and flumioxazin at a ratio of 0.1:1; a pest control composition comprising any one of the present compounds 1 to 88 and flumioxazin at a ratio of 1:1; a pest control composition comprising any one of the present compounds 1 to 88 and flumioxazin at a ratio of 1:20; a pest control composition comprising any one of the present compounds 1 to 88 and fluthiacet at a ratio of 0.1:1; a pest compounds 1 to 88 and fluthiacet at a ratio of 1:1; a pest control composition comprising any one of the present compounds 1 to 88 and fluthiacet at a ratio of 1:20; a pest control composition comprising any one of the present compounds 1 to 88 and fomesafen at a ratio of 0.1:1; a pest control composition comprising any one of the present compounds 1 to 88 and fomesafen at a ratio of 1:1; a pest control composition comprising any one of the present compounds 1 to 88 and fomesafen at a ratio of 1:20; a pest control composition comprising any one of the present compounds 1 to 88 and foramsulfuron at a ratio of 0.1:1; a pest control composition comprising any one of the present compounds 1 to 88 and foramsulfuron at a ratio of 1:1; a pest control composition comprising any one of the present compounds 1 to 88 and foramsulfuron at a ratio of 1:20;
a pest control composition comprising any one of the present compounds 1 to 88 and glufosinate at a ratio of 0.1:1; a pest control composition comprising any one of the present compounds 1 to 88 and glufosinate at a ratio of 1:1; a pest control composition comprising any one of the present compounds 1 to 88 and glufosinate at a ratio of 1:20; a pest control composition comprising any one of the present compounds 1 to 88 and glufosinate ammonium salt at a ratio of 0.1:1; a pest control composition comprising any one of the present compounds 1 to 88 and glufosinate ammonium salt at a ratio of 1:1; a pest control composition comprising any one of the present compounds 1 to 88 and glufosinate ammonium salt at a ratio of 1:20; a pest control composition comprising any one of the present compounds 1 to 88 and glyphosate at a ratio of 0.1:1; a pest control composition comprising any one of the present compounds 1 to 88 and glyphosate at a ratio of 1:1; a pest control composition comprising any one of the present compounds 1 to 88 and glyphosate at a ratio of 1:20; a pest control composition comprising any one of the present compounds 1 to 88 and glyphosate trimesium salt at a ratio of 0.1:1; a pest control composition comprising any one of the present compounds 1 to 88 and glyphosate trimesium salt at a ratio of 1:1; a pest control composition comprising any one of the present compounds 1 to 88 and glyphosate trimesium salt at a ratio of 1:20; a pest control composition comprising any one of the present compounds 1 to 88 and glyphosate isopropylamine salt at a ratio of 0.1:1; a pest control composition comprising any one of the present compounds 1 to 88 and glyphosate isopropylamine salt at a ratio of 1:1; a pest control composition comprising any one of the present compounds 1 to 88 and glyphosate isopropylamine salt at a ratio of 1:20; a pest control composition comprising any one of the present compounds 1 to 88 and glyphosate potassium salt at a ratio of 0.1:1; a pest control composition comprising any one of the present compounds 1 to 88 and glyphosate potassium salt at a ratio of 1:1; a pest control composition comprising any one of the present compounds 1 to 88 and glyphosate potassium salt at a ratio of 1:20; a pest control composition comprising any one of the present compounds 1 to 88 and halosulfuron at a ratio of 0.1:1;
a pest control composition comprising any one of the present compounds 1 to 88 and halosulfuron at a ratio of 1:1; a pest compounds 1 to 88 and halosulfuron at a ratio of 1:20; a pest control composition comprising any one of the present compounds 1 to 88 and halosulfuron-methyl at a ratio of 0.1:1; a pest control composition comprising any one of the present compounds 1 to 88 and halosulfuron-methyl at a ratio of 1:1; a pest control composition comprising any one of the present compounds 1 to 88 and halosulfuron-methyl at a ratio of 1:20; a pest control composition comprising any one of the present compounds 1 to 88 and haloxyfop-R-methyl at a ratio of 0.1:1; a pest control composition comprising any one of the present compounds 1 to 88 and haloxyfop-R-methyl at a ratio of 1:1; a pest control composition comprising any one of the present compounds 1 to 88 and haloxyfop-R-methyl at a ratio of 1:20; a pest control composition comprising any one of the present compounds 1 to 88 and hexazinone at a ratio of 0.1:1; a pest control composition comprising any one of the present compounds 1 to 88 and hexazinone at a ratio of 1:1; a pest control composition comprising any one of the present compounds 1 to 88 and hexazinone at a ratio of 1:20; a pest control composition comprising any one of the present compounds 1 to 88 and imazamox at a ratio of 0.1:1; a pest control composition comprising any one of the present compounds 1 to 88 and imazamox at a ratio of 1:1; a pest control composition comprising any one of the present compounds 1 to 88 and imazamox at a ratio of 1:20; a pest control composition comprising any one of the present compounds 1 to 88 and imazapic at a ratio of 0.1:1; a pest control composition comprising any one of the present compounds 1 to 88 and imazapic at a ratio of 1:1; a pest compounds 1 to 88 and imazapic at a ratio of 1:20; a pest control composition comprising any one of the present compounds 1 to 88 and imazaquine at a ratio of 0.1:1; a pest control composition comprising any one of the present compounds 1 to 88 and imazaquine at a ratio of 1:1; a pest control composition comprising any one of the present compounds 1 to 88 and imazaquine at a ratio of 1:20;

a pest control composition comprising any one of the present compounds 1 to 88 and imazethapyr at a ratio of 0.1:1; a pest control composition comprising any one of the present compounds 1 to 88 and imazethapyr at a ratio of 1:1; a pest control composition comprising any one of the present compounds 1 to 88 and imazethapyr at a ratio of 1:20; a pest control composition comprising any one of the present compounds 1 to 88 and iodosulfuron at a ratio of 0.1:1; a pest control composition comprising any one of the present compounds 1 to 88 and iodosulfuron at a ratio of 1:1; a pest control composition comprising any one of the present compounds 1 to 88 and iodosulfuron at a ratio of 1:20; a pest control composition comprising any one of the present compounds 1 to 88 and isoxaflutole at a ratio of 0.1:1; a pest control composition comprising any one of the present compounds 1 to 88 and isoxaflutole at a ratio of 1:1; a pest control composition comprising any one of the present compounds 1 to 88 and isoxaflutole at a ratio of 1:20; a pest control composition comprising any one of the present compounds 1 to 88 and lactofen at a ratio of 0.1:1; a pest control composition comprising any one of the present compounds 1 to 88 and lactofen at a ratio of 1:1; a pest control composition comprising any one of the present compounds 1 to 88 and lactofen at a ratio of 1:20; a pest control composition comprising any one of the present compounds 1 to 88 and lenacil at a ratio of 0.1:1; a pest control composition comprising any one of the present compounds 1 to 88 and lenacil at a ratio of 1:1; a pest control composition comprising any one of the present compounds 1 to 88 and lenacil at a ratio of 1:20; a pest control composition comprising any one of the present compounds 1 to 88 and linuron at a ratio of 0.1:1; a pest control composition comprising any one of the present compounds 1 to 88 and linuron at a ratio of 1:1; a pest control composition comprising any one of the present compounds 1 to 88 and linuron at a ratio of 1:20; a pest control composition comprising any one of the present compounds 1 to 88 and mesosulfuron at a ratio of 0.1:1;

a pest control composition comprising any one of the present compounds 1 to 88 and mesosulfuron at a ratio of 1:1; a pest control composition comprising any one of the present compounds 1 to 88 and mesosulfuron at a ratio of 1:20; a pest control composition comprising any one of the present compounds 1 to 88 and mesotrione at a ratio of 0.1:1; a pest control composition comprising any one of the present compounds 1 to 88 and mesotrione at a ratio of 1:1; a pest control composition comprising any one of the present compounds 1 to 88 and mesotrione at a ratio of 1:20; a pest control composition comprising any one of the present compounds 1 to 88 and metam at a ratio of 0.1:1; a pest compounds 1 to 88 and metam at a ratio of 1:1; a pest control composition comprising any one of the present compounds 1 to 88 and metam at a ratio of 1:20; a pest control composition comprising any one of the present compounds 1 to 88 and metamitron at a ratio of 0.1:1; a pest control composition comprising any one of the present compounds 1 to 88 and metamitron at a ratio of 1:1; a pest control composition comprising any one of the present compounds 1 to 88 and metamitron at a ratio of 1:20; a pest control composition comprising any one of the present compounds 1 to 88 and metolachlor at a ratio of 0.1:1; a pest control composition comprising any one of the present compounds 1 to 88 and metolachlor at a ratio of 1:1; a pest control composition comprising any one of the present compounds 1 to 88 and metolachlor at a ratio of 1:20; a pest control composition comprising any one of the present compounds 1 to 88 and metribuzin at a ratio of 0.1:1; a pest control composition comprising any one of the present compounds 1 to 88 and metribuzin at a ratio of 1:1; a pest control composition comprising any one of the present compounds 1 to 88 and metribuzin at a ratio of 1:20; a pest control composition comprising any one of the present compounds 1 to 88 and metsulfuron at a ratio of 0.1:1; a pest control composition comprising any one of the present compounds 1 to 88 and metsulfuron at a ratio of 1:1; a pest control composition comprising any one of the present compounds 1 to 88 and metsulfuron at a ratio of 1:20;

a pest control composition comprising any one of the present compounds 1 to 88 and MPCA at a ratio of 0.1:1; a pest control composition comprising any one of the present compounds 1 to 88 and MPCA at a ratio of 1:1; a pest control composition comprising any one of the present compounds 1 to 88 and MPCA at a ratio of 1:20; a pest control composition comprising any one of the present compounds 1 to 88 and MSMA at a ratio of 0.1:1; a pest control composition comprising any one of the present compounds 1 to 88 and MSMA at a ratio of 1:1; a pest control composition comprising any one of the present compounds 1 to 88 and MSMA at a ratio of 1:20; a pest control composition comprising any one of the present compounds 1 to 88 and nicosulfuron at a ratio of 0.1:1; a pest control composition comprising any one of the present compounds 1 to 88 and nicosulfuron at a ratio of 1:1; a pest control composition comprising any one of the present compounds 1 to 88 and nicosulfuron at a ratio of 1:20; a pest control composition comprising any one of the present compounds 1 to 88 and oryzalin at a ratio of 0.1:1; a pest control composition comprising any one of the present compounds 1 to 88 and oryzalin at a ratio of 1:1; a pest control composition comprising any one of the present compounds 1 to 88 and oryzalin at a ratio of 1:20; a pest control composition comprising any one of the present compounds 1 to 88 and oxyfluorfen at a ratio of 0.1:1; a pest control composition comprising any one of the present compounds 1 to 88 and oxyfluorfen at a ratio of 1:1; a pest control composition comprising any one of the present compounds 1 to 88 and oxyfluorfen at a ratio of 1:20; a pest control composition comprising any one of the present compounds 1 to 88 and paraquat at a ratio of 0.1:1; a pest control composition comprising any one of the present compounds 1 to 88 and paraquat at a ratio of 1:1; a pest control composition comprising any one of the present compounds 1 to 88 and paraquat at a ratio of 1:20; a pest control composition comprising any one of the present compounds 1 to 88 and pendimethalin at a ratio of 0.1:1; a pest control composition comprising any one of the present compounds 1 to 88 and pendimethalin at a ratio of 1:1;

a pest control composition comprising any one of the present compounds 1 to 88 and pendimethalin at a ratio of 1:20; a pest control composition comprising any one of the present compounds 1 to 88 and phenmedipham at a ratio of 0.1:1; a pest control composition comprising any one of the present compounds 1 to 88 and phenmedipham at a ratio of 1:1; a pest control composition comprising any one of the present compounds 1 to 88 and phenmedipham at a ratio of 1:20; a pest control composition comprising any one of the present compounds 1 to 88 and picloram at a ratio of 0.1:1; a pest control composition comprising any one of the present compounds 1 to 88 and picloram at a ratio of 1:1; a pest control composition comprising any one of the present compounds 1 to 88 and picloram at a ratio of 1:20; a pest control composition comprising any one of the present compounds 1 to 88 and pyrimisulfuron at a ratio of 0.1:1; a pest control composition comprising any one of the present compounds 1 to 88 and pyrimisulfuron at a ratio of 1:1; a pest control composition comprising any one of the present compounds 1 to 88 and pyrimisulfuron at a ratio of 1:20; a pest control composition comprising any one of the present compounds 1 to 88 and pinoxaden at a ratio of 0.1:1; a pest control composition comprising any one of the present compounds 1 to 88 and pinoxaden at a ratio of 1:1; a pest control composition comprising any one of the present compounds 1 to 88 and pinoxaden at a ratio of 1:20; a pest control composition comprising any one of the present compounds 1 to 88 and prometryn at a ratio of 0.1:1; a pest control composition comprising any one of the present compounds 1 to 88 and prometryn at a ratio of 1:1; a pest control composition comprising any one of the present compounds 1 to 88 and prometryn at a ratio of 1:20; a pest control composition comprising any one of the present compounds 1 to 88 and pyraflufen-ethyl at a ratio of 0.1:1; a pest control composition comprising any one of the present compounds 1 to 88 and pyraflufen-ethyl at a ratio of 1:1; a pest control composition comprising any one of the present compounds 1 to 88 and pyraflufen-ethyl at a ratio of 1:20; a pest control composition comprising any one of the present compounds 1 to 88 and pyrithiobac at a ratio of 0.1:1; a pest control composition comprising any one of the present compounds 1 to 88 and pyrithiobac at a ratio of 1:1; a pest control composition comprising any one of the present compounds 1 to 88 and pyrithiobac at a ratio of 1:20; a pest control composition comprising any one of the present compounds 1 to 88 and pyroxsulam at a ratio of 0.1:1; a pest control composition comprising any one of the present compounds 1 to 88 and pyroxsulam at a ratio of 1:1; a pest control composition comprising any one of the present compounds 1 to 88 and pyroxsulam at a ratio of 1:20; a pest control composition comprising any one of the present compounds 1 to 88 and pyroxasulfone at a ratio of 0.1:1; a pest control composition comprising any one of the present compounds 1 to 88 and pyroxasulfone at a ratio of 1:1; a pest control composition comprising any one of the present compounds 1 to 88 and pyroxasulfone at a ratio of 1:20; a pest control composition comprising any one of the present compounds 1 to 88 and quizalofop-P-ethyl at a ratio of 0.1:1; a pest control composition comprising any one of the present compounds 1 to 88 and quizalofop-P-ethyl at a ratio of 1:1; a pest control composition comprising any one of the present compounds 1 to 88 and quizalofop-P-ethyl at a ratio of 1:20; a pest control composition comprising any one of the present compounds 1 to 88 and salflufenacil at a ratio of 0.1:1; a pest control composition comprising any one of the present compounds 1 to 88 and salflufenacil at a ratio of 1:1; a pest control composition comprising any one of the present compounds 1 to 88 and salflufenacil at a ratio of 1:20; a pest control composition comprising any one of the present compounds 1 to 88 and sethoxydim at a ratio of 0.1:1; a pest control composition comprising any one of the present compounds 1 to 88 and sethoxydim at a ratio of 1:1; a pest control composition comprising any one of the present compounds 1 to 88 and sethoxydim at a ratio of 1:20; a pest control composition comprising any one of the present compounds 1 to 88 and simazine at a ratio of 0.1:1; a pest control composition comprising any one of the present compounds 1 to 88 and simazine at a ratio of 1:1; a pest control composition comprising any one of the present compounds 1 to 88 and simazine at a ratio of 1:20; a pest control composition comprising any one of the present compounds 1 to 88 and sulfentrazone at a ratio of 0.1:1; a pest control composition comprising any one of the present compounds 1 to 88 and sulfentrazone at a ratio of 1:1; a pest control composition comprising any one of the present compounds 1 to 88 and sulfentrazone at a ratio of 1:20; a pest control composition comprising any one of the present compounds 1 to 88 and tebuthiuron at a ratio of 0.1:1; a pest control composition comprising any one of the present compounds 1 to 88 and tebuthiuron at a ratio of 1:1; a pest control composition comprising any one of the present compounds 1 to 88 and tebuthiuron at a ratio of 1:20; a pest control composition comprising any one of the present compounds 1 to 88 and tembotrione at a ratio of 0.1:1; a pest control composition comprising any one of the present compounds 1 to 88 and tembotrione at a ratio of 1:1; a pest control composition comprising any one of the present compounds 1 to 88 and tembotrione at a ratio of 1:20; a pest control composition comprising any one of the present compounds 1 to 88 and tepraloxydim at a ratio of 0.1:1; a pest control composition comprising any one of the present compounds 1 to 88 and tepraloxydim at a ratio of 1:1; a pest control composition comprising any one of the present compounds 1 to 88 and tepraloxydim at a ratio of 1:20; a pest control composition comprising any one of the present compounds 1 to 88 and thifensulfuron at a ratio of 0.1:1; a pest control composition comprising any one of the present compounds 1 to 88 and thifensulfuron at a ratio of 1:1; a pest control composition comprising any one of the present compounds 1 to 88 and thifensulfuron at a ratio of 1:20; a pest control composition comprising any one of the present compounds 1 to 88 and tribenuron-methyl at a ratio of 0.1:1; a pest control composition comprising any one of the present compounds 1 to 88 and tribenuron-methyl at a ratio of 1:1; a pest control composition comprising any one of the present compounds 1 to 88 and tribenuron-methyl at a ratio of 1:20; a pest control composition comprising any one of the present compounds 1 to 88 and triclopyr at a ratio of 0.1:1; a pest control composition comprising any one of the present compounds 1 to 88 and triclopyr at a ratio of 1:1; a pest control composition comprising any one of the present compounds 1 to 88 and triclopyr at a ratio of 1:20; a pest control composition comprising any one of the present compounds 1 to 88 and trifloxysulfuron at a ratio of 0.1:1; a pest control composition comprising any one of the present compounds 1 to 88 and trifloxysulfuron at a ratio of 1:1; a pest control composition comprising any one of the present compounds 1 to 88 and trifloxysulfuron at a ratio of 1:20; a pest control composition comprising any one of the present compounds 1 to 88 and trifluralin at a ratio of 0.1:1; a pest control composition comprising any one of the present compounds 1 to 88 and trifluralin at a ratio of 1:1; a pest control composition comprising any one of the present compounds 1 to 88 and trifluralin at a ratio of 1:20; a pest control composition comprising any one of the present compounds 1 to 88 and triflusulfuron-methyl at a ratio of 0.1:1; a pest control composition comprising any one of the present compounds 1 to 88 and triflusulfuron-methyl at a ratio of 1:1; and a pest control composition comprising any one of the present compounds 1 to 88 and triflusulfuron-methyl at a ratio of 1:20.

Formulation Examples will be shown below. Parts are by weight.

Formulation Example 1

Fifty parts (50 parts) of any one of the present compounds 1 to 88, 3 parts of calcium ligninsulfonate, 2 parts of laurylmagnesium sulfate, and 45 parts of synthetic hydrated silicon oxide are thoroughly ground and mixed to obtain each formulation.

Formulation Example 2

Twenty parts (20 parts) of any one of the present compounds 1 to 88 and 1.5 parts of sorbitan trioleate are mixed with 28.5 parts of an aqueous solution containing 2 parts of polyvinyl alcohol, and the mixture was finely ground by a wet grinding method. Then, 40 parts of an aqueous solution containing 0.05 part of xanthan gum and 0.1 part of aluminum magnesium silicate is added thereto and 10 parts of propylene glycol is further added, followed by stirring and mixing to obtain each formulation.

Formulation Example 3

Two parts (2 parts) of any one of the present compounds 1 to 88, 88 parts of kaolin clay, and 10 parts of talc are thoroughly ground and mixed to obtain each formulation.

Formulation Example 4

Five parts (5 parts) of any one of the present compounds 1 to 88, 14 parts of polyoxyethylene styryl phenyl ether, 6 parts of calcium dodecylbenzenesulfonate, and 75 parts of xylene are thoroughly ground and mixed to obtain each formulation.

Formulation Example 5

Two parts (2 parts) of any one of the present compounds 1 to 88, 1 part of synthetic hydrated silicon oxide, 2 parts of calcium ligninsulfonate, 30 parts of bentonite, and 65 parts of kaolin clay are thoroughly ground and mixed. After the addition of water, the mixture is thoroughly kneaded and further granulated and dried to obtain each formulation.

Formulation Example 6

Ten parts (10 parts) of any one of the present compounds 1 to 88, 35 parts of white carbon containing 50 parts of a polyoxyethylene alkyl ether sulfate ammonium salt, and 55 parts of water were finely ground by a wet grinding method to obtain each formulation.

The following Test Examples will show that the present compounds are useful for controlling plant diseases.

The control effect was evaluated by visually observing the area of lesion spots on each of test plants at the time of investigation, and comparing the area of lesion spots on a plant treated with the present compound with that on an untreated plant.

Test Example 1

Each of plastic pots was filled with sandy loam and rice (cultivar: NIHONBARE) was sowed and grown in a greenhouse for 20 days. Then, each water dilution containing a surfactant prepared by adjusting so as to contain a predetermined concentration (500 ppm) of any one compound of the present compounds 1, 2, 3, 18, 19, 20, 25, 26, 29, 30, and 38 was sprayed over stems and leaves so that it sufficiently adhered to the surface of the leaves of the rice. After spraying, the plant was air-dried and subjected to a spraying treatment and the rice seedling (cultivar: NIHONBARE) infected by the rice blast fungus (*Magnaporthe grisea*) left to stand for 6 days at 24° C. in the daytime and 20° C. at night under high humidity condition, while being in contact with each other, and then the area of lesion spots was investigated. As a result, the lesion areas on the plant treated with the present compound 1, 2, 3, 18, 19, 20, 25, 26, 29, 30, or 38 were 30% or less with respect to the lesion area on the non-treated plant.

Test Example 2

Each of plastic pots was filled with sandy loam and rice (cultivar: NIHONBARE) was sowed and grown in a greenhouse for 20 days. Then, each water dilution containing a surfactant prepared by adjusting so as to contain a predetermined concentration (200 ppm) of any one compound of the present compounds 1, 2, 3, 4, 5, 18, 19, 20, 21, 23, 25, and 26 was sprayed over stems and leaves so that it sufficiently adhered to the surface of the leaves of the rice. After spraying, the plant was air-dried and subjected to a spraying treatment and the rice seedling (cultivar: NIHONBARE) infected by the rice blast fungus (*Magnaporthe grisea*) left to stand for 6 days at 24° C. in the daytime and 20° C. at night under high humidity condition, while being in contact with each other, and then the area of lesion spots was investigated. As a result, the lesion areas on the plant treated with the present compound 1, 2, 3, 4, 5, 18, 19, 20, 21, 23, 25, or 26 were 30% or less with respect to the lesion area on the non-treated plant.

Test Example 3

Each of plastic pots was filled with sandy loam and wheat (cultivar: SHIROGANE) was sowed and grown in a greenhouse for 9 days. Then, each water dilution containing a surfactant prepared by adjusting so as to contain a predetermined concentration (500 ppm) of any one compound of the present compounds 1, 18, 19, 20, 21, 27, 30, and 38 was sprayed over stems and leaves of the wheat so that it sufficiently adhered to the surface of the leaves of the wheat. After spraying, the plant was air-dried so as to dry the dilution on the surface of the leaves. After spraying, the plant was air-dried and cultivated at 20° C. for 5 days under illumination, and then inoculated by sprinkling with spores of wheat rust fungus (*Puccinia recondita*). After the inoculation, the plant was left to stand at 23° C. for one day under dark and high humidity condition, and cultivated under illumination at 20° C. for 8 days, and then the area of lesion spots was investigated. As a result, it has been found that the area of lesion spots on the plant treated with the present compound 1, 18, 19, 20, 21, 27, 30, or 38 was 30% or less of that on an untreated plant.

Test Example 4

Each of plastic pots was filled with sandy loam and wheat (cultivar: SHIROGANE) was sowed and grown in a greenhouse for 9 days. Then, each water dilution containing a surfactant prepared by adjusting so as to contain a predetermined concentration (200 ppm) of any one compound of the present compounds 1, 2, 3, 4, 5, 18, 19, 20, 21, 23, 25, and 26 was sprayed over stems and leaves of the wheat so that it sufficiently adhered to the surface of the leaves of the wheat. After spraying, the plant was air-dried and cultivated at 20° C. for 5 days under illumination, and then inoculated by sprinkling with spores of wheat rust fungus (*Puccinia recondita*). After the inoculation, the plant was left to stand at 23° C. for one day under dark and high humidity condition, and cultivated under illumination at 20° C. for 8 days, and then the area of lesion spots was investigated. As a result, it has been found that the area of lesion spots on the plant treated with the present compound 1, 2, 3, 4, 5, 18, 19, 20, 21, 23, 25, or 26 was 30% or less of that on an untreated plant.

Test Example 5

Each of plastic pots was filled with sandy loam and barley (cultivar: MIKAMO GOLDEN) was sowed and grown in a greenhouse for 7 days. Then, each water dilution containing a surfactant prepared by adjusting so as to contain a predetermined concentration (500 ppm) of any one compound of the present compounds 1, 2, 3, 4, 5, 6, 7, 8, 10, 11, 12, 13, 14, 15, 16, 17, 18, 19, 20, 21, 23, 25, 26, 27, 28, 29, 30, 31, 32, 33, 34, 35, 36, 37, 38, 39, 40, 41, 42, 43, 44, 45, 46, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, and 87 was sprayed over stems and leaves of the barley so that it sufficiently adhered to the surface of the leaves of the barley. After spraying, the plant was air-dried. After 2 days, an aqueous suspension containing spores of barley net blotch fungus (*Pyrenophora teres*) was sprayed to inoculate the spores. After completion of the inoculation, the plant was left to stand for 3 days in a greenhouse at 23° C. in the daytime and 20° C. at night under high humidity condition and cultivated in a greenhouse for 7 days, and then the area of lesion spots was investigated. As a result, the area of lesion spots on the plant treated with the present compound 1, 2, 3, 4, 5, 6, 7, 8, 10, 11, 12, 13, 14, 15, 16, 17, 18, 19, 20, 21, 23, 25, 26, 27, 28, 29, 30, 31, 32, 33, 34, 35, 36, 37, 38, 39, 40, 41, 42, 43, 44, 45, 46, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, or 87 was 30% or less of that on an untreated plant.

Test Example 6

Each of plastic pots was filled with sandy loam and barley (cultivar: MIKAMO GOLDEN) was sowed and grown in a greenhouse for 7 days. Then, each water dilution containing a surfactant prepared by adjusting so as to contain a predetermined concentration (200 ppm) of any one compound of the present compounds 1, 2, 3, 4, 5, 18, 19, 20, 21, 23, 25, and 26 was sprayed over stems and leaves of the barley so that it sufficiently adhered to the surface of the leaves of the barley. After spraying, the plant was air-dried. After 2 days, an aqueous suspension containing spores of barley net blotch fungus (*Pyrenophora teres*) was sprayed to inoculate the spores. After completion of the inoculation, the plant was left to stand for 3 days in a greenhouse at 23° C. in the daytime and 20° C. at night under high humidity condition and cultivated in a greenhouse for 7 days, and then the area of lesion spots was investigated. As a result, the area of lesion spots on the plant treated with the present compound 1, 2, 3, 4, 5, 18, 19, 20, 21, 23, 25, or 26 was 30% or less of that on an untreated plant.

Test Example 7

Each of plastic pots was filled with sandy loam and kidney bean (cultivar: NAGAUZURA SAITOU) was sowed and grown in a greenhouse for 8 days. Then, each water dilution containing a surfactant prepared by adjusting so as to contain a predetermined concentration (500 ppm) of any one compound of the present compounds 1, 2, 3, 4, 5, 18, 19, 20, 21, 22, 23, 25, 26, 27, 29, 37, and 38 was sprayed over stems and leaves of the kidney bean so that it sufficiently adhered to the surface of the leaves of the kidney bean. After spraying, the plant was air-dried and a PDA medium containing hyphae of the kidney bean stem rot fungus (*Sclerotinia sclerotiorum*) was placed on the leaves of the kidney bean. After the inoculation, all kidney beans were left to stand under high humidity condition only at night. Four days after the inoculation, the area of lesion spots was investigated. As a result, the area of lesion spots on the plant treated with the present compound 1, 2, 3, 4, 5, 18, 19, 20, 21, 22, 23, 25, 26, 27, 29, 37, or 38 was 30% or less of that on an untreated plant.

Test Example 8

Each of plastic pots was filled with sandy loam and kidney bean (cultivar: NAGAUZURA SAITOU) was sowed and grown in a greenhouse for 8 days. Then, each water dilution containing a surfactant prepared by adjusting so as to contain a predetermined concentration (200 ppm) of any one compound of the present compounds 1, 2, 3, 4, 5, 18, 19, 20, 21, 23, 25, and 26 was sprayed over stems and leaves of the kidney bean so that it sufficiently adhered to the surface of the leaves of the kidney bean. After spraying, the plant was air-dried and a PDA medium containing hyphae of the kidney bean stem rot fungus (*Sclerotinia sclerotiorum*) was placed on the leaves of the kidney bean. After the inoculation, all kidney beans were left to stand under high humidity condition only at night. Four days after the inoculation, the area of lesion spots was investigated. As a result, the area of lesion spots on the plant treated with the present compound 1, 2, 3, 4, 5, 18, 19, 20, 21, 23, 25, or 26 was 30% or less of that on an untreated plant.

Test Example 9

Each of plastic pots was filled with sandy loam and wheat (cultivar: APOGEE) was sowed and grown in a greenhouse for 10 days. Then, each water dilution containing a surfactant prepared by adjusting so as to contain a predetermined concentration (500 ppm) of any one compound of the present compounds 1, 2, 3, 4, 5, 6, 7, 8, 10, 11, 12, 13, 14, 15, 16, 17, 18, 19, 20, 21, 23, 25, 26, 27, 29, 30, 31, 32, 33, 34, 35, 37, 38, 39, 40, 41, 42, 43, 44, 46, 48, 49, 50, 51, 52, 53, 54, 55, 56, 57, 58, 59, 60, 61, and 62 was sprayed over stems and leaves of the wheat so that it sufficiently adhered to the surface of the leaves of the wheat. After spraying, the plant was air-dried. After 4 days, an aqueous suspension containing spores of wheat leaf blotch fungus (*Septoria tritici*) was sprayed to inoculate the spores. After completion of the inoculation, the plant was left to stand at 18° C. under high humidity condition for 3 days and left to stand under illumination for 14 to 18 days, and then the area of lesion spots was investigated. As a result, the area of lesion spots

Test Example 10

Each of plastic pots was filled with sandy loam and wheat (cultivar: APOGEE) was sowed and grown in a greenhouse for 10 days. Then, each water dilution containing a surfactant prepared by adjusting so as to contain a predetermined concentration (200 ppm) of any one compound of the present compounds 1, 2, 3, 4, 5, 18, 19, 20, 21, 23, 24, 25, and 26 was sprayed over stems and leaves of the wheat so that it sufficiently adhered to the surface of the leaves of the wheat. After spraying, the plant was air-dried. After 4 days, an aqueous suspension containing spores of wheat leaf blotch fungus (Septoria tritici) was sprayed to inoculate the spores. After completion of the inoculation, the plant was left to stand at 18° C. under high humidity condition for 3 days and left to stand under illumination for 14 to 18 days, and then the area of lesion spots was investigated. As a result, the area of lesion spots on the plant treated with the present compound 1, 2, 3, 4, 5, 18, 19, 20, 21, 23, 24, 25, or 26 was 30% or less of that on an untreated plant.

Test Example 11

Each of plastic pots was filled with sandy loam and wheat (cultivar: APOGEE) was sowed and grown in a greenhouse for 10 days. Then, an aqueous suspension containing spores of wheat leaf blotch fungus (Septoria tritici) was sprayed to inoculate the spores. The wheat was left to stand at 18° C. under high humidity condition for 3 days, and then air-dried. Each water dilution containing a surfactant prepared by adjusting so as to contain a predetermined concentration (200 ppm) of any one compound of the present compounds 1, 3, 4, 19, 20, 21, 23, and 26 was sprayed over stems and leaves of the wheat so that it sufficiently adhered to the surface of the leaves of the wheat. After spraying, the plant was air-dried and left to stand under illumination for 14 to 18 days, and then the area of lesion spots was investigated. As a result, the area of lesion spots on the plant treated with the present compound 1, 3, 4, 19, 20, 21, 23, or 26 was 30% or less of that on an untreated plant.

Test Example 12

Each of plastic pots was filled with sandy loam and cucumber (cultivar: SAGAMI HANJIRO) was sowed and grown in a greenhouse for 12 days. Then, each water dilution containing a surfactant prepared by adjusting so as to contain a predetermined concentration (500 ppm) of any one compound of the present compounds 1, 2, 3, 4, 5, 6, 7, 8, 9, 10, 11, 12, 13, 14, 15, 16, 17, 18, 19, 20, 21, 23, 25, 26, 27, 28, 29, 30, 31, 32, 33, 34, 35, 36, 37, 38, 39, 40, 41, 42, 43, 44, 45, 46, 48, 49, 50, 51, 52, 53, 54, 55, 56, 57, 58, 59, 60, 61, or 62 was sprayed over stems and leaves of the cucumber so that it sufficiently adhered to the surface of the leaves of the cucumber. After spraying, the plant was air-dried and then inoculated by sprinkling with spores of cucumber powdery mildew fungus (Sphaerotheca fuliginea). After the inoculation, the plant was cultivated in a greenhouse at 24° C. in the daytime and 20° C. at night for 8 days, and then the area of lesion spots was investigated. As a result, the area of lesion spots on the plant treated with the present compound 1, 2, 3, 4, 5, 6, 7, 8, 9, 10, 11, 12, 13, 14, 15, 16, 17, 18, 19, 20, 21, 23, 25, 26, 27, 28, 29, 30, 31, 32, 33, 34, 35, 36, 37, 38, 39, 40, 41, 42, 43, 44, 45, 46, 48, 49, 50, 51, 52, 53, 54, 55, 56, 57, 58, 59, 60, 61, or 62 was 30% or less of that on an untreated plant.

Test Example 13

Each of plastic pots was filled with sandy loam and cucumber (cultivar: SAGAMI HANJIRO) was sowed and grown in a greenhouse for 12 days. Then, each water dilution containing a surfactant prepared by adjusting so as to contain a predetermined concentration (200 ppm) of any one compound of the present compounds 1, 2, 3, 4, 5, 18, 19, 20, 21, 22, 24, 25, and 26 was sprayed over stems and leaves of the cucumber so that it sufficiently adhered to the surface of the leaves of the cucumber. After spraying, the plant was air-dried and then inoculated by sprinkling with spores of cucumber powdery mildew fungus (Sphaerotheca fuliginea). After the inoculation, the plant was cultivated in a greenhouse at 24° C. in the daytime and 20° C. at night for 8 days, and then the area of lesion spots was investigated. As a result, the area of lesion spots on the plant treated with the present compound 1, 2, 3, 4, 5, 18, 19, 20, 21, 22, 24, 25, or 26 was 30% or less of that on an untreated plant.

Test Example 14

Each of plastic pots was filled with sandy loam and soybean (cultivar: KUROSENGOKU) was sowed and grown in a greenhouse for 13 days. Then, each water dilution containing a surfactant prepared by adjusting so as to contain a predetermined concentration (200 ppm) of any one compound of the present compounds 1, 2, 3, 4, 5, 19, 20, 21, 23, 25, and 26 was sprayed over stems and leaves of the soybean so that it sufficiently adhered to the surface of the leaves of the soybean. After spraying, the plant was air-dried. After 2 days, an aqueous suspension containing spores of soybean rust fungus (Phakopsora pachyrhizi) was sprayed to inoculate the spores. After completion of the inoculation, the plant was left to stand for 3 days in a greenhouse at 23° C. in the daytime and 20° C. at night under high humidity condition and cultivated in a greenhouse for 14 days, and then the area of lesion spots was investigated. As a result, it has been found that the area of lesion spots on the plant treated with the present compound 1, 2, 3, 4, 5, 19, 20, 21, 23, 25, or 26 was 30% or less of that on an untreated plant.

Test Example 15

Each of plastic pots was filled with sandy loam and barley (cultivar: MIKAMO GOLDEN) was sowed and grown in a greenhouse for 7 days. Then, each water dilution containing a surfactant prepared by adjusting so as to contain a predetermined concentration (200 ppm) of any one compound of the present compounds 1, 2, 3, 4, 5, 18, 19, 20, 21, 22, 23, 24, 25, and 26 was sprayed over stems and leaves of the barley so that it sufficiently adhered to the surface of the leaves of the barley. After spraying, the plant was air-dried. After 2 days, an aqueous suspension containing spores of barley leaf blotch fungus (Rhynchosporium secalis) was sprayed to inoculate the spores. After completion of the inoculation, the plant was left to stand for 3 days in a greenhouse at 23° C. in the daytime and 20° C. at night under high humidity condition and cultivated in a greenhouse for 7 days, and then the area of lesion spots was investigated. As a result, the area of lesion spots on the plant treated with the present compound 1, 2, 3, 4, 5, 18, 19, 20, 21, 22, 23, 24, 25, or 26 was 30% or less of that on an untreated plant.

Test Example 16

Each of plastic pots was filled with sandy loam and tomato (cultivar: PATIO) was sowed and grown in a greenhouse for 20 days. Then, each water dilution containing a surfactant prepared by adjusting so as to contain a predetermined concentration (200 ppm) of any one compound of the present compounds 1, 4, and 26 was sprayed over stems and leaves of the tomato seedling so that it sufficiently adhered to the surface of the leaves of the tomato seedling. After air-drying so as to dry the dilution on the leaves, an aqueous suspension containing spores of tomato late blight fungus (*Phytophthora infestans*) was sprayed to inoculate the spores. After completion of the inoculation, the seedling was at first left to stand at 23° C. under high humidity condition for one day and then cultivated in an air-conditioned room at 20° C. for 4 days. Thereafter, the area of lesion spots was investigated. As a result, it has been found that the area of lesion spots on the plant treated with the present compound 1, 4, or 26 was 30% or less of that on an untreated plant.

Test Example 17

Each of plastic pots was filled with sandy loam and cucumber (cultivar: SAGAMI HANJIRO) was sowed and grown in a greenhouse for 19 days. Then, each water dilution containing a surfactant prepared by adjusting so as to contain a predetermined concentration (200 ppm) of any one compound of the present compounds 18, 19, 20, 21, 23, and 26 was sprayed over stems and leaves of the cucumber so that it sufficiently adhered to the surface of the leaves of the cucumber. After spraying, the plant was air-dried. After one day, the plant was inoculated by sprinkling with spores of cucumber target leaf spot fungus (*Corynespora cassiicola*). After the inoculation, the plant was cultivated at 24° C. in the daytime and 20° C. at night under high humidity condition for 7 days. Thereafter, the area of lesion spots was investigated. As a result, the area of lesion spots on the plant treated with the present compound 18, 19, 20, 21, 23, or 26 was 30% or less of that on an untreated plant.

Test Example 18

Each of plastic pots was filled with sandy loam and cucumber (cultivar: SAGAMI HANJIRO) was sowed and grown in a greenhouse for 19 days. Then, each water dilution containing a surfactant prepared by adjusting so as to contain a predetermined concentration (200 ppm) of any one compound of the present compounds 1, 2, 3, 4, 5, 18, 19, 20, 21, 23, 24, 25, and 26 was sprayed over stems and leaves of the cucumber so that it sufficiently adhered to the surface of the leaves of the cucumber. After spraying, the plant was air-dried. After one day, the plant was inoculated by sprinkling with spores of cucumber anthracnose fungus (*Colletotrichum lagenarium*). After the inoculation, the plant was at first left to stand at 23° C. under high humidity condition for one day and then cultivated in a greenhouse at 24° C. in the daytime and 20° C. at night for 6 days. Thereafter, the area of lesion spots was investigated. As a result, the area of lesion spots on the plant treated with the present compound 1, 2, 3, 4, 5, 18, 19, 20, 21, 23, 24, 25, or 26 was 30% or less of that on an untreated plant.

Test Example 19

A water dilution (test chemical solution) containing a surfactant prepared by adjusting so as to contain a predetermined concentration (500 ppm) of the present compound 21 was used as a test chemical solution. Thirty (30) heads of cotton aphid (*Aphis gossypii*) (including adults and larvae) were released on the leaves of cucumber (cultivar; SAGAMI HANJORO FUSHINARI) grown in a polyethylene cup until the first true leaf was developed. Next day, 20 mL of the above test chemical solution was sprayed. After 6 days, the number of the surviving insects was counted and the control value was calculated by the following equation.

Control value (%)={1−(Cb×Tai)/(Cai×Tb)}×100 wherein symbols in the equation represent the followings:
Cb: Number of insects before spraying chemical solution in untreated area;
Cai: Number of surviving insects in untreated area;
Tb: Number of insects before spraying chemical solution in treated area; and
Tai: Number of surviving insects in treated area.
As a result, the present compound 21 showed 90% or more of the control value.

Comparative Test Example

Each of plastic pots was filled with sandy loam and wheat (cultivar: SHIROGANE) was sowed and grown in a greenhouse for 9 days. Then, each water dilution containing a surfactant prepared by adjusting so as to contain a predetermined concentration (200 ppm) of any one compound of 1-[2-{5-phenoxypyridin-3-yloxymethyl}-3-methylphenyl]-4-methyl-1,4-dihydrotetrazol-5-one and the present compound 63 was sprayed over stems and leaves of the wheat so that it sufficiently adhered to the surface of the leaves of the wheat. After spraying, the plant was air-dried and cultivated at 20° C. for 5 days under illumination, and then inoculated by sprinkling with spores of wheat rust fungus (*Puccinia recondita*). After the inoculation, the plant was left to stand at 23° C. for one day under dark and high humidity condition, and cultivated under illumination at 20° C. for 8 days, and then the area of lesion spots was investigated. As a result, the area of lesion spots on the plant treated with 1-[2-{5-phenoxypyridin-3-yloxymethyl}-3-methylphenyl]-4-methyl-1,4-dihydrotetrazol-5-one was 70% or more of that on an untreated plant, whereas, the area of lesion spots on the plant treated with the present compound 63 was 30% or less of that on an untreated plant.

The invention claimed is:

1. A tetrazolinone compound represented by formula (1):

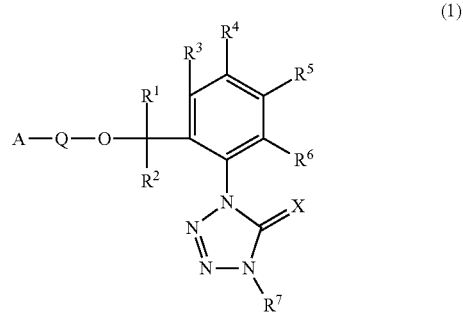

wherein
$R^1$ and $R^2$ each independently represents a hydrogen atom, a halogen atom, or a C1-C3 alkyl group;
$R^3$ represents a C1-C6 alkyl group, a C3-C6 cycloalkyl group, a halogen atom, a C1-C6 haloalkyl group, a C2-C6 alkenyl group, a C1-C6 alkoxy group, a C1-C6 alkylthio group, a C2-C6 alkynyl group, a nitro group, a cyano group, an aminocarbonyl group optionally having a C1-C6 alkyl group, a C2-C6 haloalkenyl group, a C2-C6 haloalkynyl group, a C3-C6 halocycloalkyl group, a C1-C6 haloalkoxy group, a C1-C6 haloalkylthio group, a C3-C6 cycloalkyloxy group, a C3-C6 halocycloalkyloxy group, a C3-C6 cycloalkylthio group, a C2-C6 alkenyloxy group, a C2-C6 alkynyloxy group, a C2-C6 haloalkenyloxy group, a C2-C6 haloalkynyloxy group, a C2-C6 alkenylthio group, a C2-C6 alkynylthio group, a C2-C6 haloalkenylthio group, a C2-C6 haloalkynylthio group, a C2-C6 alkylcarbonyl group, a C2-C6 haloalkylcarbonyl group, a C2-C6 alkylcarbonyloxy group, a C2-C6 alkylcarbonylthio group, a C2-C6 alkoxycarbonyl group, a hydroxy group, a sulfanyl group, an amino group optionally having a C1-C6 alkyl group, a pentafluorosulfanyl group, a C3-C9 trialkylsilyl group, a C5-C14 trialkylsilylethynyl group, a C1-C4 alkylsulfonyl group, a C1-C4 haloalkylsulfonyl group, a C1-C4 alkylsulfinyl group, a C1-C4 haloalkylsulfinyl group, a C2-C5 alkoxyalkyl group, or a C2-C5 alkylthioalkyl group;

$R^4$, $R^5$, and $R^6$ each independently represents a hydrogen atom, a halogen atom, a C1-C3 alkyl group, a C1-C3 haloalkyl group, or a C1-C3 alkoxy group;

$R^7$ represents a C1-C3 alkyl group optionally having one or more halogen atoms;

Q represents the following group:

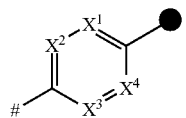

in which $X^1$, $X^2$, $X^3$, and $X^4$ each independently represents a nitrogen atom or $CR^x$, $R^x$ represents a hydrogen atom, or one or more atoms or groups selected from Group $P^2$ (provided that one or more of $X^1$, $X^2$, $X^3$, and $X^4$ represent a nitrogen atom, the symbol # represents a binding site for A, and the symbol ● represents a binding site for an oxygen atom;

X represents an oxygen atom or a sulfur atom;

A represents a C6-C10 aryl group optionally having one or more atoms or groups selected from Group $P^1$,
a C6-C10 aryloxy group optionally having one or more atoms or groups selected from Group $P^1$,
a C6-C10 arylthio group optionally having one or more atoms or groups selected from Group $P^1$,
a C6-C10 acylamino group optionally having one or more atoms or groups selected from Group $P^1$,
a 6-membered aromatic heterocyclic group having one, two, three, or four nitrogen atoms as a ring-constituent atom, provided that the heterocyclic group optionally has one or more groups or atoms selected from Group $P^1$,
a 5-membered heterocyclic group optionally having one or more atoms or groups selected from Group $P^1$ (provided that the 5-membered heterocyclic group has, as a ring-constituent atom, one or more atoms selected from the group consisting of a nitrogen atom, an oxygen atom, and a sulfur atom and, when the 5-membered heterocyclic group has two or more atoms selected from the group consisting of a nitrogen atom, an oxygen atom, and a sulfur atom, the atoms may be the same or different to each other),
an aliphatic C2-C9 heterocyclic group optionally having one or more atoms or groups selected from Group $P^1$,
provided that the aliphatic C2-C9 heterocyclic group has, as a ring-constituent atom, one or more atoms selected from the group consisting of a nitrogen atom, an oxygen atom, and a sulfur atom and, when the aliphatic C2-C9 heterocyclic group has two or more atoms selected from the group consisting of a nitrogen atom, an oxygen atom, and a sulfur atom, the atoms may be the same or different to each other, and also a carbon or nitrogen atom constituting a ring of the aliphatic C2-C9 heterocyclic group is bound to Q,
a C3-C10 cycloalkyl group optionally having one or more atoms or groups selected from Group $P^1$,
a C7-C18 aralkyl group, a C7-C18 haloaralkyl group, a C7-C18 arylalkoxy group, a C7-C18 haloarylalkoxy group, or an oxime ether group optionally having one or more groups selected from Group $P^3$:

Group $P^1$ is selected from the group consisting of a halogen atom, a C1-C6 alkyl group, a C1-C6 haloalkyl group, a C2-C6 alkenyl group, a C2-C6 haloalkenyl group, a C2-C6 alkynyl group, a C2-C6 haloalkynyl group, a C3-C6 cycloalkyl group, a C3-C6 halocycloalkyl group, a C1-C6 alkoxy group, a C1-C6 haloalkoxy group, a C1-C6 alkylthio group, a C1-C6 haloalkylthio group, a C3-C6 cycloalkyloxy group, a C3-C6 halocycloalkyloxy group, a C3-C6 cycloalkylthio group, a C3-C6 alkenyloxy group, a C3-C6 alkynyloxy group, a C3-C6 haloalkenyloxy group, a C3-C6 haloalkynyloxy group, a C3-C6 alkenylthio group, a C3-C6 alkynylthio group, a C3-C6 haloalkenylthio group, a C3-C6 haloalkynylthio group, a C2-C6 alkylcarbonyl group, a C2-C6 haloalkylcarbonyl group, a C2-C6 alkylcarbonyloxy group, a C2-C6 alkylcarbonylthio group, a hydroxycarbonyl group, a formyl group, a C2-C6 alkoxycarbonyl group, a nitro group, a cyano group, a hydroxy group, a C1-C6 alkylsulfonyl group, a C1-C6 haloalkylsulfonyl group, a C6-C10 arylsulfonyl group, a C6-C10 haloarylsulfonyl group, a C1-C6 alkylsulfinyl group, a C1-C6 haloalkylsulfinyl group, an amino group optionally having a C1-C6 alkyl group, an aminosulfonyl group optionally having a C1-C6 alkyl group, and an aminocarbonyl group optionally having a C1-C6 alkyl group;

Group $P^2$ is selected from the group consisting of a C1-C4 alkyl group, a C1-C4 haloalkyl group, a halogen atom, a cyano group, a nitro group, a C3-C6 cycloalkyl group, a C3-C6 halocycloalkyl group, a C1-C4 alkoxy group, a C1-C4 haloalkoxy group, a C1-C4 alkylthio group, and a C1-C4 haloalkylthio group; and Group $P^3$ is selected from the group consisting of a halogen atom, a C1-C6 alkyl group, a C1-C6 haloalkyl group, a C1-C6 cycloalkyl group, and a C1-C6 halocycloalkyl group.

2. The tetrazolinone compound according to claim 1, wherein $R^1$, $R^2$, $R^4$, $R^5$, and $R^6$ are hydrogen atoms, $R^3$ is a C1-C6 alkyl group, a C3-C6 cycloalkyl group, a halogen atom, a C1-C6 haloalkyl group, or a C1-C6 alkoxy group, and Q is the following group Q11:

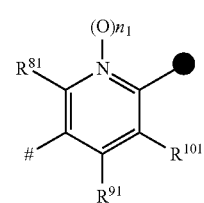

(Q11)

in which $R^{81}$, $R^{91}$, and $R^{101}$ each independently represents a hydrogen atom, a halogen atom, a C1-C4 alkyl group, or a C1-C4 haloalkyl group, $n_1$ represents 0, X represents an oxygen atom, the symbol # represents a binding site for A, and the symbol ● represents a binding site for an oxygen atom.

3. The tetrazolinone compound according to claim 1, wherein A is the following group A111:

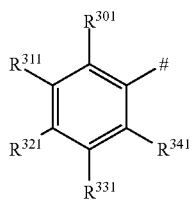

(A111)

in which $R^{301}$, $R^{311}$, $R^{321}$, $R^{331}$, and $R^{341}$ each independently represents a hydrogen atom, a halogen atom, a C1-C6 alkyl group, a C1-C6 haloalkyl group, a C1-C6 alkoxy group, a C1-C6 haloalkoxy group, a C1-C6 alkylthio group, a C1-C6 haloalkylthio group, a C1-C6 alkylsulfinyl group, a C1-C6 haloalkylsulfinyl group, a C1-C6 alkylsulfonyl group, a C1-C6 haloalkylsulfonyl group, or a cyano group, and the symbol # represents a binding site for Q.

4. The tetrazolinone compound according to claim 1, wherein A is the following group A131:

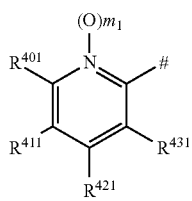

(A131)

in which $m_1$ presents 0, $R^{404}$, $R^{411}$, $R^{421}$, and $R^{431}$ each independently represents a hydrogen atom, a halogen atom, a C1-C6 alkyl group, a C1-C6 haloalkyl group, a C1-C6 alkoxy group, a C1-C6 haloalkoxy group, a C1-C6 alkylthio group, a C1-C6 haloalkylthio group, a C1-C6 alkylsulfinyl group, a C1-C6 haloalkylsulfinyl group, a C1-C6 alkylsulfonyl group, a C1-C6 haloalkylsulfonyl group, or a cyano group, and the symbol # represents a binding site for Q.

5. The tetrazolinone compound according to claim 1, wherein A is the following group A311:

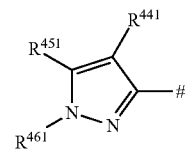

(A311)

in which $R^{441}$ represents a hydrogen atom, a C1-C3 alkyl group, or a halogen atom, $R^{451}$ represents a hydrogen atom, a halogen atom, a C1-C6 alkyl group, a C1-C3 alkoxy group, a C1-C3 alkylthio group, or a cyano group, $R^{461}$ represents a C1-C3 alkyl group, and the symbol # represents a binding site for Q.

6. The tetrazolinone compound according to claim 1, wherein $R^1$, $R^2$, $R^4$, $R^5$, and $R^6$ are hydrogen atoms, $R^3$ is a C1-C6 alkyl group, a C3-C6 cycloalkyl group, a halogen atom, or a C1-C6 alkoxy group, Q is Q11:

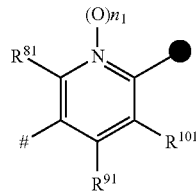

(Q11)

$R^{81}$, $R^{91}$, and $R^{101}$ each independently represents a hydrogen atom, a halogen atom, or a C1-C4 alkyl group, $n_1$ is 0, A is a group A111:

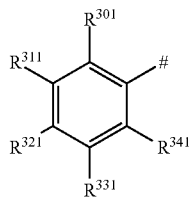

(A111)

and $R^{301}$, $R^{311}$, $R^{321}$, $R^{331}$, and $R^{341}$ each independently represents a hydrogen atom, a halogen atom, a C1-C6 alkyl group, a C1-C6 haloalkyl group, a C1-C6 alkoxy group, or a cyano group.

7. The tetrazolinone compound according to claim 1, wherein $R^1$, $R^2$, $R^4$, $R^5$, and $R^6$ are hydrogen atoms, $R^3$ is a C1-C6 alkyl group, a C3-C6 cycloalkyl group, a halogen atom, or a C1-C6 alkoxy group, Q is Q11:

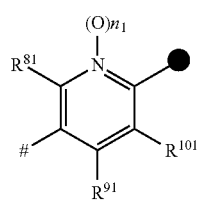

(Q11)

$R^{81}$, $R^{91}$, and $R^{101}$ each independently represents a hydrogen atom or a C1-C4 alkyl group, $n_1$ is 0, A is a group A131:

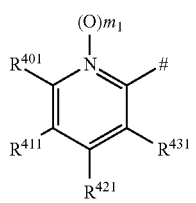

(A131)

$m_1$ is 0, $R^{401}$, $R^{411}$, $R^{421}$, and $R^{431}$ each independently represents a hydrogen atom, a halogen atom, a C1-C6 alkyl group, a C1-C6 haloalkyl group, a C1-C6 alkoxy group, or a cyano group.

8. The tetrazolinone compound according to claim 1, wherein $R^1$, $R^2$, $R^4$, $R^5$, and $R^6$ are hydrogen atoms, $R^3$ is a C1-C6 alkyl group, Q is the following group Q21:

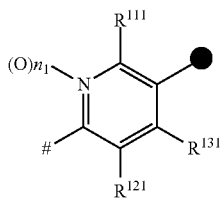

(Q21)

in which $R^{121}$ and $R^{131}$ represent a hydrogen atom, $R^{111}$ represents a C1-C4 alkyl group, $n_1$ is 0, the symbol # represents a binding site for A, and the symbol ● represents a binding site for an oxygen atom), X is an oxygen atom, A is a group A111:

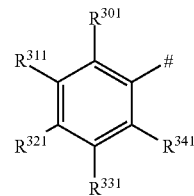

(A111)

and $R^{301}$, $R^{311}$, $R^{321}$, $R^{331}$, and $R^{341}$ each independently represents a hydrogen atom, a C1-C6 alkyl group, a C1-C6 alkoxy group, or a cyano group.

9. A pest control agent comprising the tetrazolinone compound according to claim 1.

10. A method for controlling pests, which comprises treating plants or soil with an effective amount of the tetrazolinone compound according to claim 1.

* * * * *